(12) United States Patent
Radakovits et al.

(10) Patent No.: US 8,709,766 B2
(45) Date of Patent: Apr. 29, 2014

(54) USE OF ENDOGENOUS PROMOTERS IN GENETIC ENGINEERING OF NANNOCHLOROPSIS GADITANA

(71) Applicant: Colorado School of Mines, Golden, CO (US)

(72) Inventors: Randor Radakovits, Denver, CO (US); Robert Jinkerson, Golden, CO (US); Matthew Posewitz, Golden, CO (US)

(73) Assignee: Colorado School of Mines, Golden, CO (US)

( * ) Notice: Subject to any disclaimer, the term of this patent is extended or adjusted under 35 U.S.C. 154(b) by 0 days.

(21) Appl. No.: 13/654,347

(22) Filed: Oct. 17, 2012

(65) Prior Publication Data
US 2013/0102040 A1    Apr. 25, 2013

Related U.S. Application Data

(60) Provisional application No. 61/548,157, filed on Oct. 17, 2011, provisional application No. 61/578,110, filed on Dec. 20, 2011.

(51) Int. Cl.
| | |
|---|---|
| C12P 7/64 | (2006.01) |
| C12N 9/10 | (2006.01) |
| C12N 1/13 | (2006.01) |
| C07H 21/04 | (2006.01) |

(52) U.S. Cl.
USPC ..... 435/134; 435/193; 435/257.2; 435/173.5; 435/470; 536/23.7; 536/24.1

(58) Field of Classification Search
None
See application file for complete search history.

(56) References Cited

PUBLICATIONS

Armbrust et al., "The genome of the diatom *Thalassiosira pseudonana*: Ecology, evolution, and metabolism", *Science*, 79-86 (2004).
Atsumi et al., "Direct photosynthetic recycling of carbon dioxide to isobutyraldehyde", *Nature Biotechnology*, pp. 1177-1180 (2009).
Blanc et al. "The *Chlorella variabilis* NC64A genome reveals adaptation to photosymbiosis, coevolution with viruses, and cryptic sex", *The Plant Cell* (2010).
Blüthgen et al. "Biological Profiling of Gene groups utilizing Gene ontology—A statistical and software framework", (2004), Gossip software, http://www.microdiscovery.de/.
Blüthgen et al. "Biological Profiling of Gene Groups utilizing Gene Ontology", Genome Informatics, 16 (1): 106-115, 2005.
Bowler et al., "The Phaeodactylum genome reveals the evolutionary history of diatom genomes". *Nature*, pp. 239-244 (2008).
Chen et al., "Conditional production of a functional fish growth hormone in the transgenic line of *Nannochloropsis oculata* (Eustigmatophyceae)". *Journal of Phycology*, pp. 768-776 (2008).
Cock et al. "The Ectocarpus genome and the independent evolution of multicellularity in brown algae", *Nature*, pp. 617-621 (2010).
Conesa et al., "Blast2GO: a universal tool for annotation, visualization and analysis in functional genomics research", *Bioinformatics* 21, pp. 3674-3676 (2005).
Gobler et al. "Niche of harmful alga *Aureococcus anophagefferens* revealed through ecogenomics", *Proceedings of the National Academy of Sciences*, pp. 4352-4357 (2011).
Götz et al., "B2G-FAR, a species centered GO annotation repository", *Bioinformatics* (2011).
Götz et al. "High-throughput functional annotation and data mining with the Blast2GO suite", Nucleic Acids Research 36, pp. 3420-3435 (2008).
Gouveia et al., "Microalgae as a raw material for biofuels production", *Journal of Industrial Microbiology & Biotechnology*, pp. 269-274 (2009).
Hu et al. "Microalgal triacylglycerols as feedstocks for biofuel production: perspectives and advances", *The Plant Journal*, pp. 621-639 (2008).
Karpowicz et al., "The GreenCut2 resource, a phylogenomically derived inventory of proteins specific to the plant lineage", *Journal of Biological Chemistry*, pp. 21427-21439 (2011).
Kindle, K.L. "High-frequency nuclear transformation of *Chlamydomonas reinhardtii*", *Proceedings of the National Academy of Sciences*, pp. 1228-1232 (1990).
Le Corguille et al., "Plastid genomes of two brown algae, *Ectocarpus siliculosus* and *Fucus vesiculosus*: further insights on the evolution of red-algal derived plastids", *BMC Evolutionary Biology* 9, p. 253 (2009).
Li et al., "Chloroplast-encoded chlB is required for light-independent protochlorophyllide reductase activity in *Chlamydomonas reinhardtii*", *The Plant Cell* 5, pp. 1817-1829 (1993).
Li et al. "Chlamydomonas starchless mutant defective in ADP-glucose pyrophosphorylase hyper-accumulates triacylglycerol.", *Metabolic Engineering*, pp. 387-391 (2010).
Marchler-Bauer et al., "CDD: a Conserved Domain Database for the functional annotation of proteins", Nucleic Acids Research 39, 225-229 (2011).
Matsuzaki et al., "Genome sequence of the ultrasmall unicellular red alga *Cyanidioschyzon merolae* 10D", *Nature*, pp. 653-657 (2004).
Merchant et al., "The Chlamydomonas genome reveals the evolution of key animal and plant functions", *Science*, pp. 245-250 (2007).
Oudot-Le Secq et al., "Chloroplast genomes of the diatoms *Phaeodactylum tricornutum* and *Thalassiosira pseudonana* comparison with other plastid genomes of the red lineage", *Molecular Genetics and Genomics* 277, pp. 427-439 (2007).

(Continued)

*Primary Examiner* — David T Fox
*Assistant Examiner* — Matthew Keogh
(74) *Attorney, Agent, or Firm* — Dorsey & Whitney LLP

(57) ABSTRACT

The present disclosure is directed to novel polynucleotide sequences for use in *Nannochloropsis gaditana*. The novel polynucleotide sequences include control sequences and coding sequences. Also disclosed are novel gene expression constructs wherein *N. gaditana* promoters/control regions are operatively linked to *N. gaditana* or non-*N. gaditana* coding sequences. These novel polynucleotide sequences and expression constructs can be introduced into *N. gaditana* and can recombine into the *N. gaditana* genome. Expression from these polynucleotide sequences and expression constructs can enhance *N. gaditana* biomass and/or lipid biosynthesis. Also disclosed are methods for modifying *N. gaditana*, for example by stably transforming *N. gaditana* with nucleic acid sequences, growing the modified *N. gaditana*, and obtaining biomass and biofuels from the modified *N. gaditana*.

13 Claims, 198 Drawing Sheets

(56) References Cited

PUBLICATIONS

Pal et al., "The effect of light, salinity, and nitrogen availability on lipid production by *Nannochloropsis* sp.", *Applied Microbiology and Biotechnology*, pp. 1429-1441 (2011).

Radakovits et al, "Genetic engineering of fatty acid chain length in *Phaeodactylum tricornutum*", *Metabolic Engineering*, pp. 1-7 (2010).

Radakovits et al., "Genetic engineering of algae for enhanced biofuel production", Eukaryotic Cell 9, pp. 486-501 (2010).

Samstag, Antisense Nucleic Acid Drug Dev 6: pp. 153-156 (1996).

Steen et al., "Microbial production of fatty-acid-derived fuels and chemicals from plant biomass", Nature 463, pp. 559-562 (2010).

Wang et al. Algal Lipid Bodies: Stress induction, purification, and biochemical characterization in wild-type and starchless *Chlamydomonas reinhardtii*. *Eukaryotic Cell*, pp. 1856-1868 (2009).

Work et al. "Increased lipid accumulation in the *Chlamydomonas reinhardtii* sta7-10 starchless isoamylase mutant and increased carbohydrate synthesis in complemented strains", *Eukaryotic Cell*, pp. 1251-1261 (2010).

Zaslavskaia et al., "Transformation of the diatom *Phaeodactylum tricornutum* (Bacillariophyceae) with a variety of selectable marker and reporter genes", *Journal of Phycology*, pp. 379-386 (2000).

Zou et al. "Production of cell mass and eicosapentaenoic acid (EPA) in ultrahigh cell density cultures of *Nannochloropsis* sp. (Eustigmatophyceae)", *European Journal of Phycology*, pp. 127-133 (2000).

| Supplementary Table 3. Chlorophyll (tetrapyrrole), carotenoid and sterol biosynthesis genes ||||||
|---|---|---|---|---|---|
| Enzyme | Description | EC number | N. gaditana model[a] | Transcript Support[b] | Gene Location[c] |
| Tetrapyrrole Synthesis ||||||
| GTS | glutamyl-tRNA synthetase | 6.1.1.17 | Nga04989 | Y | N |
| GTS | glutamyl-tRNA synthetase | 6.1.1.24 | Nga02834 | Y | N |
| GTR | glutamyl-tRNA reductase | 1.2.1.70 | Nga02604 | Y | N |
| GSA | glutamate-1-semialdehyde aminotransferase / glutamate-1-semialdehyde 21-aminomutase | 5.4.3.8 | Nga30045 | Y | N |
| ALAD (HemB) | 5-aminolevulinic acid dehydratase / porphobilinogen synthase | 4.2.1.24 | Nga00585 | Y | N |
| PBGD (HemC) | porphobilinogen deaminase / hydroxymethylbilane synthase | 2.5.1.61 | Nga03248 | Y | N |
| UROS (HemD) | uroporphyrinogen III synthase | 4.2.1.75 | Nga00807 | Y | N |
| UROD | uroporphyrinogen III decarboxylase | 4.1.1.37 | Nga04120 | Y | N |
| UROD | uroporphyrinogen III decarboxylase | 4.1.1.37 | Nga05706 | Y | N |
| CPX1 (HemF) | coproporphyrinogen III oxidase | 1.3.3.3 | Nga05151 | Y | N |
| CPX1 (HemF) | coproporphyrinogen III oxidase | 1.3.3.3 | Nga04278 (partial) | Y | N |
| PPX | protoporphyrinogen IX oxidase | 1.3.3.4 | Nga03873 | Y | N |
| ChlD | protoporphyrin IX Mg-chelatase subunit D | 6.6.1.1 | Nga30773 | Y | N |
| ChlI | protoporphyrin IX MG-chelatase subuint I | 6.6.1.1 | Nga40092 | N | C |
| ChlH1 | protoporphyrin IX Mg-chelatase subunit H | 6.6.1.1 | Nga30995 | Y | N |
| ChlH2 | protoporphyrin IX Mg-chelatase subunit H | 6.6.1.1 | Nga06242 | Y | N |
| PPMT (ChlM) | Mg-protoporphyrin IX methyltransferase | 2.1.1.11 | Nga04808 | Y | N |
| AcsF (ycf59) | Mg-protoporphyrin IX monomethyl ester (oxidative) cyclase | 1.14.13.81 | Nga40091 | N | C |
| DVR | divinyl protochlorophyllide a 8-vinyl-reductase | 1.3.1.75 | Nga05945 | Y | N |
| POR | light-dependent NADPH:protochlorophyllide oxidoreductase | 1.3.1.33 | Nga04959 | Y | N |
| POR | light-dependent NADPH:protochlorophyllide oxidoreductase | 1.3.1.33 | Nga00683 | Y | N |
| ChlB | light-independent:protochlorophyllide oxidoreductase subunit B | 1.18.-.- | Nga40089 | N | C |
| ChlL | light-independent:protochlorophyllide oxidoreductase subunit L | 1.18.-.- | Nga40044 | Y | C |
| ChlN | light-independent:protochlorophyllide oxidoreductase subunit N | 1.18.-.- | Nga40045 | N | C |
| CHS (ChlG) | chlorophyll synthase | 2.5.1.62 | Nga31097 | Y | N |

FIGURE 1 A

| Enzyme | Description | EC number | N. gaditana model[a] | Transcript Support[b] | Gene Location[c] |
|---|---|---|---|---|---|
| GGR (ChlP) | geranylgeranyl reductase | 1.3.1.- | Nga04895 | Y | N |
| UMT | uroporphyrinogen III C-methyltransferase | 2.1.1.107 | Nga05160 | Y | N |
| SirB | sirohydrochlorin ferrochelatase | 4.99.1.4 | Nga00339 | Y | N |
| FC (HemH) | ferrochelatase | 4.99.1.1 | Nga00748 | Y | N |
| Carotenoid Biosynthesis | | | | | |
| DXS | 1-deoxy-D-xylulose-5-phosphate synthase | 2.2.1.7 | Nga02203 | Y | N |
| DXR (IspC) | 1-deoxy-D-xylulose-5-phosphate reductoisomerase | 1.1.1.267 | Nga30771 | Y | N |
| MCT (IspD) | 2-C-methyl-D-erythritol 4-phosphate cytidyltransferase | 2.7.7.60 | Nga06198 | Y | N |
| CMK (IspE) | 4-(cytidine 5'-diphospho)-2-C-methyl-D-erythritol kinase | 2.7.1.148 | Nga04584 | Y | N |
| MDS (IspF) | 2-C-methyl-D-erythritol 24-cyclodiphosphate synthase | 4.6.1.12 | Nga02651 | Y | N |
| HDS (IspG) | 4-hydroxy-3-methylbut-2-enyl diphosphate synthase | 1.17.4.3 | Nga30806 | Y | N |
| HDR (IspH) | 4-hydroxy-3-methylbut-2-enyl diphosphate reductase | 1.17.1.2 | Nga05308 | Y | N |
| IDI | isopentenyl diphosphate:dimethylallyl diphosphate isomerase type I | 5.3.3.2 | Nga03838 | Y | N |
| IDI | isopentenyl diphosphate:dimethylallyl diphosphate isomerase type I | 5.3.3.2 | Nga10002 | Y | N |
| GGPPS (CrtE) | geranylgeranyl pyrophosphate synthase | 2.5.1.29 | Nga02636 | Y | N |
| PSY1 (CrtB) | phytoene synthase | 2.5.1.32 | Nga02957 | Y | N |
| PDS (CrtP) | phytoene desaturase | 1.14.99.- | Nga05064 | Y | N |
| ZDS (CrtQ) | zeta-carotene desaturase | 1.14.99.30 | Nga07310 | Y | N |
| CRTISO | carotenoid isomerase | | No Homolog | - | - |
| LCYB (CrtL-b) | lycopene β-cyclase | 1.14.-.- | Nga00640 | Y | N |
| CYP97E | cytochrome P450 enzyme related to CYP97A carotene β-hydroxylase | | Nga30077 | Y | N |
| CYP97F | cytochrome P450 enzyme related to CYP97A carotene β-hydroxylase | | Nga00100 | Y | N |
| ZEP | zeaxanthin epoxidase | 1.14.13.90 | Nga01534 | Y | N |
| VDE | violaxanthin de-epoxidase | 1.10.99.3 | Nga02700 | Y | N |
| NSY | neoxanthin synthase | 5.3.99.9 | Nga10001 | Y | N |
| Sterol Synthesis | | | | | |
| ACAT | acetyl-CoA C-acetyltransferase | 2.3.1.9 | Nga20998 | Y | N |
| ACAT | acetyl-CoA C-acetyltransferase | 2.3.1.9 | Nga30830 | Y | N |
| HMGS | hydroxymethylglutaryl-CoA synthase | 2.3.3.10 | Nga06246 | Y | N |

FIGURE 1B

| Enzyme | Description | EC number | N. gaditana model[a] | Transcript Support[b] | Gene Location[c] |
|---|---|---|---|---|---|
| HMGR | hydroxymethylglutaryl-CoA reductase | 1.1.1.34 | No Homolog | - | - |
| MVK | mevalonate kinase | 2.7.1.36 | No Homolog | - | - |
| PMK | phosphomevalonate kinase | 2.7.4.2 | No Homolog | - | - |
| MVD | diphosphomevalonate decarboxylase | 4.1.1.33 | No Homolog | - | - |
| GPPS | geranyl-disphosphate synthase / dimethylallyltransferase | 2.5.1.1 | Nga02865 | Y | N |
| GPPS | geranyl-disphosphate synthase / dimethylallyltransferase | 2.5.1.1 | Nga01978 | Y | N |
| FPPS | farnesyl-diphosphate synthase | 2.5.1.68 | Nga02874 | Y | N |
| IDI | isopentenyl diphosphate:dimethylallyl diphosphate isomerase type I | 5.3.3.2 | Nga03838 | Y | N |
| IDI | isopentenyl diphosphate:dimethylallyl diphosphate isomerase type I | 5.3.3.2 | Nga10002 | Y | N |
| SQE (SQP) | squalene monoxygenase / squalene epoxidase | 1.14.99.7 | Nga01590 | Y | N |
| CAS | cycloartenol synthase | 5.4.99.8 | Nga30790 | Y | N |
| CYP51 | C14-demethylase (sterol 14-demethylase) | 1.14.13.70 | Nga03733.1 | Y | N |
| FACKEL | D14-sterol reductase | 1.3.1.70 | Nga00758 | N | N |
| SMO | Sterol methyl-oxidase (C4-methylsterol monooxygenase) | 1.14.13.72 | No Homolog | - | - |
| HSD-D | C4-decarboxylase (sterol-4-alpha-carboxylate 3-dehydrogenase) | 1.1.1.170 | Nga06114 | Y | N |
| SMT1 | sterol-C24-methyl transferase (sterol 24-C-methyltransferase) | 2.1.1.41 | Nga05943 | Y | N |
| SMT1 | sterol-C24-methyl transferase (sterol 24-C-methyltransferase) | 2.1.1.41 | Nga02534 | Y | N |
| HYD1 | D8-D7-sterol-isomerase (cholestenol delta-isomerase) | 5.3.3.5 | No Homolog | - | - |
| DWF7 (STE1) | C5-desaturase (lathosterol oxidase) | 1.14.21.6 | Nga02795 | Y | N |
| DWF5 | D7-sterol reductase (7-dehydrocholesterol reductase) | 1.3.1.21 | Nga03254 | Y | N |
| DWF1 | D24-sterol reductase (24-dehydrocholesterol reductase) | 1.3.1.72 | Nga03764 | Y | N |
| DWF1 | D24-sterol reductase (24-dehydrocholesterol reductase) | 1.3.1.72 | Nga05293 | Y | N |
| CPI (CCI) | cyclopropyl sterol isomerase (cycloeucalenol cycloisomerase) | 5.5.1.9 | Nga30196 | Y | N |
| DET2 | D5-sterol reductase | 1.3.1.30 | Nga00656 | Y | N |

FIGURE 1C

| Gene Name | Guillardia theta | Odontella sinensis | Phaeodactylum tricornutum | Thalassiosira pseudonana | Emiliania huxleyi | Ectocarpus siliculosus | N. gaditana |
|---|---|---|---|---|---|---|---|
| acpP | + | + | + | - | - | - | - |
| atpA | + | + | + | + | + | + | + |
| atpB | + | + | + | + | + | + | + |
| atpD | + | + | + | + | + | + | - |
| atpE | + | + | + | + | + | + | + |
| atpF | + | + | + | + | + | + | + |
| atpG | + | + | + | + | + | + | + |
| atpH | + | + | + | + | + | + | + |
| atpI | + | + | + | + | + | + | + |
| cbbX | + | + | + | + | + | + | + |
| ccs1 (ycf44) | + | + | + | + | + | + | + |
| ccsA (ycf5) | + | + | + | + | + | + | + |
| cemA (ycf10) | + | - | - | - | - | - | - |
| chlB | - | - | - | - | - | + | + |
| chlI | + | + | + | + | + | + | + |
| chlJ | - | - | - | - | - | - | - |
| chlL | - | - | - | - | - | + | + |
| chlN | - | - | - | - | - | + | + |
| clpA | - | - | - | - | - | - | + |
| clpC | + | + | + | + | + | + | + |
| cpeB | + | - | - | - | - | - | - |
| dfr | - | - | - | - | + | - | - |
| dnaB | + | + | + | + | - | + | - |
| dnaK | + | + | + | + | + | + | + |
| ftrB | + | - | - | - | - | + | - |
| ftsH (ycf25) | + | + | + | + | - | + | + |
| groL | + | + | + | + | + | + | + |
| hlip (ycf17) | + | - | - | - | - | + | - |
| hupA | + | - | - | - | - | - | - |
| ilvB | + | - | - | - | - | + | + |

FIGURE 6A

| Gene Name | Guillardia theta | Odontella sinensis | Phaeodactylum tricornutum | Thalassiosira pseudonana | Emiliania huxleyi | Ectocarpus siliculosus | N. gaditana |
|---|---|---|---|---|---|---|---|
| ilvH | + | - | - | - | - | + | - |
| infB | + | - | - | - | - | - | - |
| minD | + | - | - | - | + | - | - |
| minE | + | - | - | - | - | - | - |
| pbsA | + | - | - | - | - | - | - |
| petA | + | + | + | + | + | + | + |
| petB | + | + | + | + | + | + | + |
| petD | + | + | + | + | + | + | + |
| petF | + | + | + | + | - | + | + |
| petG | + | + | + | + | + | + | + |
| petL (ycf7) | + | + | + | + | + | + | - |
| petM (ycf31) | + | + | + | + | + | + | - |
| petN (ycf6) | + | + | + | + | + | + | + |
| psaA | + | + | + | + | + | + | + |
| psaB | + | + | + | + | + | + | + |
| psaC | + | + | + | + | + | + | + |
| psaD | + | + | + | + | + | + | + |
| psaE | + | + | + | + | - | + | + |
| psaF | + | + | + | + | + | + | + |
| psaI | + | + | + | + | + | + | + |
| psaJ | + | + | + | + | + | + | + |
| psaK | + | - | - | - | - | - | - |
| psaL | + | + | + | + | + | + | + |
| psaM | + | + | + | + | + | + | + |
| psb28 (ycf79) | + | + | + | + | - | + | + |
| psbA | + | + | + | + | + | + | + |
| psbB | + | + | + | + | + | + | + |
| psbC | + | + | + | + | + | + | + |
| psbD | + | + | + | + | + | + | + |
| psbE | + | + | + | + | + | + | + |
| psbF | + | + | + | + | + | + | + |
| psbH | + | + | + | + | + | + | + |
| psbI | + | + | + | + | + | + | + |
| psbJ | + | + | + | + | + | + | + |
| psbK | + | + | + | + | + | + | + |

FIGURE 6 B

| Gene Name | Guillardia theta | Odontella sinensis | Phaeodactylum tricornutum | Thalassiosira pseudonana | Emiliania huxleyi | Ectocarpus siliculosus | N. gaditana |
|---|---|---|---|---|---|---|---|
| psbL | + | + | + | + | + | + | + |
| psbN | + | + | + | + | + | + | + |
| psbT (ycf8) | + | + | + | + | + | + | + |
| psbV | + | + | + | + | + | + | + |
| psbW | - | - | - | - | - | + | + |
| psbX | + | + | + | + | + | + | - |
| psbY (ycf32) | + | + | + | + | + | + | + |
| psbZ (ycf9) | + | + | + | + | + | - | + |
| rbcL | + | + | + | + | + | + | + |
| rbcR (ycf30) | + | + | + | + | + | + | - |
| rbcS | + | + | + | + | + | + | + |
| rne | + | - | - | - | - | - | - |
| rpl1 | + | + | + | + | - | + | + |
| rpl11 | + | + | + | + | - | + | + |
| rpl12 | + | + | + | + | - | + | + |
| rpl13 | + | + | + | + | - | + | + |
| rpl14 | + | + | + | + | + | + | + |
| rpl16 | + | + | + | + | + | + | + |
| rpl18 | + | + | + | + | - | + | + |
| rpl19 | + | + | + | + | + | + | + |
| rpl2 | + | + | + | + | + | + | + |
| rpl20 | + | + | + | + | + | + | + |
| rpl21 | + | + | + | + | + | + | + |
| rpl22 | + | + | + | + | + | + | + |
| rpl23 | + | + | + | + | + | + | + |
| rpl24 | + | + | + | + | - | + | - |
| rpl27 | + | + | + | + | + | + | + |
| rpl29 | + | + | + | + | - | + | - |
| rpl3 | + | + | + | + | + | + | + |
| rpl31 | + | + | + | + | + | + | + |
| rpl32 | + | + | + | + | - | + | + |
| rpl33 | + | + | + | + | + | + | + |
| rpl34 | + | + | + | + | + | + | + |
| rpl35 | + | + | + | + | - | + | + |
| rpl36 | + | + | + | + | + | + | + |

FIGURE 6 C

| Gene Name | Guillardia theta | Odontella sinensis | Phaeodactylum tricornutum | Thalassiosira pseudonana | Emiliania huxleyi | Ectocarpus siliculosus | N. gaditana |
|---|---|---|---|---|---|---|---|
| rpl4 | + | + | + | + | - | + | + |
| rpl5 | + | + | + | + | + | + | + |
| rpl6 | + | + | + | + | + | + | + |
| rpmC | - | - | - | - | - | + | + |
| rpoA | + | + | + | + | + | + | + |
| rpoB | + | + | + | + | + | + | + |
| rpoC1 | + | + | + | + | + | + | + |
| rpoC2 | + | + | + | + | + | + | + |
| rpoZ (ycf61) | + | - | - | - | - | - | - |
| rps10 | + | + | + | + | + | + | + |
| rps11 | + | + | + | + | + | + | + |
| rps12 | + | + | + | + | + | + | + |
| rps13 | + | + | + | + | + | + | + |
| rps14 | + | + | + | + | + | + | + |
| rps16 | + | + | + | + | + | + | + |
| rps17 | + | + | + | + | + | + | + |
| rps18 | + | + | + | + | + | + | + |
| rps19 | + | + | + | + | + | + | + |
| rps2 | + | + | + | + | + | + | + |
| rps20 | + | + | + | + | - | + | + |
| rps3 | + | + | + | + | + | + | + |
| rps4 | + | + | + | + | + | + | + |
| rps5 | + | + | + | + | + | + | + |
| rps6 | + | + | + | + | + | - | + |
| rps7 | + | + | + | + | + | + | + |
| rps8 | + | + | + | + | + | + | + |
| rps9 | + | + | + | + | + | + | + |
| secA | + | + | + | + | + | + | + |
| secG (ycf47) | + | + | + | + | + | + | - |
| secY | + | + | + | + | + | + | + |
| sufB (ycf24) | + | + | + | + | + | + | + |
| sufC (ycf16) | + | + | + | + | - | + | + |
| syfB | - | - | + | - | - |  | - |
| tatC (ycf43) | + | + | + | + | + |  | + |

FIGURE 6 D

| Gene Name | Guillardia theta | Odontella sinensis | Phaeodactylum tricornutum | Thalassiosira pseudonana | Emiliania huxleyi | Ectocarpus siliculosus | N. gaditana |
|---|---|---|---|---|---|---|---|
| thiG | - | + | + | + | + | + | + |
| thiS (ycf40) | - | + | + | + | + | + | + |
| tsf | + | - | + | - | - | + | - |
| tufA | + | + | + | + | + | + | + |
| ycf12 | + | + | + | + | + | + | + |
| ycf19 | + | - | - | - | + | + | + |
| ycf20 | + | - | - | - | + | - | - |
| ycf27 | + | - | - | - | + | - | - |
| ycf29 | + | - | - | - | - | - | - |
| ycf3 | + | + | + | + | + | + | + |
| ycf33 | + | + | + | + | - | + | - |
| ycf34 | - | - | - | - | - | + | + |
| ycf35 | + | + | + | + | + | + | - |
| ycf36 | + | - | - | - | - | - | - |
| ycf37 | + | - | - | - | - | + | - |
| ycf39 | + | + | + | + | + | + | - |
| ycf4 | + | + | + | + | + | + | + |
| ycf41 | - | + | + | + | - | + | - |
| ycf42 | - | + | + | + | - | + | - |
| ycf45 | - | + | + | + | + | - | - |
| ycf46 | + | + | + | + | + | + | + |
| ycf54 | - | - | - | - | - | + | + |
| ycf55 | - | - | - | - | + | - | - |
| ycf59 | - | - | - | - | - | - | + |
| ycf60 | - | - | - | - | + | + | - |
| ycf65 | + | - | - | - | + | + | - |
| ycf66 | - | + | + | + | - | + | + |
| ycf80 | + | - | - | - | + | - | - |
| ycf88 | - | + | + | + | - | - | - |
| ycf89 | - | + | + | + | - | - | - |
| ycf90 | - | + | + | + | - | - | - |

FIGURE 6 E

| Supplementary Table 9. Gene clusters |||
|---|---|---|
| GO-term | GO-term description | Contig |
| N. gaditana model[d] | Gene model description[e] | Gene #[f] |
| GO:0042967 | acyl-carrier-protein biosynthetic process | merged000123 |
| Nga02737 | phospholipid:diacylglycerol acyltransferase | 1 |
| Nga02743 | serine palmitoyltransferase | 9 |
| Nga02741 | pyruvate dehydrogenase component x | 10 |
| GO:0006807 | nitrogen compound metabolic process | merged000138 |
| Nga00713 | guanine deaminase | 1 |
| Nga00717 | cytohesin-1 isoform 2 | 3 |
| Nga00702 | serine threonine-protein kinase tousled-like 1 isoform 2 | 5 |
| GO:0008610 | lipid biosynthetic process | merged000154 |
| Nga00818 | monogalactosyldiacylglycerol synthase | 1 |
| Nga00817 | fatty acid desaturase | 3 |
| GO:0046394 | carboxylic acid biosynthetic process | merged000212 |
| Nga05525 | anthranilate synthase | 1 |
| Nga05530 | cystathionine beta-synthase | 5 |
| Nga05522 | dihydroxy-acid dehydratase | 11 |
| GO:0006778 | porphyrin metabolic process | merged000288 |
| Nga03876 | protoporphyrinogen oxidase | 1 |
| Nga03879 | protoporphyrinogen oxidase | 2 |
| Nga03873 | protoporphyrinogen oxidase | 5 |
| GO:0006397 | mRNA processing | merged000340 |
| Nga20580 | rrna processing protein rrp17 | 1 |
| Nga30171 | u4 u6 small nuclear ribonucleoprotein prp3 | 2 |
| Nga30821 | u4 u6 small nuclear ribonucleoprotein prp4 | 3 |
| Nga05511 | prp4 pre-mrna processing factor 4 homolog | 4 |
| Nga30351 | u4 u6 small nuclear ribonucleoprotein prp4 | 6 |
| GO:0016070 | RNA metabolic process | merged000438 |
| Nga03294 | tfiih subunit | 1 |
| Nga30114 | protein | 2 |
| Nga03302 | polyadenlyte binding protein | 3 |
| Nga03296 | b chain structure of the mlle domain of poly-binding protein in complex with the binding region of paip2 | 5 |
| GO:0006810 | transport | merged000462 |
| Nga31189 | abc transporter | 1 |
| Nga03486 | abc atp-binding permease protein | 3 |
| Nga03479 | atp-binding cassette superfamily | 6 |
| GO:0034641 | cellular nitrogen compound metabolic process | NODE_3127 |
| Nga03304 | s-adenosylmethionine synthetase | 1 |
| Nga03314 | glutamyl-trna amidotransferase subunit a | 2 |
| Nga03312 | cytidine and deoxycytidylate deaminase family protein | 3 |
| Nga03305 | rna pseudouridylate synthase family protein | 4 |
| Nga03303 | carbamoyl-phosphate small subunit | 5 |
| Nga03313 | dihydropteroate synthase | 6 |

FIGURE 8A

| | | |
|---|---|---|
| Nga03316 | aspartate aminotransferase | 10 |
| Nga03306 | thymidylate synthase | 11 |
| Nga03310 | dihydrofolate reductase | 12 |
| Nga03311 | threonyl-trna synthetase | 13 |
| GO:0006139 | nucleobase, nucleoside, nucleotide and nucleic acid metabolic process | NODE_4378 |
| Nga30490 | polymerase (dna directed) epsilon 2 (p59 subunit) | 1 |
| Nga03669 | uv-damaged dna-binding | 2 |
| Nga30761 | gtp-binding protein | 3 |
| Nga30709 | dna damage-binding | 4 |
| GO:0006139; GO:0006310 | nucleobase, nucleoside, nucleotide and nucleic acid metabolic process; DNA recombination | NODE_5200 |
| Nga30978 | deah (asp-glu-ala-his) box polypeptide 8-like | 1 |
| Nga03202 | dna mismatch repair protein msh2 | 3 |
| Nga03203 | dna mismatch repair protein msh2 | 5 |
| Nga30317 | dna mismatch repair protein msh2 | 10 |
| Nga30528 | protein | 13 |
| GO:0006810 | transport | NODE_521 |
| Nga01558 | chromate transporter | 1 |
| Nga01560 | translocase of inner mitochondrial membrane 13 homolog | 4 |
| Nga01563 | lipid a export atp-binding permease protein msba | 5 |
| Nga20851 | at2g36910-like protein | 6 |
| Nga20388 | atp-binding sub-family b (mdr tap) member 10 | 7 |
| GO:0042967 | acyl-carrier-protein biosynthetic process | NODE_5292 |
| Nga04041 | dihydrolipoamide acetyltransferase | 1 |
| Nga04043 | branched-chain alpha-keto acid dehydrogenase subunit e2 | 3 |
| Nga04040 | branched-chain alpha-keto acid dehydrogenase subunit e2 | 6 |
| GO:0006260 | DNA replication | NODE_5379 |
| Nga30513 | dna replication licensing factor mcm3 | 1 |
| Nga01778 | dna replication licensing factor mcm3 | 5 |
| GO:0009081 | branched chain family amino acid metabolic process | NODE_5711 |
| Nga04063 | dihydroxy-acid dehydratase | 1 |
| Nga30327 | dihydroxy-acid dehydratase | 3 |
| Nga30644 | methylmalonate-semialdehyde dehydrogenase | 8 |
| GO:0006536 | glutamate metabolic process | NODE_5865 |
| Nga30142 | glutamate--cysteine ligase catalytic subunit | 1 |
| Nga30765 | glutamate-cysteine catalytic subunit | 2 |
| GO:0006732 | coenzyme metabolic process | NODE_653 |
| Nga02623.2 | molybdenum cofactor synthesis 1 | 1 |
| Nga01769.1 | 5-oxoprolinase | 2 |
| Nga01765.01 | cystathionine gamma-lyase | 6 |
| GO:0010467; GO:0016070 | gene expression; RNA metabolic process | merged000024 |
| Nga00538 | small nuclear ribonucleoprotein associated protein b | 1 |
| Nga00552 | translesion dna polymerase-rev1 deoxycytidyl transferase | 14 |

FIGURE 8B

| Nga00540 | ash1 ( or homeotic)-like | 15 |
| Nga20782 | 50s ribosomal protein l9 | 17 |
| Nga00535 | histone-lysine n-methyltransferase | 19 |
| Nga00543 | ef-1 guanine nucleotide exchange domain-containing | 20 |
| Nga00558 | ribosomal protein s16 | 21 |
| Nga00583 | cg9383-pa | 26 |
| Nga00593 | polyribonucleotide nucleotidyltransferase | 27 |
| Nga21110 | polyribonucleotide nucleotidyltransferase | 28 |
| Nga00596 | rna helicase rnase | 37 |
| Nga00595 | dicer-like protein 2 | 38 |
| Nga20178 | dicer-1 | 39 |
| Nga00568 | cdc2-like protein kinase | 43 |
| Nga00562 | 5 -3 exoribonuclease 2 | 63 |
| Nga00557 | glycyl-trna synthetase | 70 |
| Nga00581.01 | dna polymerase v family | 73 |
| Nga00566.01 | protein bud31 homolog | 74 |

[a] Gene ontology term that defines gene cluster.

[b] Gene ontology term description.

[c] Name of contig that gene cluster is found on.

[d] N. gaditana gene model.

[e] N. gaditana gene model description.

[f] Gene location in cluster.

FIGURE 8 C

| N. gaditana Gene ID | Gene Name[a] | Conserved Domain ID[b] | Conserved Domain Description[c] | Algal group[d] | Found in GreenCut2[e] |
|---|---|---|---|---|---|
| Nga00879 | | COG0618; cl15354 | Exopolyphosphatase-related proteins; cystathionine beta-synthase (CBS)_pair superfamily | BD | |
| Nga01062 | | cd00353; cl00349 | Ribosomal protein S15 (prokaryotic)/S13 (eukaryotic); S15/NS1/EPRS_RNA-binding domain | BD | |
| Nga01241 | | cl00999 | YCII-related domain | BD | |
| Nga02101 | | cl05363 | Oxygen evolving enhancer protein 3 (PsbQ) | BD | |
| Nga02601.01 | | cl14643 | START/RHO_alpha_C/PITP/Bet_v1/CoxG/CalC (SRPBCC) ligand-binding domain superfamily | BD | |
| Nga02755 | | cl10900 | Axonemal dynein light chain | BD | |
| Nga02799 | | | | BD | |
| Nga03348 | | cd00204 | ankyrin repeats | BD | |
| Nga03586 | | cl12031; pfam00561 | Esterase_lipase superfamily; alpha/beta hydrolase 1 fold | BD | |
| Nga03779 | | cd04301 | N-Acyltransferase superfamily | BD | |
| Nga03868 | | | | BD | |
| Nga04312.01 | | cl10460 | Sulfatase superfamily | BD | |
| Nga04890 | | cl12031 | Esterase lipase superfamily | BD | |
| Nga05077 | | cl11394 | Glycosyltransferase family A (GT-A) type superfamily | BD | |
| Nga05710 | | | | BD | |
| Nga05790.1 | | cd06174 | Major Facilitator Superfamily (MFS) | BD | |
| Nga05820 | | | | BD | |
| Nga05889 | | PRK00107 | 16S rRNA methyltransferase GidB | BD | |
| Nga06056 | | | | BD | |
| Nga06213 | | cl10460 | Sulfatase | BD | |
| Nga06321 | | | | BD | |
| Nga06681 | | cl12381 | GDP-fucose protein O-fucosyltransferase | BD | |
| Nga06717 | | cd09271 | Ribonuclease H2-C | BD | |
| Nga20030 | | cl10638 | Protein of unknown function (DUF726) | BD | |
| Nga20064 | | cl02660 | TAZ zinc finger | BD | |
| Nga20089 | | cl02576 | bZIP transcription factor | BD | |
| Nga20138 | | | | BD | |

FIGURE 11 A

| N. gaditana Gene ID | Gene Name[a] | Conserved Domain ID[b] | Conserved Domain Description[c] | Algal group[d] | Found in GreenCut2[e] |
|---|---|---|---|---|---|
| Nga20219 | | cl14780 | Crotonase/Enoyl-Coenzyme A (CoA) hydratase like superfamily | BD | |
| Nga20313 | | | | BD | |
| Nga20943 | | cl03381 | von Hippel-Landau (pVHL) tumor suppressor protein | BD | |
| Nga21039 | | cl12207 | MgtC family (unknown function) | BD | |
| Nga21144 | | cl09931; COG0644 | Rossmann-fold NAD(P)(+)-binding proteins; Dehydrogenases (flavoproteins) (FixC) | BD | |
| Nga30278 | | cl00161 | Dihydrofolate reductase (DHFR) | BD | |
| Nga30454 | | cl12011 | S-adenosylmethionine-dependent methyltransferases (SAM or AdoMet-MTase), class I superfamily | BD | |
| Nga30564 | | | | BD | |
| Nga30653 | | cl14643 | START/RHO_alpha_C/PITP/Bet_v1/CoxG/CalC (SRPBCC) ligand-binding domain superfamily | BD | |
| Nga30880 | | cl14603; cl09931 | C2 superfamily; Rossmann-fold NAD(P)(+)-binding proteins | BD | |
| Nga30943 | | cd00051; cl07216 | EF-hand, calcium binding motif; COPI associated protein | BD | |
| Nga40029 | | cl03567 | Ycf4 superfamily | BD | |
| Nga00093 | | PLN02584; cl00303 | 5'-methylthioadenosine nucleosidase; Phosphorylase superfamily | BDG | GreenCut2 |
| Nga00146 | | COG5070; cl01037 | Nucleotide-sugar transporter (VRG4); EamA-like transporter family | BDG | GreenCut2 |
| Nga00382 | | | | BDG | GreenCut2 |
| Nga00539 | | cl10013 | Glycosyltransferase GTB type superfamily | BDG | GreenCut2 |
| Nga00957 | | cl01977 | Ferredoxin thioredoxin reductase catalytic beta chain | BDG | GreenCut2 |
| Nga01759.01 | | cd03407 | band 7 domain of flotillin (reggie) like proteins | BDG | GreenCut2 |
| Nga02012 | | PLN02518; cl00938; cl14643 | pheophorbide a oxygenase; Rieske [2Fe-2S] cluster binding domain; START/RHO_alpha_C/PITP/Bet_v1/CoxG/CalC (SRPBCC) ligand-binding domain superfamily | BDG | GreenCut2 |

FIGURE 11 B

| N. gaditana Gene ID | Gene Name[a] | Conserved Domain ID[b] | Conserved Domain Description[c] | Algal group[d] | Found in GreenCut2[e] |
|---|---|---|---|---|---|
| Nga02567 | | cl00938; PLN02518; cl14643 | Rieske [2Fe-2S] cluster binding domain; pheophorbide a oxygenase; START/RHO_alpha_C/PITP/Bet_v1/CoxG/CalC (SRPBCC) ligand-binding domain superfamily | BDG | GreenCut2 |
| Nga02700.01 | | cl06253 | Violaxanthin de-epoxidase (VDE) | BDG | GreenCut2 |
| Nga02877 | | cd03407 | band 7 domain of flotillin (reggie) like proteins (lipid raft-associated) | BDG | GreenCut2 |
| Nga03047 | | | | BDG | GreenCut2 |
| Nga03349 | | COG1141 | Ferredoxin | BDG | GreenCut2 |
| Nga03361 | | cd06660; COG0667 | Aldo-keto reductases, Predicted oxidoreductases | BDG | GreenCut2 |
| Nga03364 | | cl01154; cl09109 | CreA superfamily; Nuclear transport factor 2 superfamily | BDG | GreenCut2 |
| Nga05945 | DVR | PLN02657; cd05243; cl09931 | 3,8-divinyl protochlorophyllide a 8-vinyl reductase; atypical (a) SDRs, subgroup 5; Rossmann-fold NAD(P)(+)-binding proteins | BDG | GreenCut2 |
| Nga20955 | | | | BDG | GreenCut2 |
| Nga20977.1 | | | | BDG | GreenCut2 |
| Nga21190 | | | | BDG | GreenCut2 |
| Nga30820 | | cl13479 | Protein of unknown function (DUF3529) | BDG | GreenCut2 |
| Nga30882 | | cl10080 | Retinal pigment epithelial 65 membrane protein | BDG | GreenCut2 |
| Nga40028 | psaL | cl03651 | Photosystem I reaction centre subunit XI | BDG | GreenCut2 |
| Nga00206 | | cd05243; cl09931; pfam01370 | atypical (a) SDRs, subgroup 5; Rossmann-fold NAD(P)(+)-binding proteins; NAD dependent epimerase/dehydratase family | BDRG | GreenCut2 |
| Nga00244 | | cd07560 | C-terminal processing peptidase, serine protease family S41 | BDRG | GreenCut2 |
| Nga00352 | | PLN02679; cl12031 | hydrolase, alpha/beta fold family protein; Esterase lipase superfamily | BDRG | GreenCut2 |
| Nga00432 | | PRK13474 | cytochrome b6-f complex iron-sulfur subunit | BDRG | GreenCut2 |
| Nga00448.01 | | cl02879 | Chlorophyll A-B binding protein | BDRG | GreenCut2 |
| Nga00462 | | cd00207 | 2Fe-2S iron-sulfur cluster binding domain (fer2) superfamily | BDRG | GreenCut2 |
| Nga00522.01 | | cl02879 | Chlorophyll A-B binding protein | BDRG | GreenCut2 |
| Nga00631 | | cl11841 | photosystem II protein Psb27 | BDRG | GreenCut2 |

FIGURE 11 C

| N. gaditana Gene ID | Gene Name[a] | Conserved Domain ID[b] | Conserved Domain Description[c] | Algal group[d] | Found in GreenCut2[e] |
|---|---|---|---|---|---|
| Nga00640 | LCYB (CrtL-b) | cl09931 | Rossmann-fold NAD(P)(+)-binding proteins | BDRG | GreenCut2 |
| Nga00679.01 | | cl12011 | S-adenosylmethionine-dependent methyltransferases (SAM or AdoMet-MTase), class I superfamily | BDRG | GreenCut2 |
| Nga00694 | | cl10080; COG3670 | Retinal pigment epithelial 65 membrane protein superfamily; Lignostilbene-alpha,beta-dioxygenase and related enzymes | BDRG | GreenCut2 |
| Nga00774.01 | | cl02879 | Chlorophyll A-B binding protein | BDRG | GreenCut2 |
| Nga00782 | | cd02947; cl00388 | TRX family; Thioredoxin_like superfamily | BDRG | GreenCut2 |
| Nga00807 | UROS (HemD) | cd06578 | Uroporphyrinogen-III synthase (HemD) | BDRG | GreenCut2 |
| Nga00818 | MGD1 | PLN02605 | monogalactosyldiacylglycerol (MGDG) synthase | BDRG | GreenCut2 |
| Nga00935.01 | | COG0534; cl10513 | Na+-driven multidrug efflux pump (NorM); MatE superfamily | BDRG | GreenCut2 |
| Nga00964 | | cd05265; cl09931; COG0451 | atypical (a) SDRs, subgroup 1; Rossmann-fold NAD(P)(+)-binding proteins; Nucleoside-diphosphate-sugar epimerases | BDRG | GreenCut2 |
| Nga00965.01 | | cl03326 | Manganese-stabilising protein / photosystem II polypeptide | BDRG | GreenCut2 |
| Nga00983.01 | | cl00197 | cyclophilin-type peptidylprolyl cis- trans isomerase | BDRG | GreenCut2 |
| Nga01068 | | cl00484 | NifU-like domain | BDRG | GreenCut2 |
| Nga01167 | | cl11228; cl00381 | Protein of unknown function (DUF2470); Pyridoxine 5'-phosphate (PNP) oxidase-like proteins | BDRG | GreenCut2 |
| Nga01264 | | TIGR01292; cl00388; cl09931 | thioredoxin-disulfide reductase; Thioredoxin_like superfamily; Rossmann-fold NAD(P)(+)-binding proteins | BDRG | GreenCut2 |
| Nga01344 | | cd07560 | C-terminal processing peptidase, serine protease family S41 | BDRG | GreenCut2 |
| Nga01483 | | cl00484; cl15257 | NifU-like domain; GIY-YIG nuclease domain superfamily | BDRG | GreenCut2 |
| Nga01705 | | cl01535 | Domain of unknown function (DUF477) | BDRG | GreenCut2 |
| Nga01771.01 | | cl09611 | Domain of unknown function (DUF1995) | BDRG | GreenCut2 |
| Nga01898.01 | | cl02879 | Chlorophyll A-B binding protein | BDRG | GreenCut2 |

FIGURE 11 D

| N. gaditana Gene ID | Gene Name[a] | Conserved Domain ID[b] | Conserved Domain Description[c] | Algal group[d] | Found in GreenCut2[e] |
|---|---|---|---|---|---|
| Nga01936 | | cl11587 | FKBP-type peptidyl-prolyl cis-trans isomerase | BDRG | GreenCut2 |
| Nga01968 | | COG0546; cd01427 | Predicted phosphatases (Gph); Haloacid dehalogenase-like hydrolases | BDRG | GreenCut2 |
| Nga01980.01 | | PLN02824; cl12031 | hydrolase, alpha/beta fold family protein; Esterase_lipase superfamily | BDRG | GreenCut2 |
| Nga02139 | | TIGR00745 | 2-dehydropantoate 2-reductase (apbA/panE) | BDRG | GreenCut2 |
| Nga02243 | | cl00337 | UbiA prenyltransferase family | BDRG | GreenCut2 |
| Nga02246 | | PLN02775; cl09931; cl04965 | Probable dihydrodipicolinate reductase; Rossmann-fold NAD(P)(+)-binding proteins; Dihydrodipicolinate reductase, C-terminus | BDRG | GreenCut2 |
| Nga02340 | | TIGR00225; cd00988 | C-terminal peptidase (prc); PDZ domain of C-terminal processing-, tail-specific-, and tricorn proteases | BDRG | GreenCut2 |
| Nga02348.01 | | COG1092; cd02440; cl00607 | Predicted SAM-dependent methyltransferases ; S-adenosylmethionine-dependent methyltransferases (SAM or AdoMet-MTase), class I superfamily; Pseudouridine synthase and Archaeosine transglycosylase domain | BDRG | GreenCut2 |
| Nga02385 | | PLN02679 | hydrolase, alpha/beta fold family protein | BDRG | GreenCut2 |
| Nga02586 | | COG0317; cd05399 | Guanosine polyphosphate pyrophosphohydrolases/synthetases (SpoT); Nucleotidyltransferase (NT) domain of RelA- and SpoT-like ppGpp synthetases and hydrolases | BDRG | GreenCut2 |
| Nga02777 | | cl05142 | GUN4-like (involved in plastid-to-nucleus signaling) | BDRG | GreenCut2 |
| Nga02785 | | cl02879 | Chlorophyll A-B binding protein | BDRG | GreenCut2 |
| Nga02790 | | cl02879 | Chlorophyll A-B binding protein | BDRG | GreenCut2 |
| Nga02810 | | COG2267; COG1075 | Lysophospholipase; Predicted acetyltransferases and hydrolases with the alpha/beta hydrolase fold | BDRG | GreenCut2 |
| Nga03075 | | cl09931; COG1233 | Rossmann-fold NAD(P)(+)-binding proteins; Phytoene dehydrogenase and related proteins | BDRG | GreenCut2 |
| Nga03116 | | cl02879 | Chlorophyll A-B binding protein | BDRG | GreenCut2 |

FIGURE 11 E

| N. gaditana Gene ID | Gene Name[a] | Conserved Domain ID[b] | Conserved Domain Description[c] | Algal group[d] | Found in GreenCut2[e] |
|---|---|---|---|---|---|
| Nga03131.1 | | cd05243; cl09931; COG0702 | atypical (a) SDRs, subgroup 5; Rossmann-fold NAD(P)(+)-binding proteins; Predicted nucleoside-diphosphate-sugar epimerases | BDRG | GreenCut2 |
| Nga03355 | | cl00388; cl01729 | Protein Disulfide Oxidoreductases and Other Proteins with a Thioredoxin fold; Vitamin K epoxide reductase family; | BDRG | GreenCut2 |
| Nga03454.01 | | TIGR02009; cd01427 | beta-phosphoglucomutase family hydrolase; Haloacid dehalogenase-like hydrolases | BDRG | GreenCut2 |
| Nga03465.01 | | cl12031; COG1075 | Esterase lipase superfamily; Predicted acetyltransferases and hydrolases with the alpha/beta hydrolase fold | BDRG | GreenCut2 |
| Nga03470 | | COG0534 | Na+-driven multidrug efflux pump | BDRG | GreenCut2 |
| Nga03545 | AOX | cd01053 | Alternative oxidase, ferritin-like diiron-binding domain | BDRG | GreenCut2 |
| Nga03581 | | cl02879 | Chlorophyll A-B binding protein | BDRG | GreenCut2 |
| Nga03884 | | cl12011 | S-adenosylmethionine-dependent methyltransferases (SAM or AdoMet-MTase), class I | BDRG | GreenCut2 |
| Nga03886 | | cl11414 | Cytochrome C superfamily | BDRG | GreenCut2 |
| Nga04175 | | cl02879 | Chlorophyll A-B binding protein | BDRG | GreenCut2 |
| Nga04177 | | cl02879 | Chlorophyll A-B binding protein | BDRG | GreenCut2 |
| Nga04484 | | cl04786 | SOUL heme-binding protein | BDRG | GreenCut2 |
| Nga04536.01 | | cl02879 | Chlorophyll A-B binding protein | BDRG | GreenCut2 |
| Nga04565 | | COG1748; cd00590 | Saccharopine dehydrogenase and related proteins; RNA recognition motif (RRM) | BDRG | GreenCut2 |
| Nga04644 | | cd07560 | C-terminal processing peptidase, serine protease family S41 | BDRG | GreenCut2 |
| Nga04808.01 | | PRK07580; cl12011 | Mg-protoporphyrin IX methyl transferase; S-adenosylmethionine-dependent methyltransferases (SAM or AdoMet-MTase), class I superfamily | BDRG | GreenCut2 |
| Nga05064 | PDS (CrtP) | PLN02612; cl09931 | phytoene desaturase; Rossmann-fold NAD(P)(+)-binding proteins | BDRG | GreenCut2 |
| Nga05492 | | cl05808 | Protein of unknown function (DUF1092) superfamily | BDRG | GreenCut2 |
| Nga05523 | | | Ribosomal protein S1-like RNA-binding domain | BDRG | GreenCut2 |

FIGURE 11 F

| N. gaditana Gene ID | Gene Name[a] | Conserved Domain ID[b] | Conserved Domain Description[c] | Algal group[d] | Found in GreenCut2[e] |
|---|---|---|---|---|---|
| Nga05636 | | COG0317 | Guanosine polyphosphate pyrophosphohydrolases/synthetases (SpoT) | BDRG | GreenCut2 |
| Nga05671 | | COG1357 | Pentapeptide repeats containing protein | BDRG | GreenCut2 |
| Nga05697 | | cl02879 | Chlorophyll A-B binding protein | BDRG | GreenCut2 |
| Nga05732 | | cd03041; cl00388 | GST_N family, 2 repeats of the N-terminal domain of soluble GSTs (2 GST_N) subfamily; Thioredoxin_like superfamily | BDRG | GreenCut2 |
| Nga05831.01 | | cl02971 | Pentapeptide repeats | BDRG | GreenCut2 |
| Nga05995.1 | | cd01924 | cyclophilin-type peptidylprolyl cis- trans isomerases (cyclophilins) similar to the Spinach thylakoid lumen protein TLP40 | BDRG | GreenCut2 |
| Nga06121 | | PLN00049; cd07560 | carboxyl-terminal processing protease; C-terminal processing peptidase; serine protease family S41 | BDRG | GreenCut2 |
| Nga06454 | | cl02879 | Chlorophyll A-B binding protein | BDRG | GreenCut2 |
| Nga06512 | | cl00197 | cyclophilin-type peptidylprolyl cis- trans isomerases | BDRG | GreenCut2 |
| Nga06539 | | cl11228; COG0748 | Protein of unknown function (DUF2470); Putative heme iron utilization protein | BDRG | GreenCut2 |
| Nga06745 | | pfam01458; cl03223 | Uncharacterized protein family (UPF0051); cysteine desulfurase activator complex subunit (SufB) | BDRG | GreenCut2 |
| Nga06853 | | cl02879 | Chlorophyll A-B binding protein | BDRG | GreenCut2 |
| Nga07310 | ZDS (CrtQ) | PLN02487; cl09931 | zeta-carotene desaturase; Rossmann-fold NAD(P)(+)-binding proteins | BDRG | GreenCut2 |
| Nga21031 | | cl00508 | YGGT family | BDRG | GreenCut2 |
| Nga30083 | | cl09931; COG0451 | Rossmann-fold NAD(P)(+)-binding proteins; Nucleoside-diphosphate-sugar epimerases | BDRG | GreenCut2 |
| Nga30145 | | cl01792; cl12011 | Uncharacterized protein conserved in bacteria (DUF2256); S-adenosylmethionine-dependent methyltransferases (SAM or AdoMet-MTase), class I superfamily | BDRG | GreenCut2 |
| Nga30371 | | cl09931 | Rossmann-fold NAD(P)(+)-binding proteins | BDRG | GreenCut2 |
| Nga30374 | | PRK00122 | 16S rRNA-processing protein RimM | BDRG | GreenCut2 |

FIGURE 11 G

| N. gaditana Gene ID | Gene Name[a] | Conserved Domain ID[b] | Conserved Domain Description[c] | Algal group[d] | Found in GreenCut2[e] |
|---|---|---|---|---|---|
| Nga30421 | | PLN02578 | hydrolase | BDRG | GreenCut2 |
| Nga30571 | | cd07560; cd00988 | C-terminal processing peptidase; serine protease family S41; PDZ domain of C-terminal processing | BDRG | GreenCut2 |
| Nga30762 | | pfam01593; cl09931 | Flavin containing amine oxidoreductase; Rossmann-fold NAD(P)(+)-binding proteins | BDRG | GreenCut2 |
| Nga30773 | ChlD | cl09099; TIGR02030 | P-loop containing Nucleoside Triphosphate Hydrolases; magnesium chelatase ATPase subunit I | BDRG | GreenCut2 |
| Nga30837 | AOX | cl00264 | Ferritin-like superfamily of diiron-containing four-helix-bundle proteins | BDRG | GreenCut2 |
| Nga30961 | | PLN02578 | hydrolase | BDRG | GreenCut2 |
| Nga31097 | CHS (ChlG) | cl00337 | UbiA prenyltransferase family | BDRG | GreenCut2 |
| Nga40001 | petF | cd00207 | 2Fe-2S iron-sulfur cluster binding domain (fer2) superfamily | BDRG | GreenCut2 |
| Nga40006 | psaE | cl03585 | Photosystem I reaction centre subunit IV / PsaE | BDRG | GreenCut2 |
| Nga40042 | psaD | cl03639 | PsaD superfamily | BDRG | GreenCut2 |
| Nga40047 | rbcS | cd03527 | Ribulose bisphosphate carboxylase/oxygenase (Rubisco), small subunit superfamily | BDRG | GreenCut2 |
| Nga40072 | sufB (ycf24) | cl03223; CHL00085 | cysteine desulfurase activator complex subunit SufB; putative ABC transporter (ycf24) | BDRG | GreenCut2 |
| Nga40087 | psaF | cl03627 | Photosystem I reaction centre subunit III (PsaF) | BDRG | GreenCut2 |
| Nga40092 | ChlI | cl09099; TIGR02030 | P-loop containing Nucleoside Triphosphate Hydrolases; magnesium chelatase ATPase subunit I (BchI-ChlI) | BDRG | GreenCut2 |
| Nga00022.01 | | cl03831 | Haemolysin-III related | BDG | |
| Nga00046 | | pfam12697 | Alpha/beta hydrolase 6 family | BDG | |
| Nga00157.01 | | PRK13557; cl02576; cl09965 | histidine kinase; bZIP transcription factor; Motif C-terminal to PAS motifs (likely to contribute to PAS structural domain) | BDG | |
| Nga00185 | | cl06868 | Ferredoxin reductase (FNR like superfamily) | BDG | |
| Nga00317 | | cd00130 | PAS domain | BDG | |
| Nga00379.01 | | | | BDG | |

FIGURE 11 H

| N. gaditana Gene ID | Gene Name[a] | Conserved Domain ID[b] | Conserved Domain Description[c] | Algal group[d] | Found in GreenCut2[e] |
|---|---|---|---|---|---|
| Nga00763 | | cl14813; pfam03152 | Peptidase Gluzincin family; Ubiquitin fusion degradation protein UFD1 | BDG | |
| Nga00791 | | cl00524 | Transmembrane amino acid transporter protein | BDG | |
| Nga00897 | | cl00927 | Formate/nitrite transporter | BDG | |
| Nga01225 | | cd07751; cl11964; cl02238; cl09954 | Polyphosphate(polyP) polymerase domain of yeast vacuolar transport chaperone (VTC) protein VTC4; CYTH-like (also known as triphosphate tunnel metalloenzyme (TTM)-like) Phosphatases; SPX domain; Domain of unknown function (DUF202) | BDG | |
| Nga01418.01 | | COG0665 | Glycine/D-amino acid oxidases (deaminating) (DadA) | BDG | |
| Nga01437.01 | | PRK14875 | acetoin dehydrogenase E2 subunit dihydrolipoyllysine-residue acetyltransferase | BDG | |
| Nga01497 | | cl12031; pfam12695 | Esterase_lipase superfamily; Alpha/beta hydrolase family | BDG | |
| Nga01527 | | cl01018 | YeeE/YedE family (DUF395) | BDG | |
| Nga01585 | | cl02988 | Glycosyltransferase family 10 (fucosyltransferase) | BDG | |
| Nga01597.01 | | cl00447 | Nudix_Hydrolase superfamily | BDG | |
| Nga01790 | | COG0654; cl09931 | 2-polyprenyl-6-methoxyphenol hydroxylase and related FAD-dependent oxidoreductases (UbiH); Rossmann-fold NAD(P)(+)-binding proteins | BDG | |
| Nga02655 | | cl00218 | glycosyl hydrolase family 16 | BDG | |
| Nga02821 | | PLN02378; cl00388 | glutathione S-transferase DHAR1; Thioredoxin like superfamily | BDG | |
| Nga02918 | | cd04301 | N-Acyltransferase superfamily | BDG | |
| Nga03200 | | | | BDG | |
| Nga03278 | | | | BDG | |
| Nga03403 | | cd04730; cl09108 | 2-Nitropropane dioxygenase (NPD)-like; TIM phosphate binding superfamily | BDG | |
| Nga03436 | | cl02813 | Mitochondrial carrier protein | BDG | |
| Nga03614.01 | | cl03589 | Chalcone-flavanone isomerase | BDG | |
| Nga03952.01 | | cl09954 | Domain of unknown function 202 superfamily | BDG | |
| Nga04174 | | PRK09525 | beta-D-galactosidase (lacZ) | BDG | |

FIGURE 11 I

| N. gaditana Gene ID | Gene Name[a] | Conserved Domain ID[b] | Conserved Domain Description[c] | Algal group[d] | Found in GreenCut2[e] |
|---|---|---|---|---|---|
| Nga04243 | | pfam12697 | Alpha/beta hydrolase 6 family | BDG | |
| Nga04411 | | cl02813 | Mitochondrial carrier protein superfamily | BDG | |
| Nga04754.1 | | cl07118 | RAP domain superfamily | BDG | |
| Nga04844.01 | | COG0654; cl09931 | 2-polyprenyl-6-methoxyphenol hydroxylase and related FAD-dependent oxidoreductases (UbiH); Rossmann-fold NAD(P)(+)-binding proteins | BDG | |
| Nga04864 | | cl01544 | Bestrophin, RFP-TM, chloride channel superfamily | BDG | |
| Nga05116 | | cl03951; cl07248; cl07247 | Cdc37 N terminal kinase binding; Cdc37 Hsp90 binding domain; Cdc37 C terminal domain | BDG | |
| Nga05302 | | cl00447 | Nudix_Hydrolase superfamily | BDG | |
| Nga05344 | | cl01544 | Bestrophin, RFP-TM, chloride channel superfamily | BDG | |
| Nga05424 | | cl00473 | BAX inhibitor (BI)-1/YccA-like protein family | BDG | |
| Nga05532 | | COG2850 | Uncharacterized conserved protein | BDG | |
| Nga05999 | | PRK13559; cl02576 | hypothetical protein; bZIP transcription factor superfamily | BDG | |
| Nga06125 | | | | BDG | |
| Nga06186 | | cl00456 | Sodium:solute symporter family | BDG | |
| Nga06677 | | cl00927 | Formate/nitrite transporter | BDG | |
| Nga06705 | | cl09109 | Nuclear transport factor 2 (NTF2-like) superfamily | BDG | |
| Nga06712 | | | | BDG | |
| Nga06740 | | pfam08449 | UAA transporter family | BDG | |
| Nga06994 | | cl02879 | Chlorophyll A-B binding protein | BDG | |
| Nga07089 | | PRK11752; cd10292; cl00388 | putative S-transferase; Glutathione S-transferase (GST) C-terminal domain family, YghU-like subfamily; Thioredoxin_like superfamily | BDG | |
| Nga07273 | | cl00447 | Nudix_Hydrolase superfamily | BDG | |
| Nga20078 | | cl06253 | Violaxanthin de-epoxidase-like protein of unknown function | BDG | |
| Nga20139 | | cl01206 | 2OG-Fe(II) oxygenase superfamily | BDG | |
| Nga20168.1 | | | | BDG | |
| Nga20308.1 | | | | BDG | |
| Nga20591 | | cl02776 | Glutathione S-transferase (GST) family, C-terminal alpha helical domain superfamily | BDG | |

FIGURE 11 J

| N. gaditana Gene ID | Gene Name[a] | Conserved Domain ID[b] | Conserved Domain Description[c] | Algal group[d] | Found in GreenCut2[e] |
|---|---|---|---|---|---|
| Nga20879 | | cl12011 | S-adenosylmethionine-dependent methyltransferases (SAM or AdoMet-MTase), class I superfamily | BDG | |
| Nga21269 | | cl00938 | Rieske [2Fe-2S] cluster binding domain | BDG | |
| Nga30150 | | | | BDG | |
| Nga30186 | | cl02144 | TLD superfamily | BDG | |
| Nga30196 | CPl (CCl) | | | BDG | |
| Nga30242 | | cl11587 | FKBP-type peptidyl-prolyl cis-trans isomerase | BDG | |
| Nga30516 | | cl00731 | Domain of unknown function (DUF179) | BDG | |
| Nga30567 | | cl00042 | Caspase, interleukin-1 beta converting enzyme (ICE) homologues | BDG | |
| Nga30598 | | cl00524 | Transmembrane amino acid transporter protein | BDG | |
| Nga30679 | | cl00042 | Caspase, interleukin-1 beta converting enzyme (ICE) homologues | BDG | |
| Nga40030 | psbE | CHL00064 | photosystem II protein V (psbE) | BDG | |
| Nga40063 | atpH | cl00466 | ATP synthase subunit C | BDG | |
| Nga00901 | | | | BDR | |
| Nga01689 | | cd00552 | RaiA "ribosome-associated inhibitor A", also known as Protein Y (PY), YfiA, and SpotY | BDR | |
| Nga01690 | | | | BDR | |
| Nga02056 | | cl09931 | Rossmann-fold NAD(P)(+)-binding proteins | BDR | |
| Nga02342 | | cd08255; cl14614 | 2-desacetyl-2-hydroxyethyl bacteriochlorophyllide and other MDR family members; Medium chain reductase/dehydrogenase (MDR)/zinc-dependent alcohol dehydrogenase-like family | BDR | |
| Nga02943 | | | | BDR | |
| Nga02945 | | cl11446 | Rhomboid family | BDR | |
| Nga03038.01 | | | | BDR | |
| Nga03117 | | | | BDR | |
| Nga03879 | | cl09931 | Rossmann-fold NAD(P)(+)-binding proteins | BDR | |
| Nga04065 | | cl01139 | Protein of unknown function, DUF399 | BDR | |

FIGURE 11 K

| N. gaditana Gene ID | Gene Name[a] | Conserved Domain ID[b] | Conserved Domain Description[c] | Algal group[d] | Found in GreenCut2[e] |
|---|---|---|---|---|---|
| Nga04422 | | | | BDR | |
| Nga04641 | | cl02879 | Chlorophyll A-B binding protein superfamily | BDR | |
| Nga05526 | | cl00933 | ATP-dependent Clp protease adaptor protein ClpS | BDR | |
| Nga20136 | | TIGR02352; cl14881 | glycine oxidase ThiO; Malate:quinone oxidoreductase (Mqo) | BDR | |
| Nga20468 | | cd04728 | Thiazole synthase (ThiG) | BDR | |
| Nga20657 | | cl08232 | Ribulose bisphosphate carboxylase large chain superfamily | BDR | |
| Nga20670 | | cl08224 | Photosystem I psaA/psaB protein superfamily | BDR | |
| Nga20759 | | cl08232 | Ribulose bisphosphate carboxylase large chain superfamily | BDR | |
| Nga20849 | | cd09294 | Small protein B (SmpB) superfamily | BDR | |
| Nga20900 | | cl08223 | Photosystem II protein | BDR | |
| Nga21024 | | cl08232 | Ribulose bisphosphate carboxylase large chain superfamily | BDR | |
| Nga21037 | | cl01024 | Putative small multi-drug export protein | BDR | |
| Nga21157 | | | | BDR | |
| Nga21279 | | cl08232 | Ribulose bisphosphate carboxylase large chain superfamily | BDR | |
| Nga30886 | | cl02526 | C-terminal processing peptidase family S41 | BDR | |
| Nga30899 | | pfam06514 | Photosystem II 12 kDa extrinsic protein (PsbU) | BDR | |
| Nga40021 | psbV | cl11414 | Cytochrome c | BDR | |
| Nga40082 | thiG | cd04728; cl09108 | Thiazole synthase (ThiG); TIM_phosphate_binding superfamily | BDR | |
| Nga00068 | | cd05685 | Ribosomal protein S1-like RNA-binding domain (S1 Tex) | BDRG | |
| Nga00223.01 | | TIGR01172; cd03354 | serine O-acetyltransferase (cysE); Serine acetyltransferase (SAT) | BDRG | |
| Nga00251.01 | | cd03013; cl00388 | Peroxiredoxin 5 like; Thioredoxin like superfamily | BDRG | |
| Nga00361 | | cl10013 | Glycosyltransferase GTB type superfamily | BDRG | |

FIGURE 11 L

| N. gaditana Gene ID | Gene Name[a] | Conserved Domain ID[b] | Conserved Domain Description[c] | Algal group[d] | Found in GreenCut2[e] |
|---|---|---|---|---|---|
| Nga00482.01 | FABZ_2 | cd01288 | beta-hydroxyacyl-acyl carrier protein (ACP) dehydratase (FabZ) | BDRG | |
| Nga00950 | | cl12022 | Ribosomal protein L18e/L15 | BDRG | |
| Nga01002 | | cd03467 | Rieske [2Fe-2S] cluster binding domain | BDRG | |
| Nga01031 | | cl00630 | YdcF-like superfamily | BDRG | |
| Nga01037 | | cl01132 | Fatty acid hydroxylase superfamily | BDRG | |
| Nga01210 | | | | BDRG | |
| Nga01230 | | TIGR03156; cl10444 | GTP-binding protein HflX; Ras-like GTPase superfamily | BDRG | |
| Nga01305.1 | | cl03940 | TLC ATP/ADP transporter | BDRG | |
| Nga01316 | | cd00320; COG3435 | Chaperonin 10 Kd subunit (cpn10 or GroES); Gentisate 1,2-dioxygenase | BDRG | |
| Nga01515 | | TIGR00841; cl09117 | Bile Acid:Na+ Symporter (BASS) Family; Membrane transport protein | BDRG | |
| Nga01605 | | cd03013; cl00388 | Peroxiredoxin (PRX) family, PRX5-like subfamily; Thioredoxin_like superfamily | BDRG | |
| Nga01793.01 | | cl09807 | Conserved hypothetical protein (Lin0512_fam) | BDRG | |
| Nga01805 | | cl03940 | TLC ATP/ADP transporter superfamily | BDRG | |
| Nga01914 | | cl10468 | Integral membrane protein TerC family | BDRG | |
| Nga01942 | | cd03013; cl00388 | Peroxiredoxin (PRX) family, PRX5-like subfamily; Thioredoxin_like superfamily | BDRG | |
| Nga02160 | | cl01037; COG0697 | EamA-like transporter family; Permeases of the drug/metabolite transporter (DMT) superfamily (RhaT) | BDRG | |
| Nga02379 | | cd07211; cl11396 | Patatin-like phospholipase domain containing protein 8; Patatins and Phospholipases | BDRG | |
| Nga02651.01 | | cd00554 | MECDP_synthase (2-C-methyl-D-erythritol-2,4-cyclodiphosphate synthase) (IspF) | BDRG | |
| Nga02662 | | cl08419 | Sigma-70 region 2 | BDRG | |
| Nga02686 | SQD1 | cl09931; PLN02572 | Rossmann-fold NAD(P)(+)-binding proteins; UDP-sulfoquinovose synthase | BDRG | |

FIGURE 11 M

| N. gaditana Gene ID | Gene Name[a] | Conserved Domain ID[b] | Conserved Domain Description[c] | Algal group[d] | Found in GreenCut2[e] |
|---|---|---|---|---|---|
| Nga02690 | | cd00170; COG0456; cd04301 | Sec14p-like lipid-binding domain; Acetyltransferases (RimI); N-Acyltransferase superfamily: Various enzymes that characteristically catalyze the transfer of an acyl group to a substrate | BDRG | |
| Nga02746 | | cd00498 | Heat shock protein 33-like chaperonin | BDRG | |
| Nga02754 | | TIGR02997 | RNA polymerase sigma factor 70-like | BDRG | |
| Nga02798 | | cl01467 | Uncharacterized conserved protein | BDRG | |
| Nga02900 | | pfam06325 | Ribosomal protein L11 methyltransferase (PrmA) | BDRG | |
| Nga02957 | PSY1 (CrtB) | cd00683; cl00210 | Trans-Isoprenyl Diphosphate Synthases, head-to-head; Isoprenoid Biosynthesis enzymes, Class 1 | BDRG | |
| Nga03147 | | cd05399 | Nucleotidyltransferase (NT) domain of RelA- and SpoT-like ppGpp synthetases and hydrolases.; | BDRG | |
| Nga03217 | | cl00951; cl00386 | Fe-S metabolism associated domain, SufE-related proteins; BolA-like protein | BDRG | |
| Nga03341 | | cd02440 | S-adenosylmethionine-dependent methyltransferases (SAM or AdoMet-MTase), class I | BDRG | |
| Nga03442 | | cd01517; cl00289 | PAP-phosphatase_like domain; FIG, FBPase/IMPase/glpX-like domain | BDRG | |
| Nga03565 | | PRK00517 | ribosomal protein L11 methyltransferase | BDRG | |
| Nga03664 | | cl02879 | Chlorophyll A-B binding protein | BDRG | |
| Nga03732 | | TIGR02227 | signal peptidase I, bacterial typ | BDRG | |
| Nga03876 | | cl09931 | Rossmann-fold NAD(P)(+)-binding proteins | BDRG | |
| Nga03950 | | cd07233 | Glyoxalase I | BDRG | |
| Nga04047.1 | | cl09117; TIGR00841 | Membrane transport protein; Bile Acid:Na+ Symporter (BASS) Family | BDRG | |
| Nga04073 | | cl09925 | Protein Kinases, catalytic domain | BDRG | |
| Nga04218 | | cl08419 | Sigma-70 region 2 | BDRG | |
| Nga04326.01 | | cl10468 | Integral membrane protein TerC family | BDRG | |

FIGURE 11 N

| N. gaditana Gene ID | Gene Name[a] | Conserved Domain ID[b] | Conserved Domain Description[c] | Algal group[d] | Found in GreenCut2[e] |
|---|---|---|---|---|---|
| Nga04512 | | cd00831 | Chalcone and stilbene synthases like | BDRG | |
| Nga04526 | | cl09925 | Protein Kinases, catalytic domain-like superfamily | BDRG | |
| Nga04584.1 | | COG1947 | 4-diphosphocytidyl-2C-methyl-D-erythritol 2-phosphate synthase (IspE) | BDRG | |
| Nga04742 | | COG1506; cl12031; cl00020 | Dipeptidyl aminopeptidases/acylaminoacyl-peptidases (DAP2); Esterase lipase superfamily; Type 1 glutamine amidotransferase (GATase1)-like domain | BDRG | |
| Nga04777.1 | | cd00948; cl09108 | Fructose-1,6-bisphosphate aldolase; TIM phosphate binding superfamily | BDRG | |
| Nga04801 | | cl01037 | EamA-like transporter family | BDRG | |
| Nga04846 | | cl12050 | TraB superfamily | BDRG | |
| Nga04895 | GGR (ChlP) | PLN00093; cl09931 | geranylgeranyl diphosphate reductase; Rossmann-fold NAD(P)(+)-binding proteins | BDRG | |
| Nga05141 | | COG1842 | Phage shock protein A (IM30) | BDRG | |
| Nga05308 | HDR (IspH) | PLN02821 | 1-hydroxy-2-methyl-2-(E)-butenyl 4-diphosphate reductase (HDR) | BDRG | |
| Nga05494.01 | | PRK04184 | DNA topoisomerase VI subunit B | BDRG | |
| Nga05568 | | cd03017; cl00388 | Peroxiredoxin (PRX) family, Bacterioferritin comigratory protein (BCP) subfamily; Thioredoxin_like superfamily | BDRG | |
| Nga05781 | | cl01379 | Tryptophan-rich sensory protein (TspO)/MBR family | BDRG | |
| Nga05803 | | cl09611 | Domain of unknown function (DUF1995) | BDRG | |
| Nga05850 | | PLN00033; cl10130 | photosystem II stability/assembly factor; Ycf48-like protein | BDRG | |
| Nga05921 | | cl14656 | Phosphoenolpyruvate carboxylase | BDRG | |
| Nga06059.1 | | cl00489 | 60Kd inner membrane protein | BDRG | |
| Nga06149 | | cl01379 | Tryptophan-rich sensory protein (TspO)/MBR family | BDRG | |
| Nga06200 | | cl03940 | TLC ATP/ADP transporter | BDRG | |
| Nga06242 | ChlH2 | PLN03241 | magnesium chelatase subunit H | BDRG | |
| Nga06284 | | cl01697 | NnrU protein (exact function unclear) | BDRG | |
| Nga06431 | | cd04451 | Translation Initiation Factor IF1, S1-like RNA-binding domain | BDRG | |

FIGURE 11 O

| N. gaditana Gene ID | Gene Name[a] | Conserved Domain ID[b] | Conserved Domain Description[c] | Algal group[d] | Found in GreenCut2[e] |
|---|---|---|---|---|---|
| Nga06432 | | PRK12902 | preprotein translocase subunit (SecA) | BDRG | |
| Nga06516 | | TIGR00691 | (p)ppGpp synthetase, RelA/SpoT family | BDRG | |
| Nga06559 | | cd02440 | S-adenosylmethionine-dependent methyltransferases (SAM or AdoMet-MTase), class I superfamily | BDRG | |
| Nga06584 | | cl03037 | HCO3- transporter family | BDRG | |
| Nga07147 | | cd07211 | Patatin-like phospholipase domain containing protein 8 | BDRG | |
| Nga20052 | | PLN03241; cl13412 | magnesium chelatase subunit H; Domain of unknown function (DUF3479) | BDRG | |
| Nga20056 | | pfam09258 | Glycosyl transferase family 64 domain | BDRG | |
| Nga20192 | | pfam02536 | mitochondrial transcription termination factor (mTERF) | BDRG | |
| Nga20325 | | PRK00131 | shikimate kinase (aroK) | BDRG | |
| Nga20417 | | cl08224 | Photosystem I psaA/psaB protein | BDRG | |
| Nga20459 | | cl08224 | Photosystem I psaA/psaB protein | BDRG | |
| Nga20492 | | cl08232 | Ribulose bisphosphate carboxylase large chain superfamily | BDRG | |
| Nga20546.1 | | cl12011 | S-adenosylmethionine-dependent methyltransferases (SAM or AdoMet-MTase), class I superfamily | BDRG | |
| Nga20664 | | cl08224 | Photosystem I psaA/psaB protein superfamily | BDRG | |
| Nga20720 | | cl08232 | Ribulose bisphosphate carboxylase large chain superfamily | BDRG | |
| Nga20725 | | cl08224 | Photosystem I psaA/psaB protein superfamily | BDRG | |
| Nga20738 | | cl08224 | Photosystem I psaA/psaB protein superfamily | BDRG | |
| Nga20923 | | cl08223 | Photosystem II protein | BDRG | |
| Nga20940 | | pfam09258 | Glycosyl transferase family 64 domain | BDRG | |
| Nga21049 | | cl08224 | Photosystem I psaA/psaB protein | BDRG | |
| Nga21063 | | cl08224 | Photosystem I psaA/psaB protein | BDRG | |
| Nga21066 | | cl08224 | Photosystem I psaA/psaB protein | BDRG | |
| Nga21084 | | cl08224 | Photosystem I psaA/psaB protein | BDRG | |

FIGURE 11 P

| N. gaditana Gene ID | Gene Name[a] | Conserved Domain ID[b] | Conserved Domain Description[c] | Algal group[d] | Found in GreenCut2[e] |
|---|---|---|---|---|---|
| Nga21158 | | cl08224 | Photosystem I psaA/psaB protein | BDRG | |
| Nga21178 | | cl08232 | Ribulose bisphosphate carboxylase large chain superfamily | BDRG | |
| Nga21247 | | cl08224 | Photosystem I psaA/psaB protein | BDRG | |
| Nga21271 | | cd09289 | D1 subunit of photosystem II | BDRG | |
| Nga30090 | | smart00487; cd00079; COG1197 | DEAD-like helicases superfamily (DEXDc); Helicase superfamily c-terminal domain (HELICc); Transcription-repair coupling factor (Mfd) | BDRG | |
| Nga30125 | | cd00412 | Inorganic pyrophosphatase | BDRG | |
| Nga30126 | | cl03940 | TLC ATP/ADP transporter | BDRG | |
| Nga30194 | | cl09931; PRK07208 | Rossmann-fold NAD(P)(+)-binding proteins; hypothetical protein | BDRG | |
| Nga30232 | | cl02879 | Chlorophyll A-B binding protein | BDRG | |
| Nga30264 | | cl09925 | Protein Kinases, catalytic domain | BDRG | |
| Nga30614 | | cd00170 | Sec14p-like lipid-binding domain superfamily | BDRG | |
| Nga30622 | | TIGR02997; cl08419 | RNA polymerase sigma factor, cyanobacterial RpoD-like family; Sigma-70 region 2 | BDRG | |
| Nga30671 | | PRK07379; cl06150 | coproporphyrinogen III oxidase; HemN C-terminal region | BDRG | |
| Nga30751 | | PRK11132 | Serine acetyltransferase (SAT) | BDRG | |
| Nga30761 | | COG2262; cd01878 | GTPases; HflX subfamily | BDRG | |
| Nga30766 | | cl12138; TIGR03060 | Thylakoid formation protein (THF1); photosystem II biogenesis protein Psp29 | BDRG | |
| Nga30790 | CAS | cd02892 | Squalene cyclase (SQCY) domain subgroup 1 | BDRG | |
| Nga30806 | HDS (IspG) | PLN02925 | 4-hydroxy-3-methylbut-2-en-1-yl diphosphate synthase (IspG) | BDRG | |
| Nga30840 | | TIGR02997; cl08419 | RNA polymerase sigma factor, cyanobacterial RpoD-like family; Sigma-70 region 2 | BDRG | |
| Nga30855 | | cd03013; cl00388 | Peroxiredoxin (PRX) family, PRX5-like subfamily; Thioredoxin_like superfamily | BDRG | |
| Nga30862 | | cl00938 | Rieske [2Fe-2S] cluster binding domain | BDRG | |

FIGURE 11 Q

| N. gaditana Gene ID | Gene Name[a] | Conserved Domain ID[b] | Conserved Domain Description[c] | Algal group[d] | Found in GreenCut2[e] |
|---|---|---|---|---|---|
| Nga30939 | | cd02440 | S-adenosylmethionine-dependent methyltransferases (SAM or AdoMet-MTase), class I superfamily | BDRG | |
| Nga30995 | ChlH1 | PRK12493; cl13412 | magnesium chelatase subunit H; Domain of unknown function (DUF3479) | BDRG | |
| Nga31026 | | PLN02536 | Diaminopimelate epimerase | BDRG | |
| Nga40002 | psbB | cl08223 | Photosystem II protein | BDRG | |
| Nga40005 | psbH | cl02951 | Photosystem II 10 kDa phosphoprotein | BDRG | |
| Nga40009 | petB | cd00284 | Cytochrome b (N-terminus)/b6/petB | BDRG | |
| Nga40010 | petD | cd00290 | Cytochrome b(C-terminus)/b6/petD | BDRG | |
| Nga40017 | rps14 | cl00355 | Ribosomal protein S14p/S29e | BDRG | |
| Nga40018 | psaB | cl08224 | Photosystem I psaA/psaB protein | BDRG | |
| Nga40019 | psaA | cl08224 | Photosystem I psaA/psaB protein | BDRG | |
| Nga40020 | petJ | cl11414 | Cytochrome c | BDRG | |
| Nga40024 | rpl19 | cl00406 | Ribosomal protein L19 | BDRG | |
| Nga40046 | psbA | cd09289; cl08220 | D1 subunit of photosystem II (PS II); D1, D2 subunits of photosystem II (PSII) | BDRG | |
| Nga40048 | rbcL | cd08212 | Ribulose bisphosphate carboxylase large chain, Form I superfamily | BDRG | |
| Nga40050 | petA | cl03168 | Apocytochrome F, C-terminal | BDRG | |
| Nga40051 | tatC | cl00521 | Sec-independent protein translocase protein (TatC) | BDRG | |
| Nga40054 | ycf3 | CHL00033 | photosystem I assembly protein (Ycf3) | BDRG | |
| Nga40056 | rpl33 | cl00383 | Ribosomal protein L33 | BDRG | |
| Nga40060 | rpoC2 | TIGR02388 | DNA-directed RNA polymerase, beta' subunit (rpoC2 cyan) | BDRG | |
| Nga40061 | rps2 | cd01425 | Ribosomal protein S2 (RPS2) | BDRG | |
| Nga40062 | atpI | cl00413 | ATP synthase A chain | BDRG | |
| Nga40073 | ccsA | cl00504 | Cytochrome C assembly protein | BDRG | |
| Nga40078 | secA | CHL00122 | preprotein translocase subunit SecA | BDRG | |
| Nga40084 | psaC | CHL00065 | photosystem I subunit VII (psaC) | BDRG | |
| Nga40093 | psbC | cl08223; TIGR01153 | Photosystem II protein; psbC | BDRG | |
| Nga40094 | psbD | cd09288; cl08220 | D2 subunit of photosystem II (PS II); D1, D2 subunits of photosystem II (PSII) | BDRG | |

FIGURE 11 R

| N. gaditana Gene ID | Gene Name[a] | Conserved Domain ID[b] | Conserved Domain Description[c] | Algal group[d] | Found in GreenCut2[e] |
|---|---|---|---|---|---|
| Nga40113 | secY | CHL00161 | preprotein translocase subunit SecY | BDRG | |
| Nag50013 | | | | BDRG | |

[a] Name given to *N. gaditana* gene model by manual curation.

[b] Conserved protein domain(s) ID assigned from NCBI-curated domains, Pfam, SMART, COG, PRK, or TIGRFAM databases.

[c] Description(s) of conserved protein domain given.

[d] Algal lineages with homologs to *N. gaditana* gene model. B – Brown, D – diatom, R – red, G – green.

[e] Indicates if *N. gaditana* gene model has homology to a GreenCut2 gene[37].

FIGURE 11 S

| Enzyme | Description | EC number | N. gaditana model[a] | Transcript support[b] |
|---|---|---|---|---|
| Fatty acid biosynthesis | | | | |
| ACS | acetyl-CoA synthetase | 6.2.1.1 | Nga30020 | Y |
| ACS | acetyl-CoA synthetase | 6.2.1.1 | Nga02166 | Y |
| ACC | acetyl-CoA carboxylase | 6.4.1.2 | Nga30028 | Y |
| ACC | acetyl-CoA carboxylase | 6.4.1.2 | Nga30783 | Y |
| MAT | malonyl-CoA:ACP-trans-acylase | 2.3.1.39 | Nga00899 | Y |
| KASIII | 3-oxoacyl-ACP synthase III | 2.3.1.180 | Nga30106 | Y |
| KASII | 3-oxoacyl-ACP synthase II | 2.3.1.179 | Nga02138 | Y |
| KASII | 3-oxoacyl-ACP synthase II | 2.3.1.179 | Nga30755 | Y |
| KASII | 3-oxoacyl-ACP synthase II | 2.3.1.179 | Nga04201.01 | Y |
| KASI/II | fatty acid synthase | 2.3.1.- | Nga05827 | Y |
| KAR | 3-oxoacyl-ACP reductase | 1.1.1.100 | Nga20022 | Y |
| KAR | 3-oxoacyl-ACP reductase | 1.1.1.100 | Nga01542 | Y |
| HD | 3-hydroxy acyl-CoA dehydratase | 4.2.1.- | Nga05985.01 | Y |
| ENR | enoyl-ACP reductase I | 1.3.1.9 | Nga05091 | Y |
| ENR | enoyl-ACP reductase I | 1.3.1.9 | Nga10004 | Y |
| KAR | 3-oxoacyl-ACP reductase | 1.1.1.100 | Nga00602 | Y |
| KAR | 3-oxoacyl-ACP reductase | 1.1.1.100 | Nga05627 | Y |
| FAT | oleyl-ACP hydrolase | 3.1.2.14 | Nga01045.01 | Y |
| ELOVL | elongation of very long chain fatty acids | 2.3.1.- | Nga03084 | Y |
| ELOVL | elongation of very long chain fatty acids | 2.3.1.- | Nga00451 | Y |
| DESA | acyl-ACP desaturase | 1.14.19.2 | Nga01458.01 | Y |
| DESC | stearoyl-CoA desaturase | 1.14.19.1 | Nga00524 | Y |
| DES | omega-6 fatty acid desaturase delta-12 | 1.14.19.- | Nga02019 | Y |
| DES | omega-6 fatty acid desaturase delta-12 | 1.14.19.- | Nga00817 | Y |
| DEGS | sphingolipid delta-4 desaturase | 1.14.-.- | Nga06739.1 | Y |
| FAD7 | glycerolipid omega-3 fatty acid desaturase | 1.14.19.- | Nga30138 | Y |
| TAG assembly | | | | |
| G3PDH | glycerol-3-phosphate dehydrogenase | 1.1.1.8 | Nga06665.1 | Y |
| G3PDH | glycerol-3-phosphate dehydrogenase | 1.1.1.8 | Nga01869 | Y |
| G3PDH | glycerol-3-phosphate dehydrogenase | 1.1.1.8 | Nga04914 | Y |
| G3PDH | glycerol-3-phosphate dehydrogenase | 1.1.1.8 | Nga05226 | Y |
| G3PDH | glycerol-3-phosphate dehydrogenase | 1.1.1.8 | Nga30015 | Y |
| GPAT | glycerol-3-phosphate acyltransferase | 2.3.1.15 | Nga04759 | Y |
| GPAT | glycerol-3-phosphate acyltransferase | 2.3.1.15 | Nga10005 | Y |
| GPAT | glycerol-3-phosphate acyltransferase | 2.3.1.15 | Nga04850 | Y |

FIGURE 15 A

| Enzyme | Description | EC number | N. gaditana model[a] | Transcript support[b] |
|---|---|---|---|---|
| LPAAT | 1-acylglycerol-3-phosphate O-acyltransferase | 2.3.1.51 | Nga00059 | Y |
| LPAAT | 1-acylglycerol-3-phosphate O-acyltransferase | 2.3.1.51 | Nga30581 | Y |
| LPAAT | 1-acylglycerol-3-phosphate O-acyltransferase | 2.3.1.51 | Nga30809 | Y |
| LPAAT | 1-acylglycerol-3-phosphate O-acyltransferase | 2.3.1.51 | Nga02265 | Y |
| LPAAT | 1-acylglycerol-3-phosphate O-acyltransferase | 2.3.1.51 | Nga21122.1 | Y |
| PAP | phosphatidic acid phosphatase | 3.1.3.4 | Nga21116 | Y |
| DAGK | diacylglycerol kinase | 2.7.1.107 | Nga02796 | Y |
| DAGK | diacylglycerol kinase | 2.7.1.107 | Nga05586.1 | Y |
| PDAT | phospholipid:diacylglycerol acyltransferase | 2.3.1.158 | Nga02737 | Y |
| DGAT | diacylglycerol acyltransferase | 2.3.1.20 | Nga10003 | Y |
| DGAT | diacylglycerol acyltransferase | 2.3.1.20 | Nga30544 | Y |
| LPAT | lysophosphatidylglycerol acyltransferase | 2.3.1.-KO | Nga05465 | Y |
| PKS5 | polyketide synthase 5 | K12433 | Nga00335 | Y |
| MGD | monogalactosyldiacylglycerol synthase | 2.4.1.46 | Nga00818 | Y |
| SQD2 | sulfoquinovosyltransferase | 2.4.1.- | Nga00561 | Y |
| SQD1 | UDP-sulfoquinovose synthase | 3.13.1.1 | Nga02686 | Y |
| Lipid activation | | | | |
| TAGL | TAG-lipase | 3.1.1.3 | Nga30958 | Y |
| TAGL | TAG-lipase | 3.1.1.3 | Nga30749 | Y |
| AASDH | acyl-CoA synthetase | 6.2.1.- | Nga03422 | Y |
| AASDH | acyl-CoA synthase | 6.2.1.- | Nga05597 | Y |
| ACSL | long-chain acyl-CoA synthetase | 6.2.1.3 | Nga30170 | Y |
| ACSL | long-chain acyl-CoA synthetase | 6.2.1.3 | Nga03113 | Y |
| ACSL | long-chain acyl-CoA synthetase | 6.2.1.3 | Nga00675 | Y |
| ACSL | long-chain acyl-CoA synthetase | 6.2.1.3 | Nga30631 | Y |
| ACSL | long-chain acyl-CoA ligase | 6.2.1.3 | Nga00919 | Y |
| ACSL | long-chain acyl-CoA ligase | 6.2.1.3 | Nga02299 | Y |
| FADD9 | long-chain acyl-CoA ligase | 6.2.1.- | Nga00006 | Y |
| ACSL | long-chain acyl-CoA ligase | 6.2.1.3 | Nga30568 | Y |
| HADH | 3-hydroxyacyl-CoA dehydrogenase | 1.1.1.35 | Nga00482.01 | Y |
| HADH | 3-hydroxyacyl-CoA dehydrogenase | 1.1.1.35 | Nga02679 | Y |
| HADH | 3-hydroxyacyl-CoA dehydrogenase | 1.1.1.35 | Nga06144.1 | Y |
| LCD | long-chain hydroxyacyl-CoA dehydrogenase | 1.1.1.211 | Nga03480 | Y |
| ACADS | short-chain acyl-CoA dehydrogenase | 1.3.8.1 | Nga31130 | Y |
| ACADSB | short-branched-chain acyl-CoA dehydrogenase | 1.3.99.12 | Nga05705 | Y |
| ACDH | Acyl-CoA dehydrogenase | 1.3.99.3 | Nga04204.01 | Y |

FIGURE 15 B

| Enzyme | Description | EC number | *N. gaditana* model[a] | Transcript support[b] |
|---|---|---|---|---|
| ACOX | acyl-CoA oxidase | 1.3.3.6 | Nga03053 | Y |
| PTER | peroxisomal trans-2-enoyl-CoA reductase | 1.3.1.38 | Nga06128 | Y |
| AOX | alternative oxidase | 1.-.-.- | Nga03545 | Y |
| AOX | alternative oxidase | 1.-.-.- | Nga30837 | Y |
| AOX | alternative oxidase | 1.-.-.- | Nga03289 | Y |
| ACOX | acyl-CoA oxidase | 1.3.3.6 | Nga04370.1 | Y |
| ACOX | acyl-CoA oxidase | 1.3.3.6 | Nga30819 | Y |
| ECH | enyol-CoA hydratase | 4.2.1.17 | Nga01761.01 | Y |
| ECH | enyol-CoA hydratase | 4.2.1.17 | Nga00171 | Y |
| ECH | enyol-CoA hydratase | 4.2.1.17 | Nga20152 | Y |
| ECH | enyol-CoA hydratase | 4.2.1.17 | Nga06135 | Y |
| KCT1 | beta-ketoacyl-CoA thiolase | 2.3.1.16 | Nga01710 | Y |
| KCT2 | beta-ketoacyl-CoA thiolase | 2.3.1.16 | Nga04504.01 | Y |
| KCT3 | beta-ketoacyl-CoA thiolase | 2.3.1.16 | Nga30830 | Y |
| ACAT | acetyl-CoA acetyltransferase | 2.3.1.9 | Nga20998 | Y |
| KCT3 | beta-ketoacyl-CoA thiolase | 2.3.1.16 | Nga30830 | Y |
| FATP2 | solute carrier family (fatty acid transporter) | 6.2.1.- | Nga06551 | Y |
| DECR2 | peroxisomal 2,4-dienoyl-CoA reductase | 1.3.1.34 | Nga05502.01 | Y |
| PNPLA | patatin-like phospholipase | 3.1.1.- | Nga03028.01 | Y |

[a] Candidate *N. gaditana* gene model encoding corresponding enzyme.

[b] Indicates if given gene model has transcript support from RNAseq of a pool of conditions including: +/- nitrate, logarithmic phase, stationary phase, heat shocked culture (2h at 37°C), cold treated culture (2h at 4°C), culture after 12h dark, +/- $CO_2$..

FIGURE 15 C

|  | N. gaditana | E. siliculosus | P. tricornutum | C. merolae | C. reinhardtii |
|---|---|---|---|---|---|
| Total # of genes[b] | 9,052 | 16,256 | 10,402 | 5,331 | 15,143 |
| Fatty acid biosynthesis[c] | | | | | |
| ACC | 2 | 5 | 1 | 1 | 1 |
| MAT | 1 | 1 | 1 | 1 | 2 |
| KASIII | 1 | 1 | 1 | 0 | 1 |
| KASI/II | 4 | 6 | 4 | 2 | 3 |
| KAR | 4 | 5 | 2 | 4 | 4 |
| HD | 1 | 1 | 1 | 1 | 1 |
| ENR | 2 | 2 | 2 | 1 | 1 |
| Total[d] | 15 | 21 | 12 | 10 | 13 |
| TAG assembly[c] | | | | | |
| G3PDH | 5 | 1 | 2 | 3 | 6 |
| GPAT | 3 | 2 | 1 | 0 | 0 |
| LPAAT | 5 | 5 | 4 | 6 | 1 |
| PAP | 1 | 1 | 1 | 0 | 2 |
| DAGK | 2 | 2 | 1 | 1 | 2 |
| PDAT | 1 | 0 | 1 | 0 | 1 |
| DGAT | 2 | 2 | 2 | 1 | 1 |
| Total[d] | 19 | 13 | 12 | 11 | 13 |
| Lipid degradation[c] | | | | | |
| TAGL | 2 | 1 | 2 | 1 | 1 |
| AASDH | 2 | 0 | 0 | 0 | 1 |
| ACSL | 7 | 6 | 5 | 4 | 4 |
| FADD9 | 1 | 0 | 0 | 0 | 0 |
| HADH | 3 | 2 | 3 | 2 | 2 |
| LCD | 1 | 1 | 1 | 0 | 0 |
| ACADS | 1 | 1 | 5 | 1 | 3 |
| ACADSB | 1 | 0 | 0 | 0 | 0 |
| ACDH | 1 | 1 | 1 | 0 | 0 |
| ACOX | 3 | 0 | 1 | 1 | 3 |
| AOX | 3 | 2 | 2 | 3 | 5 |
| ECH | 4 | 8 | 8 | 3 | 3 |
| KCT1 | 1 | 1 | 1 | 0 | 1 |
| KCT2 | 1 | 1 | 1 | 0 | 0 |
| KCT3 | 2 | 1 | 1 | 0 | 0 |
| ACAT | 1 | 0 | 1 | 2 | 1 |
| Total[d] | 34 | 25 | 32 | 17 | 24 |
| Total in all categories[e] | 68 | 59 | 56 | 38 | 50 |

FIGURE 17

| GO term[b] | Over- or Under-represented[c] | p-value[d] P. tricornutum | p-value[d] C. reinhardtii |
|---|---|---|---|
| auxin biosynthetic process | over | 2.20E-53 | 1.26E-55 |
| acyl-carrier-protein biosynthetic process | over | 2.22E-25 | 1.35E-30 |
| pyruvate metabolic process | over | 1.96E-06 | 1.45E-09 |
| carbon utilization | over | 2.44E-07 | 2.54E-04 |
| response to stress | over | 8.46E-07 | 1.87E-12 |
| response to chemical stimulus | over | 6.11E-08 | 1.97E-16 |
| posttranscriptional regulation of gene expression | over | 2.76E-04 | 2.38E-04 |
| halogenated hydrocarbon metabolic process | over | 3.15E-05 | 3.51E-06 |
| chlorinated hydrocarbon metabolic process | over | 3.15E-05 | 3.51E-06 |
| cellular ketone metabolic process | over | 3.88E-14 | 2.63E-21 |
| carboxylic acid metabolic process | over | 5.51E-13 | 7.07E-20 |
| organic acid metabolic process | over | 1.55E-12 | 8.11E-20 |
| response to temperature stimulus | over | - | 5.55E-06 |
| response to salt stress | over | - | 1.95E-04 |
| acetyl-CoA catabolic process | over | - | 2.46E-03 |
| C-acyltransferase activity | over | - | 3.58E-03 |
| regulation of growth rate | under | 6.37E-13 | 1.15E-09 |
| regulation of growth | under | 2.89E-09 | 1.92E-08 |
| transcription factor activity | under | 1.33E-10 | 6.07E-04 |
| reproduction | under | 1.64E-18 | 2.00E-19 |
| meiotic cell cycle | under | 1.27E-03 | 3.04E-03 |
| multicellular organismal development | under | 1.17E-27 | 1.18E-37 |
| cell wall | under | 6.24E-07 | 3.30E-12 |
| vitamin binding | under | 2.52E-13 | 2.24E-07 |
| transmembrane transport | under | 1.96E-32 | 3.09E-25 |
| phagocytosis | under | 6.78E-06 | 2.14E-05 |
| cytokinesis | under | 1.82E-03 | 5.65E-04 |
| response to water deprivation | under | - | 8.40E-04 |

[a] Expansions and reduction of GO-terms. Green indicates over-representation in comparison with both P. tricornutum and C. reinhardtii, while red indicates under-representation. Lighter green and red indicates over-representation and under-representation in comparison with C. reinhardtii alone.

[b] Gene ontology term description.

[c] Signifies whether the GO-term is over- or under-represented in comparison with P. tricornutum and C. reinhardtii.

[d] Probability for over/under-representation in comparison with C. reinhardtii and P. tricornutum calculated by Fisher exact test..

FIGURE 18

| GO term[b] | Over- or Under-represented[c] | p-value[d] P. tricornutum | p-value[d] C. reinhardtii |
|---|---|---|---|
| serine family amino acid metabolic process | over | 3.39E-23 | 3.37E-28 |
| isoleucine metabolic process | over | 2.81E-12 | 3.10E-16 |
| cellular amino acid metabolic process | over | 2.10E-11 | 8.37E-22 |
| valine metabolic process | over | 6.23E-10 | 3.86E-15 |
| cellular amino acid and derivative metabolic process | over | 3.47E-09 | 2.03E-17 |
| tyrosine metabolic process | over | 7.89E-09 | 4.25E-10 |
| leucine metabolic process | over | 5.65E-08 | 5.39E-12 |
| isoleucine catabolic process | over | 8.54E-08 | 1.19E-10 |
| aspartate family amino acid metabolic process | over | 4.62E-07 | 1.57E-10 |
| valine catabolic process | over | 5.92E-07 | 1.74E-09 |
| valine biosynthetic process | over | 7.25E-07 | 3.62E-08 |
| leucine catabolic process | over | 2.86E-06 | 1.33E-08 |
| tryptophan metabolic process | over | 2.86E-06 | 1.63E-08 |
| tyrosine biosynthetic process | over | 7.36E-06 | 2.42E-06 |
| isoleucine biosynthetic process | over | 7.36E-06 | 4.06E-07 |
| lysine catabolic process | over | 1.23E-05 | 1.12E-06 |
| aromatic amino acid family metabolic process | over | 2.90E-05 | 3.46E-07 |
| lysine metabolic process | over | 7.78E-05 | 1.99E-05 |
| L-phenylalanine metabolic process | over | 1.36E-04 | 1.43E-06 |
| cellular amino acid derivative metabolic process | over | 3.08E-04 | 1.43E-03 |
| aspartate metabolic process | over | 4.60E-04 | 5.07E-05 |
| branched chain family amino acid metabolic process | over | 5.22E-04 | 2.01E-08 |
| tryptophan biosynthetic process | over | 5.43E-04 | 7.31E-04 |
| leucine biosynthetic process | over | 5.43E-04 | 3.41E-05 |
| branched chain family amino acid catabolic process | over | 6.73E-04 | 2.98E-07 |
| L-serine metabolic process | over | 6.95E-04 | 8.19E-05 |
| threonine metabolic process | over | 8.29E-04 | 7.83E-07 |
| glycine metabolic process | over | 9.27E-04 | 5.07E-05 |
| aspartate family amino acid catabolic process | over | 2.13E-03 | 3.51E-06 |
| alanine metabolic process | over | 2.13E-03 | 1.86E-05 |
| aromatic amino acid family biosynthetic process, prephenate pathway | over | 1.73E-05 | 8.66E-07 |
| L-phenylalanine biosynthetic process | over | 7.36E-06 | 4.06E-07 |
| pyruvate family amino acid metabolic process | over | 2.13E-03 | 1.86E-05 |
| amino acid binding | under | 2.65E-03 | 1.14E-03 |
| cysteine-type endopeptidase activity | under | 1.27E-03 | 3.59E-05 |
| serine-type peptidase activity | under | 1.79E-04 | 1.32E-03 |
| serine hydrolase activity | under | 1.79E-04 | 1.32E-03 |
| serine-type endopeptidase activity | under | 8.53E-04 | 5.59E-04 |

FIGURE 19

| N. gaditana model[a] | Fold regulation[b] | Description[c] | Conserved Domain ID[d] | Conserved Domain definition[e] |
|---|---|---|---|---|
| Nga06526 | 7.25 | copper amine oxidase | cl08309; PRK11504 | Copper amine oxidase, enzyme domain; tyramine oxidase |
| Nga04678 | 4.33 | no hit | no hit | no hit |
| Nga02936 | 4.23 | midasin-like protein | cl09099; COG5271 | P-loop containing Nucleoside Triphosphate Hydrolases; AAA ATPase containing von Willebrand factor type A (vWA) domain |
| Nga31211 | 3.79 | no hit | no hit | no hit |
| Nga01342.01 | 3.79 | urease accessory protein ureD | cl00530 | UreD urease accessory protein |
| Nga20676.1 | 3.61 | no hit | no hit | no hit |
| Nga20915 | 3.47 | no hit | no hit | no hit |
| Nga20972 | 3.45 | ammonium transporter | cl03012 | Ammonium Transporter Family |
| Nga04280 | 3.25 | no hit | no hit | no hit |
| Nga20680 | 3.25 | no hit | no hit | no hit |
| Nga06280.01 | 3.25 | no hit | no hit | no hit |
| Nga04146 | 3.16 | atp-dependent rna | no hit | no hit |
| Nga20823 | 3.11 | midasin-like protein | COG5271 | AAA ATPase containing von Willebrand factor type A (vWA) domain |
| Nga01883.01 | 3.05 | no hit | no hit | no hit |
| Nga30731 | 3.03 | ribonuclease hii | cl14782 | Ribonuclease H (RNase H) |
| Nga03789 | 2.98 | no hit | no hit | no hit |
| Nga20714 | 2.98 | polyketide synthase | cl14614 | Medium chain reductase/dehydrogenase (MDR)/zinc-dependent alcohol dehydrogenase-like family |
| Nga03637 | 2.97 | monovalent cation:proton antiporter-1 family | TIGR00831 | Na+/H+ antiporter |
| Nga03295 | 2.95 | no hit | no hit | no hit |
| Nga07000 | 2.92 | formin like protein | cl11068 | C2 domain of PTEN tumour-suppressor protein |

FIGURE 20 A

| N. gaditana model[a] | Fold regulation[b] | Description[c] | Conserved Domain ID[d] | Conserved Domain definition[e] |
|---|---|---|---|---|
| Nga02041 | 2.83 | hypothetical protein FB2170_06015 [Maribacter sp. HTCC2170] | no hit | no hit |
| Nga07101 | 2.8 | no hit | no hit | no hit |
| Nga21265 | 2.74 | rme1-like gtpase atpase without a c-terminal eh domain | no hit | no hit |
| Nga06490 | 2.71 | no hit | no hit | no hit |
| Nga00341 | 2.71 | no hit | no hit | no hit |
| Nga20547 | 2.65 | 3-5 exoribonuclease rna-binding protein | cl03114 | 3' exoribonuclease family, domain 1 |
| Nga07033 | 2.6 | no hit | no hit | no hit |
| Nga00173 | 2.6 | no hit | no hit | no hit |
| Nga03960 | 2.6 | protein | cd09857; cl14815 | PIN domain of Exonuclease-1; H3TH domains of structure-specific 5' nucleases |
| Nga20524.1 | 2.57 | dna-directed rna polymerase iii largest | cl04880 | RNA polymerase Rpb1, domain 1 |
| Nga00028.01 | 2.57 | no hit | no hit | no hit |
| Nga01948 | 2.57 | no hit | no hit | no hit |
| Nga20592 | 2.5 | alpha-galactosidase | cl11402 | Glycosyl hydrolase family 31 (GH31) |
| Nga04495 | 2.49 | fatty acid elongase | cl03120 | GNS1/SUR4 family |
| Nga30495 | 2.49 | no hit | no hit | no hit |
| Nga03619 | 2.48 | no hit | no hit | no hit |
| Nga00231.01 | 2.46 | phd zinc finger-containing protein | cl15348 | RING-finger |
| Nga02632 | 2.44 | no hit | no hit | no hit |
| Nga04597 | 2.44 | no hit | no hit | no hit |
| Nga06236 | 2.41 | no hit | no hit | no hit |
| Nga01424 | 2.41 | no hit | no hit | no hit |
| Nga00280 | 2.37 | no hit | no hit | no hit |
| Nga30460 | 2.36 | no hit | no hit | no hit |
| Nga31210 | 2.35 | no hit | no hit | no hit |
| Nga20586 | 2.34 | no hit | no hit | no hit |

FIGURE 20 B

| N. gaditana model[a] | Fold regulation[b] | Description[c] | Conserved Domain ID[d] | Conserved Domain definition[e] |
|---|---|---|---|---|
| Nga05509 | 2.29 | predicted protein [Thalassiosira pseudonana CCMP1335] | cl00117 | PDZ domain |
| Nga20741 | 2.29 | fbox protein | no hit | no hit |
| Nga04500 | 2.29 | no hit | no hit | no hit |
| Nga30473 | 2.28 | no hit | no hit | no hit |
| Nga20390 | 2.27 | rna polymerase ii elongator | cl02567 | WD40 domain |
| Nga06889 | 2.26 | no hit | no hit | no hit |
| Nga07058 | 2.25 | no hit | no hit | no hit |
| Nga20704 | 2.24 | no hit | no hit | no hit |
| Nga05678 | 2.23 | glutamine synthetase | cl08245 | Glutamine synthetase |
| Nga30260 | 2.22 | nuclear condensin complex subunit smc4 | cl05797 | SMC proteins Flexible Hinge Domain |
| Nga01032 | 2.21 | notch-regulated ankyrin repeat-containing protein b | cd00204 | Ankyrin repeats |
| Nga20904 | 2.21 | tetratricopeptide repeat family protein | no hit | no hit |
| Nga06186 | 2.2 | protein | cl00456 | Urea/Na+ high-affinity symporter |
| Nga04596 | 2.2 | no hit | no hit | no hit |
| Nga31101 | 2.17 | tetratricopeptide repeat | no hit | no hit |
| Nga21159 | 2.17 | ribosome biogenesis atpase rix7 | cl09099; cl03209; cd00009 | P-loop containing Nucleoside Triphosphate Hydrolases; Peptidase family M41; The AAA+ (ATPases Associated with a wide variety of cellular Activities) superfamily |
| Nga02039 | 2.13 | no hit | no hit | no hit |
| Nga21141 | 2.13 | protein | cl10757 | Guanylyl cyclase |
| Nga21257 | 2.08 | no hit | no hit | no hit |
| Nga21076 | 2.08 | vacuolar protein sorting-associated protein vps13 | cl01386 | 2-hydroxycarboxylate transporter family |
| Nga02799 | 2.06 | protein | no hit | no hit |

FIGURE 20 C

| N. gaditana model[a] | Fold regulation[b] | Description[c] | Conserved Domain ID[d] | Conserved Domain definition[e] |
|---|---|---|---|---|
| Nga40094 | 2.06 | photosystem ii d2 protein | cd09288 | D2 subunit of photosystem II (PS II) |
| Nga04295 | 2.05 | hypothetical protein Tcur_2694 [Thermomonospora curvata DSM 43183] | no hit | no hit |
| Nga00509 | 2.05 | no hit | no hit | no hit |
| Nga30431 | 2.04 | calcineurin-like phosphoesterase | cl09501 | EF-hand, calcium binding motif |
| Nga07039 | 2.04 | no hit | no hit | no hit |
| Nga20583.1 | 2.03 | protein | TIGR01241 | ATP-dependent metalloprotease FtsH |
| Nga07207 | 2.02 | no hit | no hit | no hit |
| Nga20327 | 2.02 | zinc finger fyve domain-containing protein | cd00065 | FYVE domain |
| Nga04524 | 2.01 | no hit | no hit | no hit |
| Nga05615.1 | 2.01 | phosphoribosylformylglycinamidine synthase | cd01740; cl10019; cd02204 | Type 1 glutamine amidotransferase (GATase1)-like domain; AIR (aminoimidazole ribonucleotide) synthase related protein; PurL subunit of the formylglycinamide ribonucleotide amidotransferase (FGAR-AT), second repeat |
| Nga40046 | 0.5 | photosystem ii 32 kda protein | cd09289 | D1 subunit of photosystem II (PS II) |
| Nga04641 | 0.5 | light-harvesting protein | cl02879 | Chlorophyll A-B binding protein |
| Nga01578.01 | 0.5 | auxin efflux carrier-like protein | cl09117 | Membrane transport protein |
| Nga20668.1 | 0.5 | protein kinase domain containing protein | no hit | no hit |
| Nga20029.1 | 0.49 | abc subfamily abcg | cl11417 | ABC-2 type transporter |
| Nga20678 | 0.49 | no hit | no hit | no hit |
| Nga20579 | 0.49 | no hit | no hit | no hit |
| Nga03015 | 0.49 | protein kinase wee1 | cl09925 | Protein Kinases, catalytic domain |

FIGURE 20 D

| N. gaditana model[a] | Fold regulation[b] | Description[c] | Conserved Domain ID[d] | Conserved Domain definition[e] |
|---|---|---|---|---|
| Nga04225 | 0.48 | low molecular mass early light-inducible protein hv60 | no hit | no hit |
| Nga40088 | 0.48 | ycf66 family protein | cd06468 | Ycf66 protein N-terminus |
| Nga05473 | 0.48 | no hit | no hit | no hit |
| Nga06871 | 0.47 | bnr asp-box repeat-containing protein | COG4447 | Uncharacterized protein related to plant photosystem II stability/assembly factor |
| Nga20458 | 0.47 | chaperone protein | cd06257 | DnaJ domain or J-domain |
| Nga30457 | 0.46 | stip-like protein | cl02611 | G-patch domain |
| Nga20417 | 0.46 | photosystem i p700 chlorophyll a apoprotein a1 | cl08224 | Photosystem I psaA/psaB protein |
| Nga00448.01 | 0.46 | light harvesting complex protein | cl02879 | Chlorophyll A-B binding protein |
| Nga03116 | 0.45 | light-harvesting protein | cl02879 | Chlorophyll A-B binding protein |
| Nga20981 | 0.45 | myb-like dna-binding domain containing protein | cl00132 | 'SWI3, ADA2, N-CoR and TFIIIB' DNA-binding domains |
| Nga01043 | 0.45 | no hit | no hit | no hit |
| Nga40023 | 0.45 | hypothetical protein [uncultured delta proteobacterium HF0130_19C20] | no hit | no hit |
| Nga30860 | 0.45 | no hit | no hit | no hit |
| Nga06456 | 0.45 | no hit | no hit | no hit |
| Nga03667 | 0.44 | glutathione s-transferase | cl02776; cl00388 | C-terminal, alpha helical domain of the Glutathione S-transferase family; Protein Disulfide Oxidoreductases and Other Proteins with a Thioredoxin fold |
| Nga40124 | 0.43 | 30s ribosomal protein s10 | cl00314 | Ribosomal protein S20e |
| Nga00253.1 | 0.43 | no hit | no hit | no hit |
| Nga02520.01 | 0.43 | phytochelatin synthase | pfam05023 | Phytochelatin synthase |
| Nga40090 | 0.43 | no hit | no hit | no hit |

FIGURE 20 E

| N. gaditana model[a] | Fold regulation[b] | Description[c] | Conserved Domain ID[d] | Conserved Domain definition[e] |
|---|---|---|---|---|
| Nga02790 | 0.42 | light-harvesting protein | cl02879 | Chlorophyll A-B binding protein |
| Nga03527 | 0.42 | no hit | no hit | no hit |
| Nga30169 | 0.41 | no hit | no hit | no hit |
| Nga00347 | 0.41 | cap family transcription factor | cd00038; cl00446 | Effector domain of the CAP family of transcription factors; Metallo-beta-lactamase superfamily |
| Nga01885.01 | 0.39 | no hit | no hit | no hit |
| Nga04558 | 0.39 | no hit | no hit | no hit |
| Nga00243.01 | 0.39 | no hit | no hit | no hit |
| Nga30680 | 0.39 | zinc finger protein 598 | COG5236 | Uncharacterized conserved protein, contains RING Zn-finger |
| Nga20514 | 0.39 | peptide chain release factor 2 | cl02875 | RF-1 domain |
| Nga01194 | 0.39 | no hit | no hit | no hit |
| Nga01460.01 | 0.38 | riken cdna 6720467c03 isoform cra_a | no hit | no hit |
| Nga07186 | 0.38 | no hit | no hit | no hit |
| Nga05697 | 0.37 | light-harvesting protein | cl02879 | Chlorophyll A-B binding protein |
| Nga06201 | 0.37 | no hit | no hit | no hit |
| Nga04536.01 | 0.37 | light-harvesting protein | cl02879 | Chlorophyll A-B binding protein |
| Nga30207 | 0.37 | ammonium transporter | cl03012 | Ammonium Transporter Family |
| Nga06069 | 0.37 | protein | cl01841 | Protein of unknown function (DUF1499) |
| Nga50010 | 0.36 | nadh dehydrogenase subunit 9 | cl00539 | Respiratory-chain NADH dehydrogenase |
| Nga06056 | 0.36 | predicted protein [Thalassiosira pseudonana CCMP1335] | no hit | no hit |
| Nga05289 | 0.36 | protein fucoxanthin chlorophyll a c protein | cl02879 | Chlorophyll A-B binding protein |

FIGURE 20 F

| N. gaditana model[a] | Fold regulation[b] | Description[c] | Conserved Domain ID[d] | Conserved Domain definition[e] |
|---|---|---|---|---|
| Nga20601 | 0.35 | wd40 repeat-containing protein | cl02567 | WD40 domain |
| Nga05030 | 0.34 | no hit | no hit | no hit |
| Nga06911.1 | 0.34 | ankyrin repeat and kh domain-containing protein 1 | cd00204 | Ankyrin repeats |
| Nga30730 | 0.33 | no hit | no hit | no hit |
| Nga01282 | 0.32 | no hit | no hit | no hit |
| Nga00736 | 0.32 | no hit | no hit | no hit |
| Nga21288.1 | 0.31 | udp-sulfoquinovose synthase | cl09931 | Rossmann-fold NAD(P)(+)-binding proteins |
| Nga40020 | 0.31 | cytochrome c553 | cl11414 | Cytochrome c |
| Nga02267 | 0.3 | ferredoxin-nitrite reductase | PRK09568 | Ferredoxin-nitrite reductase |
| Nga02416 | 0.3 | no hit | no hit | no hit |
| Nga07010 | 0.3 | protein fucoxanthin chlorophyll a c protein | cl02879 | Chlorophyll A-B binding protein |
| Nga02785 | 0.28 | light-harvesting protein | cl02879 | Chlorophyll A-B binding protein |
| Nga02325.01 | 0.24 | rna binding protein | cd00105 | K homology RNA-binding domain, type I |
| Nga01100.1 | 0.24 | poly -binding protein 3 isoform 2 | cd00105 | K homology RNA-binding domain, type I |
| Nga40044 | 0.22 | light-independent protochlorophyllide iron-sulfur atp-binding protein | cl10444; CHL00072 | Ras-like GTPase superfamily; photochlorophyllide reductase subunit L |
| Nga03568 | 0.21 | no hit | no hit | no hit |
| Nga40018 | 0.19 | photosystem i p700 chlorophyll a apoprotein a2 | cl09224 | Photosystem I psaA/psaB protein |
| Nga20911.1 | 0.18 | myo-inositol-1-phosphate synthase | cl00554 | Myo-inositol-1-phosphate synthase |
| Nga50007 | 0.18 | 30s ribosomal protein s3 | cl00098; cl02819 | K homology RNA-binding domain, type I; Ribosomal protein S3, C-terminal domain |
| Nga06064 | 0.11 | protein | cl02429 | Tetratricopeptide repeat domain |

FIGURE 20 G

| N. gaditana model[a] | Fold regulation[b] | Description[c] | Conserved Domain ID[d] | Conserved Domain definition[e] |
|---|---|---|---|---|
| Nga20756 | 0.11 | photosystem I p700 chlorophyll a apoprotein a1 | cl08224 | Photosystem I psaA/psaB protein |
| Nga00124 | 0.1 | no hit | no hit | no hit |
| Nga05257 | 0.1 | no hit | no hit | no hit |
| Nga30862 | 0.1 | rieske (2fe-2s) region protein | cl00938 | Rieske domain |
| Nga04958 | 0.09 | no hit | no hit | no hit |

[a] *N. gaditana* gene models differentially regulated during nitrogen deprivation.

[b] Fold regulation of gene, >1 signifies up-regulation, <1 signifies down-regulation.

[c] *N. gaditana* gene model description. A green label indicates a function in photosynthesis; a blue label indicates a function in nitrogen utilization or protein degradation/recycling.

[d] Conserved protein domain ID assigned from NCBI-curated domains, Pfam, SMART, COG, PRK, or TIGRFAM databases.

[e] Description of conserved protein domain given.

FIGURE 20 H

|  | pep# | Nga model | Description |
|---|---|---|---|
| Chlorophyll, carotenoid and sterol biosynthesis genes | | | |
| SEQ ID NO: 8722 | 59 | Nga02834 | glutamyl-tRNA synthetase |
| SEQ ID NO: 8713 | 50 | Nga02604 | glutamyl-tRNA reductase |
| SEQ ID NO: 8804 | 141 | Nga30045 | glutamate-1-semialdehyde aminotransferase / glutamate-1-semialdehyde 21-aminomutase |
| SEQ ID NO: 8678 | 15 | Nga00585 | 5-aminolevulinic acid dehydratase / porphobilinogen synthase |
| SEQ ID NO: 8730 | 67 | Nga03248 | porphobilinogen deaminase / hydroxymethylbilane synthase |
| SEQ ID NO: 8686 | 23 | Nga00807 | uroporphyrinogen III synthase |
| SEQ ID NO: 8745 | 82 | Nga04120 | uroporphyrinogen III decarboxylase |
| SEQ ID NO: 8774 | 111 | Nga05706 | uroporphyrinogen III decarboxylase |
| SEQ ID NO: 8763 | 100 | Nga05151 | coproporphyrinogen III oxidase |
| SEQ ID NO: 8749 | 86 | Nga04278 | coproporphyrinogen III oxidase |
| SEQ ID NO: 8744 | 81 | Nga03873 | protoporphyrinogen IX oxidase |
| SEQ ID NO: 8818 | 155 | Nga30773 | protoporphyrin IX Mg-chelatase subunit D |
| SEQ ID NO: 8838 | 175 | Nga40092 | protoporphyrin IX MG-chelatase subuint I |
| SEQ ID NO: 8831 | 168 | Nga30995 | protoporphyrin IX Mg-chelatase subunit H |
| SEQ ID NO: 8785 | 122 | Nga06242 | protoporphyrin IX Mg-chelatase subunit H |
| SEQ ID NO: 8837 | 174 | Nga40091 | Mg-protoporphyrin IX monomethyl ester (oxidative) cyclase |
| SEQ ID NO: 8777 | 114 | Nga05945 | divinyl protochlorophyllide a 8-vinyl-reductase |
| SEQ ID NO: 8759 | 96 | Nga04959 | light-dependent NADPH:protochlorophyllide oxidoreductase |
| SEQ ID NO: 8683 | 20 | Nga00683 | light-dependent NADPH:protochlorophyllide oxidoreductase |
| SEQ ID NO: 8836 | 173 | Nga40089 | light-independent:protochlorophyllide oxidoreductase subunit B |
| SEQ ID NO: 8834 | 171 | Nga40044 | light-independent:protochlorophyllide oxidoreductase subunit L |
| SEQ ID NO: 8835 | 172 | Nga40045 | light-independent:protochlorophyllide oxidoreductase subunit N |
| SEQ ID NO: 8832 | 169 | Nga31097 | chlorophyll synthase |
| SEQ ID NO: 8757 | 94 | Nga04895 | geranylgeranyl reductase |
| SEQ ID NO: 8764 | 101 | Nga05160 | uroporphyrinogen III C-methyltransferase |
| SEQ ID NO: 8671 | 8 | Nga00339 | sirohydrochlorin ferrochelatase |
| SEQ ID NO: 8684 | 21 | Nga00748 | ferrochelatase |
| SEQ ID NO: 8817 | 154 | Nga30771 | 1-deoxy-D-xylulose-5-phosphate reductoisomerase |
| SEQ ID NO: 8784 | 121 | Nga06198 | 2-C-methyl-D-erythritol 4-phosphate cytidyltransferase |
| SEQ ID NO: 8821 | 158 | Nga30806 | 4-hydroxy-3-methylbut-2-enyl diphosphate synthase |
| SEQ ID NO: 8767 | 104 | Nga05308 | 4-hydroxy-3-methylbut-2-enyl diphosphate reductase |
| SEQ ID NO: 8742 | 79 | Nga03838 | isopentenyl diphosphate:dimethylallyl diphosphate isomerase type I |
| SEQ ID NO: 8714 | 51 | Nga02636 | geranylgeranyl pyrophosphate synthase |
| SEQ ID NO: 8725 | 62 | Nga02957 | phytoene synthase |
| SEQ ID NO: 8761 | 98 | Nga05064 | phytoene desaturase |
| SEQ ID NO: 8792 | 129 | Nga07310 | zeta-carotene desaturase |
| SEQ ID NO: 8680 | 17 | Nga00640 | lycopene β-cyclase |
| SEQ ID NO: 8805 | 142 | Nga30077 | cytochrome P450 enzyme related to CYP97A carotene β-hydroxylase |
| SEQ ID NO: 8666 | 3 | Nga00100 | cytochrome P450 enzyme related to CYP97A carotene β-hydroxylase |
| SEQ ID NO: 8797 | 134 | Nga20998 | acetyl-CoA C-acetyltransferase |
| SEQ ID NO: 8824 | 161 | Nga30830 | acetyl-CoA C-acetyltransferase |
| SEQ ID NO: 8786 | 123 | Nga06246 | hydroxymethylglutaryl-CoA synthase |
| SEQ ID NO: 8723 | 60 | Nga02865 | geranyl-disphosphate synthase / dimethylallyltranstransferase |
| SEQ ID NO: 8724 | 61 | Nga02874 | farnesyl-diphosphate synthase |
| SEQ ID NO: 8742 | 79 | Nga03838 | isopentenyl diphosphate:dimethylallyl diphosphate isomerase type I |
| SEQ ID NO: 8698 | 35 | Nga01590 | squalene monooxygenase / squalene epoxidase |
| SEQ ID NO: 8820 | 157 | Nga30790 | cycloartenol synthase |
| SEQ ID NO: 8740 | 77 | Nga03733.1 | C14-demethylase (sterol 14-demethylase) |
| SEQ ID NO: 8685 | 22 | Nga00758 | D14-sterol reductase |
| SEQ ID NO: 8779 | 116 | Nga06114 | C4-decarboxylase (sterol-4-alpha-carboxylate 3-dehydrogenase) |
| SEQ ID NO: 8776 | 113 | Nga05943 | sterol-C24-methyl transferase (sterol 24-C-methyltransferase) |
| SEQ ID NO: 8712 | 49 | Nga02534 | sterol-C24-methyl transferase (sterol 24-C-methyltransferase) |
| SEQ ID NO: 8720 | 57 | Nga02795 | C5-desaturase (lathosterol oxidase) |
| SEQ ID NO: 8731 | 68 | Nga03254 | D7-sterol reductase (7-dehydrocholesterol reductase) |
| SEQ ID NO: 8766 | 103 | Nga05293 | D24-sterol reductase (24-dehydrocholesterol reductase) |
| SEQ ID NO: 8809 | 146 | Nga30196 | cyclopropyl sterol isomerase (cycloeucalenol cycloisomerase) |
| SEQ ID NO: 8681 | 18 | Nga00656 | D5-sterol reductase |
| Lipid metabolic pathway genes | | | |
| SEQ ID NO: 8802 | 139 | Nga30020 | acetyl-CoA synthetase |
| SEQ ID NO: 8706 | 43 | Nga02166 | acetyl-CoA synthetase |
| SEQ ID NO: 8803 | 140 | Nga30028 | acetyl-CoA carboxylase |
| SEQ ID NO: 8819 | 156 | Nga30783 | acetyl-CoA carboxylase |
| SEQ ID NO: 8690 | 27 | Nga00899 | malonyl-CoA:ACP-trans-acylase |
| SEQ ID NO: 8806 | 143 | Nga30106 | 3-oxoacyl-ACP synthase III |
| SEQ ID NO: 8705 | 42 | Nga02138 | 3-oxoacyl-ACP synthase II |
| SEQ ID NO: 8816 | 153 | Nga30755 | 3-oxoacyl-ACP synthase II |
| SEQ ID NO: 8747 | 84 | Nga04201.01 | 3-oxoacyl-ACP synthase II |

FIGURE 23A

| | pep# | Nga model | Description |
|---|---|---|---|
| SEQ ID NO: 8775 | 112 | Nga05827 | fatty acid synthase |
| SEQ ID NO: 8793 | 130 | Nga20022 | 3-oxoacyl-ACP reductase |
| SEQ ID NO: 8697 | 34 | Nga01542 | 3-oxoacyl-ACP reductase |
| SEQ ID NO: 8778 | 115 | Nga05985.01 | 3-hydroxy acyl-CoA dehydratase |
| SEQ ID NO: 8762 | 99 | Nga05091 | enoyl-ACP reductase I |
| SEQ ID NO: 8679 | 16 | Nga00602 | 3-oxoacyl-ACP reductase |
| SEQ ID NO: 8772 | 109 | Nga05627 | 3-oxoacyl-ACP reductase |
| SEQ ID NO: 8692 | 29 | Nga01045.01 | oleyl-ACP hydrolase |
| SEQ ID NO: 8728 | 65 | Nga03084 | elongation of very long chain fatty acids |
| SEQ ID NO: 8673 | 10 | Nga00451 | elongation of very long chain fatty acids |
| SEQ ID NO: 8695 | 32 | Nga01458.01 | acyl-ACP desaturase |
| SEQ ID NO: 8675 | 12 | Nga00524 | stearoyl-CoA desaturase |
| SEQ ID NO: 8704 | 41 | Nga02019 | omega-6 fatty acid desaturase delta-12 |
| SEQ ID NO: 8687 | 24 | Nga00817 | omega-6 fatty acid desaturase delta-12 |
| SEQ ID NO: 8791 | 128 | Nga06739.1 | sphingolipid delta-4 desaturase |
| SEQ ID NO: 8807 | 144 | Nga30138 | glycerolipid omega-3 fatty acid desaturase |
| SEQ ID NO: 8789 | 126 | Nga06665.1 | glycerol-3-phosphate dehydrogenase |
| SEQ ID NO: 8702 | 39 | Nga01869 | glycerol-3-phosphate dehydrogenase |
| SEQ ID NO: 8758 | 95 | Nga04914 | glycerol-3-phosphate dehydrogenase |
| SEQ ID NO: 8765 | 102 | Nga05226 | glycerol-3-phosphate dehydrogenase |
| SEQ ID NO: 8801 | 138 | Nga30015 | glycerol-3-phosphate dehydrogenase |
| SEQ ID NO: 8754 | 91 | Nga04759 | glycerol-3-phosphate acyltransferase |
| SEQ ID NO: 8756 | 93 | Nga04850 | glycerol-3-phosphate acyltransferase |
| SEQ ID NO: 8665 | 2 | Nga00059 | 1-acylglycerol-3-phosphate O-acyltransferase |
| SEQ ID NO: 8813 | 150 | Nga30581 | 1-acylglycerol-3-phosphate O-acyltransferase |
| SEQ ID NO: 8822 | 159 | Nga30809 | 1-acylglycerol-3-phosphate O-acyltransferase |
| SEQ ID NO: 8708 | 45 | Nga02265 | 1-acylglycerol-3-phosphate O-acyltransferase |
| SEQ ID NO: 8799 | 136 | Nga21116 | phosphatidic acid phosphatase |
| SEQ ID NO: 8721 | 58 | Nga02796 | diacylglycerol kinase |
| SEQ ID NO: 8770 | 107 | Nga05586.1 | diacylglycerol kinase |
| SEQ ID NO: 8719 | 56 | Nga02737 | phospholipid:diacylglycerol acyltransferase |
| SEQ ID NO: 8811 | 148 | Nga30544 | diacylglycerol acyltransferase |
| SEQ ID NO: 8768 | 105 | Nga05465 | lysophosphatidylglycerol acyltransferase |
| SEQ ID NO: 8670 | 7 | Nga00335 | polyketide synthase 5 |
| SEQ ID NO: 8688 | 25 | Nga00818 | monogalactosyldiacylglycerol synthase |
| SEQ ID NO: 8677 | 14 | Nga00561 | sulfoquinovosyltransferase |
| SEQ ID NO: 8717 | 54 | Nga02686 | UDP-sulfoquinovose synthase |
| SEQ ID NO: 8830 | 167 | Nga30958 | TAG-lipase |
| SEQ ID NO: 8815 | 152 | Nga30749 | TAG-lipase |
| SEQ ID NO: 8734 | 71 | Nga03422 | acyl-CoA synthetase |
| SEQ ID NO: 8771 | 108 | Nga05597 | acyl-CoA synthase |
| SEQ ID NO: 8808 | 145 | Nga30170 | long-chain acyl-CoA synthetase |
| SEQ ID NO: 8729 | 66 | Nga03113 | long-chain acyl-CoA synthetase |
| SEQ ID NO: 8682 | 19 | Nga00675 | long-chain acyl-CoA synthetase |
| SEQ ID NO: 8814 | 151 | Nga30631 | long-chain acyl-CoA synthetase |
| SEQ ID NO: 8691 | 28 | Nga00919 | long-chain acyl-CoA ligase |
| SEQ ID NO: 8711 | 48 | Nga02299 | long-chain acyl-CoA ligase |
| SEQ ID NO: 8664 | 1 | Nga00006 | long-chain acyl-CoA ligase |
| SEQ ID NO: 8812 | 149 | Nga30568 | long-chain acyl-CoA ligase |
| SEQ ID NO: 8674 | 11 | Nga00482.01 | 3-hydroxyacyl-CoA dehydrogenase |
| SEQ ID NO: 8716 | 53 | Nga02679 | 3-hydroxyacyl-CoA dehydrogenase |
| SEQ ID NO: 8782 | 119 | Nga06144.1 | 3-hydroxyacyl-CoA dehydrogenase |
| SEQ ID NO: 8735 | 72 | Nga03480 | long-chain hydroxyacyl-CoA dehydrogenase |
| SEQ ID NO: 8833 | 170 | Nga31130 | short-chain acyl-CoA dehydrogenase |
| SEQ ID NO: 8773 | 110 | Nga05705 | short-branched-chain acyl-CoA dehydrogenase |
| SEQ ID NO: 8748 | 85 | Nga04204.01 | Acyl-CoA dehydrogenase |
| SEQ ID NO: 8727 | 64 | Nga03053 | acyl-CoA oxidase |
| SEQ ID NO: 8780 | 117 | Nga06128 | peroxisomal trans-2-enoyl-CoA reductase |
| SEQ ID NO: 8736 | 73 | Nga03545 | alternative oxidase |
| SEQ ID NO: 8827 | 164 | Nga30837 | alternative oxidase |
| SEQ ID NO: 8732 | 69 | Nga03289 | alternative oxidase |
| SEQ ID NO: 8750 | 87 | Nga04370.1 | acyl-CoA oxidase |
| SEQ ID NO: 8823 | 160 | Nga30819 | acyl-CoA oxidase |
| SEQ ID NO: 8701 | 38 | Nga01761.01 | enyol-CoA hydratase |
| SEQ ID NO: 8668 | 5 | Nga00171 | enyol-CoA hydratase |
| SEQ ID NO: 8794 | 131 | Nga20152 | enyol-CoA hydratase |
| SEQ ID NO: 8781 | 118 | Nga06135 | enyol-CoA hydratase |
| SEQ ID NO: 8699 | 36 | Nga01710 | beta-ketoacyl-CoA thiolase |

FIGURE 23 B

|  | pep# | Nga model | Description |
|---|---|---|---|
| SEQ ID NO: 8752 | 89 | Nga04504.01 | beta-ketoacyl-CoA thiolase |
| SEQ ID NO: 8824 | 161 | Nga30830 | beta-ketoacyl-CoA thiolase |
| SEQ ID NO: 8797 | 134 | Nga20998 | acetyl-CoA acetyltransferase |
| SEQ ID NO: 8824 | 161 | Nga30830 | beta-ketoacyl-CoA thiolase |
| SEQ ID NO: 8787 | 124 | Nga06551 | solute carrier family (fatty acid transporter) |
| SEQ ID NO: 8769 | 106 | Nga05502.01 | peroxisomal 2,4-dienoyl-CoA reductase |
| SEQ ID NO: 8726 | 63 | Nga03028.01 | patatin-like phospholipase |
| Carbon assimilation genes | | | |
| SEQ ID NO: 8693 | 30 | Nga01240 | Carbonic anhydrase |
| SEQ ID NO: 8700 | 37 | Nga01717 | Carbonic anhydrase |
| SEQ ID NO: 8739 | 76 | Nga03728 | Carbonic anhydrase |
| SEQ ID NO: 8828 | 165 | Nga30848 | Carbonic anhydrase |
| SEQ ID NO: 8800 | 137 | Nga21222 | Carbonic anhydrase |
| SEQ ID NO: 8667 | 4 | Nga00165.01 | Bicarbonate transporter |
| SEQ ID NO: 8788 | 125 | Nga06584 | Bicarbonate transporter |
| Nitrate assimilation genes | | | |
| SEQ ID NO: 8710 | 47 | Nga02268 | NAD(P)H nitrate reductase |
| SEQ ID NO: 8709 | 46 | Nga02267 | Ferredoxin nitrite reductase |
| SEQ ID NO: 8738 | 75 | Nga03713 | Urease |
| SEQ ID NO: 8669 | 6 | Nga00207.01 | Urease accessory protein ureG |
| SEQ ID NO: 8694 | 31 | Nga01342.01 | Urease accessory protein ureD |
| SEQ ID NO: 8829 | 166 | Nga30904 | Nitrate high affinity transporter |
| SEQ ID NO: 8746 | 83 | Nga04130 | Putative nitrate / peptide transporter |
| SEQ ID NO: 8689 | 26 | Nga00897 | Nitrite transporter |
| SEQ ID NO: 8790 | 127 | Nga06677 | Nitrite transporter |
| SEQ ID NO: 8796 | 133 | Nga20972 | Ammonium transporter |
| SEQ ID NO: 8810 | 147 | Nga30207 | Ammonium transporter |
| SEQ ID NO: 8783 | 120 | Nga06186 | Urea/Na+ high affinity symporter |
| SEQ ID NO: 8672 | 9 | Nga00381 | carbamoyl-phosphate synthetase I large subunit |
| SEQ ID NO: 8733 | 70 | Nga03303 | carbamoyl-phosphate synthetase I small subunit |
| SEQ ID NO: 8795 | 132 | Nga20220 | ornithine carbamoyltransferase |
| SEQ ID NO: 8751 | 88 | Nga04487 | argininosuccinate synthetase |
| SEQ ID NO: 8737 | 74 | Nga03647 | argininosuccinate lyase |
| SEQ ID NO: 8676 | 13 | Nga00526 | arginase |

FIGURE 23 C

| # | Nga model | +N rpkb | -N rpkb | GO |
|---|---|---|---|---|
| SEQ ID NO: 1 | Nga00398 | 207.6225 | 207.99664 | beta adaptin |
| SEQ ID NO: 2 | Nga00392 | 784.4507 | 773.59444 | glutamine-trna ligase |
| SEQ ID NO: 3 | Nga00399 | 457.2264 | 413.26353 | glutathione synthetase |
| SEQ ID NO: 4 | Nga00401 | 202.9731 | 154.21684 | protein |
| SEQ ID NO: 5 | Nga00403 | 951.5608 | 963.13373 | ---NA--- |
| SEQ ID NO: 6 | Nga00407 | 97.71078 | 92.235162 | epidermal growth factor receptor pathway substrate 15 |
| SEQ ID NO: 7 | Nga00428 | 561.6046 | 534.89202 | uridine diphosphate-n-acetylglucosamine transporter hut1 |
| SEQ ID NO: 8 | Nga00426.2 | 1419.718 | 1439.0992 | chromatin modification-related protein eaf3 |
| SEQ ID NO: 9 | Nga00396 | 393.3464 | 576.59419 | protein |
| SEQ ID NO: 10 | Nga00394 | 739.9037 | 811.52243 | puromycin-sensitive aminopeptidase |
| SEQ ID NO: 11 | Nga00393 | 6558.025 | 6146.3496 | pumpkin fruit trypsin inhibitor |
| SEQ ID NO: 12 | Nga00405 | 418.0791 | 381.47787 | s-adenosylmethionine-dependent methyltransferase domain-containing protein |
| SEQ ID NO: 13 | Nga20048.1 | 923.9281 | 819.54214 | nudix hydrolase |
| SEQ ID NO: 14 | Nga00391 | 586.6781 | 621.63382 | protein |
| SEQ ID NO: 15 | Nga00404 | 353.5354 | 361.76184 | domain-containing histone demethylation protein 3c |
| SEQ ID NO: 16 | Nga00400.1 | 317.6551 | 342.24876 | cell division control protein 45 |
| SEQ ID NO: 17 | Nga00395 | 472.3931 | 462.21181 | protein |
| SEQ ID NO: 18 | Nga00408 | 1374.384 | 1291.3429 | ---NA--- |
| SEQ ID NO: 19 | Nga00397.01 | 144.845 | 165.12295 | fidgetin-like protein |
| SEQ ID NO: 20 | Nga20104 | 607.9952 | 643.08936 | protein |
| SEQ ID NO: 21 | Nga00406 | 266.4756 | 325.90133 | ---NA--- |
| SEQ ID NO: 22 | Nga20131.1 | 392.5466 | 476.35381 | hypothetical protein AURANDRAFT_63258 [Aureococcus anophagefferens] |
| SEQ ID NO: 23 | Nga03946.2 | 7492.188 | 6006.6103 | ---NA--- |
| SEQ ID NO: 24 | Nga03460 | 47.35376 | 56.525299 | phosphatidylinositol kinase (pik-I4) |
| SEQ ID NO: 25 | Nga03458.01 | 2169.955 | 2504.3321 | ---NA--- |
| SEQ ID NO: 26 | Nga03461 | 364.3791 | 396.47778 | ---NA--- |
| SEQ ID NO: 27 | Nga03453.01 | 210.8067 | 224.78066 | structural maintenance of chromosomes protein 3 |
| SEQ ID NO: 28 | Nga03459 | 428.2946 | 300.19855 | membrane protein |
| SEQ ID NO: 29 | Nga03456 | 397.3903 | 370.07281 | transcription elongation factor |
| SEQ ID NO: 30 | Nga03455 | 1262.334 | 1416.0045 | ankyrin partial |
| SEQ ID NO: 31 | Nga03454.01 | 651.7944 | 688.18451 | protein |
| SEQ ID NO: 32 | Nga03457.1 | 132.216 | 183.56478 | protein |
| SEQ ID NO: 33 | Nga21127 | 205.5514 | 237.28755 | solute carrier family member 27 |
| SEQ ID NO: 34 | Nga05422 | 108.4813 | 110.03264 | ---NA--- |
| SEQ ID NO: 35 | Nga03210.02 | 259.3477 | 279.21066 | protein |
| SEQ ID NO: 36 | Nga03209.02 | 131.5789 | 98.187872 | ---NA--- |
| SEQ ID NO: 37 | Nga05414.01 | 2174.783 | 2062.8542 | peptide methionine sulfoxide reductase |
| SEQ ID NO: 38 | Nga05415.01 | 1324.324 | 1401.0941 | protein |
| SEQ ID NO: 39 | Nga05420.01 | 13110.33 | 13438.712 | ribosomal protein l27 |
| SEQ ID NO: 40 | Nga05418 | 808.2192 | 788.93066 | ---NA--- |
| SEQ ID NO: 41 | Nga05416 | 386.2816 | 297.20498 | protein |
| SEQ ID NO: 42 | Nga05417 | 755.0471 | 727.98764 | tryptophan synthetase |
| SEQ ID NO: 43 | Nga05421 | 1873.007 | 2142.0519 | protein |
| SEQ ID NO: 44 | Nga05424 | 1797.619 | 1782.1777 | nmda receptor glutamate-binding chain |
| SEQ ID NO: 45 | Nga05426 | 298.0501 | 256.476 | ---NA--- |
| SEQ ID NO: 46 | Nga04327.02 | 178.0576 | 211.06177 | protein |
| SEQ ID NO: 47 | Nga05764 | 1305.814 | 1340.1871 | membrane-associated protein in eicosanoid and glutathione metabolism |
| SEQ ID NO: 48 | Nga05771 | 137.3737 | 146.61954 | lysophosphatidic acid |
| SEQ ID NO: 49 | Nga20723 | 93.75 | 74.472333 | serine threonine protein kinase |
| SEQ ID NO: 50 | Nga20343 | 194.6565 | 202.58955 | traf2 and nck-interacting protein kinase-like |
| SEQ ID NO: 51 | Nga04326.02 | 428.1109 | 438.60149 | protein |
| SEQ ID NO: 52 | Nga05768.1 | 229.0076 | 219.40311 | probable serca-type calcium atpase |
| SEQ ID NO: 53 | Nga20086.1 | 274.6067 | 437.6752 | serine threonine protein |
| SEQ ID NO: 54 | Nga05767 | 562.2776 | 488.29051 | protein |
| SEQ ID NO: 55 | Nga02263.02 | 11320.72 | 10950.608 | fructose-bisphosphate aldolase |
| SEQ ID NO: 56 | Nga05770 | 1349.741 | 1449.9245 | nucleosome chromatin assembly complex protein |
| SEQ ID NO: 57 | Nga02264.02 | 153.2385 | 168.5601 | cyclopropane-fatty-acyl-phospholipid synthase |
| SEQ ID NO: 58 | Nga04304.02 | 390.411 | 650.43499 | protein |
| SEQ ID NO: 59 | Nga04302.02 | 284.5426 | 377.93588 | pak1ip1 protein |
| SEQ ID NO: 60 | Nga05096.1 | 346.4912 | 404.62905 | retinoblastoma binding protein 4 |
| SEQ ID NO: 61 | Nga04303.02 | 490.0872 | 462.58642 | n-ethylmaleimide-sensitive fusion protein |

FIGURE 24 A

| # | Nga model | +N rpkb | -N rpkb | GO |
|---|---|---|---|---|
| SEQ ID NO: 62 | Nga05101 | 683.6066 | 701.43837 | ---NA--- |
| SEQ ID NO: 63 | Nga04401.02 | 420.6799 | 494.05287 | ---NA--- |
| SEQ ID NO: 64 | Nga21200.1 | 802.2388 | 1023.9525 | c19orf60 homolog |
| SEQ ID NO: 65 | Nga04400.2 | 159.6107 | 175.00422 | minichromosome maintenance protein 2 |
| SEQ ID NO: 66 | Nga05100.1 | 272.9104 | 285.80795 | dna replication licensing factor mcm2 |
| SEQ ID NO: 67 | Nga20255.1 | 331.1966 | 290.48261 | probable palmitoyltransferase zdhhc11-like |
| SEQ ID NO: 68 | Nga01865.2 | 128.6667 | 163.9294 | protein |
| SEQ ID NO: 69 | Nga04340.2 | 661.3295 | 756.31909 | mitochondrion protein |
| SEQ ID NO: 70 | Nga05117 | 666.6667 | 797.81039 | protein |
| SEQ ID NO: 71 | Nga05131.1 | 333.6481 | 322.89032 | calcium-transporting atpase type 2c member 1-like |
| SEQ ID NO: 72 | Nga05125 | 19.23077 | 93.741399 | ---NA--- |
| SEQ ID NO: 73 | Nga01335.02 | 703.7594 | 567.67974 | protein |
| SEQ ID NO: 74 | Nga20059.1 | 1173.2 | 1059.2993 | protein |
| SEQ ID NO: 75 | Nga01334.02 | 6031.915 | 6632.5672 | 40s ribosomal protein s2 |
| SEQ ID NO: 76 | Nga01088.02 | 700.4539 | 686.64905 | protein |
| SEQ ID NO: 77 | Nga20927.1 | 5178.976 | 5806.8178 | protein |
| SEQ ID NO: 78 | Nga05116 | 1110.123 | 993.58188 | cdc37 protein |
| SEQ ID NO: 79 | Nga05122.1 | 256.9061 | 266.31995 | ---NA--- |
| SEQ ID NO: 80 | Nga05123 | 7665.007 | 5768.8004 | ---NA--- |
| SEQ ID NO: 81 | Nga01087.2 | 793.6937 | 779.73326 | ---NA--- |
| SEQ ID NO: 82 | Nga05124 | 596 | 682.43738 | sister chromatid cohesion protein dcc1 |
| SEQ ID NO: 83 | Nga05136 | 623.6324 | 711.8846 | cytochrome b5 domain-containing |
| SEQ ID NO: 84 | Nga02421.02 | 1065.574 | 1197.3921 | phosphoglycerate kinase |
| SEQ ID NO: 85 | Nga20253.1 | 907.1895 | 718.61598 | lrr and pyd domains-containing protein 3-like |
| SEQ ID NO: 86 | Nga04768.02 | 315.6342 | 389.8364 | ---NA--- |
| SEQ ID NO: 87 | Nga05137 | 2510.606 | 2473.3842 | predicted protein [Phaeodactylum tricornutum CCAP 1055/1] |
| SEQ ID NO: 88 | Nga20778 | 292.1028 | 226.74735 | transducin wd-40 repeat |
| SEQ ID NO: 89 | Nga05132 | 505.1238 | 572.60616 | ca2 :cation antiporter family |
| SEQ ID NO: 90 | Nga02203.02 | 2106.762 | 1790.8269 | protein |
| SEQ ID NO: 91 | Nga20097.1 | 190.1932 | 218.09539 | type i inositol polyphosphate 5- |
| SEQ ID NO: 92 | Nga06060 | 463.5193 | 538.51759 | protease |
| SEQ ID NO: 93 | Nga06063 | 1310.484 | 1311.8196 | 50s ribosomal protein l3 |
| SEQ ID NO: 94 | Nga06056 | 3280.692 | 1172.6975 | predicted protein [Thalassiosira pseudonana CCMP1335] |
| SEQ ID NO: 95 | Nga06058 | 923.2915 | 826.40023 | ---NA--- |
| SEQ ID NO: 96 | Nga06059.1 | 1347.354 | 1430.8389 | protein |
| SEQ ID NO: 97 | Nga06061 | 1233.25 | 1223.7322 | cell adhesion domain-containing protein |
| SEQ ID NO: 98 | Nga06062 | 1048.626 | 1144.6859 | rieske (2fe-2s) domain protein |
| SEQ ID NO: 99 | Nga06057 | 1101.551 | 1477.9243 | phenylalanine hydroxylase |
| SEQ ID NO: 100 | Nga04012.02 | 785.3695 | 857.9792 | t-complex protein 1 subunit alpha |
| SEQ ID NO: 101 | Nga20296 | 342.8928 | 329.56245 | conserved unknown protein [Ectocarpus siliculosus] |
| SEQ ID NO: 102 | Nga06468 | 353.4994 | 345.65828 | apicomplexan specific region near n-terminus |
| SEQ ID NO: 103 | Nga06469 | 948.6166 | 1161.8589 | mate efflux family protein |
| SEQ ID NO: 104 | Nga06581 | 533.7079 | 416.8625 | syntaxin 6 |
| SEQ ID NO: 105 | Nga00063.2 | 543.497 | 530.88726 | lao ao transport system atpase |
| SEQ ID NO: 106 | Nga06584 | 856.3218 | 540.0606 | anion exchanger family |
| SEQ ID NO: 107 | Nga00070.02 | 910.2384 | 770.26593 | ---NA--- |
| SEQ ID NO: 108 | Nga00057.02 | 412.6568 | 515.55491 | conserved hypothetical protein [Phytophthora infestans T30-4] |
| SEQ ID NO: 109 | Nga00061.02 | 734.1954 | 684.80307 | ---NA--- |
| SEQ ID NO: 110 | Nga00052.02 | 725.0415 | 763.11406 | isoleucyl-trna synthetase |
| SEQ ID NO: 111 | Nga00054.02 | 1480.13 | 1451.604 | gamma tubulin |
| SEQ ID NO: 112 | Nga00053.02 | 6413.408 | 6296.6755 | expressed unknown protein [Ectocarpus siliculosus] |
| SEQ ID NO: 113 | Nga00062.2 | 197.3856 | 174.16703 | folate biopterin transporter |
| SEQ ID NO: 114 | Nga20370.1 | 283.0189 | 324.45922 | autophagy ubiquitin-activating enzyme |
| SEQ ID NO: 115 | Nga01899.2 | 238.9046 | 301.23928 | autophagy-related protein 7 |
| SEQ ID NO: 116 | Nga06246 | 3098.947 | 4042.4285 | hydroxymethylglutaryl- synthase |
| SEQ ID NO: 117 | Nga01898.02 | 25470.99 | 15573.132 | light-harvesting protein |
| SEQ ID NO: 118 | Nga01900.02 | 3330.409 | 3329.9414 | protein |
| SEQ ID NO: 119 | Nga06249 | 696.7509 | 875.97257 | acyl- wax alcohol acyltransferase 2 |
| SEQ ID NO: 120 | Nga04989.02 | 994.8893 | 888.85465 | protein |
| SEQ ID NO: 121 | Nga06270 | 122.3097 | 151.25471 | pathogenesis-related transcriptional factor and erf |
| SEQ ID NO: 122 | Nga06272.1 | 183.6115 | 300.39606 | ---NA--- |
| SEQ ID NO: 123 | Nga20972 | 5904.439 | 20343.027 | ammonium transporter |
| SEQ ID NO: 124 | Nga06269.01 | 1489.596 | 1356.3627 | ---NA--- |
| SEQ ID NO: 125 | Nga06267 | 469.2982 | 542.97441 | like protein n-terminal domain of phosphotransacetylase-like protein |

FIGURE 24 B

| # | Nga model | +N rpkb | -N rpkb | GO |
|---|---|---|---|---|
| SEQ ID NO: 126 | Nga06271.01 | 2306.054 | 2335.2678 | thiol-disulfide oxidoreductase dcc |
| SEQ ID NO: 127 | Nga06273.01 | 77.77778 | 96.287461 | ---NA--- |
| SEQ ID NO: 128 | Nga06266.01 | 780.5841 | 1109.7377 | gdsl lipase acylhydrolase family protein |
| SEQ ID NO: 129 | Nga06280.01 | 13.10044 | 42.572513 | ---NA--- |
| SEQ ID NO: 130 | Nga06268 | 5536.43 | 7500.7538 | ---NA--- |
| SEQ ID NO: 131 | Nga06431 | 1476.19 | 1080.3682 | translation initiation factor if-1 |
| SEQ ID NO: 132 | Nga20399 | 130.2521 | 220.74305 | stelar k+ outward rectifying channel |
| SEQ ID NO: 133 | Nga06437 | 272.7273 | 247.01016 | protein |
| SEQ ID NO: 134 | Nga20161 | 289.2263 | 449.58516 | shaker-like potassium channel |
| SEQ ID NO: 135 | Nga21210.1 | 396.8254 | 554.18196 | 6-phosphofructo-2-kinase fructose- -biphosphatase-1-like protein |
| SEQ ID NO: 136 | Nga06438 | 4389.199 | 3892.1786 | cyclophilin |
| SEQ ID NO: 137 | Nga06436 | 173.4612 | 189.63088 | rna family |
| SEQ ID NO: 138 | Nga06434 | 867.7897 | 856.52342 | phosphatase ptc7 family protein |
| SEQ ID NO: 139 | Nga06435 | 4999.031 | 6118.3824 | l-ascorbate peroxidase |
| SEQ ID NO: 140 | Nga06433 | 8604.491 | 8276.7305 | 60s ribosomal protein l44 |
| SEQ ID NO: 141 | Nga06432 | 1185.586 | 1034.83 | preprotein translocase subunit |
| SEQ ID NO: 142 | Nga20950.1 | 1581.604 | 1600.1298 | conserved unknown protein [Ectocarpus siliculosus] |
| SEQ ID NO: 143 | Nga01308.1 | 383.8764 | 369.2226 | methionyl-trna synthetase |
| SEQ ID NO: 144 | Nga01304 | 1096.552 | 1065.0911 | protein |
| SEQ ID NO: 145 | Nga01309.01 | 1077.348 | 825.89107 | protein |
| SEQ ID NO: 146 | Nga01314.01 | 517.0604 | 329.80351 | conserved unknown protein [Ectocarpus siliculosus] |
| SEQ ID NO: 147 | Nga01305.1 | 2472.452 | 2697.7859 | carrier protein |
| SEQ ID NO: 148 | Nga01306 | 103.6036 | 88.643018 | phosphoserine aminotransferase |
| SEQ ID NO: 149 | Nga01307 | 1448.664 | 1523.9187 | nadh:ubiquinone oxidoreductase complex i intermediate-associated protein 30 |
| SEQ ID NO: 150 | Nga00790 | 4971.613 | 4377.6628 | ---NA--- |
| SEQ ID NO: 151 | Nga00792.01 | 188.2394 | 194.48459 | nmda receptor regulated 1-like |
| SEQ ID NO: 152 | Nga20855.1 | 288.7597 | 417.75883 | ---NA--- |
| SEQ ID NO: 153 | Nga00796 | 1002.509 | 1043.8189 | copper ion binding protein |
| SEQ ID NO: 154 | Nga00791 | 117.0483 | 119.21086 | tryptophan tyrosine permease family protein |
| SEQ ID NO: 155 | Nga00797 | 216.33 | 253.48404 | cyclin l1 |
| SEQ ID NO: 156 | Nga00795 | 426.2102 | 470.63765 | probable alpha-ketoglutarate-dependent dioxygenase abh6-like |
| SEQ ID NO: 157 | Nga00794 | 1639.733 | 1699.1275 | fatty acid desaturase domain protein |
| SEQ ID NO: 158 | Nga00793 | 9758.47 | 9081.4072 | 50s ribosomal protein l28 |
| SEQ ID NO: 159 | Nga01153 | 233.9565 | 256.16649 | amino acid transport protein |
| SEQ ID NO: 160 | Nga01154.01 | 513.587 | 528.8615 | class 3 |
| SEQ ID NO: 161 | Nga01152.01 | 187.3016 | 257.91284 | ---NA--- |
| SEQ ID NO: 162 | Nga01150.1 | 730.5062 | 797.23647 | ll-diaminopimelate aminotransferase |
| SEQ ID NO: 163 | Nga01155.01 | 3923.423 | 4163.9854 | s-adenosylmethionine mitochondrial carrier protein |
| SEQ ID NO: 164 | Nga01156.01 | 309.6192 | 286.54685 | ---NA--- |
| SEQ ID NO: 165 | Nga01151.01 | 2026.278 | 2082.6096 | ribosome biogenesis protein nsa2 homolog |
| SEQ ID NO: 166 | Nga01149.01 | 371.1584 | 514.72818 | short chain dehydrogenase |
| SEQ ID NO: 167 | Nga01515 | 643.8095 | 701.52293 | sodium bile acid symporter family protein |
| SEQ ID NO: 168 | Nga01524 | 377.3585 | 245.26051 | ---NA--- |
| SEQ ID NO: 169 | Nga01525.01 | 170.5202 | 169.05963 | ---NA--- |
| SEQ ID NO: 170 | Nga20615.1 | 117.4935 | 141.41435 | c-myc promoter-binding protein irlb |
| SEQ ID NO: 171 | Nga01520 | 963.1206 | 1084.7704 | glutaredoxin 2 |
| SEQ ID NO: 172 | Nga20595.1 | 14.81481 | 56.167686 | ---NA--- |
| SEQ ID NO: 173 | Nga06576.2 | 178.2274 | 170.10321 | brefeldin a-inhibited guanine nucleotide-exchange |
| SEQ ID NO: 174 | Nga01532 | 144.4665 | 141.41623 | oligopeptidase b |
| SEQ ID NO: 175 | Nga01522.1 | 173.0959 | 192.32492 | brefeldin a-inhibited guanine nucleotide-exchange |
| SEQ ID NO: 176 | Nga01518 | 1066.289 | 981.65339 | ---NA--- |
| SEQ ID NO: 177 | Nga01516 | 427.4892 | 480.65575 | nitroreductase-like protein |
| SEQ ID NO: 178 | Nga01521 | 278.9474 | 225.19864 | inosine-uridine preferring nucleoside hydrolase |
| SEQ ID NO: 179 | Nga01517 | 1802.653 | 1682.336 | fructose- -bisphosphate 2-phosphatase |
| SEQ ID NO: 180 | Nga01523 | 150 | 165.8702 | ---NA--- |
| SEQ ID NO: 181 | Nga20384 | 220.5607 | 198.42416 | predicted protein [Thalassiosira pseudonana CCMP1335] |
| SEQ ID NO: 182 | Nga20236 | 221.458 | 184.76067 | conserved unknown protein [Ectocarpus siliculosus] |
| SEQ ID NO: 183 | Nga01519 | 862.4879 | 1397.4665 | ---NA--- |
| SEQ ID NO: 184 | Nga01193 | 695.1081 | 488.00983 | ---NA--- |
| SEQ ID NO: 185 | Nga01194 | 120.6897 | 46.691118 | ---NA--- |
| SEQ ID NO: 186 | Nga01192 | 565.0558 | 512.22066 | v-myb myeloblastosis viral oncogene homologue |
| SEQ ID NO: 187 | Nga01191 | 3554.609 | 3521.5591 | nadh-cytochrome b5 reductase 2-like isoform 2 |
| SEQ ID NO: 188 | Nga01130.1 | 2190.024 | 2291.2585 | luminal binding protein |

FIGURE 24 C

| # | Nga model | +N rpkb | -N rpkb | GO |
|---|---|---|---|---|
| SEQ ID NO: 189 | Nga01137 | 302.682 | 278.07155 | 3-mercaptopyruvate sulfurtransferase |
| SEQ ID NO: 190 | Nga01138 | 323.4323 | 303.87751 | 3-mercaptopyruvate sulfurtransferase |
| SEQ ID NO: 191 | Nga01131 | 1779.286 | 2313.264 | protein |
| SEQ ID NO: 192 | Nga20010 | 690.5738 | 654.8238 | dienoyl- reductase |
| SEQ ID NO: 193 | Nga20721 | 317.3653 | 350.26726 | ---NA--- |
| SEQ ID NO: 194 | Nga20697 | 222.7273 | 256.03711 | protein |
| SEQ ID NO: 195 | Nga20437 | 303.6364 | 289.51889 | serine threonine protein kinase |
| SEQ ID NO: 196 | Nga01265 | 1622.817 | 1581.345 | ---NA--- |
| SEQ ID NO: 197 | Nga01264 | 366.9372 | 438.66116 | thioredoxin reductase |
| SEQ ID NO: 198 | Nga01262 | 157.8947 | 175.94122 | sphingosine-1-phosphate lyase |
| SEQ ID NO: 199 | Nga01263 | 218.3236 | 224.8819 | phosphoadenosine phosphosulfate reductase family protein |
| SEQ ID NO: 200 | Nga01266.01 | 264.8115 | 275.18421 | dhhc zinc finger domain-containing protein |
| SEQ ID NO: 201 | Nga00751 | 104.9223 | 116.46168 | retrograde transporter |
| SEQ ID NO: 202 | Nga00747.01 | 1671.614 | 1771.8947 | sugar transporter |
| SEQ ID NO: 203 | Nga00566.02 | 651.7572 | 609.10279 | protein bud31 homolog |
| SEQ ID NO: 204 | Nga00750 | 1565.502 | 1291.3662 | 1-like protein |
| SEQ ID NO: 205 | Nga00748 | 662.9297 | 707.58331 | ferrochelatase |
| SEQ ID NO: 206 | Nga00745 | 9752.981 | 9653.1461 | ---NA--- |
| SEQ ID NO: 207 | Nga00746.1 | 106.9114 | 139.20609 | pre-rrna-processing protein tsr1 |
| SEQ ID NO: 208 | Nga20529 | 439.7163 | 455.36333 | clathrin-adaptor gamma chain |
| SEQ ID NO: 209 | Nga20705 | 312.2066 | 300.05072 | ap-1 complex subunit gamma-1 |
| SEQ ID NO: 210 | Nga00833 | 595.6938 | 507.40958 | glucose-6-phosphate 1-dehydrogenase |
| SEQ ID NO: 211 | Nga00835 | 64.58797 | 77.201528 | ---NA--- |
| SEQ ID NO: 212 | Nga00834 | 176.7422 | 162.34866 | y8236_dicdi ame: full=tpr-containing protein ddb_g0280363 |
| SEQ ID NO: 213 | Nga01489 | 204.4502 | 268.62525 | conserved unknown protein [Ectocarpus siliculosus] |
| SEQ ID NO: 214 | Nga01487 | 130.137 | 103.87175 | zinc transporter |
| SEQ ID NO: 215 | Nga01488 | 553.3553 | 546.97951 | protein |
| SEQ ID NO: 216 | Nga01486 | 569.6546 | 693.57237 | bifunctional aspartokinase i homeserine dehydrogenase i |
| SEQ ID NO: 217 | Nga20977.1 | 692.3783 | 601.79663 | protein |
| SEQ ID NO: 218 | Nga00861.2 | 321.6031 | 379.07894 | ferrochelatase [Actinomyces viscosus C505] |
| SEQ ID NO: 219 | Nga01106.01 | 1262.956 | 1069.7195 | chalcone isomerase-like protein |
| SEQ ID NO: 220 | Nga20761.1 | 418.5293 | 517.04204 | serine threonine-protein kinase smg1 |
| SEQ ID NO: 221 | Nga01107.01 | 535.2381 | 451.8633 | isoamyl acetate-hydrolyzing esterase 1 homolog ( cerevisiae) |
| SEQ ID NO: 222 | Nga01108.01 | 2068.654 | 1876.8227 | predicted protein [Thalassiosira pseudonana CCMP1335] |
| SEQ ID NO: 223 | Nga21000 | 326.6453 | 317.31973 | ania-6a type cyclin |
| SEQ ID NO: 224 | Nga01041 | 528.6329 | 500.56093 | alpha-glucosidase ii |
| SEQ ID NO: 225 | Nga01044 | 983.6852 | 1031.2553 | protein |
| SEQ ID NO: 226 | Nga01040 | 419.0317 | 484.65225 | ubiquitin-conjugating enzyme |
| SEQ ID NO: 227 | Nga01042.01 | 765.3333 | 615.27688 | rae1-like protein |
| SEQ ID NO: 228 | Nga01045.01 | 3785.006 | 3574.5526 | microcystin synthetase-associated thioesterase |
| SEQ ID NO: 229 | Nga01043 | 52.28758 | 23.599868 | ---NA--- |
| SEQ ID NO: 230 | Nga21140.1 | 134.7068 | 151.06908 | d-2-hydroxyglutarate mitochondrial precursor |
| SEQ ID NO: 231 | Nga20552.1 | 125.3264 | 178.18208 | ---NA--- |
| SEQ ID NO: 232 | Nga20751.1 | 250.6427 | 261.75833 | protein |
| SEQ ID NO: 233 | Nga01510 | 556.2588 | 622.36437 | sjogren syndrome antigen b |
| SEQ ID NO: 234 | Nga01509 | 637.621 | 555.85033 | aspartyl aminopeptidase |
| SEQ ID NO: 235 | Nga21163.1 | 233.0827 | 154.74771 | myb-like dna-binding |
| SEQ ID NO: 236 | Nga01480 | 1645.643 | 1647.7741 | protein |
| SEQ ID NO: 237 | Nga20898.1 | 116.3265 | 132.64089 | ---NA--- |
| SEQ ID NO: 238 | Nga01479.01 | 3896.409 | 4264.1115 | translationally controlled tumor protein |
| SEQ ID NO: 239 | Nga04160.01 | 2642.633 | 2382.096 | brain protein 44-like protein |
| SEQ ID NO: 240 | Nga04163 | 60.10929 | 47.354489 | ---NA--- |
| SEQ ID NO: 241 | Nga04157 | 1099.129 | 997.09442 | ---NA--- |
| SEQ ID NO: 242 | Nga04159 | 1494.46 | 1292.5291 | 26s proteasome subunit rpn6a |
| SEQ ID NO: 243 | Nga04161 | 348.0315 | 411.97007 | metal ion transporter family |
| SEQ ID NO: 244 | Nga20961 | 443.3333 | 528.07655 | magnesium and cobalt transport protein |
| SEQ ID NO: 245 | Nga04158 | 419.5046 | 360.51904 | glyoxalase bleomycin resistance protein dioxygenase |
| SEQ ID NO: 246 | Nga04162.1 | 351.8519 | 272.24133 | ---NA--- |
| SEQ ID NO: 247 | Nga20375.1 | 288.8147 | 339.97993 | protein |
| SEQ ID NO: 248 | Nga03952.01 | 4710.142 | 4386.2837 | protein |
| SEQ ID NO: 249 | Nga03956.01 | 679.941 | 627.89224 | pyridoxamine 5 -phosphate oxidase |
| SEQ ID NO: 250 | Nga03954 | 4982.488 | 5552.9077 | choline-phosphate cytidylyltransferase b |
| SEQ ID NO: 251 | Nga03955 | 16857.14 | 18321.732 | alcohol dehydrogenase |
| SEQ ID NO: 252 | Nga03953 | 809.2567 | 1112.8596 | ---NA--- |

FIGURE 24 D

| # | Nga model | +N rpkb | -N rpkb | GO |
|---|---|---|---|---|
| SEQ ID NO: 253 | Nga03501 | 777.7778 | 845.07612 | protein |
| SEQ ID NO: 254 | Nga03503 | 199.0741 | 260.77854 | ---NA--- |
| SEQ ID NO: 255 | Nga03500 | 611.1888 | 645.39533 | 5 deoxy cytosolic type c protein domain containing protein |
| SEQ ID NO: 256 | Nga03502 | 371.3592 | 283.95453 | dt1p1a10l protein |
| SEQ ID NO: 257 | Nga02234.02 | 420.6049 | 304.08363 | ---NA--- |
| SEQ ID NO: 258 | Nga03537 | 131.2336 | 85.294011 | ---NA--- |
| SEQ ID NO: 259 | Nga03536 | 1911.173 | 1979.2887 | serine threonine-protein phosphatase pp1-gamma catalytic subunit |
| SEQ ID NO: 260 | Nga03534 | 2398.051 | 2516.6155 | ring zinc finger-containing protein |
| SEQ ID NO: 261 | Nga03535 | 746.0908 | 904.17368 | dual specificity phosphatase 10 |
| SEQ ID NO: 262 | Nga21251.1 | 32.52033 | 52.84068 | ---NA--- |
| SEQ ID NO: 263 | Nga04223.01 | 669.0939 | 1243.6157 | trna (guanine-n -)-methyltransferase-like |
| SEQ ID NO: 264 | Nga04222.01 | 558.6457 | 647.05873 | protein |
| SEQ ID NO: 265 | Nga20765 | 608.209 | 633.5706 | traf and tnf receptor associated protein |
| SEQ ID NO: 266 | Nga04221 | 907.8014 | 882.20826 | protein |
| SEQ ID NO: 267 | Nga03914 | 1839.734 | 1903.2596 | oxidoreductase domain protein |
| SEQ ID NO: 268 | Nga03913 | 757.7808 | 749.02915 | replication factor c subunit 2 |
| SEQ ID NO: 269 | Nga03629 | 1434.009 | 2048.7684 | protein phosphatase pp2a regulatory subunit b |
| SEQ ID NO: 270 | Nga03630 | 125.9542 | 89.924955 | protein |
| SEQ ID NO: 271 | Nga21180.1 | 252.2523 | 243.97161 | gtp-binding protein parf-like |
| SEQ ID NO: 272 | Nga20137.1 | 310.0522 | 349.29345 | ras superfamily gtpase |
| SEQ ID NO: 273 | Nga03043.02 | 2702.461 | 2792.9018 | mgc84239 protein |
| SEQ ID NO: 274 | Nga03020.02 | 2188.825 | 1948.3601 | golgi snap receptor complex member 1 |
| SEQ ID NO: 275 | Nga20668.1 | 585.3659 | 290.62374 | protein kinase domain containing protein |
| SEQ ID NO: 276 | Nga21011.1 | 964.775 | 1131.9901 | copia ltr rider |
| SEQ ID NO: 277 | Nga21010.1 | 1209.77 | 1048.9938 | gag-pol polyprotein |
| SEQ ID NO: 278 | Nga20110 | 353.9463 | 274.11371 | nad-dependent epimerase dehydratase |
| SEQ ID NO: 279 | Nga04230 | 1039.88 | 786.2356 | protein |
| SEQ ID NO: 280 | Nga03893 | 1742.857 | 1535.4411 | fkbp-type peptidyl-prolyl cis-trans isomerase |
| SEQ ID NO: 281 | Nga03895 | 876.7507 | 901.17782 | protein |
| SEQ ID NO: 282 | Nga03896 | 1639.269 | 1283.558 | protein |
| SEQ ID NO: 283 | Nga03894 | 3576.208 | 2613.4529 | ---NA--- |
| SEQ ID NO: 284 | Nga03892 | 1051.075 | 1026.4515 | ist1-like protein |
| SEQ ID NO: 285 | Nga01896.02 | 626.2712 | 569.15682 | arrestin domain protein |
| SEQ ID NO: 286 | Nga20588 | 572.327 | 551.83616 | conserved unknown protein [Ectocarpus siliculosus] |
| SEQ ID NO: 287 | Nga03971 | 402.2843 | 427.51999 | loc100145185 related |
| SEQ ID NO: 288 | Nga03970 | 5975.518 | 6111.8058 | expressed unknown protein [Ectocarpus siliculosus] |
| SEQ ID NO: 289 | Nga03725 | 657.1072 | 885.1363 | ef hand domain protein |
| SEQ ID NO: 290 | Nga21162.1 | 119.4539 | 129.39655 | lysine ornithine decarboxylase |
| SEQ ID NO: 291 | Nga03729 | 201.909 | 203.60344 | folic acid synthesis protein |
| SEQ ID NO: 292 | Nga03724 | 3311.798 | 3436.8335 | actin depolymerizing factor 8 |
| SEQ ID NO: 293 | Nga04192 | 382.7751 | 266.40299 | ---NA--- |
| SEQ ID NO: 294 | Nga04190 | 1060.047 | 1166.9848 | mitochondrial phosphate carrier protein |
| SEQ ID NO: 295 | Nga02088.02 | 2302.264 | 2571.7791 | protein |
| SEQ ID NO: 296 | Nga20976.1 | 455.051 | 416.62844 | conserved hypothetical protein [Phytophthora infestans T30-4] |
| SEQ ID NO: 297 | Nga03785 | 886.3496 | 1010.3047 | ring finger protein 13 |
| SEQ ID NO: 298 | Nga20229 | 155.5324 | 131.16403 | trna (uracil-5-)-methyltransferase |
| SEQ ID NO: 299 | Nga20749 | 272.1713 | 228.5723 | trna (uracil-5-)-methyltransferase |
| SEQ ID NO: 300 | Nga03783 | 576.6962 | 430.5775 | tpr repeat-containing protein |
| SEQ ID NO: 301 | Nga21044 | 847.1338 | 812.42546 | polymerase (dna directed) epsilon 3 (p17 subunit) |
| SEQ ID NO: 302 | Nga20783 | 772.9779 | 852.25023 | short-chain dehydrogenase reductase sdr |
| SEQ ID NO: 303 | Nga05796.2 | 149.2637 | 234.19315 | n -dimethylguanosine trna methyltransferase |
| SEQ ID NO: 304 | Nga03852.01 | 338.7755 | 446.55767 | ---NA--- |
| SEQ ID NO: 305 | Nga03853 | 89.20188 | 76.28408 | ---NA--- |
| SEQ ID NO: 306 | Nga03851 | 261.9522 | 277.28199 | ---NA--- |
| SEQ ID NO: 307 | Nga03850 | 226.4631 | 222.34318 | deoxyhypusine synthase |
| SEQ ID NO: 308 | Nga03750.1 | 133.9995 | 198.71778 | dna binding |
| SEQ ID NO: 309 | Nga21172 | 295.203 | 299.78799 | protein |
| SEQ ID NO: 310 | Nga20575 | 325.9005 | 343.73633 | sulfotransferase member 1-like |
| SEQ ID NO: 311 | Nga20608 | 355.2124 | 334.58963 | kin17 protein |
| SEQ ID NO: 312 | Nga20272 | 275.5299 | 296.37615 | ---NA--- |
| SEQ ID NO: 313 | Nga20934 | 1618.502 | 1985.1007 | ---NA--- |
| SEQ ID NO: 314 | Nga20367 | 215.8648 | 195.79911 | transcription factor e2 dimerization partner protein |
| SEQ ID NO: 315 | Nga03491.02 | 1636.641 | 1347.8407 | ---NA--- |
| SEQ ID NO: 316 | Nga04018.1 | 2458.194 | 2300.5136 | type iii effector protein |

FIGURE 24 E

| # | Nga model | +N rpkb | -N rpkb | GO |
|---|---|---|---|---|
| SEQ ID NO: 317 | Nga01851 | 1371.485 | 1378.1402 | protein kinase |
| SEQ ID NO: 318 | Nga01850 | 1510.73 | 1237.5832 | ---NA--- |
| SEQ ID NO: 319 | Nga01849.1 | 165.4275 | 245.64041 | ---NA--- |
| SEQ ID NO: 320 | Nga01773 | 41.99354 | 73.981829 | pentatricopeptide repeat-containing protein |
| SEQ ID NO: 321 | Nga01771.01 | 653.7196 | 566.93284 | protein |
| SEQ ID NO: 322 | Nga04098.2 | 440.7895 | 793.71829 | phosphoribosylformylglycinamidine cyclo-ligase |
| SEQ ID NO: 323 | Nga01754 | 369.0037 | 279.80212 | protein |
| SEQ ID NO: 324 | Nga01757.01 | 527.2109 | 633.7287 | 2-oxoisovalerate dehydrogenase alpha mitochondrial expressed |
| SEQ ID NO: 325 | Nga01755.01 | 547.7583 | 711.59812 | ---NA--- |
| SEQ ID NO: 326 | Nga01756 | 631.8632 | 583.05481 | protein |
| SEQ ID NO: 327 | Nga01855 | 656.8978 | 579.17011 | loc495188 protein |
| SEQ ID NO: 328 | Nga01999 | 96.2406 | 117.28247 | fan partial |
| SEQ ID NO: 329 | Nga01597.02 | 519.4468 | 640.39068 | nucleoside diphosphate-linked moiety x motif 6 |
| SEQ ID NO: 330 | Nga07239.2 | 581.0306 | 773.39182 | splicing factor 3b |
| SEQ ID NO: 331 | Nga02160 | 401.99 | 575.56908 | protein |
| SEQ ID NO: 332 | Nga02159 | 2863.456 | 3006.0456 | natural killer enhancing factor |
| SEQ ID NO: 333 | Nga02176 | 406.0797 | 460.77184 | intron-binding protein aquarius |
| SEQ ID NO: 334 | Nga02174 | 2205.747 | 2269.8109 | expressed unknown protein [Ectocarpus siliculosus] |
| SEQ ID NO: 335 | Nga20457 | 254.818 | 211.07985 | ---NA--- |
| SEQ ID NO: 336 | Nga21075 | 102.0408 | 99.480668 | protein |
| SEQ ID NO: 337 | Nga20717 | 125.9843 | 85.294011 | ---NA--- |
| SEQ ID NO: 338 | Nga02193.01 | 1625.663 | 1479.539 | upf0414 transmembrane protein c20orf30-like protein |
| SEQ ID NO: 339 | Nga02194 | 148.4552 | 132.24107 | nucleic acid binding |
| SEQ ID NO: 340 | Nga02195.01 | 3082.659 | 3114.4192 | pyruvate kinase |
| SEQ ID NO: 341 | Nga01669 | 409.3908 | 538.88472 | kh domain protein |
| SEQ ID NO: 342 | Nga01736 | 673.1107 | 834.47723 | ubiquitin family |
| SEQ ID NO: 343 | Nga20243 | 351.4894 | 396.41753 | ---NA--- |
| SEQ ID NO: 344 | Nga20374 | 313.6247 | 364.79086 | grip and coiled-coil domain-containing protein 1 |
| SEQ ID NO: 345 | Nga02051.01 | 393.8547 | 450.84318 | ---NA--- |
| SEQ ID NO: 346 | Nga21186 | 431.2977 | 351.43086 | nucleotidyl transferase domain-containing protein |
| SEQ ID NO: 347 | Nga02050 | 206.0988 | 232.36564 | protein |
| SEQ ID NO: 348 | Nga03605.2 | 115.0342 | 112.2714 | mitochondrial carrier protein |
| SEQ ID NO: 349 | Nga01673 | 83.83234 | 110.26932 | ---NA--- |
| SEQ ID NO: 350 | Nga01672 | 523.5911 | 638.86668 | cell division cycle protein 123 homolog |
| SEQ ID NO: 351 | Nga02287 | 1085.133 | 937.33458 | ---NA--- |
| SEQ ID NO: 352 | Nga02288 | 364.726 | 443.30978 | zinc finger protein |
| SEQ ID NO: 353 | Nga20830.1 | 373.5294 | 270.80849 | retrovirus-related pol polyprotein from transposon tnt 1-94 |
| SEQ ID NO: 354 | Nga06718.2 | 2232.103 | 2335.0459 | elongation factor 3 |
| SEQ ID NO: 355 | Nga01709.1 | 390.2676 | 366.34919 | protein |
| SEQ ID NO: 356 | Nga01712 | 116.6415 | 114.36859 | ---NA--- |
| SEQ ID NO: 357 | Nga02133 | 596.577 | 458.18942 | predicted protein [Thalassiosira pseudonana CCMP1335] |
| SEQ ID NO: 358 | Nga02131 | 380.7711 | 504.23741 | asparagine synthetase |
| SEQ ID NO: 359 | Nga02132.1 | 327.3273 | 357.82503 | dynamin like protein |
| SEQ ID NO: 360 | Nga00253.2 | 3745.673 | 1601.4958 | ---NA--- |
| SEQ ID NO: 361 | Nga02325.01 | 763.4409 | 183.45091 | rna binding protein |
| SEQ ID NO: 362 | Nga02324 | 353.8296 | 369.25774 | ---NA--- |
| SEQ ID NO: 363 | Nga01800.02 | 3475.895 | 4617.9188 | gcn5-related n-acetyltransferase |
| SEQ ID NO: 364 | Nga01825.1 | 561.6883 | 637.74812 | conserved hypothetical protein [Phytophthora infestans T30-4] |
| SEQ ID NO: 365 | Nga01829 | 93.02326 | 94.468076 | ---NA--- |
| SEQ ID NO: 366 | Nga02333.2 | 316.0652 | 324.08745 | dna polymerase delta subunit 1 |
| SEQ ID NO: 367 | Nga01704 | 482.4825 | 413.12526 | short-chain dehydrogenase reductase sdr |
| SEQ ID NO: 368 | Nga01707 | 1393.6 | 1562.0233 | ---NA--- |
| SEQ ID NO: 369 | Nga01705 | 835.6998 | 689.92993 | protein |
| SEQ ID NO: 370 | Nga02125 | 1000.459 | 832.95067 | hypothetical protein PPL_04681 [Polysphondylium pallidum PN500] |
| SEQ ID NO: 371 | Nga02123 | 773.2191 | 542.59374 | nadh:ubiquinone oxidoreductase complex i intermediate-associated protein 30 |
| SEQ ID NO: 372 | Nga02124 | 336.7232 | 305.99829 | protein |
| SEQ ID NO: 373 | Nga02042 | 663.75 | 686.49951 | protein |
| SEQ ID NO: 374 | Nga02038 | 432.5203 | 361.07798 | ---NA--- |
| SEQ ID NO: 375 | Nga03606.2 | 1402.083 | 1990.4424 | agc ndr protein kinase |
| SEQ ID NO: 376 | Nga02411 | 8.333333 | 6.0179663 | ---NA--- |
| SEQ ID NO: 377 | Nga05034 | 410.5431 | 474.13115 | ---NA--- |
| SEQ ID NO: 378 | Nga04270.01 | 132.8125 | 93.090417 | ---NA--- |
| SEQ ID NO: 379 | Nga04915 | 852.9584 | 771.65347 | ---NA--- |

FIGURE 24 F

| # | Nga model | +N rpkb | -N rpkb | GO |
|---|---|---|---|---|
| SEQ ID NO: 380 | Nga20305 | 527.0555 | 450.64968 | glycosyl group 2 family protein |
| SEQ ID NO: 381 | Nga04536.02 | 8371.486 | 3099.6152 | light-harvesting protein |
| SEQ ID NO: 382 | Nga04607.01 | 198.1567 | 219.64191 | ---NA--- |
| SEQ ID NO: 383 | Nga04606.1 | 91.6129 | 101.33479 | intraflagellar transport protein 52 |
| SEQ ID NO: 384 | Nga04635 | 601.1905 | 725.84043 | protein |
| SEQ ID NO: 385 | Nga04634 | 6594.635 | 5790.7007 | protein |
| SEQ ID NO: 386 | Nga04633 | 3442.519 | 3280.3653 | aspartic protease |
| SEQ ID NO: 387 | Nga21002.1 | 133.5227 | 184.64215 | phytochelatin synthase |
| SEQ ID NO: 388 | Nga04697 | 66.66667 | 48.143731 | ---NA--- |
| SEQ ID NO: 389 | Nga04696.1 | 255.4865 | 258.36139 | pheromone-regulated membrane protein |
| SEQ ID NO: 390 | Nga04523 | 1712.789 | 1689.3433 | glyoxalase domain-containing protein 4-like |
| SEQ ID NO: 391 | Nga04524 | 55.55556 | 111.76223 | ---NA--- |
| SEQ ID NO: 392 | Nga04525 | 290.4452 | 321.08889 | conserved unknown protein [Ectocarpus siliculosus] |
| SEQ ID NO: 393 | Nga20151 | 480.8511 | 450.1951 | protein phosphatase 2c-related protein |
| SEQ ID NO: 394 | Nga20221.1 | 202.5478 | 164.20999 | protein |
| SEQ ID NO: 395 | Nga20745.1 | 496.5035 | 545.4045 | ---NA--- |
| SEQ ID NO: 396 | Nga21300.1 | 473.4694 | 530.56356 | udp-n-acetylglucosamine pyrophosphorylase |
| SEQ ID NO: 397 | Nga04998 | 241.2141 | 301.09058 | udp-n-acetylglucosamine pyrophosphorylase |
| SEQ ID NO: 398 | Nga04997 | 1405.213 | 1450.3014 | protein |
| SEQ ID NO: 399 | Nga03706.02 | 591.2863 | 553.97752 | protein |
| SEQ ID NO: 400 | Nga04405 | 587.8565 | 658.70988 | conserved unknown protein [Ectocarpus siliculosus] |
| SEQ ID NO: 401 | Nga04407 | 214.0221 | 239.83039 | ---NA--- |
| SEQ ID NO: 402 | Nga20779 | 450.1816 | 502.26753 | perq amino acid-rich with gyf domain-containing protein 1 |
| SEQ ID NO: 403 | Nga20093.1 | 189.7856 | 187.1413 | exportin 4 |
| SEQ ID NO: 404 | Nga21159 | 34.59119 | 74.940713 | ribosome biogenesis atpase rix7 |
| SEQ ID NO: 405 | Nga20583.1 | 42.32804 | 85.970948 | protein |
| SEQ ID NO: 406 | Nga20400.1 | 81.76101 | 74.940713 | ---NA--- |
| SEQ ID NO: 407 | Nga20359.1 | 1231.905 | 1166.4365 | ---NA--- |
| SEQ ID NO: 408 | Nga04678 | 26.08696 | 113.03311 | ---NA--- |
| SEQ ID NO: 409 | Nga04590 | 7654.321 | 8003.2874 | ---NA--- |
| SEQ ID NO: 410 | Nga04591 | 2558.065 | 2291.098 | ef-1 guanine nucleotide exchange domain-containing |
| SEQ ID NO: 411 | Nga04761 | 347.2222 | 280.83843 | ---NA--- |
| SEQ ID NO: 412 | Nga04446 | 162.1622 | 93.685098 | ---NA--- |
| SEQ ID NO: 413 | Nga04441 | 1111.922 | 1059.5135 | ---NA--- |
| SEQ ID NO: 414 | Nga04440 | 1710.95 | 1671.948 | ---NA--- |
| SEQ ID NO: 415 | Nga04443 | 315.7895 | 459.89932 | ---NA--- |
| SEQ ID NO: 416 | Nga04902 | 450.8475 | 376.37789 | ---NA--- |
| SEQ ID NO: 417 | Nga04903 | 320.8396 | 302.07123 | tetracycline resistance protein |
| SEQ ID NO: 418 | Nga04904.1 | 134.0206 | 174.95531 | cysteine protease family |
| SEQ ID NO: 419 | Nga01250.02 | 11149.22 | 11737.134 | ---NA--- |
| SEQ ID NO: 420 | Nga04581 | 63.88889 | 93.278478 | selenoprotein t |
| SEQ ID NO: 421 | Nga04705 | 135.2381 | 165.06422 | ---NA--- |
| SEQ ID NO: 422 | Nga01343.02 | 695.6522 | 897.88395 | ---NA--- |
| SEQ ID NO: 423 | Nga04491 | 198.032 | 178.5404 | ---NA--- |
| SEQ ID NO: 424 | Nga20981 | 114.3617 | 51.856944 | myb-like dna-binding domain containing protein |
| SEQ ID NO: 425 | Nga04831 | 4350.14 | 3858.3761 | conserved unknown protein [Ectocarpus siliculosus] |
| SEQ ID NO: 426 | Nga20929 | 7248.269 | 6437.4189 | pap2_haloperoxidase domain-containing protein |
| SEQ ID NO: 427 | Nga04622.1 | 578.1742 | 558.09849 | ---NA--- |
| SEQ ID NO: 428 | Nga20871.1 | 1056.358 | 926.69724 | pterin-4-alpha-carbinolamine dehydratase |
| SEQ ID NO: 429 | Nga04554 | 2118.163 | 3447.5681 | ---NA--- |
| SEQ ID NO: 430 | Nga20772.1 | 554.8246 | 701.9641 | protein |
| SEQ ID NO: 431 | Nga20330 | 822.9842 | 936.66104 | uncharacterized udp-glucosyltransferase |
| SEQ ID NO: 432 | Nga04735.1 | 258.0466 | 349.25578 | aldehyde dehydrogenase family |
| SEQ ID NO: 433 | Nga04361 | 8.364312 | 6.5436995 | protein |
| SEQ ID NO: 434 | Nga02230.02 | 1230.58 | 956.34464 | ---NA--- |
| SEQ ID NO: 435 | Nga04973.1 | 902.7778 | 1079.762 | px domain containing protein |
| SEQ ID NO: 436 | Nga03201.02 | 325.5172 | 340.6584 | trigger factor |
| SEQ ID NO: 437 | Nga04972.1 | 198.7578 | 224.27204 | conserved unknown protein [Ectocarpus siliculosus] |
| SEQ ID NO: 438 | Nga03844.02 | 2072.273 | 1940.1417 | 10 kda heat shock mitochondrial |
| SEQ ID NO: 439 | Nga04391.1 | 223.2754 | 293.1976 | dead box rna helicase |
| SEQ ID NO: 440 | Nga04760.1 | 284.9462 | 241.68929 | uncharacterized protein |
| SEQ ID NO: 441 | Nga07054.1 | 473.025 | 488.39449 | ---NA--- |
| SEQ ID NO: 442 | Nga03620.02 | 513.8554 | 614.05008 | endonuclease exonuclease phosphatase |
| SEQ ID NO: 443 | Nga20555.1 | 1400.729 | 1298.3022 | retrotransposon ty1-copia subclass |

FIGURE 24 G

| # | Nga model | +N rpkb | -N rpkb | GO |
|---|---|---|---|---|
| SEQ ID NO: 444 | Nga05790.2 | 953.0201 | 993.34998 | major facilitator superfamily mfs_1 |
| SEQ ID NO: 445 | Nga06926 | 147.8873 | 228.85224 | ---NA--- |
| SEQ ID NO: 446 | Nga07217 | 196.5602 | 150.37523 | egf-like protein |
| SEQ ID NO: 447 | Nga07216 | 281.8229 | 296.20121 | ---NA--- |
| SEQ ID NO: 448 | Nga07183 | 935.7683 | 854.03583 | conserved unknown protein [Ectocarpus siliculosus] |
| SEQ ID NO: 449 | Nga07184 | 3520 | 3149.711 | ---NA--- |
| SEQ ID NO: 450 | Nga06894 | 184.9148 | 187.128 | ---NA--- |
| SEQ ID NO: 451 | Nga20032.1 | 659.7222 | 541.61697 | glutathione s-transferase |
| SEQ ID NO: 452 | Nga00239.02 | 309.4001 | 285.51939 | integral membrane protein gpr155-like |
| SEQ ID NO: 453 | Nga07164 | 7902.349 | 7868.9549 | ---NA--- |
| SEQ ID NO: 454 | Nga21013.1 | 801.3857 | 1023.1933 | hypothetical protein VITISV_004538 [Vitis vinifera] |
| SEQ ID NO: 455 | Nga07115 | 60.9319 | 58.238384 | ---NA--- |
| SEQ ID NO: 456 | Nga06941 | 608.1871 | 574.34626 | ---NA--- |
| SEQ ID NO: 457 | Nga21017.1 | 312.1827 | 316.17234 | nad-dependent epimerase dehydratase |
| SEQ ID NO: 458 | Nga07291 | 108.2251 | 79.718515 | ---NA--- |
| SEQ ID NO: 459 | Nga07292 | 410.6383 | 493.21716 | ribosome biogenesis protein rlp24 |
| SEQ ID NO: 460 | Nga07181.1 | 133.9901 | 140.87377 | glycosyl hydrolase |
| SEQ ID NO: 461 | Nga20581 | 502.2288 | 350.8841 | duf563 domain protein |
| SEQ ID NO: 462 | Nga07139 | 483.3333 | 531.30046 | ---NA--- |
| SEQ ID NO: 463 | Nga07214 | 607.8125 | 626.24462 | ---NA--- |
| SEQ ID NO: 464 | Nga07213 | 3279.232 | 2599.3834 | ---NA--- |
| SEQ ID NO: 465 | Nga07028 | 292.654 | 252.84015 | conserved unknown protein [Ectocarpus siliculosus] |
| SEQ ID NO: 466 | Nga07065 | 3104.61 | 2738.8149 | purple acid phosphatase |
| SEQ ID NO: 467 | Nga07066 | 1356.725 | 1265.8845 | ---NA--- |
| SEQ ID NO: 468 | Nga07156.1 | 329.2568 | 355.64313 | protein |
| SEQ ID NO: 469 | Nga07178 | 919.2913 | 710.07264 | prefoldin subunit 5 |
| SEQ ID NO: 470 | Nga07155 | 233.8028 | 288.86238 | protein |
| SEQ ID NO: 471 | Nga03591.02 | 688.0223 | 748.30646 | possible sulfotransferase |
| SEQ ID NO: 472 | Nga05479.02 | 231.5789 | 228.04925 | ---NA--- |
| SEQ ID NO: 473 | Nga20629 | 49.0566 | 53.139778 | ---NA--- |
| SEQ ID NO: 474 | Nga07277 | 401.9461 | 771.07446 | protein |
| SEQ ID NO: 475 | Nga06901 | 234.5191 | 279.7284 | protein |
| SEQ ID NO: 476 | Nga06953 | 558.8526 | 413.57893 | ---NA--- |
| SEQ ID NO: 477 | Nga07091 | 529.2259 | 612.63468 | ---NA--- |
| SEQ ID NO: 478 | Nga07172 | 204.955 | 224.45388 | ---NA--- |
| SEQ ID NO: 479 | Nga06912 | 141.4655 | 198.20291 | wd repeat |
| SEQ ID NO: 480 | Nga06944 | 228.8288 | 208.8397 | uncharacterized protein |
| SEQ ID NO: 481 | Nga06920 | 62.99213 | 85.294011 | ---NA--- |
| SEQ ID NO: 482 | Nga06793 | 1735.88 | 1399.9269 | proteasome ( macropain) beta 6 |
| SEQ ID NO: 483 | Nga07042 | 265.0794 | 238.99923 | ---NA--- |
| SEQ ID NO: 484 | Nga07050 | 447.9638 | 511.39099 | ---NA--- |
| SEQ ID NO: 485 | Nga07290 | 523.1388 | 699.63399 | ---NA--- |
| SEQ ID NO: 486 | Nga20667.1 | 79.81221 | 81.369686 | ---NA--- |
| SEQ ID NO: 487 | Nga20924 | 78.43137 | 74.339584 | ---NA--- |
| SEQ ID NO: 488 | Nga07279 | 202.1505 | 172.38562 | ---NA--- |
| SEQ ID NO: 489 | Nga06811 | 73.23944 | 125.10589 | ---NA--- |
| SEQ ID NO: 490 | Nga06900 | 645.9948 | 579.4042 | ---NA--- |
| SEQ ID NO: 491 | Nga07302 | 829.2135 | 925.61732 | atp-binding cassette superfamily |
| SEQ ID NO: 492 | Nga07000 | 64.86486 | 189.32197 | formin like protein |
| SEQ ID NO: 493 | Nga06977 | 17.85714 | 12.895642 | myb domain-containing protein |
| SEQ ID NO: 494 | Nga06897 | 181.9923 | 184.68931 | adenylate kinase |
| SEQ ID NO: 495 | Nga06832 | 453.5256 | 430.51605 | aldehyde reductase i |
| SEQ ID NO: 496 | Nga00443.1 | 195.2645 | 257.81767 | serine threonine protein |
| SEQ ID NO: 497 | Nga00437 | 1226.667 | 1155.4495 | high mobility group protein b3 |
| SEQ ID NO: 498 | Nga00434 | 1569.892 | 1562.5806 | hypothetical protein Osl_22634 [Oryza sativa Indica Group] |
| SEQ ID NO: 499 | Nga00442.1 | 326.9136 | 360.00812 | sh2 domain containing protein |
| SEQ ID NO: 500 | Nga00432 | 23043.6 | 20055.906 | cytochrome b6-f complex iron-sulfur subunit |
| SEQ ID NO: 501 | Nga00438 | 1556.914 | 1784.3299 | lipoic acid synthetase |
| SEQ ID NO: 502 | Nga00471 | 11.36364 | 49.237906 | ribosomal large subunit pseudouridine synthase d |
| SEQ ID NO: 503 | Nga00445 | 318.9087 | 348.50989 | ---NA--- |
| SEQ ID NO: 504 | Nga20019 | 573.2722 | 501.07724 | protein |
| SEQ ID NO: 505 | Nga00436 | 1288.955 | 1058.6635 | ddb1- and cul4-associated factor 7 |
| SEQ ID NO: 506 | Nga00441 | 382.716 | 596.78166 | 3 -5 exonuclease domain-containing protein |
| SEQ ID NO: 507 | Nga20469 | 534.1098 | 409.1416 | conserved unknown protein [Ectocarpus siliculosus] |

FIGURE 24 H

| # | Nga model | +N rpkb | -N rpkb | GO |
|---|---|---|---|---|
| SEQ ID NO: 508 | Nga00430 | 1072.738 | 1048.0016 | methionine aminopeptidase 2b |
| SEQ ID NO: 509 | Nga00470 | 445.9907 | 484.54799 | cys met metabolism pyridoxal-phosphate-dependent enzyme |
| SEQ ID NO: 510 | Nga00431 | 469.8391 | 425.27097 | atp-binding cassette superfamily |
| SEQ ID NO: 511 | Nga00435 | 838.1692 | 750.33982 | n-myristoyltransferase 2 |
| SEQ ID NO: 512 | Nga00440 | 196.0784 | 217.30032 | dual specificity phosphatase 15 |
| SEQ ID NO: 513 | Nga00439 | 292.9624 | 284.54836 | arp1 actin-related protein 1 homolog centractin beta |
| SEQ ID NO: 514 | Nga00433 | 2908.56 | 2649.076 | u6 snrna-associated sm-like protein lsm6 |
| SEQ ID NO: 515 | Nga00429.01 | 7422.336 | 5958.4819 | thioredoxin f |
| SEQ ID NO: 516 | Nga00444 | 879.4051 | 886.40967 | ---NA--- |
| SEQ ID NO: 517 | Nga20025 | 194.6903 | 249.23967 | ---NA--- |
| SEQ ID NO: 518 | Nga21267 | 149.5327 | 101.23682 | ---NA--- |
| SEQ ID NO: 519 | Nga21266 | 73.3945 | 139.13096 | trna modification gtpase |
| SEQ ID NO: 520 | Nga00269 | 717.8423 | 750.62269 | protein |
| SEQ ID NO: 521 | Nga00275 | 3345.168 | 3719.7442 | conserved unknown protein [Ectocarpus siliculosus] |
| SEQ ID NO: 522 | Nga00277 | 222.0249 | 219.98179 | c transferase |
| SEQ ID NO: 523 | Nga00276 | 7134.314 | 7549.7158 | beta-lactamase |
| SEQ ID NO: 524 | Nga21179 | 171.1712 | 300.08508 | pentatricopeptide repeat-containing |
| SEQ ID NO: 525 | Nga20706 | 295.0495 | 375.3781 | salt-inducible protein |
| SEQ ID NO: 526 | Nga00274 | 127.5862 | 159.37235 | fidgetin-like 1 |
| SEQ ID NO: 527 | Nga00265 | 1312.013 | 1549.5427 | t-complex protein 1 subunit delta |
| SEQ ID NO: 528 | Nga00280 | 275.8621 | 655.1123 | ---NA--- |
| SEQ ID NO: 529 | Nga00270 | 481.5972 | 740.58598 | protein |
| SEQ ID NO: 530 | Nga00273 | 278.5388 | 247.31369 | ---NA--- |
| SEQ ID NO: 531 | Nga00278 | 504.1597 | 493.55335 | novel protein vertebrate deah (asp-glu-ala-asp his) box polypeptide 57 |
| SEQ ID NO: 532 | Nga00282 | 166.7969 | 134.9811 | conserved hypothetical protein [Capsaspora owczarzaki ATCC 30864] |
| SEQ ID NO: 533 | Nga00260 | 18877.38 | 11804.309 | luminal binding protein |
| SEQ ID NO: 534 | Nga00259 | 493.7676 | 533.55914 | nuclear pore complex protein |
| SEQ ID NO: 535 | Nga00268 | 723.055 | 516.48842 | protein |
| SEQ ID NO: 536 | Nga21168 | 77.44108 | 43.767028 | ---NA--- |
| SEQ ID NO: 537 | Nga00283 | 256.351 | 281.85764 | ---NA--- |
| SEQ ID NO: 538 | Nga00262 | 1462.753 | 1667.9341 | 30s ribosomal protein s1 |
| SEQ ID NO: 539 | Nga20639 | 57.85124 | 71.618773 | ---NA--- |
| SEQ ID NO: 540 | Nga00271 | 795.6587 | 652.6971 | protein |
| SEQ ID NO: 541 | Nga00272 | 484.5447 | 460.62329 | hypothetical protein LNTAR_19477 [Lentisphaera araneosa HTCC2155] |
| SEQ ID NO: 542 | Nga00263 | 2198.137 | 2177.4745 | phosphoglycerate mutase |
| SEQ ID NO: 543 | Nga00264.01 | 515.7685 | 588.96792 | ccr4-not transcription complex subunit 10 |
| SEQ ID NO: 544 | Nga00266 | 1552.022 | 1528.06 | 5-methyltetrahydropteroyltriglutamate--homocysteine s-methyltransferase |
| SEQ ID NO: 545 | Nga00284 | 194.3128 | 112.94382 | ---NA--- |
| SEQ ID NO: 546 | Nga20165 | 330.1304 | 249.80549 | protein |
| SEQ ID NO: 547 | Nga00281 | 11729.49 | 12331.093 | protein |
| SEQ ID NO: 548 | Nga00279 | 462.1212 | 589.68255 | protein |
| SEQ ID NO: 549 | Nga00267.01 | 818.779 | 835.86483 | px domain containing protein |
| SEQ ID NO: 550 | Nga20441 | 245.1253 | 211.21553 | mannosyloligosaccharid alpha-mannosidase |
| SEQ ID NO: 551 | Nga00261 | 362.6506 | 316.48702 | translation initiation factor eif-2b subunit delta isoform 1 |
| SEQ ID NO: 552 | Nga00485 | 654.0084 | 626.17321 | ---NA--- |
| SEQ ID NO: 553 | Nga00486 | 632 | 623.94275 | ---NA--- |
| SEQ ID NO: 554 | Nga00507 | 972.2719 | 968.90335 | peptidyl-prolyl cis-trans isomerase 10 |
| SEQ ID NO: 555 | Nga00480 | 7953.103 | 8292.3426 | ribosomal protein s18 |
| SEQ ID NO: 556 | Nga00473 | 314.6517 | 235.90043 | dihydrodipicolinate synthase |
| SEQ ID NO: 557 | Nga00510 | 165.4224 | 223.4569 | small rna degrading nuclease 5 |
| SEQ ID NO: 558 | Nga00475 | 710.1193 | 787.41486 | transmembrane protein |
| SEQ ID NO: 559 | Nga20859 | 2137.755 | 2024.1553 | conserved unknown protein [Ectocarpus siliculosus] |
| SEQ ID NO: 560 | Nga00515 | 209.0164 | 213.0952 | ---NA--- |
| SEQ ID NO: 561 | Nga00481 | 719.7279 | 791.42398 | fat-free protein |
| SEQ ID NO: 562 | Nga00476.01 | 472.374 | 546.54973 | 4-hydroxyphenylpyruvate dioxygenase |
| SEQ ID NO: 563 | Nga00511 | 240.7407 | 259.44122 | ---NA--- |
| SEQ ID NO: 564 | Nga00498 | 639.7849 | 681.38909 | ---NA--- |
| SEQ ID NO: 565 | Nga00482.01 | 3534.884 | 2768.9643 | beta-hydroxyacyl-acp dehydratase precursor |
| SEQ ID NO: 566 | Nga20160 | 142.7796 | 182.89129 | rrna biogenesis protein rrp5 |
| SEQ ID NO: 567 | Nga00499.01 | 3887.179 | 3369.1353 | ---NA--- |
| SEQ ID NO: 568 | Nga00487 | 4163.636 | 3749.2428 | phosphatidylinositol n-acetylglucosaminyltransferase subunit h-like |
| SEQ ID NO: 569 | Nga00513 | 998.1651 | 991.80502 | ---NA--- |
| SEQ ID NO: 570 | Nga00503 | 1485.666 | 1622.7198 | p-type atpase |

FIGURE 24 I

| # | Nga model | +N rpkb | -N rpkb | GO |
|---|---|---|---|---|
| SEQ ID NO: 571 | Nga00501 | 8380.399 | 7881.3366 | protein |
| SEQ ID NO: 572 | Nga00472 | 5885.945 | 3934.2108 | permease |
| SEQ ID NO: 573 | Nga00534 | 389.7436 | 388.85321 | ---NA--- |
| SEQ ID NO: 574 | Nga20028 | 78.94737 | 57.012313 | atp-dependent dead h dna helicase recq |
| SEQ ID NO: 575 | Nga00477.01 | 134.8601 | 100.80258 | conserved hypothetical protein [Phytophthora infestans T30-4] |
| SEQ ID NO: 576 | Nga00478 | 459.695 | 441.31753 | rrna biogenesis protein rrp5 |
| SEQ ID NO: 577 | Nga20628 | 207.2829 | 221.50162 | atp-dependent dna family expressed |
| SEQ ID NO: 578 | Nga00512.01 | 74.11424 | 81.849564 | ---NA--- |
| SEQ ID NO: 579 | Nga00474 | 549.5164 | 512.92699 | ---NA--- |
| SEQ ID NO: 580 | Nga00514 | 700.8514 | 838.83557 | family |
| SEQ ID NO: 581 | Nga20483 | 190.9722 | 206.86759 | prematurely terminated mrna decay factor-like |
| SEQ ID NO: 582 | Nga00506 | 890.5752 | 951.10254 | splicing factor 3b subunit 1 |
| SEQ ID NO: 583 | Nga00509 | 78.55626 | 160.99018 | ---NA--- |
| SEQ ID NO: 584 | Nga00533 | 214.2305 | 196.87546 | protein |
| SEQ ID NO: 585 | Nga00488 | 1245.968 | 1131.2806 | predicted protein [Phaeodactylum tricornutum CCAP 1055/1] |
| SEQ ID NO: 586 | Nga00483 | 235.651 | 299.74696 | ubiquitin-protein ligase |
| SEQ ID NO: 587 | Nga00484 | 1071.582 | 1189.4638 | eukaryotic translation initiation factor 3 subunit |
| SEQ ID NO: 588 | Nga00500.01 | 4996.238 | 4992.331 | glutaryl- mitochondrial precursor |
| SEQ ID NO: 589 | Nga00508.01 | 6980.9 | 6051.6275 | glutathione peroxidase |
| SEQ ID NO: 590 | Nga00504 | 258.1903 | 306.71913 | low-density lipoprotein |
| SEQ ID NO: 591 | Nga00479 | 491.0973 | 451.23534 | atp-binding cassette sub-family b member 9 |
| SEQ ID NO: 592 | Nga00505 | 1501.88 | 1518.2477 | amino acid-polyamine-organocation family |
| SEQ ID NO: 593 | Nga00502 | 3516.592 | 5094.725 | c14c577g12199 |
| SEQ ID NO: 594 | Nga00663 | 2639.663 | 2428.0167 | chaperonin |
| SEQ ID NO: 595 | Nga20429.1 | 246.0137 | 199.86777 | elongator complex protein 4 |
| SEQ ID NO: 596 | Nga00671 | 227.4939 | 202.94164 | ---NA--- |
| SEQ ID NO: 597 | Nga00688.1 | 444.6123 | 587.43351 | atp-dependent rna helicase |
| SEQ ID NO: 598 | Nga20297 | 315.4762 | 214.92737 | mitochondrial protein |
| SEQ ID NO: 599 | Nga00664 | 109.2896 | 136.14416 | phd finger protein 8 |
| SEQ ID NO: 600 | Nga00673 | 981.88 | 1018.2154 | ---NA--- |
| SEQ ID NO: 601 | Nga20068 | 320.2576 | 393.21138 | pentatricopeptide repeat10 |
| SEQ ID NO: 602 | Nga00668 | 1057.707 | 1043.3426 | s-adenosylmethionine-dependent methyltransferase domain-containing protein |
| SEQ ID NO: 603 | Nga00669.01 | 324.263 | 434.2761 | sumo ligase |
| SEQ ID NO: 604 | Nga00656 | 2106.164 | 2248.0814 | 3-oxo-5-alpha-steroid 4-dehydrogenase |
| SEQ ID NO: 605 | Nga00662 | 2118.433 | 2170.9606 | nadp-dependent malic enzyme |
| SEQ ID NO: 606 | Nga00657 | 2076.51 | 1616.8539 | zinc finger hit domain-containing protein 1 |
| SEQ ID NO: 607 | Nga00658 | 4937.87 | 4748.4959 | mpv17-like protein |
| SEQ ID NO: 608 | Nga00670 | 266.1064 | 379.28359 | ---NA--- |
| SEQ ID NO: 609 | Nga00659 | 825.2662 | 824.74685 | cobalamin synthesis protein p47k |
| SEQ ID NO: 610 | Nga00654 | 820.3971 | 785.05131 | ---NA--- |
| SEQ ID NO: 611 | Nga21199 | 1297.583 | 1148.6861 | upf0587 protein c1orf123 homolog |
| SEQ ID NO: 612 | Nga00661 | 607.4534 | 527.48783 | protein |
| SEQ ID NO: 613 | Nga00667.1 | 895.9508 | 1007.724 | lipoate-protein ligase b |
| SEQ ID NO: 614 | Nga00672 | 62.89308 | 84.024436 | flagellar outer dynein arm-docking complex |
| SEQ ID NO: 615 | Nga00665 | 183.3539 | 208.88071 | uncharacterized protein c9orf114-like |
| SEQ ID NO: 616 | Nga00660 | 9375 | 9082.3422 | ribosomal protein l12 |
| SEQ ID NO: 617 | Nga00681.2 | 1095.077 | 1240.4002 | ---NA--- |
| SEQ ID NO: 618 | Nga20187 | 228.1803 | 304.0223 | protein |
| SEQ ID NO: 619 | Nga20024 | 326.5027 | 279.68745 | conserved hypothetical protein [Albugo laibachii Nc14] |
| SEQ ID NO: 620 | Nga00666 | 994.763 | 919.28809 | protein |
| SEQ ID NO: 621 | Nga00011 | 449.3464 | 430.10759 | tf1-like protein |
| SEQ ID NO: 622 | Nga00018 | 88.88889 | 100.29944 | dynein light chain |
| SEQ ID NO: 623 | Nga00015.01 | 3272.989 | 2182.0316 | ferredoxin |
| SEQ ID NO: 624 | Nga00004 | 1060.413 | 715.55438 | methyltransferase family |
| SEQ ID NO: 625 | Nga00009 | 435.1088 | 468.07408 | protein |
| SEQ ID NO: 626 | Nga00001 | 5567.879 | 5567.0727 | 40s ribosomal protein s4 |
| SEQ ID NO: 627 | Nga00010 | 7007.191 | 7870.276 | ---NA--- |
| SEQ ID NO: 628 | Nga00005 | 765 | 895.02204 | homoserine kinase |
| SEQ ID NO: 629 | Nga00012 | 123.8913 | 115.91688 | phosphoethanolamine n- |
| SEQ ID NO: 630 | Nga00038 | 250.4105 | 287.26155 | protein |
| SEQ ID NO: 631 | Nga00014 | 65.30214 | 104.52257 | histone deacetylase |
| SEQ ID NO: 632 | Nga00008 | 437.8472 | 545.00208 | repeat-containing protein a_04 |
| SEQ ID NO: 633 | Nga00006 | 297.7194 | 266.64633 | fatty-acid- ligase fadd9 |

FIGURE 24 J

| # | Nga model | +N rpkb | -N rpkb | GO |
|---|---|---|---|---|
| SEQ ID NO: 634 | Nga20828 | 266.9231 | 198.31514 | alg2 protein |
| SEQ ID NO: 635 | Nga00016 | 2230.867 | 1908.0945 | 2fe-2s iron-sulfur cluster binding domain protein |
| SEQ ID NO: 636 | Nga00017 | 80.71473 | 67.410122 | rna recognition motif-containing protein |
| SEQ ID NO: 637 | Nga00007 | 563.786 | 483.66618 | methyltransferase family |
| SEQ ID NO: 638 | Nga00013 | 294.7368 | 341.19676 | protein |
| SEQ ID NO: 639 | Nga00003.01 | 13762.2 | 16785.777 | ethylmalonic encephalopathy 1 |
| SEQ ID NO: 640 | Nga00002 | 344.1842 | 437.33581 | protein |
| SEQ ID NO: 641 | Nga20792 | 260.2378 | 320.53422 | ---NA--- |
| SEQ ID NO: 642 | Nga02883 | 168.3168 | 220.46015 | conserved hypothetical protein [Albugo laibachii Nc14] |
| SEQ ID NO: 643 | Nga02882 | 224.4898 | 231.1167 | fha domain containing protein |
| SEQ ID NO: 644 | Nga20557 | 409.7065 | 448.69848 | dhhc zinc finger domain containing protein |
| SEQ ID NO: 645 | Nga02880.2 | 960.1407 | 1295.3091 | ras-related protein rab-2-a |
| SEQ ID NO: 646 | Nga02872 | 4786.309 | 3947.1401 | histone 2 |
| SEQ ID NO: 647 | Nga02881 | 1240.246 | 1118.8227 | conserved unknown protein [Ectocarpus siliculosus] |
| SEQ ID NO: 648 | Nga20407 | 1363.897 | 1145.3104 | protein |
| SEQ ID NO: 649 | Nga20428 | 237.1542 | 181.25258 | alanyl-trna synthetase |
| SEQ ID NO: 650 | Nga20209 | 1189.607 | 1134.9614 | protein |
| SEQ ID NO: 651 | Nga02874 | 1032.068 | 922.34856 | farnesyl diphosphate synthase |
| SEQ ID NO: 652 | Nga02871 | 1024.259 | 873.01064 | ubiquitin-conjugating enzyme e2 i |
| SEQ ID NO: 653 | Nga02876 | 304.8303 | 231.91954 | calcium-dependent protein |
| SEQ ID NO: 654 | Nga02873 | 1300.479 | 1416.8789 | protein |
| SEQ ID NO: 655 | Nga02878 | 1588.435 | 1447.9964 | protein |
| SEQ ID NO: 656 | Nga02879 | 1459.848 | 2282.177 | hypothetical protein Esi_0209_0049 [Ectocarpus siliculosus] |
| SEQ ID NO: 657 | Nga02870 | 1575.112 | 1360.7216 | protein |
| SEQ ID NO: 658 | Nga02884 | 650.237 | 769.04476 | ---NA--- |
| SEQ ID NO: 659 | Nga02877 | 3319.838 | 3433.8954 | hypersensitive-induced response protein |
| SEQ ID NO: 660 | Nga02189.2 | 538.6473 | 556.26941 | violaxanthin de-epoxidase-related protein |
| SEQ ID NO: 661 | Nga00161.01 | 760.492 | 1253.322 | had-superfamily subfamily iia hydrolase |
| SEQ ID NO: 662 | Nga00150 | 234.2342 | 231.77303 | gamma complex associated protein 2 |
| SEQ ID NO: 663 | Nga00165.01 | 1802.676 | 1561.4509 | anion exchanger family |
| SEQ ID NO: 664 | Nga21119 | 2242.798 | 1887.8583 | retinol retinaldehyde reductase |
| SEQ ID NO: 665 | Nga00166 | 231.1396 | 270.66359 | ---NA--- |
| SEQ ID NO: 666 | Nga00143.01 | 842.3308 | 907.80017 | conserved uncharacterized protein |
| SEQ ID NO: 667 | Nga20066.1 | 799.1845 | 721.05175 | receptor-interacting serine-threonine kinase 4 |
| SEQ ID NO: 668 | Nga00194 | 103.7037 | 157.80445 | ---NA--- |
| SEQ ID NO: 669 | Nga00149.01 | 1285.985 | 1033.996 | ---NA--- |
| SEQ ID NO: 670 | Nga00163 | 1542.049 | 1652.793 | nuclear receptor coactivator 7 |
| SEQ ID NO: 671 | Nga00167 | 2613.397 | 2935.4726 | l-aspartate oxidase |
| SEQ ID NO: 672 | Nga00170 | 1444.444 | 1633.0572 | peroxiredoxin-like protein |
| SEQ ID NO: 673 | Nga00168 | 4507.298 | 4185.0861 | molecular chaperone |
| SEQ ID NO: 674 | Nga00172 | 4215.859 | 4080.0221 | conserved unknown protein [Ectocarpus siliculosus] |
| SEQ ID NO: 675 | Nga00193 | 1161.348 | 1054.4245 | zinc finger protein |
| SEQ ID NO: 676 | Nga20242 | 463.0503 | 446.23788 | rna polymerase ii ctd phosphatase |
| SEQ ID NO: 677 | Nga00171 | 1501.247 | 1407.3937 | enoyl- hydratase isomerase |
| SEQ ID NO: 678 | Nga20286 | 491.8605 | 530.2808 | rna polymerase ii ctd phosphatase |
| SEQ ID NO: 679 | Nga00169 | 185.7143 | 219.46038 | tumor suppressor candidate 4 |
| SEQ ID NO: 680 | Nga20422 | 139.8176 | 186.0265 | conserved unknown protein [Ectocarpus siliculosus] |
| SEQ ID NO: 681 | Nga00144 | 799.2767 | 605.279 | caltractin |
| SEQ ID NO: 682 | Nga20351 | 152.5886 | 152.49887 | pentatricopeptide repeat-containing protein |
| SEQ ID NO: 683 | Nga21250 | 137.4408 | 97.542393 | protein |
| SEQ ID NO: 684 | Nga20271 | 157.6037 | 188.69236 | ---NA--- |
| SEQ ID NO: 685 | Nga00147 | 1786.268 | 1309.9573 | abc subfamily abcg |
| SEQ ID NO: 686 | Nga00151 | 185.0534 | 185.0364 | copine family protein |
| SEQ ID NO: 687 | Nga00164 | 19765.55 | 15222.287 | heat shock protein hsp20 |
| SEQ ID NO: 688 | Nga00145 | 177.2535 | 226.73862 | u3 small nucleolar rna-interacting protein 2 |
| SEQ ID NO: 689 | Nga00162 | 979.8658 | 984.17983 | serine threonine-protein kinase ctr1 |
| SEQ ID NO: 690 | Nga00146 | 621.4689 | 479.10589 | protein |
| SEQ ID NO: 691 | Nga00173 | 38.75969 | 100.76595 | ---NA--- |
| SEQ ID NO: 692 | Nga00174 | 78.125 | 118.47871 | ---NA--- |
| SEQ ID NO: 693 | Nga20762 | 713.5632 | 946.27333 | fha domain protein |
| SEQ ID NO: 694 | Nga03257 | 622.0096 | 645.79401 | rna binding motif protein 17 |
| SEQ ID NO: 695 | Nga03264 | 84.50704 | 45.770448 | metal ion transporter family |
| SEQ ID NO: 696 | Nga03260 | 559.6591 | 518.02381 | protein |
| SEQ ID NO: 697 | Nga03262 | 345.3608 | 352.88858 | protein |

FIGURE 24 K

| # | Nga model | +N rpkb | -N rpkb | GO |
|---|---|---|---|---|
| SEQ ID NO: 698 | Nga03267 | 413.9768 | 408.37682 | ---NA--- |
| SEQ ID NO: 699 | Nga20709.1 | 107.6923 | 168.50306 | protein |
| SEQ ID NO: 700 | Nga20491.1 | 112.5731 | 158.36754 | atp-dependent clp protease adaptor protein containing protein |
| SEQ ID NO: 701 | Nga21277 | 577.111 | 627.41394 | pentatricopeptide repeat-containing |
| SEQ ID NO: 702 | Nga03254 | 577.2931 | 533.62647 | 7-dehydrocholesterol reductase |
| SEQ ID NO: 703 | Nga03261 | 491.9499 | 434.0687 | rna recognition motif-containing protein |
| SEQ ID NO: 704 | Nga03263 | 194.7484 | 165.92205 | ---NA--- |
| SEQ ID NO: 705 | Nga03256 | 977.5281 | 964.33099 | trehalase-like isoform 1 |
| SEQ ID NO: 706 | Nga03266 | 95.63994 | 62.464967 | ---NA--- |
| SEQ ID NO: 707 | Nga20643 | 318.9369 | 212.32825 | ---NA--- |
| SEQ ID NO: 708 | Nga03258 | 643.2584 | 651.15748 | ---NA--- |
| SEQ ID NO: 709 | Nga03265 | 447.6651 | 415.15246 | protein |
| SEQ ID NO: 710 | Nga03259 | 718.6761 | 624.84416 | immature colon carcinoma transcript 1 |
| SEQ ID NO: 711 | Nga03255 | 163.9833 | 196.36441 | fad nad -binding oxidoreductase family protein |
| SEQ ID NO: 712 | Nga20184 | 191.5104 | 221.35185 | conserved unknown protein [Ectocarpus siliculosus] |
| SEQ ID NO: 713 | Nga00198 | 315.2318 | 359.40411 | single-stranded nucleic acid binding r3h protein |
| SEQ ID NO: 714 | Nga00196.01 | 469.4271 | 500.67626 | ---NA--- |
| SEQ ID NO: 715 | Nga00202 | 149.4642 | 165.57044 | pentafunctional arom polypeptide |
| SEQ ID NO: 716 | Nga00197.01 | 501.9973 | 375.74227 | proly 4-hydroxylase |
| SEQ ID NO: 717 | Nga00205 | 753.7609 | 807.06503 | transcription factor iie |
| SEQ ID NO: 718 | Nga00207.01 | 2368.566 | 2338.2092 | urease accessory protein ureg |
| SEQ ID NO: 719 | Nga00206 | 359.589 | 395.7019 | nad -binding rossmann-fold-containing protein |
| SEQ ID NO: 720 | Nga00212 | 764.0879 | 839.0666 | ---NA--- |
| SEQ ID NO: 721 | Nga00209 | 805.5556 | 926.33696 | protein |
| SEQ ID NO: 722 | Nga00200.01 | 608.4316 | 561.54786 | dna gyrase subunit a |
| SEQ ID NO: 723 | Nga00211.01 | 160.0424 | 132.60574 | nlr card domain containing 3 |
| SEQ ID NO: 724 | Nga00208 | 1932.836 | 1980.5397 | protein disulfide-isomerase |
| SEQ ID NO: 725 | Nga00203.01 | 242.0765 | 225.52575 | beta-adaptin-like protein a |
| SEQ ID NO: 726 | Nga20546.1 | 1033.708 | 983.05587 | n6-adenine-specific methylase |
| SEQ ID NO: 727 | Nga00195.01 | 617.7215 | 606.06253 | conserved hypothetical protein [Phytophthora infestans T30-4] |
| SEQ ID NO: 728 | Nga00201.01 | 99.67846 | 118.42429 | dmc1 |
| SEQ ID NO: 729 | Nga00204.01 | 1006.969 | 929.74435 | atp-binding cassette transporter |
| SEQ ID NO: 730 | Nga20535.1 | 648.855 | 613.74069 | pseudouridine synthase |
| SEQ ID NO: 731 | Nga20949.1 | 223.9289 | 183.02012 | protein |
| SEQ ID NO: 732 | Nga20254.1 | 389.5112 | 359.05565 | protein |
| SEQ ID NO: 733 | Nga20878.1 | 554.0037 | 444.79159 | aspartate carbamoyltransferase |
| SEQ ID NO: 734 | Nga00199.01 | 1643.221 | 1667.3632 | dna-directed rna polymerase ii 19 kda polypeptide |
| SEQ ID NO: 735 | Nga00210.01 | 206.4632 | 259.30196 | uncharacterized protein c16orf7 homolog |
| SEQ ID NO: 736 | Nga02630 | 138.9728 | 130.9044 | hypothetical protein Esi_0116_0070 [Ectocarpus siliculosus] |
| SEQ ID NO: 737 | Nga01767.02 | 2941.606 | 3178.5405 | h aca ribonucleoprotein complex subunit 2-like protein |
| SEQ ID NO: 738 | Nga02628 | 884.0852 | 809.71058 | phd zn finger-containing protein |
| SEQ ID NO: 739 | Nga01765.02 | 492.6185 | 522.67931 | cystathionine gamma-lyase |
| SEQ ID NO: 740 | Nga02645 | 125.9259 | 88.263506 | ---NA--- |
| SEQ ID NO: 741 | Nga02622 | 847.8261 | 902.36789 | serine threonine phosphatase 2c ptc2 |
| SEQ ID NO: 742 | Nga01764.02 | 4929.6 | 5797.4681 | protein |
| SEQ ID NO: 743 | Nga02624 | 4731.634 | 4153.7501 | endonuclease exonuclease phosphatase family protein |
| SEQ ID NO: 744 | Nga02621 | 596.2644 | 566.00011 | atp-dependent dna helicase pif1 |
| SEQ ID NO: 745 | Nga02631 | 136.4594 | 138.11518 | amino acid permease-associated region |
| SEQ ID NO: 746 | Nga02620 | 4806.452 | 4279.6017 | ubiquinol-cytochrome c reductase subunit 7 |
| SEQ ID NO: 747 | Nga02623.1 | 3232.196 | 3711.7164 | molybdenum cofactor synthesis 1 |
| SEQ ID NO: 748 | Nga02632 | 23.25581 | 56.680846 | ---NA--- |
| SEQ ID NO: 749 | Nga02625 | 1965.352 | 2248.0016 | sulfate permease family |
| SEQ ID NO: 750 | Nga02627 | 142.4522 | 171.96627 | mrna decapping protein 2 |
| SEQ ID NO: 751 | Nga02626 | 379.37 | 430.44395 | lysine-specific demethylase 5c |
| SEQ ID NO: 752 | Nga05087 | 1530.34 | 1172.4792 | predicted protein [Naegleria gruberi] |
| SEQ ID NO: 753 | Nga05088 | 122.3022 | 83.125866 | serine threonine-protein |
| SEQ ID NO: 754 | Nga05084 | 159.5205 | 170.80037 | protein |
| SEQ ID NO: 755 | Nga05083 | 3769.884 | 3502.317 | succinyl- ligase subunit mitochondrial precursor |
| SEQ ID NO: 756 | Nga20444 | 224.2424 | 439.85863 | cytochrome p450 |
| SEQ ID NO: 757 | Nga20671 | 295.082 | 399.5535 | cholesterol 24-hydroxylase-like |
| SEQ ID NO: 758 | Nga05086 | 1375.543 | 1434.1075 | succinic semialdehyde dehydrogenase |
| SEQ ID NO: 759 | Nga20512 | 539.6825 | 406.92915 | protein |
| SEQ ID NO: 760 | Nga05085 | 345.9583 | 330.6975 | isoleucyl-trna synthetase |
| SEQ ID NO: 761 | Nga20051 | 644.2335 | 742.32228 | oxidation resistance 1 |

FIGURE 24 L

| # | Nga model | +N rpkb | -N rpkb | GO |
|---|---|---|---|---|
| SEQ ID NO: 762 | Nga20290 | 445.1754 | 450.15972 | zn-dependent protease with chaperone function |
| SEQ ID NO: 763 | Nga02969 | 1224.479 | 1329.2183 | dnaj-like sec63 |
| SEQ ID NO: 764 | Nga02979 | 272.7273 | 262.60217 | ---NA--- |
| SEQ ID NO: 765 | Nga20152 | 911.1303 | 894.43907 | enoyl- hydratase isomerase |
| SEQ ID NO: 766 | Nga02975 | 922.9885 | 973.0429 | stomatal cytokinesis defective scd1 protein |
| SEQ ID NO: 767 | Nga02968 | 587.3606 | 464.43487 | protein |
| SEQ ID NO: 768 | Nga02967 | 498.5755 | 556.82722 | conserved hypothetical protein [Albugo laibachii Nc14] |
| SEQ ID NO: 769 | Nga02977 | 702.6556 | 881.86655 | ---NA--- |
| SEQ ID NO: 770 | Nga02966 | 1955.729 | 1932.3314 | glutaredoxin |
| SEQ ID NO: 771 | Nga02976 | 204.4025 | 173.7262 | 2-octaprenyl-3-methyl-6-methoxy- -benzoquinol hydroxylase |
| SEQ ID NO: 772 | Nga02971 | 1662.572 | 1669.653 | protein |
| SEQ ID NO: 773 | Nga02974 | 2705.443 | 2519.3645 | gamma-glutamyl phosphate reductase |
| SEQ ID NO: 774 | Nga02980 | 806.4516 | 896.03914 | ---NA--- |
| SEQ ID NO: 775 | Nga02972 | 826.2911 | 1042.5491 | ---NA--- |
| SEQ ID NO: 776 | Nga02993 | 98.76543 | 120.35933 | s-adenosylmethionine:trna ribosyltransferase-isomerase |
| SEQ ID NO: 777 | Nga02995 | 62.5 | 203.10636 | ---NA--- |
| SEQ ID NO: 778 | Nga20080 | 740.9639 | 703.12324 | hypothetical protein Esi_0058_0057 [Ectocarpus siliculosus] |
| SEQ ID NO: 779 | Nga02978 | 116.6667 | 117.35034 | ---NA--- |
| SEQ ID NO: 780 | Nga02970 | 4316.161 | 4561.4488 | leucine rich repeat protein |
| SEQ ID NO: 781 | Nga02973 | 1285.761 | 1224.7103 | ccr4-not transcription complex subunit 3 |
| SEQ ID NO: 782 | Nga03007 | 1712.928 | 1896.6891 | ---NA--- |
| SEQ ID NO: 783 | Nga01574.02 | 1614.892 | 1529.24 | kazal-type serine protease inhibitor domain |
| SEQ ID NO: 784 | Nga03001 | 1710.496 | 1762.9101 | protein binding protein |
| SEQ ID NO: 785 | Nga03003 | 312.2711 | 293.62385 | ---NA--- |
| SEQ ID NO: 786 | Nga21166.1 | 195.7295 | 231.2955 | aec family transporter: auxin efflux |
| SEQ ID NO: 787 | Nga01578.02 | 240.8027 | 119.55425 | auxin efflux carrier-like protein |
| SEQ ID NO: 788 | Nga03008 | 593.9902 | 585.90012 | ---NA--- |
| SEQ ID NO: 789 | Nga03006 | 298.6279 | 334.84956 | ---NA--- |
| SEQ ID NO: 790 | Nga03002 | 956.1875 | 1042.852 | ---NA--- |
| SEQ ID NO: 791 | Nga03000 | 3461.353 | 2902.5785 | ---NA--- |
| SEQ ID NO: 792 | Nga02998 | 376.3838 | 331.76538 | protein |
| SEQ ID NO: 793 | Nga01575.02 | 767.9924 | 915.00443 | tumor protein p53 inducible protein 3 |
| SEQ ID NO: 794 | Nga02997 | 1074.631 | 929.28665 | coatomer subunit beta |
| SEQ ID NO: 795 | Nga01577.02 | 349.4624 | 423.68424 | ---NA--- |
| SEQ ID NO: 796 | Nga03377 | 318.4524 | 361.07798 | hypothetical protein AURANDRAFT_63220 [Aureococcus anophagefferens] |
| SEQ ID NO: 797 | Nga00844.02 | 102.0408 | 51.582569 | ---NA--- |
| SEQ ID NO: 798 | Nga03354 | 2333.971 | 2325.9497 | homoaconitate hydratase family protein |
| SEQ ID NO: 799 | Nga03353.1 | 115.1762 | 79.627969 | insulin-degrading enzyme |
| SEQ ID NO: 800 | Nga03355 | 537.2168 | 788.76258 | vitamin k epoxide reductase family |
| SEQ ID NO: 801 | Nga03357 | 16.85393 | 10.14264 | sperm associated antigen 1 |
| SEQ ID NO: 802 | Nga03352 | 147.6744 | 167.52339 | major facilitator superfamily |
| SEQ ID NO: 803 | Nga00841.02 | 1149.094 | 1359.2105 | inorganic pyrophosphatase |
| SEQ ID NO: 804 | Nga03125.01 | 120.2186 | 139.10381 | ---NA--- |
| SEQ ID NO: 805 | Nga20189.1 | 117.338 | 185.91406 | conserved unknown protein [Ectocarpus siliculosus] |
| SEQ ID NO: 806 | Nga03119 | 3781.176 | 3466.3486 | expressed unknown protein [Ectocarpus siliculosus] |
| SEQ ID NO: 807 | Nga03120 | 437.4461 | 426.1904 | syntaxin-like protein |
| SEQ ID NO: 808 | Nga03122 | 1355.675 | 1270.0652 | dcp1-like decapping family protein |
| SEQ ID NO: 809 | Nga03124 | 7230.667 | 6512.4025 | thioredoxin |
| SEQ ID NO: 810 | Nga03117 | 3725.264 | 3056.1557 | protein |
| SEQ ID NO: 811 | Nga03118 | 2968.661 | 1677.0066 | peptidase membrane alanine aminopeptidase |
| SEQ ID NO: 812 | Nga03116 | 15449.28 | 7019.2164 | light-harvesting protein |
| SEQ ID NO: 813 | Nga20975 | 2033.856 | 2185.2523 | metallo-beta-lactamase family protein |
| SEQ ID NO: 814 | Nga21152 | 1194.376 | 1150.4321 | short-chain dehydrogenase reductase family protein |
| SEQ ID NO: 815 | Nga20056 | 164.859 | 160.56613 | n-acetylglucosaminyltransferase-like protein |
| SEQ ID NO: 816 | Nga03127 | 7677.5 | 7539.3082 | ---NA--- |
| SEQ ID NO: 817 | Nga20113.1 | 756.9767 | 779.67652 | transcription initiation factor tfiid subunit |
| SEQ ID NO: 818 | Nga03121 | 367.1875 | 271.74879 | dhhc zinc finger domain containing protein |
| SEQ ID NO: 819 | Nga03128 | 66.66667 | 61.899082 | ---NA--- |
| SEQ ID NO: 820 | Nga20750 | 237.7688 | 247.73512 | short-chain dehydrogenase reductase sdr |
| SEQ ID NO: 821 | Nga03126.01 | 9669.355 | 7501.5198 | protein |
| SEQ ID NO: 822 | Nga20990 | 432.8358 | 436.52711 | aerobic respiration control sensor protein |
| SEQ ID NO: 823 | Nga20941 | 342.437 | 416.45338 | aminoadipate-semialdehyde dehydrogenase-phosphopantetheinyl transferase |

FIGURE 24 M

| # | Nga model | +N rpkb | -N rpkb | GO |
|---|---|---|---|---|
| SEQ ID NO: 824 | Nga02551 | 761.924 | 813.95792 | ---NA--- |
| SEQ ID NO: 825 | Nga21222 | 239.3443 | 251.45234 | mitochondrial protein 18 kda |
| SEQ ID NO: 826 | Nga02564.2 | 844.6111 | 826.95277 | protein |
| SEQ ID NO: 827 | Nga02552 | 1049.405 | 1182.3404 | fam49 family protein |
| SEQ ID NO: 828 | Nga02546 | 553.2915 | 516.14909 | ohcu decarboxylase |
| SEQ ID NO: 829 | Nga20070 | 406.4039 | 344.71386 | conserved oligomeric golgi complex subunit 2 |
| SEQ ID NO: 830 | Nga06481.2 | 915.6985 | 913.82738 | protein |
| SEQ ID NO: 831 | Nga20681 | 609.0014 | 536.2846 | component of oligomeric golgi complex 2 |
| SEQ ID NO: 832 | Nga02550 | 902.4 | 724.46686 | ---NA--- |
| SEQ ID NO: 833 | Nga02554 | 1555.27 | 1484.2254 | tetratricopeptide repeat family |
| SEQ ID NO: 834 | Nga02547.01 | 1214.516 | 1151.3729 | 26s proteasome non-atpase regulatory subunit 2 |
| SEQ ID NO: 835 | Nga02549 | 7600 | 6319.0374 | voltage-dependent anion-selective channel protein 2 |
| SEQ ID NO: 836 | Nga02548.01 | 817.3913 | 679.86089 | peroxisomal membrane 22 kda (mpv17 pmp22) family protein |
| SEQ ID NO: 837 | Nga20978.1 | 205.2023 | 219.15138 | mate efflux multi antimicrobial extrusion family |
| SEQ ID NO: 838 | Nga21293.1 | 263.9692 | 265.06881 | ---NA--- |
| SEQ ID NO: 839 | Nga20832.1 | 327.6451 | 223.67117 | multidrug oligosaccharidyl-lipid polysaccharide flippase superfamily |
| SEQ ID NO: 840 | Nga02553 | 3816.801 | 3283.5831 | integral membrane protein |
| SEQ ID NO: 841 | Nga02695 | 303.6702 | 386.13015 | protein |
| SEQ ID NO: 842 | Nga02696.01 | 1319.672 | 1235.2862 | hypothetical protein Dole_0419 [Desulfococcus oleovorans Hxd3] |
| SEQ ID NO: 843 | Nga02698 | 1454.075 | 1396.4329 | protein |
| SEQ ID NO: 844 | Nga02700.01 | 1149.425 | 1155.1728 | violaxanthin de-epoxidase |
| SEQ ID NO: 845 | Nga02702 | 368.9205 | 291.04684 | ---NA--- |
| SEQ ID NO: 846 | Nga02701 | 434.4942 | 388.9223 | myo inositol monophosphatase |
| SEQ ID NO: 847 | Nga20690 | 776.9857 | 1081.0278 | set domain protein |
| SEQ ID NO: 848 | Nga20033 | 1092.025 | 1265.3236 | set domain-containing protein 3 |
| SEQ ID NO: 849 | Nga02703 | 833.0658 | 814.30909 | solute carrier family member b2 |
| SEQ ID NO: 850 | Nga02699 | 393.5018 | 348.04267 | expressed unknown protein [Ectocarpus siliculosus] |
| SEQ ID NO: 851 | Nga21139.1 | 113.253 | 107.01829 | pot1 protection of telomeres 1 homolog |
| SEQ ID NO: 852 | Nga02320.02 | 509.7907 | 517.11438 | duf1688 domain-containing protein |
| SEQ ID NO: 853 | Nga02705 | 185.654 | 207.20087 | transcription factor |
| SEQ ID NO: 854 | Nga20944.1 | 3347.214 | 3327.7288 | dna-directed rna polymerase iii subunit rpc10 |
| SEQ ID NO: 855 | Nga20568 | 514.8438 | 527.23027 | oxidoreductase domain protein |
| SEQ ID NO: 856 | Nga02697 | 489.9598 | 514.20985 | eukaryotic translation initiation factor 4e member 2 |
| SEQ ID NO: 857 | Nga02704 | 324.9476 | 304.30471 | ---NA--- |
| SEQ ID NO: 858 | Nga03236.02 | 290.8257 | 319.00743 | ---NA--- |
| SEQ ID NO: 859 | Nga20853 | 1055.085 | 1767.1401 | breast cancer 2 like |
| SEQ ID NO: 860 | Nga03233.2 | 466.9269 | 514.95311 | blue cheese |
| SEQ ID NO: 861 | Nga03223.2 | 2371.736 | 2031.6876 | ---NA--- |
| SEQ ID NO: 862 | Nga05325.1 | 974.0562 | 1018.3058 | plastid atp adp translocase |
| SEQ ID NO: 863 | Nga20719.1 | 255.137 | 341.29289 | coiled-coil domain containing 76 |
| SEQ ID NO: 864 | Nga03228.02 | 227.8594 | 231.39844 | calcium-dependent protein |
| SEQ ID NO: 865 | Nga05323.1 | 876.5432 | 1084.5713 | protein |
| SEQ ID NO: 866 | Nga03225.02 | 843.5606 | 1355.2734 | nadph--cytochrome p450 reductase |
| SEQ ID NO: 867 | Nga05327 | 4.504505 | 34.156025 | ---NA--- |
| SEQ ID NO: 868 | Nga21130 | 230.6397 | 187.83349 | protein |
| SEQ ID NO: 869 | Nga05337 | 271.0623 | 190.45871 | ---NA--- |
| SEQ ID NO: 870 | Nga04345.02 | 633.4215 | 637.85789 | amine oxidase |
| SEQ ID NO: 871 | Nga05348 | 63.61323 | 115.76546 | ---NA--- |
| SEQ ID NO: 872 | Nga05339 | 3347.973 | 2995.7274 | beta-lactamase |
| SEQ ID NO: 873 | Nga20320 | 420.2335 | 356.16058 | nuclease domain containing protein |
| SEQ ID NO: 874 | Nga05341 | 451.6765 | 519.18313 | ---NA--- |
| SEQ ID NO: 875 | Nga03059 | 437.8109 | 420.71872 | protein |
| SEQ ID NO: 876 | Nga03047 | 62.7763 | 72.790256 | protein |
| SEQ ID NO: 877 | Nga03051.01 | 599.3512 | 581.59032 | sentrin-specific protease 8 |
| SEQ ID NO: 878 | Nga03052 | 202.8302 | 163.50701 | uncharacterized protein |
| SEQ ID NO: 879 | Nga03061 | 60.27397 | 84.086653 | ---NA--- |
| SEQ ID NO: 880 | Nga03057 | 1445.333 | 1458.755 | iron-sulfur cluster assembly 2 mitochondrial-like |
| SEQ ID NO: 881 | Nga03062 | 60.60606 | 82.063177 | ---NA--- |
| SEQ ID NO: 882 | Nga03050 | 1356.15 | 1422.1066 | aldo keto reductase family protein |
| SEQ ID NO: 883 | Nga03053 | 323.5816 | 277.53068 | peroxisomal acyl-coenzyme a oxidase 1 |
| SEQ ID NO: 884 | Nga03046 | 587.5262 | 637.27993 | protein |
| SEQ ID NO: 885 | Nga03045.01 | 422.5352 | 411.93403 | proteasome subunit alpha |
| SEQ ID NO: 886 | Nga03058.01 | 293.4473 | 271.58002 | transmembrane protein 144 |
| SEQ ID NO: 887 | Nga03049.1 | 1050.495 | 1231.2402 | iron-sulfur cluster scaffold protein nfu-like protein |

FIGURE 24 N

| # | Nga model | +N rpkb | -N rpkb | GO |
|---|---|---|---|---|
| SEQ ID NO: 888 | Nga03055 | 650.6922 | 685.24064 | tim21-like mitochondrial precursor |
| SEQ ID NO: 889 | Nga03056 | 354.8387 | 336.61786 | tbc1 domain member 20 |
| SEQ ID NO: 890 | Nga03044 | 506.2657 | 559.26364 | chaperone protein dnaj |
| SEQ ID NO: 891 | Nga03060 | 282.2086 | 299.05231 | atp-binding cassette superfamily |
| SEQ ID NO: 892 | Nga03048 | 278.8314 | 283.16213 | protein |
| SEQ ID NO: 893 | Nga03054 | 255.7078 | 206.09474 | soluble nsf attachment protein receptor |
| SEQ ID NO: 894 | Nga00357.01 | 1129.63 | 1157.8567 | dihydrolipoyllysine-residue acetyltransferase component of pyruvate dehydrogenase mitochondrial |
| SEQ ID NO: 895 | Nga00372 | 34.52855 | 40.279615 | ---NA--- |
| SEQ ID NO: 896 | Nga00371 | 112.2807 | 193.84186 | conserved hypothetical protein [Phytophthora infestans T30-4] |
| SEQ ID NO: 897 | Nga00351.01 | 7803.557 | 7858.4813 | atp synthase gamma |
| SEQ ID NO: 898 | Nga00389.01 | 155.303 | 164.12635 | eukaryotic translation initiation factor 2-alpha kinase 1 |
| SEQ ID NO: 899 | Nga00368.01 | 282.2528 | 304.32702 | eukaryotic translation initiation factor 2-alpha kinase 1 |
| SEQ ID NO: 900 | Nga00367 | 675.6453 | 686.89919 | malate dehydrogenase |
| SEQ ID NO: 901 | Nga00353 | 758.1428 | 842.26506 | phosphatidate cytidylyltransferase |
| SEQ ID NO: 902 | Nga00390.01 | 251.7986 | 311.722 | ---NA--- |
| SEQ ID NO: 903 | Nga00362 | 903.0934 | 1018.6092 | atp-dependent clp protease atp-binding subunit |
| SEQ ID NO: 904 | Nga20758 | 163.0435 | 164.83995 | ---NA--- |
| SEQ ID NO: 905 | Nga00358 | 491.8191 | 516.42144 | pheromone processing carboxypeptidase |
| SEQ ID NO: 906 | Nga00352 | 735.6882 | 684.77273 | protein |
| SEQ ID NO: 907 | Nga00365 | 347.032 | 401.88474 | serine protease family s09x |
| SEQ ID NO: 908 | Nga00359 | 854.8535 | 919.55848 | protein |
| SEQ ID NO: 909 | Nga00369 | 993.5691 | 1033.31 | carbon-nitrogen family protein |
| SEQ ID NO: 910 | Nga00363 | 230.198 | 214.50177 | ---NA--- |
| SEQ ID NO: 911 | Nga00355 | 531.8163 | 561.47398 | a chain crystal structure of the protein bh0493 from bacillus halodurans c-125 complexed with zn |
| SEQ ID NO: 912 | Nga00356 | 827.5862 | 816.42755 | peptidyl-prolyl cis-trans isomerase |
| SEQ ID NO: 913 | Nga00364 | 470.8141 | 441.77974 | protein |
| SEQ ID NO: 914 | Nga20736 | 465.1163 | 577.30491 | 50s ribosomal protein l27 |
| SEQ ID NO: 915 | Nga00366 | 597.2716 | 621.92791 | tha domain |
| SEQ ID NO: 916 | Nga00370 | 166.1631 | 199.62922 | ---NA--- |
| SEQ ID NO: 917 | Nga00354 | 281.4313 | 423.76028 | set and zf-mynd domain-containing protein |
| SEQ ID NO: 918 | Nga00361 | 555.4342 | 541.91277 | glycosyl group 1 |
| SEQ ID NO: 919 | Nga00360 | 847.4702 | 886.5754 | eukaryotic translation initiation factor 5 |
| SEQ ID NO: 920 | Nga02480 | 1609.689 | 2169.4384 | ---NA--- |
| SEQ ID NO: 921 | Nga02482.01 | 461.488 | 468.30074 | pre-mrna-splicing factor syf1 |
| SEQ ID NO: 922 | Nga02486.1 | 775.3004 | 706.73992 | atp-binding sub-family c (cftr mrp) member 3 |
| SEQ ID NO: 923 | Nga02485.1 | 1718.162 | 1876.166 | protein |
| SEQ ID NO: 924 | Nga02328.02 | 304.9645 | 320.61676 | signal recognition particle 72kda |
| SEQ ID NO: 925 | Nga02483.01 | 1542.857 | 1293.6908 | peptide methionine sulfoxide reductase |
| SEQ ID NO: 926 | Nga02484.1 | 8670.943 | 10558.3 | Aardvark [Ectocarpus siliculosus] |
| SEQ ID NO: 927 | Nga02593 | 690.8345 | 637.19644 | trafficking protein particle complex subunit 3 |
| SEQ ID NO: 928 | Nga02604 | 2590.909 | 2356.6614 | glutamyl-trna reductase |
| SEQ ID NO: 929 | Nga02600 | 419.7012 | 519.36567 | tkl family protein kinase |
| SEQ ID NO: 930 | Nga02605 | 3395.317 | 3428.7488 | isoform c |
| SEQ ID NO: 931 | Nga02603 | 6181.495 | 5675.7347 | ---NA--- |
| SEQ ID NO: 932 | Nga02599 | 423.3668 | 449.53301 | two-pore calcium channel |
| SEQ ID NO: 933 | Nga02596 | 285.7143 | 257.91284 | dnaj homolog subfamily b member 12 |
| SEQ ID NO: 934 | Nga02597.1 | 555.1331 | 626.05156 | u2 small nuclear ribonucleoprotein auxiliary factor u2af |
| SEQ ID NO: 935 | Nga02595 | 49.46237 | 62.315071 | dna polymerase epsilon catalytic subunit a |
| SEQ ID NO: 936 | Nga02607 | 374.2489 | 356.11897 | ---NA--- |
| SEQ ID NO: 937 | Nga02592.01 | 324.4253 | 366.05837 | thiamine monophosphate synthase |
| SEQ ID NO: 938 | Nga02598 | 2450.573 | 2299.5796 | si: (novel protein vertebrate udp-galactose transporters) |
| SEQ ID NO: 939 | Nga02601.01 | 1569.873 | 1348.6361 | protein |
| SEQ ID NO: 940 | Nga06487.2 | 139.5349 | 178.1398 | transportin 1 |
| SEQ ID NO: 941 | Nga21191 | 254.9575 | 300.72784 | mitochondrial inner membrane protein oxa1l-like |
| SEQ ID NO: 942 | Nga02606 | 87.11303 | 87.344997 | protein |
| SEQ ID NO: 943 | Nga02602 | 282.1782 | 422.30036 | dead box atp-dependent rna helicase |
| SEQ ID NO: 944 | Nga00539 | 997.8669 | 988.03505 | digalactosyldiacylglycerol synthase 1 |
| SEQ ID NO: 945 | Nga00564 | 1872.2 | 1631.2732 | hsp90-like protein |
| SEQ ID NO: 946 | Nga00556 | 1823.432 | 1410.3491 | nuclear transport |
| SEQ ID NO: 947 | Nga20874 | 423.9195 | 445.7357 | casein kinase 2 subunit beta |
| SEQ ID NO: 948 | Nga20782 | 1705.882 | 1532.685 | 50s ribosomal protein l9 |
| SEQ ID NO: 949 | Nga00537 | 510.4432 | 554.76882 | protein |

FIGURE 24 O

| # | Nga model | +N rpkb | -N rpkb | GO |
|---|---|---|---|---|
| SEQ ID NO: 950 | Nga00563 | 2255.952 | 1841.9276 | peptide methionine sulfoxide reductase b5 |
| SEQ ID NO: 951 | Nga20573 | 404.8193 | 339.32629 | uncharacterized protein |
| SEQ ID NO: 952 | Nga20405 | 311.2339 | 383.02195 | uncharacterized protein |
| SEQ ID NO: 953 | Nga00568 | 316.8142 | 285.667 | cdc2-like protein kinase |
| SEQ ID NO: 954 | Nga21265 | 154.5455 | 423.446 | rme1-like gtpase atpase without a c-terminal eh domain |
| SEQ ID NO: 955 | Nga00569 | 355.0725 | 382.01004 | rme1-like gtpase atpase without a c-terminal eh domain |
| SEQ ID NO: 956 | Nga00586.2 | 3477.536 | 3371.7408 | nucleoredoxin |
| SEQ ID NO: 957 | Nga00565 | 246.6509 | 222.7928 | transcriptional sir2 family |
| SEQ ID NO: 958 | Nga00557 | 847.185 | 1039.6723 | glycyl-trna synthetase |
| SEQ ID NO: 959 | Nga20199 | 1761.337 | 1789.0164 | mrna (2 -o-methyladenosine-n -)- |
| SEQ ID NO: 960 | Nga00594 | 572.6817 | 635.28006 | wd repeat domain 18 |
| SEQ ID NO: 961 | Nga00572 | 612.6533 | 561.54736 | protein |
| SEQ ID NO: 962 | Nga00535 | 827.0295 | 750.96892 | histone-lysine n-methyltransferase |
| SEQ ID NO: 963 | Nga00560 | 531.4201 | 569.7564 | tetratricopeptide repeat protein 30a |
| SEQ ID NO: 964 | Nga00538 | 1563.501 | 1539.8801 | small nuclear ribonucleoprotein associated protein b |
| SEQ ID NO: 965 | Nga20185 | 464.5197 | 584.18948 | hnrnp arginine n-methyltransferase |
| SEQ ID NO: 966 | Nga00558 | 12029.89 | 12677.572 | ribosomal protein s16 |
| SEQ ID NO: 967 | Nga00570 | 142.7713 | 143.91025 | retrograde transporter |
| SEQ ID NO: 968 | Nga00596 | 165.0485 | 192.80863 | rna helicase rnase |
| SEQ ID NO: 969 | Nga20986 | 255.3191 | 237.06032 | wd40 repeat domain-containing protein |
| SEQ ID NO: 970 | Nga00541 | 169.8718 | 190.9547 | neural precursor cell developmentally down-regulated 1 |
| SEQ ID NO: 971 | Nga00595 | 289.1414 | 298.16288 | dicer-like protein 2 |
| SEQ ID NO: 972 | Nga00562 | 691.5094 | 805.27202 | 5 -3 exoribonuclease 2 |
| SEQ ID NO: 973 | Nga00573 | 1462.664 | 1313.3899 | taurine catabolism dioxygenase |
| SEQ ID NO: 974 | Nga00559 | 764.2105 | 1000.376 | ---NA--- |
| SEQ ID NO: 975 | Nga20178 | 475.1773 | 433.10151 | dicer-1 |
| SEQ ID NO: 976 | Nga00536 | 923.2323 | 1088.7048 | ---NA--- |
| SEQ ID NO: 977 | Nga00561 | 3143.882 | 2544.8223 | glycosyl group 1 family protein |
| SEQ ID NO: 978 | Nga00542 | 369.5324 | 356.17647 | ---NA--- |
| SEQ ID NO: 979 | Nga00571 | 156.4356 | 218.79181 | ---NA--- |
| SEQ ID NO: 980 | Nga03381 | 450.0805 | 394.2204 | trna-dihydrouridine synthase 1-like |
| SEQ ID NO: 981 | Nga03384 | 729.8637 | 710.07528 | cytosolic iron-sulfur protein assembly 1 homolog ( cerevisiae) |
| SEQ ID NO: 982 | Nga03382 | 906.0119 | 868.60503 | ---NA--- |
| SEQ ID NO: 983 | Nga20887 | 197.8346 | 215.36738 | helicase mov-10 |
| SEQ ID NO: 984 | Nga03383 | 1518.848 | 1790.1717 | rna helicase |
| SEQ ID NO: 985 | Nga03385 | 4139.18 | 3538.8396 | conserved unknown protein [Ectocarpus siliculosus] |
| SEQ ID NO: 986 | Nga03380 | 1726.364 | 1951.2648 | protein |
| SEQ ID NO: 987 | Nga03388 | 388.6463 | 373.69206 | ---NA--- |
| SEQ ID NO: 988 | Nga03379.01 | 1003.876 | 948.87934 | conserved hypothetical protein [Phytophthora infestans T30-4] |
| SEQ ID NO: 989 | Nga03386 | 523.0927 | 627.40851 | protein |
| SEQ ID NO: 990 | Nga03387 | 4681.694 | 4936.7055 | ---NA--- |
| SEQ ID NO: 991 | Nga20108 | 248.2447 | 344.41841 | eukaryotic translation initiation factor 4b |
| SEQ ID NO: 992 | Nga03389 | 60.34483 | 102.72046 | ---NA--- |
| SEQ ID NO: 993 | Nga01429.02 | 3957.888 | 4347.0705 | xylulose kinase |
| SEQ ID NO: 994 | Nga02900 | 487.8517 | 518.06091 | ribosomal protein l11 methyltransferase |
| SEQ ID NO: 995 | Nga02908.1 | 1334.945 | 1391.3009 | protein |
| SEQ ID NO: 996 | Nga01433.02 | 155.3154 | 150.8197 | ---NA--- |
| SEQ ID NO: 997 | Nga01432.02 | 137.793 | 204.38376 | amidophosphoribosyltransferase |
| SEQ ID NO: 998 | Nga02906 | 459.6062 | 421.38021 | arabinose 5-phosphate isomerase |
| SEQ ID NO: 999 | Nga01427.02 | 422.5513 | 474.99438 | mitochondrial inner membrane protease atp23 homolog |
| SEQ ID NO: 1000 | Nga01426.02 | 551.8035 | 429.80196 | udp-glucose 4-epimerase |
| SEQ ID NO: 1001 | Nga01425.02 | 1500.775 | 1598.8197 | protein |
| SEQ ID NO: 1002 | Nga01431.02 | 8.438819 | 7.3129718 | protein |
| SEQ ID NO: 1003 | Nga02903 | 6260.047 | 7722.63 | cytochrome c1 |
| SEQ ID NO: 1004 | Nga01428.02 | 796.5368 | 725.67295 | snf7 family protein |
| SEQ ID NO: 1005 | Nga02904 | 1660.081 | 1686.311 | calcium-dependent protein kinase |
| SEQ ID NO: 1006 | Nga04498.02 | 165.4135 | 222.61951 | conserved hypothetical protein [Phytophthora infestans T30-4] |
| SEQ ID NO: 1007 | Nga06724 | 513.5135 | 576.33065 | lipase class 3 |
| SEQ ID NO: 1008 | Nga06728 | 719.0476 | 964.59403 | serine threonine protein kinase |
| SEQ ID NO: 1009 | Nga06729 | 1141.35 | 1285.1024 | conserved unknown protein [Ectocarpus siliculosus] |
| SEQ ID NO: 1010 | Nga06726 | 2934.808 | 2558.6515 | malate synthase |
| SEQ ID NO: 1011 | Nga06725 | 1471.335 | 1440.2214 | atp-dependent rna helicase |
| SEQ ID NO: 1012 | Nga20336 | 552.4862 | 560.56858 | conserved plasmodium protein |
| SEQ ID NO: 1013 | Nga20947 | 539.5778 | 477.30889 | mitochondrial protein |

FIGURE 24 P

| # | Nga model | +N rpkb | -N rpkb | GO |
|---|---|---|---|---|
| SEQ ID NO: 1014 | Nga20205 | 500.4292 | 577.41483 | protein memo1 |
| SEQ ID NO: 1015 | Nga20380 | 277.4451 | 337.2944 | ---NA--- |
| SEQ ID NO: 1016 | Nga21193 | 459.4595 | 653.84391 | ---NA--- |
| SEQ ID NO: 1017 | Nga20064 | 2607.602 | 2232.0582 | conserved unknown protein [Ectocarpus siliculosus] |
| SEQ ID NO: 1018 | Nga20046 | 560.0248 | 658.25231 | imidazoleglycerol-phosphate dehydratase |
| SEQ ID NO: 1019 | Nga21189 | 122.1591 | 187.71952 | ---NA--- |
| SEQ ID NO: 1020 | Nga21068.1 | 156.0976 | 195.51052 | glutamate carboxypeptidase 2 |
| SEQ ID NO: 1021 | Nga20401.1 | 232.8767 | 204.03379 | glutamate carboxypeptidase |
| SEQ ID NO: 1022 | Nga20577.1 | 202.7027 | 146.38296 | ---NA--- |
| SEQ ID NO: 1023 | Nga06109 | 1195.153 | 1418.9812 | ---NA--- |
| SEQ ID NO: 1024 | Nga06113 | 556.7568 | 543.24345 | hypothetical protein RHA1_ro04171 [Rhodococcus jostii RHA1] |
| SEQ ID NO: 1025 | Nga06116 | 577.6892 | 565.35317 | ---NA--- |
| SEQ ID NO: 1026 | Nga06114 | 196.7871 | 181.26405 | nad dependent steroid dehydrogenase-like |
| SEQ ID NO: 1027 | Nga06115 | 250.1005 | 246.96166 | c2h2-type zinc finger-containing protein |
| SEQ ID NO: 1028 | Nga06111 | 6255.613 | 6012.3537 | protein |
| SEQ ID NO: 1029 | Nga06110 | 746.8847 | 710.345 | histidyl-trna synthetase |
| SEQ ID NO: 1030 | Nga03152.1 | 319.5793 | 293.59496 | metallo-beta-lactamase domain-containing protein |
| SEQ ID NO: 1031 | Nga03154 | 88 | 87.019793 | protein |
| SEQ ID NO: 1032 | Nga03144 | 966.4778 | 1127.2179 | ---NA--- |
| SEQ ID NO: 1033 | Nga03147 | 353.6836 | 370.08638 | ppgpp synthetase |
| SEQ ID NO: 1034 | Nga03145 | 358.9744 | 342.56116 | vacuolar amino acid |
| SEQ ID NO: 1035 | Nga03157 | 360.4336 | 299.43052 | ---NA--- |
| SEQ ID NO: 1036 | Nga03153 | 237.6812 | 345.37894 | trna (guanine-n -)-methyltransferase |
| SEQ ID NO: 1037 | Nga21223 | 313.2184 | 289.48493 | thioesterase family protein |
| SEQ ID NO: 1038 | Nga03155 | 289.5377 | 271.46739 | protein |
| SEQ ID NO: 1039 | Nga21154 | 581.1733 | 610.33509 | mediator of rna polymerase ii transcription subunit 31 |
| SEQ ID NO: 1040 | Nga03148 | 42.64871 | 52.277283 | kinesin-like protein |
| SEQ ID NO: 1041 | Nga03150 | 131.6726 | 187.60635 | toxin biosynthesis |
| SEQ ID NO: 1042 | Nga03151 | 691.2669 | 767.45726 | dna-3-methyladenine glycosylase |
| SEQ ID NO: 1043 | Nga03156 | 332.3782 | 364.1818 | lysine decarboxylase |
| SEQ ID NO: 1044 | Nga03149 | 46.2204 | 67.82544 | protein |
| SEQ ID NO: 1045 | Nga20073 | 668.5117 | 702.83629 | abl-philin partial |
| SEQ ID NO: 1046 | Nga01458.02 | 7968.763 | 9166.4674 | delta-9 acyl-desaturase |
| SEQ ID NO: 1047 | Nga01459.02 | 828.3642 | 775.11018 | methionine aminopeptidase |
| SEQ ID NO: 1048 | Nga21224.1 | 93.61702 | 69.142592 | conserved unknown protein [Ectocarpus siliculosus] |
| SEQ ID NO: 1049 | Nga01460.02 | 97.11286 | 36.960738 | riken cdna 6720467c03 isoform cra_a |
| SEQ ID NO: 1050 | Nga05263 | 160.3053 | 140.57234 | ---NA--- |
| SEQ ID NO: 1051 | Nga05276 | 195.1477 | 164.54186 | protein |
| SEQ ID NO: 1052 | Nga20764.1 | 329.5924 | 273.84768 | tubulin tyrosine ligase |
| SEQ ID NO: 1053 | Nga05260 | 675.3103 | 650.83683 | nicotinamide nucleotide transhydrogenase |
| SEQ ID NO: 1054 | Nga05261 | 915.1751 | 842.56212 | protein |
| SEQ ID NO: 1055 | Nga04994.02 | 756.4935 | 695.19235 | stromal cell-derived factor 2 |
| SEQ ID NO: 1056 | Nga05636 | 2555.225 | 2617.1447 | ppgpp synthetase |
| SEQ ID NO: 1057 | Nga05641 | 235.5123 | 349.5275 | mucolipin-like protein |
| SEQ ID NO: 1058 | Nga04806.02 | 6873.897 | 6980.2338 | 60s ribosomal protein l39 |
| SEQ ID NO: 1059 | Nga05635 | 1593.084 | 2002.2593 | pkd domain-containing protein |
| SEQ ID NO: 1060 | Nga20957.1 | 523.0461 | 366.86681 | cytochrome c oxidase assembly protein cox19 |
| SEQ ID NO: 1061 | Nga20109.1 | 316.7128 | 290.06264 | folate-binding protein |
| SEQ ID NO: 1062 | Nga05640 | 124.5902 | 149.16664 | ---NA--- |
| SEQ ID NO: 1063 | Nga04995.02 | 2294.228 | 2284.0334 | nad-dependent epimerase dehydratase |
| SEQ ID NO: 1064 | Nga04996.02 | 1387.654 | 1414.8908 | ntp pyrophosphohydrolase |
| SEQ ID NO: 1065 | Nga02527 | 941.8239 | 1137.7363 | predicted protein [Thalassiosira pseudonana CCMP1335] |
| SEQ ID NO: 1066 | Nga02522 | 1190.734 | 1207.7211 | membrane protein |
| SEQ ID NO: 1067 | Nga02528 | 2026.354 | 1517.7963 | expressed unknown protein [Ectocarpus siliculosus] |
| SEQ ID NO: 1068 | Nga02523 | 407.0568 | 542.54919 | intraflagellar transport protein 72 74 |
| SEQ ID NO: 1069 | Nga02524.01 | 18205.19 | 18242.249 | predicted protein [Phaeodactylum tricornutum CCAP 1055/1] |
| SEQ ID NO: 1070 | Nga02545 | 224.1379 | 219.96705 | ---NA--- |
| SEQ ID NO: 1071 | Nga02526 | 204.1467 | 211.63662 | ---NA--- |
| SEQ ID NO: 1072 | Nga02529 | 74.91857 | 85.858933 | ---NA--- |
| SEQ ID NO: 1073 | Nga02531 | 131.9444 | 180.53899 | ---NA--- |
| SEQ ID NO: 1074 | Nga02530 | 150.6173 | 230.02005 | ubiquitin-specific protease, putative [Phytophthora infestans T30-4] |
| SEQ ID NO: 1075 | Nga02525 | 281.0373 | 343.40447 | dead-box atp-dependent rna helicase 13 |
| SEQ ID NO: 1076 | Nga20966 | 406.8182 | 502.22665 | ubiquitin carboxyl-terminal hydrolase 24 |
| SEQ ID NO: 1077 | Nga05070 | 508.7719 | 459.45217 | 50s ribosomal protein l15 |

FIGURE 24 Q

| # | Nga model | +N rpkb | -N rpkb | GO |
|---|---|---|---|---|
| SEQ ID NO: 1078 | Nga05071 | 661.9965 | 508.41803 | acetylornithine deacetylase |
| SEQ ID NO: 1079 | Nga05072 | 1534.29 | 1215.3988 | anion-transporting atpase |
| SEQ ID NO: 1080 | Nga04814.2 | 297.8036 | 270.10872 | ---NA--- |
| SEQ ID NO: 1081 | Nga05081 | 129.2517 | 162.11664 | subtilisin-like serine peptidase |
| SEQ ID NO: 1082 | Nga05074 | 131.4741 | 93.865889 | n-ethylmaleimide-sensitive factor attachment gamma |
| SEQ ID NO: 1083 | Nga05073 | 318.232 | 293.25118 | ---NA--- |
| SEQ ID NO: 1084 | Nga05056 | 266.6667 | 238.31147 | neuro-oncological ventral antigen 2 |
| SEQ ID NO: 1085 | Nga05053.01 | 3648.168 | 3444.6372 | vacuolar h+ atpase b subunit |
| SEQ ID NO: 1086 | Nga05055 | 502.1699 | 558.74187 | sedoheptulose- -bisphosphatase |
| SEQ ID NO: 1087 | Nga04458.02 | 20072.77 | 23208.969 | inorganic phosphate |
| SEQ ID NO: 1088 | Nga05052 | 2484.892 | 2467.2796 | ---NA--- |
| SEQ ID NO: 1089 | Nga05057 | 24.74527 | 21.286256 | inorganic phosphate |
| SEQ ID NO: 1090 | Nga05620.01 | 2161.398 | 1892.5052 | polyubiquitin-like protein |
| SEQ ID NO: 1091 | Nga05622 | 462.7615 | 599.17794 | trna pseudouridine synthase a |
| SEQ ID NO: 1092 | Nga05623 | 304 | 358.18936 | tata-box binding protein |
| SEQ ID NO: 1093 | Nga05621 | 688.7822 | 747.05789 | crystal protein |
| SEQ ID NO: 1094 | Nga05624 | 6611.679 | 6088.2492 | ribosomal protein s15a |
| SEQ ID NO: 1095 | Nga04451.2 | 984.6697 | 1532.1933 | deah (asp-glu-ala-his) box polypeptide 36 |
| SEQ ID NO: 1096 | Nga06094 | 1360.065 | 1292.4346 | mitotic spindle-associated mmxd complex subunit mip18 |
| SEQ ID NO: 1097 | Nga06098 | 140.4682 | 178.72756 | methyltransferase type 11 |
| SEQ ID NO: 1098 | Nga06096 | 134.3202 | 150.2512 | ctp synthase |
| SEQ ID NO: 1099 | Nga06095 | 1733.026 | 2393.5881 | 6-phosphofructo-2-kinase fructose- -bisphosphatase short form |
| SEQ ID NO: 1100 | Nga06097 | 560.7537 | 611.65061 | protein |
| SEQ ID NO: 1101 | Nga06203 | 161.079 | 189.09633 | protein |
| SEQ ID NO: 1102 | Nga06199 | 358.484 | 406.7777 | pre-mrna-processing protein 40a |
| SEQ ID NO: 1103 | Nga06198 | 343.4685 | 242.75175 | protein |
| SEQ ID NO: 1104 | Nga06204 | 1927.728 | 2155.1764 | ---NA--- |
| SEQ ID NO: 1105 | Nga06200 | 781.1121 | 753.86581 | carrier protein |
| SEQ ID NO: 1106 | Nga06197 | 1064.14 | 1029.9971 | seryl-trna synthetase |
| SEQ ID NO: 1107 | Nga06202 | 1434.806 | 1354.763 | protein |
| SEQ ID NO: 1108 | Nga06201 | 1527.867 | 566.57895 | ---NA--- |
| SEQ ID NO: 1109 | Nga06196 | 272.6406 | 335.60632 | ---NA--- |
| SEQ ID NO: 1110 | Nga04202.02 | 741.7783 | 699.28622 | udp-glucuronate decarboxylase 1 |
| SEQ ID NO: 1111 | Nga04201.02 | 917.2619 | 756.97419 | 3-oxoacyl-(acyl-carrier-protein) synthase 2 |
| SEQ ID NO: 1112 | Nga06687 | 483.7641 | 551.30793 | ---NA--- |
| SEQ ID NO: 1113 | Nga04206.02 | 698.4127 | 747.94724 | ---NA--- |
| SEQ ID NO: 1114 | Nga04203.02 | 23497.08 | 20695.47 | ---NA--- |
| SEQ ID NO: 1115 | Nga06689 | 240.1919 | 265.38161 | exosome component 10 |
| SEQ ID NO: 1116 | Nga06686 | 323.9247 | 324.67899 | protein high chlorophyll fluorescent 107 |
| SEQ ID NO: 1117 | Nga02345.02 | 1162.684 | 1729.2092 | glutamate dehydrogenase |
| SEQ ID NO: 1118 | Nga06372 | 21606.13 | 22502.413 | ---NA--- |
| SEQ ID NO: 1119 | Nga06375.1 | 985.9296 | 1047.8519 | protein |
| SEQ ID NO: 1120 | Nga06376 | 3891.015 | 4130.8012 | tpa_inf: von willebrand factor |
| SEQ ID NO: 1121 | Nga06371 | 2529.624 | 1893.3113 | gdp-mannose -epimerase |
| SEQ ID NO: 1122 | Nga06377 | 148.855 | 184.67347 | ---NA--- |
| SEQ ID NO: 1123 | Nga20771 | 314.4154 | 297.55121 | suppression of tumorigenicity 5 |
| SEQ ID NO: 1124 | Nga06374 | 705.2519 | 565.41749 | ---NA--- |
| SEQ ID NO: 1125 | Nga05670 | 744.1077 | 694.80157 | ---NA--- |
| SEQ ID NO: 1126 | Nga05667 | 560.462 | 484.95324 | protein |
| SEQ ID NO: 1127 | Nga05675 | 90.46625 | 66.335829 | ---NA--- |
| SEQ ID NO: 1128 | Nga05674.01 | 1694.783 | 1273.9773 | light harvesting complex protein |
| SEQ ID NO: 1129 | Nga05669 | 969.5274 | 1081.8866 | cysteine subfamily |
| SEQ ID NO: 1130 | Nga05672 | 479.1224 | 354.94502 | endoplasmic reticulum protein |
| SEQ ID NO: 1131 | Nga01541.2 | 738.3513 | 652.2699 | ---NA--- |
| SEQ ID NO: 1132 | Nga05666.1 | 1267.76 | 1299.2888 | protein |
| SEQ ID NO: 1133 | Nga05687 | 105.0375 | 125.39042 | hypothetical protein (Partial) [Ectocarpus siliculosus] |
| SEQ ID NO: 1134 | Nga01539.2 | 338.326 | 507.73609 | hypothetical protein GLRG_11977 [Glomerella graminicola M1.001] |
| SEQ ID NO: 1135 | Nga05673 | 628.5714 | 394.60665 | nudix (nucleoside diphosphate linked moiety x)-type motif isoform cra_a |
| SEQ ID NO: 1136 | Nga02810 | 981.32 | 914.61097 | protein |
| SEQ ID NO: 1137 | Nga21290.1 | 2242.386 | 1954.7699 | transmembrane protein 222 |
| SEQ ID NO: 1138 | Nga02806 | 504.5045 | 472.86134 | udp-n-acetylglucosamine transporter |
| SEQ ID NO: 1139 | Nga02807 | 400.8547 | 492.5474 | zinc finger mynd domain-containing protein 10 |
| SEQ ID NO: 1140 | Nga02803.01 | 1532.258 | 2007.8153 | x-pro dipeptidyl-peptidase domain-containing protein |

FIGURE 24 R

| # | Nga model | +N rpkb | -N rpkb | GO |
|---|---|---|---|---|
| SEQ ID NO: 1141 | Nga02804 | 1168.84 | 1122.6378 | protein |
| SEQ ID NO: 1142 | Nga02808.01 | 152.0681 | 125.19127 | cysteine synthase |
| SEQ ID NO: 1143 | Nga02809 | 448.9572 | 575.50519 | vesicle-associated membrane protein 4 |
| SEQ ID NO: 1144 | Nga20044.1 | 243.6364 | 319.97064 | protein |
| SEQ ID NO: 1145 | Nga20890 | 399.4823 | 462.6409 | iws1 c-terminus family protein |
| SEQ ID NO: 1146 | Nga20954 | 138.5224 | 175.77543 | atp-dependent rna |
| SEQ ID NO: 1147 | Nga20617 | 859.4164 | 959.68206 | u5 small nuclear ribonucleoprotein 40 kda protein |
| SEQ ID NO: 1148 | Nga21041 | 557.6756 | 405.86042 | bzip transcription factor |
| SEQ ID NO: 1149 | Nga20204 | 170.0913 | 210.21663 | deah (asp-glu-ala-his) box polypeptide 16 |
| SEQ ID NO: 1150 | Nga20197 | 218.1373 | 198.23889 | pre-mrna-splicing factor atp-dependent rna helicase dhx16 |
| SEQ ID NO: 1151 | Nga20933 | 2507.644 | 2549.7885 | pas pac sensor hybrid histidine kinase |
| SEQ ID NO: 1152 | Nga21085 | 16120.79 | 16179.915 | f-type h-atpase beta subunit |
| SEQ ID NO: 1153 | Nga21038 | 685.5576 | 695.09161 | beclin-1-like protein |
| SEQ ID NO: 1154 | Nga20049 | 1594.843 | 2070.0444 | transmembrane and coiled-coil domains 4 |
| SEQ ID NO: 1155 | Nga20078 | 848.8111 | 704.66093 | violaxanthin de-epoxidase |
| SEQ ID NO: 1156 | Nga20799.1 | 224.7765 | 242.10209 | competence-like protein |
| SEQ ID NO: 1157 | Nga21114 | 410.8619 | 358.09386 | protein |
| SEQ ID NO: 1158 | Nga20812 | 553.9247 | 622.15096 | phd zinc finger-containing protein |
| SEQ ID NO: 1159 | Nga20906 | 327.7512 | 308.38478 | ---NA--- |
| SEQ ID NO: 1160 | Nga05829.1 | 946.2366 | 938.39761 | myb-like dna-binding domain containing protein |
| SEQ ID NO: 1161 | Nga05825 | 425.2598 | 386.62187 | ---NA--- |
| SEQ ID NO: 1162 | Nga05826.1 | 245.4268 | 257.04789 | signal recognition particle receptor |
| SEQ ID NO: 1163 | Nga05827 | 935.4866 | 1116.1801 | beta-ketoacyl synthase |
| SEQ ID NO: 1164 | Nga04858.2 | 142.8571 | 152.42417 | endoribonuclease |
| SEQ ID NO: 1165 | Nga04857.02 | 2722.667 | 2415.8524 | signal peptidase complex catalytic subunit sec11a |
| SEQ ID NO: 1166 | Nga05839 | 803.9807 | 1238.7283 | atp-binding cassette |
| SEQ ID NO: 1167 | Nga20872.1 | 585.3081 | 720.01687 | ubiquitin carboxyl-terminal hydrolase 10 |
| SEQ ID NO: 1168 | Nga06401 | 1986.053 | 1589.3474 | pre-mrna-processing factor 17 |
| SEQ ID NO: 1169 | Nga06400 | 283.3333 | 252.75459 | predicted protein [Phaeodactylum tricornutum CCAP 1055/1] |
| SEQ ID NO: 1170 | Nga01885.02 | 3082.192 | 1211.3874 | ---NA--- |
| SEQ ID NO: 1171 | Nga06404 | 977.8963 | 1145.9822 | tryptophanyl-trna synthetase |
| SEQ ID NO: 1172 | Nga06406.1 | 4746.489 | 4117.57 | fatty-acyl |
| SEQ ID NO: 1173 | Nga01884.2 | 524.6727 | 603.25113 | s-adenosyl-l-methionine-dependent methyltransferase domain-containing protein |
| SEQ ID NO: 1174 | Nga06405 | 163.242 | 187.34012 | non-ribosomal peptide synthase |
| SEQ ID NO: 1175 | Nga03329 | 200 | 248.3512 | peroxin 3 |
| SEQ ID NO: 1176 | Nga03326 | 1255.692 | 1327.3252 | seryl-trna synthetase |
| SEQ ID NO: 1177 | Nga03321 | 4297.498 | 4343.5557 | ---NA--- |
| SEQ ID NO: 1178 | Nga03320 | 964.2276 | 1012.7797 | conserved unknown protein [Ectocarpus siliculosus] |
| SEQ ID NO: 1179 | Nga03318 | 475.5678 | 547.95385 | protein |
| SEQ ID NO: 1180 | Nga03330 | 610.2362 | 588.52868 | ---NA--- |
| SEQ ID NO: 1181 | Nga03325 | 591.8367 | 502.5616 | thioredoxin domain containing 9 |
| SEQ ID NO: 1182 | Nga03322.01 | 2959.641 | 2797.9496 | ubiquitin-conjugating enzyme |
| SEQ ID NO: 1183 | Nga03328 | 141.3502 | 107.40927 | dna binding protein |
| SEQ ID NO: 1184 | Nga03317.1 | 646.7331 | 730.55312 | splicing factor subunit 49kda |
| SEQ ID NO: 1185 | Nga03319 | 493.7076 | 494.95297 | protein |
| SEQ ID NO: 1186 | Nga03327 | 50.05688 | 65.314447 | uncharacterized protein |
| SEQ ID NO: 1187 | Nga03324 | 371.7949 | 441.62615 | s-adenosylmethionine mitochondrial carrier protein |
| SEQ ID NO: 1188 | Nga03323 | 1321.357 | 1457.2848 | radical sam cfr family |
| SEQ ID NO: 1189 | Nga05176 | 1786.078 | 1919.108 | atp-dependent clp protease proteolytic subunit |
| SEQ ID NO: 1190 | Nga05177 | 327.8167 | 435.30946 | serine hydroxymethyltransferase |
| SEQ ID NO: 1191 | Nga21108 | 173.3615 | 160.30946 | protein arginine n- |
| SEQ ID NO: 1192 | Nga20154 | 198.3095 | 174.66971 | protein arginine n-methyltransferase 5 |
| SEQ ID NO: 1193 | Nga05179 | 359.7734 | 452.11464 | methionyl-trna formyltransferase |
| SEQ ID NO: 1194 | Nga05181 | 362.5378 | 356.7145 | anaphase-promoting complex subunit 11 |
| SEQ ID NO: 1195 | Nga05175 | 582.3666 | 676.07872 | conserved unknown protein [Ectocarpus siliculosus] |
| SEQ ID NO: 1196 | Nga05178 | 230.9368 | 231.61585 | voltage-gated ion channel superfamily |
| SEQ ID NO: 1197 | Nga05180 | 322.4044 | 366.99729 | ---NA--- |
| SEQ ID NO: 1198 | Nga00607 | 1118.23 | 1343.6321 | ferredoxin-dependent glutamate synthase |
| SEQ ID NO: 1199 | Nga00603 | 1680.412 | 1756.998 | mitochondrial import inner membrane translocase subunit tim23 |
| SEQ ID NO: 1200 | Nga00608 | 747.0862 | 761.29378 | subfamily member 9 |
| SEQ ID NO: 1201 | Nga00617.01 | 240.0794 | 208.47955 | hexose-6-phosphate dehydrogenase (glucose 1-dehydrogenase) |
| SEQ ID NO: 1202 | Nga21227.1 | 293.5636 | 255.07864 | hexose-6-phosphate dehydrogenase (glucose 1-dehydrogenase) |
| SEQ ID NO: 1203 | Nga00609 | 563.7025 | 540.77201 | folate biopterin transporter |

FIGURE 24 S

| # | Nga model | +N rpkb | -N rpkb | GO |
|---|---|---|---|---|
| SEQ ID NO: 1204 | Nga00601.01 | 1153.053 | 973.70791 | protein |
| SEQ ID NO: 1205 | Nga00619 | 434.903 | 414.08943 | hypothetical protein AURANDRAFT_66563 [Aureococcus anophagefferens] |
| SEQ ID NO: 1206 | Nga00627 | 1028.249 | 1389.2322 | ---NA--- |
| SEQ ID NO: 1207 | Nga00602 | 2057.908 | 1588.8055 | short-chain dehydrogenase reductase acting with nad or nadp as acceptor |
| SEQ ID NO: 1208 | Nga20886 | 612.3596 | 702.88494 | n-acetylglucosaminylphosphatidylinositol de-n-acetylase family protein |
| SEQ ID NO: 1209 | Nga00612 | 2266.667 | 2563.6537 | atp-dependent clp protease proteolytic subunit |
| SEQ ID NO: 1210 | Nga20353 | 1054.28 | 893.27225 | n-acetylglucosaminylphosphatidylinositol de-n-acetylase family protein |
| SEQ ID NO: 1211 | Nga20647 | 79.09605 | 73.439589 | hypothetical protein AURANDRAFT_66563 [Aureococcus anophagefferens] |
| SEQ ID NO: 1212 | Nga21169 | 119.469 | 119.82676 | hypothetical protein AURANDRAFT_69090 [Aureococcus anophagefferens] |
| SEQ ID NO: 1213 | Nga20614 | 283.7838 | 204.93615 | hypothetical protein AURANDRAFT_66563 [Aureococcus anophagefferens] |
| SEQ ID NO: 1214 | Nga00653 | 1924.554 | 1907.9182 | proteasome component domain protein |
| SEQ ID NO: 1215 | Nga00604 | 957.2471 | 696.92945 | glutathione peroxidase |
| SEQ ID NO: 1216 | Nga00615 | 258.2799 | 247.37314 | phosphatidylinositol kinase |
| SEQ ID NO: 1217 | Nga00611 | 6168.681 | 6815.1069 | exo-beta- -glucanase |
| SEQ ID NO: 1218 | Nga00620 | 2981.685 | 3436.1926 | hypothetical protein DFA_07107 [Dictyostelium fasciculatum] |
| SEQ ID NO: 1219 | Nga00616 | 2996.366 | 2567.17 | ---NA--- |
| SEQ ID NO: 1220 | Nga00600 | 2286.137 | 1933.5212 | fructose- -bisphosphatase |
| SEQ ID NO: 1221 | Nga00625 | 457.0528 | 463.51145 | protein kinase |
| SEQ ID NO: 1222 | Nga00598 | 825.7669 | 688.48489 | 30s ribosomal protein s6 |
| SEQ ID NO: 1223 | Nga00599 | 1840.718 | 1780.6835 | dna binding protein |
| SEQ ID NO: 1224 | Nga00623 | 1570.136 | 1499.8624 | ---NA--- |
| SEQ ID NO: 1225 | Nga00618.1 | 305.6332 | 288.66042 | conserved unknown protein putative [Albugo laibachii Nc14] |
| SEQ ID NO: 1226 | Nga00606 | 375.3056 | 354.89816 | ---NA--- |
| SEQ ID NO: 1227 | Nga00613 | 230.1943 | 255.83104 | protein |
| SEQ ID NO: 1228 | Nga00610 | 2349.867 | 2328.8085 | protein |
| SEQ ID NO: 1229 | Nga00622 | 286.2903 | 323.22303 | atp-binding cassette superfamily |
| SEQ ID NO: 1230 | Nga00624 | 1312.399 | 1465.244 | fumarylacetoacetase |
| SEQ ID NO: 1231 | Nga00614 | 438.2494 | 563.04786 | atp-binding cassette superfamily |
| SEQ ID NO: 1232 | Nga00621 | 1619.741 | 1482.8736 | fumarylacetoacetate hydrolase |
| SEQ ID NO: 1233 | Nga00626 | 938.6503 | 881.65053 | ---NA--- |
| SEQ ID NO: 1234 | Nga20007.1 | 373.1988 | 415.18765 | butyrylcholinesterase precursor |
| SEQ ID NO: 1235 | Nga05927 | 1015.251 | 931.01479 | aldose 1- |
| SEQ ID NO: 1236 | Nga05926 | 308.046 | 328.70547 | u1 small nuclear |
| SEQ ID NO: 1237 | Nga20285 | 213.6752 | 198.12997 | e3 ubiquitin-protein ligase ubr2 |
| SEQ ID NO: 1238 | Nga21181 | 100.9174 | 69.565482 | ---NA--- |
| SEQ ID NO: 1239 | Nga21105 | 338.1309 | 410.05701 | protein |
| SEQ ID NO: 1240 | Nga20023 | 67.96117 | 73.617841 | cell cycle switch protein |
| SEQ ID NO: 1241 | Nga21053 | 47.24409 | 85.294011 | protein |
| SEQ ID NO: 1242 | Nga05925 | 1973.97 | 1978.488 | ---NA--- |
| SEQ ID NO: 1243 | Nga20754 | 269.9115 | 196.51589 | golgi transport complex subunit cog6 |
| SEQ ID NO: 1244 | Nga20347 | 134.6154 | 156.23566 | component of oligomeric golgi complex 6 |
| SEQ ID NO: 1245 | Nga20223 | 221.8845 | 238.70657 | component of oligomeric golgi complex 6 |
| SEQ ID NO: 1246 | Nga21133 | 305.2109 | 263.41669 | conserved unknown protein [Ectocarpus siliculosus] |
| SEQ ID NO: 1247 | Nga05930 | 325.5287 | 347.71482 | protein |
| SEQ ID NO: 1248 | Nga05924 | 2836.425 | 3850.6866 | phosphoinositol transporter |
| SEQ ID NO: 1249 | Nga05928 | 1358.41 | 1484.0636 | chaperonin containing tcp1 theta subunit |
| SEQ ID NO: 1250 | Nga05929 | 472.4221 | 488.36446 | pre-mrna-splicing factor cwc25-like protein |
| SEQ ID NO: 1251 | Nga05229.2 | 755.8411 | 843.21832 | glycosyl hydrolase family 81 protein |
| SEQ ID NO: 1252 | Nga20860.1 | 1766.687 | 2124.0141 | isovaleryl- dehydrogenase |
| SEQ ID NO: 1253 | Nga05995.1 | 1085.29 | 843.36289 | peptidyl-prolyl cis-trans isomerase |
| SEQ ID NO: 1254 | Nga20235.1 | 36 | 38.996422 | protein |
| SEQ ID NO: 1255 | Nga06005 | 343.5115 | 223.26196 | mekhla domain protein |
| SEQ ID NO: 1256 | Nga20456.1 | 69.29134 | 51.176407 | ribokinase |
| SEQ ID NO: 1257 | Nga05996.1 | 576.412 | 509.22792 | cytosolic phosphoglucose isomerase |
| SEQ ID NO: 1258 | Nga05999 | 807.0761 | 793.98589 | protein |
| SEQ ID NO: 1259 | Nga06000 | 155.6225 | 174.01348 | protein |
| SEQ ID NO: 1260 | Nga05998 | 10922.08 | 12835.351 | nadp-dependent glyceraldehyde-3-phosphate dehydrogenase |

FIGURE 24 T

| # | Nga model | +N rpkb | -N rpkb | GO |
|---|---|---|---|---|
| SEQ ID NO: 1261 | Nga20596.1 | 62.0155 | 100.76595 | vacuolar protein sorting-associated |
| SEQ ID NO: 1262 | Nga05973 | 1112.971 | 951.79551 | adenylate kinase |
| SEQ ID NO: 1263 | Nga20598 | 1377.953 | 1264.0572 | adenylate kinase 3 |
| SEQ ID NO: 1264 | Nga20884 | 531.3653 | 636.54983 | hsp70-binding protein 1-like |
| SEQ ID NO: 1265 | Nga20777 | 426.1662 | 524.42515 | vacuolar protein sorting-associated |
| SEQ ID NO: 1266 | Nga05970 | 704.0404 | 827.19683 | conserved unknown protein [Ectocarpus siliculosus] |
| SEQ ID NO: 1267 | Nga05967 | 1652.556 | 1988.2361 | sorting nexin-29-like |
| SEQ ID NO: 1268 | Nga05972 | 250 | 145.07597 | ---NA--- |
| SEQ ID NO: 1269 | Nga20553 | 443.4524 | 399.76491 | cathepsin a |
| SEQ ID NO: 1270 | Nga05971 | 500.8013 | 481.72663 | protein |
| SEQ ID NO: 1271 | Nga02181.2 | 494.4148 | 529.25369 | vesicle transport through interaction with t-snares homolog 1a |
| SEQ ID NO: 1272 | Nga05969 | 200.3968 | 200.59888 | deoxyribodipyrimidine photo-lyase |
| SEQ ID NO: 1273 | Nga05855 | 67.96117 | 71.865035 | pdx1 c-terminal inhibiting factor 1 |
| SEQ ID NO: 1274 | Nga20675 | 37.73585 | 51.095941 | ---NA--- |
| SEQ ID NO: 1275 | Nga05841 | 17633.25 | 17364.735 | iron-sulfur cluster scaffold homolog ( coli) |
| SEQ ID NO: 1276 | Nga21174 | 46.43963 | 73.78064 | ---NA--- |
| SEQ ID NO: 1277 | Nga05840 | 2179.762 | 1240.5608 | selenoprotein h |
| SEQ ID NO: 1278 | Nga05842 | 1313.021 | 1450.7987 | transferring glycosyl |
| SEQ ID NO: 1279 | Nga20115 | 108.7786 | 109.56374 | phd zinc finger-containing protein |
| SEQ ID NO: 1280 | Nga05843 | 163.8955 | 137.65562 | activating signal cointegrator 1 complex subunit 3 |
| SEQ ID NO: 1281 | Nga05847 | 210.6383 | 186.685 | set domain-containing protein |
| SEQ ID NO: 1282 | Nga05846 | 3655.148 | 4091.9572 | ---NA--- |
| SEQ ID NO: 1283 | Nga20450 | 166.6667 | 124.12056 | glycoside hydrolase family 31 protein |
| SEQ ID NO: 1284 | Nga05844 | 221.7544 | 229.56958 | glycoside hydrolase family 31 protein |
| SEQ ID NO: 1285 | Nga05845 | 739.6789 | 702.48715 | nop16_tetng ame: full=nucleolar protein 16 |
| SEQ ID NO: 1286 | Nga05219 | 2880.379 | 2944.8675 | ---NA--- |
| SEQ ID NO: 1287 | Nga05215 | 414.8148 | 470.07004 | protein |
| SEQ ID NO: 1288 | Nga05216 | 459.7701 | 343.64663 | ---NA--- |
| SEQ ID NO: 1289 | Nga05221 | 211.0672 | 228.63515 | serine threonine protein kinase |
| SEQ ID NO: 1290 | Nga05209 | 1098.325 | 912.03091 | ---NA--- |
| SEQ ID NO: 1291 | Nga05220 | 1600.614 | 1757.6899 | myb dna binding protein transcription factor-like protein |
| SEQ ID NO: 1292 | Nga05213 | 651.9174 | 724.81878 | conserved unknown protein [Ectocarpus siliculosus] |
| SEQ ID NO: 1293 | Nga05211 | 982.151 | 1063.4036 | cad protein |
| SEQ ID NO: 1294 | Nga05214 | 13241.8 | 12013.542 | linoleoyl- desaturase |
| SEQ ID NO: 1295 | Nga20988 | 542.7215 | 812.42546 | ---NA--- |
| SEQ ID NO: 1296 | Nga05217 | 203.4588 | 211.57774 | ---NA--- |
| SEQ ID NO: 1297 | Nga05212 | 1979.616 | 1979.4347 | ---NA--- |
| SEQ ID NO: 1298 | Nga05218 | 150.8333 | 187.76055 | potential inositol polyphosphate-5-phosphatase inp51p |
| SEQ ID NO: 1299 | Nga05210 | 1682.886 | 1932.6154 | glutathione reductase |
| SEQ ID NO: 1300 | Nga20980 | 2636.542 | 2921.965 | conserved unknown protein [Ectocarpus siliculosus] |
| SEQ ID NO: 1301 | Nga02763 | 15.65558 | 18.371874 | kinesin family-like protein |
| SEQ ID NO: 1302 | Nga02753 | 706.2147 | 625.7665 | holliday junction resolvase |
| SEQ ID NO: 1303 | Nga02749 | 810.3976 | 759.92008 | peptidase d |
| SEQ ID NO: 1304 | Nga02764 | 38.41932 | 49.54418 | ---NA--- |
| SEQ ID NO: 1305 | Nga02750 | 776.1194 | 732.93441 | bola-like protein |
| SEQ ID NO: 1306 | Nga02752 | 719.4139 | 897.53669 | rimp_proma ame: full=ribosome maturation factor rimp |
| SEQ ID NO: 1307 | Nga02754 | 912.7726 | 740.15362 | rna polymerase sigma factor |
| SEQ ID NO: 1308 | Nga02748 | 747.8788 | 628.93219 | suppressor enhancer of lin-12 protein 9 |
| SEQ ID NO: 1309 | Nga02751 | 151.9644 | 184.68777 | dna mismatch repair protein |
| SEQ ID NO: 1310 | Nga02745 | 10661.19 | 9104.0154 | ---NA--- |
| SEQ ID NO: 1311 | Nga20177 | 462.6866 | 396.64686 | peptidyl-prolyl cis-trans isomerase cyclophilin type |
| SEQ ID NO: 1312 | Nga02755 | 635.0168 | 441.31753 | protein |
| SEQ ID NO: 1313 | Nga02746 | 639.379 | 613.85805 | chaperonin |
| SEQ ID NO: 1314 | Nga02747 | 2917.146 | 2970.4793 | histone family protein dna-binding protein |
| SEQ ID NO: 1315 | Nga01017 | 268.5851 | 361.94387 | ribosome maturation protein sbds |
| SEQ ID NO: 1316 | Nga01016 | 82.91457 | 81.6508 | queuine trna-ribosyltransferase |
| SEQ ID NO: 1317 | Nga01014 | 6748.933 | 6773.2185 | lipocalin protein |
| SEQ ID NO: 1318 | Nga01019 | 443.4524 | 498.09418 | ---NA--- |
| SEQ ID NO: 1319 | Nga01018 | 596.5217 | 570.81719 | conserved hypothetical protein [Phytophthora infestans T30-4] |
| SEQ ID NO: 1320 | Nga01021 | 52.17391 | 65.935979 | ---NA--- |
| SEQ ID NO: 1321 | Nga01020 | 449.012 | 465.2272 | ubiquitin protein ligase e3a |
| SEQ ID NO: 1322 | Nga01015 | 10992.84 | 9131.288 | glycerophosphoryl diester phosphodiesterase |
| SEQ ID NO: 1323 | Nga06237 | 77.97271 | 105.57836 | atpbinding cassette superfamily |
| SEQ ID NO: 1324 | Nga04419.02 | 1411.924 | 1395.5811 | trigger factor |

FIGURE 24 U

| # | Nga model | +N rpkb | -N rpkb | GO |
|---|---|---|---|---|
| SEQ ID NO: 1325 | Nga06233 | 465.5397 | 615.56987 | adp-ribose pyrophosphatase |
| SEQ ID NO: 1326 | Nga06234 | 400.6734 | 322.78183 | potential dna binding component of sbf |
| SEQ ID NO: 1327 | Nga06236 | 22.55639 | 54.297441 | ---NA--- |
| SEQ ID NO: 1328 | Nga06235.01 | 963.3508 | 921.59956 | signal peptidase |
| SEQ ID NO: 1329 | Nga20648 | 105.5046 | 149.06889 | hypothetical protein PTSG_00045 [Salpingoeca sp. ATCC 50818] |
| SEQ ID NO: 1330 | Nga20905 | 239.1304 | 259.0342 | ring finger-like protein |
| SEQ ID NO: 1331 | Nga06622 | 6324.859 | 6432.084 | rpel repeat protein |
| SEQ ID NO: 1332 | Nga06623 | 350.3528 | 252.25996 | amine oxidase |
| SEQ ID NO: 1333 | Nga06617 | 157.5 | 183.24708 | protein |
| SEQ ID NO: 1334 | Nga06619 | 63.88889 | 48.143731 | c2h2 finger domain-containing protein |
| SEQ ID NO: 1335 | Nga01978.02 | 1568.285 | 1993.2907 | geranyl diphosphate synthase |
| SEQ ID NO: 1336 | Nga06620 | 74.25541 | 87.065315 | sulphonylurea receptor 2b |
| SEQ ID NO: 1337 | Nga20618.1 | 318.75 | 230.18721 | ---NA--- |
| SEQ ID NO: 1338 | Nga01980.02 | 748.1172 | 702.51574 | alpha beta fold family protein |
| SEQ ID NO: 1339 | Nga01981.02 | 2059.333 | 2352.2456 | ---NA--- |
| SEQ ID NO: 1340 | Nga05980.01 | 464.0523 | 445.02608 | gcn5-like n-acetyltransferase |
| SEQ ID NO: 1341 | Nga21036.1 | 568.5686 | 455.41367 | egl nine homolog 1 ( elegans) |
| SEQ ID NO: 1342 | Nga05979.01 | 323.0303 | 344.9936 | peptidase m1 membrane alanine aminopeptidase |
| SEQ ID NO: 1343 | Nga01175 | 200 | 244.90506 | ---NA--- |
| SEQ ID NO: 1344 | Nga01173 | 12800.93 | 14910.545 | ---NA--- |
| SEQ ID NO: 1345 | Nga20181 | 392.6302 | 352.36072 | mkiaa0609 protein |
| SEQ ID NO: 1346 | Nga01174 | 424.8826 | 419.56244 | protein |
| SEQ ID NO: 1347 | Nga01172 | 289.9408 | 391.82581 | protein phosphatase |
| SEQ ID NO: 1348 | Nga02657 | 524.1433 | 650.44655 | methyltransfer with n-terminal ankyrin repeats |
| SEQ ID NO: 1349 | Nga20176 | 379.3478 | 346.16389 | sel-1 suppressor of lin-12-like 2 ( elegans) |
| SEQ ID NO: 1350 | Nga02652 | 563.5684 | 562.44839 | carboxylesterase type b |
| SEQ ID NO: 1351 | Nga02659 | 870.4581 | 867.61391 | ---NA--- |
| SEQ ID NO: 1352 | Nga02649 | 279.2128 | 283.7993 | s-adenosylmethionine-dependent methyltransferase methyltransferase thiopurine s-methyltransferase |
| SEQ ID NO: 1353 | Nga02658 | 4052.305 | 3925.7627 | uncharacterized oxidoreductase ycsn |
| SEQ ID NO: 1354 | Nga02647 | 2148.564 | 2136.04 | fibronectin type iii domain protein |
| SEQ ID NO: 1355 | Nga20787 | 2104.753 | 2365.419 | -related protein kinase 2 |
| SEQ ID NO: 1356 | Nga02656 | 186.4407 | 147.49118 | protein |
| SEQ ID NO: 1357 | Nga02654 | 853.264 | 808.5143 | protein |
| SEQ ID NO: 1358 | Nga02651.01 | 1413.223 | 1125.0116 | 2c-methyl-d-erythritol -cyclodiphosphate synthase |
| SEQ ID NO: 1359 | Nga02655 | 701.4925 | 579.88046 | beta- -glucan-binding |
| SEQ ID NO: 1360 | Nga02653 | 806.6784 | 670.12012 | heterogeneous nuclear |
| SEQ ID NO: 1361 | Nga02646 | 3516.278 | 3519.7088 | ---NA--- |
| SEQ ID NO: 1362 | Nga02648 | 1573.273 | 1899.4608 | sphinganine c4-hydroxylase |
| SEQ ID NO: 1363 | Nga02650 | 1679.654 | 1795.4251 | protein |
| SEQ ID NO: 1364 | Nga05581 | 2001.678 | 3129.7464 | ---NA--- |
| SEQ ID NO: 1365 | Nga05579 | 5212.963 | 5971.1599 | kid repeat family protein |
| SEQ ID NO: 1366 | Nga05577 | 1721.336 | 1446.1119 | conserved protein |
| SEQ ID NO: 1367 | Nga02025.02 | 940.1709 | 742.98738 | signal peptidase complex subunit 1 |
| SEQ ID NO: 1368 | Nga02024.2 | 257.9473 | 334.51366 | histone acetyltransferase |
| SEQ ID NO: 1369 | Nga05578 | 1580.867 | 1853.8644 | peptidyl-prolyl cis-trans |
| SEQ ID NO: 1370 | Nga21120.1 | 134.6154 | 160.24171 | bromodomain phd finger transcription factor |
| SEQ ID NO: 1371 | Nga05373 | 624.8042 | 604.9706 | rna polymerase ii second largest subunit |
| SEQ ID NO: 1372 | Nga05374 | 452.2989 | 611.96492 | guanine nucleotide binding 2 |
| SEQ ID NO: 1373 | Nga05375 | 631.5789 | 614.46604 | protein |
| SEQ ID NO: 1374 | Nga05372 | 14386.19 | 12269.282 | expressed unknown protein [Ectocarpus siliculosus] |
| SEQ ID NO: 1375 | Nga01064 | 580.0866 | 517.38879 | actin related protein |
| SEQ ID NO: 1376 | Nga01063 | 400.1883 | 403.91774 | cop9 signalosome complex subunit 6a |
| SEQ ID NO: 1377 | Nga01066.01 | 143.6782 | 143.1861 | ---NA--- |
| SEQ ID NO: 1378 | Nga01065.01 | 307.4627 | 219.88032 | ---NA--- |
| SEQ ID NO: 1379 | Nga01062 | 6518.284 | 5480.92 | 30s ribosomal protein s15 |
| SEQ ID NO: 1380 | Nga00951 | 141.7323 | 132.20572 | ---NA--- |
| SEQ ID NO: 1381 | Nga00950 | 8120.546 | 7621.2365 | ribosomal protein l15 |
| SEQ ID NO: 1382 | Nga21306 | 9.52381 | 10.316514 | dynein heavy chain |
| SEQ ID NO: 1383 | Nga00952 | 1712.367 | 1980.7217 | like protein |
| SEQ ID NO: 1384 | Nga00953 | 726.1905 | 797.38054 | ---NA--- |
| SEQ ID NO: 1385 | Nga06154 | 125.3071 | 113.55769 | cyclin delta-3 |
| SEQ ID NO: 1386 | Nga06151 | 6808.732 | 6481.3873 | histone h2a isoform 2 |
| SEQ ID NO: 1387 | Nga20642 | 214.8438 | 186.18083 | regulator of ribonuclease activity a |

FIGURE 24 V

| # | Nga model | +N rpkb | -N rpkb | GO |
|---|---|---|---|---|
| SEQ ID NO: 1388 | Nga20731 | 341.7722 | 370.21919 | regulator of ribonuclease activity a |
| SEQ ID NO: 1389 | Nga02495.02 | 994.5227 | 955.24621 | heme steroid binding domain-containing |
| SEQ ID NO: 1390 | Nga02497.02 | 1070.802 | 1097.487 | protein |
| SEQ ID NO: 1391 | Nga20138 | 594.3971 | 719.07734 | n-acetyltransferase subunit |
| SEQ ID NO: 1392 | Nga02499.02 | 9351.421 | 9217.2852 | ribosomal protein l35a |
| SEQ ID NO: 1393 | Nga06149 | 1127.001 | 1101.1294 | mbr-related protein |
| SEQ ID NO: 1394 | Nga20436.1 | 76.31579 | 51.311081 | ---NA--- |
| SEQ ID NO: 1395 | Nga20650.1 | 41.18993 | 49.575924 | retinal pigment epithelial membrane protein |
| SEQ ID NO: 1396 | Nga02505.2 | 127.5322 | 75.806427 | nucleolar mif4g domain-containing protein 1 |
| SEQ ID NO: 1397 | Nga06559 | 1746.078 | 1799.0179 | methyltransferase type 11 |
| SEQ ID NO: 1398 | Nga06564 | 1260.7 | 1171.7472 | 26s proteasome non-atpase regulatory |
| SEQ ID NO: 1399 | Nga06565 | 920.6939 | 1289.9477 | purine nucleoside phosphorylase |
| SEQ ID NO: 1400 | Nga06567.01 | 13.7931 | 7.4705789 | ---NA--- |
| SEQ ID NO: 1401 | Nga06562 | 291.2874 | 296.93851 | polyadenylate-binding protein 1-like |
| SEQ ID NO: 1402 | Nga01530.02 | 735.0427 | 701.58172 | tpr repeat-containing protein |
| SEQ ID NO: 1403 | Nga07224.2 | 147.4954 | 165.80111 | protein |
| SEQ ID NO: 1404 | Nga06563 | 174.4548 | 115.85991 | transmembrane protein 184c |
| SEQ ID NO: 1405 | Nga06561 | 1135.762 | 903.89057 | glutamine cyclotransferase |
| SEQ ID NO: 1406 | Nga03762.02 | 964.1898 | 915.4636 | subunit of proteaseome activator |
| SEQ ID NO: 1407 | Nga20282.1 | 245.4545 | 256.03711 | cgi-01 protein isoform 1 |
| SEQ ID NO: 1408 | Nga20207.1 | 175.3813 | 175.81902 | methyltransferase-like protein 13 |
| SEQ ID NO: 1409 | Nga05604 | 312.7854 | 351.18543 | predicted protein [Thalassiosira pseudonana CCMP1335] |
| SEQ ID NO: 1410 | Nga05605 | 404.9409 | 335.09278 | soluble nsf attachment protein receptor |
| SEQ ID NO: 1411 | Nga05607 | 240.73 | 167.56863 | kinesin family member 11 |
| SEQ ID NO: 1412 | Nga05606 | 5832.871 | 7229.1029 | aconitate mitochondrial |
| SEQ ID NO: 1413 | Nga05610 | 190.9465 | 187.22562 | cyclin h |
| SEQ ID NO: 1414 | Nga20964.1 | 406.8323 | 363.3207 | hsbp1-like protein |
| SEQ ID NO: 1415 | Nga20264 | 586.6983 | 611.51686 | fumarate hydratase |
| SEQ ID NO: 1416 | Nga20993 | 755.597 | 679.04217 | 26s protease regulatory subunit 6a |
| SEQ ID NO: 1417 | Nga20186 | 792.8496 | 741.51976 | 26s protease regulatory subunit 6a |
| SEQ ID NO: 1418 | Nga04755.02 | 367.3966 | 342.62874 | short-chain dehydrogenase reductase sdr |
| SEQ ID NO: 1419 | Nga05609 | 333.1671 | 327.40138 | wd40 domain-containing protein |
| SEQ ID NO: 1420 | Nga20331 | 168.26 | 130.48516 | ---NA--- |
| SEQ ID NO: 1421 | Nga20740 | 100 | 93.880275 | ---NA--- |
| SEQ ID NO: 1422 | Nga05403 | 292.6182 | 326.75352 | zinc cchc domain containing 17 |
| SEQ ID NO: 1423 | Nga05396 | 1669.568 | 1421.4024 | glu leu phe val dehydrogenase |
| SEQ ID NO: 1424 | Nga05399 | 1183.333 | 1113.3238 | d-glycerate 3-kinase |
| SEQ ID NO: 1425 | Nga05393 | 936.8351 | 1018.4128 | rna pseudouridylate synthase domain-containing protein 1 |
| SEQ ID NO: 1426 | Nga05395 | 641.9647 | 651.52718 | phosphatidylinositol-4-phosphate 5-kinase |
| SEQ ID NO: 1427 | Nga05397 | 1760.386 | 1628.514 | electron transfer alpha subunit |
| SEQ ID NO: 1428 | Nga05398 | 3380.265 | 3922.8945 | glucokinase |
| SEQ ID NO: 1429 | Nga05400.1 | 1037.525 | 1019.0529 | proliferation-associated protein 2g4 |
| SEQ ID NO: 1430 | Nga05401 | 384.535 | 381.45229 | ---NA--- |
| SEQ ID NO: 1431 | Nga04774.02 | 8119.114 | 8316.7961 | mosc domain protein |
| SEQ ID NO: 1432 | Nga20854 | 222.5352 | 186.13316 | hypothetical protein CHLNCDRAFT_136762 [Chlorella variabilis] |
| SEQ ID NO: 1433 | Nga05402 | 195.7511 | 266.28816 | hypothetical protein VOLCADRAFT_105929 [Volvox carteri f. nagariensis] |
| SEQ ID NO: 1434 | Nga05438 | 589.2099 | 832.44274 | protein |
| SEQ ID NO: 1435 | Nga05442 | 384.7981 | 398.81535 | udp-n-acetylglucosamine transferase subunit alg13 homolog isoform 6 |
| SEQ ID NO: 1436 | Nga02620 | 138.6139 | 107.25089 | ---NA--- |
| SEQ ID NO: 1437 | Nga05446 | 517.0732 | 449.14578 | ---NA--- |
| SEQ ID NO: 1438 | Nga05444 | 850.385 | 931.29519 | protein |
| SEQ ID NO: 1439 | Nga05440 | 10219.82 | 8949.7022 | adp-ribosylation factor |
| SEQ ID NO: 1440 | Nga05443 | 258.4615 | 373.29908 | ---NA--- |
| SEQ ID NO: 1441 | Nga05439 | 2086.19 | 2344.8544 | ---NA--- |
| SEQ ID NO: 1442 | Nga05445 | 56 | 8.6658715 | ---NA--- |
| SEQ ID NO: 1443 | Nga05441 | 3148.618 | 3215.5908 | peptidase caspase catalytic subunit p20 |
| SEQ ID NO: 1444 | Nga06036.1 | 598.4556 | 518.61393 | protein |
| SEQ ID NO: 1445 | Nga06034 | 2208.706 | 2585.6801 | carboxyl transferase |
| SEQ ID NO: 1446 | Nga06033.01 | 1056.995 | 1318.0282 | gtp-binding protein |
| SEQ ID NO: 1447 | Nga06037 | 1366.412 | 1174.1925 | 26s protease regulatory subunit s10b |
| SEQ ID NO: 1448 | Nga06038 | 150.5532 | 178.19433 | rho gtpase activating protein 2 |
| SEQ ID NO: 1449 | Nga06035 | 174.6287 | 157.85384 | nad synthetase |
| SEQ ID NO: 1450 | Nga01543 | 257.8445 | 255.66094 | alcohol dehydrogenase |
| SEQ ID NO: 1451 | Nga01546.1 | 686.0405 | 739.20739 | solute carrier family 29 (nucleoside transporters) member 2 |

FIGURE 24 W

| # | Nga model | +N rpkb | -N rpkb | GO |
|---|---|---|---|---|
| SEQ ID NO: 1452 | Nga20142 | 367.2727 | 392.59024 | phosphatidylinositol kinase |
| SEQ ID NO: 1453 | Nga01551 | 353.7778 | 435.21933 | phosphatidylinositol kinase (pik-5) |
| SEQ ID NO: 1454 | Nga01544 | 4987.429 | 4585.484 | peptidylprolyl isomerase f (cyclophilin f) |
| SEQ ID NO: 1455 | Nga01542 | 3103.521 | 2785.8946 | 3-oxoacyl-(acyl-carrier-protein) reductase |
| SEQ ID NO: 1456 | Nga01378 | 564.5798 | 829.07414 | folate-biopterin transporter family |
| SEQ ID NO: 1457 | Nga04873.2 | 4269.746 | 3098.8901 | ---NA--- |
| SEQ ID NO: 1458 | Nga01376.01 | 265.6514 | 284.09689 | flap endonuclease-1 |
| SEQ ID NO: 1459 | Nga01377.01 | 421.0526 | 445.23901 | flap endonuclease-1 |
| SEQ ID NO: 1460 | Nga01375.01 | 437.799 | 290.2445 | flap endonuclease 1 |
| SEQ ID NO: 1461 | Nga20676.1 | 24.19355 | 87.357576 | ---NA--- |
| SEQ ID NO: 1462 | Nga00777 | 140.4255 | 176.69774 | transcription factor |
| SEQ ID NO: 1463 | Nga00776 | 2372.871 | 2142.9331 | undecaprenyl diphosphate synthase |
| SEQ ID NO: 1464 | Nga00775 | 838.9313 | 785.55133 | anthranilate phosphoribosyltransferase |
| SEQ ID NO: 1465 | Nga00778 | 154.3568 | 176.19407 | ankyrin repeat-containing protein |
| SEQ ID NO: 1466 | Nga00774.01 | 7425.419 | 5973.5619 | light-harvesting protein |
| SEQ ID NO: 1467 | Nga00784 | 254.2735 | 296.26911 | short-chain dehydrogenase reductase sdr |
| SEQ ID NO: 1468 | Nga20471.1 | 391.0806 | 343.73633 | wd repeat and hmg-box dna-binding protein 1 |
| SEQ ID NO: 1469 | Nga20781.1 | 866.3559 | 771.8147 | protein |
| SEQ ID NO: 1470 | Nga05503.2 | 1697.917 | 1685.0306 | glycoprotease m22 family protein |
| SEQ ID NO: 1471 | Nga05893 | 5327.88 | 4818.8035 | beta alanine--pyruvate transaminase |
| SEQ ID NO: 1472 | Nga05506.02 | 360.9467 | 301.25441 | ---NA--- |
| SEQ ID NO: 1473 | Nga05892 | 759.6458 | 670.76915 | 3-phosphoinositide-dependent protein |
| SEQ ID NO: 1474 | Nga20875.1 | 1243.391 | 985.47627 | protein |
| SEQ ID NO: 1475 | Nga05502.02 | 1425.926 | 1289.8508 | peroxisomal -dienoyl- reductase |
| SEQ ID NO: 1476 | Nga05890 | 201.7837 | 138.87615 | udp-sugar transporter ust74c (fringe connection protein) |
| SEQ ID NO: 1477 | Nga05895.1 | 422.2846 | 434.61212 | ---NA--- |
| SEQ ID NO: 1478 | Nga05889 | 2055.18 | 2218.9218 | ribosomal rna small subunit methyltransferase g |
| SEQ ID NO: 1479 | Nga21035 | 1109.005 | 944.62107 | protein |
| SEQ ID NO: 1480 | Nga05499.02 | 1387.165 | 1469.0119 | peptidase dimerization domain-containing protein |
| SEQ ID NO: 1481 | Nga05500.02 | 1186.111 | 978.92252 | rna (guanine-9-)-methyltransferase domain-containing |
| SEQ ID NO: 1482 | Nga05888 | 762.2413 | 842.27226 | protein |
| SEQ ID NO: 1483 | Nga21122.1 | 467.1875 | 504.3808 | lysocardiolipin acyltransferase 1 |
| SEQ ID NO: 1484 | Nga06829.2 | 48.85057 | 54.472971 | protein shq1 homolog isoform 2 |
| SEQ ID NO: 1485 | Nga01353 | 398.7241 | 323.06977 | ---NA--- |
| SEQ ID NO: 1486 | Nga01351.01 | 1830.59 | 2111.6756 | eukaryotic translation initiation factor 3 subunit g |
| SEQ ID NO: 1487 | Nga01354 | 631.8052 | 557.13608 | expressed unknown protein [Ectocarpus siliculosus] |
| SEQ ID NO: 1488 | Nga02827.1 | 233.5827 | 222.40963 | ubx domain-containing protein 7 |
| SEQ ID NO: 1489 | Nga02825 | 2231.366 | 2354.8564 | gtp-binding protein ypt1 |
| SEQ ID NO: 1490 | Nga20157 | 193.7322 | 175.90979 | phosphatidylinositol- -trisphosphate 5-phosphatase 1 |
| SEQ ID NO: 1491 | Nga20958 | 1066.978 | 1097.5758 | protein arginine serine-rich 45 |
| SEQ ID NO: 1492 | Nga02828 | 106.1752 | 117.40154 | protein |
| SEQ ID NO: 1493 | Nga02822 | 927.1565 | 840.28499 | protein |
| SEQ ID NO: 1494 | Nga02823 | 2258.128 | 2118.4427 | nucleoside diphosphate kinase |
| SEQ ID NO: 1495 | Nga02824 | 358.4229 | 408.96287 | 5-enolpyruvylshikimate-3-phosphate synthase |
| SEQ ID NO: 1496 | Nga03090 | 663.3565 | 496.97525 | F-box protein, putative [Phytophthora infestans T30-4] |
| SEQ ID NO: 1497 | Nga21086 | 781.9473 | 798.32657 | protein sel-1 homolog 1 |
| SEQ ID NO: 1498 | Nga03087 | 716.271 | 821.67716 | ---NA--- |
| SEQ ID NO: 1499 | Nga03096 | 606.7416 | 585.32253 | aspartyl-trna synthetase |
| SEQ ID NO: 1500 | Nga03097 | 471.3764 | 602.96944 | pre-mrna-splicing factor slu7 |
| SEQ ID NO: 1501 | Nga03085 | 809.1658 | 809.80754 | otu-like cysteine type protease |
| SEQ ID NO: 1502 | Nga03089 | 1624.242 | 1744.1161 | conserved unknown protein [Ectocarpus siliculosus] |
| SEQ ID NO: 1503 | Nga03092 | 1117.212 | 1255.6426 | ribosomal rna assembly protein mis3 |
| SEQ ID NO: 1504 | Nga03094 | 334.2199 | 299.13774 | cullin 3 |
| SEQ ID NO: 1505 | Nga03099 | 532.9768 | 714.43237 | hypothetical protein Esi_0081_0011 [Ectocarpus siliculosus] |
| SEQ ID NO: 1506 | Nga03100 | 844.375 | 751.49355 | exodeoxyribonuclease iii |
| SEQ ID NO: 1507 | Nga07097.2 | 706.486 | 893.8014 | gtp-binding protein |
| SEQ ID NO: 1508 | Nga03098 | 654.8148 | 680.43139 | ---NA--- |
| SEQ ID NO: 1509 | Nga03084 | 669.507 | 630.29315 | gns1 sur4 family protein |
| SEQ ID NO: 1510 | Nga03095 | 1002.151 | 983.06392 | nad-dependent epimerase dehydratase |
| SEQ ID NO: 1511 | Nga03091 | 301.8242 | 418.56303 | serine threonine protein kinase |
| SEQ ID NO: 1512 | Nga03086 | 1336.815 | 975.75903 | ferredoxin (2fe-2s) |
| SEQ ID NO: 1513 | Nga03088 | 538.6289 | 486.80698 | cytochrome b-561 domain containing 2 |
| SEQ ID NO: 1514 | Nga05303 | 359.944 | 300.39261 | conserved unknown protein [Ectocarpus siliculosus] |
| SEQ ID NO: 1515 | Nga05301 | 1665.58 | 1779.094 | propionyl- alpha subunit |

FIGURE 24 X

| # | Nga model | +N rpkb | -N rpkb | GO |
|---|---|---|---|---|
| SEQ ID NO: 1516 | Nga05304 | 266.6667 | 212.74324 | atp-binding cassette sub-family b member mitochondrial |
| SEQ ID NO: 1517 | Nga20922 | 169.9346 | 304.4383 | abc transporter |
| SEQ ID NO: 1518 | Nga05297 | 2164.684 | 2012.6406 | mannitol dehydrogenase |
| SEQ ID NO: 1519 | Nga05302 | 236.4066 | 326.50668 | nudix hydrolase |
| SEQ ID NO: 1520 | Nga05298 | 5700.475 | 5767.4491 | white |
| SEQ ID NO: 1521 | Nga05299 | 3574.202 | 2930.6912 | endosomal p24a protein |
| SEQ ID NO: 1522 | Nga05300 | 10436.2 | 10902.839 | cazy family gt2 |
| SEQ ID NO: 1523 | Nga05305 | 53.23591 | 64.451289 | e3 ubiquitin-protein ligase shprh |
| SEQ ID NO: 1524 | Nga01228 | 1208.453 | 1194.575 | ---NA--- |
| SEQ ID NO: 1525 | Nga01227 | 187.5792 | 194.95465 | hypothetical protein PTSG_03392 [Salpingoeca sp. ATCC 50818] |
| SEQ ID NO: 1526 | Nga01225 | 8943.038 | 9082.9394 | vacuolar transporter chaperone |
| SEQ ID NO: 1527 | Nga01229 | 3633.406 | 3039.3994 | conserved unknown protein [Ectocarpus siliculosus] |
| SEQ ID NO: 1528 | Nga01226 | 1012.112 | 1167.7304 | hypothetical membrane spanning protein |
| SEQ ID NO: 1529 | Nga20334 | 196.2482 | 189.13608 | myb-like dna-binding domain-containing protein |
| SEQ ID NO: 1530 | Nga20421.1 | 323.8866 | 350.845 | ---NA--- |
| SEQ ID NO: 1531 | Nga01418.01 | 692.9023 | 666.07849 | protein |
| SEQ ID NO: 1532 | Nga01419.1 | 357.5143 | 406.42397 | cullin-associated and neddylation-dissociated 1 |
| SEQ ID NO: 1533 | Nga01416 | 413.7495 | 415.74985 | trna (5-methylaminomethyl-2-thiouridylate)-methyltransferase |
| SEQ ID NO: 1534 | Nga01417 | 1390.653 | 2177.9307 | lysine decarboxylase domain-containing protein |
| SEQ ID NO: 1535 | Nga01420 | 453.252 | 770.59325 | ---NA--- |
| SEQ ID NO: 1536 | Nga05988.1 | 2033.517 | 2206.4515 | protein |
| SEQ ID NO: 1537 | Nga05990 | 139.7038 | 131.65878 | kinesin-related protein klpa-like protein |
| SEQ ID NO: 1538 | Nga05989 | 1090.932 | 1097.1524 | aminopeptidase n |
| SEQ ID NO: 1539 | Nga05861 | 644.4159 | 522.84462 | ---NA--- |
| SEQ ID NO: 1540 | Nga05859 | 876.4143 | 903.16633 | s-adenosyl-methyltransferase |
| SEQ ID NO: 1541 | Nga05857 | 1561.716 | 1448.8418 | protein |
| SEQ ID NO: 1542 | Nga05863 | 150.3831 | 118.28417 | ---NA--- |
| SEQ ID NO: 1543 | Nga05862 | 8278.788 | 9992.0125 | ---NA--- |
| SEQ ID NO: 1544 | Nga05856 | 336.1763 | 322.58353 | udp-galactopyranose mutase |
| SEQ ID NO: 1545 | Nga20654 | 486.6221 | 336.92561 | protein |
| SEQ ID NO: 1546 | Nga05858 | 802.4901 | 826.98505 | transmembrane protein |
| SEQ ID NO: 1547 | Nga05860 | 857.9235 | 786.08452 | eukaryotic translation initiation factor 3 subunit 12 |
| SEQ ID NO: 1548 | Nga01028 | 72.07207 | 41.475173 | ---NA--- |
| SEQ ID NO: 1549 | Nga20866.1 | 1586.207 | 1755.586 | ---NA--- |
| SEQ ID NO: 1550 | Nga01029.1 | 376.3713 | 480.82789 | ---NA--- |
| SEQ ID NO: 1551 | Nga20896.1 | 343.0532 | 468.22462 | ---NA--- |
| SEQ ID NO: 1552 | Nga02089.02 | 2521.918 | 2368.0285 | rhamnose biosynthetic enzyme expressed |
| SEQ ID NO: 1553 | Nga02093.02 | 595.3109 | 560.94072 | short-chain dehydrogenase |
| SEQ ID NO: 1554 | Nga06174 | 582.5893 | 464.24312 | sys1_dicdi ame: full=protein sys1 homolog |
| SEQ ID NO: 1555 | Nga02090.2 | 59.20206 | 83.647409 | nudix hydrolase |
| SEQ ID NO: 1556 | Nga02091.02 | 212.4183 | 166.37907 | ---NA--- |
| SEQ ID NO: 1557 | Nga06178 | 358.871 | 339.23859 | abc transporter family protein |
| SEQ ID NO: 1558 | Nga20908 | 94.73684 | 148.23201 | ---NA--- |
| SEQ ID NO: 1559 | Nga20662 | 157.3034 | 97.369343 | ---NA--- |
| SEQ ID NO: 1560 | Nga06180 | 473.2824 | 446.52391 | ---NA--- |
| SEQ ID NO: 1561 | Nga20521 | 383.0645 | 464.45111 | protein |
| SEQ ID NO: 1562 | Nga21171 | 681.8811 | 621.77329 | conserved hypothetical protein [Phytophthora infestans T30-4] |
| SEQ ID NO: 1563 | Nga06529 | 233.8889 | 330.98815 | ribosome biogenesis protein nob1 |
| SEQ ID NO: 1564 | Nga06527 | 1435.414 | 1696.9093 | eukaryotic translation initiation factor 3 |
| SEQ ID NO: 1565 | Nga06538 | 373.581 | 394.61463 | pyridoxamine 5 -phosphate oxidase- fmn-binding |
| SEQ ID NO: 1566 | Nga06526 | 171.1045 | 1240.2708 | copper amine oxidase |
| SEQ ID NO: 1567 | Nga06532 | 600.795 | 589.90423 | ---NA--- |
| SEQ ID NO: 1568 | Nga06531 | 398.8285 | 407.22213 | inorganic phosphate |
| SEQ ID NO: 1569 | Nga20089 | 1202.669 | 1285.6063 | protein |
| SEQ ID NO: 1570 | Nga06530 | 341.1033 | 352.9418 | alanyl-trna synthetase |
| SEQ ID NO: 1571 | Nga06528 | 1225.36 | 1408.3241 | potential zinc ring finger protein |
| SEQ ID NO: 1572 | Nga06533 | 807.6923 | 795.06594 | protein |
| SEQ ID NO: 1573 | Nga06359 | 473.4625 | 453.55288 | conserved unknown protein [Ectocarpus siliculosus] |
| SEQ ID NO: 1574 | Nga20953 | 285.4223 | 259.00212 | multidrug resistance protein 2 (atp-binding cassette protein c) |
| SEQ ID NO: 1575 | Nga21115 | 216.4846 | 235.57918 | atp-dependent bile acid permease |
| SEQ ID NO: 1576 | Nga20835 | 418.3192 | 372.84114 | abc transporter c family protein |
| SEQ ID NO: 1577 | Nga20587 | 162.3489 | 159.02398 | impact homolog |
| SEQ ID NO: 1578 | Nga06363 | 190.4762 | 151.06324 | ---NA--- |
| SEQ ID NO: 1579 | Nga06361 | 1032.932 | 891.81911 | 26s proteasome regulatory subunit n7 |

FIGURE 24 Y

| # | Nga model | +N rpkb | -N rpkb | GO |
|---|---|---|---|---|
| SEQ ID NO: 1580 | Nga06362 | 3924.299 | 4638.671 | translation initiation factor eif-5a |
| SEQ ID NO: 1581 | Nga06360 | 3093.82 | 3670.8242 | enolase |
| SEQ ID NO: 1582 | Nga06632 | 93.06987 | 94.302153 | rsc complex subunit |
| SEQ ID NO: 1583 | Nga02313.02 | 777.4914 | 613.2742 | zinc fyve domain containing 21 |
| SEQ ID NO: 1584 | Nga02316.2 | 51.3308 | 32.950082 | transducin wd40 domain-containing protein |
| SEQ ID NO: 1585 | Nga06630 | 300.7136 | 356.66112 | brf1 subunit of rna polymerase iii transcription initiation factor iiib |
| SEQ ID NO: 1586 | Nga20132 | 196.0656 | 198.88885 | n-terminal asparagine amidohydrolase |
| SEQ ID NO: 1587 | Nga06631 | 256.656 | 237.64238 | translation initiation factor eif-2b alpha subunit |
| SEQ ID NO: 1588 | Nga20261 | 121.2654 | 104.70627 | gdsl-like protein |
| SEQ ID NO: 1589 | Nga00325 | 3018.395 | 2650.1192 | ---NA--- |
| SEQ ID NO: 1590 | Nga00322 | 516.6003 | 584.05442 | zinc finger (c3hc4-type ring finger) family protein |
| SEQ ID NO: 1591 | Nga00316 | 375.8287 | 340.82373 | conserved protein |
| SEQ ID NO: 1592 | Nga00347 | 6.245121 | 2.5368476 | cap family transcription factor |
| SEQ ID NO: 1593 | Nga00319 | 1177.994 | 1479.9523 | protein |
| SEQ ID NO: 1594 | Nga00312 | 1069.463 | 1105.9492 | nuclear lim factor interactor-interacting protein cleavage-specific form |
| SEQ ID NO: 1595 | Nga00324 | 293.7853 | 299.87832 | ectonucleoside triphosphate diphosphohydrolase 4 |
| SEQ ID NO: 1596 | Nga00309 | 768.6782 | 757.1743 | atp synthase mitochondrial f1 complex assembly factor 2 |
| SEQ ID NO: 1597 | Nga00310 | 7792.723 | 8849.7944 | serine hydroxymethyltransferase |
| SEQ ID NO: 1598 | Nga00314.1 | 772.2772 | 646.0589 | protein |
| SEQ ID NO: 1599 | Nga00318.01 | 315.1042 | 373.77213 | expressed unknown protein [Ectocarpus siliculosus] |
| SEQ ID NO: 1600 | Nga00313 | 469.3878 | 569.67562 | dead deah box helicase |
| SEQ ID NO: 1601 | Nga00326 | 582.9384 | 532.20499 | ---NA--- |
| SEQ ID NO: 1602 | Nga00317 | 3870.263 | 4661.3348 | aureochrome1-like protein |
| SEQ ID NO: 1603 | Nga00320 | 1751.299 | 1941.2968 | protein |
| SEQ ID NO: 1604 | Nga00321 | 1558.491 | 1453.8498 | early-responsive to dehydration stress-related protein |
| SEQ ID NO: 1605 | Nga00350 | 30.30303 | 49.237906 | ---NA--- |
| SEQ ID NO: 1606 | Nga00315 | 393.5428 | 397.94196 | serine racemase |
| SEQ ID NO: 1607 | Nga00346 | 38.65074 | 59.37614 | kinesin motor protein |
| SEQ ID NO: 1608 | Nga00323 | 2103.635 | 2368.37 | heat shock protein |
| SEQ ID NO: 1609 | Nga00311 | 800 | 715.59091 | fgfr1 oncogene partner |
| SEQ ID NO: 1610 | Nga04197.01 | 2880.819 | 2549.735 | protein |
| SEQ ID NO: 1611 | Nga20607.1 | 124.6291 | 208.93236 | e3 ubiquitin-protein ligase ubr4 |
| SEQ ID NO: 1612 | Nga20308.1 | 251.6171 | 386.0685 | protein |
| SEQ ID NO: 1613 | Nga20168.1 | 528.1921 | 655.2994 | protein |
| SEQ ID NO: 1614 | Nga02949 | 513.8889 | 500.78077 | anaphase promoting complex subunit 1 |
| SEQ ID NO: 1615 | Nga02948 | 13.75476 | 9.1933814 | arf-gap with coiled- ank repeat and ph domain-containing protein 1 |
| SEQ ID NO: 1616 | Nga02938 | 487.3684 | 454.95826 | protein |
| SEQ ID NO: 1617 | Nga02945 | 549.1924 | 432.65732 | der1-like domain member 1 |
| SEQ ID NO: 1618 | Nga02942 | 389.3037 | 419.07366 | phosphoribosylformylglycinamidine synthase |
| SEQ ID NO: 1619 | Nga02943 | 2212.867 | 1748.3416 | peptidase s8 s53 subtilisin kexin sedolisin |
| SEQ ID NO: 1620 | Nga02944 | 387.808 | 403.22716 | metal dependent phosphohydrolase |
| SEQ ID NO: 1621 | Nga02946.1 | 2234.012 | 1934.7062 | dna-formamidopyrimidine glycosylase |
| SEQ ID NO: 1622 | Nga02947 | 75.09881 | 68.504913 | ---NA--- |
| SEQ ID NO: 1623 | Nga02950 | 501.9225 | 579.90341 | protein |
| SEQ ID NO: 1624 | Nga02939 | 241.0304 | 277.03683 | rio kinase |
| SEQ ID NO: 1625 | Nga02941 | 234.5779 | 240.03479 | dna-directed rna polymerase i subunit rpa2 |
| SEQ ID NO: 1626 | Nga02951 | 145.0777 | 151.5405 | ---NA--- |
| SEQ ID NO: 1627 | Nga02940 | 230.8276 | 195.75526 | chaperone -domain containing protein |
| SEQ ID NO: 1628 | Nga06743.2 | 377.7006 | 458.86993 | ---NA--- |
| SEQ ID NO: 1629 | Nga06739.1 | 1392.58 | 1334.6489 | sphingolipid delta 4 desaturase c-4 hydroxylase protein des2 |
| SEQ ID NO: 1630 | Nga06744 | 377.7778 | 349.04205 | ---NA--- |
| SEQ ID NO: 1631 | Nga06740 | 625.7036 | 461.33978 | solute carrier family member b3 |
| SEQ ID NO: 1632 | Nga06741 | 1342.806 | 1481.51 | dihydrolipoyllysine-residue acetyltransferase component 1 of pyruvate dehydrogenase complex |
| SEQ ID NO: 1633 | Nga06743.1 | 377.7006 | 458.86993 | ---NA--- |
| SEQ ID NO: 1634 | Nga06738 | 4765.01 | 4385.913 | hypothetical protein GOALK_097_02160 [Gordonia alkanivorans NBRC 16433] |
| SEQ ID NO: 1635 | Nga02678 | 312.4448 | 348.01161 | replication factor c subunit 4 |
| SEQ ID NO: 1636 | Nga02677 | 1277.234 | 1483.1755 | rna helicase |
| SEQ ID NO: 1637 | Nga02671 | 559.0043 | 634.28228 | nucleoprotein tpr |
| SEQ ID NO: 1638 | Nga02679 | 944.385 | 824.87975 | protein |
| SEQ ID NO: 1639 | Nga02676 | 554.6489 | 593.71613 | protein |
| SEQ ID NO: 1640 | Nga02681 | 617.7778 | 526.37146 | conserved unknown protein [Ectocarpus siliculosus] |
| SEQ ID NO: 1641 | Nga02674 | 779.4038 | 835.46986 | conserved unknown protein [Ectocarpus siliculosus] |

FIGURE 24 Z

| # | Nga model | +N rpkb | -N rpkb | GO |
|---|---|---|---|---|
| SEQ ID NO: 1642 | Nga20519 | 4586.698 | 5084.8957 | ---NA--- |
| SEQ ID NO: 1643 | Nga02673 | 527.4295 | 662.16495 | protein |
| SEQ ID NO: 1644 | Nga02675 | 226.3993 | 239.8137 | phosphatidylserine receptor |
| SEQ ID NO: 1645 | Nga02680 | 522.646 | 457.69539 | protein |
| SEQ ID NO: 1646 | Nga02682 | 64.35644 | 94.738282 | conserved unknown protein [Ectocarpus siliculosus] |
| SEQ ID NO: 1647 | Nga02672 | 1097.561 | 1355.5667 | abc transporter atp-binding protein |
| SEQ ID NO: 1648 | Nga06348 | 1944.215 | 1797.1836 | proteasome maturation factor ump1 family protein |
| SEQ ID NO: 1649 | Nga03952.02 | 4710.142 | 4386.2837 | protein |
| SEQ ID NO: 1650 | Nga03956.02 | 679.941 | 627.89224 | pyridoxamine 5 -phosphate oxidase |
| SEQ ID NO: 1651 | Nga06347 | 1766.458 | 1845.5726 | protein |
| SEQ ID NO: 1652 | Nga06346 | 1403.037 | 1762.0306 | serine threonine-protein kinase dclk3-like |
| SEQ ID NO: 1653 | Nga06344 | 912.0952 | 1003.0474 | retinol retinaldehyde reductase |
| SEQ ID NO: 1654 | Nga01357.1 | 879.9571 | 986.86908 | ---NA--- |
| SEQ ID NO: 1655 | Nga01358.01 | 440.5405 | 482.57584 | dna gyrase subunit b |
| SEQ ID NO: 1656 | Nga21070.1 | 576.6284 | 442.00925 | trafficking protein particle complex subunit 4 |
| SEQ ID NO: 1657 | Nga01356 | 3829.361 | 3494.9845 | udp-glucose 6- |
| SEQ ID NO: 1658 | Nga01359 | 132.3764 | 153.76048 | atp-binding cassette superfamily |
| SEQ ID NO: 1659 | Nga20289 | 91.33489 | 86.25282 | atp-binding cassette sub-family g member 2 |
| SEQ ID NO: 1660 | Nga20029.1 | 184.7015 | 90.943148 | abc subfamily abcg |
| SEQ ID NO: 1661 | Nga02467.02 | 721.6981 | 742.59434 | 50s ribosomal protein l25 general stress protein ctc |
| SEQ ID NO: 1662 | Nga01056.02 | 26.21723 | 14.199696 | ---NA--- |
| SEQ ID NO: 1663 | Nga01053.02 | 266.0819 | 191.62472 | ---NA--- |
| SEQ ID NO: 1664 | Nga01050.02 | 211.8877 | 198.52334 | lipase domain-containing protein |
| SEQ ID NO: 1665 | Nga06297 | 75.72016 | 73.107147 | dna rna non-specific nuclease |
| SEQ ID NO: 1666 | Nga06306 | 83.10249 | 68.014689 | tata-binding protein-associated factor 172 |
| SEQ ID NO: 1667 | Nga06307 | 82.25108 | 82.063177 | tata-binding protein-associated factor 172 |
| SEQ ID NO: 1668 | Nga04152 | 379.1349 | 365.21246 | ---NA--- |
| SEQ ID NO: 1669 | Nga04156 | 83.94161 | 101.47082 | hnh endonuclease |
| SEQ ID NO: 1670 | Nga04151 | 1295.841 | 1376.2752 | serine carboxypeptidase |
| SEQ ID NO: 1671 | Nga04150 | 698.2025 | 691.75299 | acetylserotonin o-methyltransferase-like |
| SEQ ID NO: 1672 | Nga03826 | 262.1083 | 262.32161 | ---NA--- |
| SEQ ID NO: 1673 | Nga03820.1 | 594.7137 | 774.64747 | predicted protein [Thalassiosira pseudonana CCMP1335] |
| SEQ ID NO: 1674 | Nga06683.2 | 417.1843 | 427.23823 | ---NA--- |
| SEQ ID NO: 1675 | Nga03818.01 | 401.5317 | 394.65744 | cop9 complex subunit 7a |
| SEQ ID NO: 1676 | Nga03817.01 | 595.4495 | 658.23594 | soluble pyridine nucleotide transhydrogenase |
| SEQ ID NO: 1677 | Nga06678.2 | 3382.787 | 2908.7495 | protein |
| SEQ ID NO: 1678 | Nga03043.01 | 2702.461 | 2792.9018 | mgc84239 protein |
| SEQ ID NO: 1679 | Nga03021 | 774.9172 | 901.56617 | ---NA--- |
| SEQ ID NO: 1680 | Nga03020.01 | 2188.825 | 1948.3601 | golgi snap receptor complex member 1 |
| SEQ ID NO: 1681 | Nga20672 | 612.9032 | 377.09354 | protein kinase domain protein |
| SEQ ID NO: 1682 | Nga03023.01 | 1230.971 | 1157.1554 | protein |
| SEQ ID NO: 1683 | Nga03026 | 1096.096 | 1166.1843 | ---NA--- |
| SEQ ID NO: 1684 | Nga03022 | 2081.91 | 2078.2149 | abc subfamily abcg |
| SEQ ID NO: 1685 | Nga03027.01 | 1082.492 | 1021.2307 | protein |
| SEQ ID NO: 1686 | Nga03029 | 212.1212 | 164.12635 | ---NA--- |
| SEQ ID NO: 1687 | Nga20536 | 245.6814 | 261.97212 | dna ligase |
| SEQ ID NO: 1688 | Nga03024 | 328.2313 | 288.30971 | dna ligase i |
| SEQ ID NO: 1689 | Nga03025.01 | 1242.206 | 1453.4038 | protein |
| SEQ ID NO: 1690 | Nga20148.1 | 242.963 | 224.67074 | dna-apurinic or apyrimidinic site lyase 2 |
| SEQ ID NO: 1691 | Nga03028.01 | 324.1913 | 305.46892 | protein |
| SEQ ID NO: 1692 | Nga06127 | 441.906 | 531.71797 | ---NA--- |
| SEQ ID NO: 1693 | Nga06126 | 260.8696 | 260.22352 | nudix hydrolase |
| SEQ ID NO: 1694 | Nga06124 | 747.9167 | 674.76448 | mitochondrial phosphate carrier protein |
| SEQ ID NO: 1695 | Nga06123.01 | 752.5355 | 799.79139 | mitochondrial protein translocase family |
| SEQ ID NO: 1696 | Nga06125 | 182.3944 | 180.79327 | cyclic nucleotide-binding domain protein |
| SEQ ID NO: 1697 | Nga20217 | 258.6873 | 313.67778 | gamma complex associated protein 3 |
| SEQ ID NO: 1698 | Nga20091 | 158.8527 | 193.584 | abc subfamily abcg |
| SEQ ID NO: 1699 | Nga20499 | 199.7919 | 206.2766 | ---NA--- |
| SEQ ID NO: 1700 | Nga06600 | 4222.222 | 3849.702 | nadh dehydrogenase |
| SEQ ID NO: 1701 | Nga21177 | 125.7143 | 111.41835 | ser thr protein phosphatase family |
| SEQ ID NO: 1702 | Nga21231.1 | 518.8811 | 534.79941 | rna binding protein |
| SEQ ID NO: 1703 | Nga06598 | 226.1905 | 184.83754 | adp-ribosylation factor-like protein 2 |
| SEQ ID NO: 1704 | Nga06599.1 | 176.8293 | 249.95032 | chromosome region maintenance protein 5 exportin |
| SEQ ID NO: 1705 | Nga06597 | 505.9133 | 549.44586 | tho complex 7 |

FIGURE 24 AA

| # | Nga model | +N rpkb | -N rpkb | GO |
|---|---|---|---|---|
| SEQ ID NO: 1706 | Nga03239.1 | 1841.419 | 2086.3256 | casein kinase i |
| SEQ ID NO: 1707 | Nga20497 | 144.6384 | 167.48255 | atp-binding sub-family c (cftr mrp) member 2 |
| SEQ ID NO: 1708 | Nga03243 | 306.3584 | 270.98241 | multidrug-resistance like protein isoform e |
| SEQ ID NO: 1709 | Nga03245.01 | 476.3713 | 413.63996 | e3 ubiquitin-protein ligase rnf14 |
| SEQ ID NO: 1710 | Nga03242 | 697.0492 | 668.40862 | conserved unknown protein [Ectocarpus siliculosus] |
| SEQ ID NO: 1711 | Nga03238 | 702.9973 | 601.14072 | transmembrane protein 115 |
| SEQ ID NO: 1712 | Nga03241 | 5336.549 | 5478.8649 | vacuolar h+-atpase a subunit |
| SEQ ID NO: 1713 | Nga03244 | 722.2222 | 678.5257 | gtp-binding protein era |
| SEQ ID NO: 1714 | Nga03240 | 5466.374 | 5159.6143 | nadh dehydrogenase subunit 10 |
| SEQ ID NO: 1715 | Nga05902.2 | 2056.911 | 1804.9896 | ---NA--- |
| SEQ ID NO: 1716 | Nga05498.01 | 3419.098 | 2738.2545 | ---NA--- |
| SEQ ID NO: 1717 | Nga05489 | 12153.85 | 10402.554 | ---NA--- |
| SEQ ID NO: 1718 | Nga05497.01 | 1666.924 | 1441.5215 | dolichyl-diphosphooligosaccharide--protein glycosyltransferase subunit dad1 |
| SEQ ID NO: 1719 | Nga05493 | 248.227 | 223.27295 | unc45 family protein |
| SEQ ID NO: 1720 | Nga20081 | 1131.985 | 943.39449 | pseudouridine synthase homolog 1 ( coli) |
| SEQ ID NO: 1721 | Nga05492 | 1087.874 | 985.38659 | rna binding protein |
| SEQ ID NO: 1722 | Nga20055.1 | 2043.287 | 1900.2292 | conserved unknown protein [Ectocarpus siliculosus] |
| SEQ ID NO: 1723 | Nga05495 | 376.1468 | 549.07042 | mitochondrial carrier domain-containing protein |
| SEQ ID NO: 1724 | Nga20804.1 | 2625.498 | 2593.7195 | mitochondrial carrier domain-containing protein |
| SEQ ID NO: 1725 | Nga21076 | 62.82723 | 130.44178 | vacuolar protein sorting-associated protein vps13 |
| SEQ ID NO: 1726 | Nga05509 | 96.01449 | 219.7866 | predicted protein [Thalassiosira pseudonana CCMP1335] |
| SEQ ID NO: 1727 | Nga05897.2 | 895.2703 | 834.3829 | ---NA--- |
| SEQ ID NO: 1728 | Nga05508 | 146.7991 | 198.47333 | syt3 protein |
| SEQ ID NO: 1729 | Nga05494.01 | 967.684 | 874.49586 | topoisomerase 6 subunit b |
| SEQ ID NO: 1730 | Nga05496 | 270.6311 | 326.02187 | vacuolar protein sorting-associated protein 13 family protein |
| SEQ ID NO: 1731 | Nga04128.01 | 25708.25 | 33515.408 | fructose-bisphosphate aldolase |
| SEQ ID NO: 1732 | Nga04129.01 | 2357.423 | 2462.0057 | ---NA--- |
| SEQ ID NO: 1733 | Nga05546.2 | 360.4411 | 368.04572 | ---NA--- |
| SEQ ID NO: 1734 | Nga04133 | 467.5325 | 769.0492 | ---NA--- |
| SEQ ID NO: 1735 | Nga04132 | 410.6231 | 479.10143 | mono-or diacylglycerol acyltransferase type 2 |
| SEQ ID NO: 1736 | Nga04130 | 192.2807 | 231.08991 | nitrate transporter |
| SEQ ID NO: 1737 | Nga20404 | 323.913 | 207.22736 | dna topoisomerase |
| SEQ ID NO: 1738 | Nga20335 | 265.8824 | 145.28079 | dna topoisomerase |
| SEQ ID NO: 1739 | Nga03611 | 1292.655 | 1408.2041 | serine threonine protein kinase |
| SEQ ID NO: 1740 | Nga03610 | 1474.63 | 1592.0304 | atp-binding cassette sub-family g member 2 |
| SEQ ID NO: 1741 | Nga03608 | 248.1618 | 291.38462 | protein |
| SEQ ID NO: 1742 | Nga03609 | 411.6766 | 483.77963 | protein |
| SEQ ID NO: 1743 | Nga21043 | 540 | 363.73855 | ser thr kinase |
| SEQ ID NO: 1744 | Nga20895 | 500 | 362.34938 | ser thr kinase |
| SEQ ID NO: 1745 | Nga20101 | 588.3377 | 465.7246 | ser thr kinase |
| SEQ ID NO: 1746 | Nga02505.1 | 127.5322 | 75.806427 | nucleolar mif4g domain-containing protein 1 |
| SEQ ID NO: 1747 | Nga02501.02 | 4314.115 | 5050.0668 | dihydrolipoyl dehydrogenase |
| SEQ ID NO: 1748 | Nga02498 | 4942.308 | 4534.3062 | histone h4 |
| SEQ ID NO: 1749 | Nga02500 | 108.31 | 107.21083 | cyclin delta-3 |
| SEQ ID NO: 1750 | Nga02501.01 | 4314.115 | 5050.0668 | dihydrolipoyl dehydrogenase |
| SEQ ID NO: 1751 | Nga02495.01 | 994.5227 | 955.24621 | heme steroid binding domain-containing |
| SEQ ID NO: 1752 | Nga02507 | 128.3167 | 111.37729 | conserved unknown protein [Ectocarpus siliculosus] |
| SEQ ID NO: 1753 | Nga02504 | 916.7816 | 853.63815 | protein |
| SEQ ID NO: 1754 | Nga02497.01 | 1070.802 | 1097.487 | protein |
| SEQ ID NO: 1755 | Nga02499.01 | 9351.421 | 9217.2852 | ribosomal protein l35a |
| SEQ ID NO: 1756 | Nga02502 | 490.0344 | 544.96718 | isoform a |
| SEQ ID NO: 1757 | Nga02496 | 3411.514 | 2940.2064 | nadh dehydrogenase |
| SEQ ID NO: 1758 | Nga20863 | 991.404 | 1066.1629 | protein |
| SEQ ID NO: 1759 | Nga02506 | 389.071 | 410.80019 | protein |
| SEQ ID NO: 1760 | Nga01606 | 551.0888 | 449.98663 | u6 snrna-associated sm-like protein lsm8 |
| SEQ ID NO: 1761 | Nga01610 | 342.8962 | 388.45479 | aspartyl glutamyl-trna amidotransferase subunit a |
| SEQ ID NO: 1762 | Nga01616 | 127.0125 | 155.02454 | ---NA--- |
| SEQ ID NO: 1763 | Nga01609 | 1611.903 | 1526.8025 | protein |
| SEQ ID NO: 1764 | Nga20814 | 322.1258 | 287.84416 | probable methyltransferase bcdin3d-like |
| SEQ ID NO: 1765 | Nga01608 | 28330.88 | 23337.319 | expressed unknown protein [Ectocarpus siliculosus] |
| SEQ ID NO: 1766 | Nga01607 | 977.5227 | 1125.7137 | homoaconitase |
| SEQ ID NO: 1767 | Nga07299.2 | 2197.878 | 2503.6802 | solute carrier family 35 member b1 |
| SEQ ID NO: 1768 | Nga06703.1 | 927.3743 | 1104.6472 | uncharacterized protein |

FIGURE 24 AB

| # | Nga model | +N rpkb | -N rpkb | GO |
|---|---|---|---|---|
| SEQ ID NO: 1769 | Nga06699 | 1065.029 | 901.65137 | mitochondrial ribosomal protein l11 |
| SEQ ID NO: 1770 | Nga06697 | 3123.953 | 3304.1357 | ---NA--- |
| SEQ ID NO: 1771 | Nga06700 | 641.6465 | 773.73853 | endonuclease |
| SEQ ID NO: 1772 | Nga20171 | 225.2986 | 184.06744 | fibronectin-binding a domain-containing protein |
| SEQ ID NO: 1773 | Nga20686 | 250 | 273.12309 | fibronectin-binding a domain-containing protein |
| SEQ ID NO: 1774 | Nga06702 | 2292 | 1808.2785 | protein |
| SEQ ID NO: 1775 | Nga06701 | 342.5358 | 268.03948 | proteasome subunit beta type-6 |
| SEQ ID NO: 1776 | Nga20669 | 129.771 | 90.958575 | ---NA--- |
| SEQ ID NO: 1777 | Nga03837 | 306.7485 | 331.17275 | coq7 family protein |
| SEQ ID NO: 1778 | Nga03838 | 466.1469 | 464.94161 | squalene synthase |
| SEQ ID NO: 1779 | Nga20134 | 1234.158 | 1354.0424 | vacuolar sorting protein 9 domain-containing protein |
| SEQ ID NO: 1780 | Nga01200 | 633.1878 | 636.22255 | potential rn mrp complex component |
| SEQ ID NO: 1781 | Nga01198.01 | 154.661 | 172.12404 | ---NA--- |
| SEQ ID NO: 1782 | Nga01197.01 | 2927.435 | 2518.5728 | peptide deformylase |
| SEQ ID NO: 1783 | Nga01199 | 1094.29 | 1182.4944 | pas-domain protein |
| SEQ ID NO: 1784 | Nga21026 | 578.9474 | 527.36389 | rna methylase |
| SEQ ID NO: 1785 | Nga01501 | 281.909 | 351.05917 | cox11 cytochrome c oxidase assembly protein |
| SEQ ID NO: 1786 | Nga01500.01 | 378.1903 | 335.94494 | ---NA--- |
| SEQ ID NO: 1787 | Nga04084.2 | 1391.663 | 1262.367 | pyridoxal kinase |
| SEQ ID NO: 1788 | Nga05539.1 | 400.8715 | 348.09805 | cysteinyl-trna synthetase |
| SEQ ID NO: 1789 | Nga05544 | 466.6667 | 393.48241 | protein |
| SEQ ID NO: 1790 | Nga04136.02 | 176.7358 | 235.4007 | protein |
| SEQ ID NO: 1791 | Nga05542 | 5735.736 | 5819.5361 | transmembrane bax inhibitor motif-containing protein 4 |
| SEQ ID NO: 1792 | Nga04134.02 | 716.0563 | 560.23029 | activating transcription factor 1 |
| SEQ ID NO: 1793 | Nga05543 | 611.6006 | 644.21402 | protein |
| SEQ ID NO: 1794 | Nga20225 | 377.0701 | 329.79989 | rna guanylyltransferase and 5-phosphatase |
| SEQ ID NO: 1795 | Nga05545 | 158.2609 | 207.85532 | homolog of coli closely related to ydj1p |
| SEQ ID NO: 1796 | Nga05538 | 671.3911 | 690.88149 | conserved hypothetical protein [Phytophthora infestans T30-4] |
| SEQ ID NO: 1797 | Nga05541 | 414.9001 | 342.48826 | 6-phosphofructo-2- isoform a |
| SEQ ID NO: 1798 | Nga01218 | 1524.8 | 1274.4608 | abc transporter g family member 7 |
| SEQ ID NO: 1799 | Nga20368.1 | 1223.301 | 1139.3237 | transthyretin family protein |
| SEQ ID NO: 1800 | Nga01221.01 | 112.069 | 93.382236 | ---NA--- |
| SEQ ID NO: 1801 | Nga01220.01 | 140.8451 | 85.67289 | ---NA--- |
| SEQ ID NO: 1802 | Nga01219 | 190.5263 | 141.39054 | ---NA--- |
| SEQ ID NO: 1803 | Nga06134 | 987.2979 | 1053.839 | ---NA--- |
| SEQ ID NO: 1804 | Nga06133.1 | 325.7373 | 374.63051 | dna replication complex gins protein psf2 |
| SEQ ID NO: 1805 | Nga06137 | 1353.991 | 1166.6379 | mitochondrial carrier |
| SEQ ID NO: 1806 | Nga06135 | 1176.416 | 1078.8983 | 3-hydroxyacyl- dehydrogenase |
| SEQ ID NO: 1807 | Nga06142 | 502.8681 | 488.80155 | transporter belonging to the mfs superfamily |
| SEQ ID NO: 1808 | Nga21238 | 280.8989 | 216.03823 | ---NA--- |
| SEQ ID NO: 1809 | Nga06141 | 543.7352 | 513.02096 | major facilitator superfamily protein |
| SEQ ID NO: 1810 | Nga06136 | 3119.735 | 3234.3223 | fumarate hydratase |
| SEQ ID NO: 1811 | Nga21203.1 | 622.3092 | 735.58156 | protein |
| SEQ ID NO: 1812 | Nga06138 | 1791.444 | 1958.8963 | ---NA--- |
| SEQ ID NO: 1813 | Nga04845.02 | 295.9223 | 316.76705 | nadph dependent diflavin oxidoreductase 1 |
| SEQ ID NO: 1814 | Nga04844.02 | 224.1888 | 218.08471 | salicylate hydroxylase |
| SEQ ID NO: 1815 | Nga06783 | 100 | 117.35034 | ---NA--- |
| SEQ ID NO: 1816 | Nga06779 | 4436.236 | 4418.6799 | protein-l-isoaspartated-aspartate o-methyltransferase |
| SEQ ID NO: 1817 | Nga20295.1 | 569.7413 | 470.33555 | jmjc domain-containing protein 4-like |
| SEQ ID NO: 1818 | Nga06780 | 901.1765 | 1027.1607 | protein fucu homolog |
| SEQ ID NO: 1819 | Nga04328.02 | 440.3748 | 418.89967 | ---NA--- |
| SEQ ID NO: 1820 | Nga04329.02 | 180.8874 | 162.66994 | ---NA--- |
| SEQ ID NO: 1821 | Nga06781 | 6658.182 | 6686.5077 | ribosomal protein |
| SEQ ID NO: 1822 | Nga21161 | 245.4955 | 351.31912 | nad h dehydrogenase |
| SEQ ID NO: 1823 | Nga06789 | 463.9017 | 450.93149 | nad h dehydrogenase |
| SEQ ID NO: 1824 | Nga03624 | 87.03375 | 117.36638 | n-acetylglucosamine-1-phosphate transferase |
| SEQ ID NO: 1825 | Nga03625 | 300 | 241.57836 | ketose-bisphosphate aldolase class-ii-like protein |
| SEQ ID NO: 1826 | Nga01634.01 | 76.14213 | 67.816677 | ---NA--- |
| SEQ ID NO: 1827 | Nga20962 | 241.2935 | 266.76657 | tetratricopeptide repeat protein 26 |
| SEQ ID NO: 1828 | Nga00882 | 2295.918 | 2300.4092 | protein |
| SEQ ID NO: 1829 | Nga00884.1 | 36.52058 | 31.888029 | dna replication atp-dependent helicase dna2 |
| SEQ ID NO: 1830 | Nga00881.01 | 3447.703 | 3984.5643 | succinate fumarate mitochondrial transporter |
| SEQ ID NO: 1831 | Nga01403 | 10142.86 | 12660.655 | ---NA--- |
| SEQ ID NO: 1832 | Nga01404 | 372.093 | 268.70919 | ---NA--- |

FIGURE 24 AC

| # | Nga model | +N rpkb | -N rpkb | GO |
|---|---|---|---|---|
| SEQ ID NO: 1833 | Nga20494 | 371.308 | 292.51887 | short-chain dehydrogenase reductase sdr |
| SEQ ID NO: 1834 | Nga01400 | 1717.678 | 1625.3273 | transmembrane protein 56 |
| SEQ ID NO: 1835 | Nga01402 | 624.1747 | 670.62579 | hsp70 hsp90 organizing protein |
| SEQ ID NO: 1836 | Nga21131 | 163.7168 | 105.44755 | ---NA--- |
| SEQ ID NO: 1837 | Nga01401 | 328.152 | 437.78367 | ufm1-conjugating enzyme 1 |
| SEQ ID NO: 1838 | Nga01238 | 475.1082 | 618.99082 | phyhd1 protein |
| SEQ ID NO: 1839 | Nga01239 | 982.7246 | 1037.2526 | uncharacterized protein |
| SEQ ID NO: 1840 | Nga01237 | 716.8142 | 752.51207 | homeobox prox 1 |
| SEQ ID NO: 1841 | Nga03808 | 2240.779 | 2098.7058 | protein |
| SEQ ID NO: 1842 | Nga20061 | 618.888 | 598.97177 | dna primase |
| SEQ ID NO: 1843 | Nga06320 | 2054.688 | 1970.0108 | mannitol 1-phosphate dehydrogenase |
| SEQ ID NO: 1844 | Nga06319 | 282.2832 | 341.93161 | phosphatidylinositol 3-kinase |
| SEQ ID NO: 1845 | Nga06314 | 470.2277 | 476.16763 | translation initiation factor eif-2b subunit beta |
| SEQ ID NO: 1846 | Nga06316 | 255.2422 | 260.03881 | slc30a9 protein |
| SEQ ID NO: 1847 | Nga06317 | 1006.623 | 1046.5682 | ---NA--- |
| SEQ ID NO: 1848 | Nga06318.1 | 203.6082 | 234.51456 | protein |
| SEQ ID NO: 1849 | Nga06315 | 384.4508 | 431.90283 | bifunctional coenzyme a synthase |
| SEQ ID NO: 1850 | Nga01317 | 310.0437 | 264.89564 | didehydrogluconate reductase |
| SEQ ID NO: 1851 | Nga01316 | 2941.298 | 3026.6962 | protein |
| SEQ ID NO: 1852 | Nga01315 | 1364.583 | 1351.478 | methionine synthase |
| SEQ ID NO: 1853 | Nga21150.1 | 299.8776 | 234.67859 | protein |
| SEQ ID NO: 1854 | Nga06047 | 1942.127 | 1438.9662 | ---NA--- |
| SEQ ID NO: 1855 | Nga06048 | 615.4482 | 636.24893 | myb-like dna-binding |
| SEQ ID NO: 1856 | Nga06049 | 351.6721 | 255.90964 | ---NA--- |
| SEQ ID NO: 1857 | Nga20180 | 171.1957 | 192.80387 | rna polymerase ii associated protein 3 |
| SEQ ID NO: 1858 | Nga20208 | 101.0989 | 134.51147 | nad-specific glutamate dehydrogenase encoded in antisense gene pair with dnakj |
| SEQ ID NO: 1859 | Nga02731.01 | 1963.609 | 1938.1593 | hypothetical protein VOLCADRAFT_89537 [Volvox carteri f. nagariensis] |
| SEQ ID NO: 1860 | Nga20216 | 536.6492 | 561.46681 | ubiquitin carboxyl-terminal hydrolase and or f-box |
| SEQ ID NO: 1861 | Nga02735.01 | 456.2118 | 452.26672 | conserved unknown protein [Ectocarpus siliculosus] |
| SEQ ID NO: 1862 | Nga02729 | 257.3099 | 250.22071 | isoform a |
| SEQ ID NO: 1863 | Nga20748 | 758.567 | 757.02642 | ubiquitin carboxyl-terminal hydrolase and or f-box |
| SEQ ID NO: 1864 | Nga06813.2 | 1161.026 | 1004.3523 | protein |
| SEQ ID NO: 1865 | Nga02725.01 | 954.0785 | 1002.0732 | ---NA--- |
| SEQ ID NO: 1866 | Nga02723.01 | 176.7956 | 214.2529 | expressed unknown protein [Ectocarpus siliculosus] |
| SEQ ID NO: 1867 | Nga02728 | 3966.667 | 4339.0319 | h+-translocating pyrophosphatase family |
| SEQ ID NO: 1868 | Nga02726 | 447.5806 | 481.92263 | sugar fermentation stimulation protein |
| SEQ ID NO: 1869 | Nga02733 | 439.4753 | 397.89631 | leucyl aminopeptidase |
| SEQ ID NO: 1870 | Nga02734 | 408.7452 | 333.61958 | dihydrofolate reductase-thymidylate synthase |
| SEQ ID NO: 1871 | Nga02727 | 2606.964 | 2381.0574 | phosphoglucomutase |
| SEQ ID NO: 1872 | Nga02724 | 2800.532 | 2484.8119 | ---NA--- |
| SEQ ID NO: 1873 | Nga02730 | 1702.29 | 1590.3969 | protein |
| SEQ ID NO: 1874 | Nga01462 | 174.3827 | 185.55396 | tubulin-specific chaperone e |
| SEQ ID NO: 1875 | Nga01461 | 2782.575 | 2911.2975 | pyruvate dehydrogenase e1 component alpha subunit |
| SEQ ID NO: 1876 | Nga21022 | 212.766 | 220.59779 | ---NA--- |
| SEQ ID NO: 1877 | Nga01464 | 304.3478 | 290.82476 | nad-dependent deacetylase |
| SEQ ID NO: 1878 | Nga01465 | 1107.784 | 1312.9617 | conserved unknown protein [Ectocarpus siliculosus] |
| SEQ ID NO: 1879 | Nga01463 | 408.2251 | 426.72852 | cytochrome p450 |
| SEQ ID NO: 1880 | Nga01467 | 126.8293 | 133.86306 | u3 small nucleolar ribonucleoprotein protein mpp10 |
| SEQ ID NO: 1881 | Nga20838 | 141.0473 | 207.68083 | u3 small nucleolar ribonucleoprotein protein mpp10 |
| SEQ ID NO: 1882 | Nga04006 | 140.9432 | 164.28468 | breast cancer type 2 susceptibility protein homolog |
| SEQ ID NO: 1883 | Nga04004 | 894.9275 | 772.19666 | peptide chain release factor 1 |
| SEQ ID NO: 1884 | Nga04005.01 | 1076.887 | 1047.7602 | protease required for anti-sigma degradation |
| SEQ ID NO: 1885 | Nga04140.2 | 262.3336 | 318.9475 | uncharacterized membrane protein |
| SEQ ID NO: 1886 | Nga03645 | 301.9432 | 306.83532 | protein |
| SEQ ID NO: 1887 | Nga03643 | 1371.827 | 1151.9671 | protein |
| SEQ ID NO: 1888 | Nga20563 | 713.7405 | 756.60997 | protein |
| SEQ ID NO: 1889 | Nga03644 | 619.8663 | 707.67146 | protein |
| SEQ ID NO: 1890 | Nga00807 | 282.4742 | 304.86893 | uroporphyrinogen-iii synthase |
| SEQ ID NO: 1891 | Nga00805 | 3169.899 | 3540.469 | sulfite ferredoxin dependent |
| SEQ ID NO: 1892 | Nga00803 | 4287.931 | 4515.0311 | rnp-1 like rna-binding protein |
| SEQ ID NO: 1893 | Nga21102 | 2178.94 | 1937.537 | expressed unknown protein [Ectocarpus siliculosus] |
| SEQ ID NO: 1894 | Nga00804 | 1746.439 | 971.10431 | ---NA--- |
| SEQ ID NO: 1895 | Nga00806 | 73.21773 | 139.83945 | conserved hypothetical protein [Ricinus communis] |

FIGURE 24 AD

| # | Nga model | +N rpkb | -N rpkb | GO |
|---|---|---|---|---|
| SEQ ID NO: 1896 | Nga04125 | 459.1492 | 468.47491 | protein |
| SEQ ID NO: 1897 | Nga04124.1 | 341.5233 | 460.44096 | transcription antitermination protein nusg |
| SEQ ID NO: 1898 | Nga04123.01 | 522.1122 | 655.66041 | ---NA--- |
| SEQ ID NO: 1899 | Nga20969 | 549.8688 | 602.74435 | serine threonine-protein kinase eg2 |
| SEQ ID NO: 1900 | Nga20328 | 181.2689 | 206.17444 | component of oligomeric golgi complex 8 |
| SEQ ID NO: 1901 | Nga02573 | 555.3838 | 643.46663 | eukaryotic translation initiation factor 2a |
| SEQ ID NO: 1902 | Nga20425 | 203.3582 | 198.05397 | conserved oligomeric golgi complex subunit |
| SEQ ID NO: 1903 | Nga02108.2 | 580.3595 | 681.99438 | swi snf-related matrix-associated actin-dependent regulator of chromatin a1 isoform a isoform 19 |
| SEQ ID NO: 1904 | Nga20362 | 210.6227 | 200.37844 | serine threonine protein kinase |
| SEQ ID NO: 1905 | Nga20813 | 444.4024 | 427.72172 | protein kinase |
| SEQ ID NO: 1906 | Nga02109.02 | 1408.063 | 1229.1563 | gualynate kinase-1 |
| SEQ ID NO: 1907 | Nga20883 | 385.8447 | 576.24089 | mitochondrial ribosomal l36 protein |
| SEQ ID NO: 1908 | Nga02110.02 | 210.356 | 183.1682 | phosphoinositol transporter |
| SEQ ID NO: 1909 | Nga02578.1 | 520.9165 | 520.55346 | protein |
| SEQ ID NO: 1910 | Nga02580 | 285.4167 | 293.37586 | protein |
| SEQ ID NO: 1911 | Nga02574 | 429.4809 | 403.16249 | leukotriene a4 hydrolase |
| SEQ ID NO: 1912 | Nga02575 | 1068.664 | 1246.1924 | methyltransferase small |
| SEQ ID NO: 1913 | Nga02581 | 251.1166 | 293.52145 | conserved unknown protein [Ectocarpus siliculosus] |
| SEQ ID NO: 1914 | Nga03684 | 496.1182 | 600.11632 | histone acetylase complex subunit paf400 |
| SEQ ID NO: 1915 | Nga03402 | 508.6022 | 462.99515 | kelch repeat |
| SEQ ID NO: 1916 | Nga20038 | 2171.219 | 2215.5418 | c2h2-type zinc finger-containing protein |
| SEQ ID NO: 1917 | Nga03406 | 3095.548 | 2954.4882 | phosphoinositol transporter |
| SEQ ID NO: 1918 | Nga03401 | 400.8097 | 426.86142 | folylpolyglutamate synthase |
| SEQ ID NO: 1919 | Nga03405 | 283.906 | 321.2484 | abc1 protein |
| SEQ ID NO: 1920 | Nga03404 | 580.581 | 554.76406 | protein |
| SEQ ID NO: 1921 | Nga03408 | 4650.206 | 4488.9571 | ---NA--- |
| SEQ ID NO: 1922 | Nga03400 | 8735.661 | 7629.9109 | protein |
| SEQ ID NO: 1923 | Nga03399 | 6236.411 | 4757.7242 | cellulase 2 |
| SEQ ID NO: 1924 | Nga03407 | 1545.671 | 1497.943 | protein |
| SEQ ID NO: 1925 | Nga06481.1 | 915.6985 | 913.82738 | glutathione-regulated potassium-efflux system protein |
| SEQ ID NO: 1926 | Nga02547.02 | 1214.516 | 1151.3729 | 26s proteasome non-atpase regulatory subunit 2 |
| SEQ ID NO: 1927 | Nga02614.02 | 352.1657 | 411.0577 | choline ethanolaminephosphotransferase 1 |
| SEQ ID NO: 1928 | Nga02548.02 | 817.3913 | 679.86089 | peroxisomal membrane 22 kda (mpv17 pmp22) family protein |
| SEQ ID NO: 1929 | Nga02608.02 | 5491.917 | 5974.0477 | expressed unknown protein [Ectocarpus siliculosus] |
| SEQ ID NO: 1930 | Nga06477 | 198.5636 | 139.12257 | ribonucleoside-diphosphate reductase large subunit |
| SEQ ID NO: 1931 | Nga06475 | 716.8317 | 589.87987 | novel protein |
| SEQ ID NO: 1932 | Nga06655 | 115.2211 | 93.953964 | ---NA--- |
| SEQ ID NO: 1933 | Nga06660 | 1050.773 | 970.84543 | ---NA--- |
| SEQ ID NO: 1934 | Nga06656 | 1025.258 | 1004.2361 | actin binding protein |
| SEQ ID NO: 1935 | Nga06023.2 | 1939.289 | 2664.3985 | protein |
| SEQ ID NO: 1936 | Nga06657 | 375.4109 | 356.09268 | bud13 homolog |
| SEQ ID NO: 1937 | Nga06658 | 1810.726 | 1684.6509 | protein |
| SEQ ID NO: 1938 | Nga20150 | 334.2287 | 322.76714 | poly rna polymerase |
| SEQ ID NO: 1939 | Nga00046 | 1486.328 | 1419.0999 | conserved unknown protein [Ectocarpus siliculosus] |
| SEQ ID NO: 1940 | Nga00049 | 392.5128 | 471.87956 | drug metabolite transporter superfamily |
| SEQ ID NO: 1941 | Nga00042.01 | 832.1649 | 913.49007 | dna replication licensing factor mcm9 |
| SEQ ID NO: 1942 | Nga00045 | 2257.962 | 2228.5641 | nucleoside diphosphate kinase a |
| SEQ ID NO: 1943 | Nga20293 | 1037.52 | 1005.3712 | inositol 5-phosphatase |
| SEQ ID NO: 1944 | Nga00050 | 948.7399 | 845.85717 | ---NA--- |
| SEQ ID NO: 1945 | Nga00040 | 1443.492 | 1629.4945 | peptidase |
| SEQ ID NO: 1946 | Nga00041 | 536.1822 | 617.63932 | exocyst complex |
| SEQ ID NO: 1947 | Nga20074.1 | 1108.252 | 1092.1733 | hypothetical protein CHLNCDRAFT_136236 [Chlorella variabilis] |
| SEQ ID NO: 1948 | Nga00044 | 4000 | 3841.5249 | ubiquitin conjugating enzyme |
| SEQ ID NO: 1949 | Nga00048 | 571.9468 | 561.91942 | macrophage erythroblast attacher |
| SEQ ID NO: 1950 | Nga00043.01 | 365.3846 | 399.81712 | myosin light chain kinase |
| SEQ ID NO: 1951 | Nga21125 | 274.4043 | 295.57882 | tpr repeat nuclear phosphoprotein |
| SEQ ID NO: 1952 | Nga20797 | 299.4393 | 360.80802 | ctr9 protein |
| SEQ ID NO: 1953 | Nga20955 | 406.2827 | 389.0568 | protein |
| SEQ ID NO: 1954 | Nga01535 | 174.7212 | 240.27122 | afg1 family |
| SEQ ID NO: 1955 | Nga20562.1 | 152.0468 | 190.04104 | ---NA--- |
| SEQ ID NO: 1956 | Nga01534.1 | 3648.79 | 2991.1035 | zeaxanthin epoxidase |
| SEQ ID NO: 1957 | Nga06644 | 932.4222 | 962.32628 | fe-s oxidoreductase |
| SEQ ID NO: 1958 | Nga20916.1 | 595.9821 | 459.40725 | protein |

FIGURE 24 AE

| # | Nga model | +N rpkb | -N rpkb | GO |
|---|---|---|---|---|
| SEQ ID NO: 1959 | Nga06647 | 106.0851 | 98.581872 | tbc1 domain member 13 |
| SEQ ID NO: 1960 | Nga06645 | 549.2578 | 554.04273 | prolyl carboxypeptidase like protein |
| SEQ ID NO: 1961 | Nga06646 | 1916.94 | 1977.0499 | protein |
| SEQ ID NO: 1962 | Nga06643 | 138.322 | 178.49206 | chorismate mutase |
| SEQ ID NO: 1963 | Nga06642 | 1342.894 | 1380.9378 | atp-dependent metalloprotease |
| SEQ ID NO: 1964 | Nga20543 | 638.79 | 481.86563 | glutamyl-trna amidotransferase subunit c |
| SEQ ID NO: 1965 | Nga20599 | 195.4023 | 204.19582 | ---NA--- |
| SEQ ID NO: 1966 | Nga20194 | 267.0873 | 277.92753 | sterol 3-beta- |
| SEQ ID NO: 1967 | Nga00705 | 627.081 | 543.42036 | ---NA--- |
| SEQ ID NO: 1968 | Nga00692 | 526.8293 | 607.66782 | exosome component 8 |
| SEQ ID NO: 1969 | Nga00711 | 854.4153 | 708.36778 | ---NA--- |
| SEQ ID NO: 1970 | Nga00707 | 13.88889 | 15.044916 | low quality protein: 60 kda lysophospholipase-like |
| SEQ ID NO: 1971 | Nga00701 | 1813.62 | 970.63973 | ---NA--- |
| SEQ ID NO: 1972 | Nga00697 | 848.763 | 713.65492 | carbamoyltransferase |
| SEQ ID NO: 1973 | Nga00696 | 23297.15 | 23184.629 | enolase |
| SEQ ID NO: 1974 | Nga00703 | 319.7625 | 309.16728 | protein |
| SEQ ID NO: 1975 | Nga00706 | 275.2902 | 377.24565 | atp-dependent protease la |
| SEQ ID NO: 1976 | Nga00710.1 | 880 | 765.48532 | cytochrome c oxidase biogenesis protein cmc1-like protein |
| SEQ ID NO: 1977 | Nga00708 | 2069.307 | 2049.8325 | cyclin-dependent kinase 2 |
| SEQ ID NO: 1978 | Nga00699.01 | 156.6667 | 192.27402 | phosphatidylinositol kinase (pik-k) |
| SEQ ID NO: 1979 | Nga00693 | 557.0825 | 589.70981 | rab family gtpase |
| SEQ ID NO: 1980 | Nga00695 | 650.0921 | 703.20435 | protein |
| SEQ ID NO: 1981 | Nga00700 | 180.7732 | 232.04071 | phosphatidylinositol 4-kinase |
| SEQ ID NO: 1982 | Nga00698 | 438.3117 | 466.00161 | riboflavin kinase |
| SEQ ID NO: 1983 | Nga00702 | 321.499 | 293.42037 | serine threonine-protein kinase tousled-like 1 isoform 2 |
| SEQ ID NO: 1984 | Nga00694 | 441.1303 | 459.14154 | retinal pigment epithelial membrane protein |
| SEQ ID NO: 1985 | Nga00709 | 287.9652 | 245.42709 | atpase aaa domain containing 5 |
| SEQ ID NO: 1986 | Nga00704 | 1031.308 | 909.67712 | adp-ribosylation factor 3 |
| SEQ ID NO: 1987 | Nga05195.2 | 38.13559 | 32.12982 | elegans protein partially confirmed by transcript evidence |
| SEQ ID NO: 1988 | Nga00943.01 | 72.56236 | 58.951507 | dna repair and recombination protein rad54 |
| SEQ ID NO: 1989 | Nga00932 | 504.9248 | 617.70728 | protein |
| SEQ ID NO: 1990 | Nga00935.01 | 212.3552 | 201.45084 | mate efflux family protein |
| SEQ ID NO: 1991 | Nga05196.2 | 1679.558 | 1479.2228 | spermidine synthase |
| SEQ ID NO: 1992 | Nga00934 | 27757.31 | 24354.446 | heat shock protein 90 |
| SEQ ID NO: 1993 | Nga00933 | 1067.098 | 1094.618 | diacylglycerol acyltransferase family protein |
| SEQ ID NO: 1994 | Nga00938 | 537.2993 | 387.67296 | predicted protein [Phaeodactylum tricornutum CCAP 1055/1] |
| SEQ ID NO: 1995 | Nga21051 | 468.8399 | 508.90185 | ---NA--- |
| SEQ ID NO: 1996 | Nga20027 | 213.7405 | 136.43786 | protein |
| SEQ ID NO: 1997 | Nga03963 | 588.1122 | 599.20203 | cell surface |
| SEQ ID NO: 1998 | Nga03964 | 904.8132 | 906.58588 | exported nucleotide-binding protein |
| SEQ ID NO: 1999 | Nga03966 | 225.6569 | 220.99981 | prefoldin subunit 3 |
| SEQ ID NO: 2000 | Nga03965 | 106.1703 | 94.096847 | atp-binding cassette superfamily |
| SEQ ID NO: 2001 | Nga07110.2 | 99.28571 | 177.95986 | bromodomain containing protein |
| SEQ ID NO: 2002 | Nga01056.01 | 26.21726 | 14.199696 | ---NA--- |
| SEQ ID NO: 2003 | Nga01053.01 | 266.0819 | 191.62472 | ---NA--- |
| SEQ ID NO: 2004 | Nga01050.01 | 211.8877 | 198.52334 | lipase domain-containing protein |
| SEQ ID NO: 2005 | Nga01051 | 553.0303 | 746.77491 | ---NA--- |
| SEQ ID NO: 2006 | Nga01054 | 1369.528 | 1263.0545 | otu domain-containing protein 7b |
| SEQ ID NO: 2007 | Nga01052 | 1038.439 | 1053.7669 | eukaryotic translation initiation factor subunit e |
| SEQ ID NO: 2008 | Nga05705 | 1194.636 | 1318.1421 | isobutyryl- mitochondrial |
| SEQ ID NO: 2009 | Nga05703 | 1344.229 | 1006.6875 | phosphomannomutase |
| SEQ ID NO: 2010 | Nga05707 | 123.2068 | 91.412147 | methyltransferase type 11 |
| SEQ ID NO: 2011 | Nga05706 | 488.6481 | 375.61053 | probable dolichyl pyrophosphate glc1man9 c2 alpha- -glucosyltransferase |
| SEQ ID NO: 2012 | Nga05704 | 281.8018 | 275.19997 | guanylate-binding protein |
| SEQ ID NO: 2013 | Nga05702 | 335.119 | 358.49885 | ankyrin repeat family protein |
| SEQ ID NO: 2014 | Nga20864 | 1480.652 | 1381.0681 | uncharacterized protein |
| SEQ ID NO: 2015 | Nga05708 | 41.37931 | 14.941158 | ---NA--- |
| SEQ ID NO: 2016 | Nga02451.01 | 757.2407 | 824.83216 | zinc transporter |
| SEQ ID NO: 2017 | Nga02460 | 1658.027 | 2003.4759 | conserved unknown protein [Ectocarpus siliculosus] |
| SEQ ID NO: 2018 | Nga02461 | 322.1477 | 225.37082 | ---NA--- |
| SEQ ID NO: 2019 | Nga02462 | 314.6417 | 303.71045 | ---NA--- |
| SEQ ID NO: 2020 | Nga02459.01 | 69.37799 | 76.016417 | metallo-beta-lactamase superfamily protein |
| SEQ ID NO: 2021 | Nga20655 | 135.4167 | 157.97162 | glutathione s-transferase |

FIGURE 24 AF

| # | Nga model | +N rpkb | -N rpkb | GO |
|---|---|---|---|---|
| SEQ ID NO: 2022 | Nga02453.01 | 857.3643 | 952.90998 | protein |
| SEQ ID NO: 2023 | Nga04049.2 | 808.4186 | 789.84033 | 5 -3 exoribonuclease 1 |
| SEQ ID NO: 2024 | Nga02452 | 92.15956 | 95.360347 | n-acetyltransferase mak3-like protein |
| SEQ ID NO: 2025 | Nga02456 | 1085.77 | 1140.2463 | ---NA--- |
| SEQ ID NO: 2026 | Nga02448 | 5468.165 | 5239.6878 | uqcrx qcr9 like ubiquinol-cytochrome c reductase family protein |
| SEQ ID NO: 2027 | Nga02457 | 215.7012 | 254.57098 | ubiquitin carboxyl-terminal hydrolase 4 |
| SEQ ID NO: 2028 | Nga02463 | 161.6162 | 257.73916 | rna polymerase ii elongator |
| SEQ ID NO: 2029 | Nga20287 | 120.3931 | 170.33654 | elongator complex protein 2 |
| SEQ ID NO: 2030 | Nga02454 | 494.3705 | 487.84333 | potential 4 histone acetyltransferase complex component yng2 |
| SEQ ID NO: 2031 | Nga20390 | 166.362 | 378.24074 | rna polymerase ii elongator |
| SEQ ID NO: 2032 | Nga20077 | 225.0242 | 289.98309 | wd-40 repeat-containing protein |
| SEQ ID NO: 2033 | Nga20372 | 243.1694 | 236.77245 | 1-acyl-sn-glycerol-3-phosphate acyltransferase |
| SEQ ID NO: 2034 | Nga20245 | 227.4775 | 241.53189 | protein |
| SEQ ID NO: 2035 | Nga21001 | 334.2391 | 341.45418 | protein |
| SEQ ID NO: 2036 | Nga02477 | 153.1823 | 179.95472 | p-type atpase |
| SEQ ID NO: 2037 | Nga02449 | 6466.234 | 5714.0444 | citrate synthase |
| SEQ ID NO: 2038 | Nga02479 | 203.5928 | 259.45723 | e1-e2 atpase family protein |
| SEQ ID NO: 2039 | Nga02458 | 311.7326 | 308.86207 | ca-transporting atpase |
| SEQ ID NO: 2040 | Nga02455 | 1801.379 | 1933.8839 | protein |
| SEQ ID NO: 2041 | Nga01622 | 1013.298 | 1064.5078 | mitogen-activated protein kinase kinase 1-interacting protein 1 |
| SEQ ID NO: 2042 | Nga01629 | 148.6111 | 176.02552 | ---NA--- |
| SEQ ID NO: 2043 | Nga06228 | 254.0773 | 297.54065 | ---NA--- |
| SEQ ID NO: 2044 | Nga06227 | 227.9849 | 320.11289 | gtp-binding protein obg |
| SEQ ID NO: 2045 | Nga06229 | 350.8647 | 358.25505 | nadph:adrenodoxin mitochondrial |
| SEQ ID NO: 2046 | Nga00417.02 | 2296.524 | 2372.4817 | ubiquitin domain containing protein |
| SEQ ID NO: 2047 | Nga06226 | 356.0732 | 431.97183 | ---NA--- |
| SEQ ID NO: 2048 | Nga01119 | 777.1781 | 666.47701 | serine threonine-protein phosphatase 4 catalytic subunit |
| SEQ ID NO: 2049 | Nga01121 | 259.7938 | 415.4258 | diacylglycerol acyltransferase family protein |
| SEQ ID NO: 2050 | Nga01120 | 176.5499 | 242.34075 | ---NA--- |
| SEQ ID NO: 2051 | Nga03781 | 148.9002 | 185.1212 | 3 -5 exoribonuclease |
| SEQ ID NO: 2052 | Nga03772 | 1148.187 | 1012.515 | protein |
| SEQ ID NO: 2053 | Nga03774 | 3114.914 | 3644.3274 | ---NA--- |
| SEQ ID NO: 2054 | Nga03776 | 1542.533 | 1374.0075 | GrpE [Atopobium rimae ATCC 49626] |
| SEQ ID NO: 2055 | Nga03773 | 9570.216 | 11926.603 | pyruvate decarboxylase |
| SEQ ID NO: 2056 | Nga03775.01 | 595.6679 | 481.0028 | 3 (2 ) -bisphosphate nucleotidase |
| SEQ ID NO: 2057 | Nga01000 | 481.7098 | 549.40842 | nhl repeat containing 2 |
| SEQ ID NO: 2058 | Nga01001 | 338.5214 | 181.24148 | muscular protein 20 |
| SEQ ID NO: 2059 | Nga00999 | 1278.696 | 1366.1949 | folate biopterin transporter |
| SEQ ID NO: 2060 | Nga01094 | 2086.988 | 2019.1861 | peptidase m48 ste24p |
| SEQ ID NO: 2061 | Nga01097.1 | 511.3772 | 527.99547 | conserved unknown protein [Ectocarpus siliculosus] |
| SEQ ID NO: 2062 | Nga01095 | 595.3421 | 693.77429 | protein |
| SEQ ID NO: 2063 | Nga01096.1 | 560.4616 | 617.98143 | dna topoisomerase i |
| SEQ ID NO: 2064 | Nga01098 | 1.219512 | 2.0549153 | dynein heavy chain |
| SEQ ID NO: 2065 | Nga01099 | 6.666667 | 4.1266055 | dynein heavy chain |
| SEQ ID NO: 2066 | Nga04654.02 | 1314.465 | 1350.636 | protein |
| SEQ ID NO: 2067 | Nga04655.02 | 722.8464 | 900.66642 | ---NA--- |
| SEQ ID NO: 2068 | Nga05808 | 748.8636 | 745.13365 | abc1 family protein |
| SEQ ID NO: 2069 | Nga20416.1 | 301.1204 | 370.18079 | ---NA--- |
| SEQ ID NO: 2070 | Nga05810 | 4962.825 | 5506.3721 | protein |
| SEQ ID NO: 2071 | Nga05816 | 280.1498 | 301.84496 | ---NA--- |
| SEQ ID NO: 2072 | Nga20877 | 320.6349 | 333.56728 | conserved c2h2 zinc finger protein |
| SEQ ID NO: 2073 | Nga05814 | 651.0264 | 627.38623 | exocyst complex component 6 |
| SEQ ID NO: 2074 | Nga05809 | 1672.316 | 1615.671 | ---NA--- |
| SEQ ID NO: 2075 | Nga20638 | 671.6418 | 659.35979 | exocyst complex component 6b |
| SEQ ID NO: 2076 | Nga20852 | 99.45387 | 106.79771 | uncharacterized protein |
| SEQ ID NO: 2077 | Nga05813 | 27709.13 | 30559.299 | glyceraldehyde 3-phosphate |
| SEQ ID NO: 2078 | Nga21005 | 24312.97 | 18319.07 | glyceraldehyde-3-phosphate dehydrogenase |
| SEQ ID NO: 2079 | Nga05812 | 299.3601 | 333.1885 | myb dna binding protein transcription factor-like protein |
| SEQ ID NO: 2080 | Nga00912 | 118.5077 | 115.69287 | hypothetical conserved protein |
| SEQ ID NO: 2081 | Nga00910 | 509.8039 | 413.21223 | ---NA--- |
| SEQ ID NO: 2082 | Nga00909 | 715.0685 | 688.5213 | oral cancer overexpressed 1 |
| SEQ ID NO: 2083 | Nga00911 | 164.1975 | 168.50306 | nad-dependent epimerase dehydratase |
| SEQ ID NO: 2084 | Nga00918 | 449.2406 | 410.43396 | protein phosphatase |
| SEQ ID NO: 2085 | Nga01324.01 | 613.4507 | 665.19143 | upf0760 protein c2orf29-like |

FIGURE 24 AG

| # | Nga model | +N rpkb | -N rpkb | GO |
|---|---|---|---|---|
| SEQ ID NO: 2086 | Nga01327.01 | 342.3019 | 362.69716 | phosphopantothenoylcysteine decarboxylase |
| SEQ ID NO: 2087 | Nga01325.01 | 1065.072 | 1237.6855 | ---NA--- |
| SEQ ID NO: 2088 | Nga01328.01 | 1213.585 | 1115.473 | heat shock protein 101 |
| SEQ ID NO: 2089 | Nga01323 | 1176.222 | 1464.3597 | 26s proteasome non-atpase regulatory |
| SEQ ID NO: 2090 | Nga01326 | 241.1504 | 276.4004 | microtubule interacting and transport domain-containing protein |
| SEQ ID NO: 2091 | Nga01328.02 | 1213.585 | 1115.473 | heat shock protein 101 |
| SEQ ID NO: 2092 | Nga00824 | 65.1341 | 74.705789 | ---NA--- |
| SEQ ID NO: 2093 | Nga00819.01 | 590.0178 | 455.692 | uncharacterized protein conserved in bacteria with a cystatin-like fold |
| SEQ ID NO: 2094 | Nga00823 | 362.3037 | 334.61153 | pre-mrna-splicing regulator female-lethal d |
| SEQ ID NO: 2095 | Nga00822 | 168.4211 | 169.77 | ---NA--- |
| SEQ ID NO: 2096 | Nga00818 | 1076.087 | 1103.6427 | monogalactosyldiacylglycerol synthase |
| SEQ ID NO: 2097 | Nga00821 | 88.7574 | 64.096683 | ---NA--- |
| SEQ ID NO: 2098 | Nga00817 | 838.2599 | 651.26949 | fatty acid desaturase |
| SEQ ID NO: 2099 | Nga00820 | 327.619 | 292.98899 | ---NA--- |
| SEQ ID NO: 2100 | Nga05243 | 1140.489 | 944.28508 | ---NA--- |
| SEQ ID NO: 2101 | Nga03614.02 | 8410.891 | 7259.0974 | protein |
| SEQ ID NO: 2102 | Nga05238.02 | 227.2109 | 191.5924 | sorbitol dehydrogenase |
| SEQ ID NO: 2103 | Nga05240 | 1185.022 | 1338.5336 | histone deacetylase complex subunit |
| SEQ ID NO: 2104 | Nga03613.02 | 3916.282 | 4065.8798 | calcium-dependent protein |
| SEQ ID NO: 2105 | Nga05232 | 817.9104 | 786.28772 | multidrug oligosaccharidyl-lipid polysaccharide flippase |
| SEQ ID NO: 2106 | Nga05237 | 171.6418 | 176.49707 | ---NA--- |
| SEQ ID NO: 2107 | Nga05234 | 1064.363 | 899.02546 | stage iv sporulation protein fb |
| SEQ ID NO: 2108 | Nga05238.01 | 227.2109 | 191.5924 | sorbitol dehydrogenase |
| SEQ ID NO: 2109 | Nga05241 | 180.9524 | 263.0711 | ---NA--- |
| SEQ ID NO: 2110 | Nga05242 | 3325.301 | 3258.4025 | ---NA--- |
| SEQ ID NO: 2111 | Nga05236 | 463.6763 | 495.40392 | tpr repeat-containing protein |
| SEQ ID NO: 2112 | Nga06288 | 135.8025 | 203.94219 | protein |
| SEQ ID NO: 2113 | Nga06286 | 287.3016 | 244.15749 | autophagyrelated protein |
| SEQ ID NO: 2114 | Nga00970.02 | 3093.06 | 2547.4792 | glutaredoxin type i |
| SEQ ID NO: 2115 | Nga00971.2 | 204.5019 | 216.8543 | glutamine-fructose-6-phosphate transaminase |
| SEQ ID NO: 2116 | Nga06282.1 | 1803.519 | 2360.2429 | biotin and thiamin synthesis associated |
| SEQ ID NO: 2117 | Nga06287.1 | 265.5367 | 321.9102 | ---NA--- |
| SEQ ID NO: 2118 | Nga06289 | 913.6691 | 1109.7303 | small gtp-binding protein |
| SEQ ID NO: 2119 | Nga20974 | 1950.318 | 2292.0402 | small gtp-binding protein |
| SEQ ID NO: 2120 | Nga06284 | 6748.981 | 7340.161 | 15-cis-zeta-carotene isomerase |
| SEQ ID NO: 2121 | Nga06285 | 1322.974 | 1419.2279 | cbs domain-containing protein |
| SEQ ID NO: 2122 | Nga00979 | 1484.127 | 1628.2897 | predicted protein [Phaeodactylum tricornutum CCAP 1055/1] |
| SEQ ID NO: 2123 | Nga00977 | 401.8605 | 500.80676 | rrp15-like protein |
| SEQ ID NO: 2124 | Nga00976 | 361.2613 | 324.97018 | serine threonine-protein phosphatase 6 regulatory ankyrin repeat subunit c |
| SEQ ID NO: 2125 | Nga20210.1 | 152.6718 | 150.90855 | transcription factor iiic-gamma subunit |
| SEQ ID NO: 2126 | Nga00978 | 422.8758 | 569.93681 | topoisomerase 6 subunit b |
| SEQ ID NO: 2127 | Nga20277 | 250 | 189.16769 | cyclin-dependent kinase d1_2 |
| SEQ ID NO: 2128 | Nga00980 | 528.2392 | 640.58353 | ---NA--- |
| SEQ ID NO: 2129 | Nga20246.1 | 1860.104 | 2120.1638 | uncharacterized protein c9orf85 homolog |
| SEQ ID NO: 2130 | Nga01274 | 366.8342 | 371.51114 | protein |
| SEQ ID NO: 2131 | Nga01275 | 1015.57 | 910.74446 | l-gulonolactone oxidase-like |
| SEQ ID NO: 2132 | Nga01283 | 34.46502 | 50.149719 | cyclin e |
| SEQ ID NO: 2133 | Nga01273 | 2766.871 | 2698.1164 | h aca ribonucleoprotein complex subunit 3 |
| SEQ ID NO: 2134 | Nga20116 | 186.6109 | 183.10733 | genomes uncoupled 1 protein |
| SEQ ID NO: 2135 | Nga20122 | 274.3083 | 248.33031 | conserved unknown protein [Ectocarpus siliculosus] |
| SEQ ID NO: 2136 | Nga20084 | 442.6952 | 374.49335 | conserved unknown protein [Ectocarpus siliculosus] |
| SEQ ID NO: 2137 | Nga03708 | 263.3797 | 270.69436 | dna repair helicase rad25 |
| SEQ ID NO: 2138 | Nga03707 | 891.8239 | 805.27202 | 26s protease regulatory subunit 7 |
| SEQ ID NO: 2139 | Nga00893 | 3678.571 | 3271.2945 | ---NA--- |
| SEQ ID NO: 2140 | Nga20096 | 1484.926 | 1463.3038 | protein |
| SEQ ID NO: 2141 | Nga00890 | 780.9355 | 856.83869 | orotidine-5-phosphate decarboxylase orotate phosphoribosyltransferase |
| SEQ ID NO: 2142 | Nga20527 | 588.8224 | 548.1034 | dtw domain containing protein |
| SEQ ID NO: 2143 | Nga00891 | 339.2948 | 357.57237 | abc1 family protein |
| SEQ ID NO: 2144 | Nga00892 | 485.1158 | 490.85904 | ---NA--- |
| SEQ ID NO: 2145 | Nga02270 | 52.91005 | 63.045362 | ---NA--- |
| SEQ ID NO: 2146 | Nga02269 | 2376.374 | 2033.5436 | l-threonine-o-3-phosphate decarboxylase |

FIGURE 24 AH

| # | Nga model | +N rpkb | -N rpkb | GO |
|---|---|---|---|---|
| SEQ ID NO: 2147 | Nga01745 | 2281.679 | 1961.0119 | triosephosphate isomerase glyceraldehyde-3-phosphate dehydrogenase |
| SEQ ID NO: 2148 | Nga01746 | 271.7391 | 233.52326 | dihydrolipoamide s-acetyltransferase |
| SEQ ID NO: 2149 | Nga01744 | 757.1885 | 694.46947 | tricarboxylate transport mitochondrial precursor |
| SEQ ID NO: 2150 | Nga20985.1 | 152 | 181.9833 | uncharacterized protein |
| SEQ ID NO: 2151 | Nga05796.1 | 149.2637 | 234.19315 | n -dimethylguanosine trna methyltransferase |
| SEQ ID NO: 2152 | Nga05798 | 5359.477 | 5111.7314 | heat shock protein |
| SEQ ID NO: 2153 | Nga05802 | 2029.72 | 2149.424 | dihydrolipoamide s-succinyltransferase |
| SEQ ID NO: 2154 | Nga05795.02 | 3420.67 | 3770.0325 | dihydrolipoamide succinyltransferase |
| SEQ ID NO: 2155 | Nga05799 | 245.7483 | 244.09608 | cyclin-dependent kinase |
| SEQ ID NO: 2156 | Nga05800.1 | 1377.297 | 1509.5011 | electron transfer flavoprotein subunit |
| SEQ ID NO: 2157 | Nga05797 | 739.6825 | 777.86513 | cell division cycle 2 |
| SEQ ID NO: 2158 | Nga05795.01 | 3420.67 | 3770.0325 | dihydrolipoamide succinyltransferase |
| SEQ ID NO: 2159 | Nga05800.2 | 1377.297 | 1509.5011 | electron-transfer- beta polypeptide |
| SEQ ID NO: 2160 | Nga20040 | 3558.26 | 4267.4305 | ---NA--- |
| SEQ ID NO: 2161 | Nga00079 | 1211.514 | 1224.769 | dna-directed rna polymerase ii subunit rpb4 |
| SEQ ID NO: 2162 | Nga00088 | 1994.444 | 1567.6802 | ---NA--- |
| SEQ ID NO: 2163 | Nga00081.01 | 451.3981 | 552.43489 | cyclin dependent kinase |
| SEQ ID NO: 2164 | Nga00084 | 656.5008 | 635.21905 | malate synthase a |
| SEQ ID NO: 2165 | Nga00071 | 3824.536 | 3974.4332 | cdgsh iron sulfur domain 1 |
| SEQ ID NO: 2166 | Nga00072 | 3163.641 | 3547.3567 | glucose-6-phosphate isomerase |
| SEQ ID NO: 2167 | Nga00083 | 620.915 | 550.46692 | phosphatidylinositide phosphatase sac1 |
| SEQ ID NO: 2168 | Nga20882 | 1043.103 | 855.38128 | ap-4 complex subunit sigma- |
| SEQ ID NO: 2169 | Nga00086 | 4351.607 | 4235.67 | 60s ribosomal protein l13a |
| SEQ ID NO: 2170 | Nga00087 | 177.1379 | 189.99129 | regulator of chromosome condensation -like protein |
| SEQ ID NO: 2171 | Nga00078 | 14765.62 | 16839.859 | cell division protein |
| SEQ ID NO: 2172 | Nga00089 | 5387.294 | 4742.5398 | ---NA--- |
| SEQ ID NO: 2173 | Nga00074 | 1040.564 | 987.71067 | dnaj subfamily b member 5 |
| SEQ ID NO: 2174 | Nga00114 | 967.8715 | 1118.0366 | cystinosin |
| SEQ ID NO: 2175 | Nga00082 | 2055.556 | 1843.9425 | glycolate oxidase |
| SEQ ID NO: 2176 | Nga20784 | 971.2121 | 1250.6428 | ---NA--- |
| SEQ ID NO: 2177 | Nga00085 | 297.9684 | 311.15467 | protein |
| SEQ ID NO: 2178 | Nga00073 | 915.0579 | 844.83883 | prefoldin subunit 2 |
| SEQ ID NO: 2179 | Nga00076 | 2075.351 | 3336.1669 | imp dehydrogenase |
| SEQ ID NO: 2180 | Nga00075 | 1472.652 | 1115.6527 | translation elongation factor p |
| SEQ ID NO: 2181 | Nga00080 | 523.774 | 557.67461 | dna nad-dependent |
| SEQ ID NO: 2182 | Nga00090 | 292.1788 | 274.13686 | postreplication repair e3 ubiquitin-protein ligase rad18 |
| SEQ ID NO: 2183 | Nga00077 | 436.3002 | 469.30685 | protein |
| SEQ ID NO: 2184 | Nga02030 | 1970.76 | 2061.9453 | cystatin b |
| SEQ ID NO: 2185 | Nga02031 | 595.6989 | 479.88428 | aldehyde dehydrogenase |
| SEQ ID NO: 2186 | Nga02032 | 382.8265 | 299.39113 | protein |
| SEQ ID NO: 2187 | Nga01783.02 | 1437.126 | 1556.7434 | tim10-like protein |
| SEQ ID NO: 2188 | Nga01781.02 | 1005.471 | 838.98776 | endomembrane protein 70 containing expressed |
| SEQ ID NO: 2189 | Nga01782.2 | 159.7494 | 158.62549 | nad-dependent histone deacetylase sir2-like protein |
| SEQ ID NO: 2190 | Nga01677.1 | 1513.24 | 1322.8277 | molecular chaperone ( superfamily) |
| SEQ ID NO: 2191 | Nga01678.01 | 756.1299 | 824.80835 | mitochondrial-processing peptidase subunit beta |
| SEQ ID NO: 2192 | Nga01679.01 | 561.5797 | 630.07383 | pleiotropic regulator 1 |
| SEQ ID NO: 2193 | Nga01680 | 355.248 | 427.29643 | protein |
| SEQ ID NO: 2194 | Nga20780 | 336.8201 | 243.99202 | protein |
| SEQ ID NO: 2195 | Nga06766 | 253.5211 | 274.62269 | dna glycosylase |
| SEQ ID NO: 2196 | Nga06759 | 277.7778 | 281.75024 | ---NA--- |
| SEQ ID NO: 2197 | Nga06758 | 857.7388 | 887.55589 | phospholipase ddhd1 |
| SEQ ID NO: 2198 | Nga20206 | 237.1202 | 271.8817 | mitogen-activated protein kinase kinase 2 |
| SEQ ID NO: 2199 | Nga06760 | 1053.704 | 1089.2519 | flj10769 protein |
| SEQ ID NO: 2200 | Nga06757 | 760.7399 | 517.70309 | cellulase 2 |
| SEQ ID NO: 2201 | Nga01656 | 558.6488 | 618.41641 | myb domain-containing protein |
| SEQ ID NO: 2202 | Nga01658 | 87.96296 | 85.254523 | glutathione s-transferase c-terminal domain-containing |
| SEQ ID NO: 2203 | Nga06216 | 589.5789 | 541.23038 | transmembrane protein 110 |
| SEQ ID NO: 2204 | Nga06212 | 637.6147 | 579.38109 | uncharacterized protein c3orf26-like |
| SEQ ID NO: 2205 | Nga06213 | 312.2476 | 287.93904 | arylsulfatase j |
| SEQ ID NO: 2206 | Nga06217 | 373.7374 | 368.73721 | protein |
| SEQ ID NO: 2207 | Nga06218 | 317.757 | 354.32886 | ---NA--- |
| SEQ ID NO: 2208 | Nga06214 | 415.1515 | 541.61697 | conserved unknown protein [Ectocarpus siliculosus] |
| SEQ ID NO: 2209 | Nga06215.1 | 576.7386 | 467.583 | conserved unknown protein [Ectocarpus siliculosus] |

FIGURE 24 AI

| # | Nga model | +N rpkb | -N rpkb | GO |
|---|---|---|---|---|
| SEQ ID NO: 2210 | Nga20085 | 154.0195 | 159.51454 | subunit of golgi mannosyltransferase complex |
| SEQ ID NO: 2211 | Nga03572.2 | 794.279 | 844.68477 | protein |
| SEQ ID NO: 2212 | Nga20635 | 166.6667 | 116.06078 | ---NA--- |
| SEQ ID NO: 2213 | Nga20691 | 129.2929 | 144.43119 | kinesin family member 2b |
| SEQ ID NO: 2214 | Nga03572.1 | 794.279 | 844.68477 | protein |
| SEQ ID NO: 2215 | Nga03571.1 | 1037.758 | 960.85087 | protein |
| SEQ ID NO: 2216 | Nga03570.1 | 262.1118 | 255.67012 | integral membrane mpv17 pmp22 |
| SEQ ID NO: 2217 | Nga02313.01 | 777.4914 | 613.2742 | zinc fyve domain containing 21 |
| SEQ ID NO: 2218 | Nga02316.1 | 51.3308 | 32.950082 | transducin wd40 domain-containing protein |
| SEQ ID NO: 2219 | Nga02315 | 3352.59 | 2942.5698 | canine-like rab-type small g protein |
| SEQ ID NO: 2220 | Nga02314 | 8992.026 | 6693.9366 | ---NA--- |
| SEQ ID NO: 2221 | Nga02067 | 752.0176 | 748.64738 | ---NA--- |
| SEQ ID NO: 2222 | Nga20237 | 331.5364 | 291.9768 | protein kinase domain protein |
| SEQ ID NO: 2223 | Nga02068 | 76.74419 | 98.246799 | ---NA--- |
| SEQ ID NO: 2224 | Nga02066 | 320.4301 | 216.64679 | acetyl-coenzyme a transporter 1 |
| SEQ ID NO: 2225 | Nga00871 | 1874.825 | 1851.3453 | small gtp-binding protein |
| SEQ ID NO: 2226 | Nga00873 | 976.7442 | 1070.331 | phosphoribosylpyrophosphate synthetase |
| SEQ ID NO: 2227 | Nga00872 | 669.0717 | 749.77087 | ---NA--- |
| SEQ ID NO: 2228 | Nga00869 | 1194.201 | 1132.0022 | oligopeptidase b |
| SEQ ID NO: 2229 | Nga00870 | 538.0711 | 419.73024 | conserved unknown protein [Ectocarpus siliculosus] |
| SEQ ID NO: 2230 | Nga00876 | 352.8571 | 340.96078 | alpha- -mannosyltransferase |
| SEQ ID NO: 2231 | Nga00874 | 463.5368 | 469.57089 | protein |
| SEQ ID NO: 2232 | Nga00875 | 524.3399 | 635.4615 | conserved unknown protein [Ectocarpus siliculosus] |
| SEQ ID NO: 2233 | Nga01846 | 216.3934 | 200.66465 | aaa family atpase |
| SEQ ID NO: 2234 | Nga01845 | 131.4554 | 76.28408 | diphosphate fructose-6-phosphate 1-phosphotransferase |
| SEQ ID NO: 2235 | Nga01843 | 185.1157 | 156.82843 | pyrophosphate-dependent phosphofructokinase alpha subunit |
| SEQ ID NO: 2236 | Nga04265.2 | 125.0936 | 116.84321 | ---NA--- |
| SEQ ID NO: 2237 | Nga01844 | 446.7509 | 381.2827 | peroxisomal membrane protein pmp47b |
| SEQ ID NO: 2238 | Nga01842 | 594.5626 | 738.8014 | glutathione s-transferase mu 1-like |
| SEQ ID NO: 2239 | Nga02391 | 564.4871 | 757.02912 | ribose-phosphate pyrophosphokinase |
| SEQ ID NO: 2240 | Nga02390.1 | 608.7654 | 536.69581 | gtp cyclohydrolase ii |
| SEQ ID NO: 2241 | Nga02392.01 | 639.0328 | 692.22203 | cd4-specific ankyrin repeat protein |
| SEQ ID NO: 2242 | Nga01983.02 | 1527.665 | 1594.8829 | conserved unknown protein [Ectocarpus siliculosus] |
| SEQ ID NO: 2243 | Nga02022.1 | 988.9503 | 906.68476 | m-aaa protease afg3 yta10-like protein |
| SEQ ID NO: 2244 | Nga20730 | 132 | 90.991651 | epsilon 1 |
| SEQ ID NO: 2245 | Nga20701 | 95.2381 | 103.16514 | epsilon 1 |
| SEQ ID NO: 2246 | Nga02082 | 126.0163 | 134.3034 | epsilon tubulin |
| SEQ ID NO: 2247 | Nga02081 | 2184.369 | 2097.002 | protein atypical group |
| SEQ ID NO: 2248 | Nga20646.1 | 237.1968 | 195.62446 | ---NA--- |
| SEQ ID NO: 2249 | Nga01645.01 | 604.0992 | 504.80805 | lysophospholipase-like protein |
| SEQ ID NO: 2250 | Nga01647 | 75.63025 | 109.23367 | ---NA--- |
| SEQ ID NO: 2251 | Nga01646.1 | 1423.3 | 1713.4221 | iojap-like protein |
| SEQ ID NO: 2252 | Nga05879 | 203.5836 | 230.56787 | cell division cycle 5-like protein |
| SEQ ID NO: 2253 | Nga05878 | 349.537 | 317.19698 | ---NA--- |
| SEQ ID NO: 2254 | Nga05877 | 719.5915 | 572.29351 | hypothetical protein Pmar_PMAR026561 [Perkinsus marinus ATCC 50983] |
| SEQ ID NO: 2255 | Nga05880 | 297.9351 | 217.28586 | ---NA--- |
| SEQ ID NO: 2256 | Nga05876 | 377.5194 | 445.46946 | cell division cycle 5-like protein |
| SEQ ID NO: 2257 | Nga05872 | 9011.161 | 7577.8017 | glutathione peroxidase |
| SEQ ID NO: 2258 | Nga05875 | 1426.564 | 1155.1728 | nad-dependent epimerase dehydratase |
| SEQ ID NO: 2259 | Nga20683 | 54.34783 | 64.758551 | protein |
| SEQ ID NO: 2260 | Nga21034 | 166.1808 | 189.48699 | hypothetical protein CaO19.1645 [Candida albicans SC5314] |
| SEQ ID NO: 2261 | Nga05873 | 296.4286 | 352.05103 | myotubularin-related protein |
| SEQ ID NO: 2262 | Nga05874 | 610.1974 | 564.77822 | loc779510 protein |
| SEQ ID NO: 2263 | Nga05871 | 323.3743 | 432.78591 | lysyl-trna synthetase |
| SEQ ID NO: 2264 | Nga03925.01 | 1104.401 | 1177.4764 | ---NA--- |
| SEQ ID NO: 2265 | Nga03921.1 | 4067.703 | 4165.822 | ribosomal protein s7 |
| SEQ ID NO: 2266 | Nga03920.01 | 772.9636 | 741.5553 | cytochrome c oxidase assembly mitochondrial |
| SEQ ID NO: 2267 | Nga03924 | 616.5703 | 666.84633 | branched-chain-amino-acid transaminase |
| SEQ ID NO: 2268 | Nga03922 | 820.3209 | 660.36722 | protein |
| SEQ ID NO: 2269 | Nga03926 | 1188.748 | 1170.7184 | ---NA--- |
| SEQ ID NO: 2270 | Nga03923 | 2248.792 | 2217.4898 | periplasmic binding protein |
| SEQ ID NO: 2271 | Nga02252 | 639.3606 | 669.85196 | atp-binding cassette protein c4-like |
| SEQ ID NO: 2272 | Nga02253 | 212.1212 | 306.3692 | ---NA--- |
| SEQ ID NO: 2273 | Nga02248 | 255.914 | 186.36283 | ---NA--- |

FIGURE 24 AJ

| # | Nga model | +N rpkb | -N rpkb | GO |
|---|---|---|---|---|
| SEQ ID NO: 2274 | Nga02247.1 | 695.0445 | 664.80558 | histone deacetylase superfamily protein |
| SEQ ID NO: 2275 | Nga02249 | 66.0066 | 89.375738 | ---NA--- |
| SEQ ID NO: 2276 | Nga01202.02 | 701.7857 | 658.96731 | magnesium-dependent phosphatase 1 |
| SEQ ID NO: 2277 | Nga03425 | 845.9445 | 722.35252 | cdc25 protein |
| SEQ ID NO: 2278 | Nga03428 | 3385.317 | 3369.2379 | ---NA--- |
| SEQ ID NO: 2279 | Nga03430.1 | 1044.761 | 980.39865 | fha domain containing protein |
| SEQ ID NO: 2280 | Nga03438 | 469.8795 | 349.7671 | pseudouridine synthase and archaeosine transglycosylase domain-containing protein |
| SEQ ID NO: 2281 | Nga03432 | 897.1471 | 907.57438 | 4fe-4s iron-sulfur binding protein |
| SEQ ID NO: 2282 | Nga20095 | 2260.87 | 2214.2576 | aldo keto reductase |
| SEQ ID NO: 2283 | Nga03431 | 542.2427 | 554.9286 | methyltransferase type 11 |
| SEQ ID NO: 2284 | Nga03437 | 555.8158 | 716.23665 | tom1 protein |
| SEQ ID NO: 2285 | Nga03426 | 426.1874 | 490.86211 | ubiquitin-conjugating enzyme e2 t |
| SEQ ID NO: 2286 | Nga03436 | 390.7886 | 372.66876 | protein |
| SEQ ID NO: 2287 | Nga03434 | 400.995 | 437.60496 | conserved unknown protein [Ectocarpus siliculosus] |
| SEQ ID NO: 2288 | Nga03435 | 610.8298 | 737.01873 | dead deah box helicase |
| SEQ ID NO: 2289 | Nga20396 | 228.5966 | 237.10681 | cap-specific mrna (nucleoside-2 -o-)-methyltransferase 1 |
| SEQ ID NO: 2290 | Nga03452 | 3679.811 | 2759.9115 | protein |
| SEQ ID NO: 2291 | Nga03427 | 12704.65 | 15826.424 | ypl260w-like protein |
| SEQ ID NO: 2292 | Nga03429 | 1508.311 | 1284.8998 | hect e3 ubiquitin |
| SEQ ID NO: 2293 | Nga21287 | 101.5625 | 101.55318 | ---NA--- |
| SEQ ID NO: 2294 | Nga20716 | 38.46154 | 53.566514 | dna helicase |
| SEQ ID NO: 2295 | Nga02368 | 879.2627 | 936.47321 | hypothetical protein VOLCADRAFT_103907 [Volvox carteri f. nagariensis] |
| SEQ ID NO: 2296 | Nga21187 | 1103.261 | 1208.8263 | sucrose-phosphate phosphatase |
| SEQ ID NO: 2297 | Nga02367 | 387.5598 | 321.34213 | sulfate permease |
| SEQ ID NO: 2298 | Nga02366.1 | 334.6614 | 379.77923 | ---NA--- |
| SEQ ID NO: 2299 | Nga02244 | 6858.185 | 5816.4571 | ---NA--- |
| SEQ ID NO: 2300 | Nga02243 | 740.0722 | 732.58421 | homogentisate solanesyltransferase |
| SEQ ID NO: 2301 | Nga21059 | 619.9295 | 685.85712 | exosome complex exonuclease rrp41 |
| SEQ ID NO: 2302 | Nga02242.01 | 502.994 | 507.88753 | drug metabolite transporter superfamily |
| SEQ ID NO: 2303 | Nga04175 | 31271.32 | 18693.283 | light-harvesting protein |
| SEQ ID NO: 2304 | Nga04176 | 1022.435 | 1013.1865 | histone acetyltransferase |
| SEQ ID NO: 2305 | Nga04174 | 664.9162 | 702.65287 | beta-galactosidase |
| SEQ ID NO: 2306 | Nga04173 | 1576.88 | 1531.846 | ap-2 complex subunit mu |
| SEQ ID NO: 2307 | Nga00239.01 | 309.4001 | 285.51939 | integral membrane protein gpr155-like |
| SEQ ID NO: 2308 | Nga00243.01 | 5108.949 | 1993.6562 | ---NA--- |
| SEQ ID NO: 2309 | Nga00236 | 628.2051 | 396.78899 | ---NA--- |
| SEQ ID NO: 2310 | Nga00249.01 | 2197.105 | 1291.9193 | ---NA--- |
| SEQ ID NO: 2311 | Nga00237 | 931.9372 | 1201.3877 | ---NA--- |
| SEQ ID NO: 2312 | Nga00242.1 | 4126.603 | 2518.8661 | ---NA--- |
| SEQ ID NO: 2313 | Nga00238.01 | 4637.011 | 3068.5203 | ---NA--- |
| SEQ ID NO: 2314 | Nga00246 | 109.7561 | 165.12713 | ---NA--- |
| SEQ ID NO: 2315 | Nga00241 | 508.4623 | 540.56936 | propionyl- carboxylase |
| SEQ ID NO: 2316 | Nga00247 | 77.50473 | 61.431036 | ---NA--- |
| SEQ ID NO: 2317 | Nga00235 | 242.9178 | 299.96067 | conserved unknown protein [Ectocarpus siliculosus] |
| SEQ ID NO: 2318 | Nga00248 | 165.9919 | 149.10913 | ---NA--- |
| SEQ ID NO: 2319 | Nga00245 | 109.7561 | 165.12713 | ---NA--- |
| SEQ ID NO: 2320 | Nga00240 | 979.4195 | 975.76799 | hypothetical protein CY0110_14003 [Cyanothece sp. CCY0110] |
| SEQ ID NO: 2321 | Nga00244 | 1148.058 | 1196.2899 | carboxyl-terminal protease |
| SEQ ID NO: 2322 | Nga06410.2 | 353.6379 | 377.57393 | nicotinate-nucleotide pyrophosphorylase |
| SEQ ID NO: 2323 | Nga00968.01 | 54.57227 | 59.114537 | hypothetical protein PTSG_07517 [Salpingoeca sp. ATCC 50818] |
| SEQ ID NO: 2324 | Nga00966.1 | 738.2107 | 652.13643 | mitogen-activated protein kinase |
| SEQ ID NO: 2325 | Nga00965.01 | 26928.68 | 20938.844 | oxygen-evolving enhancer protein |
| SEQ ID NO: 2326 | Nga00964 | 2335.029 | 1760.2552 | nad-dependent epimerase dehydratase |
| SEQ ID NO: 2327 | Nga00967.01 | 484.4479 | 507.08152 | dna polymerase beta |
| SEQ ID NO: 2328 | Nga03051.02 | 599.3512 | 581.59032 | sentrin-specific protease 8 |
| SEQ ID NO: 2329 | Nga06386 | 252.1877 | 251.6343 | hypothetical protein SKA58_14132 [Sphingomonas sp. SKA58] |
| SEQ ID NO: 2330 | Nga21046 | 432.1951 | 425.89588 | tho complex subunit 5 homolog |
| SEQ ID NO: 2331 | Nga20043 | 436.5869 | 522.00729 | nucleoporin 98kd |
| SEQ ID NO: 2332 | Nga20534 | 252.3364 | 187.28811 | gtpase activator nb4s evi5 (contains tbc domain) calmodulin-binding protein pollux (contains ptb and tbc domains) |
| SEQ ID NO: 2333 | Nga05196.1 | 1679.558 | 1479.2228 | spermidine synthase |
| SEQ ID NO: 2334 | Nga05198 | 264.7263 | 262.73866 | ---NA--- |
| SEQ ID NO: 2335 | Nga05197 | 1009.174 | 1190.0666 | ---NA--- |

FIGURE 24 AK

| # | Nga model | +N rpkb | -N rpkb | GO |
|---|---|---|---|---|
| SEQ ID NO: 2336 | Nga05194 | 50.98039 | 36.107798 | phosphatidylinositol n-acetylglucosaminyltransferase subunit |
| SEQ ID NO: 2337 | Nga05199 | 317.6329 | 329.02577 | protein |
| SEQ ID NO: 2338 | Nga05193 | 731.4619 | 762.50948 | dna photolyase |
| SEQ ID NO: 2339 | Nga05190 | 1821.705 | 1648.6429 | protein |
| SEQ ID NO: 2340 | Nga05191 | 205.8636 | 202.28652 | probable phospholipid-transporting atpase ia isoform 1 |
| SEQ ID NO: 2341 | Nga05195.1 | 38.13559 | 32.12982 | dna repair and recombination protein rad26 |
| SEQ ID NO: 2342 | Nga00943.02 | 72.56236 | 58.951507 | dna repair and recombination protein rad54 |
| SEQ ID NO: 2343 | Nga00935.02 | 212.3552 | 201.45084 | mate efflux family protein |
| SEQ ID NO: 2344 | Nga20392 | 179.34 | 161.63032 | methyltransferase small |
| SEQ ID NO: 2345 | Nga04290 | 646.7149 | 749.69921 | protein |
| SEQ ID NO: 2346 | Nga02441 | 562.0781 | 601.86729 | atp-dependent rna helicase |
| SEQ ID NO: 2347 | Nga02442 | 277.2512 | 304.60607 | ---NA--- |
| SEQ ID NO: 2348 | Nga01803 | 97.11286 | 82.450877 | ---NA--- |
| SEQ ID NO: 2349 | Nga01804 | 6029.674 | 5975.4656 | 40s ribosomal protein s23 |
| SEQ ID NO: 2350 | Nga01805 | 489.8407 | 428.89164 | carrier protein |
| SEQ ID NO: 2351 | Nga01802 | 3402.211 | 3678.6535 | mitochondrial carrier protein |
| SEQ ID NO: 2352 | Nga04343.01 | 18888.24 | 14347.115 | ---NA--- |
| SEQ ID NO: 2353 | Nga04342.01 | 517.7936 | 528.12473 | dna-directed rna polymerases and iii kda polypeptide |
| SEQ ID NO: 2354 | Nga04344 | 770.7359 | 707.25823 | trypsin 5g1 |
| SEQ ID NO: 2355 | Nga04560 | 261.4379 | 343.77141 | retinol dehydrogenase 14 |
| SEQ ID NO: 2356 | Nga04618 | 162.2103 | 204.67522 | ---NA--- |
| SEQ ID NO: 2357 | Nga04617 | 10205.34 | 15520.908 | ---NA--- |
| SEQ ID NO: 2358 | Nga01794.01 | 1708.625 | 1941.741 | ---NA--- |
| SEQ ID NO: 2359 | Nga01792.01 | 1814.887 | 1902.2904 | expressed unknown protein [Ectocarpus siliculosus] |
| SEQ ID NO: 2360 | Nga01793.01 | 333.8789 | 304.93656 | protein |
| SEQ ID NO: 2361 | Nga01791.1 | 2943.874 | 3333.4838 | beta- aspartyl asparaginyl family |
| SEQ ID NO: 2362 | Nga04213 | 256.4103 | 273.7844 | sulfate permease family |
| SEQ ID NO: 2363 | Nga04212 | 641.0749 | 704.82976 | ---NA--- |
| SEQ ID NO: 2364 | Nga03741 | 703.5461 | 815.88259 | ---NA--- |
| SEQ ID NO: 2365 | Nga03740 | 1138.486 | 948.04774 | solute carrier family member b2 |
| SEQ ID NO: 2366 | Nga03742 | 885.5932 | 900.94639 | radical sam cfr family |
| SEQ ID NO: 2367 | Nga20943 | 3762.472 | 4644.2734 | protein |
| SEQ ID NO: 2368 | Nga20613 | 662.2807 | 676.22938 | protein |
| SEQ ID NO: 2369 | Nga03739.01 | 7230.616 | 8437.329 | malate synthase |
| SEQ ID NO: 2370 | Nga03865 | 148.1481 | 176.08124 | nucleolar complex protein 3 homolog |
| SEQ ID NO: 2371 | Nga03858 | 598.4556 | 588.04128 | cystathionine beta-lyase |
| SEQ ID NO: 2372 | Nga03859 | 128.2435 | 143.78255 | atp-dependent dna helicase |
| SEQ ID NO: 2373 | Nga03860 | 5805.501 | 5448.0921 | 60s ribosomal protein l43 |
| SEQ ID NO: 2374 | Nga03861 | 203.4739 | 232.05756 | es2 protein |
| SEQ ID NO: 2375 | Nga04688 | 730.6219 | 994.80017 | histidine kinase |
| SEQ ID NO: 2376 | Nga04511 | 149.4465 | 158.88764 | msk16-like protein rbm13 |
| SEQ ID NO: 2377 | Nga04510 | 215.8399 | 204.57943 | smad nuclear interacting protein 1 |
| SEQ ID NO: 2378 | Nga02200 | 1085.137 | 1277.0594 | mitochondrial import tom22 homolog |
| SEQ ID NO: 2379 | Nga02201.1 | 474.1533 | 494.30996 | gpn-loop gtpase 2-like |
| SEQ ID NO: 2380 | Nga02199 | 706.6136 | 822.52523 | pyruvate dehydrogenase |
| SEQ ID NO: 2381 | Nga02202 | 119.9791 | 189.8626 | rwp-rk domain-containing protein |
| SEQ ID NO: 2382 | Nga06333 | 496.1464 | 415.34404 | solute carrier family 25 member 45-like |
| SEQ ID NO: 2383 | Nga21292 | 68.62745 | 95.579465 | ---NA--- |
| SEQ ID NO: 2384 | Nga21291 | 104.8951 | 166.65138 | ---NA--- |
| SEQ ID NO: 2385 | Nga06337 | 169.0909 | 196.95163 | protein |
| SEQ ID NO: 2386 | Nga20480 | 584.3972 | 852.75863 | phosphoglucomutase phosphomannomutase alpha beta alpha domain i |
| SEQ ID NO: 2387 | Nga20323 | 143.1065 | 209.84113 | ---NA--- |
| SEQ ID NO: 2388 | Nga21235 | 658.0977 | 620.97987 | phosphoglucomutase phosphomannomutase |
| SEQ ID NO: 2389 | Nga21226 | 752.7594 | 1162.145 | phosphoglucomutase phosphomannomutase family protein |
| SEQ ID NO: 2390 | Nga06335 | 68.37607 | 114.18705 | snf2-related domain-containing protein |
| SEQ ID NO: 2391 | Nga20439 | 225.1656 | 172.16963 | oligomeric golgi complex component |
| SEQ ID NO: 2392 | Nga20337 | 157.3187 | 171.89485 | ---NA--- |
| SEQ ID NO: 2393 | Nga21006 | 396.2264 | 270.24075 | uncharacterized protein |
| SEQ ID NO: 2394 | Nga06331 | 7981.792 | 7293.8804 | fatty-acyl elongase |
| SEQ ID NO: 2395 | Nga06336 | 982.7338 | 932.04877 | fatty acid elongation protein 3 |
| SEQ ID NO: 2396 | Nga06332 | 782.6087 | 1093.2242 | rhodanese domain protein |
| SEQ ID NO: 2397 | Nga06334 | 508.3415 | 553.84189 | protein |
| SEQ ID NO: 2398 | Nga03803 | 50.77031 | 70.850175 | dynein heavy chain |

FIGURE 24 AL

| # | Nga model | +N rpkb | -N rpkb | GO |
|---|---|---|---|---|
| SEQ ID NO: 2399 | Nga03804 | 1038.889 | 1060.3657 | endoglucanase e |
| SEQ ID NO: 2400 | Nga05524 | 937.1383 | 1000.6096 | serine threonine protein phosphatase 5 |
| SEQ ID NO: 2401 | Nga05527 | 178.3476 | 137.64169 | alpha-( )-fucosyltransferase |
| SEQ ID NO: 2402 | Nga05520 | 471.7322 | 525.67412 | methylisocitrate lyase |
| SEQ ID NO: 2403 | Nga20584 | 105.1136 | 95.398444 | ---NA--- |
| SEQ ID NO: 2404 | Nga05526 | 1969.194 | 1374.5777 | atp-dependent clp protease adaptor protein |
| SEQ ID NO: 2405 | Nga05522 | 1169.638 | 1507.5152 | dihydroxy-acid dehydratase |
| SEQ ID NO: 2406 | Nga05525 | 607.9772 | 623.39959 | anthranilate synthase |
| SEQ ID NO: 2407 | Nga05521 | 289.7436 | 286.08486 | yeats domain-containing protein |
| SEQ ID NO: 2408 | Nga05523 | 4374.106 | 4691.6892 | 30s ribosomal protein s1 |
| SEQ ID NO: 2409 | Nga02227.01 | 599.177 | 542.06275 | gluconolactonase |
| SEQ ID NO: 2410 | Nga02226.1 | 439.0592 | 526.56133 | far upstream binding protein |
| SEQ ID NO: 2411 | Nga02075 | 564.8415 | 577.51665 | ---NA--- |
| SEQ ID NO: 2412 | Nga02076 | 2409.051 | 2402.1585 | calcium-dependent protein |
| SEQ ID NO: 2413 | Nga02074 | 74.38795 | 98.939447 | abc transporter atpase |
| SEQ ID NO: 2414 | Nga04611 | 211.6402 | 299.94308 | conserved unknown protein [Ectocarpus siliculosus] |
| SEQ ID NO: 2415 | Nga04613 | 117.6471 | 143.3692 | ---NA--- |
| SEQ ID NO: 2416 | Nga04612 | 111.6505 | 73.617841 | ---NA--- |
| SEQ ID NO: 2417 | Nga04610.1 | 184.9837 | 172.09157 | pectinacetylesterase family protein |
| SEQ ID NO: 2418 | Nga02849 | 525.8456 | 380.89464 | ap-4 complex subunit mu- |
| SEQ ID NO: 2419 | Nga02855 | 386.0148 | 438.4665 | protein |
| SEQ ID NO: 2420 | Nga02844 | 1185.029 | 1008.5282 | estradiol 17-beta-dehydrogenase 12-b |
| SEQ ID NO: 2421 | Nga02856 | 491.9852 | 494.20044 | 3-hydroxyisobutyrate dehydrogenase |
| SEQ ID NO: 2422 | Nga20358 | 528.8684 | 485.32883 | 3-hydroxyisobutyrate dehydrogenase |
| SEQ ID NO: 2423 | Nga02848 | 976.257 | 1037.0906 | conserved hypothetical protein [Phytophthora infestans T30-4] |
| SEQ ID NO: 2424 | Nga02851 | 1228.369 | 1046.3579 | ferredoxin [Ectocarpus siliculosus] |
| SEQ ID NO: 2425 | Nga02852 | 562.0023 | 433.78652 | protein |
| SEQ ID NO: 2426 | Nga02853 | 264.3756 | 217.45765 | protein |
| SEQ ID NO: 2427 | Nga02845 | 437.5 | 424.57263 | fusca protein fus6 |
| SEQ ID NO: 2428 | Nga02850 | 368.3908 | 377.88678 | sec1-like family protein |
| SEQ ID NO: 2429 | Nga02857 | 355.042 | 299.63404 | drug metabolite transporter superfamily |
| SEQ ID NO: 2430 | Nga02847 | 1017.954 | 946.86315 | aps kinase atp sulfurlyase pyrophosphatase fusion protein |
| SEQ ID NO: 2431 | Nga02854 | 292.6829 | 314.90189 | uncharacterized protein kiaa1530-like |
| SEQ ID NO: 2432 | Nga02846 | 611.9697 | 682.14173 | prp6 pre-mrna splicing factor 6 homolog |
| SEQ ID NO: 2433 | Nga04240 | 5503.173 | 5256.0907 | cen |
| SEQ ID NO: 2434 | Nga04241 | 849.6241 | 855.18469 | 5 ampactivated protein kinase subunit beta |
| SEQ ID NO: 2435 | Nga04242 | 1462.145 | 1146.4511 | bet1 homolog |
| SEQ ID NO: 2436 | Nga20559 | 322.3767 | 340.99273 | ---NA--- |
| SEQ ID NO: 2437 | Nga20774 | 265.1254 | 273.87223 | glycosyl hydrolase family 85 protein |
| SEQ ID NO: 2438 | Nga04073 | 550.8637 | 589.43728 | fructosamine kinase |
| SEQ ID NO: 2439 | Nga04074 | 640.264 | 661.38046 | coiled-coil domain-containing |
| SEQ ID NO: 2440 | Nga04075 | 1043.021 | 1006.5998 | carbonyl reductase |
| SEQ ID NO: 2441 | Nga04072 | 890.3038 | 1397.1201 | xanthine dehydrogenase |
| SEQ ID NO: 2442 | Nga04116 | 4064.74 | 4474.4449 | protein |
| SEQ ID NO: 2443 | Nga04117 | 105.7692 | 93.741399 | ---NA--- |
| SEQ ID NO: 2444 | Nga20307 | 196.1853 | 221.36933 | dna-directed rna polymerase iii subunit rpc8 |
| SEQ ID NO: 2445 | Nga04118 | 969.4656 | 998.89053 | conserved hypothetical protein [Phytophthora infestans T30-4] |
| SEQ ID NO: 2446 | Nga04115 | 762.8205 | 1027.6835 | ---NA--- |
| SEQ ID NO: 2447 | Nga04114 | 1065.911 | 992.64457 | cinnamyl alcohol dehydrogenase-like protein |
| SEQ ID NO: 2448 | Nga01942 | 965.3036 | 871.15096 | redoxin domain protein |
| SEQ ID NO: 2449 | Nga01941 | 6220.363 | 5204.6596 | peptidyl-prolyl cis-trans isomerase fkbp2-like |
| SEQ ID NO: 2450 | Nga02010 | 221.4765 | 175.69231 | membrane protein |
| SEQ ID NO: 2451 | Nga20356 | 199.3464 | 212.39881 | membrane protein |
| SEQ ID NO: 2452 | Nga02008 | 5251.773 | 5527.5661 | 60s ribosomal protein l9 |
| SEQ ID NO: 2453 | Nga20594 | 479.5918 | 331.60223 | ---NA--- |
| SEQ ID NO: 2454 | Nga20488 | 442.8044 | 375.73428 | thioredoxin-like protein |
| SEQ ID NO: 2455 | Nga02363.2 | 196.2296 | 182.85954 | alpha- -glucosyltransferase |
| SEQ ID NO: 2456 | Nga04938.1 | 648.4099 | 700.46576 | atp-dependent protease la |
| SEQ ID NO: 2457 | Nga20344 | 126.3345 | 132.99491 | ---NA--- |
| SEQ ID NO: 2458 | Nga06450 | 138.8889 | 202.03173 | ---NA--- |
| SEQ ID NO: 2459 | Nga06451 | 377.5811 | 316.34266 | ---NA--- |
| SEQ ID NO: 2460 | Nga06448 | 592.9204 | 410.07381 | channel hemolysin iii family |
| SEQ ID NO: 2461 | Nga06447 | 657.2827 | 596.64048 | plastid-lipid associated protein pap |
| SEQ ID NO: 2462 | Nga06449 | 2687.285 | 2981.6852 | protein |

FIGURE 24 AM

| # | Nga model | +N rpkb | -N rpkb | GO |
|---|---|---|---|---|
| SEQ ID NO: 2463 | Nga03733.2 | 793.9633 | 825.93034 | protein |
| SEQ ID NO: 2464 | Nga04282 | 403.5533 | 395.90276 | ---NA--- |
| SEQ ID NO: 2465 | Nga00945 | 1495.127 | 1528.7746 | protein |
| SEQ ID NO: 2466 | Nga00944 | 624.0474 | 717.26413 | brix domain containing 1 |
| SEQ ID NO: 2467 | Nga00946 | 770.1493 | 669.34157 | peptidyl prolyl isomerase h |
| SEQ ID NO: 2468 | Nga02239.01 | 275.2881 | 249.65699 | protein |
| SEQ ID NO: 2469 | Nga01635.01 | 777.3344 | 582.68131 | ---NA--- |
| SEQ ID NO: 2470 | Nga01636 | 167.2084 | 174.47538 | ---NA--- |
| SEQ ID NO: 2471 | Nga02043.01 | 344.3443 | 345.89752 | protein phosphatase 1a isoform 2 |
| SEQ ID NO: 2472 | Nga20538.1 | 195.0887 | 227.58257 | ---NA--- |
| SEQ ID NO: 2473 | Nga02045 | 59775.8 | 59616.416 | ubiquitin ribosomal protein cep52 fusion |
| SEQ ID NO: 2474 | Nga21008.1 | 5611.111 | 5267.7265 | hypothetical protein SNOG_05870 [Phaeosphaeria nodorum SN15] |
| SEQ ID NO: 2475 | Nga02046 | 185.1852 | 154.30683 | predicted protein [Micromonas pusilla CCMP1545] |
| SEQ ID NO: 2476 | Nga20951 | 707.5306 | 638.68434 | phytanoyl- dioxygenase superfamily protein |
| SEQ ID NO: 2477 | Nga02044 | 525.6831 | 522.08324 | ubiquinone biosynthesis protein coq4 mitochondrial-like |
| SEQ ID NO: 2478 | Nga02048 | 13.0719 | 10.029944 | dna topoisomerase |
| SEQ ID NO: 2479 | Nga01874 | 396.7093 | 455.47314 | ---NA--- |
| SEQ ID NO: 2480 | Nga01873 | 700 | 596.58705 | ---NA--- |
| SEQ ID NO: 2481 | Nga02062 | 540.3987 | 477.39586 | gluconolactonase |
| SEQ ID NO: 2482 | Nga21242 | 252.8302 | 188.03306 | ---NA--- |
| SEQ ID NO: 2483 | Nga05388.2 | 1009.963 | 1033.3215 | isoform b |
| SEQ ID NO: 2484 | Nga05388.1 | 1009.963 | 1033.3215 | peptidyl-trna hydrolase mitochondrial-like |
| SEQ ID NO: 2485 | Nga05386 | 130.4771 | 101.25653 | proline glycine betaine transporter |
| SEQ ID NO: 2486 | Nga05387 | 289.2157 | 297.35834 | protein |
| SEQ ID NO: 2487 | Nga00862 | 447.1387 | 534.08722 | bifunctional aspartokinase i homoserine dehydrogenase i |
| SEQ ID NO: 2488 | Nga00861.1 | 321.6031 | 379.07894 | ---NA--- |
| SEQ ID NO: 2489 | Nga21032 | 198.6301 | 220.10918 | protein |
| SEQ ID NO: 2490 | Nga01910 | 255.9809 | 238.41513 | expressed unknown protein [Ectocarpus siliculosus] |
| SEQ ID NO: 2491 | Nga01909 | 1225.446 | 1155.7719 | cell division protein |
| SEQ ID NO: 2492 | Nga03666 | 75.39683 | 73.075306 | protein |
| SEQ ID NO: 2493 | Nga03662 | 941.6058 | 684.50445 | rab acceptor 1 |
| SEQ ID NO: 2494 | Nga03664 | 24138.41 | 12092.462 | light-harvesting protein |
| SEQ ID NO: 2495 | Nga03663 | 266.7838 | 306.69418 | dna-directed rna polymerase i subunit |
| SEQ ID NO: 2496 | Nga03665 | 1622.416 | 1460.4209 | rna binding protein |
| SEQ ID NO: 2497 | Nga03661 | 389.1129 | 736.71556 | wd40 subgroup |
| SEQ ID NO: 2498 | Nga02403.02 | 9336.989 | 8769.5509 | atp synthase subunit 5 |
| SEQ ID NO: 2499 | Nga03545 | 8422.045 | 9003.6457 | immutans protein |
| SEQ ID NO: 2500 | Nga03548 | 171.5758 | 208.1915 | mitochondrial carrier protein |
| SEQ ID NO: 2501 | Nga20627 | 179.6407 | 184.86328 | ---NA--- |
| SEQ ID NO: 2502 | Nga03543 | 3441.392 | 3536.3819 | integral inner membrane protein |
| SEQ ID NO: 2503 | Nga03541 | 2442.793 | 3708.4264 | cdgsh iron sulfur domain-containing protein 1 |
| SEQ ID NO: 2504 | Nga03550 | 210.5263 | 111.91306 | enoyl- hydratase isomerase family protein |
| SEQ ID NO: 2505 | Nga03547 | 1858.561 | 2198.723 | thiol-disulfide oxidoreductase dcc |
| SEQ ID NO: 2506 | Nga03546 | 184.5343 | 184.66378 | zinc cchc domain containing 9 |
| SEQ ID NO: 2507 | Nga04457.2 | 1102.609 | 1434.2645 | ---NA--- |
| SEQ ID NO: 2508 | Nga00990.01 | 1366.231 | 1281.5907 | cytochrome b5 |
| SEQ ID NO: 2509 | Nga06569.2 | 706.0878 | 732.69641 | tripeptidyl peptidase ii |
| SEQ ID NO: 2510 | Nga00998 | 102.5641 | 101.84251 | ---NA--- |
| SEQ ID NO: 2511 | Nga20640 | 156.4626 | 180.53899 | peroxisomal membrane protein pmp34 |
| SEQ ID NO: 2512 | Nga00989 | 510.4816 | 506.32748 | lipin-like protein |
| SEQ ID NO: 2513 | Nga00991 | 2583.47 | 2934.2774 | ---NA--- |
| SEQ ID NO: 2514 | Nga00993 | 600.6006 | 585.53186 | phosphoribosylformylglycinamidine cyclo-ligase |
| SEQ ID NO: 2515 | Nga04244 | 236.0248 | 284.82549 | ---NA--- |
| SEQ ID NO: 2516 | Nga04624 | 241.573 | 312.10352 | protein |
| SEQ ID NO: 2517 | Nga04625 | 132.5648 | 124.86847 | 5 -nucleotidase domain-containing |
| SEQ ID NO: 2518 | Nga04623 | 1235.252 | 1008.4207 | short-chain dehydrogenase reductase sdr |
| SEQ ID NO: 2519 | Nga04626 | 277.4869 | 317.59739 | pleckstrin g- interacting region; mechanosensitive ion channel |
| SEQ ID NO: 2520 | Nga01963 | 2960.99 | 3505.3079 | 60s ribosomal protein l5 |
| SEQ ID NO: 2521 | Nga06074.2 | 512.7389 | 293.23212 | ---NA--- |
| SEQ ID NO: 2522 | Nga01964 | 362.5 | 537.97147 | ---NA--- |
| SEQ ID NO: 2523 | Nga04810 | 71.2743 | 121.6591 | u3 snornp protein utp20 |
| SEQ ID NO: 2524 | Nga04809 | 276.6204 | 326.28661 | protein |
| SEQ ID NO: 2525 | Nga05692.2 | 399.6479 | 446.26187 | ---NA--- |
| SEQ ID NO: 2526 | Nga05689.2 | 698.0803 | 782.6507 | ---NA--- |

FIGURE 24 AN

| # | Nga model | +N rpkb | -N rpkb | GO |
|---|---|---|---|---|
| SEQ ID NO: 2527 | Nga01860 | 1737.3 | 1309.6283 | ---NA--- |
| SEQ ID NO: 2528 | Nga01861 | 181.6881 | 194.48621 | ---NA--- |
| SEQ ID NO: 2529 | Nga06578 | 170.7989 | 183.02575 | cell division cycle associated 8 |
| SEQ ID NO: 2530 | Nga02397.2 | 1196.039 | 1347.6936 | pre-mrna-splicing factor syf2 |
| SEQ ID NO: 2531 | Nga02397.1 | 1196.039 | 1347.6936 | myosin light chain kinase |
| SEQ ID NO: 2532 | Nga02398 | 351.3028 | 416.55357 | programmed cell death protein 2 |
| SEQ ID NO: 2533 | Nga02396 | 1347.325 | 1529.9008 | protein |
| SEQ ID NO: 2534 | Nga04880 | 1498.534 | 1405.6628 | ---NA--- |
| SEQ ID NO: 2535 | Nga20325 | 672.0947 | 742.46827 | shikimate kinase |
| SEQ ID NO: 2536 | Nga02079.1 | 798.7761 | 894.11642 | c2h2 zinc-finger protein |
| SEQ ID NO: 2537 | Nga02079.2 | 798.7761 | 894.11642 | weakly similar glutamic acid-rich protein precursor |
| SEQ ID NO: 2538 | Nga06541 | 984.4444 | 989.35367 | polymerase ii (dna directed) polypeptide h |
| SEQ ID NO: 2539 | Nga06539 | 1020.164 | 975.63864 | pyridoxamine 5 -phosphate oxidase-related fmn-binding protein |
| SEQ ID NO: 2540 | Nga06548 | 91.30435 | 64.366075 | set and mynd domain containing 3 |
| SEQ ID NO: 2541 | Nga06540 | 2596.288 | 2201.6541 | small nuclear ribonucleoprotein f |
| SEQ ID NO: 2542 | Nga06546.2 | 2396.192 | 2573.5399 | cell division protein |
| SEQ ID NO: 2543 | Nga06558 | 283.1858 | 338.71032 | iduronate 2-sulfatase |
| SEQ ID NO: 2544 | Nga05620.02 | 2161.398 | 1892.5052 | polyubiquitin-like protein |
| SEQ ID NO: 2545 | Nga06549 | 250.9713 | 216.31012 | uncharacterized protein |
| SEQ ID NO: 2546 | Nga06546.1 | 2396.192 | 2573.5399 | cell division protein |
| SEQ ID NO: 2547 | Nga06543 | 1036.622 | 914.83883 | protein |
| SEQ ID NO: 2548 | Nga06542 | 555.6309 | 532.79824 | suppressor of g2 allele of skp1 ( cerevisiae) |
| SEQ ID NO: 2549 | Nga01694.1 | 1476.454 | 1599.9455 | rna binding protein |
| SEQ ID NO: 2550 | Nga01693 | 954.9072 | 1114.8402 | charged multivesicular body protein 4b |
| SEQ ID NO: 2551 | Nga02094 | 347.6085 | 497.03448 | protein kinase domain containing protein |
| SEQ ID NO: 2552 | Nga02095 | 572.973 | 626.51909 | ankyrin partial |
| SEQ ID NO: 2553 | Nga20495 | 107.4074 | 122.36532 | esterase |
| SEQ ID NO: 2554 | Nga05689.1 | 698.0803 | 782.6507 | guanylate kinase |
| SEQ ID NO: 2555 | Nga05692.1 | 399.6479 | 446.26187 | conserved unknown protein [Ectocarpus siliculosus] |
| SEQ ID NO: 2556 | Nga05693 | 159.7542 | 148.09189 | ---NA--- |
| SEQ ID NO: 2557 | Nga05688.2 | 652.6846 | 705.19257 | cu-zn superoxide dismutase |
| SEQ ID NO: 2558 | Nga05690 | 1421.274 | 1611.446 | major facilitator superfamily domain-containing protein 1 isoform 1 |
| SEQ ID NO: 2559 | Nga05688.1 | 652.6846 | 705.19257 | superoxide dismutase |
| SEQ ID NO: 2560 | Nga03579 | 1093.254 | 1058.1591 | eh-domain containing 4 |
| SEQ ID NO: 2561 | Nga03578 | 400.8594 | 434.8895 | unknown [Medicago truncatula] |
| SEQ ID NO: 2562 | Nga03580.1 | 576.8143 | 436.96902 | wd-40 repeat protein |
| SEQ ID NO: 2563 | Nga02228.02 | 58.99705 | 67.102987 | protein unc-45 homolog a |
| SEQ ID NO: 2564 | Nga20560 | 123.2394 | 133.49714 | ---NA--- |
| SEQ ID NO: 2565 | Nga06082 | 218.9817 | 191.69439 | glycyl-trna synthetase |
| SEQ ID NO: 2566 | Nga07221 | 3385.086 | 3252.0431 | protein |
| SEQ ID NO: 2567 | Nga20322 | 191.6488 | 180.92558 | type a von willebrand factor domain-containing protein |
| SEQ ID NO: 2568 | Nga02379 | 428.0394 | 401.13372 | calcium-independent phospholipase a2-gamma |
| SEQ ID NO: 2569 | Nga02377 | 2793.417 | 3212.8153 | major facilitator superfamily mfs_1 |
| SEQ ID NO: 2570 | Nga02378.1 | 371.0451 | 370.77135 | 2-acylglycerol o-acyltransferase 1 |
| SEQ ID NO: 2571 | Nga04821 | 10536.7 | 9367.171 | predicted protein [Thalassiosira pseudonana CCMP1335] |
| SEQ ID NO: 2572 | Nga04822 | 459.364 | 514.8232 | protein |
| SEQ ID NO: 2573 | Nga20117 | 204.4674 | 284.76769 | rna recognition motif-containing protein |
| SEQ ID NO: 2574 | Nga20058 | 463.0119 | 441.45003 | conserved unknown protein [Ectocarpus siliculosus] |
| SEQ ID NO: 2575 | Nga04577 | 104.7254 | 150.79502 | expressed unknown protein [Ectocarpus siliculosus] |
| SEQ ID NO: 2576 | Nga05046 | 663.8388 | 631.79074 | ---NA--- |
| SEQ ID NO: 2577 | Nga04839 | 513.2743 | 520.847 | ---NA--- |
| SEQ ID NO: 2578 | Nga20042 | 1100.407 | 1156.7234 | mitogen-activated protein kinase kinase |
| SEQ ID NO: 2579 | Nga20593 | 241.1924 | 187.87797 | choline transporter-like protein 1-like |
| SEQ ID NO: 2580 | Nga20685 | 233.1288 | 222.62783 | isoform a |
| SEQ ID NO: 2581 | Nga20352 | 259.6401 | 297.95895 | choline transporter-like protein 5- partial |
| SEQ ID NO: 2582 | Nga04840 | 555.7743 | 428.60241 | developmentally regulated gtp binding protein 1 |
| SEQ ID NO: 2583 | Nga04897.1 | 463.7346 | 488.95977 | dnaj-like protein |
| SEQ ID NO: 2584 | Nga04896 | 378.3133 | 311.48414 | nicotinate-nucleotide--dimethylbenzimidazole phosphoribosyltransferase |
| SEQ ID NO: 2585 | Nga04895 | 13996.1 | 11049.711 | geranylgeranyl reductase |
| SEQ ID NO: 2586 | Nga04961.01 | 314.1487 | 311.722 | glutathione s-transferase |
| SEQ ID NO: 2587 | Nga04357 | 225.2066 | 234.9991 | hypothetical protein GSI_13513 [Acromyrmex echinatior] |
| SEQ ID NO: 2588 | Nga04358 | 21801.05 | 17643.669 | ---NA--- |
| SEQ ID NO: 2589 | Nga01960 | 155.9203 | 165.08841 | ---NA--- |

FIGURE 24 AO

| # | Nga model | +N rpkb | -N rpkb | GO |
|---|---|---|---|---|
| SEQ ID NO: 2590 | Nga01958 | 82.98755 | 122.85641 | arabinogalactan protein |
| SEQ ID NO: 2591 | Nga01957 | 320.197 | 341.51218 | ---NA--- |
| SEQ ID NO: 2592 | Nga01959 | 82.6972 | 100.6057 | arabinogalactan protein |
| SEQ ID NO: 2593 | Nga04506 | 441.9476 | 413.81971 | ---NA--- |
| SEQ ID NO: 2594 | Nga04296 | 349.0967 | 432.83312 | ---NA--- |
| SEQ ID NO: 2595 | Nga04297 | 169.6751 | 294.59792 | ---NA--- |
| SEQ ID NO: 2596 | Nga06925 | 1358.559 | 1357.458 | methyltransferase family |
| SEQ ID NO: 2597 | Nga06924 | 916.9454 | 1000.5121 | ---NA--- |
| SEQ ID NO: 2598 | Nga06419 | 868.0702 | 811.09517 | conserved unknown protein [Ectocarpus siliculosus] |
| SEQ ID NO: 2599 | Nga06423 | 172.2275 | 155.58365 | tbc domain-containing protein kinase-like protein |
| SEQ ID NO: 2600 | Nga06422 | 506.1444 | 586.12774 | galactose-binding protein |
| SEQ ID NO: 2601 | Nga06420 | 766.4179 | 859.3117 | sin3 histone deacetylase corepressor complex component sds3 |
| SEQ ID NO: 2602 | Nga04593 | 223.236 | 164.72536 | protein |
| SEQ ID NO: 2603 | Nga20413 | 165.6535 | 156.39396 | ---NA--- |
| SEQ ID NO: 2604 | Nga00990.02 | 1366.231 | 1281.5907 | cytochrome b5 |
| SEQ ID NO: 2605 | Nga03513 | 351.5483 | 340.68924 | ---NA--- |
| SEQ ID NO: 2606 | Nga02387 | 708.3333 | 999.73466 | chaperonin |
| SEQ ID NO: 2607 | Nga02388 | 521.3033 | 697.72211 | chaperonin |
| SEQ ID NO: 2608 | Nga02386 | 291.6667 | 258.32441 | protein fam98a |
| SEQ ID NO: 2609 | Nga04448 | 228.6213 | 228.74574 | ---NA--- |
| SEQ ID NO: 2610 | Nga06961 | 99.29078 | 119.07891 | ---NA--- |
| SEQ ID NO: 2611 | Nga20989 | 86.58744 | 110.34641 | hypothetical tyrosinase-like protein in chromosome |
| SEQ ID NO: 2612 | Nga01633 | 155.8266 | 170.26441 | ketose-bisphosphate aldolase class-ii family protein |
| SEQ ID NO: 2613 | Nga01632 | 259.058 | 253.14706 | ketose-bisphosphate aldolase class-ii-like protein |
| SEQ ID NO: 2614 | Nga01634.01 | 76.14213 | 67.816677 | ---NA--- |
| SEQ ID NO: 2615 | Nga01631 | 2312.641 | 1491.5862 | thioredoxin-1 |
| SEQ ID NO: 2616 | Nga06509 | 5954.505 | 5683.8377 | protein disulfide isomerase |
| SEQ ID NO: 2617 | Nga06510 | 164.6916 | 152.72578 | structural maintenance of chromosomes protein 5 puta |
| SEQ ID NO: 2618 | Nga06508 | 524.0156 | 596.69269 | kelch-like protein 17-like |
| SEQ ID NO: 2619 | Nga21004 | 27437.72 | 30045.686 | expressed unknown protein [Ectocarpus siliculosus] |
| SEQ ID NO: 2620 | Nga20930 | 9981.41 | 11227.442 | ---NA--- |
| SEQ ID NO: 2621 | Nga06513 | 1293.001 | 1322.2393 | protein |
| SEQ ID NO: 2622 | Nga06512 | 634.9593 | 582.12816 | peptidyl-prolyl cis-trans isomerase |
| SEQ ID NO: 2623 | Nga06511 | 363.5417 | 341.89571 | abortive infection protein |
| SEQ ID NO: 2624 | Nga02307 | 388.3735 | 466.25283 | wd repeat domain 74 |
| SEQ ID NO: 2625 | Nga02309 | 394.6557 | 473.14946 | gram domain-containing protein 1a-like |
| SEQ ID NO: 2626 | Nga02308 | 3384.735 | 3135.8104 | hypothetical protein BRAFLDRAFT_228541 [Branchiostoma floridae] |
| SEQ ID NO: 2627 | Nga02306 | 502.5773 | 681.20897 | protein |
| SEQ ID NO: 2628 | Nga02312 | 307.5506 | 307.21552 | ---NA--- |
| SEQ ID NO: 2629 | Nga05655 | 121.5278 | 116.5981 | ---NA--- |
| SEQ ID NO: 2630 | Nga05656 | 153.8462 | 111.10092 | ---NA--- |
| SEQ ID NO: 2631 | Nga05651 | 1848.282 | 2867.0607 | cbl-interacting serine threonine-protein kinase 15 |
| SEQ ID NO: 2632 | Nga04606.2 | 91.6129 | 101.33479 | intraflagellar transport |
| SEQ ID NO: 2633 | Nga05652 | 293.9189 | 376.93613 | exosome complex exonuclease rrp41 |
| SEQ ID NO: 2634 | Nga04607.02 | 198.1567 | 219.64191 | ---NA--- |
| SEQ ID NO: 2635 | Nga05653 | 35.38175 | 48.41269 | intraflagellar transport 52 homolog |
| SEQ ID NO: 2636 | Nga07057 | 250.6394 | 274.27151 | ---NA--- |
| SEQ ID NO: 2637 | Nga07058 | 62.5 | 140.6121 | ---NA--- |
| SEQ ID NO: 2638 | Nga05481 | 466.4311 | 329.18063 | smap1 protein |
| SEQ ID NO: 2639 | Nga05480 | 1415.033 | 1495.0516 | conserved unknown protein [Ectocarpus siliculosus] |
| SEQ ID NO: 2640 | Nga03875 | 29.70297 | 25.025207 | cell division cycle protein 23 |
| SEQ ID NO: 2641 | Nga03874 | 162.4549 | 218.99314 | anaphase promoting complex subunit 8 |
| SEQ ID NO: 2642 | Nga03876 | 132.3529 | 172.57403 | protoporphyrinogen oxidase |
| SEQ ID NO: 2643 | Nga03879 | 28.57143 | 5.1582569 | protoporphyrinogen oxidase |
| SEQ ID NO: 2644 | Nga03873 | 989.6319 | 939.47661 | protoporphyrinogen oxidase |
| SEQ ID NO: 2645 | Nga20695 | 43.34365 | 36.89032 | ---NA--- |
| SEQ ID NO: 2646 | Nga06011 | 158.2492 | 218.83514 | zinc knuckle family expressed |
| SEQ ID NO: 2647 | Nga06006 | 673.8411 | 512.92203 | mitochondrial ribosomal protein l37 |
| SEQ ID NO: 2648 | Nga06010 | 264.5432 | 221.15128 | abc transporter |
| SEQ ID NO: 2649 | Nga06008 | 1333.333 | 1637.341 | srrm2 protein |
| SEQ ID NO: 2650 | Nga06020 | 304.3478 | 321.83037 | ---NA--- |
| SEQ ID NO: 2651 | Nga06009 | 795.6989 | 937.63798 | ubiquitin-fold modifier 1 |
| SEQ ID NO: 2652 | Nga06019 | 213.2616 | 279.54424 | ---NA--- |
| SEQ ID NO: 2653 | Nga06007 | 837.5559 | 761.97678 | soluble nsf attachment protein receptor |

FIGURE 24 AP

| # | Nga model | +N rpkb | -N rpkb | GO |
|---|---|---|---|---|
| SEQ ID NO: 2654 | Nga06012 | 4748.494 | 4214.3891 | 40s ribosomal protein |
| SEQ ID NO: 2655 | Nga20247 | 369.2596 | 363.44681 | brca1-associated protein |
| SEQ ID NO: 2656 | Nga02429 | 875.9843 | 1018.1973 | ---NA--- |
| SEQ ID NO: 2657 | Nga03210.01 | 259.3477 | 279.21066 | protein |
| SEQ ID NO: 2658 | Nga03211 | 321.7391 | 329.6799 | ---NA--- |
| SEQ ID NO: 2659 | Nga03207 | 273.3214 | 300.5765 | major facilitator superfamily mfs_1 |
| SEQ ID NO: 2660 | Nga03209.01 | 131.5789 | 98.187872 | ---NA--- |
| SEQ ID NO: 2661 | Nga03208 | 292.1028 | 255.94966 | protein |
| SEQ ID NO: 2662 | Nga06410.1 | 353.6379 | 377.57393 | nicotinate-nucleotide pyrophosphorylase |
| SEQ ID NO: 2663 | Nga06413 | 62.5 | 87.045585 | ---NA--- |
| SEQ ID NO: 2664 | Nga06411 | 399.2347 | 425.55619 | oxidoreductase htatip2 |
| SEQ ID NO: 2665 | Nga06412 | 157.6422 | 237.58387 | ---NA--- |
| SEQ ID NO: 2666 | Nga07135 | 624.8694 | 691.5945 | protein |
| SEQ ID NO: 2667 | Nga07143.2 | 2920.635 | 3402.8864 | ---NA--- |
| SEQ ID NO: 2668 | Nga20477 | 168.3673 | 163.03776 | ribonuclease z |
| SEQ ID NO: 2669 | Nga20031 | 69.76744 | 67.177299 | ---NA--- |
| SEQ ID NO: 2670 | Nga01967 | 533.1205 | 518.70739 | serine protease family s09x |
| SEQ ID NO: 2671 | Nga20952 | 175.2888 | 229.05148 | exportin 6 |
| SEQ ID NO: 2672 | Nga04472 | 3549.561 | 3367.9469 | steroid 5-alpha reductase c-terminal domain-containing protein |
| SEQ ID NO: 2673 | Nga03949 | 464.1745 | 563.55161 | ---NA--- |
| SEQ ID NO: 2674 | Nga20493 | 258.3222 | 200.49203 | ---NA--- |
| SEQ ID NO: 2675 | Nga03948 | 90.7173 | 123.4064 | ---NA--- |
| SEQ ID NO: 2676 | Nga03947 | 197.8495 | 291.19192 | ---NA--- |
| SEQ ID NO: 2677 | Nga01165 | 923.6948 | 981.72607 | conserved unknown protein [Ectocarpus siliculosus] |
| SEQ ID NO: 2678 | Nga20602 | 278.157 | 290.21797 | fad-binding protein |
| SEQ ID NO: 2679 | Nga01164 | 585.1359 | 551.53009 | homogentisate -dioxygenase |
| SEQ ID NO: 2680 | Nga01163 | 156.3574 | 260.57174 | gtp-binding protein |
| SEQ ID NO: 2681 | Nga01166 | 165.9292 | 145.38981 | atp binding |
| SEQ ID NO: 2682 | Nga02416 | 567.0816 | 170.05125 | ---NA--- |
| SEQ ID NO: 2683 | Nga02414 | 4454.155 | 4187.0561 | succinate dehydrogenase cytochrome b subunit |
| SEQ ID NO: 2684 | Nga02415 | 438.6217 | 489.12717 | protein serine threonine kinase |
| SEQ ID NO: 2685 | Nga06834 | 350.9572 | 356.46987 | npc21_dicdi ame: full= phosphatidylglycerol phosphatidylinositol transfer protein 1 short=pg pi-tp flags: precursor |
| SEQ ID NO: 2686 | Nga20065 | 339.8058 | 428.6862 | signal recognition particle 68 kda protein |
| SEQ ID NO: 2687 | Nga01600.1 | 492.209 | 441.83236 | developmentally regulated g-protein 1 |
| SEQ ID NO: 2688 | Nga01597.01 | 519.4468 | 640.39068 | nucleoside diphosphate-linked moiety x motif 6 |
| SEQ ID NO: 2689 | Nga01598 | 136.5926 | 163.36773 | beach domain-containing protein |
| SEQ ID NO: 2690 | Nga01600.2 | 492.209 | 441.83236 | developmentally regulated g-protein 1 |
| SEQ ID NO: 2691 | Nga01601 | 1119.43 | 1158.539 | iron-sulfur protein |
| SEQ ID NO: 2692 | Nga05013 | 988.2254 | 1032.2154 | protein |
| SEQ ID NO: 2693 | Nga05015 | 4648.446 | 4934.3454 | atp-dependent clp protease proteolytic subunit |
| SEQ ID NO: 2694 | Nga05014 | 2759.637 | 2990.1514 | lysosomal acid phosphatase |
| SEQ ID NO: 2695 | Nga20169 | 160.8315 | 180.14394 | rrna processing protein |
| SEQ ID NO: 2696 | Nga20798 | 220.8545 | 216.48991 | protein |
| SEQ ID NO: 2697 | Nga01662 | 130.9942 | 79.817238 | ---NA--- |
| SEQ ID NO: 2698 | Nga01661.2 | 222.8571 | 313.62202 | serine threonine-protein kinase rio3 |
| SEQ ID NO: 2699 | Nga01661.1 | 222.8571 | 313.62202 | serine threonine-protein kinase rio3 |
| SEQ ID NO: 2700 | Nga01659 | 160.6805 | 153.57759 | ---NA--- |
| SEQ ID NO: 2701 | Nga01701 | 449.3088 | 743.78736 | ---NA--- |
| SEQ ID NO: 2702 | Nga01700 | 733.3333 | 783.47109 | otu domain-containing protein 6b |
| SEQ ID NO: 2703 | Nga20460 | 121.6578 | 102.82033 | ---NA--- |
| SEQ ID NO: 2704 | Nga01124.02 | 1733.86 | 1392.9332 | mannose-p-dolichol utilization defect 1 |
| SEQ ID NO: 2705 | Nga02234.01 | 420.6049 | 304.08363 | ---NA--- |
| SEQ ID NO: 2706 | Nga07107 | 2516.19 | 2632.7743 | ---NA--- |
| SEQ ID NO: 2707 | Nga20678 | 129.1667 | 63.188647 | ---NA--- |
| SEQ ID NO: 2708 | Nga04348 | 651.8987 | 662.281 | protein phosphatase |
| SEQ ID NO: 2709 | Nga06033.02 | 1056.995 | 1318.0282 | gtp-binding protein |
| SEQ ID NO: 2710 | Nga20451 | 49.85337 | 76.239339 | protein |
| SEQ ID NO: 2711 | Nga06356 | 25081.14 | 25774.316 | p-type h+-atpase |
| SEQ ID NO: 2712 | Nga06354.1 | 15057.44 | 14114.816 | p-type h+-atpase |
| SEQ ID NO: 2713 | Nga06358 | 696.6667 | 877.41949 | ---NA--- |
| SEQ ID NO: 2714 | Nga06354.2 | 15057.44 | 14114.816 | p-type h+-atpase |
| SEQ ID NO: 2715 | Nga06357 | 17908.3 | 20710.739 | p-type h+-atpase |
| SEQ ID NO: 2716 | Nga05597 | 17.40295 | 23.926854 | amp-dependent synthetase and ligase |

FIGURE 24 AQ

| # | Nga model | +N rpkb | -N rpkb | GO |
|---|---|---|---|---|
| SEQ ID NO: 2717 | Nga05596 | 195.8457 | 295.71965 | dna cross-link repair protein pso2 |
| SEQ ID NO: 2718 | Nga05595 | 355.4084 | 362.2736 | ---NA--- |
| SEQ ID NO: 2719 | Nga05594 | 213.1148 | 168.70037 | ---NA--- |
| SEQ ID NO: 2720 | Nga04924 | 154.386 | 148.23201 | dna mismatch repair protein homolog |
| SEQ ID NO: 2721 | Nga04923 | 1275.352 | 1606.5427 | hypothetical protein ACP_2683 [Acidobacterium capsulatum ATCC 51196] |
| SEQ ID NO: 2722 | Nga02014 | 3.703704 | 0 | ---NA--- |
| SEQ ID NO: 2723 | Nga03694 | 1089.73 | 1128.7433 | gcn5-related n-acetyltransferase |
| SEQ ID NO: 2724 | Nga03695 | 399.8624 | 388.41355 | hydrolase |
| SEQ ID NO: 2725 | Nga03693 | 1649.215 | 1905.5843 | electron-transferring-flavoprotein dehydrogenase |
| SEQ ID NO: 2726 | Nga03696.01 | 1150.15 | 933.59802 | ---NA--- |
| SEQ ID NO: 2727 | Nga01832.2 | 96.84685 | 89.049637 | protein phosphatase 2c containing protein |
| SEQ ID NO: 2728 | Nga01830 | 146.4968 | 136.84165 | smad nuclear interacting protein 1 |
| SEQ ID NO: 2729 | Nga01831 | 2487.594 | 2280.9845 | protein |
| SEQ ID NO: 2730 | Nga01832.1 | 96.84685 | 89.049637 | protein phosphatase |
| SEQ ID NO: 2731 | Nga01440 | 2914.552 | 2853.7991 | ---NA--- |
| SEQ ID NO: 2732 | Nga01442 | 810.9375 | 855.58556 | deoxycytidylate deaminase |
| SEQ ID NO: 2733 | Nga01441 | 440.5797 | 372.74043 | ---NA--- |
| SEQ ID NO: 2734 | Nga01444 | 1043.956 | 778.8401 | cell division topological specificity factor |
| SEQ ID NO: 2735 | Nga05996.2 | 576.412 | 509.22792 | cytosolic phosphoglucose isomerase |
| SEQ ID NO: 2736 | Nga20997 | 1196.833 | 1477.8056 | ankyrin |
| SEQ ID NO: 2737 | Nga20158 | 1311.456 | 1472.3192 | ankyrin repeat-containing protein |
| SEQ ID NO: 2738 | Nga20833 | 394.2112 | 443.36196 | indigoidine synthase a family protein |
| SEQ ID NO: 2739 | Nga05980.02 | 464.0523 | 445.02608 | gcn5-like n-acetyltransferase |
| SEQ ID NO: 2740 | Nga05979.02 | 323.0303 | 344.9936 | peptidase m1 membrane alanine aminopeptidase |
| SEQ ID NO: 2741 | Nga01890.1 | 3082.353 | 4085.3394 | ---NA--- |
| SEQ ID NO: 2742 | Nga01891.01 | 302.9661 | 327.03567 | protein |
| SEQ ID NO: 2743 | Nga01892 | 534.3915 | 555.94546 | ca -dependent phospholipid-binding family protein |
| SEQ ID NO: 2744 | Nga20357 | 160.1732 | 161.78169 | tubulin-specific chaperone c |
| SEQ ID NO: 2745 | Nga07021 | 47.4359 | 43.051605 | high-affinity glucose |
| SEQ ID NO: 2746 | Nga02279 | 260.8868 | 331.05962 | phytanoyl- dioxygenase domain-containing protein 1 homolog |
| SEQ ID NO: 2747 | Nga02278.1 | 881.6348 | 1017.113 | fe-only |
| SEQ ID NO: 2748 | Nga04069 | 258.9532 | 293.93538 | ---NA--- |
| SEQ ID NO: 2749 | Nga04068 | 547.8088 | 564.27425 | mitochondrial 2-oxoglutarate malate carrier protein |
| SEQ ID NO: 2750 | Nga06942 | 384.2593 | 481.43731 | ---NA--- |
| SEQ ID NO: 2751 | Nga05513 | 611.7216 | 484.08257 | ---NA--- |
| SEQ ID NO: 2752 | Nga05510 | 614.4578 | 611.22236 | ---NA--- |
| SEQ ID NO: 2753 | Nga05512 | 3160.804 | 3242.444 | ---NA--- |
| SEQ ID NO: 2754 | Nga20580 | 136.5854 | 171.73221 | rrna processing protein rrp17 |
| SEQ ID NO: 2755 | Nga05511 | 330.4196 | 312.47133 | prp4 pre-mrna processing factor 4 homolog |
| SEQ ID NO: 2756 | Nga05518 | 121.5805 | 154.74771 | ---NA--- |
| SEQ ID NO: 2757 | Nga02770 | 320.5538 | 333.96829 | tpr repeat-containing protein |
| SEQ ID NO: 2758 | Nga02772 | 592.4479 | 476.73577 | had family hydrolase |
| SEQ ID NO: 2759 | Nga02779 | 627.6648 | 586.46081 | alkyl sulfatase or beta-lactamase |
| SEQ ID NO: 2760 | Nga02778 | 352.349 | 407.12148 | methionyl-trna synthetase |
| SEQ ID NO: 2761 | Nga02767 | 493.6709 | 543.5758 | protein |
| SEQ ID NO: 2762 | Nga02783 | 225.8553 | 291.55161 | argininosuccinate partial |
| SEQ ID NO: 2763 | Nga02774 | 311.0048 | 362.80563 | family s49 |
| SEQ ID NO: 2764 | Nga02771 | 147.6035 | 175.81902 | pyridine nucleotide-disulfide oxidoreductase domain-containing protein 1 |
| SEQ ID NO: 2765 | Nga02782 | 476.5258 | 694.18513 | ---NA--- |
| SEQ ID NO: 2766 | Nga02776 | 771.1214 | 745.45131 | uridine phosphorylase |
| SEQ ID NO: 2767 | Nga02766 | 613.2797 | 1185.6726 | amidophosphoribosyltransferase |
| SEQ ID NO: 2768 | Nga02781 | 213.7255 | 195.40691 | ---NA--- |
| SEQ ID NO: 2769 | Nga02768 | 1876.61 | 1811.7547 | elongation of very long chain fatty acids protein 6 |
| SEQ ID NO: 2770 | Nga02777 | 1653.74 | 1513.8269 | gun4-like protein |
| SEQ ID NO: 2771 | Nga02769 | 676.8061 | 638.40784 | spliceosomal protein |
| SEQ ID NO: 2772 | Nga02773 | 479.4352 | 444.53155 | protein |
| SEQ ID NO: 2773 | Nga02780 | 768.2468 | 724.60118 | protein |
| SEQ ID NO: 2774 | Nga02775 | 2030.822 | 2037.3701 | dna-binding horma domain-containing protein |
| SEQ ID NO: 2775 | Nga01297 | 226.1029 | 232.97495 | ---NA--- |
| SEQ ID NO: 2776 | Nga04742 | 360.2781 | 455.2313 | peptidase s9 prolyl oligopeptidase |
| SEQ ID NO: 2777 | Nga04743 | 221.6117 | 308.50344 | mitogen-activated protein kinase |
| SEQ ID NO: 2778 | Nga04745 | 2363.144 | 1899.3289 | major facilitator superfamily mfs_1 |
| SEQ ID NO: 2779 | Nga04744 | 513.2159 | 656.93923 | ---NA--- |

FIGURE 24 AR

| # | Nga model | +N rpkb | -N rpkb | GO |
|---|---|---|---|---|
| SEQ ID NO: 2780 | Nga04746 | 132.6861 | 150.74129 | ---NA--- |
| SEQ ID NO: 2781 | Nga05945 | 953.3528 | 803.74064 | protein |
| SEQ ID NO: 2782 | Nga05946 | 3405.437 | 3139.5858 | 40s ribosomal protein s10 |
| SEQ ID NO: 2783 | Nga05943 | 1494.771 | 1583.7871 | delta-24-sterol methyltransferase |
| SEQ ID NO: 2784 | Nga05944 | 312.7351 | 292.19959 | ---NA--- |
| SEQ ID NO: 2785 | Nga20773 | 322.4941 | 418.69552 | dna binding |
| SEQ ID NO: 2786 | Nga21148.1 | 365.6286 | 273.61965 | protein phosphatase methylesterase 1 |
| SEQ ID NO: 2787 | Nga05947 | 635.2838 | 702.21963 | chromodomain-helicase-dna-binding protein 7 |
| SEQ ID NO: 2788 | Nga02219.2 | 191.4894 | 269.84817 | peroxisome assembly protein 12 |
| SEQ ID NO: 2789 | Nga02219.1 | 191.4894 | 269.84817 | protein |
| SEQ ID NO: 2790 | Nga05917 | 296.544 | 204.08755 | ---NA--- |
| SEQ ID NO: 2791 | Nga05913 | 747.6636 | 742.40332 | transmembrane protein |
| SEQ ID NO: 2792 | Nga05915 | 766.9841 | 561.90611 | protein |
| SEQ ID NO: 2793 | Nga05916 | 11794.87 | 10263.503 | conserved hypothetical protein [Albugo laibachii Nc14] |
| SEQ ID NO: 2794 | Nga21088 | 1545.657 | 1504.6256 | short-chain dehydrogenase reductase sdr |
| SEQ ID NO: 2795 | Nga05918 | 3097.308 | 3000.7599 | peptidylprolyl isomerase |
| SEQ ID NO: 2796 | Nga05914 | 1546.926 | 1510.9185 | ---NA--- |
| SEQ ID NO: 2797 | Nga05912 | 788.6815 | 781.28493 | eukaryotic peptide chain release factor subunit 1 |
| SEQ ID NO: 2798 | Nga04416 | 2302.682 | 1996.3047 | protein |
| SEQ ID NO: 2799 | Nga04418 | 893.5811 | 1114.3403 | branched-chain amino acid |
| SEQ ID NO: 2800 | Nga04417 | 294.5488 | 234.70896 | fungal zn binuclear cluster domain containing protein |
| SEQ ID NO: 2801 | Nga07186 | 83.33333 | 31.594323 | ---NA--- |
| SEQ ID NO: 2802 | Nga03992 | 243.3862 | 177.67329 | ---NA--- |
| SEQ ID NO: 2803 | Nga03993 | 20.20202 | 21.883514 | ---NA--- |
| SEQ ID NO: 2804 | Nga03991 | 28.67384 | 46.590707 | set domain protein |
| SEQ ID NO: 2805 | Nga03990 | 3169.643 | 3191.6714 | conserved hypothetical protein [Phytophthora infestans T30-4] |
| SEQ ID NO: 2806 | Nga02209.01 | 545.8554 | 533.97511 | mfs monosaccharide |
| SEQ ID NO: 2807 | Nga07113 | 231.0008 | 275.49516 | small ubiquitin-like modifier-1 |
| SEQ ID NO: 2808 | Nga07114 | 62.5 | 33.851061 | ---NA--- |
| SEQ ID NO: 2809 | Nga05250 | 1297.737 | 1237.2156 | ---NA--- |
| SEQ ID NO: 2810 | Nga05252 | 5.50055 | 4.766706 | testis 14 |
| SEQ ID NO: 2811 | Nga05251 | 193.2059 | 234.58569 | inositol monophosphatase |
| SEQ ID NO: 2812 | Nga04832 | 514.4509 | 544.7477 | ---NA--- |
| SEQ ID NO: 2813 | Nga04833 | 289.5377 | 210.84846 | protein |
| SEQ ID NO: 2814 | Nga04481 | 89.20188 | 101.71211 | ---NA--- |
| SEQ ID NO: 2815 | Nga04482 | 192.959 | 190.67621 | sun domain protein |
| SEQ ID NO: 2816 | Nga00852 | 214.2162 | 224.66293 | two component transcriptional family |
| SEQ ID NO: 2817 | Nga00853 | 362.8205 | 399.9633 | retinitis pigmentosa 9 (autosomal dominant) |
| SEQ ID NO: 2818 | Nga00854 | 1463.758 | 1546.7148 | dihydroxy-3-keto-5-methylthiopentene dioxygenase |
| SEQ ID NO: 2819 | Nga07266 | 2168.699 | 2356.6943 | rrna methyltransferase |
| SEQ ID NO: 2820 | Nga04466 | 206.3492 | 189.13608 | hypoxanthine-guanine phosphoribosyltransferase-like |
| SEQ ID NO: 2821 | Nga07307 | 89.65517 | 52.294052 | ---NA--- |
| SEQ ID NO: 2822 | Nga07242 | 1067.751 | 1115.5255 | dephospho- kinase |
| SEQ ID NO: 2823 | Nga06615.2 | 346.6851 | 382.52322 | apicomplexan specific pf 23612804 and py 23478322 |
| SEQ ID NO: 2824 | Nga06970 | 319.8198 | 409.8723 | ---NA--- |
| SEQ ID NO: 2825 | Nga06521 | 333.3333 | 375.61803 | ---NA--- |
| SEQ ID NO: 2826 | Nga06519 | 8847.328 | 9393.5401 | protein |
| SEQ ID NO: 2827 | Nga06522 | 332.2215 | 334.58126 | dash family |
| SEQ ID NO: 2828 | Nga06520 | 448.4127 | 477.13876 | cysteine synthase a |
| SEQ ID NO: 2829 | Nga07144 | 301.8868 | 362.78118 | ---NA--- |
| SEQ ID NO: 2830 | Nga04436 | 39.27492 | 35.998711 | ---NA--- |
| SEQ ID NO: 2831 | Nga02925 | 290.5812 | 256.15552 | aspartyl asparaginyl beta-hydroxylase |
| SEQ ID NO: 2832 | Nga20434 | 19.88636 | 24.618953 | midasin |
| SEQ ID NO: 2833 | Nga02926 | 721.8391 | 763.86669 | duf747 family protein |
| SEQ ID NO: 2834 | Nga21303 | 0 | 21.239881 | ---NA--- |
| SEQ ID NO: 2835 | Nga02924 | 606.8237 | 684.61089 | abc subfamily abcg |
| SEQ ID NO: 2836 | Nga20408 | 431.6667 | 534.39541 | folylpolyglutamate synthase |
| SEQ ID NO: 2837 | Nga02923 | 5602.484 | 5840.0439 | protein |
| SEQ ID NO: 2838 | Nga21309 | 5.076142 | 0 | ---NA--- |
| SEQ ID NO: 2839 | Nga21310 | 15.26718 | 0 | ---NA--- |
| SEQ ID NO: 2840 | Nga06940 | 716.129 | 743.58769 | ---NA--- |
| SEQ ID NO: 2841 | Nga06828 | 369.5652 | 507.76591 | s-adenosylmethionine mitochondrial carrier protein |
| SEQ ID NO: 2842 | Nga04654.01 | 1314.465 | 1350.636 | protein |
| SEQ ID NO: 2843 | Nga04655.01 | 722.8464 | 900.66642 | ---NA--- |

FIGURE 24 AS

| # | Nga model | +N rpkb | -N rpkb | GO |
|---|---|---|---|---|
| SEQ ID NO: 2844 | Nga02434 | 764.3396 | 771.15179 | 116 kda u5 small nuclear ribonucleoprotein component |
| SEQ ID NO: 2845 | Nga02430 | 1029.206 | 1034.4024 | protein |
| SEQ ID NO: 2846 | Nga02431 | 126.1172 | 162.16238 | ap3d1 protein |
| SEQ ID NO: 2847 | Nga04064 | 575.227 | 559.88162 | predicted protein [Nematostella vectensis] |
| SEQ ID NO: 2848 | Nga20067 | 193.1385 | 199.57932 | protein |
| SEQ ID NO: 2849 | Nga04065 | 253.5613 | 217.88124 | protein |
| SEQ ID NO: 2850 | Nga06847 | 52.63158 | 38.008208 | ---NA--- |
| SEQ ID NO: 2851 | Nga21215.1 | 599.1903 | 469.25519 | uncharacterized protein |
| SEQ ID NO: 2852 | Nga20817 | 66.86047 | 91.31914 | ---NA--- |
| SEQ ID NO: 2853 | Nga07122 | 642.2535 | 576.70765 | ---NA--- |
| SEQ ID NO: 2854 | Nga04813.01 | 691.4095 | 580.0135 | protein |
| SEQ ID NO: 2855 | Nga20574.1 | 116.7883 | 229.2977 | purine nucleoside phosphoramidase |
| SEQ ID NO: 2856 | Nga20513.1 | 198.3806 | 188.57919 | aprataxin |
| SEQ ID NO: 2857 | Nga07236 | 1196.078 | 1241.0159 | ---NA--- |
| SEQ ID NO: 2858 | Nga07235 | 795.3504 | 700.51966 | subtilisin-like serine peptidase |
| SEQ ID NO: 2859 | Nga06808 | 249.4005 | 179.24015 | ---NA--- |
| SEQ ID NO: 2860 | Nga20567 | 118.9591 | 208.05609 | ---NA--- |
| SEQ ID NO: 2861 | Nga20260 | 145.5274 | 231.39844 | conserved unknown protein [Ectocarpus siliculosus] |
| SEQ ID NO: 2862 | Nga20195 | 119.403 | 176.37459 | predicted protein [Phaeodactylum tricornutum CCAP 1055/1] |
| SEQ ID NO: 2863 | Nga07074 | 190.7895 | 153.22059 | protein |
| SEQ ID NO: 2864 | Nga07117 | 47.72234 | 35.246224 | ---NA--- |
| SEQ ID NO: 2865 | Nga07098 | 2193.076 | 2747.7505 | ---NA--- |
| SEQ ID NO: 2866 | Nga03634 | 169.6833 | 183.80666 | ---NA--- |
| SEQ ID NO: 2867 | Nga20224 | 317.0732 | 453.21045 | translation elongation factor 1- |
| SEQ ID NO: 2868 | Nga20431 | 362.4242 | 456.92777 | hbs1-like protein |
| SEQ ID NO: 2869 | Nga03633 | 263.6816 | 309.88036 | ---NA--- |
| SEQ ID NO: 2870 | Nga21198 | 436.0313 | 477.98051 | expressed unknown protein [Ectocarpus siliculosus] |
| SEQ ID NO: 2871 | Nga06898 | 110.5121 | 131.38956 | tether containing ubx domain for glut4 |
| SEQ ID NO: 2872 | Nga07027 | 1959.77 | 2037.8079 | ---NA--- |
| SEQ ID NO: 2873 | Nga04958 | 219.0476 | 20.633027 | ---NA--- |
| SEQ ID NO: 2874 | Nga04957 | 356.236 | 544.44843 | di-n-acetylchitobiase |
| SEQ ID NO: 2875 | Nga04183.1 | 125 | 114.24733 | ---NA--- |
| SEQ ID NO: 2876 | Nga04182 | 712.931 | 563.09488 | ---NA--- |
| SEQ ID NO: 2877 | Nga06984 | 1474.164 | 1790.2993 | ---NA--- |
| SEQ ID NO: 2878 | Nga06858.2 | 154.5894 | 167.45645 | snf2 family helicase atpase |
| SEQ ID NO: 2879 | Nga06856 | 162.1005 | 153.33448 | chromatin-remodeling factor chd3 |
| SEQ ID NO: 2880 | Nga06857 | 172.5888 | 109.97299 | phosphoinositol transporter |
| SEQ ID NO: 2881 | Nga06858.1 | 154.5894 | 167.45645 | snf2 family helicase atpase |
| SEQ ID NO: 2882 | Nga05021 | 496.769 | 465.4931 | protein |
| SEQ ID NO: 2883 | Nga05023 | 468.1335 | 561.34202 | ---NA--- |
| SEQ ID NO: 2884 | Nga04423.2 | 220.405 | 345.89246 | calmodulin-like protein 12 |
| SEQ ID NO: 2885 | Nga04425.02 | 316.0377 | 226.09954 | ---NA--- |
| SEQ ID NO: 2886 | Nga04408.2 | 740.3509 | 847.58305 | ribosome biogenesis protein brx1 homolog |
| SEQ ID NO: 2887 | Nga03704.1 | 92.89617 | 119.57009 | ---NA--- |
| SEQ ID NO: 2888 | Nga07048 | 12838.98 | 18994.625 | ---NA--- |
| SEQ ID NO: 2889 | Nga07047 | 274.6365 | 257.24619 | ---NA--- |
| SEQ ID NO: 2890 | Nga01920 | 613.9438 | 566.97885 | ---NA--- |
| SEQ ID NO: 2891 | Nga03290 | 131.5789 | 102.62216 | ---NA--- |
| SEQ ID NO: 2892 | Nga03289 | 3990.159 | 5229.2073 | alternative oxidase mitochondrial |
| SEQ ID NO: 2893 | Nga03291 | 202.1277 | 159.41209 | ---NA--- |
| SEQ ID NO: 2894 | Nga03287 | 132.1696 | 108.05326 | ---NA--- |
| SEQ ID NO: 2895 | Nga03288 | 513.7514 | 738.83943 | protein kinase domain containing protein |
| SEQ ID NO: 2896 | Nga03293 | 351.9695 | 349.6079 | expressed unknown protein [Ectocarpus siliculosus] |
| SEQ ID NO: 2897 | Nga03286 | 324.7588 | 271.67925 | sh2 domain containing protein |
| SEQ ID NO: 2898 | Nga03292 | 64.10256 | 32.404434 | ---NA--- |
| SEQ ID NO: 2899 | Nga20423 | 304.3478 | 353.22846 | novel protein anaphase promoting complex subunit 1 |
| SEQ ID NO: 2900 | Nga01496 | 8046.358 | 8891.8442 | heat shock protein hsp20 |
| SEQ ID NO: 2901 | Nga05016 | 1983.957 | 1758.4047 | manganese lipoxygenase |
| SEQ ID NO: 2902 | Nga20995 | 73.02534 | 122.69118 | hect e3 ubiquitin |
| SEQ ID NO: 2903 | Nga01838 | 1139.481 | 1079.7202 | protein |
| SEQ ID NO: 2904 | Nga01840 | 11.49425 | 49.803859 | ---NA--- |
| SEQ ID NO: 2905 | Nga01839 | 246.1629 | 266.65204 | myb-like protein |
| SEQ ID NO: 2906 | Nga21255 | 98.03922 | 117.99934 | wd repeat-containing protein 3 |
| SEQ ID NO: 2907 | Nga01037 | 206.4057 | 236.4354 | c-5 sterol desaturase |

FIGURE 24 AT

| # | Nga model | +N rpkb | -N rpkb | GO |
|---|---|---|---|---|
| SEQ ID NO: 2908 | Nga01035 | 418.2622 | 531.24728 | ---NA--- |
| SEQ ID NO: 2909 | Nga01036 | 247.7341 | 222.53749 | ---NA--- |
| SEQ ID NO: 2910 | Nga20476 | 121.6216 | 156.14183 | ---NA--- |
| SEQ ID NO: 2911 | Nga07014 | 273.9726 | 430.32581 | ---NA--- |
| SEQ ID NO: 2912 | Nga07191 | 324.3243 | 529.23072 | lipase family protein |
| SEQ ID NO: 2913 | Nga20843 | 195.4315 | 206.19935 | ---NA--- |
| SEQ ID NO: 2914 | Nga00195.02 | 617.7215 | 606.06253 | conserved hypothetical protein [Phytophthora infestans T30-4] |
| SEQ ID NO: 2915 | Nga00201.02 | 99.67846 | 118.42429 | dmc1 |
| SEQ ID NO: 2916 | Nga05351 | 2383.464 | 2251.8008 | abortive infection protein |
| SEQ ID NO: 2917 | Nga00204.02 | 1006.969 | 929.74435 | atp-binding cassette transporter |
| SEQ ID NO: 2918 | Nga00199.02 | 1643.221 | 1667.3632 | dna-directed rna polymerase ii 19 kda polypeptide |
| SEQ ID NO: 2919 | Nga00210.02 | 206.4632 | 259.30196 | uncharacterized protein c16orf7 homolog |
| SEQ ID NO: 2920 | Nga05361 | 203.125 | 334.27922 | g-patch domain-contaning protein |
| SEQ ID NO: 2921 | Nga00196.02 | 469.4271 | 500.67626 | ---NA--- |
| SEQ ID NO: 2922 | Nga00197.02 | 501.9973 | 375.74227 | proly 4-hydroxylase |
| SEQ ID NO: 2923 | Nga00207.02 | 2368.566 | 2338.2092 | urease accessory protein ureg |
| SEQ ID NO: 2924 | Nga00200.02 | 608.4316 | 561.54786 | dna gyrase subunit a |
| SEQ ID NO: 2925 | Nga00211.02 | 160.0424 | 132.60574 | nlr card domain containing 3 |
| SEQ ID NO: 2926 | Nga00203.02 | 242.0765 | 225.52575 | beta-adaptin-like protein a |
| SEQ ID NO: 2927 | Nga01268.02 | 330.4843 | 253.83473 | protein |
| SEQ ID NO: 2928 | Nga03485 | 50.13333 | 83.770091 | elongation protein 1 |
| SEQ ID NO: 2929 | Nga03476.01 | 3646.76 | 2977.1728 | predicted protein [Phaeodactylum tricornutum CCAP 1055/1] |
| SEQ ID NO: 2930 | Nga03490.01 | 855.7214 | 986.22792 | dynein light chain roadblock-type 1-like |
| SEQ ID NO: 2931 | Nga03474 | 415.2047 | 530.53124 | ---NA--- |
| SEQ ID NO: 2932 | Nga03481 | 165.7356 | 177.5132 | abc transporter-like protein |
| SEQ ID NO: 2933 | Nga03486 | 98.03922 | 100.40671 | abc atp-binding permease protein |
| SEQ ID NO: 2934 | Nga03484 | 152.9582 | 189.13608 | diacylglycerol acyltransferase |
| SEQ ID NO: 2935 | Nga03489 | 190.4762 | 138.87615 | ---NA--- |
| SEQ ID NO: 2936 | Nga03483 | 221.4664 | 263.64424 | alpha-aminoadipic semialdehyde |
| SEQ ID NO: 2937 | Nga03479 | 108.307 | 152.63233 | atp-binding cassette superfamily |
| SEQ ID NO: 2938 | Nga03498 | 89.14729 | 151.14892 | ---NA--- |
| SEQ ID NO: 2939 | Nga03475 | 172.3164 | 205.01885 | ring finger protein 2 |
| SEQ ID NO: 2940 | Nga20984 | 160.7143 | 166.35378 | saccharopine dehydrogenase |
| SEQ ID NO: 2941 | Nga03480 | 1271.881 | 1551.8957 | trifunctional enzyme subunit alpha |
| SEQ ID NO: 2942 | Nga03672.2 | 490.3226 | 412.32776 | adenosine kinase |
| SEQ ID NO: 2943 | Nga03482 | 1111.396 | 1058.9617 | lipoic acid synthetase |
| SEQ ID NO: 2944 | Nga03488 | 1346.87 | 1479.1367 | ---NA--- |
| SEQ ID NO: 2945 | Nga03487 | 828.6479 | 1048.4312 | multifunctional fatty acid oxidation complex subunit alpha |
| SEQ ID NO: 2946 | Nga20692 | 95.65217 | 62.79617 | ---NA--- |
| SEQ ID NO: 2947 | Nga04849 | 293.5421 | 326.45406 | ankyrin repeat protein |
| SEQ ID NO: 2948 | Nga04846 | 392.7393 | 401.29706 | protein |
| SEQ ID NO: 2949 | Nga04847 | 50.3876 | 82.572096 | meiotic recombination 11 |
| SEQ ID NO: 2950 | Nga04848 | 22.98851 | 26.97709 | meiotic recombination 11 |
| SEQ ID NO: 2951 | Nga04835 | 590.3479 | 751.33398 | cysteine proteinase |
| SEQ ID NO: 2952 | Nga04314 | 476.3077 | 471.29009 | trna-splicing ligase homolog |
| SEQ ID NO: 2953 | Nga21092 | 2297.417 | 2378.7462 | ubiquitin-conjugating enzyme e2 8 |
| SEQ ID NO: 2954 | Nga04313 | 3082.836 | 3356.9226 | ---NA--- |
| SEQ ID NO: 2955 | Nga07085 | 629.0429 | 491.92406 | ---NA--- |
| SEQ ID NO: 2956 | Nga20315 | 272.7273 | 275.39846 | brca1-associated protein 2 containing protein |
| SEQ ID NO: 2957 | Nga07036 | 925.5556 | 872.60512 | ---NA--- |
| SEQ ID NO: 2958 | Nga06821 | 1156.338 | 770.46921 | protein |
| SEQ ID NO: 2959 | Nga06822 | 771.0526 | 839.0312 | expressed unknown protein [Ectocarpus siliculosus] |
| SEQ ID NO: 2960 | Nga04207 | 3638.422 | 4280.7127 | protein |
| SEQ ID NO: 2961 | Nga20435 | 205.4795 | 242.36741 | ---NA--- |
| SEQ ID NO: 2962 | Nga01514.02 | 213.6752 | 291.63991 | ---NA--- |
| SEQ ID NO: 2963 | Nga20472.1 | 106.383 | 98.775131 | cleavage and polyadenylation specificity factor subunit 2 |
| SEQ ID NO: 2964 | Nga20240.1 | 115.0307 | 109.65252 | cleavage and polyadenylation specificity factor subunit 2 |
| SEQ ID NO: 2965 | Nga01511.2 | 643.7423 | 700.00805 | arginine biosynthesis bifunctional protein |
| SEQ ID NO: 2966 | Nga02444 | 119.5499 | 150.83004 | chloride channel 7 |
| SEQ ID NO: 2967 | Nga02445 | 267.6768 | 289.95656 | conserved unknown protein [Ectocarpus siliculosus] |
| SEQ ID NO: 2968 | Nga02443.01 | 1509.804 | 2050.7664 | ---NA--- |
| SEQ ID NO: 2969 | Nga20107 | 535.7711 | 528.70083 | adp-ribosylation factor |
| SEQ ID NO: 2970 | Nga07265 | 156.4417 | 200.47581 | beta-ketoacyl synthase |
| SEQ ID NO: 2971 | Nga06796 | 178.2178 | 107.25089 | ---NA--- |

FIGURE 24 AU

| # | Nga model | +N rpkb | -N rpkb | GO |
|---|---|---|---|---|
| SEQ ID NO: 2972 | Nga01221.02 | 112.069 | 93.382236 | ---NA--- |
| SEQ ID NO: 2973 | Nga01220.02 | 140.8451 | 85.67289 | ---NA--- |
| SEQ ID NO: 2974 | Nga03568 | 101.9417 | 21.033669 | ---NA--- |
| SEQ ID NO: 2975 | Nga03566 | 399.2095 | 563.02476 | dnaj dnaj protein |
| SEQ ID NO: 2976 | Nga05785 | 1039.326 | 1125.833 | ---NA--- |
| SEQ ID NO: 2977 | Nga05782 | 244.6483 | 303.10674 | ---NA--- |
| SEQ ID NO: 2978 | Nga05787 | 271.1111 | 361.07798 | expressed unknown protein [Ectocarpus siliculosus] |
| SEQ ID NO: 2979 | Nga05784 | 297.1014 | 340.14592 | ---NA--- |
| SEQ ID NO: 2980 | Nga05783.01 | 151.2821 | 161.09633 | ---NA--- |
| SEQ ID NO: 2981 | Nga20127 | 247.3934 | 258.74403 | mitochondrial 28s ribosomal protein s29-related |
| SEQ ID NO: 2982 | Nga04168.02 | 1071.701 | 1663.3415 | protein |
| SEQ ID NO: 2983 | Nga06937 | 163.2373 | 222.88764 | hypothetical protein ALO_12346 [Acetonema longum DSM 6540] |
| SEQ ID NO: 2984 | Nga04890 | 490.3581 | 605.77545 | protein |
| SEQ ID NO: 2985 | Nga04888 | 311.0085 | 380.25764 | ---NA--- |
| SEQ ID NO: 2986 | Nga04363 | 490.7407 | 495.47923 | conserved unknown protein [Ectocarpus siliculosus] |
| SEQ ID NO: 2987 | Nga04295 | 286.123 | 587.33285 | hypothetical protein Tcur_2694 [Thermomonospora curvata DSM 43183] |
| SEQ ID NO: 2988 | Nga04644 | 531.1555 | 532.77023 | carboxyl-terminal protease |
| SEQ ID NO: 2989 | Nga05279 | 910.7867 | 1273.8761 | ---NA--- |
| SEQ ID NO: 2990 | Nga20525 | 10541.08 | 9100.0334 | histone h2b |
| SEQ ID NO: 2991 | Nga05286 | 1276.423 | 926.9136 | histone |
| SEQ ID NO: 2992 | Nga05284 | 232.5 | 213.9387 | ---NA--- |
| SEQ ID NO: 2993 | Nga05282 | 472.7011 | 356.40887 | cre-ntl-4 protein |
| SEQ ID NO: 2994 | Nga05281 | 145.9075 | 168.97421 | conserved hypothetical protein [Capsaspora owczarzaki ATCC 30864] |
| SEQ ID NO: 2995 | Nga20474 | 205.6962 | 202.24938 | hydrolase-like protein |
| SEQ ID NO: 2996 | Nga05283 | 2270.396 | 2422.7575 | protein |
| SEQ ID NO: 2997 | Nga05280 | 736.3434 | 611.05504 | abc transporter-like protein |
| SEQ ID NO: 2998 | Nga05285 | 947.1987 | 1056.164 | u2 small nuclear rna auxiliary factor 2 |
| SEQ ID NO: 2999 | Nga05278 | 136.0332 | 179.97656 | ---NA--- |
| SEQ ID NO: 3000 | Nga20520 | 1649.419 | 1528.1949 | cullin a |
| SEQ ID NO: 3001 | Nga01114 | 1269.076 | 1496.516 | poly binding protein 2-like |
| SEQ ID NO: 3002 | Nga01115 | 184.3288 | 203.84556 | transportin 3 |
| SEQ ID NO: 3003 | Nga01113 | 134.0388 | 166.2105 | protein |
| SEQ ID NO: 3004 | Nga04737 | 405.8389 | 571.67784 | ---NA--- |
| SEQ ID NO: 3005 | Nga21298 | 436.2934 | 500.49033 | agmatine deiminase |
| SEQ ID NO: 3006 | Nga06612 | 168.4783 | 229.5985 | ---NA--- |
| SEQ ID NO: 3007 | Nga06613 | 188.0342 | 268.49388 | ---NA--- |
| SEQ ID NO: 3008 | Nga01325.02 | 1065.072 | 1237.6855 | ---NA--- |
| SEQ ID NO: 3009 | Nga01324.02 | 613.4507 | 665.19143 | upf0760 protein c2orf29-like |
| SEQ ID NO: 3010 | Nga01327.02 | 342.3019 | 362.69716 | phosphopantothenoylcysteine decarboxylase |
| SEQ ID NO: 3011 | Nga07278 | 20.83333 | 33.851061 | ---NA--- |
| SEQ ID NO: 3012 | Nga21272 | 591.4221 | 846.04728 | homocysteine s-methyltransferase 1 |
| SEQ ID NO: 3013 | Nga07017 | 596.7994 | 664.65408 | solute carrier family 2 (facilitated glucose transporter) member 13 |
| SEQ ID NO: 3014 | Nga07016 | 834.7826 | 718.56761 | translation elongation factor p |
| SEQ ID NO: 3015 | Nga01953 | 223.0047 | 216.13823 | myosin-like protein |
| SEQ ID NO: 3016 | Nga01955 | 841.5301 | 822.78425 | expressed unknown protein [Ectocarpus siliculosus] |
| SEQ ID NO: 3017 | Nga01956 | 518.2342 | 531.22125 | ---NA--- |
| SEQ ID NO: 3018 | Nga01952 | 292.2002 | 343.00306 | ---NA--- |
| SEQ ID NO: 3019 | Nga01954 | 568.1818 | 527.549 | ---NA--- |
| SEQ ID NO: 3020 | Nga06861 | 369.1814 | 346.00892 | type i fatty acid |
| SEQ ID NO: 3021 | Nga01554 | 487.9852 | 901.02638 | ---NA--- |
| SEQ ID NO: 3022 | Nga01552 | 417.7632 | 424.02908 | wd repeat-containing protein 92 |
| SEQ ID NO: 3023 | Nga01553 | 828.2828 | 927.3139 | membrane protein |
| SEQ ID NO: 3024 | Nga01285 | 151.8207 | 173.25675 | vacuolar protein sorting 41 |
| SEQ ID NO: 3025 | Nga01286 | 6806.387 | 6820.482 | transaldolase |
| SEQ ID NO: 3026 | Nga01288 | 253.9063 | 362.48844 | testes-specific alpha4-t2 proteasome subunit |
| SEQ ID NO: 3027 | Nga01289 | 336.1244 | 390.01605 | sorting and assembly machinery component 50 putativ |
| SEQ ID NO: 3028 | Nga01046.02 | 367.3051 | 362.31286 | aspartate aminotransferase |
| SEQ ID NO: 3029 | Nga01287 | 497.8029 | 701.07608 | major facilitator superfamily |
| SEQ ID NO: 3030 | Nga02147 | 1487.603 | 1703.95 | hypothetical protein CHLNCDRAFT_49994 [Chlorella variabilis] |
| SEQ ID NO: 3031 | Nga02146.1 | 1490.266 | 2171.5862 | cysteine desulfurase |
| SEQ ID NO: 3032 | Nga06938 | 225.8065 | 209.65818 | ---NA--- |
| SEQ ID NO: 3033 | Nga20600 | 474.9722 | 365.09442 | hypothetical protein AURANDRAFT_65325 [Aureococcus anophagefferens] |
| SEQ ID NO: 3034 | Nga06123.02 | 752.5355 | 799.79139 | mitochondrial protein translocase family |

FIGURE 24 AV

| # | Nga model | +N rpkb | -N rpkb | GO |
|---|---|---|---|---|
| SEQ ID NO: 3035 | Nga06905 | 4518.065 | 4449.6455 | protein |
| SEQ ID NO: 3036 | Nga06906 | 146.1596 | 123.59045 | pentatricopeptide repeat-containing protein |
| SEQ ID NO: 3037 | Nga20076 | 1129.648 | 950.41531 | ---NA--- |
| SEQ ID NO: 3038 | Nga21217.1 | 81.08108 | 66.917927 | atp synthase alpha subunit |
| SEQ ID NO: 3039 | Nga06276.02 | 757.3436 | 708.32156 | coiled-coil domain-containing protein 124 |
| SEQ ID NO: 3040 | Nga01355.02 | 490.099 | 633.19273 | chaperone protein |
| SEQ ID NO: 3041 | Nga02122 | 380.9524 | 325.36697 | transcription elongation factor s-ii |
| SEQ ID NO: 3042 | Nga20267 | 249.1228 | 248.95377 | chromatin remodeling complex subunit |
| SEQ ID NO: 3043 | Nga02121 | 250.8961 | 337.78263 | chromatin remodeling complex subunit |
| SEQ ID NO: 3044 | Nga02120 | 485.9649 | 575.82436 | trna pseudouridine synthase |
| SEQ ID NO: 3045 | Nga20897 | 78.68852 | 152.71823 | ---NA--- |
| SEQ ID NO: 3046 | Nga20487 | 183.8741 | 219.41612 | snf2 superfamily rad5 protein |
| SEQ ID NO: 3047 | Nga07272 | 156.7649 | 122.2221 | ---NA--- |
| SEQ ID NO: 3048 | Nga07138 | 2540.96 | 1930.8492 | glycosyl bnr protein |
| SEQ ID NO: 3049 | Nga04328.01 | 440.3748 | 418.89967 | ---NA--- |
| SEQ ID NO: 3050 | Nga04329.01 | 180.8874 | 162.66994 | ---NA--- |
| SEQ ID NO: 3051 | Nga04564 | 455.4125 | 489.70233 | protein |
| SEQ ID NO: 3052 | Nga03757 | 590 | 626.10922 | ---NA--- |
| SEQ ID NO: 3053 | Nga03756 | 724.4526 | 832.1925 | domain protein |
| SEQ ID NO: 3054 | Nga03759 | 1415.07 | 1287.9831 | tubulin--tyrosine ligase-like protein 12 |
| SEQ ID NO: 3055 | Nga03758 | 50.69124 | 74.877922 | ---NA--- |
| SEQ ID NO: 3056 | Nga02378.2 | 371.0451 | 370.77135 | diacylglycerol o- |
| SEQ ID NO: 3057 | Nga07127 | 432.4324 | 522.09924 | ---NA--- |
| SEQ ID NO: 3058 | Nga01500.02 | 378.1903 | 335.94494 | ---NA--- |
| SEQ ID NO: 3059 | Nga05400.2 | 1037.525 | 1019.0529 | proliferation-associated protein 2g4 |
| SEQ ID NO: 3060 | Nga04774.01 | 8119.114 | 8316.7961 | mosc domain protein |
| SEQ ID NO: 3061 | Nga01107.02 | 535.2381 | 451.8633 | isoamyl acetate-hydrolyzing esterase 1 homolog ( cerevisiae) |
| SEQ ID NO: 3062 | Nga01108.02 | 2068.654 | 1876.8227 | predicted protein [Thalassiosira pseudonana CCMP1335] |
| SEQ ID NO: 3063 | Nga01106.02 | 1262.956 | 1069.7195 | chalcone isomerase-like protein |
| SEQ ID NO: 3064 | Nga03574.02 | 344.2249 | 390.16177 | protein |
| SEQ ID NO: 3065 | Nga03575.02 | 352.2388 | 224.1917 | protein |
| SEQ ID NO: 3066 | Nga01066.02 | 143.6782 | 143.1861 | ---NA--- |
| SEQ ID NO: 3067 | Nga01065.02 | 307.4627 | 219.88032 | ---NA--- |
| SEQ ID NO: 3068 | Nga04494.1 | 1548.544 | 1513.1095 | glutaredoxin-like protein |
| SEQ ID NO: 3069 | Nga04497 | 301.5007 | 313.29549 | uncharacterized protein c1orf53-like |
| SEQ ID NO: 3070 | Nga04496 | 9121.803 | 10300.199 | heat shock protein 70 |
| SEQ ID NO: 3071 | Nga04495 | 51.28205 | 127.76605 | fatty acid elongase |
| SEQ ID NO: 3072 | Nga07230 | 651.9274 | 650.92289 | ---NA--- |
| SEQ ID NO: 3073 | Nga07228 | 614.8459 | 699.77823 | heavy metal translocating p-type atpase |
| SEQ ID NO: 3074 | Nga07229 | 4.519774 | 3.6719795 | short-chain dehydrogenase reductase sdr |
| SEQ ID NO: 3075 | Nga06827 | 0 | 2.087156 | glycosyl bnr protein |
| SEQ ID NO: 3076 | Nga07063 | 214.5086 | 234.05289 | capsular associated protein |
| SEQ ID NO: 3077 | Nga06703.2 | 927.3743 | 1104.6472 | uncharacterized protein |
| SEQ ID NO: 3078 | Nga20498.1 | 399.1826 | 472.25458 | ---NA--- |
| SEQ ID NO: 3079 | Nga06266.02 | 780.5841 | 1109.7377 | gdsl lipase acylhydrolase family protein |
| SEQ ID NO: 3080 | Nga06280.02 | 13.10044 | 42.572513 | ---NA--- |
| SEQ ID NO: 3081 | Nga01380.02 | 473.0159 | 387.4424 | conserved unknown protein [Ectocarpus siliculosus] |
| SEQ ID NO: 3082 | Nga04932 | 104.2553 | 70.294969 | ---NA--- |
| SEQ ID NO: 3083 | Nga03763 | 422.5146 | 329.40447 | nedd8-conjugating enzyme ubc12 |
| SEQ ID NO: 3084 | Nga03762.01 | 964.1898 | 915.4636 | subunit of proteaseome activator |
| SEQ ID NO: 3085 | Nga02165 | 1593.186 | 1790.1942 | h aca ribonucleoprotein complex subunit 4 |
| SEQ ID NO: 3086 | Nga02167 | 350.9524 | 301.75803 | tpa: zn 2cys6 transcription factor |
| SEQ ID NO: 3087 | Nga02166 | 754.3398 | 707.15062 | acetyl-coenzyme a synthetase |
| SEQ ID NO: 3088 | Nga20901 | 181.8182 | 154.74771 | ---NA--- |
| SEQ ID NO: 3089 | Nga20699 | 185.1852 | 165.49407 | carbohydrate kinase fggy |
| SEQ ID NO: 3090 | Nga02225 | 713.9241 | 579.55301 | protein |
| SEQ ID NO: 3091 | Nga02224 | 752.7011 | 749.68111 | glycoside |
| SEQ ID NO: 3092 | Nga20410 | 639.7849 | 502.30606 | protein |
| SEQ ID NO: 3093 | Nga07313 | 270.1613 | 428.05212 | ---NA--- |
| SEQ ID NO: 3094 | Nga04806.01 | 6873.897 | 6980.2338 | 60s ribosomal protein l39 |
| SEQ ID NO: 3095 | Nga04005.02 | 1076.887 | 1047.7602 | protease required for anti-sigma degradation |
| SEQ ID NO: 3096 | Nga04140.1 | 262.3336 | 318.9475 | uncharacterized membrane protein |
| SEQ ID NO: 3097 | Nga04138 | 4079.327 | 4002.2369 | proteasome subunit |
| SEQ ID NO: 3098 | Nga03221 | 71.05943 | 141.35223 | ---NA--- |

FIGURE 24 AW

| # | Nga model | +N rpkb | -N rpkb | GO |
|---|---|---|---|---|
| SEQ ID NO: 3099 | Nga03220.01 | 96.58793 | 100.07831 | gc-rich sequence dna-binding factor homolog |
| SEQ ID NO: 3100 | Nga03216.01 | 358.2183 | 431.5267 | aspartyl glutamyl-trna amidotransferase subunit b |
| SEQ ID NO: 3101 | Nga05331.2 | 11.56069 | 0 | ---NA--- |
| SEQ ID NO: 3102 | Nga03219 | 124.8025 | 109.52128 | trna splicing endonuclease 2 homolog ( cerevisiae) |
| SEQ ID NO: 3103 | Nga03214 | 232.4903 | 363.00982 | drug metabolite transporter superfamily |
| SEQ ID NO: 3104 | Nga03217 | 1226.868 | 1062.9956 | protein |
| SEQ ID NO: 3105 | Nga03218 | 2388.649 | 2486.302 | s-adenosylmethionine carrier 1 |
| SEQ ID NO: 3106 | Nga03215.01 | 761.8481 | 870.92112 | ribosomal rna processing 12 homolog ( cerevisiae) |
| SEQ ID NO: 3107 | Nga00165.02 | 1802.676 | 1561.4509 | anion exchanger family |
| SEQ ID NO: 3108 | Nga04641 | 7836.066 | 3891.9471 | light-harvesting protein |
| SEQ ID NO: 3109 | Nga20249 | 210.6406 | 281.0998 | class member 1 |
| SEQ ID NO: 3110 | Nga20094 | 314.7244 | 368.13324 | class member 1 |
| SEQ ID NO: 3111 | Nga04640 | 6783.496 | 8667.3781 | phosphoenolpyruvate carboxykinase |
| SEQ ID NO: 3112 | Nga01812 | 3089.286 | 2748.9211 | pyruvate dehydrogenase e1 component beta subunit |
| SEQ ID NO: 3113 | Nga02830.02 | 727.3567 | 711.81084 | potential ankyrin repeat protein |
| SEQ ID NO: 3114 | Nga02831.02 | 751.5432 | 685.3795 | solute carrier family 25 (mitochondrial carrier citrate transporter) member 1 |
| SEQ ID NO: 3115 | Nga07020 | 322.2836 | 391.00157 | ---NA--- |
| SEQ ID NO: 3116 | Nga04863 | 742.4534 | 754.15902 | adipocyte plasma membrane-associated |
| SEQ ID NO: 3117 | Nga21104 | 2841.988 | 3492.9847 | PREDICTED: hypothetical protein [Saccoglossus kowalevskii] |
| SEQ ID NO: 3118 | Nga04864 | 2982.301 | 2549.9135 | upf0187-containing protein |
| SEQ ID NO: 3119 | Nga04865 | 3609.195 | 3626.7882 | triosephosphate isomerase |
| SEQ ID NO: 3120 | Nga03105.02 | 948.5294 | 915.96988 | conserved unknown protein [Ectocarpus siliculosus] |
| SEQ ID NO: 3121 | Nga00753.02 | 204.0609 | 232.04301 | diacylglycerol acyltransferase family protein |
| SEQ ID NO: 3122 | Nga04643 | 2725.971 | 2711.4077 | protein |
| SEQ ID NO: 3123 | Nga02172 | 285.3387 | 388.49668 | agc family protein kinase |
| SEQ ID NO: 3124 | Nga02171 | 316.0228 | 375.25584 | pyridoxine biosynthesis protein |
| SEQ ID NO: 3125 | Nga20590 | 72.72727 | 59.085488 | type i polyketide synthase |
| SEQ ID NO: 3126 | Nga00314.2 | 772.2772 | 646.0589 | protein |
| SEQ ID NO: 3127 | Nga00318.02 | 315.1042 | 373.77213 | expressed unknown protein [Ectocarpus siliculosus] |
| SEQ ID NO: 3128 | Nga06871 | 21.76871 | 10.316514 | bnr asp-box repeat-containing protein |
| SEQ ID NO: 3129 | Nga01358.02 | 440.5405 | 482.57584 | dna gyrase subunit b |
| SEQ ID NO: 3130 | Nga06626.2 | 314.7903 | 310.38359 | atp-dependent rna helicase ddx1 |
| SEQ ID NO: 3131 | Nga01982 | 21.64502 | 37.514595 | ---NA--- |
| SEQ ID NO: 3132 | Nga06567.02 | 13.7931 | 7.4705789 | ---NA--- |
| SEQ ID NO: 3133 | Nga07223 | 211.1952 | 231.7031 | arginine serine-rich splicing factor |
| SEQ ID NO: 3134 | Nga07224.1 | 147.4954 | 165.80111 | ubiquitin-like protein |
| SEQ ID NO: 3135 | Nga04045 | 4995.287 | 5618.3189 | protein |
| SEQ ID NO: 3136 | Nga04047.1 | 2199.197 | 1649.6478 | anion:sodium symporter |
| SEQ ID NO: 3137 | Nga21283.1 | 1526.012 | 1092.6261 | response regulator receiver domain-containing protein |
| SEQ ID NO: 3138 | Nga02476.02 | 1954.212 | 1454.2316 | response regulator receiver domain-containing protein |
| SEQ ID NO: 3139 | Nga02465.02 | 2351.721 | 2235.209 | ---NA--- |
| SEQ ID NO: 3140 | Nga07187 | 5097.319 | 4308.9481 | ---NA--- |
| SEQ ID NO: 3141 | Nga04874 | 807.4409 | 754.28809 | gtp-binding protein |
| SEQ ID NO: 3142 | Nga04875 | 640.2516 | 647.21525 | ---NA--- |
| SEQ ID NO: 3143 | Nga03775.02 | 595.6679 | 481.0028 | 3 (2) -bisphosphate nucleotidase |
| SEQ ID NO: 3144 | Nga03554 | 809.8464 | 1174.7266 | dead deah box rna |
| SEQ ID NO: 3145 | Nga03555 | 311.0048 | 316.15919 | alkyl sulfatase or beta-lactamase |
| SEQ ID NO: 3146 | Nga03553 | 246.0733 | 218.3482 | ankyrin repeat protein |
| SEQ ID NO: 3147 | Nga03551 | 669.5122 | 735.14596 | ribonucleoside-diphosphate alpha subunit |
| SEQ ID NO: 3148 | Nga03552 | 401.2975 | 444.73831 | |
| SEQ ID NO: 3149 | Nga20767 | 1347.633 | 1246.3108 | atp-binding cassette superfamily |
| SEQ ID NO: 3150 | Nga06946 | 374.5233 | 451.96717 | protein phosphatase 2c |
| SEQ ID NO: 3151 | Nga00641.2 | 534.2137 | 412.22708 | ---NA--- |
| SEQ ID NO: 3152 | Nga04787.1 | 439.3116 | 584.78934 | protein |
| SEQ ID NO: 3153 | Nga04702 | 111.1111 | 76.592299 | hydrolase iia |
| SEQ ID NO: 3154 | Nga05340.02 | 143.7186 | 176.36573 | ---NA--- |
| SEQ ID NO: 3155 | Nga04965 | 1143.646 | 861.79938 | lactoylglutathione lyase |
| SEQ ID NO: 3156 | Nga04964 | 434.6103 | 424.27855 | -like 2 |
| SEQ ID NO: 3157 | Nga04966 | 992.5595 | 912.36668 | ubiquitin carboxyl-terminal hydrolase isozyme l3 |
| SEQ ID NO: 3158 | Nga04967 | 259.1241 | 208.21285 | nicotinamide n-methyltransferase |
| SEQ ID NO: 3159 | Nga00710.2 | 880 | 765.48532 | protein |
| SEQ ID NO: 3160 | Nga00699.02 | 156.6667 | 192.27402 | phosphatidylinositol kinase (pik-k) |
| SEQ ID NO: 3161 | Nga01677.2 | 1513.24 | 1322.8277 | disulfide isomerase |

FIGURE 24 AX

| # | Nga model | +N rpkb | -N rpkb | GO |
|---|---|---|---|---|
| SEQ ID NO: 3162 | Nga01678.02 | 756.1299 | 824.80835 | mitochondrial-processing peptidase subunit beta |
| SEQ ID NO: 3163 | Nga01679.02 | 561.5797 | 630.07383 | pleiotropic regulator 1 |
| SEQ ID NO: 3164 | Nga04323.01 | 677.9089 | 672.83502 | cation diffusion facilitator family |
| SEQ ID NO: 3165 | Nga05773.2 | 490.2676 | 531.73345 | cystathionine gamma-synthase |
| SEQ ID NO: 3166 | Nga02114 | 743.6919 | 739.41865 | wd repeat domain phosphoinositide-interacting protein 3 |
| SEQ ID NO: 3167 | Nga20291 | 616.5919 | 655.76943 | ---NA--- |
| SEQ ID NO: 3168 | Nga02112 | 945.933 | 954.69709 | protein |
| SEQ ID NO: 3169 | Nga02115.2 | 1490.608 | 1340.8512 | protein |
| SEQ ID NO: 3170 | Nga20862.1 | 6250 | 6514.8784 | ---NA--- |
| SEQ ID NO: 3171 | Nga20996 | 172.0698 | 132.36524 | rab alpha subunit |
| SEQ ID NO: 3172 | Nga04980 | 74.07407 | 86.92618 | ---NA--- |
| SEQ ID NO: 3173 | Nga04977 | 987.4715 | 1123.9477 | protein |
| SEQ ID NO: 3174 | Nga20963 | 239.5693 | 414.04904 | activating signal cointegrator 1 complex subunit 3-like 1 |
| SEQ ID NO: 3175 | Nga05818.2 | 586.8373 | 778.59502 | trehalose-phosphate synthase |
| SEQ ID NO: 3176 | Nga00886.02 | 6284.261 | 7991.0382 | isocitrate lyase |
| SEQ ID NO: 3177 | Nga20275.1 | 178.5346 | 155.3865 | upf0533 protein c5orf44 homolog |
| SEQ ID NO: 3178 | Nga20506.1 | 354.1667 | 324.97018 | conserved unknown protein [Ectocarpus siliculosus] |
| SEQ ID NO: 3179 | Nga07161 | 137.3955 | 117.77095 | rna-binding la domain protein |
| SEQ ID NO: 3180 | Nga07162 | 387.1681 | 422.58905 | uncharacterized conserved protein |
| SEQ ID NO: 3181 | Nga07160 | 570.1754 | 755.41314 | epsin 2-like protein |
| SEQ ID NO: 3182 | Nga04943.01 | 365.5395 | 394.2204 | ainteguemnta-like protein |
| SEQ ID NO: 3183 | Nga04942.01 | 2777.103 | 2549.143 | phosphoglucomutase |
| SEQ ID NO: 3184 | Nga04941.01 | 5066.498 | 7316.4598 | wd sam and u-box domain-containing protein 1 |
| SEQ ID NO: 3185 | Nga04456 | 835.1114 | 981.66775 | u5 small nuclear ribonucleoprotein 200 kda helicase |
| SEQ ID NO: 3186 | Nga20274.1 | 132.2506 | 159.17591 | apoptosis-inducing mitochondrion-associated 1 |
| SEQ ID NO: 3187 | Nga03465.02 | 386.4119 | 365.6777 | protein |
| SEQ ID NO: 3188 | Nga03473.02 | 106.7961 | 59.595395 | ---NA--- |
| SEQ ID NO: 3189 | Nga03467.2 | 1522.52 | 1536.9981 | alpha-actinin |
| SEQ ID NO: 3190 | Nga01198.02 | 154.661 | 172.12404 | ---NA--- |
| SEQ ID NO: 3191 | Nga01197.02 | 2927.435 | 2518.5728 | peptide deformylase |
| SEQ ID NO: 3192 | Nga02369 | 262.1871 | 248.33031 | delta( )-delta( )-dienoyl- mitochondrial-like |
| SEQ ID NO: 3193 | Nga03678 | 28.57143 | 20.633027 | ---NA--- |
| SEQ ID NO: 3194 | Nga03677 | 84.65608 | 51.582569 | ---NA--- |
| SEQ ID NO: 3195 | Nga03676 | 1296.296 | 874.18879 | pin1-type peptidyl-prolyl cis-trans in1 |
| SEQ ID NO: 3196 | Nga07053 | 71.49758 | 74.308802 | ---NA--- |
| SEQ ID NO: 3197 | Nga06850 | 332.618 | 413.76747 | ---NA--- |
| SEQ ID NO: 3198 | Nga06851 | 437.3866 | 525.88944 | hypothetical protein Gbem_1483 [Geobacter bemidjiensis Bem] |
| SEQ ID NO: 3199 | Nga04710 | 63.69983 | 76.563656 | helicase domain-containing protein |
| SEQ ID NO: 3200 | Nga04709 | 1077.536 | 1056.5456 | methylmalonate-semialdehyde dehydrogenase |
| SEQ ID NO: 3201 | Nga06146.2 | 1602.181 | 1863.635 | pyrophosphate-dependent phosphofructose kinase |
| SEQ ID NO: 3202 | Nga02136 | 1252.304 | 1138.1444 | dimethyl-8-ribityllumazine synthase |
| SEQ ID NO: 3203 | Nga02138 | 119.8198 | 157.11772 | 3-oxoacyl-(acyl-carrier-protein) synthase 2 |
| SEQ ID NO: 3204 | Nga20125 | 170.7014 | 225.25349 | uncharacterized udp-glucosyltransferase |
| SEQ ID NO: 3205 | Nga20060 | 288.5439 | 266.16937 | protein |
| SEQ ID NO: 3206 | Nga02137 | 993.8776 | 966.06782 | protein |
| SEQ ID NO: 3207 | Nga07192 | 140.3509 | 122.47089 | subtilisin-like serine peptidase |
| SEQ ID NO: 3208 | Nga06969 | 213.3106 | 216.89326 | bacterial transferase hexapeptide repeat-containing protein |
| SEQ ID NO: 3209 | Nga02325.02 | 763.4409 | 183.45091 | rna binding protein |
| SEQ ID NO: 3210 | Nga04368 | 300.1912 | 347.96042 | cleavage stimulation factor subunit 3 |
| SEQ ID NO: 3211 | Nga01100.2 | 489.9206 | 115.80082 | conserved hypothetical protein [Paracoccidioides brasiliensis Pb01] |
| SEQ ID NO: 3212 | Nga05988.2 | 2033.517 | 2206.4515 | protein |
| SEQ ID NO: 3213 | Nga04311 | 60.60606 | 73.85686 | cleavage and polyadenylation specificity factor |
| SEQ ID NO: 3214 | Nga21219.1 | 230.3307 | 228.50431 | augmenter of liver regeneration |
| SEQ ID NO: 3215 | Nga07207 | 64.24242 | 129.98807 | ---NA--- |
| SEQ ID NO: 3216 | Nga04751 | 971.3115 | 1094.3326 | ---NA--- |
| SEQ ID NO: 3217 | Nga06972 | 497.992 | 569.89416 | ---NA--- |
| SEQ ID NO: 3218 | Nga04855.01 | 0 | 66.866293 | ---NA--- |
| SEQ ID NO: 3219 | Nga04854 | 108.1794 | 152.43398 | anthranilate phosphoribosyltransferase |
| SEQ ID NO: 3220 | Nga00679.02 | 1138.103 | 1014.1425 | protein |
| SEQ ID NO: 3221 | Nga04270.02 | 132.8125 | 93.090417 | ---NA--- |
| SEQ ID NO: 3222 | Nga04234 | 262.1083 | 348.73343 | protein |
| SEQ ID NO: 3223 | Nga04236 | 327.381 | 212.7781 | chord family protein |
| SEQ ID NO: 3224 | Nga04233 | 7273.639 | 7017.7419 | atp synthase subunit delta |
| SEQ ID NO: 3225 | Nga04231 | 967.3222 | 1079.4749 | importin beta- |

FIGURE 24 AY

| # | Nga model | +N rpkb | -N rpkb | GO |
|---|---|---|---|---|
| SEQ ID NO: 3226 | Nga04235 | 729.8497 | 701.80833 | cellulose synthase (udp-forming) family gt2 |
| SEQ ID NO: 3227 | Nga04232 | 510.6145 | 515.59515 | calcium calmodulin dependent protein |
| SEQ ID NO: 3228 | Nga04754.1 | 1061.605 | 769.2306 | protein |
| SEQ ID NO: 3229 | Nga04755.01 | 367.3966 | 342.62874 | short-chain dehydrogenase reductase sdr |
| SEQ ID NO: 3230 | Nga20369 | 92.55079 | 136.93251 | pentatricopeptide repeat-containing protein |
| SEQ ID NO: 3231 | Nga02180 | 101.0638 | 59.539454 | ---NA--- |
| SEQ ID NO: 3232 | Nga06879 | 917.4917 | 758.41697 | ---NA--- |
| SEQ ID NO: 3233 | Nga03045.02 | 422.5352 | 411.93403 | proteasome subunit alpha |
| SEQ ID NO: 3234 | Nga03058.02 | 293.4473 | 271.58002 | transmembrane protein 144 |
| SEQ ID NO: 3235 | Nga03049.2 | 1050.495 | 1231.2402 | iron-sulfur cluster scaffold protein nfu-like protein |
| SEQ ID NO: 3236 | Nga07299.1 | 2197.878 | 2503.6802 | solute carrier family 35 member b1 |
| SEQ ID NO: 3237 | Nga05100.2 | 272.9104 | 285.80795 | dna replication licensing factor mcm2 |
| SEQ ID NO: 3238 | Nga04401.01 | 420.6799 | 494.05287 | ---NA--- |
| SEQ ID NO: 3239 | Nga04400.1 | 159.6107 | 175.00422 | minichromosome maintenance protein 2 |
| SEQ ID NO: 3240 | Nga04948 | 238.2979 | 193.59926 | protein |
| SEQ ID NO: 3241 | Nga01903 | 788.8631 | 743.93793 | conserved unknown protein [Ectocarpus siliculosus] |
| SEQ ID NO: 3242 | Nga01904 | 3324.742 | 3802.4862 | ---NA--- |
| SEQ ID NO: 3243 | Nga01901 | 334.9436 | 374.16052 | phosphoacetylglucosamine mutase |
| SEQ ID NO: 3244 | Nga01902 | 2519.75 | 2572.4197 | ---NA--- |
| SEQ ID NO: 3245 | Nga04826 | 947.2934 | 964.41768 | aldo keto reductase |
| SEQ ID NO: 3246 | Nga04499 | 557.5888 | 584.17675 | protein |
| SEQ ID NO: 3247 | Nga04229.01 | 1672.539 | 1881.5102 | ---NA--- |
| SEQ ID NO: 3248 | Nga02099 | 1486.425 | 971.11188 | delta 5 fatty acid desaturase |
| SEQ ID NO: 3249 | Nga02100 | 2967.782 | 2464.4579 | nucleoside diphosphate kinase |
| SEQ ID NO: 3250 | Nga02098 | 857.6779 | 832.71074 | hypothetical protein CHLNCDRAFT_49994 [Chlorella variabilis] |
| SEQ ID NO: 3251 | Nga07072 | 131.4554 | 147.48256 | protein |
| SEQ ID NO: 3252 | Nga04274 | 384.6154 | 351.81957 | ---NA--- |
| SEQ ID NO: 3253 | Nga04272 | 1712.885 | 1696.1562 | ---NA--- |
| SEQ ID NO: 3254 | Nga04271 | 310.6267 | 271.54638 | ---NA--- |
| SEQ ID NO: 3255 | Nga02394 | 740.9396 | 1022.1657 | ---NA--- |
| SEQ ID NO: 3256 | Nga06318.2 | 203.6082 | 234.51456 | adp-ribosylation factor gtpase-activating |
| SEQ ID NO: 3257 | Nga02601.02 | 1569.873 | 1348.6361 | protein |
| SEQ ID NO: 3258 | Nga02061.01 | 3210.618 | 3488.5947 | peptidase s1 and chymotrypsin hap |
| SEQ ID NO: 3259 | Nga01740 | 225.7218 | 222.71214 | molecular chaperone |
| SEQ ID NO: 3260 | Nga02013.02 | 121.3788 | 210.92674 | transducin -like 3 |
| SEQ ID NO: 3261 | Nga20982.1 | 177.2429 | 154.07047 | ---NA--- |
| SEQ ID NO: 3262 | Nga06627.2 | 80.9816 | 152.84896 | transducin-like 3 |
| SEQ ID NO: 3263 | Nga02359.01 | 579.3358 | 642.87869 | u2 small nuclear ribonucleoprotein a |
| SEQ ID NO: 3264 | Nga01155.02 | 3923.423 | 4163.9854 | s-adenosylmethionine mitochondrial carrier protein |
| SEQ ID NO: 3265 | Nga01156.02 | 309.6192 | 286.54685 | ---NA--- |
| SEQ ID NO: 3266 | Nga01151.02 | 2026.278 | 2082.6096 | ribosome biogenesis protein nsa2 homolog |
| SEQ ID NO: 3267 | Nga01149.02 | 371.1584 | 514.72818 | short chain dehydrogenase |
| SEQ ID NO: 3268 | Nga01985 | 2090.659 | 1990.8888 | atp-dependent metalloprotease |
| SEQ ID NO: 3269 | Nga01986 | 3546.392 | 4076.0865 | ---NA--- |
| SEQ ID NO: 3270 | Nga01987 | 291.3486 | 311.46421 | protein |
| SEQ ID NO: 3271 | Nga01983.01 | 1527.665 | 1594.8829 | conserved unknown protein [Ectocarpus siliculosus] |
| SEQ ID NO: 3272 | Nga02022.2 | 988.9503 | 906.68476 | ---NA--- |
| SEQ ID NO: 3273 | Nga04350 | 106.817 | 144.19861 | rna polymerase largest subunit |
| SEQ ID NO: 3274 | Nga04223.02 | 669.0939 | 1243.6157 | trna (guanine-n -)-methyltransferase-like |
| SEQ ID NO: 3275 | Nga04222.02 | 558.6457 | 647.05873 | protein |
| SEQ ID NO: 3276 | Nga04354 | 60.43614 | 60.067178 | rna polymerase largest subunit |
| SEQ ID NO: 3277 | Nga06979 | 241.8112 | 304.72477 | yor006c-like protein |
| SEQ ID NO: 3278 | Nga00389.02 | 155.303 | 164.12635 | eukaryotic translation initiation factor 2-alpha kinase 1 |
| SEQ ID NO: 3279 | Nga00368.02 | 282.2528 | 304.32702 | eukaryotic translation initiation factor 2-alpha kinase 1 |
| SEQ ID NO: 3280 | Nga07040 | 142.3565 | 176.50592 | dna repair protein rev1 |
| SEQ ID NO: 3281 | Nga03469.2 | 369.7825 | 427.30745 | fad-dependent pyridine nucleotide-disulphide oxidoreductase |
| SEQ ID NO: 3282 | Nga20233.1 | 404.2934 | 389.49915 | protein |
| SEQ ID NO: 3283 | Nga03468.2 | 2891.089 | 2994.981 | small nuclear ribonucleoprotein sm d1 |
| SEQ ID NO: 3284 | Nga01209 | 1266.129 | 1068.4923 | na+-dependent inorganic phosphate cotransporter |
| SEQ ID NO: 3285 | Nga01208 | 1284.963 | 1131.0739 | coatomer subunit epsilon |
| SEQ ID NO: 3286 | Nga01211 | 207.9439 | 120.21872 | protein |
| SEQ ID NO: 3287 | Nga01210 | 659.8425 | 672.11681 | protein |
| SEQ ID NO: 3288 | Nga07168 | 91.60305 | 115.76546 | ---NA--- |
| SEQ ID NO: 3289 | Nga06803 | 171.7246 | 206.86481 | ---NA--- |

FIGURE 24 AZ

| # | Nga model | +N rpkb | -N rpkb | GO |
|---|---|---|---|---|
| SEQ ID NO: 3290 | Nga01937 | 449.5356 | 539.94014 | ariadne-like ubiquitin ligase |
| SEQ ID NO: 3291 | Nga06813.1 | 1161.026 | 1004.3523 | protein |
| SEQ ID NO: 3292 | Nga20727 | 523.0179 | 422.48894 | nad-dependent epimerase dehydratase |
| SEQ ID NO: 3293 | Nga20248 | 1464.933 | 1592.8405 | ---NA--- |
| SEQ ID NO: 3294 | Nga03691 | 87.78626 | 66.151691 | ---NA--- |
| SEQ ID NO: 3295 | Nga07131 | 697.5309 | 815.76877 | ---NA--- |
| SEQ ID NO: 3296 | Nga21232 | 236.9403 | 309.2067 | protein |
| SEQ ID NO: 3297 | Nga21270 | 147.8261 | 197.80794 | phenazine biosynthesis protein family |
| SEQ ID NO: 3298 | Nga03131.2 | 4353.203 | 4000.4485 | protein |
| SEQ ID NO: 3299 | Nga07239.1 | 581.0306 | 773.39182 | splicing factor 3b |
| SEQ ID NO: 3300 | Nga20967 | 401.7372 | 416.35702 | myb dna binding protein transcription factor-like protein |
| SEQ ID NO: 3301 | Nga01158.02 | 874.8002 | 1073.4231 | dihydroorotate dehydrogenase |
| SEQ ID NO: 3302 | Nga01162.02 | 958.1056 | 808.97252 | ---NA--- |
| SEQ ID NO: 3303 | Nga01161.02 | 1189.836 | 1233.818 | protein |
| SEQ ID NO: 3304 | Nga02719.02 | 441.8052 | 429.69137 | ---NA--- |
| SEQ ID NO: 3305 | Nga02714.2 | 1736.949 | 1771.3629 | protein |
| SEQ ID NO: 3306 | Nga03317.2 | 646.7331 | 730.55312 | splicing factor subunit 49kda |
| SEQ ID NO: 3307 | Nga03322.02 | 2959.641 | 2797.9496 | ubiquitin-conjugating enzyme |
| SEQ ID NO: 3308 | Nga01883.01 | 88.70968 | 270.80849 | ---NA--- |
| SEQ ID NO: 3309 | Nga02364 | 209.5727 | 269.21381 | translation initiation factor if-2 |
| SEQ ID NO: 3310 | Nga02187 | 149.9579 | 167.91495 | conserved unknown protein [Ectocarpus siliculosus] |
| SEQ ID NO: 3311 | Nga02184 | 514.6667 | 626.83137 | ---NA--- |
| SEQ ID NO: 3312 | Nga00157.02 | 2288.21 | 2909.1217 | protein |
| SEQ ID NO: 3313 | Nga02186 | 114.3791 | 95.579465 | pci domain-containing protein 2 |
| SEQ ID NO: 3314 | Nga02192 | 357.6288 | 316.86435 | pci domain-containing protein 2 |
| SEQ ID NO: 3315 | Nga00774.02 | 7425.419 | 5973.5619 | light-harvesting protein |
| SEQ ID NO: 3316 | Nga04588 | 98.63211 | 139.59602 | ArfGAP [Ectocarpus siliculosus] |
| SEQ ID NO: 3317 | Nga04460 | 314.3483 | 274.07124 | lysine decarboxylase-like protein |
| SEQ ID NO: 3318 | Nga04459 | 623.3635 | 776.69946 | sedoheptulose- -bisphosphatase |
| SEQ ID NO: 3319 | Nga04458.01 | 20072.77 | 23208.969 | inorganic phosphate |
| SEQ ID NO: 3320 | Nga20288.1 | 379.5276 | 370.17601 | chaperone protein |
| SEQ ID NO: 3321 | Nga20445.1 | 348.9499 | 446.24338 | heat shock protein 40 like protein domain containing protein |
| SEQ ID NO: 3322 | Nga00677.2 | 184.0234 | 226.5232 | asparagine synthetase domain-containing protein 1-like |
| SEQ ID NO: 3323 | Nga06922 | 1067.395 | 892.50058 | arachidonate 5-lipoxygenase |
| SEQ ID NO: 3324 | Nga03592 | 16.94915 | 36.719795 | ---NA--- |
| SEQ ID NO: 3325 | Nga03591.01 | 688.0223 | 748.30646 | possible sulfotransferase |
| SEQ ID NO: 3326 | Nga06913 | 256.8149 | 307.71925 | ---NA--- |
| SEQ ID NO: 3327 | Nga02426.01 | 2195.592 | 2118.722 | ---NA--- |
| SEQ ID NO: 3328 | Nga20378.1 | 105.9432 | 156.74703 | conserved unknown protein [Ectocarpus siliculosus] |
| SEQ ID NO: 3329 | Nga04766.01 | 235.0908 | 237.8059 | 2-dehydropantoate 2-reductase |
| SEQ ID NO: 3330 | Nga04767.01 | 387.6488 | 415.88446 | ---NA--- |
| SEQ ID NO: 3331 | Nga04799 | 1072.936 | 964.97262 | protein |
| SEQ ID NO: 3332 | Nga03929.02 | 1365.455 | 1483.0457 | -dihydroxy-2-butanone 4-phosphate synthase |
| SEQ ID NO: 3333 | Nga07271 | 3179.048 | 5255.2321 | phosphate dikinase |
| SEQ ID NO: 3334 | Nga05037 | 1363.601 | 1487.6525 | otu-like cysteine protease family protein |
| SEQ ID NO: 3335 | Nga05038 | 2161.337 | 1494.1701 | uncharacterized protein |
| SEQ ID NO: 3336 | Nga03852.02 | 338.7755 | 446.55767 | ---NA--- |
| SEQ ID NO: 3337 | Nga04285 | 262.4878 | 262.05562 | amino acid-polyamine-organocation family |
| SEQ ID NO: 3338 | Nga04284 | 226.219 | 207.81466 | amino acid-polyamine-organocation family |
| SEQ ID NO: 3339 | Nga07159 | 78.57143 | 123.79816 | ---NA--- |
| SEQ ID NO: 3340 | Nga03699.2 | 613.3829 | 865.78177 | n-acetyltransferase esco2 |
| SEQ ID NO: 3341 | Nga03700.02 | 801.2232 | 1132.9236 | n-acetyltransferase esco2 |
| SEQ ID NO: 3342 | Nga02485.2 | 1718.162 | 1876.166 | sorbitol transporter |
| SEQ ID NO: 3343 | Nga02328.01 | 304.9645 | 320.61676 | signal recognition particle 72kda |
| SEQ ID NO: 3344 | Nga01479.02 | 3896.409 | 4264.1115 | translationally controlled tumor protein |
| SEQ ID NO: 3345 | Nga04914 | 473.6025 | 487.79168 | glycerol-3-phosphate mitochondrial precursor |
| SEQ ID NO: 3346 | Nga20634.1 | 81.15942 | 94.194256 | protein |
| SEQ ID NO: 3347 | Nga21107.1 | 325.6113 | 338.772 | histidine kinase |
| SEQ ID NO: 3348 | Nga05829.2 | 946.2366 | 938.39761 | myb-like dna-binding domain containing protein |
| SEQ ID NO: 3349 | Nga06976 | 66203.17 | 80596.044 | ---NA--- |
| SEQ ID NO: 3350 | Nga00103.02 | 2716.834 | 3062.5209 | protein |
| SEQ ID NO: 3351 | Nga00099.02 | 257.2877 | 207.31093 | protein |
| SEQ ID NO: 3352 | Nga04793 | 1349.398 | 1631.3764 | ---NA--- |
| SEQ ID NO: 3353 | Nga01305.2 | 2472.452 | 2697.7859 | adp atp carrier protein |

FIGURE 24 BA

| # | Nga model | +N rpkb | -N rpkb | GO |
|---|---|---|---|---|
| SEQ ID NO: 3354 | Nga01309.02 | 1077.348 | 825.89107 | protein |
| SEQ ID NO: 3355 | Nga01314.02 | 517.0604 | 329.80351 | conserved unknown protein [Ectocarpus siliculosus] |
| SEQ ID NO: 3356 | Nga00425.02 | 135.4738 | 105.18481 | ---NA--- |
| SEQ ID NO: 3357 | Nga00409.02 | 677.7188 | 774.35424 | protein |
| SEQ ID NO: 3358 | Nga00411.02 | 482.5374 | 523.47299 | werner syndrome atp-dependent helicase |
| SEQ ID NO: 3359 | Nga00412.02 | 1750 | 1613.6836 | hsp12 variant c |
| SEQ ID NO: 3360 | Nga00424.02 | 745.6395 | 614.0425 | ---NA--- |
| SEQ ID NO: 3361 | Nga03843 | 297.4359 | 203.31468 | expressed unknown protein [Ectocarpus siliculosus] |
| SEQ ID NO: 3362 | Nga03844.01 | 2072.273 | 1940.1417 | 10 kda heat shock mitochondrial |
| SEQ ID NO: 3363 | Nga04391.2 | 223.2754 | 293.1976 | protein |
| SEQ ID NO: 3364 | Nga01922 | 531.2661 | 503.26993 | atp-binding sub-family f member 1 |
| SEQ ID NO: 3365 | Nga01924 | 11714.29 | 10956.849 | phosphoribulokinase |
| SEQ ID NO: 3366 | Nga01921 | 376.8977 | 408.98338 | ---NA--- |
| SEQ ID NO: 3367 | Nga01923 | 775.9197 | 947.37684 | protein |
| SEQ ID NO: 3368 | Nga01925 | 68.37607 | 104.92864 | swr1 complex snf2 family dna-dependent atpase |
| SEQ ID NO: 3369 | Nga02321 | 681.1071 | 620.48057 | zinc and ring finger 4 |
| SEQ ID NO: 3370 | Nga02320.01 | 509.7907 | 517.11438 | duf1688 domain-containing protein |
| SEQ ID NO: 3371 | Nga04993.01 | 384.5455 | 226.49437 | tpr domain-containing protein |
| SEQ ID NO: 3372 | Nga05006 | 358.2888 | 366.09832 | protein ddi1 homolog 2 |
| SEQ ID NO: 3373 | Nga01865.1 | 128.6667 | 163.9294 | protein |
| SEQ ID NO: 3374 | Nga04258 | 122.6252 | 134.70267 | ---NA--- |
| SEQ ID NO: 3375 | Nga04255 | 113.4259 | 116.58313 | dna mismatch repair protein |
| SEQ ID NO: 3376 | Nga03309 | 221.3542 | 267.98756 | ---NA--- |
| SEQ ID NO: 3377 | Nga03304 | 1223.118 | 1278.3325 | s-adenosylmethionine synthetase |
| SEQ ID NO: 3378 | Nga03308 | 1223.118 | 1278.3325 | protease subunit of atp-dependent clp protease |
| SEQ ID NO: 3379 | Nga03307 | 1223.118 | 1278.3325 | atp-dependent protease atp-binding subunit |
| SEQ ID NO: 3380 | Nga03305 | 1223.118 | 1278.3325 | rna pseudouridylate synthase family protein |
| SEQ ID NO: 3381 | Nga03303 | 1223.118 | 1278.3325 | carbamoyl-phosphate small subunit |
| SEQ ID NO: 3382 | Nga03306 | 1223.118 | 1278.3325 | thymidylate synthase |
| SEQ ID NO: 3383 | Nga03310 | 221.3542 | 267.98756 | dihydrofolate reductase |
| SEQ ID NO: 3384 | Nga07312.1 | 1236.999 | 1185.7395 | conserved unknown protein [Ectocarpus siliculosus] |
| SEQ ID NO: 3385 | Nga07311 | 1276.129 | 1329.2329 | ---NA--- |
| SEQ ID NO: 3386 | Nga04551 | 2950.104 | 2844.3336 | unknown [Picea sitchensis] |
| SEQ ID NO: 3387 | Nga04552 | 296.5779 | 238.88809 | ---NA--- |
| SEQ ID NO: 3388 | Nga20677 | 7001.497 | 7504.8004 | macrophage migration inhibitory factor |
| SEQ ID NO: 3389 | Nga07064 | 693.7442 | 764.63572 | 30s ribosomal protein s18 |
| SEQ ID NO: 3390 | Nga01991 | 5806.005 | 6485.6443 | ---NA--- |
| SEQ ID NO: 3391 | Nga01992 | 543.1818 | 767.29071 | kua-ubiquitin conjugating enzyme hybrid localisation domain-containing protein |
| SEQ ID NO: 3392 | Nga01996 | 118.8341 | 110.91409 | ethanolamine kinase 1 isoform 1 |
| SEQ ID NO: 3393 | Nga04567 | 1794.793 | 1862.897 | stomatin prohibitin-family membrane protease subunit |
| SEQ ID NO: 3394 | Nga20316 | 537.7778 | 483.0421 | protein |
| SEQ ID NO: 3395 | Nga04566 | 260.0671 | 310.79363 | cytochrome p450 |
| SEQ ID NO: 3396 | Nga01972 | 202.1661 | 172.06604 | ---NA--- |
| SEQ ID NO: 3397 | Nga01976 | 68.37607 | 55.550459 | ---NA--- |
| SEQ ID NO: 3398 | Nga01971.01 | 447.2843 | 422.21898 | nucleolar basal body binding protein bn46 51 large subunit |
| SEQ ID NO: 3399 | Nga20776 | 313.8402 | 425.12885 | riboflavin transporter 2-like |
| SEQ ID NO: 3400 | Nga05741 | 487.9867 | 481.9359 | golgi reassembly stacking protein 2 |
| SEQ ID NO: 3401 | Nga05744 | 8398.503 | 8321.3444 | member ras oncogene family |
| SEQ ID NO: 3402 | Nga05745 | 804.8048 | 722.15596 | mitochondrial import inner membrane translocase subunit tim22 |
| SEQ ID NO: 3403 | Nga05740 | 555.7075 | 693.77321 | protein |
| SEQ ID NO: 3404 | Nga05743 | 691.358 | 675.34956 | ---NA--- |
| SEQ ID NO: 3405 | Nga20306 | 382.3976 | 269.57567 | dyslexia susceptibility 1 candidate 1 |
| SEQ ID NO: 3406 | Nga20190 | 530.1103 | 519.10702 | conserved oligomeric golgi complex subunit 5 |
| SEQ ID NO: 3407 | Nga20769 | 429.3139 | 419.4435 | expressed unknown protein [Ectocarpus siliculosus] |
| SEQ ID NO: 3408 | Nga05747 | 212.1372 | 262.94861 | ---NA--- |
| SEQ ID NO: 3409 | Nga05742 | 2707.911 | 3325.14 | serine threonine-protein kinase ctr1 |
| SEQ ID NO: 3410 | Nga05746 | 1422.93 | 1370.2564 | calciumdependent protein 4 |
| SEQ ID NO: 3411 | Nga20811 | 464.0199 | 587.3117 | ---NA--- |
| SEQ ID NO: 3412 | Nga05739 | 1214.47 | 1431.4363 | ribosomal biogenesis gtpase |
| SEQ ID NO: 3413 | Nga20231.1 | 190.9161 | 226.82035 | tbc1 domain family member 23-like |
| SEQ ID NO: 3414 | Nga04988.01 | 75.51385 | 103.09599 | translation elongation factor g |
| SEQ ID NO: 3415 | Nga04987 | 79.2393 | 104.71834 | conserved unknown protein [Ectocarpus siliculosus] |
| SEQ ID NO: 3416 | Nga00841.01 | 1149.094 | 1359.2105 | inorganic pyrophosphatase |

FIGURE 24 BB

| # | Nga model | +N rpkb | -N rpkb | GO |
|---|---|---|---|---|
| SEQ ID NO: 3417 | Nga00843 | 738.5965 | 613.83257 | 2og-fe oxygenase family family |
| SEQ ID NO: 3418 | Nga00842 | 88.3874 | 109.49473 | like protein |
| SEQ ID NO: 3419 | Nga00844.01 | 102.0408 | 51.582569 | ---NA--- |
| SEQ ID NO: 3420 | Nga06806 | 357.5677 | 509.0412 | loc496093 protein |
| SEQ ID NO: 3421 | Nga04390 | 3.100775 | 1.6794325 | peroxiredoxin |
| SEQ ID NO: 3422 | Nga20465.1 | 166.6667 | 150.99625 | ---NA--- |
| SEQ ID NO: 3423 | Nga04736.2 | 79.41653 | 108.85009 | ---NA--- |
| SEQ ID NO: 3424 | Nga01835 | 211.4014 | 234.1432 | ---NA--- |
| SEQ ID NO: 3425 | Nga04083.1 | 948.0088 | 1692.7527 | sec14p-like phosphatidylinositol transfer family protein |
| SEQ ID NO: 3426 | Nga04086.1 | 245.9517 | 278.99976 | sh2 domain containing protein |
| SEQ ID NO: 3427 | Nga04085 | 279.3427 | 244.10906 | ---NA--- |
| SEQ ID NO: 3428 | Nga04087 | 247.2527 | 329.33486 | protein |
| SEQ ID NO: 3429 | Nga04084.1 | 1391.663 | 1262.367 | pyridoxal kinase |
| SEQ ID NO: 3430 | Nga20766.1 | 244.6853 | 316.07493 | ubiquitin ligase e3 |
| SEQ ID NO: 3431 | Nga20105.1 | 431.4346 | 543.90227 | protein |
| SEQ ID NO: 3432 | Nga01079 | 895.3049 | 827.77078 | rossmann-fold nad -binding domain-containing protein |
| SEQ ID NO: 3433 | Nga20022 | 581.9328 | 516.58425 | 3-hydroxybutyrate dehydrogenase |
| SEQ ID NO: 3434 | Nga01078 | 20.23988 | 25.172603 | kinesin family member 19 |
| SEQ ID NO: 3435 | Nga01077 | 269.2046 | 331.3768 | protein |
| SEQ ID NO: 3436 | Nga01076 | 3688.772 | 3663.2311 | elegans protein confirmed by transcript evidence |
| SEQ ID NO: 3437 | Nga04509 | 103.6585 | 92.47119 | ---NA--- |
| SEQ ID NO: 3438 | Nga04508 | 84.82143 | 48.358658 | ---NA--- |
| SEQ ID NO: 3439 | Nga01591.01 | 93.19899 | 98.227763 | vacuolar membrane protein |
| SEQ ID NO: 3440 | Nga20940 | 702.5365 | 830.11855 | n-acetylglucosaminyltransferase-like protein |
| SEQ ID NO: 3441 | Nga21188 | 552.8846 | 762.08285 | ---NA--- |
| SEQ ID NO: 3442 | Nga01592 | 32.95311 | 37.068842 | sumo-activating enzyme subunit 1 |
| SEQ ID NO: 3443 | Nga01590 | 322.695 | 520.49007 | squalene monooxygenase |
| SEQ ID NO: 3444 | Nga01870 | 192.3688 | 115.38422 | phosphoglycerate mutase |
| SEQ ID NO: 3445 | Nga01868 | 638.914 | 353.8891 | ---NA--- |
| SEQ ID NO: 3446 | Nga01869 | 328 | 407.29596 | glycerol-3-phosphate dehydrogenase |
| SEQ ID NO: 3447 | Nga04536.01 | 8371.486 | 3099.6152 | light-harvesting protein |
| SEQ ID NO: 3448 | Nga04535 | 744.136 | 748.48162 | acyltransferase 3 |
| SEQ ID NO: 3449 | Nga04764 | 636.1502 | 771.74061 | nitroreductase-like protein |
| SEQ ID NO: 3450 | Nga04664 | 814.5161 | 1003.1562 | protein |
| SEQ ID NO: 3451 | Nga01916.02 | 4258.001 | 4114.7956 | dynamin-like protein |
| SEQ ID NO: 3452 | Nga20936.1 | 4845.533 | 5109.6176 | dynamin-like protein |
| SEQ ID NO: 3453 | Nga01918.02 | 520.4678 | 576.45783 | protein |
| SEQ ID NO: 3454 | Nga04665.1 | 487.3418 | 523.33454 | dna-directed rna polymerase i and iii subunit |
| SEQ ID NO: 3455 | Nga20230 | 227.0742 | 304.31463 | ---NA--- |
| SEQ ID NO: 3456 | Nga03457.2 | 132.216 | 183.56478 | protein |
| SEQ ID NO: 3457 | Nga01617 | 1908.297 | 1609.8717 | clathrin assembly protein ap19 |
| SEQ ID NO: 3458 | Nga04170 | 695.6886 | 835.2101 | protein |
| SEQ ID NO: 3459 | Nga07176 | 139.726 | 166.1948 | ---NA--- |
| SEQ ID NO: 3460 | Nga01576 | 683.8235 | 618.61154 | gnat family |
| SEQ ID NO: 3461 | Nga01575.01 | 767.9924 | 915.00443 | tumor protein p53 inducible protein 3 |
| SEQ ID NO: 3462 | Nga01577.01 | 349.4624 | 423.68424 | ---NA--- |
| SEQ ID NO: 3463 | Nga01574.01 | 1614.892 | 1529.24 | kazal-type serine protease inhibitor domain |
| SEQ ID NO: 3464 | Nga01578.01 | 240.8027 | 119.55425 | auxin efflux carrier-like protein |
| SEQ ID NO: 3465 | Nga04278 | 158.3333 | 192.57492 | coproporphyrinogen oxidase |
| SEQ ID NO: 3466 | Nga04275 | 1023.415 | 815.8601 | lipolytic protein g-d-s-l family |
| SEQ ID NO: 3467 | Nga04277 | 113.6364 | 218.83514 | ---NA--- |
| SEQ ID NO: 3468 | Nga04276 | 531.5006 | 475.23322 | expressed unknown protein [Ectocarpus siliculosus] |
| SEQ ID NO: 3469 | Nga04927 | 762.3457 | 746.39499 | protein |
| SEQ ID NO: 3470 | Nga00293.02 | 1144.668 | 1073.5406 | hypoxia-inducible factor alpha subunit |
| SEQ ID NO: 3471 | Nga03786.02 | 991.1003 | 1203.3011 | pas pac sensor hybrid histidine kinase |
| SEQ ID NO: 3472 | Nga04253 | 334.7488 | 411.67489 | chromosome 20 open reading frame 4 |
| SEQ ID NO: 3473 | Nga04251 | 840.3263 | 994.22696 | serine threonine-protein phosphatase 5 |
| SEQ ID NO: 3474 | Nga04478 | 300.3072 | 379.38147 | hypothetical protein NAEGRDRAFT_78553 [Naegleria gruberi] |
| SEQ ID NO: 3475 | Nga05004 | 4582.453 | 4206.2212 | ---NA--- |
| SEQ ID NO: 3476 | Nga05003 | 2337.49 | 2567.7786 | protein |
| SEQ ID NO: 3477 | Nga00161.02 | 760.492 | 1253.322 | had-superfamily subfamily iia hydrolase |
| SEQ ID NO: 3478 | Nga07032 | 289.0947 | 325.97318 | ---NA--- |
| SEQ ID NO: 3479 | Nga04871 | 1281.218 | 1246.4457 | alcohol dehydrogenase zinc-binding domain protein |
| SEQ ID NO: 3480 | Nga04869 | 111.9792 | 93.090417 | ---NA--- |

FIGURE 24 BC

| # | Nga model | +N rpkb | -N rpkb | GO |
|---|---|---|---|---|
| SEQ ID NO: 3481 | Nga04870 | 3139.659 | 3368.6497 | 60s ribosomal protein l26 |
| SEQ ID NO: 3482 | Nga02126 | 105.8394 | 115.52738 | dna replication licensing factor mcm8 |
| SEQ ID NO: 3483 | Nga21077 | 78.21229 | 60.515863 | ---NA--- |
| SEQ ID NO: 3484 | Nga01897.01 | 683.237 | 641.17431 | yip1 domain-containing protein |
| SEQ ID NO: 3485 | Nga06537.02 | 6065.217 | 6723.115 | ribosomal protein l22 |
| SEQ ID NO: 3486 | Nga07303 | 190.4762 | 213.69921 | ---NA--- |
| SEQ ID NO: 3487 | Nga07212 | 160.5996 | 132.21485 | ---NA--- |
| SEQ ID NO: 3488 | Nga04283.2 | 960.6513 | 930.37596 | peptidyl-prolyl cis-trans fkbp-type |
| SEQ ID NO: 3489 | Nga03731 | 554.5809 | 550.06324 | protein |
| SEQ ID NO: 3490 | Nga02818.2 | 566.3377 | 582.59457 | threonine synthase |
| SEQ ID NO: 3491 | Nga07067 | 285.3437 | 236.03541 | tripeptidyl peptidase i |
| SEQ ID NO: 3492 | Nga04515.1 | 179.1725 | 196.74445 | ---NA--- |
| SEQ ID NO: 3493 | Nga04514 | 652.8146 | 594.77301 | uracil-dna glycosylase |
| SEQ ID NO: 3494 | Nga04516 | 373.9837 | 362.83934 | ---NA--- |
| SEQ ID NO: 3495 | Nga20658 | 84.375 | 145.55956 | ---NA--- |
| SEQ ID NO: 3496 | Nga20455 | 96.21993 | 145.17568 | ---NA--- |
| SEQ ID NO: 3497 | Nga06668 | 1501.706 | 1565.6982 | (aldo keto reductase ) |
| SEQ ID NO: 3498 | Nga06672 | 55.01618 | 49.07856 | ---NA--- |
| SEQ ID NO: 3499 | Nga20453.1 | 37.63441 | 34.94303 | wd repeat domain 19 |
| SEQ ID NO: 3500 | Nga20409.1 | 85.06224 | 53.93696 | elegans protein confirmed by transcript evidence |
| SEQ ID NO: 3501 | Nga06671 | 187.0748 | 156.58994 | gdp-mannose transporter |
| SEQ ID NO: 3502 | Nga06673 | 606.7616 | 333.45102 | ---NA--- |
| SEQ ID NO: 3503 | Nga03822.02 | 8692.898 | 8393.5037 | gtp-binding nuclear protein ran |
| SEQ ID NO: 3504 | Nga06670.1 | 496.124 | 501.27408 | mitochondrial phosphate carrier 1 |
| SEQ ID NO: 3505 | Nga04936 | 417.4265 | 396.19803 | conserved unknown protein [Ectocarpus siliculosus] |
| SEQ ID NO: 3506 | Nga04937 | 267.2414 | 339.91134 | ---NA--- |
| SEQ ID NO: 3507 | Nga04906 | 134.0206 | 174.95531 | ---NA--- |
| SEQ ID NO: 3508 | Nga07129 | 1189.989 | 1041.3341 | cyanate hydratase |
| SEQ ID NO: 3509 | Nga04264 | 331.4763 | 274.58019 | peroxisomal membrane protein pmp47b |
| SEQ ID NO: 3510 | Nga04265.1 | 125.0936 | 116.84321 | isoform b |
| SEQ ID NO: 3511 | Nga01687 | 1350.056 | 1463.6338 | fgd6 protein |
| SEQ ID NO: 3512 | Nga01686 | 211.6 | 204.08127 | transposon en spm sub- expressed |
| SEQ ID NO: 3513 | Nga04127.02 | 203.4483 | 291.35258 | growth arrest-specific 7 |
| SEQ ID NO: 3514 | Nga04126.02 | 3030.083 | 2953.0485 | ---NA--- |
| SEQ ID NO: 3515 | Nga02105 | 1335.992 | 1101.5938 | protein |
| SEQ ID NO: 3516 | Nga02106 | 1777.108 | 1977.2282 | ---NA--- |
| SEQ ID NO: 3517 | Nga06855 | 5806.202 | 6511.9994 | ribosomal protein l37a |
| SEQ ID NO: 3518 | Nga01733 | 1046.306 | 949.71992 | flavodoxin |
| SEQ ID NO: 3519 | Nga00787 | 683.0295 | 618.33971 | ---NA--- |
| SEQ ID NO: 3520 | Nga00786 | 171.4719 | 208.75677 | ---NA--- |
| SEQ ID NO: 3521 | Nga00785 | 11.36364 | 12.309477 | ---NA--- |
| SEQ ID NO: 3522 | Nga01410 | 179.7235 | 159.73957 | ---NA--- |
| SEQ ID NO: 3523 | Nga06989.2 | 71.9697 | 53.341065 | dna replication licensing factor mcm5 |
| SEQ ID NO: 3524 | Nga20757 | 78.94737 | 66.514365 | phytoene dehydrogenase |
| SEQ ID NO: 3525 | Nga01409 | 587.3306 | 740.53379 | dna replication licensing factor mcm5 |
| SEQ ID NO: 3526 | Nga06849 | 474.918 | 802.39551 | carbon catabolite repressor protein 4-like 4 |
| SEQ ID NO: 3527 | Nga06848 | 548.2124 | 529.29416 | ---NA--- |
| SEQ ID NO: 3528 | Nga03379.02 | 1003.876 | 948.87934 | conserved hypothetical protein [Phytophthora infestans T30-4] |
| SEQ ID NO: 3529 | Nga06792 | 2909.871 | 2800.2915 | small nuclear ribonucleoprotein sm d3 |
| SEQ ID NO: 3530 | Nga06951 | 65.57377 | 104.5745 | ---NA--- |
| SEQ ID NO: 3531 | Nga06950 | 258.1699 | 350.45804 | aldehyde oxidase |
| SEQ ID NO: 3532 | Nga03771 | 69.44444 | 77.373853 | abc transporter family protein |
| SEQ ID NO: 3533 | Nga03769 | 1673.188 | 2114.1137 | ---NA--- |
| SEQ ID NO: 3534 | Nga04548 | 149.0683 | 198.85454 | snare associated golgi protein |
| SEQ ID NO: 3535 | Nga07175 | 125.9968 | 129.57344 | ---NA--- |
| SEQ ID NO: 3536 | Nga07174 | 182.2289 | 316.48702 | p-type had subfamily ic |
| SEQ ID NO: 3537 | Nga04014 | 201.1785 | 243.45409 | conserved hypothetical protein [Phytophthora infestans T30-4] |
| SEQ ID NO: 3538 | Nga04015 | 225 | 291.87137 | ---NA--- |
| SEQ ID NO: 3539 | Nga04017 | 289.4376 | 265.97925 | ---NA--- |
| SEQ ID NO: 3540 | Nga02339 | 286.6817 | 486.59945 | n-terminal domain-containing protein |
| SEQ ID NO: 3541 | Nga02343 | 146.4646 | 196.95163 | ---NA--- |
| SEQ ID NO: 3542 | Nga02341 | 243.5897 | 254.60627 | ---NA--- |
| SEQ ID NO: 3543 | Nga02340 | 464.4128 | 380.99509 | carboxyl-terminal processing protease |
| SEQ ID NO: 3544 | Nga02338 | 451.9812 | 544.16319 | zinc finger ccch domain-containing protein 63 |

FIGURE 24 BD

| # | Nga model | +N rpkb | -N rpkb | GO |
|---|---|---|---|---|
| SEQ ID NO: 3545 | Nga04345.01 | 633.4215 | 637.85789 | amine oxidase |
| SEQ ID NO: 3546 | Nga20713 | 560.3448 | 513.6023 | ---NA--- |
| SEQ ID NO: 3547 | Nga04099 | 494.5848 | 568.33935 | conserved hypothetical protein [Albugo laibachii Nc14] |
| SEQ ID NO: 3548 | Nga01771.02 | 653.7196 | 566.93284 | protein |
| SEQ ID NO: 3549 | Nga04098.1 | 440.7895 | 793.71829 | phosphoribosylformylglycinamidine cyclo-ligase |
| SEQ ID NO: 3550 | Nga04432 | 125.2556 | 143.98815 | ---NA--- |
| SEQ ID NO: 3551 | Nga04433 | 69.95231 | 111.93991 | heat repeat containing 1 |
| SEQ ID NO: 3552 | Nga04431.1 | 381.5514 | 374.70356 | upf0598 protein c8orf82-like |
| SEQ ID NO: 3553 | Nga04765 | 49.75124 | 72.754518 | ---NA--- |
| SEQ ID NO: 3554 | Nga01549.2 | 559.9022 | 716.85897 | protein |
| SEQ ID NO: 3555 | Nga03984 | 235.6747 | 194.22124 | galactosyl transferase gma12 mnn10 family protein |
| SEQ ID NO: 3556 | Nga03982 | 298.9418 | 424.12334 | hypothetical protein Esi_0162_0021 [Ectocarpus siliculosus] |
| SEQ ID NO: 3557 | Nga03981 | 830.8622 | 854.21413 | monooxygenase fad-binding |
| SEQ ID NO: 3558 | Nga20219 | 120.4453 | 123.89214 | periplasmic protease |
| SEQ ID NO: 3559 | Nga03983 | 1810.987 | 1696.4613 | cell differentiation protein |
| SEQ ID NO: 3560 | Nga04770 | 225.976 | 181.35223 | ---NA--- |
| SEQ ID NO: 3561 | Nga03711 | 180.8279 | 162.83909 | ---NA--- |
| SEQ ID NO: 3562 | Nga20959 | 174.9681 | 175.69695 | intraflagellar transport 140 homolog |
| SEQ ID NO: 3563 | Nga04023 | 676.6382 | 924.29791 | protein |
| SEQ ID NO: 3564 | Nga04024 | 964.8241 | 1172.1426 | ---NA--- |
| SEQ ID NO: 3565 | Nga04022 | 1061.728 | 1346.8782 | ---NA--- |
| SEQ ID NO: 3566 | Nga06820 | 795.8697 | 850.92801 | 3-ketoacyl- thiolase peroxisomal |
| SEQ ID NO: 3567 | Nga04747 | 30.30303 | 32.825271 | ---NA--- |
| SEQ ID NO: 3568 | Nga04750 | 44.55446 | 66.138046 | sulfate transporter |
| SEQ ID NO: 3569 | Nga04748 | 1053.208 | 882.86109 | ---NA--- |
| SEQ ID NO: 3570 | Nga01721 | 258.3587 | 216.20779 | dc12 family protein |
| SEQ ID NO: 3571 | Nga01723 | 387.4346 | 249.5408 | ---NA--- |
| SEQ ID NO: 3572 | Nga01722 | 228.4153 | 317.27508 | hypothetical protein CHLNCDRAFT_135021 [Chlorella variabilis] |
| SEQ ID NO: 3573 | Nga04616 | 2117.958 | 2147.3969 | ---NA--- |
| SEQ ID NO: 3574 | Nga04585 | 641.2078 | 636.8569 | ankyrin unc44 |
| SEQ ID NO: 3575 | Nga06885 | 341.4376 | 301.15278 | ribosome recycling factor |
| SEQ ID NO: 3576 | Nga06886 | 306.7649 | 322.14057 | hypothetical protein HMPREF9446_02801 [Bacteroides fluxus YIT 12057] |
| SEQ ID NO: 3577 | Nga01184 | 191.7808 | 247.31369 | histone demethylase jarid1a |
| SEQ ID NO: 3578 | Nga01186 | 2016.822 | 2289.9768 | ---NA--- |
| SEQ ID NO: 3579 | Nga01187 | 225.1082 | 299.03461 | rna helicase |
| SEQ ID NO: 3580 | Nga01190 | 228.9562 | 317.31095 | atp-dependent chaperone protein |
| SEQ ID NO: 3581 | Nga20704 | 90.90909 | 203.51668 | ---NA--- |
| SEQ ID NO: 3582 | Nga01029.2 | 376.3713 | 480.82789 | pilus assembly protein |
| SEQ ID NO: 3583 | Nga04789 | 721.4171 | 769.25309 | 30s ribosomal protein s16 |
| SEQ ID NO: 3584 | Nga06790 | 167.5774 | 163.76761 | cleavage and polyadenylation specificity factor subunit 3 |
| SEQ ID NO: 3585 | Nga06791 | 692.6606 | 875.15861 | fmu domain-containing protein |
| SEQ ID NO: 3586 | Nga04410 | 3388.502 | 3763.0113 | 60s ribosomal protein |
| SEQ ID NO: 3587 | Nga04412 | 567.9012 | 677.57843 | ---NA--- |
| SEQ ID NO: 3588 | Nga04411 | 824.7214 | 812.15108 | mitochondrial carrier domain-containing protein |
| SEQ ID NO: 3589 | Nga01715 | 289.8551 | 185.02443 | phosphatidylinositol synthase |
| SEQ ID NO: 3590 | Nga05466 | 1365.177 | 1538.8932 | dj-1 family protein |
| SEQ ID NO: 3591 | Nga05478 | 175.5725 | 214.993 | ---NA--- |
| SEQ ID NO: 3592 | Nga05464 | 726.3844 | 838.00671 | farnesyl-protein transferase alpha-subunit |
| SEQ ID NO: 3593 | Nga05467 | 345.9916 | 326.79843 | 9-cis-epoxycarotenoid dioxygenase |
| SEQ ID NO: 3594 | Nga05465 | 635.7724 | 494.94104 | acyl- :lysophosphatidylglycerol acyltransferase 1 |
| SEQ ID NO: 3595 | Nga02421.01 | 1065.574 | 1197.3921 | phosphoglycerate kinase |
| SEQ ID NO: 3596 | Nga06599.2 | 176.8293 | 249.95032 | chromosome region maintenance protein 5 exportin |
| SEQ ID NO: 3597 | Nga02422 | 164.4144 | 224.45388 | ---NA--- |
| SEQ ID NO: 3598 | Nga04699 | 306.2693 | 381.85945 | ---NA--- |
| SEQ ID NO: 3599 | Nga04700 | 335.5978 | 431.23308 | trna splicing endonuclease 34 homolog |
| SEQ ID NO: 3600 | Nga04463.1 | 12506.97 | 12153.356 | 60s ribosomal protein l36 |
| SEQ ID NO: 3601 | Nga03751.02 | 6433.283 | 6577.3575 | 60s ribosomal protein l34 |
| SEQ ID NO: 3602 | Nga02087.01 | 1572.414 | 1402.3344 | conserved unknown protein [Ectocarpus siliculosus] |
| SEQ ID NO: 3603 | Nga03622 | 2187.368 | 2100.3336 | ---NA--- |
| SEQ ID NO: 3604 | Nga06161.2 | 196.2216 | 248.36708 | pescadillo-like protein |
| SEQ ID NO: 3605 | Nga02808.02 | 152.0681 | 125.19127 | cysteine synthase |
| SEQ ID NO: 3606 | Nga02803.02 | 1532.258 | 2007.8153 | x-pro dipeptidyl-peptidase domain-containing protein |
| SEQ ID NO: 3607 | Nga07109 | 97.28507 | 144.59458 | pathogenesis-related transcriptional factor and erf |
| SEQ ID NO: 3608 | Nga06272.2 | 183.6115 | 300.39606 | ---NA--- |

FIGURE 24 BE

| # | Nga model | +N rpkb | -N rpkb | GO |
|---|---|---|---|---|
| SEQ ID NO: 3609 | Nga07110.1 | 99.28571 | 177.95986 | bromodomain-containing protein |
| SEQ ID NO: 3610 | Nga04451.1 | 984.6697 | 1532.1933 | deah (asp-glu-ala-his) box polypeptide 36 |
| SEQ ID NO: 3611 | Nga01641 | 137.2549 | 164.60908 | purple acid |
| SEQ ID NO: 3612 | Nga01639 | 1829.268 | 2223.712 | thioredoxin-like protein 4a |
| SEQ ID NO: 3613 | Nga20688 | 154.4715 | 158.52204 | calcineurin-like phosphoesterase domain-containing protein 1-like |
| SEQ ID NO: 3614 | Nga01640 | 145.5939 | 128.65997 | protein |
| SEQ ID NO: 3615 | Nga01272.02 | 459.9904 | 547.58592 | trehalose-6-phosphate synthase |
| SEQ ID NO: 3616 | Nga05096.2 | 346.4912 | 404.62905 | retinoblastoma binding protein 4 |
| SEQ ID NO: 3617 | Nga01988 | 260.3406 | 303.09466 | ---NA--- |
| SEQ ID NO: 3618 | Nga01989 | 2468.966 | 2614.7026 | ---NA--- |
| SEQ ID NO: 3619 | Nga03556 | 8799.642 | 8762.7619 | ---NA--- |
| SEQ ID NO: 3620 | Nga21202 | 351.1604 | 395.69191 | abc subfamily abcg |
| SEQ ID NO: 3621 | Nga20196 | 403.0227 | 399.05029 | white |
| SEQ ID NO: 3622 | Nga03559 | 1389.234 | 1308.6273 | ---NA--- |
| SEQ ID NO: 3623 | Nga03558 | 1039.095 | 1515.636 | dna polymerase i |
| SEQ ID NO: 3624 | Nga21182 | 73.52941 | 87.61451 | tpr repeat-containing protein |
| SEQ ID NO: 3625 | Nga20302 | 95.2381 | 99.941227 | hypothetical protein AURANDRAFT_39295 [Aureococcus anophagefferens] |
| SEQ ID NO: 3626 | Nga21256 | 68.96552 | 67.23521 | conserved unknown protein [Ectocarpus siliculosus] |
| SEQ ID NO: 3627 | Nga20904 | 97.56098 | 215.13705 | tetratricopeptide repeat family protein |
| SEQ ID NO: 3628 | Nga21301 | 103.2258 | 153.74933 | ---NA--- |
| SEQ ID NO: 3629 | Nga03557 | 672.0779 | 852.28471 | bruno-like protein |
| SEQ ID NO: 3630 | Nga06985.1 | 125.9058 | 156.00924 | dead deah box helicase |
| SEQ ID NO: 3631 | Nga04715 | 1070.451 | 1197.3366 | ---NA--- |
| SEQ ID NO: 3632 | Nga04717 | 324.3243 | 310.65718 | and domain-containing protein |
| SEQ ID NO: 3633 | Nga04718 | 806.3241 | 453.84505 | ---NA--- |
| SEQ ID NO: 3634 | Nga04716 | 526.7118 | 669.17612 | loc495015 protein |
| SEQ ID NO: 3635 | Nga00015.02 | 3272.989 | 2182.0316 | ferredoxin |
| SEQ ID NO: 3636 | Nga20915 | 33.78378 | 117.10637 | ---NA--- |
| SEQ ID NO: 3637 | Nga01719 | 963.964 | 814.86517 | ---NA--- |
| SEQ ID NO: 3638 | Nga01720 | 174.8634 | 278.20762 | ---NA--- |
| SEQ ID NO: 3639 | Nga06889 | 30.81232 | 69.788181 | ---NA--- |
| SEQ ID NO: 3640 | Nga04518 | 482.3151 | 609.53678 | vacuolar protein sorting-associated protein 29 |
| SEQ ID NO: 3641 | Nga04520 | 65.42056 | 70.865772 | protein |
| SEQ ID NO: 3642 | Nga02651.02 | 1413.223 | 1125.0116 | 2c-methyl-d-erythritol -cyclodiphosphate synthase |
| SEQ ID NO: 3643 | Nga04522 | 57.97101 | 73.262199 | ---NA--- |
| SEQ ID NO: 3644 | Nga01343.01 | 695.6522 | 897.88395 | ---NA--- |
| SEQ ID NO: 3645 | Nga01344 | 833.1893 | 912.83759 | carboxyl-terminal protease |
| SEQ ID NO: 3646 | Nga05025 | 2699.13 | 2812.6405 | copper chaperone |
| SEQ ID NO: 3647 | Nga01308.2 | 383.8764 | 369.2226 | methionyl-trna synthetase |
| SEQ ID NO: 3648 | Nga04503 | 915.2047 | 1067.3972 | protein |
| SEQ ID NO: 3649 | Nga20880 | 248.7437 | 348.37674 | ---NA--- |
| SEQ ID NO: 3650 | Nga03670 | 11666.67 | 13470.616 | ---NA--- |
| SEQ ID NO: 3651 | Nga03669 | 572.2071 | 649.35005 | uv-damaged dna-binding |
| SEQ ID NO: 3652 | Nga02262 | 2375.631 | 2214.3381 | riboflavin kinase |
| SEQ ID NO: 3653 | Nga04371 | 22211.21 | 17915.683 | protein |
| SEQ ID NO: 3654 | Nga04372 | 314.4208 | 261.20535 | phosphoribosylformimino-5-aminoimidazole carboxamide ribotide isomerase |
| SEQ ID NO: 3655 | Nga04373 | 918.5004 | 808.67342 | protein |
| SEQ ID NO: 3656 | Nga04012.01 | 785.3695 | 857.9792 | t-complex protein 1 subunit alpha |
| SEQ ID NO: 3657 | Nga03868 | 5450.746 | 4067.786 | predicted protein [Thalassiosira pseudonana CCMP1335] |
| SEQ ID NO: 3658 | Nga03867 | 4748.598 | 4730.7965 | ---NA--- |
| SEQ ID NO: 3659 | Nga03869 | 99.35897 | 135.40424 | nicotinamide n-methyltransferase |
| SEQ ID NO: 3660 | Nga01643 | 275 | 352.05103 | ---NA--- |
| SEQ ID NO: 3661 | Nga01644 | 275 | 352.05103 | ---NA--- |
| SEQ ID NO: 3662 | Nga20626 | 304.2071 | 371.59481 | ribosomal rna large subunit methyltransferase n |
| SEQ ID NO: 3663 | Nga07015 | 274.5098 | 491.17225 | from coli sequence gb |
| SEQ ID NO: 3664 | Nga20526 | 117.6471 | 164.92143 | ---NA--- |
| SEQ ID NO: 3665 | Nga02263.01 | 11320.72 | 10950.608 | fructose-bisphosphate aldolase |
| SEQ ID NO: 3666 | Nga02264.01 | 153.2385 | 168.5601 | cyclopropane-fatty-acyl-phospholipid synthase |
| SEQ ID NO: 3667 | Nga02265 | 225.1244 | 245.20967 | lysocardiolipin and lysophospholipid acyltransferase |
| SEQ ID NO: 3668 | Nga20791 | 198.9967 | 271.7142 | amp-dependent synthetase and ligase |
| SEQ ID NO: 3669 | Nga04476 | 571.6599 | 497.32279 | ---NA--- |
| SEQ ID NO: 3670 | Nga04781 | 506.3841 | 568.8376 | transcription elongation factor spt6 |

FIGURE 24 BF

| # | Nga model | +N rpkb | -N rpkb | GO |
|---|---|---|---|---|
| SEQ ID NO: 3671 | Nga07149 | 391.1765 | 328.15616 | ---NA--- |
| SEQ ID NO: 3672 | Nga06235.02 | 963.3508 | 921.59956 | signal peptidase |
| SEQ ID NO: 3673 | Nga06999 | 127.3408 | 159.57753 | ---NA--- |
| SEQ ID NO: 3674 | Nga00443.2 | 195.2645 | 257.81767 | serine threonine protein |
| SEQ ID NO: 3675 | Nga04305 | 231.405 | 190.98339 | pseudouridine synthase |
| SEQ ID NO: 3676 | Nga04307 | 131.2336 | 180.53899 | ---NA--- |
| SEQ ID NO: 3677 | Nga01743 | 1891.407 | 1745.0398 | ---NA--- |
| SEQ ID NO: 3678 | Nga06826 | 116.0221 | 89.770769 | ---NA--- |
| SEQ ID NO: 3679 | Nga21196.1 | 181.1927 | 168.94474 | yth domain containing 2 |
| SEQ ID NO: 3680 | Nga01453.1 | 470.6239 | 390.38413 | dnaj domain |
| SEQ ID NO: 3681 | Nga01455.01 | 100.6711 | 87.240317 | ---NA--- |
| SEQ ID NO: 3682 | Nga01456.01 | 131.9444 | 90.269495 | ---NA--- |
| SEQ ID NO: 3683 | Nga01450.01 | 127.0627 | 184.11402 | ---NA--- |
| SEQ ID NO: 3684 | Nga01454.1 | 106.3566 | 85.986942 | phosphopantothenate--cysteine ligase |
| SEQ ID NO: 3685 | Nga01448.01 | 1506.52 | 2076.0676 | phosphoserine aminotransferase |
| SEQ ID NO: 3686 | Nga01452.01 | 175.9259 | 164.12635 | snf2 family dna-dependent atpase |
| SEQ ID NO: 3687 | Nga01451.01 | 769.6314 | 823.70914 | protein |
| SEQ ID NO: 3688 | Nga20182 | 233.0559 | 264.04632 | major intrinsic protein |
| SEQ ID NO: 3689 | Nga04330 | 1133.706 | 1708.8332 | ---NA--- |
| SEQ ID NO: 3690 | Nga04332 | 683.4925 | 1114.2679 | ---NA--- |
| SEQ ID NO: 3691 | Nga04331 | 267.4897 | 213.97214 | signal recognition particle 14kda (homologous alu rna binding protein) |
| SEQ ID NO: 3692 | Nga04784 | 602.108 | 558.02961 | protein |
| SEQ ID NO: 3693 | Nga04990 | 183.0065 | 173.45903 | histone arginine |
| SEQ ID NO: 3694 | Nga00731 | 309.2269 | 270.13315 | ---NA--- |
| SEQ ID NO: 3695 | Nga00732 | 5.733006 | 10.646034 | ---NA--- |
| SEQ ID NO: 3696 | Nga00733 | 3797.364 | 4109.8645 | ---NA--- |
| SEQ ID NO: 3697 | Nga00734 | 338.5417 | 372.36167 | surfeit locus 1 |
| SEQ ID NO: 3698 | Nga04110 | 170 | 191.37133 | ---NA--- |
| SEQ ID NO: 3699 | Nga04109 | 1478.605 | 1471.2068 | cysteine-rich pdz-binding protein |
| SEQ ID NO: 3700 | Nga20566 | 162.6374 | 180.93578 | ---NA--- |
| SEQ ID NO: 3701 | Nga20679 | 310 | 308.72167 | ataxin 3 variant ref |
| SEQ ID NO: 3702 | Nga03832 | 427.5742 | 321.37831 | sulfotransferase |
| SEQ ID NO: 3703 | Nga07304 | 213.5417 | 239.77835 | acetyl-coenzyme a transporter 1 |
| SEQ ID NO: 3704 | Nga06607 | 818.9781 | 708.45081 | hepatocyte growth factor-regulated tyrosine kinase substrate |
| SEQ ID NO: 3705 | Nga06606 | 417.2235 | 482.50955 | ---NA--- |
| SEQ ID NO: 3706 | Nga21264 | 459.8436 | 478.87101 | sec24-like transport protein |
| SEQ ID NO: 3707 | Nga03528 | 120.2186 | 100.62829 | ---NA--- |
| SEQ ID NO: 3708 | Nga20899 | 212.1212 | 339.19447 | elmo domain-containing protein 2 |
| SEQ ID NO: 3709 | Nga06881 | 448.6934 | 515.72706 | serine hydroxymethyltransferase |
| SEQ ID NO: 3710 | Nga02257 | 149.5972 | 137.11822 | ---NA--- |
| SEQ ID NO: 3711 | Nga20250 | 201.3058 | 238.0993 | protein |
| SEQ ID NO: 3712 | Nga20707 | 195.5307 | 233.99467 | trna (adenine-n -)-methyltransferase non-catalytic subunit trm6 |
| SEQ ID NO: 3713 | Nga21121 | 348.3309 | 484.2323 | conserved unknown protein [Ectocarpus siliculosus] |
| SEQ ID NO: 3714 | Nga01949 | 165.9919 | 170.15983 | ---NA--- |
| SEQ ID NO: 3715 | Nga01947 | 149.8258 | 230.23439 | ---NA--- |
| SEQ ID NO: 3716 | Nga01948 | 45.19774 | 116.27935 | ---NA--- |
| SEQ ID NO: 3717 | Nga02404 | 6454.039 | 5838.6008 | er lumen protein retaining receptor |
| SEQ ID NO: 3718 | Nga02405 | 112.7098 | 127.28648 | ---NA--- |
| SEQ ID NO: 3719 | Nga20310 | 544.9309 | 516.65766 | protein |
| SEQ ID NO: 3720 | Nga02354 | 413.7267 | 405.08364 | arsenical-resistance protein |
| SEQ ID NO: 3721 | Nga04610.2 | 184.9837 | 172.09157 | pectinacetylesterase family protein |
| SEQ ID NO: 3722 | Nga04713 | 436.4929 | 440.48091 | splicing factor 3a |
| SEQ ID NO: 3723 | Nga04879 | 828.9624 | 973.30484 | protein |
| SEQ ID NO: 3724 | Nga05028 | 474.1784 | 520.42695 | ---NA--- |
| SEQ ID NO: 3725 | Nga05026 | 115.7025 | 205.90397 | ---NA--- |
| SEQ ID NO: 3726 | Nga04919.1 | 1002.747 | 818.37729 | protein nef1 |
| SEQ ID NO: 3727 | Nga00476.02 | 472.374 | 546.54973 | 4-hydroxyphenylpyruvate dioxygenase |
| SEQ ID NO: 3728 | Nga00482.02 | 3534.884 | 2768.9643 | beta-hydroxyacyl-acp dehydratase precursor |
| SEQ ID NO: 3729 | Nga00477.02 | 134.8601 | 100.80258 | conserved hypothetical protein [Phytophthora infestans T30-4] |
| SEQ ID NO: 3730 | Nga00737 | 4459.658 | 4097.2198 | wos2 protein |
| SEQ ID NO: 3731 | Nga00740 | 1663.889 | 1366.0784 | ---NA--- |
| SEQ ID NO: 3732 | Nga00739 | 417.1322 | 399.40469 | dna-directed rna polymerase ii |
| SEQ ID NO: 3733 | Nga00738 | 312.2677 | 246.64713 | hypothetical protein Esi_0097_0005 [Ectocarpus siliculosus] |

FIGURE 24 BG

| # | Nga model | +N rpkb | -N rpkb | GO |
|---|---|---|---|---|
| SEQ ID NO: 3734 | Nga04961.02 | 314.1487 | 311.722 | glutathione s-transferase |
| SEQ ID NO: 3735 | Nga07199 | 7737.634 | 8206.9531 | 40s ribosomal protein s12 |
| SEQ ID NO: 3736 | Nga07200 | 2886.71 | 2230.1875 | conserved unknown protein [Ectocarpus siliculosus] |
| SEQ ID NO: 3737 | Nga07198 | 1092.063 | 1145.133 | queuosine biosynthesis protein |
| SEQ ID NO: 3738 | Nga03618 | 81.87135 | 107.68992 | ---NA--- |
| SEQ ID NO: 3739 | Nga03617 | 108.3845 | 106.32971 | ---NA--- |
| SEQ ID NO: 3740 | Nga03616 | 164.3836 | 201.80797 | ---NA--- |
| SEQ ID NO: 3741 | Nga03619 | 66.66667 | 165.06422 | ---NA--- |
| SEQ ID NO: 3742 | Nga21208 | 160.7143 | 162.80748 | duf51 family protein |
| SEQ ID NO: 3743 | Nga05311 | 633.0409 | 658.01711 | conserved oligomeric golgi complex |
| SEQ ID NO: 3744 | Nga05313 | 287.1972 | 172.41786 | ---NA--- |
| SEQ ID NO: 3745 | Nga05312 | 47.00855 | 37.033639 | ---NA--- |
| SEQ ID NO: 3746 | Nga05314 | 25.42373 | 27.539846 | ---NA--- |
| SEQ ID NO: 3747 | Nga04837 | 13.33333 | 0 | ---NA--- |
| SEQ ID NO: 3748 | Nga07315 | 152.5424 | 142.2892 | ---NA--- |
| SEQ ID NO: 3749 | Nga04292.01 | 3421.419 | 3302.4323 | conserved unknown protein [Ectocarpus siliculosus] |
| SEQ ID NO: 3750 | Nga02736.02 | 3124.7 | 3021.1057 | conserved unknown protein [Ectocarpus siliculosus] |
| SEQ ID NO: 3751 | Nga04982.1 | 877.3449 | 673.69961 | isoform a |
| SEQ ID NO: 3752 | Nga01259 | 355.5957 | 329.46736 | leucine rich repeat containing 5G |
| SEQ ID NO: 3753 | Nga01258 | 270.2703 | 304.96451 | ---NA--- |
| SEQ ID NO: 3754 | Nga06396 | 288.8889 | 312.93425 | ---NA--- |
| SEQ ID NO: 3755 | Nga01849.2 | 165.4275 | 245.64041 | ---NA--- |
| SEQ ID NO: 3756 | Nga06397 | 260.355 | 335.43931 | ---NA--- |
| SEQ ID NO: 3757 | Nga06395 | 142.1801 | 193.37352 | set domain protein |
| SEQ ID NO: 3758 | Nga20708 | 320.8469 | 317.56044 | protein |
| SEQ ID NO: 3759 | Nga04885 | 113.7629 | 133.573 | potassium subfamily member 2 |
| SEQ ID NO: 3760 | Nga04884 | 161.2903 | 204.78241 | trna pseudouridine synthase 3 |
| SEQ ID NO: 3761 | Nga01798.01 | 636.5233 | 572.52575 | ---NA--- |
| SEQ ID NO: 3762 | Nga01797.01 | 530.6824 | 593.46543 | serine threonine-protein kinase 4 |
| SEQ ID NO: 3763 | Nga01799.01 | 279.3522 | 276.29044 | nuclear receptor 2c2-associated protein |
| SEQ ID NO: 3764 | Nga02089.01 | 2821.918 | 2368.0285 | rhamnose biosynthetic enzyme expressed |
| SEQ ID NO: 3765 | Nga02093.01 | 595.3109 | 560.94072 | short-chain dehydrogenase |
| SEQ ID NO: 3766 | Nga02090.1 | 59.20206 | 83.647409 | nudix hydrolase 3 |
| SEQ ID NO: 3767 | Nga02091.01 | 212.4183 | 166.37907 | ---NA--- |
| SEQ ID NO: 3768 | Nga02152 | 351.4493 | 392.47607 | ---NA--- |
| SEQ ID NO: 3769 | Nga02149 | 1727.941 | 1667.3307 | ubiquitin conjugating enzyme |
| SEQ ID NO: 3770 | Nga21147 | 3329.71 | 3116.26 | ubiquitin conjugating enzyme |
| SEQ ID NO: 3771 | Nga02025.01 | 940.1709 | 742.98738 | signal peptidase complex subunit 1 |
| SEQ ID NO: 3772 | Nga02024.1 | 257.9473 | 334.51366 | histone acetyltransferase |
| SEQ ID NO: 3773 | Nga04852 | 669.3548 | 816.79333 | ---NA--- |
| SEQ ID NO: 3774 | Nga20198 | 204.8847 | 216.79377 | protein with ppr repeats |
| SEQ ID NO: 3775 | Nga04851 | 1563.241 | 1352.972 | lipolytic protein g-d-s-l family |
| SEQ ID NO: 3776 | Nga04853 | 129.771 | 186.05163 | ---NA--- |
| SEQ ID NO: 3777 | Nga02108.1 | 580.3595 | 681.99438 | swi snf-related matrix-associated actin-dependent regulator of chromatin a1 isoform a isoform 19 |
| SEQ ID NO: 3778 | Nga02109.01 | 1408.063 | 1229.1563 | gualynate kinase-1 |
| SEQ ID NO: 3779 | Nga02110.01 | 210.356 | 183.1682 | phosphoinositol transporter |
| SEQ ID NO: 3780 | Nga02578.2 | 520.9165 | 520.55346 | protein |
| SEQ ID NO: 3781 | Nga03653 | 3556.531 | 3903.8495 | heat shock protein 90 |
| SEQ ID NO: 3782 | Nga03652 | 547.5305 | 626.46934 | threonine dehydratase |
| SEQ ID NO: 3783 | Nga03650 | 1789.264 | 1493.4846 | ---NA--- |
| SEQ ID NO: 3784 | Nga03655 | 290.0543 | 298.93727 | tetratricopeptide repeat domain-containing protein |
| SEQ ID NO: 3785 | Nga03654 | 2394.02 | 2737.9548 | cug-bp- and etr-3-like |
| SEQ ID NO: 3786 | Nga03651 | 879.7386 | 875.7911 | histidinol dehydrogenase |
| SEQ ID NO: 3787 | Nga01247 | 710.4762 | 528.2055 | hypothetical protein AURANDRAFT_64930 [Aureococcus anophagefferens] |
| SEQ ID NO: 3788 | Nga01248 | 84.88613 | 58.31073 | cl- voltage gated |
| SEQ ID NO: 3789 | Nga01249 | 74.95069 | 117.51059 | cl- voltage gated |
| SEQ ID NO: 3790 | Nga01252 | 125 | 111.50938 | ---NA--- |
| SEQ ID NO: 3791 | Nga01250.01 | 11149.22 | 11737.134 | ---NA--- |
| SEQ ID NO: 3792 | Nga01251 | 2889.744 | 3635.7775 | ferredoxin component |
| SEQ ID NO: 3793 | Nga03790 | 585.5199 | 560.56567 | sac3 ganp domain protein |
| SEQ ID NO: 3794 | Nga03791 | 121.1454 | 136.00074 | conserved unknown protein [Ectocarpus siliculosus] |
| SEQ ID NO: 3795 | Nga03792 | 347.0052 | 299.0177 | glucosaminyl (n-acetyl) transferase i-branching enzyme |

FIGURE 24 BH

| # | Nga model | +N rpkb | -N rpkb | GO |
|---|---|---|---|---|
| SEQ ID NO: 3796 | Nga06966 | 276.9231 | 183.31651 | gtp-binding protein 128up |
| SEQ ID NO: 3797 | Nga06965 | 228.9973 | 256.86442 | developmentally regulated gtp binding protein 1 |
| SEQ ID NO: 3798 | Nga02375 | 300.4484 | 497.89901 | protein |
| SEQ ID NO: 3799 | Nga20666 | 19.37984 | 25.191487 | ---NA--- |
| SEQ ID NO: 3800 | Nga00986 | 844.8637 | 1179.37 | acetylornithine aminotransferase |
| SEQ ID NO: 3801 | Nga00987 | 144.7964 | 200.96195 | ---NA--- |
| SEQ ID NO: 3802 | Nga03961 | 12.39157 | 32.215136 | hypothetical protein RTM1035_12233 [Roseovarius sp. TM1035] |
| SEQ ID NO: 3803 | Nga06375.2 | 985.9296 | 1047.8519 | prolyl 4-hydroxylase |
| SEQ ID NO: 3804 | Nga02345.01 | 1162.684 | 1729.2092 | glutamate dehydrogenase |
| SEQ ID NO: 3805 | Nga02350 | 223.5772 | 281.81696 | conserved unknown protein [Ectocarpus siliculosus] |
| SEQ ID NO: 3806 | Nga02351 | 620.8651 | 686.32379 | fk506 binding protein 12-rapamycin associated protein 1 |
| SEQ ID NO: 3807 | Nga02347 | 456.4498 | 603.12364 | conserved unknown protein [Ectocarpus siliculosus] |
| SEQ ID NO: 3808 | Nga02344 | 258.7621 | 338.19086 | protein atypical group |
| SEQ ID NO: 3809 | Nga02349 | 120.108 | 198.08124 | protein atypical group |
| SEQ ID NO: 3810 | Nga03801 | 166.6667 | 159.39478 | ---NA--- |
| SEQ ID NO: 3811 | Nga03802 | 179.4872 | 175.90979 | ---NA--- |
| SEQ ID NO: 3812 | Nga02332 | 186.9984 | 204.30175 | pirin |
| SEQ ID NO: 3813 | Nga07099 | 221.519 | 169.11247 | ---NA--- |
| SEQ ID NO: 3814 | Nga03596 | 2224.111 | 1833.2939 | glutaredoxin-related protein |
| SEQ ID NO: 3815 | Nga20234 | 117.8121 | 112.4254 | ubiquinone menaquinone biosynthesis methyltransferase |
| SEQ ID NO: 3816 | Nga03595 | 55.7971 | 59.656362 | queuine trna-ribosyltransferase |
| SEQ ID NO: 3817 | Nga06982 | 2052.863 | 1911.1683 | ubiquitin-protein ligase e3 rbbp6 family involved in mrna cleavage |
| SEQ ID NO: 3818 | Nga04217 | 220.202 | 301.99249 | v-myb myeloblastosis viral oncogene homologue |
| SEQ ID NO: 3819 | Nga04218 | 286.0082 | 286.41062 | type ii alternative rna polymerase sigma sigma-70 family protein |
| SEQ ID NO: 3820 | Nga04106 | 124.1237 | 165.57473 | nxn protein |
| SEQ ID NO: 3821 | Nga20174 | 359.3482 | 327.01402 | nxn protein |
| SEQ ID NO: 3822 | Nga04107 | 377.3585 | 483.70824 | protein |
| SEQ ID NO: 3823 | Nga04102 | 555.2354 | 613.93662 | nxn protein |
| SEQ ID NO: 3824 | Nga04101 | 1836.299 | 1703.8769 | enhancer of rudimentary homolog |
| SEQ ID NO: 3825 | Nga04594 | 941.954 | 934.44491 | acyltransferase family protein |
| SEQ ID NO: 3826 | Nga03891 | 44.32624 | 78.74573 | 3-isopropylmalate dehydrogenase |
| SEQ ID NO: 3827 | Nga04199.02 | 844.1128 | 731.138 | protein |
| SEQ ID NO: 3828 | Nga20123.1 | 500.4739 | 556.50502 | predicted protein [Thalassiosira pseudonana CCMP1335] |
| SEQ ID NO: 3829 | Nga04200.02 | 2435.262 | 2111.2617 | glycine cleavage system h protein |
| SEQ ID NO: 3830 | Nga03739.02 | 7230.616 | 8437.329 | malate synthase |
| SEQ ID NO: 3831 | Nga07288 | 78.53403 | 116.26333 | ---NA--- |
| SEQ ID NO: 3832 | Nga07101 | 1471.218 | 4118.3191 | ---NA--- |
| SEQ ID NO: 3833 | Nga03906 | 477.305 | 371.06524 | aldo keto reductase |
| SEQ ID NO: 3834 | Nga03907 | 524.1302 | 560.46111 | nad-dependent deacetylase sirtuin-5 |
| SEQ ID NO: 3835 | Nga03905 | 120.9068 | 73.670822 | mad2 mitotic arrest deficient-like 2 |
| SEQ ID NO: 3836 | Nga03904 | 4352.507 | 4118.8453 | ribosomal protein l35 |
| SEQ ID NO: 3837 | Nga02053.2 | 2867.55 | 3311.3959 | ---NA--- |
| SEQ ID NO: 3838 | Nga03603.1 | 1104.2 | 1236.3567 | lipase family protein |
| SEQ ID NO: 3839 | Nga02055.02 | 56.06061 | 65.650542 | cathepsin l-like proteinase |
| SEQ ID NO: 3840 | Nga02052.02 | 8390.187 | 12092.738 | ---NA--- |
| SEQ ID NO: 3841 | Nga06957 | 244.2159 | 144.80248 | ---NA--- |
| SEQ ID NO: 3842 | Nga06958 | 160.3053 | 128.1689 | ---NA--- |
| SEQ ID NO: 3843 | Nga00906 | 213.2616 | 174.71515 | ---NA--- |
| SEQ ID NO: 3844 | Nga00904 | 1502.256 | 983.86962 | ---NA--- |
| SEQ ID NO: 3845 | Nga00905 | 308.1444 | 377.44927 | type iii restriction res subunit |
| SEQ ID NO: 3846 | Nga04631 | 3986.096 | 4091.9597 | nadh ubiquinone oxidoreductase |
| SEQ ID NO: 3847 | Nga04632 | 190.0726 | 150.81344 | ---NA--- |
| SEQ ID NO: 3848 | Nga07118 | 558.6854 | 628.91986 | ---NA--- |
| SEQ ID NO: 3849 | Nga03586 | 156.669 | 240.03914 | alpha beta hydrolase fold protein |
| SEQ ID NO: 3850 | Nga03585 | 1.491424 | 0.4038904 | kinesin-like protein kif6 |
| SEQ ID NO: 3851 | Nga04668 | 147.001 | 131.54316 | major facilitator superfamily |
| SEQ ID NO: 3852 | Nga04667 | 95.89041 | 123.65684 | ankyrin unc44 |
| SEQ ID NO: 3853 | Nga03794 | 2080.334 | 1635.2934 | zinc metalloendopeptidase |
| SEQ ID NO: 3854 | Nga03797 | 452.6316 | 543.51738 | probable e3 ubiquitin-protein ligase herc3 |
| SEQ ID NO: 3855 | Nga03798 | 119.3416 | 209.51438 | ---NA--- |
| SEQ ID NO: 3856 | Nga03796 | 988.806 | 957.93449 | protein |
| SEQ ID NO: 3857 | Nga03795 | 365.9976 | 532.02517 | ---NA--- |
| SEQ ID NO: 3858 | Nga01817 | 101.1058 | 77.007152 | amp-dependent synthetase and ligase |
| SEQ ID NO: 3859 | Nga03918.2 | 275.0166 | 319.44275 | structural maintenance of chromosomes 1 |

FIGURE 24 BI

| # | Nga model | +N rpkb | -N rpkb | GO |
|---|---|---|---|---|
| SEQ ID NO: 3860 | Nga03915.2 | 268.4073 | 229.09125 | 2 protease |
| SEQ ID NO: 3861 | Nga01386 | 301.0753 | 170.05608 | ---NA--- |
| SEQ ID NO: 3862 | Nga01390 | 108.046 | 57.274438 | ---NA--- |
| SEQ ID NO: 3863 | Nga01389 | 2416.268 | 2285.6754 | cyclin-dependent kinases regulatory subunit |
| SEQ ID NO: 3864 | Nga01391 | 249.3113 | 167.11047 | manganese-dependent inorganic pyrophosphatase |
| SEQ ID NO: 3865 | Nga04544 | 135.2941 | 143.3692 | ---NA--- |
| SEQ ID NO: 3866 | Nga02153 | 5733.068 | 5998.7856 | protein |
| SEQ ID NO: 3867 | Nga02154 | 1238.028 | 1058.823 | n-methyl-d-aspartate receptor nmdar2c subunit |
| SEQ ID NO: 3868 | Nga02156 | 1468.072 | 1981.0868 | ornithine decarboxylase |
| SEQ ID NO: 3869 | Nga02155 | 352.4306 | 372.36167 | usp37 protein |
| SEQ ID NO: 3870 | Nga01384 | 240.2235 | 401.42189 | ---NA--- |
| SEQ ID NO: 3871 | Nga20829 | 466.0033 | 499.40139 | proteasome component c11 |
| SEQ ID NO: 3872 | Nga01357.2 | 879.9571 | 986.86908 | ---NA--- |
| SEQ ID NO: 3873 | Nga05131.2 | 333.6481 | 322.89032 | calcium-transporting atpase type 2c member 1-like |
| SEQ ID NO: 3874 | Nga01085 | 797.1888 | 787.41102 | mediator of rna polymerase ii transcription |
| SEQ ID NO: 3875 | Nga01087.1 | 793.6937 | 779.73326 | trna specific adenosine deaminase |
| SEQ ID NO: 3876 | Nga01088.01 | 700.4539 | 686.64905 | protein |
| SEQ ID NO: 3877 | Nga05122.2 | 256.9061 | 266.31995 | ---NA--- |
| SEQ ID NO: 3878 | Nga01811 | 500 | 463.38341 | phenylalanyl-trna synthetase alpha chain |
| SEQ ID NO: 3879 | Nga01809 | 405.0926 | 529.07954 | conserved unknown protein [Ectocarpus siliculosus] |
| SEQ ID NO: 3880 | Nga01808 | 397.0856 | 463.67937 | phenylalanyl-trna synthetase alpha chain |
| SEQ ID NO: 3881 | Nga20564 | 235.4839 | 297.01576 | hect e3 ubiquitin |
| SEQ ID NO: 3882 | Nga20496 | 328.2675 | 352.29797 | ---NA--- |
| SEQ ID NO: 3883 | Nga03827 | 2344.978 | 2206.6753 | protein |
| SEQ ID NO: 3884 | Nga03828 | 783.4586 | 618.99082 | thioredoxin-like protein 1 |
| SEQ ID NO: 3885 | Nga03193 | 306.8783 | 171.9419 | ---NA--- |
| SEQ ID NO: 3886 | Nga03195 | 140.1869 | 161.97891 | ---NA--- |
| SEQ ID NO: 3887 | Nga03191 | 227.0742 | 222.32312 | ---NA--- |
| SEQ ID NO: 3888 | Nga20910 | 673.9812 | 631.60349 | dna mismatch repair protein msh2 |
| SEQ ID NO: 3889 | Nga04975.2 | 82.99595 | 157.88025 | ---NA--- |
| SEQ ID NO: 3890 | Nga03190 | 145.0382 | 190.18611 | ---NA--- |
| SEQ ID NO: 3891 | Nga03194 | 11947.44 | 12371.041 | ---NA--- |
| SEQ ID NO: 3892 | Nga03196 | 250 | 488.51727 | ---NA--- |
| SEQ ID NO: 3893 | Nga01557 | 805.5556 | 816.43743 | protein |
| SEQ ID NO: 3894 | Nga01559 | 241.6049 | 236.20452 | protein |
| SEQ ID NO: 3895 | Nga01558 | 978.3514 | 883.00252 | chromate transporter |
| SEQ ID NO: 3896 | Nga02003 | 427.673 | 484.68149 | zinc finger cchc domain-containing protein 7-like |
| SEQ ID NO: 3897 | Nga02004 | 206.4018 | 235.53762 | polyol transporter |
| SEQ ID NO: 3898 | Nga20703 | 133.3333 | 132.39526 | polyol monosaccharide transporter |
| SEQ ID NO: 3899 | Nga04147 | 72.89294 | 103.63514 | atp-dependent rna |
| SEQ ID NO: 3900 | Nga04146 | 25.80645 | 81.533737 | atp-dependent rna |
| SEQ ID NO: 3901 | Nga04148 | 1669.749 | 1317.9108 | ---NA--- |
| SEQ ID NO: 3902 | Nga04145 | 329.2469 | 356.65146 | tpr repeat protein |
| SEQ ID NO: 3903 | Nga01141 | 75.41899 | 66.567449 | ---NA--- |
| SEQ ID NO: 3904 | Nga01145 | 2108.824 | 2153.724 | ---NA--- |
| SEQ ID NO: 3905 | Nga01140 | 559.633 | 493.34704 | ---NA--- |
| SEQ ID NO: 3906 | Nga01142 | 406.1224 | 386.86926 | ---NA--- |
| SEQ ID NO: 3907 | Nga01146 | 193.8776 | 165.80111 | ---NA--- |
| SEQ ID NO: 3908 | Nga01144 | 209.8139 | 238.27481 | tpr repeat-containing protein |
| SEQ ID NO: 3909 | Nga01143 | 172.3164 | 192.77892 | aspartyl glutamyl-trna amidotransferase subunit b |
| SEQ ID NO: 3910 | Nga01566 | 200.4831 | 273.42499 | ---NA--- |
| SEQ ID NO: 3911 | Nga01567 | 271.1443 | 350.29953 | molybdopterin biosynthesis |
| SEQ ID NO: 3912 | Nga01568 | 332.618 | 246.40085 | ---NA--- |
| SEQ ID NO: 3913 | Nga20402 | 227.9412 | 151.33415 | c2h2 zinc finger protein |
| SEQ ID NO: 3914 | Nga01569 | 169.8113 | 183.94539 | ---NA--- |
| SEQ ID NO: 3915 | Nga01564 | 558.802 | 640.92001 | ---NA--- |
| SEQ ID NO: 3916 | Nga01565 | 409.4551 | 301.18764 | cop9 signalosome complex subunit 2 |
| SEQ ID NO: 3917 | Nga04054 | 202.381 | 219.22592 | 39s ribosomal protein mitochondrial-like |
| SEQ ID NO: 3918 | Nga04053 | 356.9068 | 390.90927 | morn repeat protein |
| SEQ ID NO: 3919 | Nga04038 | 903.8462 | 1229.0539 | ---NA--- |
| SEQ ID NO: 3920 | Nga02490.2 | 186.1925 | 169.96348 | ---NA--- |
| SEQ ID NO: 3921 | Nga02489.02 | 709.0239 | 658.31897 | ---NA--- |
| SEQ ID NO: 3922 | Nga06750 | 610.2004 | 580.09249 | signal recognition particle 19 kda |
| SEQ ID NO: 3923 | Nga06751.1 | 215.6057 | 248.62727 | nucleolar protein |

FIGURE 24 BJ

| # | Nga model | +N rpkb | -N rpkb | GO |
|---|---|---|---|---|
| SEQ ID NO: 3924 | Nga06753 | 118.608 | 117.70937 | ---NA--- |
| SEQ ID NO: 3925 | Nga06748 | 1096.591 | 900.64337 | major facilitator superfamily mfs_1 |
| SEQ ID NO: 3926 | Nga07243 | 1.754386 | 0 | inositol monophosphatase family protein |
| SEQ ID NO: 3927 | Nga00768 | 604.9383 | 713.24045 | ---NA--- |
| SEQ ID NO: 3928 | Nga00770 | 118.7215 | 183.01213 | ---NA--- |
| SEQ ID NO: 3929 | Nga00769 | 625.4296 | 409.46987 | set domain containing protein |
| SEQ ID NO: 3930 | Nga00767 | 445.7547 | 454.75387 | predicted protein [Phaeodactylum tricornutum CCAP 1055/1] |
| SEQ ID NO: 3931 | Nga20454 | 348.8024 | 285.40295 | ---NA--- |
| SEQ ID NO: 3932 | Nga00766 | 341.7031 | 402.07373 | origin recognition complex 1 protein |
| SEQ ID NO: 3933 | Nga06255 | 893.1751 | 723.22741 | tata box binding protein -associated factor |
| SEQ ID NO: 3934 | Nga06258 | 292.3351 | 282.8766 | bifunctional apoptosis regulator |
| SEQ ID NO: 3935 | Nga06257 | 560.5307 | 646.70683 | alpha beta-hydrolase domain-containing protein |
| SEQ ID NO: 3936 | Nga06259 | 116.9591 | 114.02463 | domain-containing protein |
| SEQ ID NO: 3937 | Nga02366.2 | 334.6614 | 379.77923 | ---NA--- |
| SEQ ID NO: 3938 | Nga05721 | 194.8901 | 239.43139 | poly polymerase gamma |
| SEQ ID NO: 3939 | Nga01130.2 | 2190.024 | 2291.2585 | heat shock protein 70 |
| SEQ ID NO: 3940 | Nga05725 | 1367.041 | 1541.6813 | atp-dependent metalloprotease |
| SEQ ID NO: 3941 | Nga05726 | 6136.434 | 6301.2306 | s-adenosylmethionine synthetase |
| SEQ ID NO: 3942 | Nga05727 | 8834.264 | 8308.8279 | methionine s-adenosyl transferase |
| SEQ ID NO: 3943 | Nga05723 | 310.9541 | 352.14672 | methionine aminopeptidase |
| SEQ ID NO: 3944 | Nga05722 | 102.1505 | 93.181414 | ---NA--- |
| SEQ ID NO: 3945 | Nga05738 | 1290.509 | 1381.6248 | atp-dependent metalloprotease |
| SEQ ID NO: 3946 | Nga04598 | 331.3953 | 365.27656 | ---NA--- |
| SEQ ID NO: 3947 | Nga05938 | 403.3829 | 503.02919 | protein |
| SEQ ID NO: 3948 | Nga05937 | 424.7021 | 347.77717 | translation initiation factor fusion with methylthioribose kinase |
| SEQ ID NO: 3949 | Nga05936 | 776.6082 | 733.55842 | hypothetical protein Esi_0462_0008 [Ectocarpus siliculosus] |
| SEQ ID NO: 3950 | Nga05935 | 645.6759 | 669.40401 | ---NA--- |
| SEQ ID NO: 3951 | Nga00925 | 290.8654 | 298.58371 | protein |
| SEQ ID NO: 3952 | Nga21056.1 | 42.73504 | 74.067278 | ---NA--- |
| SEQ ID NO: 3953 | Nga21047.1 | 63.82979 | 51.856944 | ---NA--- |
| SEQ ID NO: 3954 | Nga21078 | 172.4138 | 236.56833 | serine threonine protein kinase mst4 |
| SEQ ID NO: 3955 | Nga00927 | 86.95652 | 112.62357 | protein |
| SEQ ID NO: 3956 | Nga00928 | 271.0526 | 220.92271 | beta- -endoglucanase |
| SEQ ID NO: 3957 | Nga20203 | 171.0817 | 209.23393 | small nucleolar ribonucleoprotein complex subunit |
| SEQ ID NO: 3958 | Nga00929 | 187.9223 | 220.03189 | protein |
| SEQ ID NO: 3959 | Nga00926 | 508.4175 | 536.14609 | transcription factor protein |
| SEQ ID NO: 3960 | Nga01663 | 496.2406 | 613.56108 | ---NA--- |
| SEQ ID NO: 3961 | Nga01665 | 168.1416 | 178.9413 | ---NA--- |
| SEQ ID NO: 3962 | Nga01666 | 224.2424 | 210.08173 | ---NA--- |
| SEQ ID NO: 3963 | Nga01667 | 370.6897 | 420.22006 | ---NA--- |
| SEQ ID NO: 3964 | Nga01664 | 406.893 | 490.35281 | ---NA--- |
| SEQ ID NO: 3965 | Nga00825 | 343.0556 | 361.07798 | ---NA--- |
| SEQ ID NO: 3966 | Nga20313 | 370.2479 | 350.93199 | conserved unknown protein [Ectocarpus siliculosus] |
| SEQ ID NO: 3967 | Nga00829 | 124.7849 | 131.44233 | ---NA--- |
| SEQ ID NO: 3968 | Nga00828.01 | 6466.377 | 6095.2469 | ---NA--- |
| SEQ ID NO: 3969 | Nga00827 | 439.3939 | 416.88094 | transcription elongation factor spt4 |
| SEQ ID NO: 3970 | Nga00826 | 537.5 | 607.06235 | ---NA--- |
| SEQ ID NO: 3971 | Nga00761 | 542.6573 | 465.10884 | heat shock protein |
| SEQ ID NO: 3972 | Nga00759 | 3177.602 | 3462.9176 | nucleoredoxin-like protein 2 |
| SEQ ID NO: 3973 | Nga00760 | 129.8701 | 164.12635 | ---NA--- |
| SEQ ID NO: 3974 | Nga00764 | 409.7808 | 420.14133 | ---NA--- |
| SEQ ID NO: 3975 | Nga00763 | 562.6615 | 617.89119 | thermostable carboxypeptidase |
| SEQ ID NO: 3976 | Nga00762 | 727.0341 | 710.78343 | protein |
| SEQ ID NO: 3977 | Nga01753 | 92.59259 | 70.209607 | dnak protein |
| SEQ ID NO: 3978 | Nga01751 | 297.619 | 261.13675 | ccaat-box dna binding protein subunit b |
| SEQ ID NO: 3979 | Nga01752 | 86.07595 | 106.95221 | hsp70-like protein |
| SEQ ID NO: 3980 | Nga04908.01 | 6196.842 | 5891.6524 | sugar nucleotide epimerase |
| SEQ ID NO: 3981 | Nga04909.01 | 769.6335 | 764.50228 | nudix hydrolase |
| SEQ ID NO: 3982 | Nga02060 | 374.1188 | 405.80365 | oxidoreductase domain protein |
| SEQ ID NO: 3983 | Nga02059 | 78.26087 | 83.204926 | dna ligase 4-like |
| SEQ ID NO: 3984 | Nga20998 | 811.0236 | 879.7468 | acetyl- acetyltransferase |
| SEQ ID NO: 3985 | Nga20377 | 726.9373 | 833.41062 | ---NA--- |
| SEQ ID NO: 3986 | Nga01778 | 120.4819 | 95.707416 | dna replication licensing factor mcm3 |
| SEQ ID NO: 3987 | Nga01777 | 153.0139 | 140.07817 | protein |

FIGURE 24 BK

| # | Nga model | +N rpkb | -N rpkb | GO |
|---|---|---|---|---|
| SEQ ID NO: 3988 | Nga01369 | 314.1487 | 389.6525 | ---NA--- |
| SEQ ID NO: 3989 | Nga01371 | 176.4706 | 99.119446 | ---NA--- |
| SEQ ID NO: 3990 | Nga01370 | 105.8952 | 95.788154 | ---NA--- |
| SEQ ID NO: 3991 | Nga02435 | 587.5486 | 556.36918 | ---NA--- |
| SEQ ID NO: 3992 | Nga02437 | 2538.813 | 1953.7781 | 26s proteasome regulatory atpase subunit |
| SEQ ID NO: 3993 | Nga02436 | 963.3028 | 1146.1741 | 26s protease regulatory subunit 7 |
| SEQ ID NO: 3994 | Nga00887 | 521.7391 | 509.34672 | myst esa1-associated factor 6-like |
| SEQ ID NO: 3995 | Nga00888 | 3.642987 | 5.9193112 | chc1-b-prov partial |
| SEQ ID NO: 3996 | Nga01335.01 | 703.7594 | 567.67974 | protein |
| SEQ ID NO: 3997 | Nga01334.01 | 6031.915 | 6632.5672 | 40s ribosomal protein s2 |
| SEQ ID NO: 3998 | Nga01337 | 115.3846 | 62.494266 | ---NA--- |
| SEQ ID NO: 3999 | Nga01333 | 1655.844 | 1540.4431 | sulfate adenylyltransferase |
| SEQ ID NO: 4000 | Nga01336 | 1202.649 | 1265.4468 | protein |
| SEQ ID NO: 4001 | Nga06454 | 40266.56 | 27658.345 | light harvesting complex protein |
| SEQ ID NO: 4002 | Nga06455 | 417.9293 | 263.96989 | protein |
| SEQ ID NO: 4003 | Nga06453 | 426.0355 | 472.1789 | short-chain dehydrogenase reductase sdr |
| SEQ ID NO: 4004 | Nga04399 | 80 | 115.54495 | ---NA--- |
| SEQ ID NO: 4005 | Nga07309 | 162.6016 | 250.99323 | pyruvate kinase |
| SEQ ID NO: 4006 | Nga21007 | 7077.947 | 6816.5482 | ---NA--- |
| SEQ ID NO: 4007 | Nga07308 | 2.743484 | 1.4859176 | protein |
| SEQ ID NO: 4008 | Nga01473 | 1552.809 | 1304.7492 | enhancer of yellow 2 transcription factor homolog |
| SEQ ID NO: 4009 | Nga01474 | 299.9185 | 326.64756 | ubiquitin-like modifier-activating enzyme 5 |
| SEQ ID NO: 4010 | Nga01061 | 86.629 | 148.91917 | ---NA--- |
| SEQ ID NO: 4011 | Nga05569 | 66.26506 | 47.853708 | ---NA--- |
| SEQ ID NO: 4012 | Nga05568 | 1938.776 | 1691.1714 | peroxiredoxin q |
| SEQ ID NO: 4013 | Nga03517 | 129.9435 | 101.99943 | nedd8 activating enzyme |
| SEQ ID NO: 4014 | Nga03518 | 117.76 | 125.47 | ---NA--- |
| SEQ ID NO: 4015 | Nga03527 | 86.96 | 36.63 | ---NA--- |
| SEQ ID NO: 4016 | Nga02193.02 | 1625.66 | 1479.54 | upf0414 transmembrane protein c20orf30-like protein |
| SEQ ID NO: 4017 | Nga04468 | 220.27 | 214.45 | nucleic acid binding |
| SEQ ID NO: 4018 | Nga02195.02 | 3082.66 | 3114.42 | pyruvate kinase |
| SEQ ID NO: 4019 | Nga05956 | 145.90 | 199.38 | crooked neck |
| SEQ ID NO: 4020 | Nga05957 | 25.00 | 27.08 | ---NA--- |
| SEQ ID NO: 4021 | Nga05955 | 427.45 | 454.53 | crooked neck |
| SEQ ID NO: 4022 | Nga05953 | 936.88 | 918.34 | histone acetyltransferase |
| SEQ ID NO: 4023 | Nga05966 | 483.97 | 555.50 | crooked neck |
| SEQ ID NO: 4024 | Nga05958 | 486.34 | 645.20 | ---NA--- |
| SEQ ID NO: 4025 | Nga05954 | 444.66 | 445.91 | gpr7 transmembrane protein |
| SEQ ID NO: 4026 | Nga04051 | 396.06 | 485.32 | ---NA--- |
| SEQ ID NO: 4027 | Nga06172 | 96.62 | 104.66 | ---NA--- |
| SEQ ID NO: 4028 | Nga20735 | 117.12 | 185.42 | ---NA--- |
| SEQ ID NO: 4029 | Nga06168 | 168.10 | 135.40 | ---NA--- |
| SEQ ID NO: 4030 | Nga06169 | 826.09 | 894.85 | ---NA--- |
| SEQ ID NO: 4031 | Nga06170 | 1119.50 | 1243.33 | splicing arginine serine- |
| SEQ ID NO: 4032 | Nga06171 | 584.39 | 397.64 | ---NA--- |
| SEQ ID NO: 4033 | Nga01180 | 1065.11 | 795.70 | ---NA--- |
| SEQ ID NO: 4034 | Nga01181 | 315.79 | 321.71 | ---NA--- |
| SEQ ID NO: 4035 | Nga01183 | 263.57 | 159.55 | ---NA--- |
| SEQ ID NO: 4036 | Nga06911.2 | 280.63 | 95.67 | ankyrin repeat protein |
| SEQ ID NO: 4037 | Nga03806 | 138.67 | 109.77 | ---NA--- |
| SEQ ID NO: 4038 | Nga01735 | 97.13 | 105.21 | ---NA--- |
| SEQ ID NO: 4039 | Nga20200.1 | 661.93 | 594.95 | zn-binding protein |
| SEQ ID NO: 4040 | Nga05031.1 | 529.19 | 471.59 | conserved unknown protein [Ectocarpus siliculosus] |
| SEQ ID NO: 4041 | Nga01791.2 | 2943.87 | 3333.48 | protein |
| SEQ ID NO: 4042 | Nga05147 | 2930.80 | 2813.66 | PREDICTED: hypothetical protein [Vitis vinifera] |
| SEQ ID NO: 4043 | Nga05149 | 249.21 | 254.63 | ---NA--- |
| SEQ ID NO: 4044 | Nga05146 | 1294.99 | 1060.30 | protein |
| SEQ ID NO: 4045 | Nga05148 | 305.99 | 314.38 | s-adenosylmethionine decarboxylase proenzyme |
| SEQ ID NO: 4046 | Nga05150 | 1697.78 | 1537.00 | proteasome ( macropain) alpha 6 |
| SEQ ID NO: 4047 | Nga05152 | 195.15 | 252.53 | protein |
| SEQ ID NO: 4048 | Nga05145 | 1531.84 | 1892.40 | protein |
| SEQ ID NO: 4049 | Nga05151 | 2610.41 | 2552.10 | coproporphyrinogen iii oxidase |
| SEQ ID NO: 4050 | Nga04027 | 200.17 | 250.83 | ribosome biogenesis protein nob1 |
| SEQ ID NO: 4051 | Nga04026 | 531.87 | 559.47 | ---NA--- |

FIGURE 24 BL

| # | Nga model | +N rpkb | -N rpkb | GO |
|---|---|---|---|---|
| SEQ ID NO: 4052 | Nga04025 | 137.19 | 141.64 | inositol oxygenase |
| SEQ ID NO: 4053 | Nga02276.01 | 390.35 | 299.31 | phosphatidylinositol-4-phosphate 5- |
| SEQ ID NO: 4054 | Nga20053.1 | 1379.41 | 1452.23 | hypothetical protein AURANDRAFT_70731 [Aureococcus anophagefferens] |
| SEQ ID NO: 4055 | Nga02277.01 | 1101.16 | 1216.17 | hypothetical protein AURANDRAFT_70731 [Aureococcus anophagefferens] |
| SEQ ID NO: 4056 | Nga21136 | 166.15 | 129.99 | ---NA--- |
| SEQ ID NO: 4057 | Nga07268 | 251.43 | 148.56 | fatty-acyl elongase |
| SEQ ID NO: 4058 | Nga06186 | 126.71 | 279.13 | protein |
| SEQ ID NO: 4059 | Nga06195 | 280.49 | 158.52 | ---NA--- |
| SEQ ID NO: 4060 | Nga06185 | 5908.55 | 6087.20 | histone h3 |
| SEQ ID NO: 4061 | Nga06187 | 514.65 | 586.46 | ---NA--- |
| SEQ ID NO: 4062 | Nga06188 | 599.07 | 580.75 | methionine sulfoxide reductase b |
| SEQ ID NO: 4063 | Nga06189 | 25.72 | 20.90 | ankyrin repeat protein |
| SEQ ID NO: 4064 | Nga06194 | 34.19 | 27.78 | ---NA--- |
| SEQ ID NO: 4065 | Nga01096.2 | 560.46 | 617.98 | dna topoisomerase i |
| SEQ ID NO: 4066 | Nga04622.2 | 578.17 | 558.10 | ---NA--- |
| SEQ ID NO: 4067 | Nga01127 | 103.24 | 83.08 | riken cdna isoform cra_b |
| SEQ ID NO: 4068 | Nga06501 | 452.53 | 507.70 | ---NA--- |
| SEQ ID NO: 4069 | Nga06500 | 725.15 | 772.83 | eukaryotic translation initiation factor 4e |
| SEQ ID NO: 4070 | Nga03180 | 133.78 | 146.12 | transaminase transferring nitrogenous groups |
| SEQ ID NO: 4071 | Nga03179 | 3084.26 | 2892.00 | proteasome subunit beta 7 |
| SEQ ID NO: 4072 | Nga03189 | 405.34 | 341.80 | ---NA--- |
| SEQ ID NO: 4073 | Nga03181 | 1414.57 | 1544.44 | aldehyde dehydrogenase |
| SEQ ID NO: 4074 | Nga03177 | 894.74 | 963.86 | ---NA--- |
| SEQ ID NO: 4075 | Nga03178 | 240.68 | 275.40 | ---NA--- |
| SEQ ID NO: 4076 | Nga05164 | 111.50 | 143.42 | denn domain-containing protein 4b |
| SEQ ID NO: 4077 | Nga05161 | 2560.64 | 2199.93 | proteasome subunit alpha type 3 |
| SEQ ID NO: 4078 | Nga05166 | 178.95 | 267.96 | ---NA--- |
| SEQ ID NO: 4079 | Nga05163 | 95.98 | 100.61 | dynein intermediate chain 3 |
| SEQ ID NO: 4080 | Nga05162 | 160.00 | 151.65 | phospholipase carboxylesterase family expressed |
| SEQ ID NO: 4081 | Nga05165 | 98.14 | 110.14 | ---NA--- |
| SEQ ID NO: 4082 | Nga03640 | 118.81 | 85.80 | ---NA--- |
| SEQ ID NO: 4083 | Nga03639 | 256.10 | 242.63 | ---NA--- |
| SEQ ID NO: 4084 | Nga01782.1 | 159.75 | 158.63 | nad-dependent histone deacetylase sir2-like protein |
| SEQ ID NO: 4085 | Nga01783.01 | 1437.13 | 1556.74 | tim10-like protein |
| SEQ ID NO: 4086 | Nga01781.01 | 1005.47 | 838.99 | endomembrane protein 70 containing expressed |
| SEQ ID NO: 4087 | Nga04063 | 174.48 | 157.97 | dihydroxy-acid dehydratase |
| SEQ ID NO: 4088 | Nga04061 | 685.82 | 697.25 | protein |
| SEQ ID NO: 4089 | Nga04060 | 283.96 | 262.47 | fg-gap repeat domain protein |
| SEQ ID NO: 4090 | Nga04062 | 14320.21 | 12391.52 | protein |
| SEQ ID NO: 4091 | Nga20354 | 139.53 | 139.70 | ---NA--- |
| SEQ ID NO: 4092 | Nga03977 | 78.95 | 79.18 | ylr143w-like protein |
| SEQ ID NO: 4093 | Nga03980 | 111.80 | 80.74 | ---NA--- |
| SEQ ID NO: 4094 | Nga01652 | 1432.46 | 1310.09 | ---NA--- |
| SEQ ID NO: 4095 | Nga01653 | 64.52 | 78.62 | ---NA--- |
| SEQ ID NO: 4096 | Nga21299 | 260.00 | 184.15 | ---NA--- |
| SEQ ID NO: 4097 | Nga05463 | 84.85 | 75.50 | ---NA--- |
| SEQ ID NO: 4098 | Nga05452 | 627.16 | 530.47 | short-chain dehydrogenase reductase sdr |
| SEQ ID NO: 4099 | Nga05453 | 397.31 | 501.50 | soluble pyridine nucleotide transhydrogenase stha |
| SEQ ID NO: 4100 | Nga20645 | 143.65 | 137.65 | ---NA--- |
| SEQ ID NO: 4101 | Nga03969 | 639.71 | 642.51 | ---NA--- |
| SEQ ID NO: 4102 | Nga02385 | 610.79 | 768.07 | alpha beta hydrolase fold protein |
| SEQ ID NO: 4103 | Nga02374 | 69.31 | 85.80 | ---NA--- |
| SEQ ID NO: 4104 | Nga02230.01 | 1230.58 | 956.34 | ---NA--- |
| SEQ ID NO: 4105 | Nga02229 | 1983.22 | 1792.06 | conserved unknown protein [Ectocarpus siliculosus] |
| SEQ ID NO: 4106 | Nga02334.01 | 26634.92 | 28408.62 | uncharacterized protein conserved in bacteria with a cystatin-like fold |
| SEQ ID NO: 4107 | Nga02335.01 | 1068.17 | 1077.20 | ---NA--- |
| SEQ ID NO: 4108 | Nga01635.02 | 777.33 | 582.68 | ---NA--- |
| SEQ ID NO: 4109 | Nga06461 | 107.14 | 96.72 | ---NA--- |
| SEQ ID NO: 4110 | Nga06459 | 135.78 | 157.02 | ---NA--- |
| SEQ ID NO: 4111 | Nga06462 | 1379.48 | 1425.64 | ---NA--- |
| SEQ ID NO: 4112 | Nga06463 | 783.25 | 1083.23 | ---NA--- |
| SEQ ID NO: 4113 | Nga06458 | 674.36 | 633.28 | predicted protein [Phaeodactylum tricornutum CCAP 1055/1] |

FIGURE 24 BM

| # | Nga model | +N rpkb | -N rpkb | GO |
|---|---|---|---|---|
| SEQ ID NO: 4114 | Nga06464 | 240.34 | 199.91 | ---NA--- |
| SEQ ID NO: 4115 | Nga06460 | 162.02 | 171.73 | ---NA--- |
| SEQ ID NO: 4116 | Nga06076 | 1824.13 | 2040.20 | 60s ribosomal protein l5 |
| SEQ ID NO: 4117 | Nga06074.1 | 512.74 | 293.23 | ---NA--- |
| SEQ ID NO: 4118 | Nga06072 | 177.08 | 170.87 | polymerase (dna directed) alpha 2 (70kd subunit) |
| SEQ ID NO: 4119 | Nga06075 | 1240.74 | 1277.81 | 60s ribosomal protein l5 |
| SEQ ID NO: 4120 | Nga06073 | 197.99 | 160.18 | conserved unknown protein [Ectocarpus siliculosus] |
| SEQ ID NO: 4121 | Nga06071 | 232.06 | 196.95 | ---NA--- |
| SEQ ID NO: 4122 | Nga04905 | 134.02 | 174.96 | ---NA--- |
| SEQ ID NO: 4123 | Nga06120.2 | 290.91 | 317.94 | protein |
| SEQ ID NO: 4124 | Nga01815.01 | 774.27 | 649.59 | cral n-terminus family protein |
| SEQ ID NO: 4125 | Nga03737.01 | 99.17 | 102.95 | ---NA--- |
| SEQ ID NO: 4126 | Nga03736 | 141.84 | 199.75 | ---NA--- |
| SEQ ID NO: 4127 | Nga03735 | 324.73 | 316.82 | nacht and ankyrin domain protein |
| SEQ ID NO: 4128 | Nga03734 | 257.91 | 368.14 | protein fam102b-like |
| SEQ ID NO: 4129 | Nga02908.2 | 1334.95 | 1391.30 | ras-related protein rab-7a |
| SEQ ID NO: 4130 | Nga01432.01 | 137.79 | 204.38 | amidophosphoribosyltransferase |
| SEQ ID NO: 4131 | Nga01427.01 | 422.55 | 474.99 | mitochondrial inner membrane protease atp23 homolog |
| SEQ ID NO: 4132 | Nga01426.01 | 551.80 | 429.80 | udp-glucose 4-epimerase |
| SEQ ID NO: 4133 | Nga01425.01 | 1500.78 | 1598.82 | protein |
| SEQ ID NO: 4134 | Nga01431.01 | 8.44 | 7.31 | protein |
| SEQ ID NO: 4135 | Nga01428.01 | 796.54 | 725.67 | snf7 family protein |
| SEQ ID NO: 4136 | Nga01429.01 | 3957.89 | 4347.07 | xylulose kinase |
| SEQ ID NO: 4137 | Nga06021 | 4816.12 | 4517.89 | gamma-butyrobetaine dioxygenase |
| SEQ ID NO: 4138 | Nga06026 | 119.32 | 125.15 | n-acetyltransferase 9 |
| SEQ ID NO: 4139 | Nga06023.1 | 1939.29 | 2664.40 | protein |
| SEQ ID NO: 4140 | Nga06025 | 239.55 | 288.66 | calcium calmodulin-dependent protein kinase i |
| SEQ ID NO: 4141 | Nga06022 | 607.42 | 694.43 | rna binding s1 domain-containing protein |
| SEQ ID NO: 4142 | Nga06027 | 259.69 | 258.21 | paired amphipathic helix repeat-containing protein |
| SEQ ID NO: 4143 | Nga06990.2 | 221.78 | 232.49 | transcriptional repressor sin3p |
| SEQ ID NO: 4144 | Nga01393 | 173.59 | 216.05 | hydroxyacid oxidase |
| SEQ ID NO: 4145 | Nga01394 | 221.43 | 147.01 | ---NA--- |
| SEQ ID NO: 4146 | Nga01392 | 137.93 | 127.00 | ---NA--- |
| SEQ ID NO: 4147 | Nga01395 | 81.08 | 175.66 | ---NA--- |
| SEQ ID NO: 4148 | Nga07156.2 | 329.26 | 355.64 | protein |
| SEQ ID NO: 4149 | Nga05559 | 150.38 | 160.86 | ---NA--- |
| SEQ ID NO: 4150 | Nga05566 | 201.26 | 292.95 | amidase |
| SEQ ID NO: 4151 | Nga05557 | 147.77 | 253.13 | amidase |
| SEQ ID NO: 4152 | Nga05567 | 641.38 | 560.29 | ---NA--- |
| SEQ ID NO: 4153 | Nga05036.02 | 303.62 | 307.90 | ---NA--- |
| SEQ ID NO: 4154 | Nga05556 | 201.60 | 156.40 | magnesium and cobalt efflux protein |
| SEQ ID NO: 4155 | Nga04246 | 70.06 | 100.04 | expressed unknown protein [Ectocarpus siliculosus] |
| SEQ ID NO: 4156 | Nga04247 | 131.16 | 97.76 | dna repair protein rad51 |
| SEQ ID NO: 4157 | Nga06068.2 | 668.74 | 647.92 | ---NA--- |
| SEQ ID NO: 4158 | Nga03890 | 44.33 | 78.75 | 60s ribosomal export protein |
| SEQ ID NO: 4159 | Nga03889 | 110.61 | 173.25 | 60s ribosomal export protein |
| SEQ ID NO: 4160 | Nga03882 | 176.99 | 233.04 | tfiih and nucleotide excision repair factor 3 complexes subunit |
| SEQ ID NO: 4161 | Nga03881 | 180.12 | 248.49 | syntaxin-like protein |
| SEQ ID NO: 4162 | Nga03883 | 152.09 | 116.29 | ribosomal rna-processing |
| SEQ ID NO: 4163 | Nga21284 | 175.68 | 204.94 | at2g47330-like protein |
| SEQ ID NO: 4164 | Nga21297 | 195.65 | 247.26 | atp-dependent rna helicase ddx42 |
| SEQ ID NO: 4165 | Nga21083 | 66.67 | 20.63 | peptide chain release factor 2 |
| SEQ ID NO: 4166 | Nga02236 | 138.61 | 169.49 | rna polymerase i subunit |
| SEQ ID NO: 4167 | Nga02802 | 292.00 | 226.76 | ---NA--- |
| SEQ ID NO: 4168 | Nga02799 | 382.88 | 790.47 | protein |
| SEQ ID NO: 4169 | Nga02800 | 218.71 | 276.19 | ---NA--- |
| SEQ ID NO: 4170 | Nga02798 | 2581.80 | 2745.92 | hypothetical protein FRAAL3804 [Frankia alni ACN14a] |
| SEQ ID NO: 4171 | Nga02801 | 894.36 | 1143.05 | protein |
| SEQ ID NO: 4172 | Nga04558 | 242.68 | 95.18 | ---NA--- |
| SEQ ID NO: 4173 | Nga05575 | 154.59 | 172.69 | ---NA--- |
| SEQ ID NO: 4174 | Nga04669 | 94.41 | 132.56 | ---NA--- |
| SEQ ID NO: 4175 | Nga04556 | 556.86 | 606.61 | o-acetylhomoserine o-acetylserine sulfhydrylase |
| SEQ ID NO: 4176 | Nga04557 | 180.56 | 131.64 | 4-hydroxybenzoyl- thioesterase family active site protein |
| SEQ ID NO: 4177 | Nga03690.1 | 1274.73 | 1353.05 | protein |

FIGURE 24 BN

| # | Nga model | +N rpkb | -N rpkb | GO |
|---|---|---|---|---|
| SEQ ID NO: 4178 | Nga03689 | 424.80 | 440.15 | pabp-dependent poly nuclease 3 isoform 2 |
| SEQ ID NO: 4179 | Nga03686 | 308.99 | 379.82 | lipase-related protein |
| SEQ ID NO: 4180 | Nga03688 | 588.61 | 479.91 | ---NA--- |
| SEQ ID NO: 4181 | Nga03687 | 378.26 | 322.84 | glycoside |
| SEQ ID NO: 4182 | Nga04186 | 22.82 | 33.93 | ---NA--- |
| SEQ ID NO: 4183 | Nga20482 | 381.68 | 304.30 | ---NA--- |
| SEQ ID NO: 4184 | Nga04081 | 209.15 | 251.34 | ---NA--- |
| SEQ ID NO: 4185 | Nga04080 | 250.48 | 200.37 | snare ykt6 |
| SEQ ID NO: 4186 | Nga04079 | 2622.49 | 2201.27 | predicted protein [Phaeodactylum tricornutum CCAP 1055/1] |
| SEQ ID NO: 4187 | Nga02406 | 2021.81 | 1602.92 | tim10 ddp zinc finger domain-containing protein |
| SEQ ID NO: 4188 | Nga04992.02 | 200.00 | 256.04 | ---NA--- |
| SEQ ID NO: 4189 | Nga20747 | 288.95 | 346.76 | protein |
| SEQ ID NO: 4190 | Nga04991.2 | 177.95 | 180.89 | beta like 1 |
| SEQ ID NO: 4191 | Nga05174 | 21.28 | 30.73 | ---NA--- |
| SEQ ID NO: 4192 | Nga06489 | 94.02 | 115.73 | ---NA--- |
| SEQ ID NO: 4193 | Nga06491 | 1149.32 | 1548.88 | ---NA--- |
| SEQ ID NO: 4194 | Nga06490 | 51.28 | 138.88 | ---NA--- |
| SEQ ID NO: 4195 | Nga06488 | 174.96 | 178.09 | gamma-tubulin complex component 4 |
| SEQ ID NO: 4196 | Nga07034 | 1482.27 | 1361.72 | glycosyl hydrolase |
| SEQ ID NO: 4197 | Nga07211 | 139.39 | 196.95 | ---NA--- |
| SEQ ID NO: 4198 | Nga21126.1 | 152.35 | 114.02 | ---NA--- |
| SEQ ID NO: 4199 | Nga02383 | 337.02 | 418.93 | ---NA--- |
| SEQ ID NO: 4200 | Nga02382 | 331.33 | 396.27 | ---NA--- |
| SEQ ID NO: 4201 | Nga04696.2 | 255.49 | 258.36 | duf1212 domain membrane protein |
| SEQ ID NO: 4202 | Nga20818 | 728.78 | 748.22 | atp binding protein |
| SEQ ID NO: 4203 | Nga02289 | 8268.79 | 8215.05 | protein |
| SEQ ID NO: 4204 | Nga02291 | 1539.47 | 1618.20 | ---NA--- |
| SEQ ID NO: 4205 | Nga02293 | 729.97 | 754.35 | protein |
| SEQ ID NO: 4206 | Nga21209 | 536.25 | 685.61 | aminotransferase class iv |
| SEQ ID NO: 4207 | Nga02297 | 180.49 | 165.57 | at2g30800-like protein |
| SEQ ID NO: 4208 | Nga02290 | 893.10 | 778.45 | protein |
| SEQ ID NO: 4209 | Nga02292 | 111.78 | 121.08 | atp-dependent rna helicase dhx57 |
| SEQ ID NO: 4210 | Nga01585 | 183.62 | 126.48 | glycoprotein 3-alpha-l-fucosyltransferase |
| SEQ ID NO: 4211 | Nga01586 | 220.83 | 191.82 | at5g52030 msg15_11 |
| SEQ ID NO: 4212 | Nga01584 | 1170.34 | 1282.95 | mitochondrial ribosomal protein l53-like |
| SEQ ID NO: 4213 | Nga01583 | 7583.92 | 8057.97 | ---NA--- |
| SEQ ID NO: 4214 | Nga06713 | 1007.35 | 910.00 | dihydrolipoamide s-succinyltransferase |
| SEQ ID NO: 4215 | Nga06144.2 | 861.43 | 810.33 | hydroxyacyl-coenzyme a mitochondrial precursor |
| SEQ ID NO: 4216 | Nga20440 | 186.58 | 252.07 | ---NA--- |
| SEQ ID NO: 4217 | Nga06712 | 527.61 | 469.62 | protein |
| SEQ ID NO: 4218 | Nga06715 | 791.58 | 836.88 | adenylyl cyclase-associated protein 1 |
| SEQ ID NO: 4219 | Nga01790 | 311.85 | 317.40 | kynurenine 3-monooxygenase |
| SEQ ID NO: 4220 | Nga01759.02 | 1722.32 | 1588.87 | hypersensitive-induced response protein |
| SEQ ID NO: 4221 | Nga01761.02 | 3718.91 | 3827.70 | enoyl- hydratase isomerase |
| SEQ ID NO: 4222 | Nga04382 | 531.86 | 574.12 | ---NA--- |
| SEQ ID NO: 4223 | Nga01762.02 | 101.10 | 76.18 | ---NA--- |
| SEQ ID NO: 4224 | Nga03028.02 | 324.19 | 305.47 | protein |
| SEQ ID NO: 4225 | Nga03505 | 844.74 | 939.76 | protein |
| SEQ ID NO: 4226 | Nga03023.02 | 1230.97 | 1157.16 | protein |
| SEQ ID NO: 4227 | Nga03506 | 2623.25 | 2613.09 | abc subfamily abcg |
| SEQ ID NO: 4228 | Nga03027.02 | 1082.49 | 1021.23 | protein |
| SEQ ID NO: 4229 | Nga03025.02 | 1242.21 | 1453.40 | protein |
| SEQ ID NO: 4230 | Nga06862 | 9.30 | 45.34 | ---NA--- |
| SEQ ID NO: 4231 | Nga00958.01 | 980.74 | 1281.43 | ribosome biogenesis regulatory protein |
| SEQ ID NO: 4232 | Nga00957 | 2070.46 | 2101.51 | ferredoxin-thioredoxin catalytic chain |
| SEQ ID NO: 4233 | Nga20802 | 185.37 | 291.74 | rrna processing protein |
| SEQ ID NO: 4234 | Nga00959 | 89.06 | 135.06 | ---NA--- |
| SEQ ID NO: 4235 | Nga06800 | 543.11 | 590.24 | puff-specific protein bx42 |
| SEQ ID NO: 4236 | Nga00429.02 | 7422.34 | 5958.48 | thioredoxin f |
| SEQ ID NO: 4237 | Nga04442.2 | 326.91 | 360.01 | sh2 domain containing protein |
| SEQ ID NO: 4238 | Nga04300.01 | 4487.61 | 4325.42 | conserved hypothetical protein [Phytophthora infestans T30-4] |
| SEQ ID NO: 4239 | Nga04301.01 | 421.84 | 328.82 | udp-n-acetylglucosamine transporter |
| SEQ ID NO: 4240 | Nga04299.01 | 10843.09 | 11728.31 | 40s ribosomal protein |
| SEQ ID NO: 4241 | Nga06995 | 1080.94 | 937.10 | protein |

FIGURE 24 BO

| # | Nga model | +N rpkb | -N rpkb | GO |
|---|---|---|---|---|
| SEQ ID NO: 4242 | Nga02623.2 | 3232.20 | 3711.72 | molybdenum cofactor synthesis 1 |
| SEQ ID NO: 4243 | Nga01767.01 | 2941.61 | 3178.54 | h aca ribonucleoprotein complex subunit 2-like protein |
| SEQ ID NO: 4244 | Nga01765.01 | 492.62 | 522.68 | cystathionine gamma-lyase |
| SEQ ID NO: 4245 | Nga01764.01 | 4929.60 | 5797.47 | protein |
| SEQ ID NO: 4246 | Nga04484 | 3847.96 | 3777.47 | soul heme-binding protein |
| SEQ ID NO: 4247 | Nga04485 | 4519.55 | 4143.06 | ribosomal protein l7ae l30e s12e gadd45 family protein |
| SEQ ID NO: 4248 | Nga04486 | 5580.20 | 5582.36 | protein tyrosine phosphatase type iva protein 1 |
| SEQ ID NO: 4249 | Nga04340.1 | 661.33 | 756.32 | mitochondrion protein |
| SEQ ID NO: 4250 | Nga06844.1 | 3618.52 | 7053.06 | ferredoxin (2fe-2s) |
| SEQ ID NO: 4251 | Nga01222.02 | 694.92 | 575.64 | uv excision repair protein |
| SEQ ID NO: 4252 | Nga04202.01 | 741.78 | 699.29 | udp-glucuronate decarboxylase 1 |
| SEQ ID NO: 4253 | Nga04201.01 | 917.26 | 756.97 | 3-oxoacyl-(acyl-carrier-protein) synthase 2 |
| SEQ ID NO: 4254 | Nga04206.01 | 698.41 | 747.95 | ---NA--- |
| SEQ ID NO: 4255 | Nga04203.01 | 23497.08 | 20695.47 | ---NA--- |
| SEQ ID NO: 4256 | Nga02299 | 2695.44 | 2560.89 | amp-dependent synthetase and ligase |
| SEQ ID NO: 4257 | Nga02300 | 416.47 | 356.03 | udp-n-acetylglucosamine--dolichyl-phosphate n-acetylglucosaminephosphotransferase |
| SEQ ID NO: 4258 | Nga02302 | 6893.55 | 7685.14 | 60s ribosomal protein l6 |
| SEQ ID NO: 4259 | Nga02301 | 597.28 | 518.04 | peptidyl-prolyl cis-trans isomerase d-like |
| SEQ ID NO: 4260 | Nga02298 | 834.60 | 1019.95 | nacht and ankyrin domain protein |
| SEQ ID NO: 4261 | Nga01929 | 653.16 | 606.67 | leucine carboxyl methyltransferase |
| SEQ ID NO: 4262 | Nga01930 | 3133.33 | 2946.86 | protein |
| SEQ ID NO: 4263 | Nga01932 | 905.41 | 1044.20 | protein |
| SEQ ID NO: 4264 | Nga01931 | 609.03 | 758.26 | phosphoribosylaminoimidazole carboxylase |
| SEQ ID NO: 4265 | Nga20865 | 657.84 | 769.18 | protein |
| SEQ ID NO: 4266 | Nga01732 | 294.22 | 318.71 | ---NA--- |
| SEQ ID NO: 4267 | Nga01728 | 409.67 | 370.73 | ---NA--- |
| SEQ ID NO: 4268 | Nga01731 | 492.46 | 563.16 | dimethyladenosine transferase |
| SEQ ID NO: 4269 | Nga01727 | 341.69 | 344.99 | retinol retinaldehyde reductase |
| SEQ ID NO: 4270 | Nga07148 | 643.20 | 828.31 | ectonucleoside triphosphate diphosphohydrolase 7 |
| SEQ ID NO: 4271 | Nga07286 | 159.37 | 127.65 | ---NA--- |
| SEQ ID NO: 4272 | Nga05414.02 | 2174.78 | 2062.85 | peptide methionine sulfoxide reductase |
| SEQ ID NO: 4273 | Nga04891 | 838.80 | 842.75 | saccharopine dehydrogenase |
| SEQ ID NO: 4274 | Nga04892.1 | 449.06 | 410.90 | pentatricopeptide repeat-containing protein |
| SEQ ID NO: 4275 | Nga20558.1 | 308.61 | 329.47 | b chain snapshots of the rna processing factor scaf8 bound to different phosphorylated forms of the carboxy-terminal domain of rna-polymerase ii |
| SEQ ID NO: 4276 | Nga00516.02 | 4916.85 | 4334.15 | expressed unknown protein [Ectocarpus siliculosus] |
| SEQ ID NO: 4277 | Nga20382.1 | 238.26 | 167.21 | conserved unknown protein [Ectocarpus siliculosus] |
| SEQ ID NO: 4278 | Nga21003.1 | 174.83 | 208.31 | conserved unknown protein [Ectocarpus siliculosus] |
| SEQ ID NO: 4279 | Nga20361.1 | 321.43 | 236.67 | conserved unknown protein [Ectocarpus siliculosus] |
| SEQ ID NO: 4280 | Nga03718 | 904.31 | 1005.07 | endonuclease iii |
| SEQ ID NO: 4281 | Nga00522.02 | 15290.02 | 7760.55 | chloroplast light harvesting protein isoform 4 |
| SEQ ID NO: 4282 | Nga03717.1 | 403.36 | 506.72 | ankyrin repeat-containing protein |
| SEQ ID NO: 4283 | Nga06867 | 785.48 | 937.37 | ---NA--- |
| SEQ ID NO: 4284 | Nga06863 | 591.27 | 558.81 | ferredoxin |
| SEQ ID NO: 4285 | Nga07010 | 53127.19 | 15716.39 | protein fucoxanthin chlorophyll a c protein |
| SEQ ID NO: 4286 | Nga01818 | 2764.95 | 2945.25 | mitogen-activated protein kinase 4 |
| SEQ ID NO: 4287 | Nga01819 | 480.42 | 477.23 | vacuolar protein sorting-associated protein 53 homolog |
| SEQ ID NO: 4288 | Nga20522 | 174.56 | 132.37 | protein |
| SEQ ID NO: 4289 | Nga07123 | 496.11 | 554.25 | 2-alkenal reductase |
| SEQ ID NO: 4290 | Nga07124 | 297.50 | 318.20 | c3hc zinc finger-like protein |
| SEQ ID NO: 4291 | Nga04438 | 65.04 | 70.45 | ---NA--- |
| SEQ ID NO: 4292 | Nga00983.02 | 1637.10 | 1510.56 | peptidyl-prolyl cis-trans isomerase |
| SEQ ID NO: 4293 | Nga07249 | 1277.35 | 1160.41 | two component regulator propeller domain-containing protein |
| SEQ ID NO: 4294 | Nga00141 | 106.27 | 164.80 | cobalamin synthesis protein p47k |
| SEQ ID NO: 4295 | Nga20147 | 432.21 | 472.13 | hypothetical protein MMP0558 [Methanococcus maripaludis S2] |
| SEQ ID NO: 4296 | Nga00120 | 777.78 | 671.23 | protein |
| SEQ ID NO: 4297 | Nga00121 | 251.31 | 334.61 | ---NA--- |
| SEQ ID NO: 4298 | Nga20133 | 428.45 | 516.23 | e3 ubiquitin-protein ligase upl6 |
| SEQ ID NO: 4299 | Nga00123 | 4518.17 | 4161.81 | protein |
| SEQ ID NO: 4300 | Nga00115 | 5554.31 | 5648.21 | protein |
| SEQ ID NO: 4301 | Nga00124 | 919.72 | 95.41 | ---NA--- |
| SEQ ID NO: 4302 | Nga00118 | 144.66 | 132.70 | nuclear serine protease 2 |

FIGURE 24 BP

| # | Nga model | +N rpkb | -N rpkb | GO |
|---|---|---|---|---|
| SEQ ID NO: 4303 | Nga00122 | 233.72 | 219.97 | ---NA--- |
| SEQ ID NO: 4304 | Nga00117 | 3161.26 | 2770.22 | phosphoadenosine phosphosulfate reductase |
| SEQ ID NO: 4305 | Nga20939 | 595.41 | 509.42 | polycomb group ring finger protein 3 |
| SEQ ID NO: 4306 | Nga00119 | 857.71 | 819.37 | programmed cell death 6-interacting |
| SEQ ID NO: 4307 | Nga20539 | 181.11 | 167.12 | e3 ubiquitin-protein ligase listerin |
| SEQ ID NO: 4308 | Nga00116 | 1334.46 | 1362.92 | heat shock protein atpase subunit |
| SEQ ID NO: 4309 | Nga06866 | 355.79 | 322.71 | gtp-binding protein |
| SEQ ID NO: 4310 | Nga02286 | 165.08 | 123.80 | transcriptional family |
| SEQ ID NO: 4311 | Nga20034 | 234.53 | 250.52 | protein |
| SEQ ID NO: 4312 | Nga02283 | 125.38 | 162.32 | ---NA--- |
| SEQ ID NO: 4313 | Nga02284 | 199.75 | 171.92 | protein |
| SEQ ID NO: 4314 | Nga06309 | 299.35 | 291.42 | beta- -endoglucanase |
| SEQ ID NO: 4315 | Nga06308 | 1155.72 | 1408.86 | ---NA--- |
| SEQ ID NO: 4316 | Nga00357.02 | 1129.63 | 1157.86 | dihydrolipoyllysine-residue acetyltransferase component of pyruvate dehydrogenase mitochondrial |
| SEQ ID NO: 4317 | Nga00351.02 | 7803.56 | 7858.48 | atp synthase gamma |
| SEQ ID NO: 4318 | Nga00390.02 | 251.80 | 311.72 | ---NA--- |
| SEQ ID NO: 4319 | Nga03353.2 | 115.18 | 79.63 | insulin degrading enzyme |
| SEQ ID NO: 4320 | Nga00003.02 | 13762.20 | 16785.78 | ethylmalonic encephalopathy 1 |
| SEQ ID NO: 4321 | Nga03123 | 397.98 | 348.53 | hypothetical protein (Partial) [Ectocarpus siliculosus] |
| SEQ ID NO: 4322 | Nga03931 | 3914.89 | 3541.64 | ---NA--- |
| SEQ ID NO: 4323 | Nga01497 | 570.00 | 483.84 | retinoblastoma binding protein 9 |
| SEQ ID NO: 4324 | Nga05340.01 | 143.72 | 176.37 | ---NA--- |
| SEQ ID NO: 4325 | Nga03146.1 | 107.14 | 107.46 | ---NA--- |
| SEQ ID NO: 4326 | Nga06544 | 364.22 | 410.68 | auxin efflux carrier |
| SEQ ID NO: 4327 | Nga00213 | 140.63 | 263.76 | g-patch domain-contaning protein |
| SEQ ID NO: 4328 | Nga20612.1 | 157.69 | 166.65 | predicted protein [Thalassiosira pseudonana CCMP1335] |
| SEQ ID NO: 4329 | Nga01560 | 1751.16 | 1458.59 | translocase of inner mitochondrial membrane 13 homolog |
| SEQ ID NO: 4330 | Nga01545 | 99.50 | 106.17 | ---NA--- |
| SEQ ID NO: 4331 | Nga02805.1 | 1504.93 | 1312.22 | uncharacterized fam18-like protein cg5021 |
| SEQ ID NO: 4332 | Nga20318.1 | 568.29 | 583.89 | lyr family of fe s cluster biogenesis protein |
| SEQ ID NO: 4333 | Nga06421 | 1570.30 | 1529.52 | fk506-binding protein fkbp59 |
| SEQ ID NO: 4334 | Nga01185 | 3774.81 | 3533.60 | tha4 hcf106 protein |
| SEQ ID NO: 4335 | Nga01449 | 565.66 | 635.58 | pre-mrna-splicing factor sf2 |
| SEQ ID NO: 4336 | Nga20586 | 154.17 | 361.08 | ---NA--- |
| SEQ ID NO: 4337 | Nga00540 | 66.03 | 54.36 | ash1 ( or homeotic)-like |
| SEQ ID NO: 4338 | Nga00566.01 | 651.76 | 609.10 | protein bud31 homolog |
| SEQ ID NO: 4339 | Nga03403 | 151.02 | 115.69 | enoyl-(acyl-carrier-protein) reductase ii |
| SEQ ID NO: 4340 | Nga01433.01 | 155.32 | 150.82 | ---NA--- |
| SEQ ID NO: 4341 | Nga20556 | 74.58 | 128.52 | ---NA--- |
| SEQ ID NO: 4342 | Nga06659 | 112.61 | 68.31 | kinesin family member 17 |
| SEQ ID NO: 4343 | Nga20999 | 2334.57 | 2600.46 | lanc-like protein 2-like |
| SEQ ID NO: 4344 | Nga01457.02 | 2910.32 | 2344.79 | ---NA--- |
| SEQ ID NO: 4345 | Nga06215.2 | 576.74 | 467.58 | conserved unknown protein [Ectocarpus siliculosus] |
| SEQ ID NO: 4346 | Nga20279 | 226.64 | 303.71 | vacuolar protein sorting-associated protein 13b-like |
| SEQ ID NO: 4347 | Nga00860.01 | 675.03 | 625.47 | ribosomal protein l22 |
| SEQ ID NO: 4348 | Nga20485 | 390.56 | 357.98 | l-aminoadipate-semialdehyde dehydrogenase-phosphopantetheinyl |
| SEQ ID NO: 4349 | Nga02880.1 | 960.14 | 1295.31 | ras-related protein rab-2-a |
| SEQ ID NO: 4350 | Nga05781 | 1355.28 | 1178.35 | tryptophan-rich sensory-like protein |
| SEQ ID NO: 4351 | Nga01466 | 235.52 | 281.81 | ---NA--- |
| SEQ ID NO: 4352 | Nga06310 | 299.35 | 291.42 | cobalamin synthesis protein p47k |
| SEQ ID NO: 4353 | Nga05671 | 1965.21 | 1963.54 | protein |
| SEQ ID NO: 4354 | Nga00605 | 2069.28 | 1513.53 | brain protein 44 |
| SEQ ID NO: 4355 | Nga00047 | 177.27 | 169.43 | ---NA--- |
| SEQ ID NO: 4356 | Nga00019 | 220.19 | 326.12 | ---NA--- |
| SEQ ID NO: 4357 | Nga05939 | 550.22 | 691.84 | ---NA--- |
| SEQ ID NO: 4358 | Nga06378 | 319.62 | 317.54 | nucleolar complex protein 4 homolog |
| SEQ ID NO: 4359 | Nga00555 | 17193.81 | 16126.38 | ---NA--- |
| SEQ ID NO: 4360 | Nga20118.1 | 493.58 | 483.69 | protein |
| SEQ ID NO: 4361 | Nga02826.1 | 58.44 | 112.54 | ---NA--- |
| SEQ ID NO: 4362 | Nga05423 | 1400.86 | 1322.40 | short-chain dehydrogenase reductase sdr |
| SEQ ID NO: 4363 | Nga06112 | 161.70 | 208.46 | ccaat enhancer-binding protein zeta |
| SEQ ID NO: 4364 | Nga05385 | 57.32 | 85.02 | histone-lysine n- h3 lysine-36 and h4 lysine-20 specific |
| SEQ ID NO: 4365 | Nga00410 | 231.54 | 254.81 | anthranilate anthranilate chorismate lyase |

FIGURE 24 BQ

| # | Nga model | +N rpkb | -N rpkb | GO |
|---|---|---|---|---|
| SEQ ID NO: 4366 | Nga21031 | 824.51 | 617.82 | integral membrane protein |
| SEQ ID NO: 4367 | Nga00419 | 235.82 | 258.32 | protein |
| SEQ ID NO: 4368 | Nga00417.01 | 2296.52 | 2372.48 | ubiquitin domain containing protein |
| SEQ ID NO: 4369 | Nga00421 | 1069.33 | 1057.11 | protein |
| SEQ ID NO: 4370 | Nga00415 | 92.24 | 118.09 | fructose- -bisphosphatase |
| SEQ ID NO: 4371 | Nga00423 | 9133.82 | 9269.43 | ---NA--- |
| SEQ ID NO: 4372 | Nga00418 | 376.79 | 369.46 | potential zinc ring finger protein |
| SEQ ID NO: 4373 | Nga00424.01 | 745.64 | 614.04 | ---NA--- |
| SEQ ID NO: 4374 | Nga00416 | 1058.60 | 1189.17 | regulator of nonsense |
| SEQ ID NO: 4375 | Nga00426.1 | 1419.72 | 1439.10 | ---NA--- |
| SEQ ID NO: 4376 | Nga00414 | 1534.76 | 1211.72 | uncharacterized protein |
| SEQ ID NO: 4377 | Nga00412.01 | 1750.00 | 1613.68 | hsp12 variant c |
| SEQ ID NO: 4378 | Nga00427 | 709.52 | 593.20 | ---NA--- |
| SEQ ID NO: 4379 | Nga20881 | 546.32 | 601.41 | cerebion |
| SEQ ID NO: 4380 | Nga00420 | 576.55 | 556.48 | peptide chain release factor 3 |
| SEQ ID NO: 4381 | Nga00411.01 | 482.54 | 523.47 | werner syndrome atp-dependent helicase |
| SEQ ID NO: 4382 | Nga20806 | 2332.13 | 2153.72 | zinc finger family protein |
| SEQ ID NO: 4383 | Nga20973 | 2628.27 | 2906.41 | epidermal retinol dehydrogenase 2-like |
| SEQ ID NO: 4384 | Nga00422 | 5301.78 | 5447.64 | 40s ribosomal protein s6 |
| SEQ ID NO: 4385 | Nga00409.01 | 677.72 | 774.35 | protein |
| SEQ ID NO: 4386 | Nga00413 | 1640.72 | 1670.37 | ---NA--- |
| SEQ ID NO: 4387 | Nga00425.01 | 135.47 | 105.18 | ---NA--- |
| SEQ ID NO: 4388 | Nga20006.1 | 310.25 | 339.07 | trafficking protein particle complex subunit 2-like protein |
| SEQ ID NO: 4389 | Nga20233.1 | 404.29 | 389.50 | protein |
| SEQ ID NO: 4390 | Nga03468.1 | 2891.09 | 2994.98 | small nuclear ribonucleoprotein sm d1 |
| SEQ ID NO: 4391 | Nga03467.1 | 1522.52 | 1537.00 | alpha-actinin |
| SEQ ID NO: 4392 | Nga03473.01 | 106.80 | 59.60 | ---NA--- |
| SEQ ID NO: 4393 | Nga03471 | 133.69 | 193.48 | ---NA--- |
| SEQ ID NO: 4394 | Nga03465.01 | 386.41 | 365.68 | protein |
| SEQ ID NO: 4395 | Nga03463 | 900.83 | 971.74 | protein |
| SEQ ID NO: 4396 | Nga03464 | 1042.75 | 1005.51 | protein |
| SEQ ID NO: 4397 | Nga20702 | 174.11 | 169.26 | protein |
| SEQ ID NO: 4398 | Nga03466 | 334.64 | 374.53 | plasma glutamate carboxypeptidase |
| SEQ ID NO: 4399 | Nga03472 | 826.67 | 730.58 | molybdenum cofactor sulfurase |
| SEQ ID NO: 4400 | Nga20274.1 | 132.25 | 159.18 | apoptosis-inducing mitochondrion-associated 1 |
| SEQ ID NO: 4401 | Nga03469.1 | 369.78 | 427.31 | fad-dependent pyridine nucleotide-disulphide oxidoreductase |
| SEQ ID NO: 4402 | Nga03470 | 164.07 | 184.16 | mate efflux family protein |
| SEQ ID NO: 4403 | Nga05434 | 232.64 | 246.27 | ---NA--- |
| SEQ ID NO: 4404 | Nga05428.01 | 459.75 | 494.95 | aminotransferase class i and ii |
| SEQ ID NO: 4405 | Nga05436 | 11618.52 | 12300.72 | 40s ribosomal protein s28 |
| SEQ ID NO: 4406 | Nga20121.1 | 450.83 | 415.57 | oxidoreductase |
| SEQ ID NO: 4407 | Nga20193.1 | 334.91 | 301.25 | gtp-binding protein 1 |
| SEQ ID NO: 4408 | Nga05435 | 90.49 | 95.55 | nol1 nop2 sun domain member 5-like |
| SEQ ID NO: 4409 | Nga05437 | 153.65 | 180.54 | gtp-binding protein 2 |
| SEQ ID NO: 4410 | Nga05429 | 541.34 | 651.25 | trna uridine 5-carboxymethylaminomethyl modification enzyme |
| SEQ ID NO: 4411 | Nga05431 | 489.38 | 569.05 | protein |
| SEQ ID NO: 4412 | Nga05432 | 966.40 | 1017.72 | dna rna helicase |
| SEQ ID NO: 4413 | Nga05427 | 486.71 | 476.27 | transcription initiation factor tfiid subunit 13 |
| SEQ ID NO: 4414 | Nga05430 | 1323.53 | 1158.69 | transferase-like protein |
| SEQ ID NO: 4415 | Nga05433 | 729.61 | 1246.63 | phosphatidylinositol 3-and 4-kinase family protein |
| SEQ ID NO: 4416 | Nga05773.1 | 490.27 | 531.73 | cystathionine gamma-synthase |
| SEQ ID NO: 4417 | Nga05778 | 221.46 | 295.54 | conserved hypothetical protein [Albugo laibachii Nc14] |
| SEQ ID NO: 4418 | Nga20968.1 | 333.78 | 290.13 | dna methyltransferase 1-associated protein 1 |
| SEQ ID NO: 4419 | Nga05774.1 | 266.18 | 279.07 | protein |
| SEQ ID NO: 4420 | Nga04323.02 | 677.91 | 672.84 | cation diffusion facilitator family |
| SEQ ID NO: 4421 | Nga05776 | 834.76 | 1014.57 | aldehyde dehydrogenase |
| SEQ ID NO: 4422 | Nga04909.02 | 769.63 | 764.50 | nudix hydrolase |
| SEQ ID NO: 4423 | Nga04908.02 | 6196.84 | 5891.65 | sugar nucleotide epimerase |
| SEQ ID NO: 4424 | Nga04786.02 | 69.89 | 75.71 | ---NA--- |
| SEQ ID NO: 4425 | Nga05775.1 | 126.41 | 162.74 | rep helicase |
| SEQ ID NO: 4426 | Nga21302.1 | 526.74 | 512.65 | protein |
| SEQ ID NO: 4427 | Nga21093 | 138.78 | 97.27 | glucose-methanol-choline oxidoreductase |
| SEQ ID NO: 4428 | Nga21305 | 127.43 | 191.85 | glucose-methanol-choline oxidoreductase |
| SEQ ID NO: 4429 | Nga04299.02 | 10843.09 | 11728.31 | 40s ribosomal protein |

FIGURE 24 BR

| # | Nga model | +N rpkb | -N rpkb | GO |
|---|---|---|---|---|
| SEQ ID NO: 4430 | Nga21262 | 183.27 | 211.47 | chloride channel protein |
| SEQ ID NO: 4431 | Nga04301.02 | 421.84 | 328.82 | udp-n-acetylglucosamine transporter |
| SEQ ID NO: 4432 | Nga20502 | 115.27 | 115.50 | chloride channel protein |
| SEQ ID NO: 4433 | Nga21098 | 366.91 | 293.21 | cyclase dehydrase |
| SEQ ID NO: 4434 | Nga05113 | 93.48 | 98.90 | chloride channel |
| SEQ ID NO: 4435 | Nga04300.02 | 4487.61 | 4325.42 | conserved hypothetical protein [Phytophthora infestans T30-4] |
| SEQ ID NO: 4436 | Nga05110 | 177.26 | 222.47 | kynurenine-oxoglutarate transaminase |
| SEQ ID NO: 4437 | Nga04404.02 | 605.65 | 741.74 | alpha beta hydrolase fold-3 domain protein |
| SEQ ID NO: 4438 | Nga05114 | 189.72 | 256.89 | ---NA--- |
| SEQ ID NO: 4439 | Nga04403.02 | 6167.72 | 5668.70 | conserved unknown protein [Ectocarpus siliculosus] |
| SEQ ID NO: 4440 | Nga05106 | 330.77 | 385.93 | hypothetical protein LEPBi_I1092 [Leptospira biflexa serovar Patoc strain 'Patoc 1 (Paris)'] |
| SEQ ID NO: 4441 | Nga05105.1 | 914.78 | 737.06 | ---NA--- |
| SEQ ID NO: 4442 | Nga05107 | 156.93 | 100.15 | n-alpha-acetyltransferase catalytic subunit |
| SEQ ID NO: 4443 | Nga05111 | 185.93 | 126.29 | conserved unknown protein [Ectocarpus siliculosus] |
| SEQ ID NO: 4444 | Nga05126 | 399.22 | 372.03 | myo-inositol monophosphatase 1 |
| SEQ ID NO: 4445 | Nga01091.02 | 876.21 | 843.98 | ---NA--- |
| SEQ ID NO: 4446 | Nga01342.02 | 7.94 | 30.09 | urease accessory protein ured |
| SEQ ID NO: 4447 | Nga05127 | 53.65 | 42.87 | protein |
| SEQ ID NO: 4448 | Nga05130 | 1046.38 | 985.70 | methyltransferase type 11 |
| SEQ ID NO: 4449 | Nga20004.1 | 185.85 | 183.29 | cwf19-like protein 1-like |
| SEQ ID NO: 4450 | Nga02425.02 | 694.25 | 646.58 | er lumen protein retaining receptor |
| SEQ ID NO: 4451 | Nga05143 | 1353.40 | 1646.58 | hypothetical protein CHLNCDRAFT_49994 [Chlorella variabilis] |
| SEQ ID NO: 4452 | Nga02423.2 | 477.62 | 861.12 | methylenetetrahydrofolate dehydrogenase |
| SEQ ID NO: 4453 | Nga04766.02 | 235.09 | 237.81 | 2-dehydropantoate 2-reductase |
| SEQ ID NO: 4454 | Nga04767.02 | 387.65 | 415.88 | ---NA--- |
| SEQ ID NO: 4455 | Nga20746 | 207.37 | 189.69 | ---NA--- |
| SEQ ID NO: 4456 | Nga05141 | 4366.45 | 3933.67 | plastid transcriptionally active 4 |
| SEQ ID NO: 4457 | Nga02146.2 | 1490.27 | 2171.59 | cysteine desulfurase |
| SEQ ID NO: 4458 | Nga06064 | 1678.05 | 192.34 | protein |
| SEQ ID NO: 4459 | Nga06065 | 824.32 | 607.47 | nad-dependent epimerase dehydratase family protein |
| SEQ ID NO: 4460 | Nga06069 | 197.22 | 72.22 | protein |
| SEQ ID NO: 4461 | Nga06066 | 339.36 | 340.75 | sphingosine-1-phosphate lyase |
| SEQ ID NO: 4462 | Nga06068.1 | 668.74 | 647.92 | ---NA--- |
| SEQ ID NO: 4463 | Nga06070 | 74.73 | 115.65 | nonsense-mediated mrna decay protein |
| SEQ ID NO: 4464 | Nga06067 | 774.94 | 1146.49 | 3-hydroxyisobutyrate dehydrogenase |
| SEQ ID NO: 4465 | Nga06471 | 6546.79 | 6513.89 | ---NA--- |
| SEQ ID NO: 4466 | Nga06473 | 519.48 | 539.27 | protein |
| SEQ ID NO: 4467 | Nga06470 | 408.66 | 467.06 | ---NA--- |
| SEQ ID NO: 4468 | Nga04013.2 | 410.44 | 447.00 | conserved hypothetical protein [Phytophthora infestans T30-4] |
| SEQ ID NO: 4469 | Nga06595 | 378.47 | 425.02 | ---NA--- |
| SEQ ID NO: 4470 | Nga20074.1 | 1108.25 | 1092.17 | hypothetical protein CHLNCDRAFT_136236 [Chlorella variabilis] |
| SEQ ID NO: 4471 | Nga06591 | 709.87 | 546.67 | amidase |
| SEQ ID NO: 4472 | Nga06594 | 289.70 | 301.99 | protein |
| SEQ ID NO: 4473 | Nga06596 | 547.04 | 411.40 | ---NA--- |
| SEQ ID NO: 4474 | Nga00042.02 | 832.16 | 913.49 | dna replication licensing factor mcm9 |
| SEQ ID NO: 4475 | Nga00043.02 | 365.38 | 399.82 | myosin light chain kinase |
| SEQ ID NO: 4476 | Nga06254 | 1104.17 | 1431.27 | sorting nexin-16-like |
| SEQ ID NO: 4477 | Nga01897.02 | 683.24 | 641.17 | yip1 domain-containing protein |
| SEQ ID NO: 4478 | Nga20112 | 494.72 | 530.40 | transcription initiation factor subunit taf1 |
| SEQ ID NO: 4479 | Nga06253 | 51.48 | 78.61 | conserved unknown protein [Ectocarpus siliculosus] |
| SEQ ID NO: 4480 | Nga20231.1 | 190.92 | 226.82 | tbc1 domain family member 23-like |
| SEQ ID NO: 4481 | Nga04988.02 | 75.51 | 103.10 | translation elongation factor g |
| SEQ ID NO: 4482 | Nga06274 | 3964.88 | 3658.18 | ---NA--- |
| SEQ ID NO: 4483 | Nga06278 | 1836.55 | 1524.71 | choline dehydrogenase |
| SEQ ID NO: 4484 | Nga06276.01 | 757.34 | 708.32 | coiled-coil domain-containing protein 124 |
| SEQ ID NO: 4485 | Nga06279 | 5742.72 | 6029.65 | protein |
| SEQ ID NO: 4486 | Nga21217.1 | 81.08 | 66.92 | atp synthase alpha subunit |
| SEQ ID NO: 4487 | Nga06275.01 | 1840.26 | 1797.89 | protein rer1a |
| SEQ ID NO: 4488 | Nga06277 | 192.05 | 277.38 | u3 small nucleolar rna-associated |
| SEQ ID NO: 4489 | Nga06439 | 641.27 | 626.94 | ---NA--- |
| SEQ ID NO: 4490 | Nga06440 | 1500.00 | 1348.22 | protein prune homolog |
| SEQ ID NO: 4491 | Nga06444 | 368.75 | 426.52 | s-adenosylmethionine carrier 1 |
| SEQ ID NO: 4492 | Nga06443 | 1355.93 | 1356.59 | ---NA--- |

FIGURE 24 BS

| # | Nga model | +N rpkb | -N rpkb | GO |
|---|---|---|---|---|
| SEQ ID NO: 4493 | Nga06441 | 1895.96 | 2273.77 | protein |
| SEQ ID NO: 4494 | Nga06442 | 847.27 | 917.16 | topoisomerase 6 subunit a |
| SEQ ID NO: 4495 | Nga06446 | 1223.10 | 1075.87 | protein |
| SEQ ID NO: 4496 | Nga06445 | 862.99 | 860.61 | cg6554 |
| SEQ ID NO: 4497 | Nga01313 | 273.58 | 284.43 | ---NA--- |
| SEQ ID NO: 4498 | Nga01311 | 8863.72 | 10690.35 | protein kinase |
| SEQ ID NO: 4499 | Nga01310.01 | 1417.46 | 1344.22 | mfs transporter |
| SEQ ID NO: 4500 | Nga01312 | 1972.04 | 2248.00 | protein |
| SEQ ID NO: 4501 | Nga00798 | 174.16 | 178.29 | protein |
| SEQ ID NO: 4502 | Nga00800.01 | 375.00 | 371.91 | metal ion transporter family |
| SEQ ID NO: 4503 | Nga00799 | 348.12 | 409.85 | trans- -dihydrobenzene- -diol dehydrogenase |
| SEQ ID NO: 4504 | Nga00801 | 154.42 | 162.14 | serine threonine protein kinase |
| SEQ ID NO: 4505 | Nga01159 | 475.41 | 510.54 | carbohydrate kinase |
| SEQ ID NO: 4506 | Nga01161.01 | 1189.84 | 1233.82 | protein |
| SEQ ID NO: 4507 | Nga01162.01 | 958.11 | 808.97 | ---NA--- |
| SEQ ID NO: 4508 | Nga01158.01 | 874.80 | 1073.42 | dihydroorotate dehydrogenase |
| SEQ ID NO: 4509 | Nga01160.01 | 45.20 | 57.53 | ---NA--- |
| SEQ ID NO: 4510 | Nga01157.01 | 962.03 | 991.06 | ---NA--- |
| SEQ ID NO: 4511 | Nga01530.01 | 735.04 | 701.58 | tpr repeat-containing protein |
| SEQ ID NO: 4512 | Nga01528 | 567.63 | 753.30 | protein |
| SEQ ID NO: 4513 | Nga01529 | 992.28 | 949.40 | predicted protein [Phaeodactylum tricornutum CCAP 1055/1] |
| SEQ ID NO: 4514 | Nga20244 | 417.46 | 361.08 | ribosomal large subunit pseudouridine synthase a |
| SEQ ID NO: 4515 | Nga01531 | 122.58 | 142.94 | protein |
| SEQ ID NO: 4516 | Nga01526 | 713.66 | 542.80 | probable ubiquinone menaquinone biosynthesis methyltransferase |
| SEQ ID NO: 4517 | Nga01527 | 5342.92 | 5794.00 | transporter component |
| SEQ ID NO: 4518 | Nga01195 | 802.88 | 763.43 | ---NA--- |
| SEQ ID NO: 4519 | Nga01196.01 | 576.98 | 703.95 | cop9 signalosome complex subunit 2 |
| SEQ ID NO: 4520 | Nga02128.2 | 271.83 | 466.39 | ---NA--- |
| SEQ ID NO: 4521 | Nga01132 | 3546.71 | 3590.54 | cold-inducible rna-binding protein |
| SEQ ID NO: 4522 | Nga01139 | 100.36 | 89.30 | phosphatidylinositol 3-kinase vps34 |
| SEQ ID NO: 4523 | Nga01136 | 147.26 | 127.61 | phosphatidylinositol 3- |
| SEQ ID NO: 4524 | Nga01133 | 284.97 | 314.35 | pre-rrna-processing protein esf2 |
| SEQ ID NO: 4525 | Nga20418 | 385.21 | 402.25 | dienoyl- reductase |
| SEQ ID NO: 4526 | Nga01135 | 391.26 | 368.39 | dienoyl- reductase |
| SEQ ID NO: 4527 | Nga01268.01 | 330.48 | 253.83 | protein |
| SEQ ID NO: 4528 | Nga01271 | 806.70 | 798.89 | ---NA--- |
| SEQ ID NO: 4529 | Nga01270 | 954.00 | 922.69 | dna-directed rna polymerase ii subunit rpb11-a |
| SEQ ID NO: 4530 | Nga01269 | 464.29 | 499.35 | esterase lipase thioesterase family protein |
| SEQ ID NO: 4531 | Nga01267 | 217.68 | 243.85 | ras-related gtp binding c |
| SEQ ID NO: 4532 | Nga01272.01 | 459.99 | 547.59 | trehalose-6-phosphate synthase |
| SEQ ID NO: 4533 | Nga00581.02 | 395.78 | 432.88 | dna polymerase v family |
| SEQ ID NO: 4534 | Nga00757.1 | 503.26 | 513.37 | protein |
| SEQ ID NO: 4535 | Nga00754 | 771.63 | 874.00 | 50s ribosomal protein l1 |
| SEQ ID NO: 4536 | Nga00752 | 1885.25 | 2756.29 | bifunctional purine biosynthesis |
| SEQ ID NO: 4537 | Nga00758 | 51.80 | 35.29 | lamin-b receptor |
| SEQ ID NO: 4538 | Nga00756 | 653.85 | 626.51 | translocase of inner mitochondrial membrane 50 homolog |
| SEQ ID NO: 4539 | Nga00753.01 | 204.06 | 232.04 | diacylglycerol acyltransferase family protein |
| SEQ ID NO: 4540 | Nga00840.01 | 285.71 | 424.31 | ---NA--- |
| SEQ ID NO: 4541 | Nga00839 | 119.62 | 129.57 | ---NA--- |
| SEQ ID NO: 4542 | Nga20551 | 516.34 | 463.74 | clathrin-adaptor gamma chain |
| SEQ ID NO: 4543 | Nga00837 | 798.26 | 812.88 | atp dependent rna helicase |
| SEQ ID NO: 4544 | Nga00836 | 4880.46 | 5754.68 | mitochondrial-processing peptidase subunit beta |
| SEQ ID NO: 4545 | Nga00864.02 | 471.93 | 552.11 | ---NA--- |
| SEQ ID NO: 4546 | Nga01493.01 | 10521.37 | 10349.58 | triosephosphate isomerase |
| SEQ ID NO: 4547 | Nga01495 | 7157.23 | 6952.45 | ---NA--- |
| SEQ ID NO: 4548 | Nga01494 | 279.75 | 281.39 | ---NA--- |
| SEQ ID NO: 4549 | Nga00863.02 | 442.76 | 488.39 | deoxyhypusine hydroxylase monooxygenase |
| SEQ ID NO: 4550 | Nga00865.02 | 668.39 | 480.81 | expressed unknown protein [Ectocarpus siliculosus] |
| SEQ ID NO: 4551 | Nga01110 | 184.47 | 131.46 | ---NA--- |
| SEQ ID NO: 4552 | Nga01109.01 | 824.94 | 859.83 | ---NA--- |
| SEQ ID NO: 4553 | Nga01112.01 | 117.65 | 180.54 | ---NA--- |
| SEQ ID NO: 4554 | Nga01111.01 | 72.07 | 78.07 | ---NA--- |
| SEQ ID NO: 4555 | Nga01046.01 | 367.31 | 362.31 | aspartate aminotransferase |
| SEQ ID NO: 4556 | Nga01048 | 594.70 | 581.83 | histone deacetylase 1 |

FIGURE 24 BT

| # | Nga model | +N rpkb | -N rpkb | GO |
|---|---|---|---|---|
| SEQ ID NO: 4557 | Nga21294 | 426.01 | 398.43 | lysophospholipase-like 1 |
| SEQ ID NO: 4558 | Nga01047 | 4088.63 | 4213.50 | ---NA--- |
| SEQ ID NO: 4559 | Nga01049 | 149.56 | 181.00 | PREDICTED: hypothetical protein LOC100637372 [Amphimedon queenslandica] |
| SEQ ID NO: 4560 | Nga01514.01 | 213.68 | 291.64 | ---NA--- |
| SEQ ID NO: 4561 | Nga20240.1 | 115.03 | 109.65 | cleavage and polyadenylation specificity factor subunit 2 |
| SEQ ID NO: 4562 | Nga20472.1 | 106.38 | 98.78 | cleavage and polyadenylation specificity factor subunit 2 |
| SEQ ID NO: 4563 | Nga01511.1 | 643.74 | 700.01 | arginine biosynthesis bifunctional protein |
| SEQ ID NO: 4564 | Nga01513 | 7359.91 | 7656.66 | ---NA--- |
| SEQ ID NO: 4565 | Nga01512 | 566.41 | 496.51 | dna repair protein |
| SEQ ID NO: 4566 | Nga01482 | 442.07 | 548.38 | aspartate-semialdehyde dehydrogenase |
| SEQ ID NO: 4567 | Nga01484.01 | 310.61 | 434.34 | mitochondrial phosphate carrier protein 2 |
| SEQ ID NO: 4568 | Nga01483 | 1662.75 | 1524.87 | at4g01940 t7b11_20 |
| SEQ ID NO: 4569 | Nga01481 | 1622.23 | 1683.48 | peptidase u34 dipeptidase |
| SEQ ID NO: 4570 | Nga06985.2 | 125.91 | 156.01 | protein |
| SEQ ID NO: 4571 | Nga04167 | 206.67 | 173.32 | ---NA--- |
| SEQ ID NO: 4572 | Nga04168.01 | 1071.70 | 1663.34 | protein |
| SEQ ID NO: 4573 | Nga04164 | 1052.82 | 954.10 | alanine aminotransferase |
| SEQ ID NO: 4574 | Nga04165 | 220.04 | 217.12 | magnesium and cobalt transport protein |
| SEQ ID NO: 4575 | Nga04169 | 164.86 | 133.44 | coenzyme q10 homolog a |
| SEQ ID NO: 4576 | Nga03958.01 | 971.34 | 986.64 | ---NA--- |
| SEQ ID NO: 4577 | Nga03957 | 950.78 | 1078.56 | monoglyceride lipase |
| SEQ ID NO: 4578 | Nga03959 | 812.23 | 676.44 | domain protein dehydratase |
| SEQ ID NO: 4579 | Nga03960 | 12.39 | 32.22 | protein |
| SEQ ID NO: 4580 | Nga20517 | 396.40 | 513.04 | sorting and assembly machinery 35kda protein |
| SEQ ID NO: 4581 | Nga20545 | 546.01 | 568.20 | ---NA--- |
| SEQ ID NO: 4582 | Nga03504 | 1283.17 | 1202.42 | thioredoxin |
| SEQ ID NO: 4583 | Nga03538 | 1608.68 | 1943.41 | ---NA--- |
| SEQ ID NO: 4584 | Nga03540 | 440.77 | 542.36 | ---NA--- |
| SEQ ID NO: 4585 | Nga03539 | 252.70 | 218.35 | conserved unknown protein [Ectocarpus siliculosus] |
| SEQ ID NO: 4586 | Nga04228.01 | 902.97 | 885.89 | expressed unknown protein [Ectocarpus siliculosus] |
| SEQ ID NO: 4587 | Nga04227.01 | 1197.11 | 1442.35 | aaa-type atpase family protein |
| SEQ ID NO: 4588 | Nga04226.01 | 2703.62 | 3063.23 | peroxisomal biogenesis factor 11 domain-containing protein |
| SEQ ID NO: 4589 | Nga21079.1 | 17.86 | 29.02 | ---NA--- |
| SEQ ID NO: 4590 | Nga20524.1 | 29.30 | 75.39 | dna-directed rna polymerase iii largest |
| SEQ ID NO: 4591 | Nga04224.01 | 7724.92 | 8189.01 | hybrid cluster protein |
| SEQ ID NO: 4592 | Nga20726 | 231.98 | 265.93 | ankyrin repeat-containing protein |
| SEQ ID NO: 4593 | Nga04225 | 4987.96 | 2414.19 | low molecular mass early light-inducible protein hv60 |
| SEQ ID NO: 4594 | Nga03919.01 | 883.08 | 870.36 | like protein |
| SEQ ID NO: 4595 | Nga03917.01 | 409.64 | 453.68 | structural maintenance of chromosomes 1 |
| SEQ ID NO: 4596 | Nga03918.1 | 275.02 | 319.44 | structural maintenance of chromosomes 1 |
| SEQ ID NO: 4597 | Nga03916 | 173.43 | 267.81 | structural maintenance of chromosomes 1 |
| SEQ ID NO: 4598 | Nga03915.1 | 268.41 | 229.09 | trypsin family |
| SEQ ID NO: 4599 | Nga20105.1 | 431.43 | 543.90 | protein |
| SEQ ID NO: 4600 | Nga20766.1 | 244.69 | 316.07 | ubiquitin ligase e3 |
| SEQ ID NO: 4601 | Nga20378.1 | 105.94 | 156.75 | conserved unknown protein [Ectocarpus siliculosus] |
| SEQ ID NO: 4602 | Nga03631 | 141.94 | 132.78 | hypothetical protein FIC_00832 [Flavobacteriaceae bacterium 3519-10] |
| SEQ ID NO: 4603 | Nga02426.02 | 2195.59 | 2118.72 | ---NA--- |
| SEQ ID NO: 4604 | Nga21010.1 | 1209.77 | 1048.99 | gag-pol polyprotein |
| SEQ ID NO: 4605 | Nga21011.1 | 964.77 | 1131.99 | copia ltr rider |
| SEQ ID NO: 4606 | Nga21013.1 | 801.39 | 1023.19 | hypothetical protein VITISV_004538 [Vitis vinifera] |
| SEQ ID NO: 4607 | Nga03030.02 | 609.79 | 759.79 | peptidase u34 dipeptidase |
| SEQ ID NO: 4608 | Nga03037.02 | 415.64 | 402.61 | protein |
| SEQ ID NO: 4609 | Nga03041.02 | 422.87 | 487.28 | calcium calmodulin-dependent protein kinase type 1 |
| SEQ ID NO: 4610 | Nga03040.02 | 193.55 | 227.13 | ---NA--- |
| SEQ ID NO: 4611 | Nga03038.02 | 1745.28 | 1917.36 | conserved unknown protein [Ectocarpus siliculosus] |
| SEQ ID NO: 4612 | Nga03935 | 227.47 | 222.52 | glutamyl-trna a subunit |
| SEQ ID NO: 4613 | Nga03033.02 | 251.53 | 367.69 | biotin lipoate protein ligase-like protein |
| SEQ ID NO: 4614 | Nga20830.1 | 373.53 | 270.81 | retrovirus-related pol polyprotein from transposon tnt 1-94 |
| SEQ ID NO: 4615 | Nga03900 | 921.31 | 950.17 | adhesion regulating molecule 1 |
| SEQ ID NO: 4616 | Nga03902 | 209.58 | 168.65 | btb and poz domain-containing |
| SEQ ID NO: 4617 | Nga20849 | 346.85 | 290.17 | binding protein |
| SEQ ID NO: 4618 | Nga03897 | 4605.01 | 3295.67 | ---NA--- |
| SEQ ID NO: 4619 | Nga03903 | 10836.67 | 11262.96 | ribosomal protein l29 |

FIGURE 24 BU

| # | Nga model | +N rpkb | -N rpkb | GO |
|---|---|---|---|---|
| SEQ ID NO: 4620 | Nga03898 | 3971.50 | 4971.87 | 40s ribosomal protein s14 |
| SEQ ID NO: 4621 | Nga03901 | 1042.75 | 1022.53 | protein |
| SEQ ID NO: 4622 | Nga03899 | 1572.27 | 1211.05 | ubiquitin family protein |
| SEQ ID NO: 4623 | Nga01891.02 | 302.97 | 327.04 | protein |
| SEQ ID NO: 4624 | Nga01890.2 | 3082.35 | 4085.34 | ---NA--- |
| SEQ ID NO: 4625 | Nga20820 | 705.83 | 852.92 | l-galactono- -lactone dehydrogenase |
| SEQ ID NO: 4626 | Nga03974 | 1203.34 | 1430.83 | atp-binding cassette sub-family g member 2 |
| SEQ ID NO: 4627 | Nga03973 | 182.72 | 153.43 | protein prenyltransferase alpha subunit repeat-containing protein 1 |
| SEQ ID NO: 4628 | Nga03726 | 859.56 | 816.45 | transitional endoplasmic reticulum atpase |
| SEQ ID NO: 4629 | Nga03728 | 3444.44 | 3364.59 | protein |
| SEQ ID NO: 4630 | Nga03690.2 | 1274.73 | 1353.05 | translation initiation factor if-3 |
| SEQ ID NO: 4631 | Nga04195 | 3906.48 | 3301.03 | glucokinase |
| SEQ ID NO: 4632 | Nga04196 | 2274.73 | 2230.45 | r- vamp71-family |
| SEQ ID NO: 4633 | Nga02087.02 | 1572.41 | 1402.33 | conserved unknown protein [Ectocarpus siliculosus] |
| SEQ ID NO: 4634 | Nga04193 | 726.66 | 905.69 | protein |
| SEQ ID NO: 4635 | Nga03786.01 | 991.10 | 1203.30 | pas pac sensor hybrid histidine kinase |
| SEQ ID NO: 4636 | Nga20140 | 361.77 | 363.09 | protein |
| SEQ ID NO: 4637 | Nga20888 | 180.85 | 233.36 | trna (uracil-5-)-methyltransferase |
| SEQ ID NO: 4638 | Nga03787 | 58.49 | 81.75 | ---NA--- |
| SEQ ID NO: 4639 | Nga03789 | 31.75 | 94.57 | ---NA--- |
| SEQ ID NO: 4640 | Nga03788 | 342.27 | 372.69 | retinoblastoma-binding protein 8 |
| SEQ ID NO: 4641 | Nga03857.1 | 105.93 | 100.30 | 72 kda inositol polyphosphate 5-phosphatase-like |
| SEQ ID NO: 4642 | Nga03856 | 151.69 | 164.11 | dna repair protein rad50 |
| SEQ ID NO: 4643 | Nga03854 | 1672.72 | 1712.55 | conserved hypothetical protein [Albugo laibachii Nc14] |
| SEQ ID NO: 4644 | Nga20238 | 224.43 | 195.15 | phosphoglycerate bisphosphoglycerate mutase family protein |
| SEQ ID NO: 4645 | Nga03855 | 642.32 | 632.90 | ribosome biogenesis gtp-binding protein |
| SEQ ID NO: 4646 | Nga03751.01 | 6433.28 | 6577.36 | 60s ribosomal protein l34 |
| SEQ ID NO: 4647 | Nga04463.2 | 12506.97 | 12153.36 | 60s ribosomal protein l36 |
| SEQ ID NO: 4648 | Nga02335.02 | 1068.17 | 1077.20 | ---NA--- |
| SEQ ID NO: 4649 | Nga02334.02 | 26634.92 | 28408.62 | uncharacterized protein conserved in bacteria with a cystatin-like fold |
| SEQ ID NO: 4650 | Nga03753 | 912.20 | 1017.95 | protein |
| SEQ ID NO: 4651 | Nga20610 | 169.31 | 206.33 | anaphase-promoting complex |
| SEQ ID NO: 4652 | Nga04092 | 733.16 | 661.50 | 26s proteasome non-atpase regulatory subunit 13 |
| SEQ ID NO: 4653 | Nga04094 | 382.94 | 317.02 | ---NA--- |
| SEQ ID NO: 4654 | Nga04095 | 450.39 | 470.97 | ---NA--- |
| SEQ ID NO: 4655 | Nga04091 | 2566.76 | 2362.99 | eukaryotic initiation factor 4a-iii |
| SEQ ID NO: 4656 | Nga04093 | 152.61 | 87.01 | uncharacterized oxidoreductase yrbe-like |
| SEQ ID NO: 4657 | Nga04096 | 70.18 | 66.51 | ---NA--- |
| SEQ ID NO: 4658 | Nga20465.1 | 166.67 | 151.00 | ---NA--- |
| SEQ ID NO: 4659 | Nga03672.1 | 490.32 | 412.33 | adenosine kinase |
| SEQ ID NO: 4660 | Nga03490.02 | 855.72 | 986.23 | dynein light chain roadblock-type 1-like |
| SEQ ID NO: 4661 | Nga03476.02 | 3646.76 | 2977.17 | predicted protein [Phaeodactylum tricornutum CCAP 1055/1] |
| SEQ ID NO: 4662 | Nga03675 | 208.99 | 283.70 | protein |
| SEQ ID NO: 4663 | Nga04020.01 | 723.88 | 825.90 | short chain dehydrogenase reductase family |
| SEQ ID NO: 4664 | Nga02443.02 | 1509.80 | 2050.77 | ---NA--- |
| SEQ ID NO: 4665 | Nga04021 | 917.79 | 759.14 | nitric oxide synthase interacting protein |
| SEQ ID NO: 4666 | Nga01853 | 118.42 | 114.02 | ---NA--- |
| SEQ ID NO: 4667 | Nga01854 | 832.67 | 958.07 | protein |
| SEQ ID NO: 4668 | Nga01852.1 | 640.29 | 945.30 | nli interacting factor family protein |
| SEQ ID NO: 4669 | Nga01775 | 487.72 | 432.03 | protein |
| SEQ ID NO: 4670 | Nga01774 | 83.13 | 70.63 | dash family |
| SEQ ID NO: 4671 | Nga01776 | 872.69 | 769.80 | transmembrane protein |
| SEQ ID NO: 4672 | Nga20172 | 356.19 | 251.82 | pleckstriny domain-containing expressed |
| SEQ ID NO: 4673 | Nga01762.01 | 101.10 | 76.18 | ---NA--- |
| SEQ ID NO: 4674 | Nga01760 | 494.68 | 476.32 | ---NA--- |
| SEQ ID NO: 4675 | Nga01761.01 | 3718.91 | 3827.70 | enoyl- hydratase isomerase |
| SEQ ID NO: 4676 | Nga01759.01 | 1722.32 | 1588.87 | hypersensitive-induced response protein |
| SEQ ID NO: 4677 | Nga01763 | 792.11 | 893.49 | ---NA--- |
| SEQ ID NO: 4678 | Nga01758 | 416.95 | 436.25 | nuclear distribution protein |
| SEQ ID NO: 4679 | Nga01858 | 1650.13 | 1445.25 | ubiquitin-conjugating enzyme |
| SEQ ID NO: 4680 | Nga21281 | 973.57 | 722.95 | lung cancer oncogene 5 |
| SEQ ID NO: 4681 | Nga01857 | 504.96 | 548.06 | ribosomal rna methyltransferase |
| SEQ ID NO: 4682 | Nga01859 | 114.29 | 145.90 | gtpase activating protein |
| SEQ ID NO: 4683 | Nga20461 | 85.31 | 92.41 | mon1 homolog a |

FIGURE 24 BV

| # | Nga model | +N rpkb | -N rpkb | GO |
|---|---|---|---|---|
| SEQ ID NO: 4684 | Nga01856 | 326.39 | 388.85 | taz1-interacting factor 1 |
| SEQ ID NO: 4685 | Nga02002.1 | 273.62 | 277.56 | sorting nexin 1 |
| SEQ ID NO: 4686 | Nga02000 | 2244.35 | 2721.04 | ion channel |
| SEQ ID NO: 4687 | Nga01603.02 | 228.78 | 321.85 | ---NA--- |
| SEQ ID NO: 4688 | Nga02163 | 136.70 | 135.55 | fip1 motif protein family protein |
| SEQ ID NO: 4689 | Nga02161 | 222.81 | 213.58 | 2og-fe oxygenase |
| SEQ ID NO: 4690 | Nga02162 | 1247.47 | 1654.94 | predicted protein [Phaeodactylum tricornutum CCAP 1055/1] |
| SEQ ID NO: 4691 | Nga02164 | 230.48 | 261.05 | protein |
| SEQ ID NO: 4692 | Nga20269 | 143.08 | 163.60 | likely protein kinase endoribonuclease ire1 |
| SEQ ID NO: 4693 | Nga02175 | 141.55 | 165.89 | ---NA--- |
| SEQ ID NO: 4694 | Nga02197.1 | 43.30 | 47.78 | dmt superfamily drug metabolite transporter |
| SEQ ID NO: 4695 | Nga02196.01 | 1176.23 | 1143.45 | ---NA--- |
| SEQ ID NO: 4696 | Nga01670.01 | 29.53 | 27.12 | ---NA--- |
| SEQ ID NO: 4697 | Nga01671.01 | 508.33 | 559.67 | ---NA--- |
| SEQ ID NO: 4698 | Nga01739 | 409.52 | 486.25 | ---NA--- |
| SEQ ID NO: 4699 | Nga01738 | 791.79 | 815.63 | multidrug resistance protein |
| SEQ ID NO: 4700 | Nga01737 | 1210.26 | 992.50 | protein |
| SEQ ID NO: 4701 | Nga02053.1 | 2867.55 | 3311.40 | ---NA--- |
| SEQ ID NO: 4702 | Nga02055.01 | 56.06 | 65.65 | cathepsin l-like proteinase |
| SEQ ID NO: 4703 | Nga03603.2 | 1104.20 | 1236.36 | lipase class 3 |
| SEQ ID NO: 4704 | Nga02056 | 42.32 | 56.52 | hi0933 family protein |
| SEQ ID NO: 4705 | Nga02052.01 | 8390.19 | 12092.74 | ---NA--- |
| SEQ ID NO: 4706 | Nga01675.01 | 238.79 | 327.29 | ---NA--- |
| SEQ ID NO: 4707 | Nga01674 | 637.41 | 737.12 | dep domain containing 5 |
| SEQ ID NO: 4708 | Nga01676 | 27.27 | 49.24 | ---NA--- |
| SEQ ID NO: 4709 | Nga21017.1 | 312.18 | 316.17 | nad-dependent epimerase dehydratase |
| SEQ ID NO: 4710 | Nga01711 | 606.55 | 639.05 | cbl-interacting serine threonine-protein kinase 9 |
| SEQ ID NO: 4711 | Nga01710 | 825.19 | 870.96 | 3-ketoacyl- thiolase peroxisomal |
| SEQ ID NO: 4712 | Nga02135 | 457.26 | 536.22 | single-stranded dna-binding protein |
| SEQ ID NO: 4713 | Nga20200.1 | 661.93 | 594.95 | zn-binding protein |
| SEQ ID NO: 4714 | Nga05031.2 | 529.19 | 471.59 | conserved unknown protein [Ectocarpus siliculosus] |
| SEQ ID NO: 4715 | Nga00238.02 | 4637.01 | 3068.52 | ---NA--- |
| SEQ ID NO: 4716 | Nga00242.2 | 4126.60 | 2518.87 | ---NA--- |
| SEQ ID NO: 4717 | Nga00249.02 | 2197.10 | 1291.92 | ---NA--- |
| SEQ ID NO: 4718 | Nga00243.02 | 5108.95 | 1993.66 | ---NA--- |
| SEQ ID NO: 4719 | Nga04370.2 | 676.10 | 700.21 | peroxisomal acyl-coenzyme a |
| SEQ ID NO: 4720 | Nga02326 | 1515.15 | 1586.55 | spliceosomal protein |
| SEQ ID NO: 4721 | Nga01799.02 | 279.35 | 276.29 | nuclear receptor 2c2-associated protein |
| SEQ ID NO: 4722 | Nga01797.02 | 530.68 | 593.47 | serine threonine-protein kinase 4 |
| SEQ ID NO: 4723 | Nga01798.02 | 636.52 | 572.53 | ---NA--- |
| SEQ ID NO: 4724 | Nga02041 | 157.45 | 446.20 | hypothetical protein F82170_06015 [Maribacter sp. HTCC2170] |
| SEQ ID NO: 4725 | Nga02039 | 2390.75 | 5095.11 | ---NA--- |
| SEQ ID NO: 4726 | Nga02040 | 223.71 | 142.98 | ribonucleoside-diphosphate reductase |
| SEQ ID NO: 4727 | Nga02413 | 609.36 | 694.77 | protein |
| SEQ ID NO: 4728 | Nga20385 | 243.84 | 261.47 | cryptic tubulin |
| SEQ ID NO: 4729 | Nga21135 | 105.11 | 152.89 | beta-tubulin |
| SEQ ID NO: 4730 | Nga02412.1 | 517.93 | 535.71 | argonaute 1 |
| SEQ ID NO: 4731 | Nga04862 | 138.89 | 140.42 | ---NA--- |
| SEQ ID NO: 4732 | Nga04859 | 112.40 | 172.14 | ---NA--- |
| SEQ ID NO: 4733 | Nga04860 | 137.31 | 156.83 | phosphorylated ctd-interacting |
| SEQ ID NO: 4734 | Nga04861 | 176.64 | 288.55 | ---NA--- |
| SEQ ID NO: 4735 | Nga21129 | 370.02 | 287.77 | cbs domain multi-pass transmembrane |
| SEQ ID NO: 4736 | Nga05035 | 112.34 | 104.73 | protein |
| SEQ ID NO: 4737 | Nga05036.01 | 303.62 | 307.90 | ---NA--- |
| SEQ ID NO: 4738 | Nga04269.01 | 42.42 | 52.52 | kinesin-like protein |
| SEQ ID NO: 4739 | Nga04268 | 273.33 | 306.14 | conserved hypothetical protein [Albugo laibachii Nc14] |
| SEQ ID NO: 4740 | Nga04917 | 260.14 | 224.92 | ---NA--- |
| SEQ ID NO: 4741 | Nga04916 | 342.26 | 347.11 | ---NA--- |
| SEQ ID NO: 4742 | Nga04918 | 2397.29 | 2310.37 | ---NA--- |
| SEQ ID NO: 4743 | Nga05019 | 689.52 | 689.48 | u3 small nucleolar rna-associated protein 10 and nuc211 domain-containing protein |
| SEQ ID NO: 4744 | Nga20083 | 214.62 | 166.78 | conserved unknown protein [Ectocarpus siliculosus] |
| SEQ ID NO: 4745 | Nga04608.01 | 2033.00 | 1573.72 | protein |
| SEQ ID NO: 4746 | Nga04609.1 | 635.63 | 716.60 | ---NA--- |

FIGURE 24 BW

| # | Nga model | +N rpkb | -N rpkb | GO |
|---|---|---|---|---|
| SEQ ID NO: 4747 | Nga04639 | 116.75 | 148.46 | ---NA--- |
| SEQ ID NO: 4748 | Nga04637 | 1771.46 | 1571.64 | protein |
| SEQ ID NO: 4749 | Nga04638 | 389.75 | 351.47 | permease (major facilitator superfamily) |
| SEQ ID NO: 4750 | Nga04636 | 852.86 | 888.25 | ---NA--- |
| SEQ ID NO: 4751 | Nga04541 | 161.23 | 135.14 | adenylate kinase |
| SEQ ID NO: 4752 | Nga04542 | 40.74 | 41.72 | mitogen-activated protein kinase 2 |
| SEQ ID NO: 4753 | Nga03737.02 | 99.17 | 102.95 | ---NA--- |
| SEQ ID NO: 4754 | Nga04528 | 156.23 | 95.14 | dna primase small subunit |
| SEQ ID NO: 4755 | Nga04526 | 2913.15 | 2981.01 | fructosamine 3 kinase |
| SEQ ID NO: 4756 | Nga04527 | 270.24 | 270.81 | cyclin-dependent kinase 10 |
| SEQ ID NO: 4757 | Nga21218 | 346.56 | 429.85 | protein phosphatase |
| SEQ ID NO: 4758 | Nga04445 | 676.64 | 729.13 | platelet glycoprotein 4 |
| SEQ ID NO: 4759 | Nga04444 | 5514.61 | 8756.03 | phosphate dikinase |
| SEQ ID NO: 4760 | Nga04546.1 | 609.28 | 509.25 | tetratricopeptide repeat domain protein |
| SEQ ID NO: 4761 | Nga03594.02 | 586.49 | 374.75 | protein |
| SEQ ID NO: 4762 | Nga20538.1 | 195.09 | 227.58 | ---NA--- |
| SEQ ID NO: 4763 | Nga02043.02 | 344.34 | 345.90 | protein phosphatase 1a isoform 2 |
| SEQ ID NO: 4764 | Nga05000 | 234.35 | 296.48 | histone deacetylase |
| SEQ ID NO: 4765 | Nga04408.1 | 740.35 | 847.58 | ribosome biogenesis protein brx1 homolog |
| SEQ ID NO: 4766 | Nga03704.2 | 92.90 | 119.57 | ---NA--- |
| SEQ ID NO: 4767 | Nga20624.1 | 58.82 | 95.58 | ---NA--- |
| SEQ ID NO: 4768 | Nga21047.1 | 63.83 | 51.86 | ---NA--- |
| SEQ ID NO: 4769 | Nga21056.1 | 42.74 | 74.07 | ---NA--- |
| SEQ ID NO: 4770 | Nga20623 | 1184.96 | 1008.30 | protein |
| SEQ ID NO: 4771 | Nga04592 | 1082.87 | 987.48 | protein |
| SEQ ID NO: 4772 | Nga04762.01 | 191.69 | 140.79 | ---NA--- |
| SEQ ID NO: 4773 | Nga04763.01 | 1319.20 | 1103.65 | ---NA--- |
| SEQ ID NO: 4774 | Nga07095.2 | 625.00 | 780.99 | ---NA--- |
| SEQ ID NO: 4775 | Nga04442 | 83.90 | 63.86 | hypothetical protein AURANDRAFT_64743 [Aureococcus anophagefferens] |
| SEQ ID NO: 4776 | Nga04582 | 441.92 | 366.46 | patatin-like phospholipase domain-containing protein |
| SEQ ID NO: 4777 | Nga04584.1 | 488.89 | 422.59 | 4-diphosphocytidyl-2c-methyl-d-erythritol kinase |
| SEQ ID NO: 4778 | Nga04583 | 523.56 | 506.81 | ring-finger-containing e3 ubiquitin |
| SEQ ID NO: 4779 | Nga04706 | 239.39 | 219.93 | ---NA--- |
| SEQ ID NO: 4780 | Nga04707 | 349.21 | 401.20 | ---NA--- |
| SEQ ID NO: 4781 | Nga04708 | 676.61 | 589.44 | ---NA--- |
| SEQ ID NO: 4782 | Nga04289 | 1298.36 | 1551.51 | protein |
| SEQ ID NO: 4783 | Nga21090.1 | 1181.82 | 1503.22 | ankyrin repeat protein |
| SEQ ID NO: 4784 | Nga05002 | 754.42 | 845.40 | ---NA--- |
| SEQ ID NO: 4785 | Nga04492 | 883.78 | 840.44 | acetyl- hydrolase transferase |
| SEQ ID NO: 4786 | Nga04493 | 900.75 | 966.47 | protein |
| SEQ ID NO: 4787 | Nga05042 | 1484.75 | 1797.43 | glycine-rich rna-binding protein 4 |
| SEQ ID NO: 4788 | Nga05043 | 433.33 | 558.28 | ---NA--- |
| SEQ ID NO: 4789 | Nga05044.1 | 479.70 | 517.63 | homing endonuclease rb16 2 |
| SEQ ID NO: 4790 | Nga05045 | 116.43 | 79.47 | ---NA--- |
| SEQ ID NO: 4791 | Nga04555 | 1641.61 | 2128.71 | protein |
| SEQ ID NO: 4792 | Nga04769 | 193.59 | 226.37 | ---NA--- |
| SEQ ID NO: 4793 | Nga04736.1 | 79.42 | 108.85 | ---NA--- |
| SEQ ID NO: 4794 | Nga04362 | 40.82 | 36.84 | ---NA--- |
| SEQ ID NO: 4795 | Nga02232.2 | 22.22 | 6.88 | ---NA--- |
| SEQ ID NO: 4796 | Nga04976 | 71.53 | 106.93 | ---NA--- |
| SEQ ID NO: 4797 | Nga04975.1 | 83.00 | 157.88 | ---NA--- |
| SEQ ID NO: 4798 | Nga03845.02 | 493.55 | 405.34 | AF391290_4unknown [Branchiostoma floridae] |
| SEQ ID NO: 4799 | Nga03848.02 | 156.46 | 132.64 | ankyrin repeat-containing protein |
| SEQ ID NO: 4800 | Nga04758 | 158.91 | 205.73 | 1-acyl-sn-glycerol-3-phosphate acyltransferase |
| SEQ ID NO: 4801 | Nga04759 | 224.42 | 253.83 | 1-acyl-sn-glycerol-3-phosphate acyltransferase family protein |
| SEQ ID NO: 4802 | Nga07094 | 243.80 | 170.09 | ---NA--- |
| SEQ ID NO: 4803 | Nga04838.2 | 179.49 | 147.21 | ---NA--- |
| SEQ ID NO: 4804 | Nga07092 | 1163.48 | 1182.13 | cytochrome p450 |
| SEQ ID NO: 4805 | Nga07055 | 5.49 | 59.52 | ---NA--- |
| SEQ ID NO: 4806 | Nga05783.02 | 151.28 | 161.10 | ---NA--- |
| SEQ ID NO: 4807 | Nga06928 | 747.83 | 742.88 | smu-1 suppressor of mec-8 and unc-52 homolog ( elegans) |
| SEQ ID NO: 4808 | Nga07218 | 707.47 | 773.84 | serine long chain base subunit 1 |
| SEQ ID NO: 4809 | Nga00828.02 | 6466.38 | 6095.25 | ---NA--- |

FIGURE 24 BX

| # | Nga model | +N rpkb | -N rpkb | GO |
|---|---|---|---|---|
| SEQ ID NO: 4810 | Nga06895.1 | 912.42 | 1157.40 | histone deacetylase superfamily protein |
| SEQ ID NO: 4811 | Nga07250 | 1609.90 | 1613.77 | protein |
| SEQ ID NO: 4812 | Nga01718.02 | 1024.82 | 1024.72 | glutathione s-transferase |
| SEQ ID NO: 4813 | Nga20014.1 | 604.32 | 833.86 | ---NA--- |
| SEQ ID NO: 4814 | Nga20398 | 298.94 | 214.93 | udp-galactose translocator |
| SEQ ID NO: 4815 | Nga20411 | 236.26 | 172.60 | udp-galactose transporter |
| SEQ ID NO: 4816 | Nga07234 | 160.92 | 148.03 | zinc finger bed domain-containing protein 1-like |
| SEQ ID NO: 4817 | Nga00251.02 | 8641.55 | 8947.81 | redoxin domain protein |
| SEQ ID NO: 4818 | Nga20464 | 104.11 | 160.26 | regulator of chromosome condensation -like protein |
| SEQ ID NO: 4819 | Nga07165 | 224.24 | 245.58 | protein |
| SEQ ID NO: 4820 | Nga20294 | 426.64 | 474.70 | uv radiation resistance-associated gene protein |
| SEQ ID NO: 4821 | Nga06959 | 425.23 | 304.48 | kelch repeat protein |
| SEQ ID NO: 4822 | Nga07116 | 234.62 | 270.81 | ---NA--- |
| SEQ ID NO: 4823 | Nga04515.2 | 179.17 | 196.74 | ---NA--- |
| SEQ ID NO: 4824 | Nga07293 | 6025.11 | 6897.93 | 40s ribosomal protein s9 |
| SEQ ID NO: 4825 | Nga00982.02 | 2877.19 | 2455.92 | ---NA--- |
| SEQ ID NO: 4826 | Nga07142 | 2374.10 | 1778.76 | predicted protein [Thalassiosira pseudonana CCMP1335] |
| SEQ ID NO: 4827 | Nga07140 | 3466.43 | 3304.05 | conserved hypothetical protein [Phytophthora infestans T30-4] |
| SEQ ID NO: 4828 | Nga07030 | 89.33 | 127.10 | para-aminobenzoate synthase |
| SEQ ID NO: 4829 | Nga07029 | 1135.86 | 1241.26 | ---NA--- |
| SEQ ID NO: 4830 | Nga07169 | 691.11 | 599.92 | ---NA--- |
| SEQ ID NO: 4831 | Nga07170 | 190.14 | 167.82 | ---NA--- |
| SEQ ID NO: 4832 | Nga07171 | 813.48 | 608.56 | ---NA--- |
| SEQ ID NO: 4833 | Nga01168.2 | 652.21 | 843.10 | ---NA--- |
| SEQ ID NO: 4834 | Nga06974 | 187.07 | 175.12 | protein |
| SEQ ID NO: 4835 | Nga07045 | 333.33 | 369.83 | hypothetical protein CHLNCDRAFT_138448 [Chlorella variabilis] |
| SEQ ID NO: 4836 | Nga07046 | 49.28 | 48.67 | ---NA--- |
| SEQ ID NO: 4837 | Nga07252 | 253.16 | 308.52 | ---NA--- |
| SEQ ID NO: 4838 | Nga06911.1 | 280.63 | 95.67 | ankyrin repeat and kh domain-containing protein 1 |
| SEQ ID NO: 4839 | Nga20211 | 259.74 | 290.74 | rbm25 protein |
| SEQ ID NO: 4840 | Nga21204 | 144.21 | 189.50 | rbm25 protein |
| SEQ ID NO: 4841 | Nga04183.2 | 125.00 | 114.25 | ---NA--- |
| SEQ ID NO: 4842 | Nga07281 | 252.53 | 246.19 | ---NA--- |
| SEQ ID NO: 4843 | Nga07280 | 144.85 | 118.15 | domain-containing protein |
| SEQ ID NO: 4844 | Nga06838 | 159.02 | 158.38 | protein |
| SEQ ID NO: 4845 | Nga06968 | 633.18 | 573.77 | ---NA--- |
| SEQ ID NO: 4846 | Nga07179 | 2634.35 | 1732.42 | protein |
| SEQ ID NO: 4847 | Nga06990.1 | 221.78 | 232.49 | transcriptional repressor sin3p |
| SEQ ID NO: 4848 | Nga07143.1 | 2920.63 | 3402.89 | ---NA--- |
| SEQ ID NO: 4849 | Nga07215 | 2.49 | 5.39 | bacteriocin o-metyltransferase |
| SEQ ID NO: 4850 | Nga06892 | 4293.51 | 4089.45 | ---NA--- |
| SEQ ID NO: 4851 | Nga06902 | 398.84 | 312.20 | dna replication licensing factor mcm3 |
| SEQ ID NO: 4852 | Nga07173 | 227.12 | 165.24 | ---NA--- |
| SEQ ID NO: 4853 | Nga06960 | 474.07 | 473.41 | ---NA--- |
| SEQ ID NO: 4854 | Nga20857 | 648.22 | 808.76 | rna-binding expressed |
| SEQ ID NO: 4855 | Nga07190 | 420.33 | 387.12 | major facilitator superfamily mfs_1 |
| SEQ ID NO: 4856 | Nga07009 | 1154.20 | 1313.11 | ---NA--- |
| SEQ ID NO: 4857 | Nga07008 | 474.64 | 622.07 | hypothetical protein AURANDRAFT_66301 [Aureococcus anophagefferens] |
| SEQ ID NO: 4858 | Nga06987 | 1000.00 | 1179.80 | peroxiredoxin 1 |
| SEQ ID NO: 4859 | Nga07051 | 1245.02 | 1395.81 | ---NA--- |
| SEQ ID NO: 4860 | Nga07103 | 198.31 | 169.11 | ---NA--- |
| SEQ ID NO: 4861 | Nga20013.1 | 62.02 | 41.99 | ---NA--- |
| SEQ ID NO: 4862 | Nga20228 | 392.49 | 392.88 | insulin-degrading enzyme |
| SEQ ID NO: 4863 | Nga06989.1 | 71.97 | 53.34 | dna replication licensing factor mcm5 |
| SEQ ID NO: 4864 | Nga06870 | 173.01 | 146.18 | ---NA--- |
| SEQ ID NO: 4865 | Nga06932 | 238.99 | 245.26 | ---NA--- |
| SEQ ID NO: 4866 | Nga06991 | 273.76 | 313.03 | ---NA--- |
| SEQ ID NO: 4867 | Nga07246 | 264.07 | 246.19 | transcription factor |
| SEQ ID NO: 4868 | Nga07276 | 34.83 | 18.86 | zinc finger bed domain-containing protein 1-like |
| SEQ ID NO: 4869 | Nga07254 | 722.22 | 819.95 | ---NA--- |
| SEQ ID NO: 4870 | Nga07255 | 506.60 | 725.73 | ---NA--- |
| SEQ ID NO: 4871 | Nga07011 | 180.81 | 272.86 | ---NA--- |
| SEQ ID NO: 4872 | Nga06931 | 67.96 | 73.62 | ---NA--- |

FIGURE 24 BY

| # | Nga model | +N rpkb | -N rpkb | GO |
|---|---|---|---|---|
| SEQ ID NO: 4873 | Nga06930 | 439.02 | 356.67 | ---NA--- |
| SEQ ID NO: 4874 | Nga07296 | 894.60 | 941.94 | ---NA--- |
| SEQ ID NO: 4875 | Nga21275 | 161.20 | 201.26 | protein |
| SEQ ID NO: 4876 | Nga21101 | 281.90 | 298.93 | ---NA--- |
| SEQ ID NO: 4877 | Nga07090 | 22322.94 | 21377.69 | actin |
| SEQ ID NO: 4878 | Nga06992 | 81.76 | 149.88 | ---NA--- |
| SEQ ID NO: 4879 | Nga21143 | 690.14 | 570.60 | ku p70 dna |
| SEQ ID NO: 4880 | Nga00461.01 | 902.98 | 815.05 | abc subfamily abcg |
| SEQ ID NO: 4881 | Nga20932 | 1639.90 | 1233.23 | protein |
| SEQ ID NO: 4882 | Nga00457 | 780.92 | 850.46 | mitochondrial 2-oxoglutarate malate carrier |
| SEQ ID NO: 4883 | Nga00446 | 1303.08 | 1446.65 | gtp-binding protein sar1 |
| SEQ ID NO: 4884 | Nga00451 | 3271.98 | 3103.50 | fatty-acyl |
| SEQ ID NO: 4885 | Nga00462 | 4341.30 | 3758.35 | ferredoxin |
| SEQ ID NO: 4886 | Nga00448.01 | 26082.30 | 12065.79 | light harvesting complex protein |
| SEQ ID NO: 4887 | Nga21052 | 380.80 | 338.84 | 2og-fe oxygenase |
| SEQ ID NO: 4888 | Nga00463 | 408.07 | 289.83 | aminoglycoside phosphotransferase |
| SEQ ID NO: 4889 | Nga00468 | 2122.19 | 2160.81 | [Fe] hydrogenase maturation protein [Naegleria gruberi] |
| SEQ ID NO: 4890 | Nga00466 | 298.93 | 333.45 | beta subunit of the capping protein heterodimer (cap1p and cap2p) |
| SEQ ID NO: 4891 | Nga21094 | 621.35 | 697.84 | 30s ribosomal protein s5 |
| SEQ ID NO: 4892 | Nga00465 | 1218.96 | 1144.36 | splicing factor 3b subunit 5 |
| SEQ ID NO: 4893 | Nga00449 | 1092.59 | 738.87 | ---NA--- |
| SEQ ID NO: 4894 | Nga00454 | 903.74 | 975.07 | protein |
| SEQ ID NO: 4895 | Nga00455 | 209.00 | 183.02 | katanin p60 atpase-containing subunit a-like 1 |
| SEQ ID NO: 4896 | Nga00459 | 923.14 | 875.08 | cdk5 regulatory subunit associated protein 1 |
| SEQ ID NO: 4897 | Nga00453 | 3230.58 | 3154.99 | nose resistant to fluoxetine protein 6-like |
| SEQ ID NO: 4898 | Nga00464 | 1014.49 | 934.70 | ankyrin repeat and btb poz domain-containing protein 1 |
| SEQ ID NO: 4899 | Nga00456 | 118.14 | 130.37 | protein |
| SEQ ID NO: 4900 | Nga00450 | 462.02 | 361.58 | sam-dependent methyltransferase |
| SEQ ID NO: 4901 | Nga00460 | 633.47 | 500.53 | glucose-methanol-choline oxidoreductase |
| SEQ ID NO: 4902 | Nga00469 | 403.47 | 401.51 | ---NA--- |
| SEQ ID NO: 4903 | Nga00467 | 172.77 | 211.73 | dna-directed rna polymerase i subunit |
| SEQ ID NO: 4904 | Nga00458.01 | 9447.11 | 8268.63 | chaperonin 10 |
| SEQ ID NO: 4905 | Nga00452 | 542.35 | 516.92 | metal-dependent hydrolase |
| SEQ ID NO: 4906 | Nga00285 | 2874.65 | 2792.47 | 26s protease regulatory subunit 8 |
| SEQ ID NO: 4907 | Nga00303.1 | 394.52 | 401.64 | cytochrome c biogenesis protein transmembrane region |
| SEQ ID NO: 4908 | Nga00287 | 1338.96 | 1332.18 | protein |
| SEQ ID NO: 4909 | Nga00308 | 998.21 | 1193.99 | phage spo1 dna polymerase-related protein |
| SEQ ID NO: 4910 | Nga00289 | 563.75 | 494.23 | fad dependent oxidoreductase |
| SEQ ID NO: 4911 | Nga00292 | 1769.69 | 2002.31 | calcium-binding protein 39-like |
| SEQ ID NO: 4912 | Nga20284.1 | 439.26 | 454.07 | ubiquitin carboxyl-terminal hydrolase family protein |
| SEQ ID NO: 4913 | Nga00291 | 362.53 | 483.63 | uncharacterized protein |
| SEQ ID NO: 4914 | Nga20037.1 | 190.70 | 217.98 | ubiquitinspecific protease |
| SEQ ID NO: 4915 | Nga00300 | 1287.13 | 1236.96 | myo-inositol 2-dehydrogenase |
| SEQ ID NO: 4916 | Nga00307 | 2052.27 | 2104.51 | protein |
| SEQ ID NO: 4917 | Nga20603.1 | 82.49 | 125.83 | conserved unknown protein [Ectocarpus siliculosus] |
| SEQ ID NO: 4918 | Nga00296 | 1260.08 | 1291.59 | sporangia induced mitogen-activated protein |
| SEQ ID NO: 4919 | Nga00305 | 89.60 | 97.05 | conserved unknown protein [Ectocarpus siliculosus] |
| SEQ ID NO: 4920 | Nga00306 | 899.87 | 915.61 | ---NA--- |
| SEQ ID NO: 4921 | Nga00288 | 1530.67 | 1294.10 | fructose- -bisphosphatase |
| SEQ ID NO: 4922 | Nga00290 | 445.33 | 405.85 | ---NA--- |
| SEQ ID NO: 4923 | Nga00299 | 723.15 | 897.51 | adenosine trna methylthiotransferase |
| SEQ ID NO: 4924 | Nga20173 | 657.87 | 744.17 | ---NA--- |
| SEQ ID NO: 4925 | Nga00297 | 1102.27 | 1289.21 | chloroplast envelope protein translocase (cept or tic-toc) family protein |
| SEQ ID NO: 4926 | Nga00286 | 226.00 | 213.72 | ---NA--- |
| SEQ ID NO: 4927 | Nga21019 | 115.52 | 230.72 | protein |
| SEQ ID NO: 4928 | Nga00302 | 493.54 | 428.26 | phd finger-like domain-containing protein 5a |
| SEQ ID NO: 4929 | Nga00298 | 1575.73 | 1632.15 | protein |
| SEQ ID NO: 4930 | Nga00294 | 409.40 | 270.35 | lysosomal aspartic protease |
| SEQ ID NO: 4931 | Nga00295 | 1149.81 | 1389.82 | rna polymerase sigma factor |
| SEQ ID NO: 4932 | Nga00301 | 2595.06 | 2361.08 | h - or na -translocating f- v-type and a-type atpase (f-atpase) superfamily |
| SEQ ID NO: 4933 | Nga00293.01 | 1144.67 | 1073.54 | hypoxia-inducible factor alpha subunit |
| SEQ ID NO: 4934 | Nga21274 | 388.59 | 309.07 | ---NA--- |

FIGURE 24 BZ

| # | Nga model | +N rpkb | -N rpkb | GO |
|---|---|---|---|---|
| SEQ ID NO: 4935 | Nga00304 | 106.31 | 137.60 | ---NA--- |
| SEQ ID NO: 4936 | Nga20530 | 968.98 | 1062.91 | dihydrouridine synthase |
| SEQ ID NO: 4937 | Nga00518 | 17666.67 | 14291.52 | ---NA--- |
| SEQ ID NO: 4938 | Nga00517 | 706.27 | 757.04 | threonyl-trna synthetase |
| SEQ ID NO: 4939 | Nga20447 | 294.99 | 239.65 | transducin wd-40 repeat-containing protein |
| SEQ ID NO: 4940 | Nga00492 | 460.76 | 448.10 | aldo keto reductase |
| SEQ ID NO: 4941 | Nga00490.01 | 783.65 | 773.93 | adenine phosphoribosyltransferase |
| SEQ ID NO: 4942 | Nga00496 | 914.65 | 1123.17 | protein |
| SEQ ID NO: 4943 | Nga21241 | 1043.73 | 967.05 | holliday junction resolvase |
| SEQ ID NO: 4944 | Nga00519 | 8718.01 | 8478.83 | 60s ribosomal protein l14 |
| SEQ ID NO: 4945 | Nga00531 | 597.40 | 729.97 | bromodomain protein |
| SEQ ID NO: 4946 | Nga00527 | 459.72 | 588.61 | na+ h+ antiporter |
| SEQ ID NO: 4947 | Nga03717.2 | 403.36 | 506.72 | ---NA--- |
| SEQ ID NO: 4948 | Nga20867 | 338.66 | 528.64 | s-adenosylmethionine-dependent methyltransferase methyltransferase |
| SEQ ID NO: 4949 | Nga20803 | 915.05 | 952.95 | sideroflexin 5 |
| SEQ ID NO: 4950 | Nga00525 | 684.88 | 784.77 | phosphopantothenate--cysteine ligase |
| SEQ ID NO: 4951 | Nga00493.01 | 4304.25 | 4488.03 | mago nashi |
| SEQ ID NO: 4952 | Nga00522.01 | 15290.02 | 7760.55 | chloroplast light harvesting protein isoform 4 |
| SEQ ID NO: 4953 | Nga00523 | 783.31 | 931.87 | set domain |
| SEQ ID NO: 4954 | Nga00526 | 1180.56 | 1326.96 | arginase |
| SEQ ID NO: 4955 | Nga00528 | 381.82 | 518.64 | protein |
| SEQ ID NO: 4956 | Nga00489 | 1519.87 | 1523.04 | histone-lysine n-methyltransferase setd3 |
| SEQ ID NO: 4957 | Nga00521 | 688.05 | 648.58 | t-complex protein 1 subunit epsilon |
| SEQ ID NO: 4958 | Nga00497 | 262.56 | 348.81 | transcription initiation factor tfiid subunit |
| SEQ ID NO: 4959 | Nga00494.01 | 791.11 | 849.77 | serine threonine protein phosphatase |
| SEQ ID NO: 4960 | Nga00530 | 260.12 | 278.40 | endonuclease iii-like protein 1-like |
| SEQ ID NO: 4961 | Nga00524 | 5705.77 | 4778.72 | stearoyl- desaturase 5 |
| SEQ ID NO: 4962 | Nga00532.01 | 423.08 | 522.87 | sdhfb_dicdi ame: full=succinate dehydrogenase assembly factor 1 homolog mitochondrial short=sdh assembly factor 1b |
| SEQ ID NO: 4963 | Nga21212 | 432.94 | 506.36 | proteasome a type |
| SEQ ID NO: 4964 | Nga20491 | 1342.57 | 1430.90 | fad linked oxidase family protein |
| SEQ ID NO: 4965 | Nga20361.1 | 321.43 | 236.67 | conserved unknown protein [Ectocarpus siliculosus] |
| SEQ ID NO: 4966 | Nga21003.1 | 174.83 | 208.31 | conserved unknown protein [Ectocarpus siliculosus] |
| SEQ ID NO: 4967 | Nga20382.1 | 238.26 | 167.21 | conserved unknown protein [Ectocarpus siliculosus] |
| SEQ ID NO: 4968 | Nga00520 | 1748.94 | 1539.86 | aspartate aminotransferase |
| SEQ ID NO: 4969 | Nga00516.01 | 4916.85 | 4334.15 | expressed unknown protein [Ectocarpus siliculosus] |
| SEQ ID NO: 4970 | Nga00684 | 247.11 | 281.02 | thyroid hormone receptor interactor 4 isoform 4 |
| SEQ ID NO: 4971 | Nga20445.1 | 348.95 | 446.24 | heat shock protein 40 like protein domain containing protein |
| SEQ ID NO: 4972 | Nga20288.1 | 379.53 | 370.18 | chaperone protein |
| SEQ ID NO: 4973 | Nga00685 | 118.25 | 116.96 | predicted protein [Phaeodactylum tricornutum CCAP 1055/1] |
| SEQ ID NO: 4974 | Nga00681.1 | 1095.08 | 1240.40 | abc transporter atp-binding protein |
| SEQ ID NO: 4975 | Nga00674 | 2802.27 | 2544.18 | protein |
| SEQ ID NO: 4976 | Nga00676 | 2045.79 | 1962.28 | proteasome subunit alpha type 7 |
| SEQ ID NO: 4977 | Nga00687 | 339.22 | 361.44 | ---NA--- |
| SEQ ID NO: 4978 | Nga00675 | 3949.23 | 4216.28 | long chain acyl-coa synthetase |
| SEQ ID NO: 4979 | Nga00682 | 1447.58 | 1611.75 | ---NA--- |
| SEQ ID NO: 4980 | Nga00677.1 | 184.02 | 226.52 | asparagine synthase related protein |
| SEQ ID NO: 4981 | Nga00690 | 1457.98 | 1661.26 | farnesyltransferase beta subunit |
| SEQ ID NO: 4982 | Nga20956 | 1140.94 | 1446.74 | protein farnesyltransferase subunit beta |
| SEQ ID NO: 4983 | Nga00680 | 2569.25 | 2674.29 | protein |
| SEQ ID NO: 4984 | Nga00689 | 177.17 | 146.42 | asparagine-linked glycosylation 1 homolog ( beta- -mannosyltransferase) |
| SEQ ID NO: 4985 | Nga00686 | 1233.25 | 1236.45 | ---NA--- |
| SEQ ID NO: 4986 | Nga00683 | 514.49 | 499.01 | protein |
| SEQ ID NO: 4987 | Nga00679.01 | 1138.10 | 1014.14 | protein |
| SEQ ID NO: 4988 | Nga00691 | 222.22 | 235.81 | leucine-rich transmembrane protein |
| SEQ ID NO: 4989 | Nga00678 | 706.07 | 826.57 | rpot-like rna polymerase |
| SEQ ID NO: 4990 | Nga20458 | 203.19 | 94.94 | chaperone protein |
| SEQ ID NO: 4991 | Nga20427 | 419.24 | 409.47 | abc transporter atp-binding protein |
| SEQ ID NO: 4992 | Nga20508 | 152.17 | 160.92 | ---NA--- |
| SEQ ID NO: 4993 | Nga21170 | 120.16 | 109.16 | n-terminal kinase-like protein |
| SEQ ID NO: 4994 | Nga00026 | 470.44 | 508.83 | transcription factor jumonji family protein |
| SEQ ID NO: 4995 | Nga04261.2 | 719.39 | 1022.90 | adenosine deaminase |

FIGURE 24 CA

| # | Nga model | +N rpkb | -N rpkb | GO |
|---|---|---|---|---|
| SEQ ID NO: 4996 | Nga00032 | 265.24 | 305.02 | ---NA--- |
| SEQ ID NO: 4997 | Nga00031 | 1100.64 | 1026.74 | glutaredoxin 3 |
| SEQ ID NO: 4998 | Nga00020 | 154.96 | 111.91 | pyruvate kinase |
| SEQ ID NO: 4999 | Nga00028.01 | 32.92 | 84.70 | ---NA--- |
| SEQ ID NO: 5000 | Nga00035 | 345.79 | 448.82 | nuclear control of atpase protein |
| SEQ ID NO: 5001 | Nga00037 | 832.58 | 722.97 | ---NA--- |
| SEQ ID NO: 5002 | Nga20737 | 601.03 | 503.65 | fumarylacetoacetate hydrolase domain-containing protein 1 |
| SEQ ID NO: 5003 | Nga00029.01 | 164.38 | 136.85 | mmp37-like mitochondrial precursor |
| SEQ ID NO: 5004 | Nga00021 | 483.47 | 504.69 | ---NA--- |
| SEQ ID NO: 5005 | Nga20582 | 145.99 | 134.42 | conserved protein with yshh some fused to polo |
| SEQ ID NO: 5006 | Nga00025 | 328.14 | 353.20 | s-adenosylmethionine-dependent methyltransferase domain-containing protein |
| SEQ ID NO: 5007 | Nga00034 | 561.04 | 524.74 | cytochrome b5 |
| SEQ ID NO: 5008 | Nga00023 | 201.52 | 153.08 | dna primase large subunit |
| SEQ ID NO: 5009 | Nga00036 | 820.92 | 782.81 | ---NA--- |
| SEQ ID NO: 5010 | Nga00039 | 288.14 | 293.76 | chloride channel family |
| SEQ ID NO: 5011 | Nga00033 | 242.88 | 232.27 | chloride channel protein |
| SEQ ID NO: 5012 | Nga00022.01 | 707.38 | 651.38 | hemolysin iii |
| SEQ ID NO: 5013 | Nga00030 | 415.47 | 517.43 | ---NA--- |
| SEQ ID NO: 5014 | Nga00027.01 | 6926.51 | 8021.43 | fad-dependent pyridine nucleotide-disulfide oxidoreductase |
| SEQ ID NO: 5015 | Nga06088.2 | 397.20 | 587.17 | glycerophosphoryl diester phosphodiesterase |
| SEQ ID NO: 5016 | Nga21197.1 | 401.91 | 501.77 | conserved unknown protein [Ectocarpus siliculosus] |
| SEQ ID NO: 5017 | Nga02898 | 112.19 | 111.37 | myosin-like protein |
| SEQ ID NO: 5018 | Nga06085.2 | 358.28 | 384.12 | ---NA--- |
| SEQ ID NO: 5019 | Nga02885.01 | 3260.95 | 3187.80 | conserved hypothetical protein [Sporisorium reilianum SRZ2] |
| SEQ ID NO: 5020 | Nga20728 | 175.00 | 194.77 | endonuclease exonuclease phosphatase family |
| SEQ ID NO: 5021 | Nga02892.02 | 1310.42 | 1685.03 | abc transporter family protein |
| SEQ ID NO: 5022 | Nga02897 | 145.73 | 87.09 | ---NA--- |
| SEQ ID NO: 5023 | Nga02891 | 8330.79 | 7764.55 | conserved hypothetical protei |
| SEQ ID NO: 5024 | Nga02888 | 6533.13 | 7733.52 | protein |
| SEQ ID NO: 5025 | Nga02889 | 440.99 | 620.41 | protein |
| SEQ ID NO: 5026 | Nga02893 | 529.91 | 495.32 | ---NA--- |
| SEQ ID NO: 5027 | Nga02886 | 23360.30 | 24857.58 | translation elongation factor 1- |
| SEQ ID NO: 5028 | Nga20827 | 598.11 | 634.25 | nudix hydrolase |
| SEQ ID NO: 5029 | Nga02890 | 2427.10 | 3682.70 | ---NA--- |
| SEQ ID NO: 5030 | Nga02887 | 875.80 | 1112.71 | predicted protein [Phaeodactylum tricornutum CCAP 1055/1] |
| SEQ ID NO: 5031 | Nga20473 | 175.31 | 217.03 | rna 3'-terminal phosphate cyclase |
| SEQ ID NO: 5032 | Nga02892.01 | 1310.42 | 1685.03 | abc transporter family protein |
| SEQ ID NO: 5033 | Nga00186 | 123.89 | 177.80 | sulfate permease family |
| SEQ ID NO: 5034 | Nga20120 | 409.62 | 532.63 | methyltransferase |
| SEQ ID NO: 5035 | Nga00157.01 | 2288.21 | 2909.12 | protein |
| SEQ ID NO: 5036 | Nga00175.01 | 273.43 | 269.47 | alpha beta hydrolase |
| SEQ ID NO: 5037 | Nga00181 | 528.94 | 558.70 | magnesium and cobalt transport protein |
| SEQ ID NO: 5038 | Nga00156 | 389.41 | 357.70 | pci domain-containing protein 2 |
| SEQ ID NO: 5039 | Nga00178 | 191.73 | 208.88 | ---NA--- |
| SEQ ID NO: 5040 | Nga00183.1 | 199.22 | 194.04 | imidazoleglycerol phosphate cyclase subunit |
| SEQ ID NO: 5041 | Nga20540 | 219.44 | 189.57 | homolog dmc1 |
| SEQ ID NO: 5042 | Nga00185 | 670.43 | 543.01 | nadh-cytochrome b5 reductase 2-like isoform 1 |
| SEQ ID NO: 5043 | Nga20339 | 477.04 | 418.85 | protein |
| SEQ ID NO: 5044 | Nga00190 | 256.94 | 203.11 | ---NA--- |
| SEQ ID NO: 5045 | Nga00155 | 754.01 | 840.82 | hydantoin utilization protein a |
| SEQ ID NO: 5046 | Nga00159 | 851.85 | 682.79 | solute carrier family member 36 |
| SEQ ID NO: 5047 | Nga00153 | 1754.02 | 1741.53 | glyceraldehyde-3-phosphate dehydrogenase |
| SEQ ID NO: 5048 | Nga00152 | 1670.31 | 1425.83 | beta-ketoacyl synthase |
| SEQ ID NO: 5049 | Nga00177 | 688.12 | 744.47 | aspartic proteinase |
| SEQ ID NO: 5050 | Nga00191 | 6106.93 | 4806.98 | ---NA--- |
| SEQ ID NO: 5051 | Nga00189 | 475.27 | 327.68 | phosphatidylinositol class b |
| SEQ ID NO: 5052 | Nga00160 | 966.46 | 898.29 | serine threonine protein |
| SEQ ID NO: 5053 | Nga00154 | 283.26 | 297.12 | gluconate kinase |
| SEQ ID NO: 5054 | Nga00188 | 313.04 | 254.32 | phosphatidylinositol class b |
| SEQ ID NO: 5055 | Nga00179 | 333.69 | 340.23 | snf2 super family |
| SEQ ID NO: 5056 | Nga00176 | 674.73 | 759.45 | ---NA--- |
| SEQ ID NO: 5057 | Nga00184 | 409.55 | 372.09 | cytidine deaminase |
| SEQ ID NO: 5058 | Nga21039 | 350.81 | 355.98 | mg(2+) transport atpase protein c |

FIGURE 24 CB

| # | Nga model | +N rpkb | -N rpkb | GO |
|---|---|---|---|---|
| SEQ ID NO: 5059 | Nga00180 | 1155.15 | 1006.77 | retinol retinaldehyde reductase |
| SEQ ID NO: 5060 | Nga00187 | 337.80 | 296.60 | oligosaccharide translocation protein rft1 |
| SEQ ID NO: 5061 | Nga00158 | 1151.20 | 1085.10 | membrane protein |
| SEQ ID NO: 5062 | Nga03285 | 855.40 | 873.76 | histidine acid |
| SEQ ID NO: 5063 | Nga03281 | 561.47 | 520.12 | predicted protein [Thalassiosira pseudonana CCMP1335] |
| SEQ ID NO: 5064 | Nga03269 | 7940.70 | 7722.11 | receptor accessory protein 6 |
| SEQ ID NO: 5065 | Nga01741.02 | 975.28 | 958.57 | pap fibrillin family protein |
| SEQ ID NO: 5066 | Nga20687 | 289.92 | 282.19 | ---NA--- |
| SEQ ID NO: 5067 | Nga20062 | 547.85 | 533.39 | tesmin tso1-like cxc domain-containing protein |
| SEQ ID NO: 5068 | Nga03272 | 1167.81 | 1158.82 | trehalase |
| SEQ ID NO: 5069 | Nga03282 | 348.30 | 270.27 | ---NA--- |
| SEQ ID NO: 5070 | Nga03277 | 701.39 | 913.67 | atpase ii |
| SEQ ID NO: 5071 | Nga21252 | 184.43 | 235.29 | conserved unknown protein [Ectocarpus siliculosus] |
| SEQ ID NO: 5072 | Nga21138 | 178.92 | 214.84 | inositol-pentakisphosphate 2-kinase-like protein |
| SEQ ID NO: 5073 | Nga03283 | 704.79 | 670.24 | short-chain dehydrogenase reductase sdr |
| SEQ ID NO: 5074 | Nga03275 | 2491.04 | 2182.00 | proteasome subunit beta type 5 |
| SEQ ID NO: 5075 | Nga03270 | 875.96 | 885.98 | valosin containing protein p47 complex interacting protein 1 |
| SEQ ID NO: 5076 | Nga03268 | 519.31 | 457.67 | poly + rna transport protein |
| SEQ ID NO: 5077 | Nga20201 | 224.37 | 213.44 | protein |
| SEQ ID NO: 5078 | Nga03279 | 1010.13 | 1100.79 | ribonuclease p protein subunit p38-like |
| SEQ ID NO: 5079 | Nga03280 | 179.90 | 146.38 | protein |
| SEQ ID NO: 5080 | Nga03273 | 392.62 | 349.64 | 1-family small gtpase |
| SEQ ID NO: 5081 | Nga03278 | 224.81 | 224.62 | protein |
| SEQ ID NO: 5082 | Nga03271 | 164.47 | 173.39 | protein |
| SEQ ID NO: 5083 | Nga03274 | 12610.72 | 11455.70 | 40s ribosomal protein s15 |
| SEQ ID NO: 5084 | Nga00225.1 | 267.29 | 320.52 | protein |
| SEQ ID NO: 5085 | Nga00218.01 | 1682.69 | 1001.99 | protein |
| SEQ ID NO: 5086 | Nga00219 | 596.03 | 631.89 | protein binding protein |
| SEQ ID NO: 5087 | Nga00215 | 3847.65 | 4595.83 | protein |
| SEQ ID NO: 5088 | Nga00220 | 1055.87 | 1016.56 | ribosomal rna processing protein 1 homolog b-like |
| SEQ ID NO: 5089 | Nga00228 | 74.63 | 43.11 | dynein regulator |
| SEQ ID NO: 5090 | Nga00226 | 9489.18 | 9952.21 | 60s ribosomal protein l17-2 |
| SEQ ID NO: 5091 | Nga00229 | 653.70 | 653.95 | uncharacterized protein |
| SEQ ID NO: 5092 | Nga00217.01 | 13677.11 | 13639.38 | myo-inositol 2-dehydrogenase |
| SEQ ID NO: 5093 | Nga00222 | 83.21 | 66.94 | myosin-like antigen |
| SEQ ID NO: 5094 | Nga00214.01 | 684.27 | 683.71 | pleckstrin domain-containing protein |
| SEQ ID NO: 5095 | Nga00221 | 352.94 | 356.62 | peptidyl-trna hydrolase |
| SEQ ID NO: 5096 | Nga20072.1 | 318.39 | 347.35 | chloride channel 7 |
| SEQ ID NO: 5097 | Nga20531 | 207.87 | 265.55 | kinesin-like protein |
| SEQ ID NO: 5098 | Nga21229.1 | 348.84 | 268.71 | chloride channel protein 7 |
| SEQ ID NO: 5099 | Nga21126.1 | 152.35 | 114.02 | ---NA--- |
| SEQ ID NO: 5100 | Nga00231.01 | 129.11 | 317.85 | phd zinc finger-containing protein |
| SEQ ID NO: 5101 | Nga00227.01 | 631.30 | 781.54 | predicted protein [Thalassiosira pseudonana CCMP1335] |
| SEQ ID NO: 5102 | Nga00216 | 320.47 | 241.08 | sec1 family domain containing 1 |
| SEQ ID NO: 5103 | Nga21225.1 | 229.03 | 262.07 | ribosomal rna large subunit methyltransferase f |
| SEQ ID NO: 5104 | Nga00224.01 | 2630.54 | 2139.15 | alanine-2-oxoglutarate aminotransferase 2 |
| SEQ ID NO: 5105 | Nga00234.01 | 163.78 | 204.54 | methyltransferase mett10d |
| SEQ ID NO: 5106 | Nga00230.01 | 292.04 | 421.79 | amino acid permease family protein |
| SEQ ID NO: 5107 | Nga00232.01 | 3023.75 | 2957.22 | hypothetical protein tll0394 [Thermosynechococcus elongatus BP-1] |
| SEQ ID NO: 5108 | Nga20001 | 1521.93 | 1225.76 | transmembrane protein 167 precursor |
| SEQ ID NO: 5109 | Nga20338.1 | 945.78 | 846.23 | ctf2a like oxidoreductase |
| SEQ ID NO: 5110 | Nga00233.01 | 365.97 | 281.46 | ---NA--- |
| SEQ ID NO: 5111 | Nga00223.01 | 647.29 | 827.95 | serine acetyltransferase |
| SEQ ID NO: 5112 | Nga01769.2 | 448.64 | 619.83 | 5-oxoprolinase |
| SEQ ID NO: 5113 | Nga01768.02 | 13904.11 | 18448.36 | heat shock protein hsp20 |
| SEQ ID NO: 5114 | Nga02641 | 704.34 | 721.43 | mgc82338 protein |
| SEQ ID NO: 5115 | Nga02643 | 216.31 | 321.43 | protein |
| SEQ ID NO: 5116 | Nga01770.02 | 189.25 | 218.98 | zinc transport |
| SEQ ID NO: 5117 | Nga20175.1 | 274.30 | 357.71 | protein |
| SEQ ID NO: 5118 | Nga02639 | 1339.04 | 1328.07 | soluble nsf attachment protein receptor |
| SEQ ID NO: 5119 | Nga20309 | 1726.28 | 1666.79 | protein |
| SEQ ID NO: 5120 | Nga02638 | 195.42 | 176.79 | sphingosine kinase 1 |
| SEQ ID NO: 5121 | Nga02635 | 418.48 | 477.59 | ring finger domain protein |
| SEQ ID NO: 5122 | Nga02634 | 857.80 | 849.18 | elongation factor ts |

FIGURE 24 CC

| # | Nga model | +N rpkb | -N rpkb | GO |
|---|---|---|---|---|
| SEQ ID NO: 5123 | Nga02642 | 302.36 | 341.85 | aminophospholipid transporter- class type member 2 |
| SEQ ID NO: 5124 | Nga02636 | 1207.30 | 1209.58 | geranylgeranyl pyrophosphate synthase |
| SEQ ID NO: 5125 | Nga02637 | 745.43 | 669.30 | phosphoribosylglycinamide synthetase |
| SEQ ID NO: 5126 | Nga20516 | 241.99 | 215.88 | ---NA--- |
| SEQ ID NO: 5127 | Nga21184.1 | 36.04 | 9.76 | serine threonine-protein kinase eg2-like |
| SEQ ID NO: 5128 | Nga20012.1 | 68.63 | 21.24 | a chain crystal structure of the mouse aurora-a catalytic domain (asn186- |
| SEQ ID NO: 5129 | Nga05092 | 128.80 | 162.78 | sentrin-specific protease 1 |
| SEQ ID NO: 5130 | Nga20340.1 | 95.93 | 63.41 | protein kinase p46 g22 |
| SEQ ID NO: 5131 | Nga05091 | 464.45 | 470.60 | short-chain dehydrogenase reductase sdr |
| SEQ ID NO: 5132 | Nga05090 | 2040.24 | 2166.87 | mei2-like protein |
| SEQ ID NO: 5133 | Nga05089 | 302.13 | 341.51 | trna (uracil-5-)-methyltransferase |
| SEQ ID NO: 5134 | Nga02987 | 430.32 | 464.24 | myb dna binding protein transcription factor-like protein |
| SEQ ID NO: 5135 | Nga02981 | 1070.31 | 1018.61 | protein |
| SEQ ID NO: 5136 | Nga02983 | 818.87 | 805.42 | family exonuclease |
| SEQ ID NO: 5137 | Nga02990 | 1731.36 | 2821.59 | protein |
| SEQ ID NO: 5138 | Nga02984 | 413.11 | 482.58 | telomerase-binding protein est1a |
| SEQ ID NO: 5139 | Nga02994 | 323.94 | 361.08 | protein |
| SEQ ID NO: 5140 | Nga02986 | 213.51 | 234.21 | peptide chain release factor 1 |
| SEQ ID NO: 5141 | Nga02992 | 196.37 | 189.48 | protein |
| SEQ ID NO: 5142 | Nga02991 | 37.04 | 8.02 | ---NA--- |
| SEQ ID NO: 5143 | Nga02988 | 896.35 | 993.96 | 3-hydroxybutyryl- dehydratase |
| SEQ ID NO: 5144 | Nga21033 | 283.19 | 190.25 | hypothetical protein AURANDRAFT_66840 [Aureococcus anophagefferens] |
| SEQ ID NO: 5145 | Nga20263 | 186.60 | 156.19 | 72 kda inositol polyphosphate 5-phosphatase |
| SEQ ID NO: 5146 | Nga02989 | 76.30 | 100.18 | elac homolog 2 ( coli) |
| SEQ ID NO: 5147 | Nga02982 | 1058.13 | 1109.91 | cral trio domain containing protein |
| SEQ ID NO: 5148 | Nga21040 | 962.69 | 931.66 | methyltransferase type 11 |
| SEQ ID NO: 5149 | Nga02985 | 804.30 | 864.17 | rna polymerase ii largest subunit |
| SEQ ID NO: 5150 | Nga03014 | 3975.51 | 4120.71 | dienelactone hydrolase family protein |
| SEQ ID NO: 5151 | Nga21160 | 182.44 | 156.61 | setx protein |
| SEQ ID NO: 5152 | Nga21276 | 210.53 | 175.42 | trna-splicing endonuclease positive effector-related |
| SEQ ID NO: 5153 | Nga03018 | 111.11 | 82.60 | dna2 nam7 helicase family protein |
| SEQ ID NO: 5154 | Nga03015 | 96.67 | 46.94 | protein kinase wee1 |
| SEQ ID NO: 5155 | Nga03019 | 47.62 | 44.88 | ---NA--- |
| SEQ ID NO: 5156 | Nga03011 | 499.59 | 530.60 | ring u-box domain-containing protein |
| SEQ ID NO: 5157 | Nga03010 | 1041.63 | 1351.86 | dihydrolipoamide branched chain transacylase e2 |
| SEQ ID NO: 5158 | Nga01582.02 | 532.14 | 464.71 | ---NA--- |
| SEQ ID NO: 5159 | Nga03009 | 1024.57 | 1099.99 | ---NA--- |
| SEQ ID NO: 5160 | Nga03017.1 | 404.03 | 455.47 | cell division cycle 16 |
| SEQ ID NO: 5161 | Nga03012 | 466.72 | 381.46 | nicotinate-nucleotide adenylyltransferase |
| SEQ ID NO: 5162 | Nga03013 | 241.58 | 300.98 | splicing factor 3a |
| SEQ ID NO: 5163 | Nga03360.02 | 1681.41 | 1926.98 | protein |
| SEQ ID NO: 5164 | Nga00850.2 | 1465.64 | 1654.48 | ---NA--- |
| SEQ ID NO: 5165 | Nga03366 | 1547.98 | 1043.31 | tissue specific transplantation antigen p35b |
| SEQ ID NO: 5166 | Nga03360.01 | 1681.41 | 1926.98 | protein |
| SEQ ID NO: 5167 | Nga03375 | 174.57 | 119.22 | protein |
| SEQ ID NO: 5168 | Nga03362 | 1326.99 | 1314.42 | aldehyde dehydrogenase |
| SEQ ID NO: 5169 | Nga00846.02 | 193.32 | 915.00 | ---NA--- |
| SEQ ID NO: 5170 | Nga03368 | 658.30 | 546.96 | periplasmic binding protein |
| SEQ ID NO: 5171 | Nga00845.02 | 388.86 | 398.35 | at4g35080-like protein |
| SEQ ID NO: 5172 | Nga00849.02 | 242.17 | 287.01 | set domain-containing protein |
| SEQ ID NO: 5173 | Nga03378 | 205.39 | 218.84 | mixed-lineage leukemia |
| SEQ ID NO: 5174 | Nga03371 | 28.53 | 15.45 | ---NA--- |
| SEQ ID NO: 5175 | Nga03364 | 1139.26 | 1237.23 | protein |
| SEQ ID NO: 5176 | Nga03376 | 63.38 | 42.38 | ---NA--- |
| SEQ ID NO: 5177 | Nga03373 | 65.54 | 83.59 | histone-lysine n- |
| SEQ ID NO: 5178 | Nga03361 | 880.00 | 786.35 | protein |
| SEQ ID NO: 5179 | Nga20063 | 1441.67 | 1145.42 | zip transporter |
| SEQ ID NO: 5180 | Nga20510 | 245.10 | 159.30 | chaperone protein dnaj 15 |
| SEQ ID NO: 5181 | Nga20341 | 184.44 | 221.64 | chaperone protein dnaj 16 |
| SEQ ID NO: 5182 | Nga20312.1 | 213.58 | 236.73 | wd40 repeat-containing protein |
| SEQ ID NO: 5183 | Nga00851.02 | 151.62 | 199.44 | ---NA--- |
| SEQ ID NO: 5184 | Nga00848.02 | 912.07 | 750.95 | ubiquitin-conjugating enzyme |

FIGURE 24 CD

| # | Nga model | +N rpkb | -N rpkb | GO |
|---|---|---|---|---|
| SEQ ID NO: 5185 | Nga03367 | 888.69 | 1008.26 | ---NA--- |
| SEQ ID NO: 5186 | Nga20634.1 | 81.16 | 94.19 | protein |
| SEQ ID NO: 5187 | Nga03137 | 439.05 | 556.44 | cysteinyl-trna synthetase |
| SEQ ID NO: 5188 | Nga03140 | 235.55 | 258.43 | molybdenum cofactor sulfurase |
| SEQ ID NO: 5189 | Nga03132 | 784.40 | 697.31 | protein |
| SEQ ID NO: 5190 | Nga03134 | 3020.45 | 2652.70 | nuclear distribution gene c homolog (nidulans) |
| SEQ ID NO: 5191 | Nga20507 | 523.54 | 687.48 | dual specificity phosphatase 19 |
| SEQ ID NO: 5192 | Nga03129 | 958.31 | 868.88 | haloacid dehalogenase-like hydrolase domain containing 3 |
| SEQ ID NO: 5193 | Nga03142 | 985.13 | 1119.25 | nucleotide-binding protein 1 |
| SEQ ID NO: 5194 | Nga03136 | 2128.02 | 1590.84 | mitochondrial import inner membrane translocase subunit tim16 |
| SEQ ID NO: 5195 | Nga20948 | 1559.44 | 1541.97 | alpha- -mannosyltransferase |
| SEQ ID NO: 5196 | Nga03143 | 294.72 | 281.60 | fusaric acid resistance protein conserved region |
| SEQ ID NO: 5197 | Nga03130 | 1880.21 | 1739.94 | polyadenylate-binding protein 2 |
| SEQ ID NO: 5198 | Nga20786 | 554.50 | 540.45 | centromere protein v-like |
| SEQ ID NO: 5199 | Nga03135 | 5236.96 | 4477.76 | uncharacterized protein |
| SEQ ID NO: 5200 | Nga03133 | 175.61 | 191.61 | dead deah box rna |
| SEQ ID NO: 5201 | Nga03141 | 161.46 | 149.82 | poc1 centriolar protein homolog a |
| SEQ ID NO: 5202 | Nga03139 | 1266.67 | 1354.04 | protein |
| SEQ ID NO: 5203 | Nga03131.1 | 4353.20 | 4000.45 | protein |
| SEQ ID NO: 5204 | Nga21021 | 450.47 | 471.36 | trna-specific adenosine deaminase |
| SEQ ID NO: 5205 | Nga21107.1 | 325.61 | 338.77 | histidine kinase |
| SEQ ID NO: 5206 | Nga02569 | 2515.44 | 2336.77 | expressed unknown protein [Ectocarpus siliculosus] |
| SEQ ID NO: 5207 | Nga02568 | 7730.28 | 7752.15 | 60s ribosomal protein l18a |
| SEQ ID NO: 5208 | Nga02559 | 1343.94 | 1059.01 | archain 1 |
| SEQ ID NO: 5209 | Nga02560 | 1332.36 | 1147.83 | protein |
| SEQ ID NO: 5210 | Nga20256 | 407.14 | 410.26 | aaa family cdc48 subfamily |
| SEQ ID NO: 5211 | Nga02571 | 291.49 | 334.19 | cell division cycle atpase |
| SEQ ID NO: 5212 | Nga02570 | 2636.36 | 2515.90 | crai n-terminus family protein |
| SEQ ID NO: 5213 | Nga02557 | 1664.90 | 1453.90 | betaine aldehyde dehydrogenase |
| SEQ ID NO: 5214 | Nga02566 | 446.76 | 513.11 | protein |
| SEQ ID NO: 5215 | Nga20011.1 | 326.19 | 355.92 | e3 ubiquitin-protein ligase march6 (membrane-associated ring finger protein 6) |
| SEQ ID NO: 5216 | Nga02564.1 | 844.61 | 826.95 | protein |
| SEQ ID NO: 5217 | Nga02558 | 2034.23 | 1866.51 | protein |
| SEQ ID NO: 5218 | Nga02572 | 912.85 | 662.42 | ---NA--- |
| SEQ ID NO: 5219 | Nga02563.01 | 1646.55 | 1120.59 | ---NA--- |
| SEQ ID NO: 5220 | Nga02567 | 697.11 | 623.46 | lethal leaf-spot 1 |
| SEQ ID NO: 5221 | Nga02562 | 357.70 | 401.13 | in family member (ttn-1) |
| SEQ ID NO: 5222 | Nga02561 | 712.13 | 691.44 | conserved unknown protein [Ectocarpus siliculosus] |
| SEQ ID NO: 5223 | Nga02565 | 1241.35 | 1275.61 | like dehydratase |
| SEQ ID NO: 5224 | Nga02712 | 1198.88 | 1171.68 | protein |
| SEQ ID NO: 5225 | Nga20789.1 | 176.68 | 187.44 | proteasome component ecm29 |
| SEQ ID NO: 5226 | Nga02709 | 398.46 | 474.10 | tpr repeat protein |
| SEQ ID NO: 5227 | Nga02719.01 | 441.81 | 429.69 | ---NA--- |
| SEQ ID NO: 5228 | Nga20861 | 971.41 | 793.44 | nad-dependent epimerase dehydratase |
| SEQ ID NO: 5229 | Nga02708 | 985.63 | 1077.40 | xylose isomerase |
| SEQ ID NO: 5230 | Nga02707 | 249.07 | 240.46 | tryptophanyl-trna synthetase |
| SEQ ID NO: 5231 | Nga02714.1 | 1736.95 | 1771.36 | protein |
| SEQ ID NO: 5232 | Nga02711 | 810.37 | 876.47 | hypothetical protein [Aegilops comosa] |
| SEQ ID NO: 5233 | Nga02720 | 866.17 | 646.00 | conserved unknown protein [Ectocarpus siliculosus] |
| SEQ ID NO: 5234 | Nga02716 | 1045.79 | 1275.68 | mitochondrial carrier family |
| SEQ ID NO: 5235 | Nga20870 | 1167.54 | 1234.47 | mitochondrial deoxynucleotide carrier |
| SEQ ID NO: 5236 | Nga02718 | 1444.86 | 1312.03 | clathrin coat assembly protein |
| SEQ ID NO: 5237 | Nga02713 | 5202.71 | 6201.40 | cellulase 2 |
| SEQ ID NO: 5238 | Nga02722 | 550.94 | 590.67 | 8-amino-7-oxononanoate synthase |
| SEQ ID NO: 5239 | Nga02710 | 1948.09 | 2440.72 | rna binding |
| SEQ ID NO: 5240 | Nga20660.1 | 186.38 | 198.01 | incenp-like protein |
| SEQ ID NO: 5241 | Nga21207 | 200.93 | 318.90 | methyltransferase type 12 |
| SEQ ID NO: 5242 | Nga20724 | 852.33 | 823.76 | rrna-processing protein utp23 homolog |
| SEQ ID NO: 5243 | Nga02721 | 475.73 | 452.22 | nucleic-acid-binding contains pin domain |
| SEQ ID NO: 5244 | Nga02706 | 620.17 | 641.06 | cleavage stimulation factor subunit 2-like |
| SEQ ID NO: 5245 | Nga02715 | 7392.93 | 6832.71 | s-adenosyl homocysteine hydrolase |
| SEQ ID NO: 5246 | Nga02323.02 | 2494.69 | 2768.12 | elongation factor 1- |
| SEQ ID NO: 5247 | Nga05333.2 | 798.92 | 827.30 | amp deaminase |

FIGURE 24 CE

| # | Nga model | +N rpkb | -N rpkb | GO |
|---|---|---|---|---|
| SEQ ID NO: 5248 | Nga05331.1 | 11.56 | 0.00 | ---NA--- |
| SEQ ID NO: 5249 | Nga05336 | 504.17 | 437.81 | amp deaminase |
| SEQ ID NO: 5250 | Nga03220.02 | 96.59 | 100.08 | gc-rich sequence dna-binding factor homolog |
| SEQ ID NO: 5251 | Nga03216.02 | 358.22 | 431.53 | aspartyl glutamyl-trna amidotransferase subunit b |
| SEQ ID NO: 5252 | Nga05332 | 2441.03 | 2962.63 | glycolipid 2-alpha-mannosyltransferase |
| SEQ ID NO: 5253 | Nga03215.02 | 761.85 | 870.92 | ribosomal rna processing 12 homolog ( cerevisiae) |
| SEQ ID NO: 5254 | Nga05333.1 | 798.92 | 827.30 | protein |
| SEQ ID NO: 5255 | Nga04346.02 | 876.42 | 824.31 | dna replication complex gins protein psf3 |
| SEQ ID NO: 5256 | Nga05344 | 317.68 | 345.82 | upf0187-containing protein |
| SEQ ID NO: 5257 | Nga05345 | 207.25 | 213.28 | predicted protein [Naegleria gruberi] |
| SEQ ID NO: 5258 | Nga05347 | 120.69 | 127.18 | regulator of telomere elongation helicase 1 |
| SEQ ID NO: 5259 | Nga05342 | 463.75 | 292.55 | ---NA--- |
| SEQ ID NO: 5260 | Nga05346 | 619.90 | 605.46 | ---NA--- |
| SEQ ID NO: 5261 | Nga20942 | 682.31 | 722.73 | conserved unknown protein [Ectocarpus siliculosus] |
| SEQ ID NO: 5262 | Nga03073 | 821.51 | 669.27 | conserved unknown protein [Ectocarpus siliculosus] |
| SEQ ID NO: 5263 | Nga03083 | 815.85 | 888.39 | tim17_caeel ame: full=probable mitochondrial import inner membrane translocase subunit tim17 |
| SEQ ID NO: 5264 | Nga06389.2 | 645.23 | 635.62 | supt16h protein |
| SEQ ID NO: 5265 | Nga20365 | 112.39 | 144.10 | m3g-cap-specific nuclear import receptor |
| SEQ ID NO: 5266 | Nga03069 | 2784.42 | 3048.95 | nadh-ubiquinone reductase 75 kda subunit precursor |
| SEQ ID NO: 5267 | Nga03076 | 555.19 | 570.83 | pyrroline-5-carboxylate reductase |
| SEQ ID NO: 5268 | Nga03070 | 850.52 | 1031.86 | asparaginyl-trna synthetase |
| SEQ ID NO: 5269 | Nga03065.01 | 525.64 | 552.61 | adenosine 3 -phospho 5 -phosphosulfate transporter 2 |
| SEQ ID NO: 5270 | Nga03067 | 479.46 | 488.89 | phosphatidylinositol-4-phosphate 5-kinase its3 |
| SEQ ID NO: 5271 | Nga03077 | 411.33 | 398.63 | asparagine-linked glycosylation protein 11 homolog |
| SEQ ID NO: 5272 | Nga03066.01 | 1130.43 | 1118.00 | coiled-coil domain 6-like protein |
| SEQ ID NO: 5273 | Nga20129 | 333.33 | 415.24 | conserved unknown protein [Ectocarpus siliculosus] |
| SEQ ID NO: 5274 | Nga03078 | 1458.71 | 1454.39 | eukaryotic translation initiation factor 6 |
| SEQ ID NO: 5275 | Nga03072.01 | 1389.98 | 1476.31 | ---NA--- |
| SEQ ID NO: 5276 | Nga03063.01 | 1093.05 | 887.33 | ---NA--- |
| SEQ ID NO: 5277 | Nga03075 | 281.63 | 255.61 | fad dependent oxidoreductase |
| SEQ ID NO: 5278 | Nga04730.2 | 247.45 | 315.99 | sorting nexin 16 isoform 1 |
| SEQ ID NO: 5279 | Nga03074 | 741.21 | 888.44 | actin-related protein 6 |
| SEQ ID NO: 5280 | Nga03081 | 58.67 | 94.91 | ---NA--- |
| SEQ ID NO: 5281 | Nga03071 | 6554.83 | 6984.82 | 14-3-3-like protein |
| SEQ ID NO: 5282 | Nga03064 | 470.09 | 271.14 | protein of hypothetical function duf1445 |
| SEQ ID NO: 5283 | Nga00377 | 162.23 | 190.84 | rna-binding protein 26 |
| SEQ ID NO: 5284 | Nga00385 | 392.86 | 430.39 | conserved unknown protein [Ectocarpus siliculosus] |
| SEQ ID NO: 5285 | Nga00384 | 2918.39 | 2733.34 | prefoldin subunit 1 |
| SEQ ID NO: 5286 | Nga00376.01 | 2173.73 | 2140.08 | centrin 3 |
| SEQ ID NO: 5287 | Nga00373 | 762.09 | 1087.48 | 50s ribosomal protein l21 |
| SEQ ID NO: 5288 | Nga20414 | 174.11 | 280.48 | rna binding motif protein 34 |
| SEQ ID NO: 5289 | Nga00374 | 384.47 | 358.41 | sf- |
| SEQ ID NO: 5290 | Nga20509 | 250.35 | 325.42 | rna recognition motif-containing protein |
| SEQ ID NO: 5291 | Nga00379.01 | 689.68 | 757.11 | protein |
| SEQ ID NO: 5292 | Nga00383 | 463.08 | 537.05 | ---NA--- |
| SEQ ID NO: 5293 | Nga00380 | 444.30 | 528.29 | protein |
| SEQ ID NO: 5294 | Nga00386 | 835.92 | 1075.75 | ubiquinone biosynthesis protein coq9 |
| SEQ ID NO: 5295 | Nga00375 | 592.97 | 769.27 | mechanosensitive ion channel |
| SEQ ID NO: 5296 | Nga00388 | 332.64 | 331.62 | prenylcysteine oxidase |
| SEQ ID NO: 5297 | Nga20710 | 111.11 | 140.91 | phycoerythrobilin:ferredoxin oxidoreductase |
| SEQ ID NO: 5298 | Nga00378 | 824.62 | 558.14 | serologically defined breast cancer antigen ny-br-84 |
| SEQ ID NO: 5299 | Nga00387 | 559.09 | 534.05 | ribosomal rna-processing protein 7 homolog a-like |
| SEQ ID NO: 5300 | Nga00382 | 257.19 | 243.77 | protein |
| SEQ ID NO: 5301 | Nga20036 | 277.78 | 334.48 | tnf receptor-associated factor 4 |
| SEQ ID NO: 5302 | Nga00381 | 973.76 | 1309.47 | carbamoyl-phosphate synthase |
| SEQ ID NO: 5303 | Nga02488 | 102.22 | 88.58 | cof-like hydrolase |
| SEQ ID NO: 5304 | Nga02487 | 173.19 | 142.28 | ---NA--- |
| SEQ ID NO: 5305 | Nga02494 | 374.76 | 359.72 | sua5 family protein |
| SEQ ID NO: 5306 | Nga02493.1 | 102.33 | 114.38 | wd repeat-containing protein ybr281c |
| SEQ ID NO: 5307 | Nga02330.02 | 2612.90 | 2387.77 | nadh-ubiquinone oxidoreductase kda subunit |
| SEQ ID NO: 5308 | Nga06751.2 | 215.61 | 248.63 | nucleolar protein |
| SEQ ID NO: 5309 | Nga02489.01 | 709.02 | 658.32 | ---NA--- |
| SEQ ID NO: 5310 | Nga02490.1 | 186.19 | 169.96 | hypothetical protein CAOG_06333 [Capsaspora owczarzaki ATCC 30864] |

FIGURE 24 CF

| # | Nga model | +N rpkb | -N rpkb | GO |
|---|---|---|---|---|
| SEQ ID NO: 5311 | Nga02610 | 1611.61 | 1457.21 | 26s proteasome subunit 4 |
| SEQ ID NO: 5312 | Nga02609 | 1449.69 | 1763.66 | dioxygenase-like protein |
| SEQ ID NO: 5313 | Nga02615 | 510.10 | 483.69 | protein |
| SEQ ID NO: 5314 | Nga02612 | 418.81 | 317.67 | protein |
| SEQ ID NO: 5315 | Nga02617 | 295.04 | 362.02 | ---NA--- |
| SEQ ID NO: 5316 | Nga02613 | 980.62 | 971.27 | pre-mrna-splicing factor |
| SEQ ID NO: 5317 | Nga02608.01 | 5491.92 | 5974.05 | expressed unknown protein [Ectocarpus siliculosus] |
| SEQ ID NO: 5318 | Nga02616 | 136.70 | 139.97 | ---NA--- |
| SEQ ID NO: 5319 | Nga02614.01 | 352.17 | 411.06 | choline ethanolaminephosphotransferase 1 |
| SEQ ID NO: 5320 | Nga02611 | 727.27 | 997.89 | ---NA--- |
| SEQ ID NO: 5321 | Nga00554.2 | 187.18 | 217.34 | dihydrouridine synthase |
| SEQ ID NO: 5322 | Nga00585 | 1501.49 | 1132.45 | delta-aminolevulinic acid dehydratase |
| SEQ ID NO: 5323 | Nga00757.2 | 503.26 | 513.37 | protein |
| SEQ ID NO: 5324 | Nga00583 | 214.56 | 209.89 | cg9383-pa |
| SEQ ID NO: 5325 | Nga20689 | 333.33 | 380.98 | ---NA--- |
| SEQ ID NO: 5326 | Nga00589 | 414.81 | 437.31 | ---NA--- |
| SEQ ID NO: 5327 | Nga21194 | 451.30 | 517.70 | expressed unknown protein [Ectocarpus siliculosus] |
| SEQ ID NO: 5328 | Nga00545 | 802.40 | 773.47 | kinesin heavy chain |
| SEQ ID NO: 5329 | Nga00547 | 239.90 | 271.98 | protein |
| SEQ ID NO: 5330 | Nga00593 | 204.70 | 242.35 | polyribonucleotide nucleotidyltransferase |
| SEQ ID NO: 5331 | Nga00590 | 717.56 | 726.29 | low psii accumulation 3 protein |
| SEQ ID NO: 5332 | Nga21110 | 126.20 | 173.04 | polyribonucleotide nucleotidyltransferase |
| SEQ ID NO: 5333 | Nga00574 | 2288.15 | 2147.37 | aspartate aminotransferase |
| SEQ ID NO: 5334 | Nga00575 | 976.41 | 799.73 | microtubule -associated protein eb1 |
| SEQ ID NO: 5335 | Nga00591 | 1143.99 | 1161.90 | g u mismatch-specific dna glycosylase |
| SEQ ID NO: 5336 | Nga00577 | 537.44 | 447.83 | protein |
| SEQ ID NO: 5337 | Nga00584 | 1501.51 | 1661.40 | nudix hydrolase 13 |
| SEQ ID NO: 5338 | Nga00551 | 310.09 | 345.75 | xanthine molybdopterin binding subunit |
| SEQ ID NO: 5339 | Nga00587 | 1667.35 | 1980.41 | adenylosuccinate lyase |
| SEQ ID NO: 5340 | Nga00548 | 1566.67 | 1390.15 | conserved unknown protein [Ectocarpus siliculosus] |
| SEQ ID NO: 5341 | Nga20846 | 414.01 | 494.47 | tubby-like protein |
| SEQ ID NO: 5342 | Nga00597 | 363.64 | 496.03 | cleavage induced conserved hypothetical protein [Albugo laibachii Nc14] |
| SEQ ID NO: 5343 | Nga00586.1 | 3477.54 | 3371.74 | thioredoxin |
| SEQ ID NO: 5344 | Nga00544 | 1830.57 | 1760.08 | ornithine aminotransferase |
| SEQ ID NO: 5345 | Nga00553 | 503.34 | 480.90 | protein arginine n-methyltransferase 10 |
| SEQ ID NO: 5346 | Nga20965 | 921.92 | 1034.44 | predicted protein [Thalassiosira pseudonana CCMP1335] |
| SEQ ID NO: 5347 | Nga00592 | 384.76 | 386.91 | protein |
| SEQ ID NO: 5348 | Nga21289 | 1169.44 | 1207.37 | protein |
| SEQ ID NO: 5349 | Nga00543 | 3443.12 | 2936.35 | ef-1 guanine nucleotide exchange domain-containing |
| SEQ ID NO: 5350 | Nga00588 | 1016.95 | 965.42 | protein |
| SEQ ID NO: 5351 | Nga00554.1 | 187.18 | 217.34 | protein |
| SEQ ID NO: 5352 | Nga00576 | 1134.83 | 1363.17 | protein |
| SEQ ID NO: 5353 | Nga00579 | 9785.98 | 9944.01 | mitochondrial phosphate transporter |
| SEQ ID NO: 5354 | Nga00582 | 793.36 | 708.55 | methylenetetrahydrofolate reductase |
| SEQ ID NO: 5355 | Nga00550 | 605.26 | 690.98 | atp-binding cassette |
| SEQ ID NO: 5356 | Nga00546 | 1581.98 | 1639.49 | vacuolar protein sorting-associated protein 25 |
| SEQ ID NO: 5357 | Nga00580 | 665.14 | 435.61 | conserved hypothetical protein [Albugo laibachii Nc14] |
| SEQ ID NO: 5358 | Nga03390 | 839.33 | 905.57 | abc1 family protein |
| SEQ ID NO: 5359 | Nga03391 | 891.97 | 704.23 | dnaj-like protein |
| SEQ ID NO: 5360 | Nga03392 | 15773.63 | 14925.45 | chloroplast sedoheptulose- -bisphosphatase |
| SEQ ID NO: 5361 | Nga03393 | 751.24 | 703.55 | ap-2 complex subunit |
| SEQ ID NO: 5362 | Nga20087 | 435.68 | 458.01 | protein |
| SEQ ID NO: 5363 | Nga21048 | 361.18 | 393.90 | dead-box atp-dependent rna helicase 50 |
| SEQ ID NO: 5364 | Nga21124 | 4855.17 | 5145.36 | related to single-stranded dna binding protein 12k chain |
| SEQ ID NO: 5365 | Nga03394 | 449.02 | 570.99 | protein |
| SEQ ID NO: 5366 | Nga03397.1 | 957.21 | 1058.84 | ribulose-phosphate 3-epimerase |
| SEQ ID NO: 5367 | Nga03396 | 1058.46 | 1206.72 | ---NA--- |
| SEQ ID NO: 5368 | Nga03398.01 | 2625.09 | 3123.45 | ---NA--- |
| SEQ ID NO: 5369 | Nga03395.01 | 617.11 | 421.31 | alkaline phosphatase d |
| SEQ ID NO: 5370 | Nga02916 | 468.93 | 503.42 | ---NA--- |
| SEQ ID NO: 5371 | Nga01439.02 | 6.01 | 9.76 | mismatch repair protein 5 |
| SEQ ID NO: 5372 | Nga02915 | 1330.78 | 1278.30 | family with sequence similarity member a |
| SEQ ID NO: 5373 | Nga02918 | 206.71 | 173.51 | gcn5-related n-acetyltransferase |

FIGURE 24 CG

| # | Nga model | +N rpkb | -N rpkb | GO |
|---|---|---|---|---|
| SEQ ID NO: 5374 | Nga01434.02 | 1309.20 | 1273.96 | zip zinc transporter family protein |
| SEQ ID NO: 5375 | Nga01435.02 | 321.71 | 320.46 | protein polybromo-1 |
| SEQ ID NO: 5376 | Nga01436.02 | 370.20 | 472.56 | inosine triphosphate pyrophosphatase |
| SEQ ID NO: 5377 | Nga02912 | 11436.47 | 12996.71 | superoxide dismutase |
| SEQ ID NO: 5378 | Nga01437.02 | 304.95 | 306.79 | alpha beta hydrolase fold family |
| SEQ ID NO: 5379 | Nga02913 | 2211.64 | 2238.77 | abc subfamily abcg |
| SEQ ID NO: 5380 | Nga01438.02 | 276.63 | 247.29 | protein phosphatase 1 beta |
| SEQ ID NO: 5381 | Nga20379.1 | 138.85 | 143.64 | protein |
| SEQ ID NO: 5382 | Nga06732 | 855.97 | 857.37 | fatty-acyl elongase |
| SEQ ID NO: 5383 | Nga06737 | 282.11 | 272.30 | ---NA--- |
| SEQ ID NO: 5384 | Nga06735 | 8771.85 | 9608.65 | heat shock protein 70 |
| SEQ ID NO: 5385 | Nga04494.2 | 1548.54 | 1513.11 | glutaredoxin-like protein |
| SEQ ID NO: 5386 | Nga06730 | 110.98 | 128.53 | dna polymerase alpha catalytic subunit |
| SEQ ID NO: 5387 | Nga06731.1 | 552.46 | 538.02 | fad-linked oxidoreductase |
| SEQ ID NO: 5388 | Nga06733 | 227.40 | 204.90 | expressed unknown protein [Ectocarpus siliculosus] |
| SEQ ID NO: 5389 | Nga06736 | 640.06 | 815.39 | wd repeat protein 12 |
| SEQ ID NO: 5390 | Nga21263 | 893.11 | 920.14 | serine threonine protein kinase |
| SEQ ID NO: 5391 | Nga21116 | 2007.27 | 1836.25 | lipid phosphate phosphatase 3 |
| SEQ ID NO: 5392 | Nga20103 | 344.83 | 415.55 | cytochrome b5-related protein |
| SEQ ID NO: 5393 | Nga20366 | 459.00 | 468.82 | ubiquitin-conjugating enzyme e2 j1 |
| SEQ ID NO: 5394 | Nga01815.02 | 774.27 | 649.59 | cral n-terminus family protein |
| SEQ ID NO: 5395 | Nga06120.1 | 290.91 | 317.94 | protein |
| SEQ ID NO: 5396 | Nga06117 | 485.28 | 547.67 | diphthine synthase |
| SEQ ID NO: 5397 | Nga06119 | 4204.07 | 4735.95 | lipase domain-containing protein |
| SEQ ID NO: 5398 | Nga20836 | 1088.88 | 1119.58 | protein |
| SEQ ID NO: 5399 | Nga20258 | 430.41 | 399.09 | atp-binding cassette subfamily member group wbc protein 2 |
| SEQ ID NO: 5400 | Nga20166 | 377.57 | 336.72 | abc subfamily abcg |
| SEQ ID NO: 5401 | Nga06122 | 613.80 | 736.47 | alkylated dna repair protein |
| SEQ ID NO: 5402 | Nga06121 | 264.98 | 292.52 | carboxyl-terminal protease |
| SEQ ID NO: 5403 | Nga03175 | 654.28 | 665.96 | protein |
| SEQ ID NO: 5404 | Nga03165.1 | 277.12 | 337.58 | glycoside hydrolase family 37 |
| SEQ ID NO: 5405 | Nga03158 | 8200.95 | 8424.20 | 40s ribosomal protein |
| SEQ ID NO: 5406 | Nga03163 | 2082.76 | 2372.01 | cysteine desulfurase |
| SEQ ID NO: 5407 | Nga03172 | 194.95 | 189.01 | tripeptidyl peptidase i |
| SEQ ID NO: 5408 | Nga20554 | 297.49 | 283.43 | protein |
| SEQ ID NO: 5409 | Nga03161 | 333.96 | 341.36 | leucine carboxyl methyltransferase |
| SEQ ID NO: 5410 | Nga02542.02 | 3636.79 | 3271.84 | ferredoxin |
| SEQ ID NO: 5411 | Nga03162 | 536.93 | 534.44 | ureidoglycolate dehydrogenase |
| SEQ ID NO: 5412 | Nga03159 | 879.61 | 1062.02 | ---NA--- |
| SEQ ID NO: 5413 | Nga03166 | 7892.28 | 8094.39 | gtp-binding protein sas1 |
| SEQ ID NO: 5414 | Nga03168 | 332.43 | 303.66 | gtp-binding protein |
| SEQ ID NO: 5415 | Nga03160 | 1284.64 | 1150.72 | protein |
| SEQ ID NO: 5416 | Nga03169 | 1995.61 | 2344.90 | protein |
| SEQ ID NO: 5417 | Nga03170 | 362.50 | 366.88 | conserved unknown protein [Ectocarpus siliculosus] |
| SEQ ID NO: 5418 | Nga03176 | 168.75 | 142.17 | ---NA--- |
| SEQ ID NO: 5419 | Nga03167 | 4364.02 | 4906.08 | guanine nucleotide binding protein (g protein) beta polypeptide 2-like 1 |
| SEQ ID NO: 5420 | Nga03174 | 291.90 | 220.44 | gram domain family protein |
| SEQ ID NO: 5421 | Nga03164 | 375.49 | 382.49 | amino acid transporter |
| SEQ ID NO: 5422 | Nga03171 | 427.00 | 283.72 | clathrin coat assembly protein ap-1 |
| SEQ ID NO: 5423 | Nga01450.02 | 127.06 | 184.11 | ---NA--- |
| SEQ ID NO: 5424 | Nga01456.02 | 131.94 | 90.27 | ---NA--- |
| SEQ ID NO: 5425 | Nga01455.02 | 100.67 | 87.24 | ---NA--- |
| SEQ ID NO: 5426 | Nga01453.2 | 470.62 | 390.38 | dnaj domain |
| SEQ ID NO: 5427 | Nga05272 | 151.79 | 204.43 | ---NA--- |
| SEQ ID NO: 5428 | Nga05275 | 200.00 | 292.91 | adp-ribosylation factor gtpase-activating protein agd6 |
| SEQ ID NO: 5429 | Nga21196.1 | 181.19 | 168.94 | yth domain containing 2 |
| SEQ ID NO: 5430 | Nga05267 | 487.04 | 524.97 | pre-mrna-splicing factor sf2 |
| SEQ ID NO: 5431 | Nga20318.1 | 568.29 | 583.89 | lyr family of fe s cluster biogenesis protein |
| SEQ ID NO: 5432 | Nga01451.02 | 769.63 | 823.71 | protein |
| SEQ ID NO: 5433 | Nga20298 | 578.13 | 395.33 | c transferase |
| SEQ ID NO: 5434 | Nga20314 | 389.06 | 358.82 | c transferase |
| SEQ ID NO: 5435 | Nga01452.02 | 175.93 | 164.13 | snf2 family dna-dependent atpase |
| SEQ ID NO: 5436 | Nga01448.02 | 1506.52 | 2076.07 | phosphoserine aminotransferase |

FIGURE 24 CH

| # | Nga model | +N rpkb | -N rpkb | GO |
|---|---|---|---|---|
| SEQ ID NO: 5437 | Nga05264 | 183.79 | 168.17 | t-snare family protein |
| SEQ ID NO: 5438 | Nga20698 | 627.80 | 547.28 | protein |
| SEQ ID NO: 5439 | Nga05643 | 502.30 | 465.78 | pre-mrna cleavage complex ii protein |
| SEQ ID NO: 5440 | Nga05650 | 1037.45 | 883.41 | transmembrane protein 128 |
| SEQ ID NO: 5441 | Nga05644 | 399.35 | 380.72 | protein |
| SEQ ID NO: 5442 | Nga05648 | 254.80 | 335.87 | protein |
| SEQ ID NO: 5443 | Nga04808.02 | 871.60 | 961.00 | mg-protoporphyrin ix methyl transferase |
| SEQ ID NO: 5444 | Nga05647 | 804.55 | 688.80 | protein |
| SEQ ID NO: 5445 | Nga04807.02 | 788.12 | 811.47 | uncharacterized protein |
| SEQ ID NO: 5446 | Nga05642 | 900.27 | 963.32 | ccaat-box binding factor hap3 |
| SEQ ID NO: 5447 | Nga04993.02 | 384.55 | 226.49 | tpr domain-containing protein |
| SEQ ID NO: 5448 | Nga20145 | 140.26 | 152.83 | sentrin-specific protease 7 |
| SEQ ID NO: 5449 | Nga02542.01 | 3636.79 | 3271.84 | ferredoxin |
| SEQ ID NO: 5450 | Nga02543 | 65.22 | 102.04 | ---NA--- |
| SEQ ID NO: 5451 | Nga02538 | 2786.50 | 2907.07 | glycosyl hydrolase family 1 |
| SEQ ID NO: 5452 | Nga02540 | 1883.64 | 1799.30 | subfamily member 4 |
| SEQ ID NO: 5453 | Nga02544 | 156.57 | 150.40 | microfibrillar-associated protein 1 |
| SEQ ID NO: 5454 | Nga02533 | 9225.73 | 7041.02 | phosphoglycerate mutase |
| SEQ ID NO: 5455 | Nga02541 | 65.12 | 78.09 | ---NA--- |
| SEQ ID NO: 5456 | Nga20971 | 2024.18 | 2071.83 | ---NA--- |
| SEQ ID NO: 5457 | Nga02539 | 335.74 | 332.40 | ---NA--- |
| SEQ ID NO: 5458 | Nga02534 | 2248.05 | 2311.24 | 24-sterol c-methyltransferase |
| SEQ ID NO: 5459 | Nga02537 | 3500.00 | 3981.18 | hypothetical protein Esi_0341_0019 [Ectocarpus siliculosus] |
| SEQ ID NO: 5460 | Nga02536 | 298.25 | 164.70 | ---NA--- |
| SEQ ID NO: 5461 | Nga02535 | 53.39 | 56.42 | dna repair protein rad51 |
| SEQ ID NO: 5462 | Nga20490 | 396.63 | 424.08 | conserved unknown protein [Ectocarpus siliculosus] |
| SEQ ID NO: 5463 | Nga20283 | 302.97 | 354.15 | nadh dehydrogenase |
| SEQ ID NO: 5464 | Nga21099 | 1258.20 | 1488.40 | cationic amino acid transporter |
| SEQ ID NO: 5465 | Nga02532 | 1146.72 | 1472.88 | predicted protein [Thalassiosira pseudonana CCMP1335] |
| SEQ ID NO: 5466 | Nga05076 | 211.22 | 184.11 | hypothetical protein Esi_0089_0116 [Ectocarpus siliculosus] |
| SEQ ID NO: 5467 | Nga05079 | 83.33 | 112.84 | elegans protein confirmed by transcript evidence |
| SEQ ID NO: 5468 | Nga05077 | 210.76 | 178.85 | protein |
| SEQ ID NO: 5469 | Nga20513.1 | 198.38 | 188.58 | aprataxin |
| SEQ ID NO: 5470 | Nga20574.1 | 116.79 | 229.30 | purine nucleoside phosphoramidase |
| SEQ ID NO: 5471 | Nga05075 | 188.54 | 193.34 | histone deacetylase family protein |
| SEQ ID NO: 5472 | Nga04813.02 | 691.41 | 580.01 | protein |
| SEQ ID NO: 5473 | Nga05080 | 129.25 | 162.12 | ---NA--- |
| SEQ ID NO: 5474 | Nga05067 | 577.78 | 590.69 | zinc iron permease |
| SEQ ID NO: 5475 | Nga05053.02 | 3648.17 | 3444.64 | vacuolar h+ atpase b subunit |
| SEQ ID NO: 5476 | Nga05068 | 59.24 | 81.41 | vacuolar protein sorting protein |
| SEQ ID NO: 5477 | Nga20281.1 | 237.84 | 253.24 | rna-binding protein nova-2 |
| SEQ ID NO: 5478 | Nga05066.01 | 164.88 | 164.69 | ---NA--- |
| SEQ ID NO: 5479 | Nga05062 | 28.80 | 23.40 | inorganic phosphate |
| SEQ ID NO: 5480 | Nga05063 | 1711.60 | 1879.35 | sulfate large subunit |
| SEQ ID NO: 5481 | Nga05058.01 | 5137.54 | 3468.91 | ferredoxin-dependent bilin reductase |
| SEQ ID NO: 5482 | Nga05061.01 | 1195.18 | 788.67 | phosphoinositol transporter |
| SEQ ID NO: 5483 | Nga05065 | 189.25 | 230.33 | zinc iron permease |
| SEQ ID NO: 5484 | Nga05069 | 255.56 | 284.85 | vacuolar protein sorting protein |
| SEQ ID NO: 5485 | Nga04461.02 | 698.16 | 611.27 | deah (asp-glu-ala-his) box polypeptide 35 |
| SEQ ID NO: 5486 | Nga05064 | 1600.10 | 1420.39 | phytoene desaturase |
| SEQ ID NO: 5487 | Nga05630.01 | 2018.06 | 2342.56 | apolipoprotein a-i-binding protein precursor |
| SEQ ID NO: 5488 | Nga05626 | 1207.51 | 1206.68 | exportin 1 (crm1 yeast) |
| SEQ ID NO: 5489 | Nga21020 | 105.56 | 126.38 | dna excision repair protein rad2 |
| SEQ ID NO: 5490 | Nga05628 | 584.34 | 591.89 | protein |
| SEQ ID NO: 5491 | Nga20889 | 70.42 | 61.03 | protein |
| SEQ ID NO: 5492 | Nga20711 | 160.92 | 173.07 | protein |
| SEQ ID NO: 5493 | Nga05625 | 983.51 | 1005.66 | thioredoxin o |
| SEQ ID NO: 5494 | Nga05632 | 70.55 | 51.58 | peptide-n -(n-acetyl-beta-glucosaminyl)asparagine amidase |
| SEQ ID NO: 5495 | Nga05627 | 600.97 | 625.35 | b-keto acyl reductase |
| SEQ ID NO: 5496 | Nga05629 | 1184.75 | 1269.37 | ---NA--- |
| SEQ ID NO: 5497 | Nga05631 | 363.77 | 304.38 | ---NA--- |
| SEQ ID NO: 5498 | Nga05633 | 766.80 | 672.20 | ---NA--- |
| SEQ ID NO: 5499 | Nga04452.02 | 3876.38 | 5172.26 | ---NA--- |
| SEQ ID NO: 5500 | Nga20212 | 210.79 | 209.31 | dual specificity phosphatase 3 |

FIGURE 24 CI

| # | Nga model | +N rpkb | -N rpkb | GO |
|---|---|---|---|---|
| SEQ ID NO: 5501 | Nga06102 | 234.89 | 252.48 | arginyl-trna synthetase |
| SEQ ID NO: 5502 | Nga06101 | 337.35 | 242.38 | protein |
| SEQ ID NO: 5503 | Nga06100 | 325.73 | 315.78 | mitochondrial carrier protein |
| SEQ ID NO: 5504 | Nga06107 | 895.28 | 570.91 | ---NA--- |
| SEQ ID NO: 5505 | Nga06104 | 359.18 | 502.03 | major intrinsic protein |
| SEQ ID NO: 5506 | Nga06108 | 716.83 | 689.10 | protein |
| SEQ ID NO: 5507 | Nga06103 | 1903.11 | 2124.96 | histidinol-phosphate aminotransferase |
| SEQ ID NO: 5508 | Nga06106 | 159.16 | 194.47 | rna polymerase iii subunit |
| SEQ ID NO: 5509 | Nga06208 | 184.80 | 184.56 | rad1 homolog ( pombe) |
| SEQ ID NO: 5510 | Nga21151 | 162.87 | 190.54 | cirhin |
| SEQ ID NO: 5511 | Nga06210 | 205.35 | 204.85 | homodimeric type |
| SEQ ID NO: 5512 | Nga20518 | 113.35 | 190.09 | protein |
| SEQ ID NO: 5513 | Nga20616 | 54.14 | 82.79 | ---NA--- |
| SEQ ID NO: 5514 | Nga06207 | 627.82 | 582.27 | replication protein a 70 kda dna-binding subunit |
| SEQ ID NO: 5515 | Nga06206 | 537.65 | 497.23 | conserved unknown protein [Ectocarpus siliculosus] |
| SEQ ID NO: 5516 | Nga06211 | 307.38 | 421.75 | ---NA--- |
| SEQ ID NO: 5517 | Nga06209 | 735.09 | 639.56 | 4 -phosphopantetheinyl transferase |
| SEQ ID NO: 5518 | Nga06205 | 20225.50 | 18271.71 | cyclophilin |
| SEQ ID NO: 5519 | Nga21307 | 202.13 | 224.71 | conserved unknown protein [Ectocarpus siliculosus] |
| SEQ ID NO: 5520 | Nga06695 | 359.09 | 275.67 | serine threonine protein kinase |
| SEQ ID NO: 5521 | Nga06692 | 671.77 | 618.23 | riboflavin biosynthesis protein |
| SEQ ID NO: 5522 | Nga04204.02 | 12867.52 | 15623.75 | acyl- dehydrogenase |
| SEQ ID NO: 5523 | Nga06693 | 1438.04 | 1522.31 | membrane protein |
| SEQ ID NO: 5524 | Nga20303 | 571.43 | 549.54 | nuclear autoantigenic sperm protein |
| SEQ ID NO: 5525 | Nga20760.1 | 1417.03 | 1398.98 | uncharacterized protein |
| SEQ ID NO: 5526 | Nga04205.02 | 1129.97 | 1359.07 | ---NA--- |
| SEQ ID NO: 5527 | Nga06690 | 5409.46 | 5190.74 | conserved unknown protein [Ectocarpus siliculosus] |
| SEQ ID NO: 5528 | Nga06382 | 1264.24 | 1184.40 | ---NA--- |
| SEQ ID NO: 5529 | Nga02348.02 | 345.29 | 397.21 | sam-dependent methyltransferase |
| SEQ ID NO: 5530 | Nga06383 | 206.60 | 236.02 | arsenite inducible rna associated protein aip- |
| SEQ ID NO: 5531 | Nga06379 | 638.72 | 786.71 | dead-box atp-dependent rna helicase 42 |
| SEQ ID NO: 5532 | Nga06384 | 100.59 | 123.92 | ---NA--- |
| SEQ ID NO: 5533 | Nga05685 | 243.00 | 284.75 | wd repeat-containing protein 82 |
| SEQ ID NO: 5534 | Nga05678 | 9966.85 | 22234.88 | glutamine synthetase |
| SEQ ID NO: 5535 | Nga05686 | 2698.50 | 2620.86 | conserved unknown protein [Ectocarpus siliculosus] |
| SEQ ID NO: 5536 | Nga05684 | 657.37 | 455.20 | drug metabolite transporter superfamily |
| SEQ ID NO: 5537 | Nga01534.2 | 3648.79 | 2991.10 | zeaxanthin epoxidase |
| SEQ ID NO: 5538 | Nga05683 | 39.04 | 26.02 | ---NA--- |
| SEQ ID NO: 5539 | Nga05680 | 333.33 | 201.17 | pfkb-like carbohydrate kinase family protein |
| SEQ ID NO: 5540 | Nga05681 | 522.48 | 451.54 | rip metalloprotease |
| SEQ ID NO: 5541 | Nga20562.1 | 152.05 | 190.04 | ---NA--- |
| SEQ ID NO: 5542 | Nga05682 | 221.60 | 242.07 | phosphatidate cytidylyltransferase |
| SEQ ID NO: 5543 | Nga02819.01 | 385.71 | 330.13 | ---NA--- |
| SEQ ID NO: 5544 | Nga02820.1 | 871.08 | 761.16 | ---NA--- |
| SEQ ID NO: 5545 | Nga02817.01 | 1953.22 | 1704.03 | polymerase ii (dna directed) polypeptide e |
| SEQ ID NO: 5546 | Nga02821 | 857.14 | 960.07 | dehydroascorbate reductase |
| SEQ ID NO: 5547 | Nga02815 | 3479.95 | 3712.93 | succinate dehydrogenase flavoprotein subunit |
| SEQ ID NO: 5548 | Nga02814 | 1072.66 | 898.90 | protein |
| SEQ ID NO: 5549 | Nga02816 | 294.12 | 351.08 | myotubularin |
| SEQ ID NO: 5550 | Nga20252.1 | 224.86 | 176.95 | inactive receptor kinase |
| SEQ ID NO: 5551 | Nga02812 | 3833.67 | 4187.86 | atp-citrate synthase |
| SEQ ID NO: 5552 | Nga02813.01 | 226.29 | 307.50 | protein |
| SEQ ID NO: 5553 | Nga20606 | 242.06 | 214.93 | short chain dehydrogenase reductase family protein |
| SEQ ID NO: 5554 | Nga02811 | 743.52 | 736.72 | ---NA--- |
| SEQ ID NO: 5555 | Nga02818.1 | 566.34 | 582.59 | threonine synthase |
| SEQ ID NO: 5556 | Nga20030 | 3646.05 | 2345.15 | predicted protein [Phaeodactylum tricornutum CCAP 1055/1] |
| SEQ ID NO: 5557 | Nga20983 | 371.79 | 481.02 | ran protein binding protein |
| SEQ ID NO: 5558 | Nga20349 | 106.82 | 83.65 | gnat family |
| SEQ ID NO: 5559 | Nga20656 | 491.97 | 520.27 | uba thif-type nad fad binding protein |
| SEQ ID NO: 5560 | Nga20355 | 492.06 | 552.12 | molybdopterin biosynthesis protein |
| SEQ ID NO: 5561 | Nga20775 | 372.45 | 421.38 | ubiquitin specific peptidase 54 |
| SEQ ID NO: 5562 | Nga21109 | 788.85 | 672.61 | repb family protein |
| SEQ ID NO: 5563 | Nga21142 | 2363.17 | 2449.78 | trans-2-enoyl- reductase |
| SEQ ID NO: 5564 | Nga20035 | 3342.15 | 2333.70 | protein |

FIGURE 24 CJ

| # | Nga model | +N rpkb | -N rpkb | GO |
|---|---|---|---|---|
| SEQ ID NO: 5565 | Nga20816 | 419.64 | 383.03 | octopine dehydrogenase |
| SEQ ID NO: 5566 | Nga21030 | 1389.45 | 1211.50 | protein |
| SEQ ID NO: 5567 | Nga20763 | 670.37 | 812.72 | vacuolar sorting protein 35 |
| SEQ ID NO: 5568 | Nga20045 | 11066.08 | 8994.01 | calreticulin precursor |
| SEQ ID NO: 5569 | Nga21269 | 106.84 | 97.21 | accelerated cell death 1 |
| SEQ ID NO: 5570 | Nga20970 | 10396.14 | 10596.85 | protein |
| SEQ ID NO: 5571 | Nga05831.01 | 1936.49 | 1515.83 | pentapeptide repeat protein |
| SEQ ID NO: 5572 | Nga05836 | 803.98 | 1238.73 | ---NA--- |
| SEQ ID NO: 5573 | Nga05833 | 1376.64 | 1269.77 | protein |
| SEQ ID NO: 5574 | Nga05832 | 114.17 | 102.00 | anthranilate phosphoribosyltransferase |
| SEQ ID NO: 5575 | Nga04855.02 | 0.00 | 66.87 | ---NA--- |
| SEQ ID NO: 5576 | Nga05834 | 440.46 | 490.76 | protein |
| SEQ ID NO: 5577 | Nga05835.1 | 267.36 | 292.12 | ring zinc finger-containing protein |
| SEQ ID NO: 5578 | Nga05830 | 338.03 | 356.77 | ubiquitin specific peptidase 5 (isopeptidase t) |
| SEQ ID NO: 5579 | Nga06407 | 505.82 | 578.33 | alpha- -mannosyltransferase alg9 |
| SEQ ID NO: 5580 | Nga01883.02 | 88.71 | 270.81 | ---NA--- |
| SEQ ID NO: 5581 | Nga06408 | 1988.98 | 1908.13 | d-lactate dehydrogenase |
| SEQ ID NO: 5582 | Nga03337 | 357.87 | 423.10 | coiled-coil domain-containing protein 12 |
| SEQ ID NO: 5583 | Nga03333 | 497.86 | 450.28 | atpase family aaa domain-containing protein 3 |
| SEQ ID NO: 5584 | Nga00838.2 | 940.72 | 973.95 | uv excision repair protein rad23 |
| SEQ ID NO: 5585 | Nga00840.02 | 285.71 | 424.31 | ---NA--- |
| SEQ ID NO: 5586 | Nga03350 | 683.59 | 647.40 | acid phosphatase |
| SEQ ID NO: 5587 | Nga03339 | 646.01 | 828.28 | rrna (guanine-n -)-methyltransferase |
| SEQ ID NO: 5588 | Nga03331 | 1273.33 | 1108.51 | ---NA--- |
| SEQ ID NO: 5589 | Nga03346 | 572.77 | 457.70 | ubiquitin-like protein 5 |
| SEQ ID NO: 5590 | Nga03336 | 1483.00 | 2022.38 | glycoside hydrolase family 8 |
| SEQ ID NO: 5591 | Nga03338 | 977.62 | 911.26 | beta-adaptin-like protein c |
| SEQ ID NO: 5592 | Nga03343 | 305.21 | 374.99 | n-acetyltransferase 10 |
| SEQ ID NO: 5593 | Nga03340.01 | 605.67 | 647.71 | mitotic checkpoint protein |
| SEQ ID NO: 5594 | Nga03335 | 570.47 | 561.25 | chaperone -domain containing protein |
| SEQ ID NO: 5595 | Nga03345 | 354.96 | 397.73 | conserved unknown protein (Partial) [Ectocarpus siliculosus] |
| SEQ ID NO: 5596 | Nga03349 | 442.03 | 472.28 | ferredoxin |
| SEQ ID NO: 5597 | Nga03334.1 | 481.17 | 513.48 | protein of hypothetical function duf482 |
| SEQ ID NO: 5598 | Nga03348 | 89.66 | 117.87 | protein |
| SEQ ID NO: 5599 | Nga03341 | 872.08 | 819.21 | methyltransferase type 11 |
| SEQ ID NO: 5600 | Nga03332 | 1664.02 | 1835.48 | n-acetyl-gamma-glutamyl-phosphate reductase |
| SEQ ID NO: 5601 | Nga03344 | 180.21 | 148.23 | component of oligomeric golgi complex 4 |
| SEQ ID NO: 5602 | Nga03342 | 62.63 | 71.30 | protein |
| SEQ ID NO: 5603 | Nga20192 | 456.67 | 457.43 | protein |
| SEQ ID NO: 5604 | Nga05183.1 | 314.78 | 411.62 | protein |
| SEQ ID NO: 5605 | Nga06884.2 | 304.21 | 253.28 | soluble pyridine nucleotide transhydrogenase |
| SEQ ID NO: 5606 | Nga05189 | 193.65 | 127.24 | hypothetical protein BATDEDRAFT_34916 [Batrachochytrium dendrobatidis JAM81] |
| SEQ ID NO: 5607 | Nga20326 | 141.81 | 95.35 | na+ solute symporter |
| SEQ ID NO: 5608 | Nga05188 | 123.81 | 134.11 | ---NA--- |
| SEQ ID NO: 5609 | Nga05182 | 726.76 | 931.13 | protein |
| SEQ ID NO: 5610 | Nga21073 | 173.91 | 220.99 | protein arginine n-methyltransferase |
| SEQ ID NO: 5611 | Nga05185 | 577.66 | 831.80 | ---NA--- |
| SEQ ID NO: 5612 | Nga05187 | 362.77 | 470.52 | cysteine proteinase |
| SEQ ID NO: 5613 | Nga05184 | 682.56 | 687.73 | 2-hydroxy-3-oxopropionate reductase |
| SEQ ID NO: 5614 | Nga00652 | 650.66 | 747.38 | ---NA--- |
| SEQ ID NO: 5615 | Nga00633 | 1318.75 | 1093.77 | threonine synthase |
| SEQ ID NO: 5616 | Nga00649 | 1384.92 | 1207.89 | photosystem ii oxygen evolving complex protein in synechococcus |
| SEQ ID NO: 5617 | Nga00618.2 | 305.63 | 288.66 | hypothetical protein Esi_0183_0025 [Ectocarpus siliculosus] |
| SEQ ID NO: 5618 | Nga00638 | 875.75 | 948.34 | protein transporter |
| SEQ ID NO: 5619 | Nga00645 | 16154.72 | 16510.60 | adp atp |
| SEQ ID NO: 5620 | Nga00644 | 611.77 | 648.82 | anthranilate synthase |
| SEQ ID NO: 5621 | Nga00637 | 3119.95 | 4231.30 | papain family cysteine protease containing protein |
| SEQ ID NO: 5622 | Nga00642 | 212.12 | 144.75 | transmembrane protein |
| SEQ ID NO: 5623 | Nga00631 | 8587.86 | 6551.19 | photosystem ii 11 kd protein |
| SEQ ID NO: 5624 | Nga00650 | 521.32 | 587.80 | ccaat-binding factor complex subunit |
| SEQ ID NO: 5625 | Nga00639 | 4270.83 | 3776.27 | glycoprotein fp21 |
| SEQ ID NO: 5626 | Nga03580.2 | 576.81 | 436.97 | wd-40 repeat protein |
| SEQ ID NO: 5627 | Nga00636 | 2517.46 | 2402.56 | cytochrome p450 cyp102a3 |

FIGURE 24 CK

| # | Nga model | +N rpkb | -N rpkb | GO |
|---|---|---|---|---|
| SEQ ID NO: 5628 | Nga20822 | 1126.23 | 1121.38 | t-complex 11 like isoform cra_b |
| SEQ ID NO: 5629 | Nga20821 | 1169.42 | 969.55 | conserved hypothetical protein [Phytophthora infestans T30-4] |
| SEQ ID NO: 5630 | Nga00632 | 1568.58 | 1303.44 | expressed unknown protein [Ectocarpus siliculosus] |
| SEQ ID NO: 5631 | Nga00640 | 1368.59 | 1126.62 | lycopene beta cyclase |
| SEQ ID NO: 5632 | Nga00630 | 694.51 | 763.74 | pantothenate kinase 3 |
| SEQ ID NO: 5633 | Nga00641.1 | 534.21 | 412.23 | ---NA--- |
| SEQ ID NO: 5634 | Nga00647 | 1345.11 | 1150.80 | coiled-coil domain-containing |
| SEQ ID NO: 5635 | Nga00634 | 228.81 | 220.32 | histone h2b |
| SEQ ID NO: 5636 | Nga00651 | 487.46 | 561.03 | ankyrin unc44 |
| SEQ ID NO: 5637 | Nga00635 | 1621.84 | 1445.99 | protein |
| SEQ ID NO: 5638 | Nga04787.2 | 439.31 | 584.79 | protein |
| SEQ ID NO: 5639 | Nga00628 | 1188.81 | 1328.16 | cathepsin z |
| SEQ ID NO: 5640 | Nga00648 | 473.60 | 519.56 | n-6 adenine-specific dna methyltransferase 2 |
| SEQ ID NO: 5641 | Nga05934 | 133.20 | 195.67 | ---NA--- |
| SEQ ID NO: 5642 | Nga20847 | 455.51 | 469.32 | histone deacetylase superfamily protein |
| SEQ ID NO: 5643 | Nga05933 | 760.81 | 709.29 | reticulon 4 interacting protein 1 |
| SEQ ID NO: 5644 | Nga21278 | 469.31 | 465.36 | peptidase |
| SEQ ID NO: 5645 | Nga05931 | 215.22 | 195.23 | ---NA--- |
| SEQ ID NO: 5646 | Nga05932 | 448.89 | 478.44 | trehalose-6-phosphate synthase |
| SEQ ID NO: 5647 | Nga06001 | 2151.43 | 2749.81 | protein kinase |
| SEQ ID NO: 5648 | Nga06003 | 4972.91 | 5093.40 | ribomal-ubiquitin fusion protein ubi5 |
| SEQ ID NO: 5649 | Nga20862.1 | 6250.00 | 6514.88 | ---NA--- |
| SEQ ID NO: 5650 | Nga21008.1 | 5611.11 | 5267.73 | hypothetical protein SNOG_05870 [Phaeosphaeria nodorum SN15] |
| SEQ ID NO: 5651 | Nga20911.1 | 30.46 | 5.50 | myo-inositol-1-phosphate synthase |
| SEQ ID NO: 5652 | Nga20412 | 78.95 | 46.05 | ---NA--- |
| SEQ ID NO: 5653 | Nga01445.2 | 3746.55 | 4432.15 | succinate dehydrogenase |
| SEQ ID NO: 5654 | Nga06002 | 284.88 | 313.32 | prolyl-trna synthetase |
| SEQ ID NO: 5655 | Nga05978 | 1454.79 | 1913.22 | protein |
| SEQ ID NO: 5656 | Nga05974 | 777.44 | 842.62 | protein |
| SEQ ID NO: 5657 | Nga05976 | 1060.19 | 1140.91 | protein |
| SEQ ID NO: 5658 | Nga05975 | 514.26 | 442.79 | protein |
| SEQ ID NO: 5659 | Nga21308 | 374.15 | 390.55 | cathepsin a |
| SEQ ID NO: 5660 | Nga05977 | 326.77 | 413.68 | ---NA--- |
| SEQ ID NO: 5661 | Nga05852 | 1304.64 | 1214.87 | conserved unknown protein [Ectocarpus siliculosus] |
| SEQ ID NO: 5662 | Nga20712 | 525.66 | 427.06 | isochorismatase hydrolase |
| SEQ ID NO: 5663 | Nga05853 | 891.89 | 935.77 | surface protein sur1 |
| SEQ ID NO: 5664 | Nga05851 | 3444.44 | 3500.60 | alpha beta hydrolase fold-3 domain protein |
| SEQ ID NO: 5665 | Nga05854 | 194.00 | 244.54 | protein |
| SEQ ID NO: 5666 | Nga05850 | 1407.35 | 1128.90 | photosystem ii stability assembly factor hcf136 |
| SEQ ID NO: 5667 | Nga05849 | 538.46 | 592.03 | nlr card domain containing 3 |
| SEQ ID NO: 5668 | Nga05848 | 1425.30 | 1103.05 | cytochrome c peroxidase |
| SEQ ID NO: 5669 | Nga05995.2 | 1085.29 | 843.36 | peptidyl-prolyl cis-trans isomerase |
| SEQ ID NO: 5670 | Nga05226 | 1034.87 | 1275.41 | glycerol-3-phosphate dehydrogenase 1-like protein |
| SEQ ID NO: 5671 | Nga04505.02 | 1002.05 | 1358.48 | ankyrin |
| SEQ ID NO: 5672 | Nga05222 | 2130.43 | 1774.55 | ---NA--- |
| SEQ ID NO: 5673 | Nga05229.1 | 755.84 | 843.22 | glycosyl hydrolase family 81 protein |
| SEQ ID NO: 5674 | Nga05227 | 1093.39 | 1193.74 | trna (5-methylaminomethyl-2-thiouridylate)-methyltransferase |
| SEQ ID NO: 5675 | Nga05225 | 1654.49 | 1451.92 | cation diffusion facilitator family transporter |
| SEQ ID NO: 5676 | Nga05228 | 466.62 | 446.24 | ion channel |
| SEQ ID NO: 5677 | Nga05231 | 393.44 | 579.35 | conserved hypothetical protein [Perkinsus marinus ATCC 50983] |
| SEQ ID NO: 5678 | Nga04504.02 | 4897.14 | 5041.69 | 3-ketoacyl- mitochondrial |
| SEQ ID NO: 5679 | Nga02759 | 1340.03 | 1462.02 | fe-s protein assembly co-chaperone |
| SEQ ID NO: 5680 | Nga02761 | 225.87 | 316.21 | phosphatidylinositol-4-phosphate 5- 11335-7537 |
| SEQ ID NO: 5681 | Nga02756 | 728.16 | 835.43 | homoserine o-acetyltransferase |
| SEQ ID NO: 5682 | Nga20333 | 321.43 | 368.54 | l-seryl-trna kinase-like |
| SEQ ID NO: 5683 | Nga20868 | 557.84 | 647.90 | predicted protein [Phaeodactylum tricornutum CCAP 1055/1] |
| SEQ ID NO: 5684 | Nga21145 | 5579.09 | 5538.14 | ubiquitin |
| SEQ ID NO: 5685 | Nga02757 | 1947.41 | 1628.07 | vesicle transport protein sft2a-like |
| SEQ ID NO: 5686 | Nga02758 | 6362.60 | 7305.63 | ribosomal protein l23 |
| SEQ ID NO: 5687 | Nga20641 | 152.78 | 140.42 | protein |
| SEQ ID NO: 5688 | Nga02762 | 1942.33 | 2029.74 | amp-binding domain protein |
| SEQ ID NO: 5689 | Nga21015 | 132.63 | 206.88 | protein kinase |
| SEQ ID NO: 5690 | Nga02765 | 31.86 | 45.13 | spo11 meiotic protein covalently bound to dsb homolog ( cerevisiae) |
| SEQ ID NO: 5691 | Nga02760 | 1626.94 | 1777.05 | wd repeat-containing protein 5 |

FIGURE 24 CL

| # | Nga model | +N rpkb | -N rpkb | GO |
|---|---|---|---|---|
| SEQ ID NO: 5692 | Nga01024 | 791.48 | 767.77 | apoptosis-inducing factor mitochondrial isoform 1 |
| SEQ ID NO: 5693 | Nga01022 | 246.01 | 324.46 | xpa-binding protein 1 |
| SEQ ID NO: 5694 | Nga01026 | 1929.97 | 1600.60 | protein |
| SEQ ID NO: 5695 | Nga20415 | 103.26 | 133.44 | rna exonuclease 4 |
| SEQ ID NO: 5696 | Nga01025 | 10.64 | 26.89 | ---NA--- |
| SEQ ID NO: 5697 | Nga20403 | 238.05 | 265.26 | transcription initiation factor tfiid subunit |
| SEQ ID NO: 5698 | Nga01027 | 120.50 | 128.53 | ---NA--- |
| SEQ ID NO: 5699 | Nga01023 | 3581.90 | 2352.81 | hpp family protein |
| SEQ ID NO: 5700 | Nga06244 | 2219.75 | 2424.05 | short-chain dehydrogenase reductase sdr |
| SEQ ID NO: 5701 | Nga06243 | 3204.49 | 2721.28 | ---NA--- |
| SEQ ID NO: 5702 | Nga06240.01 | 938.43 | 1181.71 | glucose-methanol-choline oxidoreductase |
| SEQ ID NO: 5703 | Nga06241 | 1898.33 | 1643.67 | ---NA--- |
| SEQ ID NO: 5704 | Nga06239 | 308.53 | 357.15 | protein |
| SEQ ID NO: 5705 | Nga06238 | 1998.35 | 1566.85 | ---NA--- |
| SEQ ID NO: 5706 | Nga06242 | 698.73 | 710.75 | magnesium h subunit |
| SEQ ID NO: 5707 | Nga20052 | 406.36 | 467.23 | magnesium h subunit |
| SEQ ID NO: 5708 | Nga20741 | 72.58 | 165.98 | fbox protein |
| SEQ ID NO: 5709 | Nga06627.1 | 80.98 | 152.85 | transducin -like 3 |
| SEQ ID NO: 5710 | Nga02359.02 | 579.34 | 642.88 | u2 small nuclear ribonucleoprotein a |
| SEQ ID NO: 5711 | Nga06628 | 162.42 | 185.97 | tripartite motif-containing 26 |
| SEQ ID NO: 5712 | Nga06626.1 | 314.79 | 310.38 | atp-dependent rna helicase ddx1 |
| SEQ ID NO: 5713 | Nga05984.01 | 206.52 | 263.87 | protein |
| SEQ ID NO: 5714 | Nga05981.01 | 2019.73 | 2874.37 | ---NA--- |
| SEQ ID NO: 5715 | Nga05985.01 | 469.14 | 493.32 | protein |
| SEQ ID NO: 5716 | Nga05982.01 | 456.31 | 493.09 | triacylglycerol lipase |
| SEQ ID NO: 5717 | Nga20665.1 | 63.68 | 37.90 | protein |
| SEQ ID NO: 5718 | Nga05987.01 | 489.49 | 465.27 | ---NA--- |
| SEQ ID NO: 5719 | Nga05983.01 | 3140.04 | 2439.95 | ---NA--- |
| SEQ ID NO: 5720 | Nga05986.01 | 458.72 | 510.52 | alanine-glyoxylate aminotransferase 2-like 2 |
| SEQ ID NO: 5721 | Nga01177 | 965.36 | 1074.61 | probable inactive purple acid phosphatase 27-like |
| SEQ ID NO: 5722 | Nga01178 | 123.71 | 89.34 | ---NA--- |
| SEQ ID NO: 5723 | Nga01176 | 638.74 | 790.56 | ---NA--- |
| SEQ ID NO: 5724 | Nga02662 | 1355.97 | 1684.12 | rna polymerase sigma factor |
| SEQ ID NO: 5725 | Nga02668 | 1294.01 | 1438.62 | cytochrome p450 |
| SEQ ID NO: 5726 | Nga02667 | 274.65 | 231.40 | cell cycle checkpoint protein rad17 |
| SEQ ID NO: 5727 | Nga02660 | 513.18 | 461.97 | cellulase 2 |
| SEQ ID NO: 5728 | Nga02669 | 352.36 | 331.44 | folate-binding protein |
| SEQ ID NO: 5729 | Nga20111 | 617.85 | 665.27 | la ribonucleoprotein domain member 1 |
| SEQ ID NO: 5730 | Nga02666 | 236.90 | 280.47 | thiamine triphosphatase |
| SEQ ID NO: 5731 | Nga02663 | 3778.00 | 3550.48 | protein |
| SEQ ID NO: 5732 | Nga02665.01 | 6477.17 | 6628.01 | conserved hypothetical protein [Phytophthora infestans T30-4] |
| SEQ ID NO: 5733 | Nga02661 | 933.16 | 866.96 | tricarboxylate transport mitochondrial-like |
| SEQ ID NO: 5734 | Nga02670 | 3615.84 | 3311.65 | ---NA--- |
| SEQ ID NO: 5735 | Nga20026 | 1041.43 | 849.56 | ---NA--- |
| SEQ ID NO: 5736 | Nga02664 | 2054.59 | 1716.24 | protein |
| SEQ ID NO: 5737 | Nga04292.02 | 3421.42 | 3302.43 | conserved unknown protein [Ectocarpus siliculosus] |
| SEQ ID NO: 5738 | Nga05585 | 677.98 | 744.50 | cyclin-y-like protein |
| SEQ ID NO: 5739 | Nga02277.02 | 1101.16 | 1216.17 | hypothetical protein AURANDRAFT_70731 [Aureococcus anophagefferens] |
| SEQ ID NO: 5740 | Nga05591 | 205.72 | 193.05 | ---NA--- |
| SEQ ID NO: 5741 | Nga20053.1 | 1379.41 | 1452.21 | hypothetical protein AURANDRAFT_70731 [Aureococcus anophagefferens] |
| SEQ ID NO: 5742 | Nga05584 | 138.63 | 155.23 | phosphatidylinositol-4-phosphate 5- |
| SEQ ID NO: 5743 | Nga02276.02 | 390.35 | 299.31 | phosphatidylinositol-4-phosphate 5- |
| SEQ ID NO: 5744 | Nga05589 | 245.36 | 263.55 | ---NA--- |
| SEQ ID NO: 5745 | Nga05593 | 122.81 | 133.03 | ---NA--- |
| SEQ ID NO: 5746 | Nga05592 | 75.47 | 61.32 | ---NA--- |
| SEQ ID NO: 5747 | Nga21149.1 | 1114.05 | 1007.81 | transcriptional coactivator pterin dehydratase |
| SEQ ID NO: 5748 | Nga05586.1 | 296.20 | 249.87 | diacylglycerol kinase |
| SEQ ID NO: 5749 | Nga02026.02 | 127.45 | 159.29 | ---NA--- |
| SEQ ID NO: 5750 | Nga21155 | 142.86 | 198.27 | e1a-binding protein p400-like |
| SEQ ID NO: 5751 | Nga05384 | 129.03 | 192.19 | ---NA--- |
| SEQ ID NO: 5752 | Nga05381 | 818.79 | 534.35 | ---NA--- |
| SEQ ID NO: 5753 | Nga04229.02 | 1672.54 | 1881.51 | ---NA--- |

FIGURE 24 CM

| # | Nga model | +N rpkb | -N rpkb | GO |
|---|---|---|---|---|
| SEQ ID NO: 5754 | Nga05382 | 353.23 | 455.39 | gtp cyclohydrolase ii |
| SEQ ID NO: 5755 | Nga05383 | 442.93 | 472.43 | Aardvark [Ectocarpus siliculosus] |
| SEQ ID NO: 5756 | Nga05378 | 758.35 | 696.75 | protein |
| SEQ ID NO: 5757 | Nga05380 | 258.72 | 295.37 | protein |
| SEQ ID NO: 5758 | Nga00958.02 | 980.74 | 1281.43 | ribosome biogenesis regulatory protein |
| SEQ ID NO: 5759 | Nga05379 | 1055.25 | 1268.76 | thiamin pyrophosphokinase1 |
| SEQ ID NO: 5760 | Nga01072 | 613.49 | 542.32 | transforming growth beta- 68kda |
| SEQ ID NO: 5761 | Nga01069 | 1681.90 | 1620.18 | enoyl- hydratase domain-containing protein 1-like |
| SEQ ID NO: 5762 | Nga01067 | 584.19 | 430.27 | uracil phosphoribosyltransferase |
| SEQ ID NO: 5763 | Nga01073 | 218.79 | 241.18 | ---NA--- |
| SEQ ID NO: 5764 | Nga01068 | 2381.33 | 2115.44 | nifu like protein |
| SEQ ID NO: 5765 | Nga00400.2 | 317.66 | 342.25 | chaperone protein |
| SEQ ID NO: 5766 | Nga01074 | 134.69 | 127.15 | brca1 brca2-containing complex subunit 3 |
| SEQ ID NO: 5767 | Nga01070 | 647.77 | 700.23 | protein |
| SEQ ID NO: 5768 | Nga01071 | 2312.47 | 2426.40 | cre-cul-1 protein |
| SEQ ID NO: 5769 | Nga20873 | 1197.26 | 1530.36 | cul2 protein |
| SEQ ID NO: 5770 | Nga20106 | 407.30 | 390.24 | uncharacterized protein family upf0310 |
| SEQ ID NO: 5771 | Nga00954 | 995.84 | 850.86 | natural resistance-associated macrophage |
| SEQ ID NO: 5772 | Nga00955 | 7.34 | 6.36 | dynein heavy chain |
| SEQ ID NO: 5773 | Nga00956 | 0.36 | 3.51 | dynein heavy chain |
| SEQ ID NO: 5774 | Nga06161.1 | 196.22 | 248.37 | pescadillo-like protein |
| SEQ ID NO: 5775 | Nga06158 | 5530.41 | 4944.40 | histone h3 |
| SEQ ID NO: 5776 | Nga02516.02 | 24.04 | 35.23 | t-complex 11 like isoform cra_b |
| SEQ ID NO: 5777 | Nga02514.02 | 802.06 | 599.69 |tropinone reductase |
| SEQ ID NO: 5778 | Nga06167 | 251.43 | 237.28 | pyrimidine 5 -nucleotidase |
| SEQ ID NO: 5779 | Nga06162 | 2176.55 | 2330.59 | expressed unknown protein [Ectocarpus siliculosus] |
| SEQ ID NO: 5780 | Nga20008 | 457.91 | 593.59 | ---NA--- |
| SEQ ID NO: 5781 | Nga02511.02 | 2391.62 | 2702.49 | sporangia induced sperm flagellar protein |
| SEQ ID NO: 5782 | Nga06163 | 418.44 | 446.44 | 3-dehydroquinate synthase |
| SEQ ID NO: 5783 | Nga06159 | 240.49 | 184.66 | protein mis18-alpha |
| SEQ ID NO: 5784 | Nga02519.02 | 463.46 | 438.55 | phosphoglycerate mutase 1 family |
| SEQ ID NO: 5785 | Nga02520.02 | 902.96 | 384.44 | phytochelatin synthase |
| SEQ ID NO: 5786 | Nga02518.02 | 181.02 | 126.74 | histone h1 |
| SEQ ID NO: 5787 | Nga06571 | 559.36 | 502.05 | protein |
| SEQ ID NO: 5788 | Nga06569.1 | 706.09 | 732.70 | tripeptidyl peptidase ii |
| SEQ ID NO: 5789 | Nga06572 | 515.82 | 611.46 | protein |
| SEQ ID NO: 5790 | Nga06573 | 149.59 | 172.61 | ---NA--- |
| SEQ ID NO: 5791 | Nga06570 | 532.48 | 541.04 | phenylalanyl-trna synthetase beta chain |
| SEQ ID NO: 5792 | Nga06577 | 128.69 | 109.69 | and ph domain containing 5 |
| SEQ ID NO: 5793 | Nga06568 | 808.06 | 1054.67 | gtp cyclohydrolase i |
| SEQ ID NO: 5794 | Nga01522.2 | 173.10 | 192.32 | brefeldin a-inhibited guanine nucleotide-exchange |
| SEQ ID NO: 5795 | Nga06576.1 | 178.23 | 170.10 | brefeldin a-inhibited guanine nucleotide-exchange |
| SEQ ID NO: 5796 | Nga20595.1 | 14.81 | 56.17 | ---NA--- |
| SEQ ID NO: 5797 | Nga20615.1 | 117.49 | 141.41 | c-myc promoter-binding protein irlb |
| SEQ ID NO: 5798 | Nga01525.02 | 170.52 | 169.06 | ---NA--- |
| SEQ ID NO: 5799 | Nga20130 | 104.50 | 129.67 | atp binding protein |
| SEQ ID NO: 5800 | Nga03766.02 | 3999.10 | 3999.26 | nadh dehydrogenase |
| SEQ ID NO: 5801 | Nga05614 | 274.43 | 290.26 | trimethylguanosine synthase homolog |
| SEQ ID NO: 5802 | Nga05617 | 62.47 | 62.68 | chromatin remodeling complex subunit |
| SEQ ID NO: 5803 | Nga03764.02 | 455.84 | 534.93 | 24-dehydrocholesterol reductase |
| SEQ ID NO: 5804 | Nga05619 | 33.74 | 26.58 | snf2 family dna-dependent atpase |
| SEQ ID NO: 5805 | Nga05615.1 | 654.91 | 1315.06 | phosphoribosylformylglycinamidine synthase |
| SEQ ID NO: 5806 | Nga05618 | 5018.97 | 3974.79 | conserved hypothetical protein [Phytophthora infestans T30-4] |
| SEQ ID NO: 5807 | Nga05616 | 1550.69 | 1688.13 | vacuolar sorting protein 9 domain-containing protein |
| SEQ ID NO: 5808 | Nga04756.02 | 1614.47 | 1104.61 | conserved unknown protein [Ectocarpus siliculosus] |
| SEQ ID NO: 5809 | Nga21205 | 463.34 | 536.85 | ---NA--- |
| SEQ ID NO: 5810 | Nga20475.1 | 201.51 | 226.47 | trna pseudouridine synthase a |
| SEQ ID NO: 5811 | Nga05411 | 456.90 | 445.12 | rnf111 partial |
| SEQ ID NO: 5812 | Nga20214 | 645.42 | 644.28 | ---NA--- |
| SEQ ID NO: 5813 | Nga05410 | 528.96 | 512.34 | hypothetical protein BATDEDRAFT_22755 [Batrachochytrium dendrobatidis JAM81] |
| SEQ ID NO: 5814 | Nga05413 | 608.47 | 553.80 | serine hydroxymethyltransferase |
| SEQ ID NO: 5815 | Nga20572 | 335.60 | 328.86 | methyltransferase family protein |
| SEQ ID NO: 5816 | Nga05408 | 1963.20 | 1947.77 | proteasome ( macropain) activator subunit 1 (pa28 alpha) |

FIGURE 24 CN

| # | Nga model | +N rpkb | -N rpkb | GO |
|---|---|---|---|---|
| SEQ ID NO: 5817 | Nga05404 | 854.79 | 866.86 | protein |
| SEQ ID NO: 5818 | Nga05412 | 806.17 | 854.18 | ---NA--- |
| SEQ ID NO: 5819 | Nga04776.02 | 2722.74 | 2796.39 | aquaporin sip1-2 |
| SEQ ID NO: 5820 | Nga05405 | 1103.86 | 807.87 | photosystem ii oxygen-evolving complex 23k protein |
| SEQ ID NO: 5821 | Nga05406 | 740.27 | 820.50 | uncharacterized glycosyltransferase aer61 |
| SEQ ID NO: 5822 | Nga04777.2 | 1441.20 | 1045.24 | protein |
| SEQ ID NO: 5823 | Nga05450 | 670.89 | 761.89 | zinc metalloproteinase |
| SEQ ID NO: 5824 | Nga05448 | 157.02 | 147.71 | ---NA--- |
| SEQ ID NO: 5825 | Nga05451 | 100.67 | 116.66 | ---NA--- |
| SEQ ID NO: 5826 | Nga05447 | 401.48 | 384.08 | protein |
| SEQ ID NO: 5827 | Nga05449 | 620.77 | 744.44 | histone acetyltransferase |
| SEQ ID NO: 5828 | Nga20241 | 436.33 | 426.67 | nucleoredoxin-like protein 2 |
| SEQ ID NO: 5829 | Nga06045 | 234.65 | 216.96 | cdc14 cell division cycle 14 homolog a ( cerevisiae) |
| SEQ ID NO: 5830 | Nga06041 | 680.50 | 743.43 | sh3 domain-containing protein |
| SEQ ID NO: 5831 | Nga20128 | 511.31 | 505.35 | predicted protein [Thalassiosira pseudonana CCMP1335] |
| SEQ ID NO: 5832 | Nga06046 | 384.62 | 392.12 | ---NA--- |
| SEQ ID NO: 5833 | Nga21089 | 2128.23 | 2050.87 | hypothetical protein |
| SEQ ID NO: 5834 | Nga06044 | 1126.30 | 1139.71 | t-complex protein 1 subunit zeta |
| SEQ ID NO: 5835 | Nga06043 | 408.48 | 379.46 | protein |
| SEQ ID NO: 5836 | Nga06040 | 602.43 | 500.74 | expressed unknown protein [Ectocarpus siliculosus] |
| SEQ ID NO: 5837 | Nga06042 | 9608.51 | 8659.21 | catalase |
| SEQ ID NO: 5838 | Nga06039 | 2452.44 | 1745.06 | delta-6 fatty acid desaturase |
| SEQ ID NO: 5839 | Nga01547 | 403.19 | 377.01 | protein |
| SEQ ID NO: 5840 | Nga01549.1 | 559.90 | 716.86 | protein |
| SEQ ID NO: 5841 | Nga01550 | 571.14 | 726.56 | ---NA--- |
| SEQ ID NO: 5842 | Nga01548 | 2441.91 | 2081.07 | pre-mrna branch site protein |
| SEQ ID NO: 5843 | Nga01383 | 142.86 | 77.37 | ---NA--- |
| SEQ ID NO: 5844 | Nga21243 | 107.84 | 138.06 | intraflagellar transport protein 46 homolog isoform 2 |
| SEQ ID NO: 5845 | Nga01382 | 41.03 | 16.67 | flagellar associated protein |
| SEQ ID NO: 5846 | Nga01380.01 | 473.02 | 387.44 | conserved unknown protein [Ectocarpus siliculosus] |
| SEQ ID NO: 5847 | Nga01381 | 448.33 | 443.10 | naphthoate synthase |
| SEQ ID NO: 5848 | Nga00781 | 49.69 | 47.10 | ---NA--- |
| SEQ ID NO: 5849 | Nga00783 | 145.39 | 126.76 | ---NA--- |
| SEQ ID NO: 5850 | Nga00782 | 116.02 | 125.68 | thioredoxin |
| SEQ ID NO: 5851 | Nga00779.01 | 5335.74 | 3704.86 | ribulose-phosphate 3-epimerase |
| SEQ ID NO: 5852 | Nga20826.1 | 592.84 | 339.05 | dna ligase |
| SEQ ID NO: 5853 | Nga00780 | 81.78 | 57.37 | dna ligase 1 |
| SEQ ID NO: 5854 | Nga05497.02 | 1666.92 | 1441.52 | dolichyl-diphosphooligosaccharide--protein glycosyltransferase subunit dad1 |
| SEQ ID NO: 5855 | Nga20937 | 7508.09 | 6591.72 | mapeg family protein |
| SEQ ID NO: 5856 | Nga05909 | 435.90 | 333.30 | ---NA--- |
| SEQ ID NO: 5857 | Nga05498.02 | 3419.10 | 2738.25 | ---NA--- |
| SEQ ID NO: 5858 | Nga05903 | 725.81 | 640.62 | gpn-loop gtpase 3 |
| SEQ ID NO: 5859 | Nga05902.1 | 2056.91 | 1804.99 | predicted protein [Thalassiosira pseudonana CCMP1335] |
| SEQ ID NO: 5860 | Nga05494.02 | 967.68 | 874.50 | topoisomerase 6 subunit b |
| SEQ ID NO: 5861 | Nga05897.1 | 895.27 | 834.38 | ---NA--- |
| SEQ ID NO: 5862 | Nga05899 | 255.68 | 228.55 | protein |
| SEQ ID NO: 5863 | Nga05908 | 168.87 | 129.13 | ---NA--- |
| SEQ ID NO: 5864 | Nga05900 | 1069.06 | 809.93 | phenylalanyl-trna synthetase |
| SEQ ID NO: 5865 | Nga05905 | 1115.94 | 1287.32 | ---NA--- |
| SEQ ID NO: 5866 | Nga05911 | 492.42 | 625.73 | trna (guanine-n -)-methyltransferase |
| SEQ ID NO: 5867 | Nga20804.1 | 2625.50 | 2593.72 | mitochondrial carrier domain-containing protein |
| SEQ ID NO: 5868 | Nga05910 | 521.05 | 530.21 | ---NA--- |
| SEQ ID NO: 5869 | Nga05898 | 19.48 | 16.08 | g-protein complex alpha subunit |
| SEQ ID NO: 5870 | Nga20055.1 | 2043.29 | 1900.23 | conserved unknown protein [Ectocarpus siliculosus] |
| SEQ ID NO: 5871 | Nga05901 | 231.58 | 219.97 | unc45 family protein |
| SEQ ID NO: 5872 | Nga01355.01 | 490.10 | 633.19 | chaperone protein |
| SEQ ID NO: 5873 | Nga20420 | 199.58 | 197.79 | low quality protein: l-fucose kinase-like |
| SEQ ID NO: 5874 | Nga20342 | 186.36 | 177.26 | l-fucose kinase |
| SEQ ID NO: 5875 | Nga02831.01 | 751.54 | 685.38 | solute carrier family 25 (mitochondrial carrier citrate transporter) member 1 |
| SEQ ID NO: 5876 | Nga02833 | 5136.12 | 4585.13 | beta- -mannosyltransferase egh |
| SEQ ID NO: 5877 | Nga02830.01 | 727.36 | 711.81 | potential ankyrin repeat protein |
| SEQ ID NO: 5878 | Nga02839.01 | 1754.74 | 1803.40 | dihydrolipoamide dehydrogenase |

FIGURE 24 CO

| # | Nga model | +N rpkb | -N rpkb | GO |
|---|---|---|---|---|
| SEQ ID NO: 5879 | Nga21237.1 | 153.06 | 118.82 | protein |
| SEQ ID NO: 5880 | Nga02842.01 | 2105.04 | 2116.40 | ---NA--- |
| SEQ ID NO: 5881 | Nga02829 | 1823.71 | 1901.20 | pbs lyase heat-like repeat domain protein |
| SEQ ID NO: 5882 | Nga02834 | 741.71 | 806.44 | glutamyl-trna synthetase |
| SEQ ID NO: 5883 | Nga02832 | 2218.77 | 1834.55 | glycine decarboxylase t-protein |
| SEQ ID NO: 5884 | Nga02835 | 1163.55 | 1421.41 | protein |
| SEQ ID NO: 5885 | Nga02837 | 364.53 | 275.98 | protein kinase family protein |
| SEQ ID NO: 5886 | Nga02836 | 950.24 | 900.10 | aminophospholipid transporter- class type member 2 |
| SEQ ID NO: 5887 | Nga02843 | 1048.99 | 1101.69 | protein myg1 |
| SEQ ID NO: 5888 | Nga02838 | 712.33 | 786.46 | fk506 binding-like protein |
| SEQ ID NO: 5889 | Nga02841 | 544.22 | 704.96 | protein archease-like |
| SEQ ID NO: 5890 | Nga02840 | 566.41 | 549.06 | n-terminal acetyltransferase complex ard1 subunit |
| SEQ ID NO: 5891 | Nga03109 | 679.86 | 549.38 | solute carrier family 35 member b1 |
| SEQ ID NO: 5892 | Nga03106 | 737.73 | 634.00 | proteasome ( macropain) 26s non- 3 |
| SEQ ID NO: 5893 | Nga03102 | 588.07 | 574.58 | asparaginyl-trna synthetase |
| SEQ ID NO: 5894 | Nga03111 | 4980.48 | 5818.63 | succinate- ligase |
| SEQ ID NO: 5895 | Nga03103 | 2239.08 | 2012.46 | protein |
| SEQ ID NO: 5896 | Nga03113 | 1667.10 | 2035.47 | amp-dependent synthetase and ligase |
| SEQ ID NO: 5897 | Nga03110 | 413.18 | 531.32 | hypoxanthine phosphoribosyltransferase 1 |
| SEQ ID NO: 5898 | Nga03114 | 104.07 | 117.64 | ---NA--- |
| SEQ ID NO: 5899 | Nga03105.01 | 948.53 | 915.97 | conserved unknown protein [Ectocarpus siliculosus] |
| SEQ ID NO: 5900 | Nga03108 | 667.69 | 733.57 | atp-dependent dna helicase |
| SEQ ID NO: 5901 | Nga03115 | 525.94 | 455.11 | expressed unknown protein [Ectocarpus siliculosus] |
| SEQ ID NO: 5902 | Nga03107 | 517.01 | 526.14 | udp-n-acetylglucosamine transferase subunit alg14 homolog |
| SEQ ID NO: 5903 | Nga03112 | 16980.97 | 17325.40 | ribosomal protein s25 |
| SEQ ID NO: 5904 | Nga03104 | 387.98 | 547.30 | protein |
| SEQ ID NO: 5905 | Nga03101 | 1905.63 | 1692.08 | xenotropic and polytropic murine leukemia virus receptor xpr1 |
| SEQ ID NO: 5906 | Nga20360 | 416.96 | 458.23 | conserved unknown protein [Ectocarpus siliculosus] |
| SEQ ID NO: 5907 | Nga05309 | 1512.68 | 1590.09 | cysteine synthase |
| SEQ ID NO: 5908 | Nga05310 | 804.46 | 835.01 | adenine guanine permease azg1 |
| SEQ ID NO: 5909 | Nga05308 | 4440.73 | 4333.69 | 4-hydroxy-3-methylbut-2-enyl diphosphate reductase |
| SEQ ID NO: 5910 | Nga05306 | 1451.65 | 1402.41 | protein |
| SEQ ID NO: 5911 | Nga05307 | 362.23 | 411.50 | lon protease-like mitochondrial |
| SEQ ID NO: 5912 | Nga01235 | 512.91 | 432.55 | ribokinase |
| SEQ ID NO: 5913 | Nga01236 | 101.45 | 146.52 | solute carrier family member 35-like |
| SEQ ID NO: 5914 | Nga00985.2 | 231.15 | 248.73 | cation transporting atpase |
| SEQ ID NO: 5915 | Nga20143 | 560.12 | 507.24 | s-adenosylmethionine mitochondrial carrier protein |
| SEQ ID NO: 5916 | Nga01230 | 585.08 | 723.67 | gtp-binding proten |
| SEQ ID NO: 5917 | Nga01231 | 178.52 | 145.40 | diacylglycerol cholinephosphotransferase |
| SEQ ID NO: 5918 | Nga01233 | 408.33 | 456.51 | protein |
| SEQ ID NO: 5919 | Nga01232 | 453.33 | 418.13 | aminopeptidase-like 1 |
| SEQ ID NO: 5920 | Nga20099 | 1342.18 | 1592.32 | ring finger protein 126 |
| SEQ ID NO: 5921 | Nga01422 | 2443.47 | 1967.98 | ---NA--- |
| SEQ ID NO: 5922 | Nga01421 | 56.66 | 52.89 | protein |
| SEQ ID NO: 5923 | Nga01423 | 1731.93 | 1801.60 | atp-dependent clp protease adaptor protein |
| SEQ ID NO: 5924 | Nga01424 | 104.05 | 250.46 | ---NA--- |
| SEQ ID NO: 5925 | Nga05993 | 1155.89 | 1171.10 | protein |
| SEQ ID NO: 5926 | Nga04312.02 | 962.73 | 1403.02 | galactosamine (n-acetyl)-6-sulfate sulfatase-like |
| SEQ ID NO: 5927 | Nga05991 | 2536.14 | 3505.07 | p-type h+-atpase |
| SEQ ID NO: 5928 | Nga05870 | 112.90 | 64.06 | phosphoinositol transporter |
| SEQ ID NO: 5929 | Nga07312.2 | 1237.00 | 1185.74 | phosphatidylinositol n-acetylglucosaminyltransferase subunit |
| SEQ ID NO: 5930 | Nga05867 | 1168.20 | 1075.77 | phosphatidate cytidylyltransferase |
| SEQ ID NO: 5931 | Nga05865 | 1085.06 | 1194.08 | protein |
| SEQ ID NO: 5932 | Nga20808 | 301.47 | 298.69 | ---NA--- |
| SEQ ID NO: 5933 | Nga20879 | 1019.81 | 1100.18 | methyltransferase type 11 |
| SEQ ID NO: 5934 | Nga05868 | 125.65 | 129.84 | chloride channel protein |
| SEQ ID NO: 5935 | Nga05864 | 301.47 | 321.25 | hippocampus abundant transcript 1 |
| SEQ ID NO: 5936 | Nga05866 | 6452.44 | 7184.28 | 40s ribosomal protein s19 |
| SEQ ID NO: 5937 | Nga20935 | 841.34 | 774.90 | atp-binding cassette sub-family g member 2 |
| SEQ ID NO: 5938 | Nga20215 | 294.90 | 361.83 | probable atp-dependent rna helicase ddx31 |
| SEQ ID NO: 5939 | Nga21103 | 194.82 | 245.83 | dead box atp-dependent rna |
| SEQ ID NO: 5940 | Nga01031 | 768.42 | 722.50 | protein |
| SEQ ID NO: 5941 | Nga01033 | 222.77 | 267.86 | ---NA--- |
| SEQ ID NO: 5942 | Nga01030.01 | 2352.40 | 2701.89 | ---NA--- |

FIGURE 24 CP

| # | Nga model | +N rpkb | -N rpkb | GO |
|---|---|---|---|---|
| SEQ ID NO: 5943 | Nga01034 | 441.86 | 541.62 | splicing arginine serine-rich 9 |
| SEQ ID NO: 5944 | Nga01032 | 211.16 | 467.28 | notch-regulated ankyrin repeat-containing protein b |
| SEQ ID NO: 5945 | Nga21215.1 | 599.19 | 469.26 | uncharacterized protein |
| SEQ ID NO: 5946 | Nga06181 | 2250.00 | 2302.78 | conserved plasmodium protein |
| SEQ ID NO: 5947 | Nga06183 | 516.93 | 546.08 | ---NA--- |
| SEQ ID NO: 5948 | Nga21280 | 104.90 | 98.48 | ---NA--- |
| SEQ ID NO: 5949 | Nga06184 | 114.09 | 72.70 | ---NA--- |
| SEQ ID NO: 5950 | Nga02092.02 | 1547.45 | 2155.74 | alternative nadh-dehydrogenase |
| SEQ ID NO: 5951 | Nga06534 | 156.86 | 148.68 | hypothetical protein CHLNCDRAFT_138430 [Chlorella variabilis] |
| SEQ ID NO: 5952 | Nga20651 | 666.67 | 644.68 | tp53 regulating kinase |
| SEQ ID NO: 5953 | Nga06535 | 3016.23 | 2719.65 | bacterioferritin comigratory protein |
| SEQ ID NO: 5954 | Nga06536 | 2909.77 | 3307.62 | trehalose-6-phosphate phosphatase |
| SEQ ID NO: 5955 | Nga06537.01 | 6065.22 | 6723.12 | ribosomal protein l22 |
| SEQ ID NO: 5956 | Nga20503 | 245.76 | 309.06 | gpi-anchored wall transfer protein 1 |
| SEQ ID NO: 5957 | Nga06364 | 281.21 | 283.07 | ---NA--- |
| SEQ ID NO: 5958 | Nga20743 | 145.60 | 145.82 | gpi-anchored wall transfer protein 1 |
| SEQ ID NO: 5959 | Nga06369 | 3536.93 | 2667.00 | secreted salivary gland |
| SEQ ID NO: 5960 | Nga06367 | 935.90 | 805.48 | phospholipid n-methyltransferase |
| SEQ ID NO: 5961 | Nga06365 | 151.41 | 248.47 | conserved hypothetical protein [Phytophthora infestans T30-4] |
| SEQ ID NO: 5962 | Nga06368 | 106.23 | 107.79 | trpc4apa protein |
| SEQ ID NO: 5963 | Nga21257 | 82.80 | 172.49 | ---NA--- |
| SEQ ID NO: 5964 | Nga06366 | 125.27 | 85.71 | ---NA--- |
| SEQ ID NO: 5965 | Nga06370 | 792.34 | 761.89 | amidase family protein |
| SEQ ID NO: 5966 | Nga06636 | 2072.50 | 2410.60 | uncharacterized protein |
| SEQ ID NO: 5967 | Nga04941.02 | 5066.50 | 7316.46 | wd sam and u-box domain-containing protein 1 |
| SEQ ID NO: 5968 | Nga04942.02 | 2777.10 | 2549.14 | phosphoglucomutase |
| SEQ ID NO: 5969 | Nga04943.02 | 365.54 | 394.22 | aintegumenta-like protein |
| SEQ ID NO: 5970 | Nga02317.02 | 2491.88 | 2067.26 | expressed unknown protein [Ectocarpus siliculosus] |
| SEQ ID NO: 5971 | Nga06638 | 707.18 | 716.12 | sulphate transporter |
| SEQ ID NO: 5972 | Nga06640 | 116.57 | 168.54 | gtp binding protein |
| SEQ ID NO: 5973 | Nga21112 | 1048.96 | 874.49 | short-chain dehydrogenase reductase sdr |
| SEQ ID NO: 5974 | Nga06635 | 614.58 | 508.71 | predicted protein [Thalassiosira pseudonana CCMP1335] |
| SEQ ID NO: 5975 | Nga00331 | 2033.25 | 2377.17 | ---NA--- |
| SEQ ID NO: 5976 | Nga00340 | 135.77 | 234.83 | ---NA--- |
| SEQ ID NO: 5977 | Nga00342 | 936.51 | 1053.76 | ribosome biogenesis gtpase |
| SEQ ID NO: 5978 | Nga00338 | 925.57 | 1205.93 | mitochondrial carrier protein |
| SEQ ID NO: 5979 | Nga00348 | 572.78 | 625.29 | protein |
| SEQ ID NO: 5980 | Nga00343 | 651.43 | 598.36 | dna replication complex gins protein psf1 |
| SEQ ID NO: 5981 | Nga00349 | 250.00 | 346.82 | predicted protein [Thalassiosira pseudonana CCMP1335] |
| SEQ ID NO: 5982 | Nga00344 | 1025.04 | 1085.95 | conserved hypothetical protein [Albugo laibachii Nc14] |
| SEQ ID NO: 5983 | Nga00330 | 1951.10 | 2021.27 | clathrin heavy chain |
| SEQ ID NO: 5984 | Nga00337 | 451.13 | 336.39 | methylenetetrahydrofolate reductase |
| SEQ ID NO: 5985 | Nga00328 | 900.22 | 810.90 | nucleotide sugar transporter family protein |
| SEQ ID NO: 5986 | Nga20149 | 951.28 | 784.65 | transmembrane emp24 domain trafficking protein 2 |
| SEQ ID NO: 5987 | Nga00327 | 8169.65 | 8650.17 | rubisco expression protein |
| SEQ ID NO: 5988 | Nga00329 | 276.36 | 288.01 | peptidyl-prolyl cis-trans isomerase-like protein |
| SEQ ID NO: 5989 | Nga00336 | 397.11 | 401.02 | major facilitator superfamily mfs_1 |
| SEQ ID NO: 5990 | Nga00334 | 638.40 | 712.65 | ---NA--- |
| SEQ ID NO: 5991 | Nga00332 | 1290.44 | 1379.26 | protein kinase c inhibitor |
| SEQ ID NO: 5992 | Nga00335 | 3111.78 | 3765.06 | polyketide synthase |
| SEQ ID NO: 5993 | Nga00333 | 458.61 | 527.08 | phosphatidylinositol phosphate kinase pipk5 |
| SEQ ID NO: 5994 | Nga00341 | 41.67 | 112.84 | ---NA--- |
| SEQ ID NO: 5995 | Nga00345 | 100.92 | 99.38 | ---NA--- |
| SEQ ID NO: 5996 | Nga00339 | 3222.22 | 3278.02 | protein |
| SEQ ID NO: 5997 | Nga04200.01 | 2435.26 | 2111.26 | glycine cleavage system h protein |
| SEQ ID NO: 5998 | Nga04199.01 | 844.11 | 731.14 | protein |
| SEQ ID NO: 5999 | Nga20123.1 | 500.47 | 556.51 | predicted protein [Thalassiosira pseudonana CCMP1335] |
| SEQ ID NO: 6000 | Nga02061.02 | 3210.62 | 3488.59 | peptidase s1 and chymotrypsin hap |
| SEQ ID NO: 6001 | Nga20785 | 605.52 | 862.54 | protein |
| SEQ ID NO: 6002 | Nga02954 | 3985.99 | 3621.40 | protein disulfide isomerase |
| SEQ ID NO: 6003 | Nga02960 | 921.97 | 1162.55 | polysaccharide deacetylase family protein |
| SEQ ID NO: 6004 | Nga02962 | 9144.93 | 9393.26 | ribosomal protein l32 |
| SEQ ID NO: 6005 | Nga20633 | 280.13 | 310.50 | protein arginine n-methyltransferase 7 |
| SEQ ID NO: 6006 | Nga02955 | 359.95 | 407.92 | protein |

FIGURE 24 CQ

| # | Nga model | +N rpkb | -N rpkb | GO |
|---|---|---|---|---|
| SEQ ID NO: 6007 | Nga02961 | 329.42 | 322.09 | protein |
| SEQ ID NO: 6008 | Nga02965 | 887.32 | 929.39 | ---NA--- |
| SEQ ID NO: 6009 | Nga02953 | 895.42 | 818.90 | protein |
| SEQ ID NO: 6010 | Nga02956 | 1779.14 | 2084.51 | plasma membrane intrinsic protein |
| SEQ ID NO: 6011 | Nga02958 | 548.88 | 517.58 | protein kinase-like |
| SEQ ID NO: 6012 | Nga02963 | 501.20 | 688.39 | fe-s-cluster oxidoreductase-like |
| SEQ ID NO: 6013 | Nga02946.2 | 2234.01 | 1934.71 | ---NA--- |
| SEQ ID NO: 6014 | Nga02957 | 2336.83 | 2590.37 | phytoene synthase |
| SEQ ID NO: 6015 | Nga02959 | 664.86 | 647.85 | adiponutrin and related vesicular transport proteins alpha beta hydrolase |
| SEQ ID NO: 6016 | Nga02964 | 416.48 | 425.64 | ---NA--- |
| SEQ ID NO: 6017 | Nga06747 | 315.33 | 314.68 | dynamin family protein |
| SEQ ID NO: 6018 | Nga06745 | 861.87 | 943.50 | assembly protein |
| SEQ ID NO: 6019 | Nga06746 | 151.76 | 106.66 | protein |
| SEQ ID NO: 6020 | Nga02693 | 268.10 | 326.15 | protein mon2 homolog |
| SEQ ID NO: 6021 | Nga02691 | 239.11 | 216.65 | transmembrane protein |
| SEQ ID NO: 6022 | Nga02689 | 551.55 | 528.06 | protein |
| SEQ ID NO: 6023 | Nga02690 | 574.31 | 561.29 | gcn5-related n-acetyltransferase |
| SEQ ID NO: 6024 | Nga02688 | 1167.21 | 1010.43 | ribosomal protein l17 |
| SEQ ID NO: 6025 | Nga02685 | 296.86 | 323.63 | AlNc14C116G6546 [Albugo laibachii Nc14] |
| SEQ ID NO: 6026 | Nga02684 | 338.70 | 361.34 | actin-like protein 6a |
| SEQ ID NO: 6027 | Nga02686 | 1598.07 | 1329.45 | udp-sulfoquinovose synthase |
| SEQ ID NO: 6028 | Nga02683 | 311.62 | 351.19 | protein |
| SEQ ID NO: 6029 | Nga20909 | 162.07 | 179.29 | glutathione synthetase |
| SEQ ID NO: 6030 | Nga20438 | 125.44 | 67.94 | glutathione synthetase |
| SEQ ID NO: 6031 | Nga02687 | 246.89 | 272.49 | abc transporter |
| SEQ ID NO: 6032 | Nga02692 | 97.39 | 120.36 | glutathione synthetase |
| SEQ ID NO: 6033 | Nga06352 | 517.45 | 499.08 | ---NA--- |
| SEQ ID NO: 6034 | Nga03958.02 | 971.34 | 986.64 | ---NA--- |
| SEQ ID NO: 6035 | Nga06349 | 1677.11 | 1777.57 | sulfate transporter |
| SEQ ID NO: 6036 | Nga06350 | 541.64 | 490.83 | fructose-bisphosphate aldolase |
| SEQ ID NO: 6037 | Nga06353 | 387.81 | 517.73 | ---NA--- |
| SEQ ID NO: 6038 | Nga01360.01 | 2706.83 | 2504.43 | transport protein sec61 alpha subunit |
| SEQ ID NO: 6039 | Nga01092.02 | 455.84 | 478.35 | rpa-interacting protein a |
| SEQ ID NO: 6040 | Nga01090.02 | 3969.61 | 4630.68 | transketolase |
| SEQ ID NO: 6041 | Nga01367 | 237.00 | 295.24 | lipase class 3 family protein |
| SEQ ID NO: 6042 | Nga20327 | 134.73 | 272.43 | zinc finger fyve domain-containing protein |
| SEQ ID NO: 6043 | Nga01368 | 139.57 | 176.11 | ---NA--- |
| SEQ ID NO: 6044 | Nga01363 | 508.73 | 459.23 | mpn pad-1 domain-containing protein |
| SEQ ID NO: 6045 | Nga01365 | 2289.17 | 2818.00 | lipase class 2 |
| SEQ ID NO: 6046 | Nga01362 | 653.23 | 528.51 | peptidase c13-like protein |
| SEQ ID NO: 6047 | Nga01361 | 6650.02 | 6478.26 | protein |
| SEQ ID NO: 6048 | Nga21165.1 | 101.93 | 80.57 | cupin 4 family protein |
| SEQ ID NO: 6049 | Nga02453.02 | 857.36 | 952.91 | protein |
| SEQ ID NO: 6050 | Nga02459.02 | 69.38 | 76.02 | metallo-beta-lactamase superfamily protein |
| SEQ ID NO: 6051 | Nga02451.02 | 757.24 | 824.83 | zinc transporter |
| SEQ ID NO: 6052 | Nga20718.1 | 229.86 | 261.82 | conserved unknown protein [Ectocarpus siliculosus] |
| SEQ ID NO: 6053 | Nga06303 | 2276.20 | 2171.49 | sideroflexin 3 |
| SEQ ID NO: 6054 | Nga06300 | 351.08 | 353.53 | protein |
| SEQ ID NO: 6055 | Nga06301 | 112.79 | 154.10 | protein |
| SEQ ID NO: 6056 | Nga06304 | 110.65 | 78.20 | glycoside hydrolase family 3 domain protein |
| SEQ ID NO: 6057 | Nga04154 | 480.66 | 450.42 | insulin-degrading enzyme |
| SEQ ID NO: 6058 | Nga04153 | 230.48 | 211.12 | chromosome 3 open reading frame 23 |
| SEQ ID NO: 6059 | Nga04155 | 19464.65 | 15657.65 | ---NA--- |
| SEQ ID NO: 6060 | Nga03824 | 459.05 | 518.27 | zinc finger ccch type domain containing protein expressed |
| SEQ ID NO: 6061 | Nga20409.1 | 85.06 | 53.94 | elegans protein confirmed by transcript evidence |
| SEQ ID NO: 6062 | Nga20453.1 | 37.63 | 34.94 | wd repeat domain 19 |
| SEQ ID NO: 6063 | Nga03825 | 16.67 | 27.08 | ---NA--- |
| SEQ ID NO: 6064 | Nga06670.2 | 496.12 | 501.27 | mitochondrial phosphate carrier protein |
| SEQ ID NO: 6065 | Nga03034 | 267.68 | 279.70 | glutamyl-trna a subunit |
| SEQ ID NO: 6066 | Nga03036 | 325.30 | 395.88 | ---NA--- |
| SEQ ID NO: 6067 | Nga03033.01 | 251.53 | 367.69 | biotin lipoate protein ligase-like protein |
| SEQ ID NO: 6068 | Nga03042.01 | 75.30 | 123.56 | protein |
| SEQ ID NO: 6069 | Nga03030.01 | 609.79 | 759.79 | peptidase u34 dipeptidase |

FIGURE 24 CR

| # | Nga model | +N rpkb | -N rpkb | GO |
|---|---|---|---|---|
| SEQ ID NO: 6070 | Nga03032 | 734.19 | 606.05 | ---NA--- |
| SEQ ID NO: 6071 | Nga03039 | 690.05 | 698.47 | ---NA--- |
| SEQ ID NO: 6072 | Nga03035 | 507.88 | 646.52 | Aardvark [Ectocarpus siliculosus] |
| SEQ ID NO: 6073 | Nga03037.01 | 415.64 | 402.61 | protein |
| SEQ ID NO: 6074 | Nga03031 | 479.89 | 486.21 | protein |
| SEQ ID NO: 6075 | Nga03041.01 | 422.87 | 487.28 | calcium calmodulin-dependent protein kinase type 1 |
| SEQ ID NO: 6076 | Nga03040.01 | 193.55 | 227.13 | ---NA--- |
| SEQ ID NO: 6077 | Nga03038.01 | 1745.28 | 1917.36 | conserved unknown protein [Ectocarpus siliculosus] |
| SEQ ID NO: 6078 | Nga06129 | 157.67 | 137.22 | dna topoisomerase 3-beta-1 |
| SEQ ID NO: 6079 | Nga06131 | 2535.79 | 2315.44 | ---NA--- |
| SEQ ID NO: 6080 | Nga06132 | 234.29 | 174.86 | ---NA--- |
| SEQ ID NO: 6081 | Nga06130 | 1083.33 | 1018.56 | chaperone protein |
| SEQ ID NO: 6082 | Nga06128 | 1112.69 | 833.60 | peroxisomal trans-2-enoyl- reductase |
| SEQ ID NO: 6083 | Nga20501 | 278.63 | 270.81 | ---NA--- |
| SEQ ID NO: 6084 | Nga20653 | 168.46 | 190.25 | ---NA--- |
| SEQ ID NO: 6085 | Nga06601.1 | 394.31 | 433.70 | ribonucleoside triphosphate reductase |
| SEQ ID NO: 6086 | Nga06602 | 347.14 | 443.35 | ufd1 like protein |
| SEQ ID NO: 6087 | Nga20848.1 | 284.96 | 214.36 | ---NA--- |
| SEQ ID NO: 6088 | Nga21244 | 151.32 | 149.66 | adp-ribosylation factor-like protein 2 |
| SEQ ID NO: 6089 | Nga06605 | 556.95 | 561.58 | arginine methyltransferase 4 |
| SEQ ID NO: 6090 | Nga06604 | 147.92 | 206.58 | atp-dependent rna helicase dbp4 |
| SEQ ID NO: 6091 | Nga20532 | 270.49 | 261.93 | serine threonine protein kinase cki3 |
| SEQ ID NO: 6092 | Nga21012 | 236.67 | 187.76 | cellular apoptosis susceptibility protein |
| SEQ ID NO: 6093 | Nga06603 | 267.67 | 217.34 | exportin-2-like protein |
| SEQ ID NO: 6094 | Nga20047 | 278.86 | 314.34 | pentatricopeptide repeat-containing protein |
| SEQ ID NO: 6095 | Nga20800 | 742.07 | 800.67 | aldo keto reductase family protein |
| SEQ ID NO: 6096 | Nga03247 | 2238.76 | 1592.10 | nudc domain-containing protein 2 |
| SEQ ID NO: 6097 | Nga03251 | 922.80 | 1038.64 | protein |
| SEQ ID NO: 6098 | Nga20831 | 536.52 | 582.62 | conserved unknown protein [Ectocarpus siliculosus] |
| SEQ ID NO: 6099 | Nga20839 | 515.54 | 603.46 | conserved unknown protein [Ectocarpus siliculosus] |
| SEQ ID NO: 6100 | Nga03252 | 4215.18 | 4347.34 | mpv17 protein |
| SEQ ID NO: 6101 | Nga03250 | 400.25 | 405.30 | ubiquitin-conjugating enzyme catalytic domain |
| SEQ ID NO: 6102 | Nga03249 | 1108.16 | 1129.33 | p21-activated protein kinase |
| SEQ ID NO: 6103 | Nga03248 | 3231.71 | 2687.33 | porphobilinogen deaminase |
| SEQ ID NO: 6104 | Nga21100 | 1144.02 | 1117.18 | ribophorin ii family protein |
| SEQ ID NO: 6105 | Nga03246 | 1849.38 | 1665.81 | high mobility group protein |
| SEQ ID NO: 6106 | Nga03253 | 453.70 | 702.10 | ---NA--- |
| SEQ ID NO: 6107 | Nga21042 | 439.10 | 427.42 | conserved unknown protein [Ectocarpus siliculosus] |
| SEQ ID NO: 6108 | Nga05503.1 | 1697.92 | 1685.03 | glycoprotease m22 family protein |
| SEQ ID NO: 6109 | Nga20781.1 | 866.36 | 771.81 | protein |
| SEQ ID NO: 6110 | Nga20471.1 | 391.08 | 343.74 | wd repeat and hmg-box dna-binding protein 1 |
| SEQ ID NO: 6111 | Nga21122.1 | 467.19 | 504.38 | lysocardiolipin acyltransferase 1 |
| SEQ ID NO: 6112 | Nga05507 | 180.09 | 168.12 | chromosome segregation protein |
| SEQ ID NO: 6113 | Nga05504 | 726.43 | 648.30 | protein |
| SEQ ID NO: 6114 | Nga05500.01 | 1186.11 | 978.92 | rna (guanine-9-)-methyltransferase domain-containing |
| SEQ ID NO: 6115 | Nga05499.01 | 1387.17 | 1469.01 | peptidase dimerization domain-containing protein |
| SEQ ID NO: 6116 | Nga21050 | 1748.68 | 1679.30 | erg28 like protein |
| SEQ ID NO: 6117 | Nga05501 | 4994.52 | 4540.79 | ---NA--- |
| SEQ ID NO: 6118 | Nga05895.2 | 422.28 | 434.61 | ---NA--- |
| SEQ ID NO: 6119 | Nga05502.01 | 1425.93 | 1289.85 | peroxisomal -dienoyl- reductase |
| SEQ ID NO: 6120 | Nga21071 | 95.59 | 143.37 | conserved unknown protein [Ectocarpus siliculosus] |
| SEQ ID NO: 6121 | Nga20875.1 | 1243.39 | 985.48 | protein |
| SEQ ID NO: 6122 | Nga04134.01 | 716.06 | 560.23 | activating transcription factor 1 |
| SEQ ID NO: 6123 | Nga04136.01 | 176.74 | 235.40 | protein |
| SEQ ID NO: 6124 | Nga05539.2 | 400.87 | 348.10 | isoform cra_a |
| SEQ ID NO: 6125 | Nga04137 | 429.43 | 645.17 | nucleolar protein 10 |
| SEQ ID NO: 6126 | Nga03613.01 | 3916.28 | 4065.88 | calcium-dependent protein |
| SEQ ID NO: 6127 | Nga03614.01 | 8410.89 | 7259.10 | protein |
| SEQ ID NO: 6128 | Nga20926 | 2883.01 | 2567.18 | protein |
| SEQ ID NO: 6129 | Nga03612 | 532.95 | 670.72 | protein |
| SEQ ID NO: 6130 | Nga03615 | 280.08 | 322.50 | twy3 methyltransferase |
| SEQ ID NO: 6131 | Nga02521 | 28.84 | 52.48 | ---NA--- |
| SEQ ID NO: 6132 | Nga02520.01 | 902.96 | 384.44 | phytochelatin synthase |
| SEQ ID NO: 6133 | Nga02512.02 | 644.84 | 653.19 | prolyl-trna |

FIGURE 24 CS

| # | Nga model | +N rpkb | -N rpkb | GO |
|---|---|---|---|---|
| SEQ ID NO: 6134 | Nga02518.01 | 181.02 | 126.74 | histone h1 |
| SEQ ID NO: 6135 | Nga02513 | 273.58 | 233.68 | xylosyltransferase i |
| SEQ ID NO: 6136 | Nga02509 | 4202.99 | 3776.77 | 40s ribosomal protein s21 |
| SEQ ID NO: 6137 | Nga02516.01 | 24.04 | 35.23 | t-complex 11 like isoform cra_b |
| SEQ ID NO: 6138 | Nga02512.01 | 644.84 | 653.19 | prolyl-trna |
| SEQ ID NO: 6139 | Nga02514.01 | 802.06 | 599.69 | tropinone reductase |
| SEQ ID NO: 6140 | Nga02508 | 4665.88 | 4659.18 | nadh-ubiquinone oxidoreductase b18 subunit family protein |
| SEQ ID NO: 6141 | Nga02511.01 | 2391.62 | 2702.49 | sporangia induced sperm flagellar protein |
| SEQ ID NO: 6142 | Nga02510 | 226.67 | 250.89 | protein |
| SEQ ID NO: 6143 | Nga02517 | 1349.68 | 1276.22 | protein |
| SEQ ID NO: 6144 | Nga02519.01 | 463.46 | 438.55 | phosphoglycerate mutase 1 family |
| SEQ ID NO: 6145 | Nga01612 | 1181.36 | 1299.88 | dna-directed rna polymerases i and iii subunit rpac2 |
| SEQ ID NO: 6146 | Nga01611 | 1717.82 | 1751.83 | glycerol kinase |
| SEQ ID NO: 6147 | Nga01613 | 1026.92 | 783.26 | proliferating cell nuclear antigen |
| SEQ ID NO: 6148 | Nga01614 | 393.84 | 368.97 | tyrosine aminotransferase |
| SEQ ID NO: 6149 | Nga01615 | 182.27 | 159.03 | alkylated dna repair protein alkb-like protein |
| SEQ ID NO: 6150 | Nga21025 | 963.21 | 778.91 | family with sequence similarity member a |
| SEQ ID NO: 6151 | Nga20876 | 1048.52 | 957.54 | protein |
| SEQ ID NO: 6152 | Nga06705 | 1078.84 | 1015.19 | protein |
| SEQ ID NO: 6153 | Nga04379.02 | 1007.44 | 1088.61 | ---NA--- |
| SEQ ID NO: 6154 | Nga04378.02 | 10024.63 | 8667.28 | like protein |
| SEQ ID NO: 6155 | Nga06704 | 1002.82 | 1049.67 | hydroxyacylglutathione hydrolase |
| SEQ ID NO: 6156 | Nga06710 | 184.24 | 259.24 | ---NA--- |
| SEQ ID NO: 6157 | Nga06707 | 1142.86 | 1049.97 | conserved unknown protein [Ectocarpus siliculosus] |
| SEQ ID NO: 6158 | Nga06711 | 83.77 | 124.77 | ---NA--- |
| SEQ ID NO: 6159 | Nga06706 | 677.48 | 737.77 | 1-aminocyclopropane-1-carboxylate deaminase |
| SEQ ID NO: 6160 | Nga21230 | 100.78 | 75.57 | ---NA--- |
| SEQ ID NO: 6161 | Nga03839 | 461.47 | 409.36 | prolyl endopeptidase |
| SEQ ID NO: 6162 | Nga03840 | 873.86 | 858.34 | protein serine threonine kinase |
| SEQ ID NO: 6163 | Nga03841 | 568.14 | 612.25 | beta-ketoacyl synthase |
| SEQ ID NO: 6164 | Nga20632 | 160.51 | 259.07 | polyketide synthase |
| SEQ ID NO: 6165 | Nga20637 | 139.30 | 169.76 | polyketide synthase |
| SEQ ID NO: 6166 | Nga20733 | 181.47 | 156.84 | polyketide synthase |
| SEQ ID NO: 6167 | Nga20163 | 139.19 | 174.20 | beta-ketoacyl synthase |
| SEQ ID NO: 6168 | Nga01202.01 | 701.79 | 658.97 | magnesium-dependent phosphatase 1 |
| SEQ ID NO: 6169 | Nga01205 | 853.93 | 709.98 | ---NA--- |
| SEQ ID NO: 6170 | Nga01203 | 452.20 | 538.47 | sulfotransferase |
| SEQ ID NO: 6171 | Nga01207 | 374.28 | 272.37 | trna splicing endonuclease 54 homolog |
| SEQ ID NO: 6172 | Nga01206 | 1929.29 | 2415.61 | glycoside hydrolase family 8 |
| SEQ ID NO: 6173 | Nga01204.01 | 11063.86 | 12214.44 | hypothetical protein THAPSDRAFT_268059 [Thalassiosira pseudonana CCMP1335] |
| SEQ ID NO: 6174 | Nga01201.01 | 567.13 | 655.45 | l-allo-threonine aldolase |
| SEQ ID NO: 6175 | Nga20807.1 | 2369.09 | 2461.90 | conserved unknown protein [Ectocarpus siliculosus] |
| SEQ ID NO: 6176 | Nga01508.1 | 2612.36 | 3093.51 | threonine aldolase |
| SEQ ID NO: 6177 | Nga01504 | 455.49 | 703.47 | uncharacterized protein |
| SEQ ID NO: 6178 | Nga04086.2 | 245.95 | 279.00 | atpase-like protein |
| SEQ ID NO: 6179 | Nga01506 | 361.54 | 351.63 | ---NA--- |
| SEQ ID NO: 6180 | Nga01503 | 623.17 | 654.33 | escrt-ii complex subunit vps22 |
| SEQ ID NO: 6181 | Nga04083.2 | 948.01 | 1692.75 | sec14p-like phosphatidylinositol transfer family protein |
| SEQ ID NO: 6182 | Nga05546.1 | 360.44 | 368.05 | ---NA--- |
| SEQ ID NO: 6183 | Nga04129.02 | 2357.42 | 2462.01 | ---NA--- |
| SEQ ID NO: 6184 | Nga20544 | 198.16 | 304.50 | rdd domain containing protein |
| SEQ ID NO: 6185 | Nga05548 | 467.30 | 419.98 | citrate synthase |
| SEQ ID NO: 6186 | Nga04128.02 | 25708.25 | 33515.41 | fructose-bisphosphate aldolase |
| SEQ ID NO: 6187 | Nga20625 | 305.56 | 259.11 | protein |
| SEQ ID NO: 6188 | Nga05552 | 252.33 | 232.95 | protein pelota homolog |
| SEQ ID NO: 6189 | Nga20680 | 29.20 | 94.88 | ---NA--- |
| SEQ ID NO: 6190 | Nga04228.02 | 902.97 | 885.89 | expressed unknown protein [Ectocarpus siliculosus] |
| SEQ ID NO: 6191 | Nga20805 | 503.09 | 579.23 | protein |
| SEQ ID NO: 6192 | Nga04227.02 | 1197.11 | 1442.35 | aaa-type atpase family protein |
| SEQ ID NO: 6193 | Nga05554 | 441.75 | 476.65 | acid phosphatase-1 |
| SEQ ID NO: 6194 | Nga04226.02 | 2703.62 | 3063.23 | peroxisomal biogenesis factor 11 domain-containing protein |
| SEQ ID NO: 6195 | Nga20348 | 490.09 | 460.49 | conserved unknown protein [Ectocarpus siliculosus] |
| SEQ ID NO: 6196 | Nga01224 | 529.65 | 748.31 | ---NA--- |

FIGURE 24 CT

| # | Nga model | +N rpkb | -N rpkb | GO |
|---|---|---|---|---|
| SEQ ID NO: 6197 | Nga01222.01 | 694.92 | 575.64 | uv excision repair protein |
| SEQ ID NO: 6198 | Nga06844.2 | 3618.52 | 7053.06 | ferredoxin (2fe-2s) |
| SEQ ID NO: 6199 | Nga06144.1 | 861.43 | 810.33 | hydroxyacyl-coenzyme a mitochondrial precursor |
| SEQ ID NO: 6200 | Nga06148 | 287.08 | 417.23 | major facilitator superfamily mfs_1 |
| SEQ ID NO: 6201 | Nga06145 | 2327.49 | 2308.50 | vacuolar atpase subunit dva41 |
| SEQ ID NO: 6202 | Nga06147 | 138.18 | 182.08 | ---NA--- |
| SEQ ID NO: 6203 | Nga06143 | 3092.62 | 2830.61 | high mobility group b3 protein |
| SEQ ID NO: 6204 | Nga06146.1 | 1602.18 | 1863.63 | pyrophosphate-dependent phosphofructose kinase |
| SEQ ID NO: 6205 | Nga06788 | 228.59 | 183.95 | cellulase 2 |
| SEQ ID NO: 6206 | Nga06786 | 239.09 | 287.81 | protein phosphatase |
| SEQ ID NO: 6207 | Nga06784 | 148.15 | 100.30 | ---NA--- |
| SEQ ID NO: 6208 | Nga06785 | 2124.70 | 2027.01 | ubiquitin-like domain-containing ctd phosphatase 1 |
| SEQ ID NO: 6209 | Nga06787 | 645.16 | 570.17 | ---NA--- |
| SEQ ID NO: 6210 | Nga21268 | 33.33 | 36.11 | transmembrane protein 97 |
| SEQ ID NO: 6211 | Nga03628 | 33.24 | 22.24 | ---NA--- |
| SEQ ID NO: 6212 | Nga03627 | 83.95 | 56.17 | ---NA--- |
| SEQ ID NO: 6213 | Nga20636 | 185.04 | 213.24 | ---NA--- |
| SEQ ID NO: 6214 | Nga00885 | 177.26 | 142.63 | condensin complex components subunit |
| SEQ ID NO: 6215 | Nga20506.1 | 354.17 | 324.97 | conserved unknown protein [Ectocarpus siliculosus] |
| SEQ ID NO: 6216 | Nga20275.1 | 178.53 | 155.39 | upf0533 protein c5orf44 homolog |
| SEQ ID NO: 6217 | Nga00886.01 | 6284.26 | 7991.04 | isocitrate lyase |
| SEQ ID NO: 6218 | Nga01406 | 1488.32 | 1530.94 | conserved unknown protein [Ectocarpus siliculosus] |
| SEQ ID NO: 6219 | Nga01407 | 1385.96 | 1435.54 | ribonuclease h |
| SEQ ID NO: 6220 | Nga01405 | 610.77 | 734.76 | mitochondrial dna replication protein yhm2 |
| SEQ ID NO: 6221 | Nga01408 | 57.68 | 42.55 | zinc ran-binding domain containing 3 |
| SEQ ID NO: 6222 | Nga20732 | 181.82 | 166.18 | ---NA--- |
| SEQ ID NO: 6223 | Nga20452 | 215.74 | 208.44 | protein |
| SEQ ID NO: 6224 | Nga20753 | 265.63 | 225.67 | ---NA--- |
| SEQ ID NO: 6225 | Nga20515 | 162.71 | 168.91 | ---NA--- |
| SEQ ID NO: 6226 | Nga20054 | 348.19 | 417.40 | protein |
| SEQ ID NO: 6227 | Nga01243.2 | 837.84 | 803.64 | mitogen-activated protein |
| SEQ ID NO: 6228 | Nga20542 | 164.35 | 203.11 | ---NA--- |
| SEQ ID NO: 6229 | Nga01240 | 920.97 | 1304.03 | carbonic anhydrase |
| SEQ ID NO: 6230 | Nga01246 | 492.46 | 480.83 | protein |
| SEQ ID NO: 6231 | Nga01242 | 403.05 | 462.51 | protein kinase-like |
| SEQ ID NO: 6232 | Nga01241 | 2189.13 | 2124.59 | ycii-related domain protein |
| SEQ ID NO: 6233 | Nga01244 | 236.29 | 202.63 | protein |
| SEQ ID NO: 6234 | Nga01243.1 | 837.84 | 803.64 | protein |
| SEQ ID NO: 6235 | Nga03809 | 290.85 | 306.16 | mn2+ fe2+ nramp family |
| SEQ ID NO: 6236 | Nga03811 | 2050.19 | 2062.61 | ---NA--- |
| SEQ ID NO: 6237 | Nga03810 | 200.60 | 210.81 | protein |
| SEQ ID NO: 6238 | Nga06329 | 387.03 | 555.34 | atp-dependent clp atp-binding subunit |
| SEQ ID NO: 6239 | Nga06325 | 610.17 | 411.57 | protein |
| SEQ ID NO: 6240 | Nga06322 | 1308.41 | 1356.57 | molybdenum cofactor synthesis isoform cra_a |
| SEQ ID NO: 6241 | Nga06328 | 1832.45 | 1846.68 | cell division protein |
| SEQ ID NO: 6242 | Nga06327 | 937.98 | 1016.06 | protein |
| SEQ ID NO: 6243 | Nga20605 | 825.08 | 799.02 | predicted protein [Phaeodactylum tricornutum CCAP 1055/1] |
| SEQ ID NO: 6244 | Nga06323 | 387.08 | 327.63 | mitogen-activated protein kinase |
| SEQ ID NO: 6245 | Nga06324.01 | 2670.06 | 2608.04 | dna repair protein nse1 |
| SEQ ID NO: 6246 | Nga06330 | 309.48 | 291.99 | fg-gap repeat family protein |
| SEQ ID NO: 6247 | Nga06321 | 12408.16 | 9381.89 | extrinsic protein in photosystem ii |
| SEQ ID NO: 6248 | Nga06326 | 1569.87 | 1313.92 | 26s proteasome non-atpase regulatory subunit 14 |
| SEQ ID NO: 6249 | Nga01322 | 138.00 | 133.39 | intraflagellar transport protein ift88 |
| SEQ ID NO: 6250 | Nga20569 | 115.89 | 114.78 | ---NA--- |
| SEQ ID NO: 6251 | Nga01321 | 131.00 | 66.22 | intraflagellar transport protein 88 homolog |
| SEQ ID NO: 6252 | Nga20597 | 122.56 | 120.69 | intraflagellar transport protein 88 homolog |
| SEQ ID NO: 6253 | Nga01319 | 339.57 | 423.71 | 60s ribosomal export protein |
| SEQ ID NO: 6254 | Nga01318 | 4676.56 | 5307.80 | chaperonin |
| SEQ ID NO: 6255 | Nga20071 | 1048.85 | 1212.72 | hit zinc finger family protein |
| SEQ ID NO: 6256 | Nga01320 | 1176.86 | 1267.71 | eukaryotic translation initiation factor iso4e |
| SEQ ID NO: 6257 | Nga01785.02 | 1113.07 | 1258.03 | protein |
| SEQ ID NO: 6258 | Nga06051 | 1828.77 | 1937.09 | peptidase c26 family protein |
| SEQ ID NO: 6259 | Nga06054 | 389.91 | 427.62 | ---NA--- |
| SEQ ID NO: 6260 | Nga06052 | 653.74 | 435.78 | ---NA--- |

FIGURE 24 CU

| # | Nga model | +N rpkb | -N rpkb | GO |
|---|---|---|---|---|
| SEQ ID NO: 6261 | Nga06055 | 2352.14 | 2984.16 | ---NA--- |
| SEQ ID NO: 6262 | Nga06050 | 430.08 | 367.71 | high density lipoprotien binding protein vigilin |
| SEQ ID NO: 6263 | Nga02741 | 1096.55 | 1111.46 | pyruvate dehydrogenase component x |
| SEQ ID NO: 6264 | Nga02742 | 291.67 | 248.24 | chaperone protein dnak |
| SEQ ID NO: 6265 | Nga02737 | 830.75 | 964.31 | phospholipid:diacylglycerol acyltransferase |
| SEQ ID NO: 6266 | Nga04982.2 | 877.34 | 673.70 | isoform a |
| SEQ ID NO: 6267 | Nga02736.01 | 3124.70 | 3021.11 | conserved unknown protein [Ectocarpus siliculosus] |
| SEQ ID NO: 6268 | Nga02739 | 1093.14 | 1109.78 | thymidylate kinase |
| SEQ ID NO: 6269 | Nga02744 | 434.78 | 399.45 | selw selh selenoprotein |
| SEQ ID NO: 6270 | Nga02740 | 100.60 | 156.14 | root hairless 1 |
| SEQ ID NO: 6271 | Nga01469 | 649.82 | 600.09 | caib baif -transferase family protein c7orf10-like isoform 1 |
| SEQ ID NO: 6272 | Nga01468 | 1832.78 | 1706.48 | abortive infection protein |
| SEQ ID NO: 6273 | Nga20537 | 327.82 | 371.32 | indole-3-glycerol-phosphate synthase |
| SEQ ID NO: 6274 | Nga01471 | 346.83 | 391.78 | u4 tri-snrnp-associated |
| SEQ ID NO: 6275 | Nga01470 | 302.22 | 334.96 | u4 tri-snrnp-associated protein 2 |
| SEQ ID NO: 6276 | Nga04009 | 356.12 | 429.49 | aarf domain containing kinase 2 |
| SEQ ID NO: 6277 | Nga04010.1 | 968.23 | 1108.62 | protein |
| SEQ ID NO: 6278 | Nga04011.01 | 136.51 | 204.59 | atp synthetase alpha chain -like |
| SEQ ID NO: 6279 | Nga04008.01 | 768.78 | 714.71 | emp24 gp25l p24 family protein |
| SEQ ID NO: 6280 | Nga03649 | 1523.72 | 1529.97 | protein |
| SEQ ID NO: 6281 | Nga03647 | 512.20 | 497.36 | argininosuccinate lyase |
| SEQ ID NO: 6282 | Nga03648 | 351.05 | 362.09 | ---NA--- |
| SEQ ID NO: 6283 | Nga20299 | 578.85 | 543.15 | amine oxidase |
| SEQ ID NO: 6284 | Nga03646 | 169.83 | 195.08 | general transcription factor polypeptide 3 |
| SEQ ID NO: 6285 | Nga00815 | 31086.73 | 24649.10 | expressed unknown protein [Ectocarpus siliculosus] |
| SEQ ID NO: 6286 | Nga00813 | 242.94 | 134.64 | conserved unknown protein [Ectocarpus siliculosus] |
| SEQ ID NO: 6287 | Nga00816 | 95.91 | 72.22 | hypothetical protein Esi_0189_0054 [Ectocarpus siliculosus] |
| SEQ ID NO: 6288 | Nga00808 | 372.03 | 407.68 | histone acetylase complex subunit mrg15-2 |
| SEQ ID NO: 6289 | Nga00809 | 8606.19 | 6021.06 | expressed unknown protein [Ectocarpus siliculosus] |
| SEQ ID NO: 6290 | Nga00810 | 1986.52 | 2210.28 | betacateninlike protein |
| SEQ ID NO: 6291 | Nga00812 | 1461.19 | 1501.69 | clusterin associated protein 1 |
| SEQ ID NO: 6292 | Nga00814 | 1292.50 | 1369.72 | protein |
| SEQ ID NO: 6293 | Nga00811 | 10958.01 | 11253.50 | predicted protein [Thalassiosira pseudonana CCMP1335] |
| SEQ ID NO: 6294 | Nga04126.01 | 3030.08 | 2953.05 | ---NA--- |
| SEQ ID NO: 6295 | Nga04127.01 | 203.45 | 291.35 | growth arrest-specific 7 |
| SEQ ID NO: 6296 | Nga20183 | 690.06 | 753.43 | kynurenine alpha-aminoadipate mitochondrial-like |
| SEQ ID NO: 6297 | Nga21057 | 517.29 | 582.20 | aromatic aminotransferase |
| SEQ ID NO: 6298 | Nga21219.1 | 230.33 | 228.50 | augmenter of liver regeneration |
| SEQ ID NO: 6299 | Nga02583 | 2572.73 | 2578.84 | ---NA--- |
| SEQ ID NO: 6300 | Nga02111.02 | 525.58 | 463.05 | carbohydratebinding protein |
| SEQ ID NO: 6301 | Nga20179 | 210.32 | 223.48 | protein |
| SEQ ID NO: 6302 | Nga02588 | 178.67 | 194.98 | sterol desaturase family protein |
| SEQ ID NO: 6303 | Nga20126 | 376.51 | 268.63 | dna repair and transcription protein |
| SEQ ID NO: 6304 | Nga02591 | 151.99 | 132.14 | mms19 nucleotide excision repair protein |
| SEQ ID NO: 6305 | Nga02586 | 423.84 | 498.22 | ppgpp synthetase |
| SEQ ID NO: 6306 | Nga02587 | 934.37 | 925.42 | 6-phosphogluconate dehydrogenase |
| SEQ ID NO: 6307 | Nga02582 | 2173.54 | 2373.53 | ---NA--- |
| SEQ ID NO: 6308 | Nga02590 | 146.55 | 150.66 | abc subfamily abcg |
| SEQ ID NO: 6309 | Nga02585 | 1421.11 | 1459.82 | protein |
| SEQ ID NO: 6310 | Nga02589 | 75.84 | 91.70 | abc transporter g family protein |
| SEQ ID NO: 6311 | Nga03685 | 883.37 | 901.24 | ccr4-associated factor |
| SEQ ID NO: 6312 | Nga03419 | 1677.78 | 1368.49 | mitochondrial carrier |
| SEQ ID NO: 6313 | Nga03418 | 527.71 | 608.84 | activating signal cointegrator 1 complex subunit 2 |
| SEQ ID NO: 6314 | Nga03422 | 406.24 | 516.38 | non-ribosomal peptide synthetase |
| SEQ ID NO: 6315 | Nga03411 | 554.52 | 600.67 | pseudouridine family |
| SEQ ID NO: 6316 | Nga03420 | 136.36 | 140.42 | ---NA--- |
| SEQ ID NO: 6317 | Nga03417 | 453.67 | 498.36 | ---NA--- |
| SEQ ID NO: 6318 | Nga03413 | 738.11 | 812.23 | cytoplasm protein |
| SEQ ID NO: 6319 | Nga03410 | 369.19 | 437.12 | protein |
| SEQ ID NO: 6320 | Nga03421 | 200.00 | 171.51 | ---NA--- |
| SEQ ID NO: 6321 | Nga03409 | 5319.15 | 5066.94 | translation elongation factor g |
| SEQ ID NO: 6322 | Nga02839.02 | 1754.74 | 1803.40 | dihydrolipoamide dehydrogenase |
| SEQ ID NO: 6323 | Nga03423 | 2415.07 | 2341.26 | uncharacterized protein |
| SEQ ID NO: 6324 | Nga03414 | 1062.63 | 992.39 | ---NA--- |

FIGURE 24 CV

| # | Nga model | +N rpkb | -N rpkb | GO |
|---|---|---|---|---|
| SEQ ID NO: 6325 | Nga02842.02 | 2105.04 | 2116.40 | ---NA--- |
| SEQ ID NO: 6326 | Nga03415 | 849.81 | 760.89 | uncharacterized protein |
| SEQ ID NO: 6327 | Nga03412 | 1441.04 | 1358.46 | protein sco1 mitochondrial-like |
| SEQ ID NO: 6328 | Nga20825 | 237.61 | 261.06 | karyopherin beta 2b isoform 2 |
| SEQ ID NO: 6329 | Nga06487.1 | 139.53 | 178.14 | transportin 1 |
| SEQ ID NO: 6330 | Nga02592.02 | 324.43 | 366.06 | thiamine monophosphate synthase |
| SEQ ID NO: 6331 | Nga02563.02 | 1646.55 | 1120.59 | ---NA--- |
| SEQ ID NO: 6332 | Nga02597.2 | 555.13 | 626.05 | u2 small nuclear ribonucleoprotein auxiliary factor u2af |
| SEQ ID NO: 6333 | Nga06485 | 857.93 | 1099.22 | serine threonine-protein phosphatase 1 regulatory subunit 10 |
| SEQ ID NO: 6334 | Nga06486 | 3845.15 | 4297.50 | glucan -beta-glucosidase precursor |
| SEQ ID NO: 6335 | Nga06665.2 | 558.54 | 566.24 | protein |
| SEQ ID NO: 6336 | Nga06662 | 144.48 | 159.86 | mitochondrial carrier protein |
| SEQ ID NO: 6337 | Nga20262.1 | 647.28 | 605.12 | myosin-like protein |
| SEQ ID NO: 6338 | Nga06666 | 290.63 | 282.22 | protein kinase domain containing protein |
| SEQ ID NO: 6339 | Nga20744 | 170.10 | 217.76 | myosin 29 |
| SEQ ID NO: 6340 | Nga06667 | 140.61 | 157.64 | class v myosin |
| SEQ ID NO: 6341 | Nga06663 | 6510.15 | 5646.23 | ---NA--- |
| SEQ ID NO: 6342 | Nga21009 | 291.67 | 376.70 | rna binding identical |
| SEQ ID NO: 6343 | Nga06665.1 | 558.54 | 566.24 | protein |
| SEQ ID NO: 6344 | Nga06661 | 208.20 | 156.89 | protein |
| SEQ ID NO: 6345 | Nga00060 | 421.44 | 364.03 | l-asparaginase i |
| SEQ ID NO: 6346 | Nga00053.01 | 6413.41 | 6296.68 | expressed unknown protein [Ectocarpus siliculosus] |
| SEQ ID NO: 6347 | Nga00055 | 207.07 | 280.84 | deah (asp-glu-ala-his) box polypeptide 35 |
| SEQ ID NO: 6348 | Nga00056 | 1521.01 | 1609.98 | protein high chlorophyll fluorescent 107 |
| SEQ ID NO: 6349 | Nga00054.01 | 1480.13 | 1451.60 | gamma tubulin |
| SEQ ID NO: 6350 | Nga00065 | 6234.67 | 5507.78 | transport protein sec61 subunit gamma |
| SEQ ID NO: 6351 | Nga00068 | 6583.39 | 6152.26 | rna binding s1 domain protein |
| SEQ ID NO: 6352 | Nga00058 | 704.45 | 750.35 | diaminopimelate decarboxylase |
| SEQ ID NO: 6353 | Nga00052.01 | 725.04 | 763.11 | isoleucyl-trna synthetase |
| SEQ ID NO: 6354 | Nga00064 | 1084.32 | 1043.27 | uncharacterized protein |
| SEQ ID NO: 6355 | Nga00061.01 | 734.20 | 684.80 | ---NA--- |
| SEQ ID NO: 6356 | Nga00057.01 | 412.66 | 515.55 | conserved hypothetical protein [Phytophthora infestans T30-4] |
| SEQ ID NO: 6357 | Nga00051 | 836.72 | 833.62 | beta glucosidase |
| SEQ ID NO: 6358 | Nga00070.01 | 910.24 | 770.27 | ---NA--- |
| SEQ ID NO: 6359 | Nga00067 | 625.30 | 535.03 | ---NA--- |
| SEQ ID NO: 6360 | Nga00063.1 | 543.50 | 530.89 | methylmalonic aciduria type a mitochondrial |
| SEQ ID NO: 6361 | Nga00069 | 1767.30 | 1941.65 | ---NA--- |
| SEQ ID NO: 6362 | Nga00059 | 1511.53 | 1363.96 | 1-acyl-sn-glycerol-3-phosphate acyltransferase |
| SEQ ID NO: 6363 | Nga01540 | 375.39 | 457.27 | tetratricopeptide repeat |
| SEQ ID NO: 6364 | Nga01536 | 994.48 | 830.38 | 30s ribosomal protein s17 |
| SEQ ID NO: 6365 | Nga21106 | 243.78 | 264.07 | tetrapyrrole methylase family protein |
| SEQ ID NO: 6366 | Nga21220 | 251.57 | 200.68 | uncharacterized protein |
| SEQ ID NO: 6367 | Nga01538 | 300.21 | 352.11 | ---NA--- |
| SEQ ID NO: 6368 | Nga01539.1 | 338.33 | 507.74 | hypothetical protein GLRG_11977 [Glomerella graminicola M1.001] |
| SEQ ID NO: 6369 | Nga05666.2 | 1267.76 | 1299.29 | protein |
| SEQ ID NO: 6370 | Nga01541.1 | 738.35 | 652.27 | ---NA--- |
| SEQ ID NO: 6371 | Nga04044 | 221.40 | 279.80 | atp-citrate synthase |
| SEQ ID NO: 6372 | Nga20541 | 271.13 | 226.31 | predicted protein [Thalassiosira pseudonana CCMP1335] |
| SEQ ID NO: 6373 | Nga20463 | 149.35 | 189.92 | ---NA--- |
| SEQ ID NO: 6374 | Nga21144 | 220.53 | 240.38 | all-trans-retinol -reductase-like |
| SEQ ID NO: 6375 | Nga06648 | 1432.49 | 1654.41 | aara_dicdi ame: full=protein aardvark ame: full=suppressor of amib protein 16 |
| SEQ ID NO: 6376 | Nga21240 | 231.40 | 153.98 | wd repeat-containing protein 59 |
| SEQ ID NO: 6377 | Nga06652 | 242.35 | 204.49 | protein |
| SEQ ID NO: 6378 | Nga01591.02 | 93.20 | 98.23 | vacuolar membrane protein |
| SEQ ID NO: 6379 | Nga21123 | 194.56 | 166.56 | protein |
| SEQ ID NO: 6380 | Nga06650 | 814.72 | 820.07 | ras-related protein rab-22a |
| SEQ ID NO: 6381 | Nga06651 | 1937.24 | 2038.05 | predicted protein [Thalassiosira pseudonana CCMP1335] |
| SEQ ID NO: 6382 | Nga06649 | 757.74 | 643.49 | integral membrane protein gpr180-like |
| SEQ ID NO: 6383 | Nga00719 | 1790.17 | 1911.41 | aspartate-semialdehyde dehydrogenase |
| SEQ ID NO: 6384 | Nga20795 | 566.49 | 620.66 | endothelin-converting enzyme 2 |
| SEQ ID NO: 6385 | Nga00730 | 956.35 | 1017.04 | elongation factor |
| SEQ ID NO: 6386 | Nga00727 | 402.50 | 321.46 | mitochondrial carrier family |
| SEQ ID NO: 6387 | Nga00726 | 520.54 | 579.21 | elongation factor 2 |

FIGURE 24 CW

| # | Nga model | +N rpkb | -N rpkb | GO |
|---|---|---|---|---|
| SEQ ID NO: 6388 | Nga00720 | 1057.08 | 906.89 | hypothetical protein PITG_19672 [Albugo laibachii Nc14] |
| SEQ ID NO: 6389 | Nga20017 | 676.21 | 696.71 | conserved unknown protein [Ectocarpus siliculosus] |
| SEQ ID NO: 6390 | Nga00722 | 931.69 | 889.71 | protein |
| SEQ ID NO: 6391 | Nga21249 | 334.15 | 417.86 | conserved unknown protein (Partial) [Ectocarpus siliculosus] |
| SEQ ID NO: 6392 | Nga00725 | 158.83 | 219.15 | conserved hypothetical protein [Phytophthora infestans T30-4] |
| SEQ ID NO: 6393 | Nga00715 | 6589.02 | 6689.63 | snf7 family protein |
| SEQ ID NO: 6394 | Nga00713 | 1355.48 | 2633.31 | guanine deaminase |
| SEQ ID NO: 6395 | Nga00712.01 | 1387.79 | 1547.99 | ---NA--- |
| SEQ ID NO: 6396 | Nga00718 | 3675.62 | 3501.73 | nuclear cap-binding protein subunit 2 |
| SEQ ID NO: 6397 | Nga00721 | 500.00 | 422.91 | ---NA--- |
| SEQ ID NO: 6398 | Nga00714 | 10613.76 | 10849.80 | isocitrate dehydrogenase |
| SEQ ID NO: 6399 | Nga00717 | 164.81 | 132.69 | cytohesin-1 isoform 2 |
| SEQ ID NO: 6400 | Nga20430 | 126.87 | 113.17 | ---NA--- |
| SEQ ID NO: 6401 | Nga00729 | 1094.19 | 1099.84 | 50s ribosomal protein l34 |
| SEQ ID NO: 6402 | Nga00723 | 585.90 | 710.29 | mediator of rna polymerase ii transcription subunit 14 |
| SEQ ID NO: 6403 | Nga00724 | 306.56 | 389.08 | ---NA--- |
| SEQ ID NO: 6404 | Nga00716 | 2835.95 | 2836.94 | ---NA--- |
| SEQ ID NO: 6405 | Nga00939.1 | 1862.83 | 2384.66 | protein |
| SEQ ID NO: 6406 | Nga00941 | 786.93 | 706.58 | trna rrna methyltransferase |
| SEQ ID NO: 6407 | Nga00942 | 2361.64 | 2083.58 | haloacid dehalogenase-like hydrolase domain-containing protein |
| SEQ ID NO: 6408 | Nga00940 | 401.71 | 300.24 | unc-50 family protein |
| SEQ ID NO: 6409 | Nga01651 | 1432.46 | 1310.09 | proteasome subunit alpha |
| SEQ ID NO: 6410 | Nga01650 | 98.90 | 92.53 | rad54-like protein |
| SEQ ID NO: 6411 | Nga20810 | 143.76 | 176.34 | dna helicase aaa atpase |
| SEQ ID NO: 6412 | Nga03967 | 97.83 | 113.82 | ---NA--- |
| SEQ ID NO: 6413 | Nga03968 | 214.29 | 165.80 | ---NA--- |
| SEQ ID NO: 6414 | Nga01057.01 | 382.95 | 325.41 | protein |
| SEQ ID NO: 6415 | Nga01058 | 510.97 | 495.55 | notchless protein homolog 1 |
| SEQ ID NO: 6416 | Nga01060 | 169.96 | 184.11 | beta-lactamase-like protein |
| SEQ ID NO: 6417 | Nga05713 | 431.57 | 502.01 | predicted protein [Phaeodactylum tricornutum CCAP 1055/1] |
| SEQ ID NO: 6418 | Nga05720 | 1510.74 | 1313.32 | nucleotide-sensitive chloride conductance regulator family protein |
| SEQ ID NO: 6419 | Nga05712.1 | 588.89 | 489.93 | transmembrane protein 30a |
| SEQ ID NO: 6420 | Nga05715 | 865.64 | 808.88 | zinc matrin type 2 |
| SEQ ID NO: 6421 | Nga05719 | 131.08 | 155.48 | set and mynd domain containing 3 |
| SEQ ID NO: 6422 | Nga05710 | 669.16 | 546.35 | hypothetical protein AURANDRAFT_70357 [Aureococcus anophagefferens] |
| SEQ ID NO: 6423 | Nga05711 | 1342.40 | 1381.25 | serine threonine protein phosphatase |
| SEQ ID NO: 6424 | Nga05714 | 684.50 | 754.85 | ---NA--- |
| SEQ ID NO: 6425 | Nga00800.02 | 375.00 | 371.91 | metal ion transporter family |
| SEQ ID NO: 6426 | Nga05718 | 146.84 | 159.93 | protein ilityhia |
| SEQ ID NO: 6427 | Nga05709 | 512.78 | 391.22 | ---NA--- |
| SEQ ID NO: 6428 | Nga05716 | 426.14 | 457.50 | ankyrin unc44 |
| SEQ ID NO: 6429 | Nga02465.01 | 2351.72 | 2235.21 | ---NA--- |
| SEQ ID NO: 6430 | Nga02473 | 355.34 | 362.33 | general transcription factor 3c polypeptide 5 |
| SEQ ID NO: 6431 | Nga02476.01 | 1954.21 | 1454.23 | response regulator receiver domain-containing protein |
| SEQ ID NO: 6432 | Nga02471 | 312.15 | 201.96 | protein |
| SEQ ID NO: 6433 | Nga20591 | 108.28 | 151.79 | glutathione s-transferase |
| SEQ ID NO: 6434 | Nga21283.1 | 1526.01 | 1092.63 | response regulator receiver domain-containing protein |
| SEQ ID NO: 6435 | Nga02475 | 44.12 | 55.75 | ---NA--- |
| SEQ ID NO: 6436 | Nga04047.2 | 2199.20 | 1649.65 | anion:sodium symporter |
| SEQ ID NO: 6437 | Nga02464 | 5103.83 | 4208.76 | heat shock protein 90 |
| SEQ ID NO: 6438 | Nga02467.01 | 721.70 | 742.59 | 50s ribosomal protein l25 general stress protein ctc |
| SEQ ID NO: 6439 | Nga02469 | 998.18 | 941.56 | protein |
| SEQ ID NO: 6440 | Nga02472 | 55.94 | 39.84 | kinesin-like protein |
| SEQ ID NO: 6441 | Nga20500 | 197.18 | 208.51 | anaphase promoting complex subunit 4 |
| SEQ ID NO: 6442 | Nga02470 | 942.47 | 1041.08 | predicted protein [Thalassiosira pseudonana CCMP1335] |
| SEQ ID NO: 6443 | Nga02478 | 1076.61 | 1313.28 | novel protein vertebrate fuse-binding protein-interacting repressor |
| SEQ ID NO: 6444 | Nga02466 | 1740.09 | 2158.98 | nadh-dependent fumarate reductase |
| SEQ ID NO: 6445 | Nga02474 | 9615.69 | 10326.79 | ---NA--- |
| SEQ ID NO: 6446 | Nga01624 | 1559.28 | 1289.22 | glutaredoxin-like protein |
| SEQ ID NO: 6447 | Nga20885 | 1682.57 | 1421.12 | grx5 |
| SEQ ID NO: 6448 | Nga01626 | 267.91 | 319.69 | ---NA--- |
| SEQ ID NO: 6449 | Nga01623 | 899.33 | 703.38 | hypothetical protein AURANDRAFT_61437 [Aureococcus anophagefferens] |

FIGURE 24 CX

| # | Nga model | +N rpkb | -N rpkb | GO |
|---|---|---|---|---|
| SEQ ID NO: 6450 | Nga01625 | 96.59 | 117.71 | transmembrane protein |
| SEQ ID NO: 6451 | Nga01627 | 663.38 | 741.48 | ---NA--- |
| SEQ ID NO: 6452 | Nga01628 | 484.08 | 499.84 | histone methylation dot1 family protein |
| SEQ ID NO: 6453 | Nga06231 | 781.30 | 787.51 | stress-inducible protein |
| SEQ ID NO: 6454 | Nga06230 | 282.95 | 197.57 | protein |
| SEQ ID NO: 6455 | Nga01122 | 389.79 | 365.19 | hsp90 chloroplast targeted |
| SEQ ID NO: 6456 | Nga01123 | 272.47 | 213.00 | ---NA--- |
| SEQ ID NO: 6457 | Nga03777 | 366.67 | 482.60 | protein |
| SEQ ID NO: 6458 | Nga03779 | 50.40 | 70.73 | gcn5-related n-acetyltransferase |
| SEQ ID NO: 6459 | Nga03782 | 822.82 | 847.69 | ---NA--- |
| SEQ ID NO: 6460 | Nga03778 | 1017.69 | 1157.82 | rrm-containing rna-binding |
| SEQ ID NO: 6461 | Nga07071.2 | 398.76 | 385.02 | tpr domain-containing protein |
| SEQ ID NO: 6462 | Nga00532.02 | 423.08 | 522.87 | sdhfb_dicdi ame: full=succinate dehydrogenase assembly factor 1 homolog mitochondrial short=sdh assembly factor 1b |
| SEQ ID NO: 6463 | Nga01006 | 569.73 | 632.31 | protein |
| SEQ ID NO: 6464 | Nga01005 | 702.11 | 782.49 | homeodomain transcription factor 2 |
| SEQ ID NO: 6465 | Nga01003 | 1626.04 | 2396.14 | conserved unknown protein [Ectocarpus siliculosus] |
| SEQ ID NO: 6466 | Nga01004 | 6757.16 | 7228.41 | atpase |
| SEQ ID NO: 6467 | Nga01008 | 323.02 | 279.18 | abhydrolase domain-containing protein |
| SEQ ID NO: 6468 | Nga01002 | 29606.59 | 24538.77 | rieske (2fe-2s) region protein |
| SEQ ID NO: 6469 | Nga01007 | 183.29 | 227.74 | ---NA--- |
| SEQ ID NO: 6470 | Nga21214 | 311.59 | 300.97 | t-complex protein 10a-like |
| SEQ ID NO: 6471 | Nga01100.1 | 489.92 | 115.80 | poly -binding protein 3 isoform 2 |
| SEQ ID NO: 6472 | Nga01103.1 | 1040.00 | 1014.42 | endoribonuclease l-psp |
| SEQ ID NO: 6473 | Nga21211 | 469.91 | 451.35 | tubulin binding cofactor c domain-containing protein |
| SEQ ID NO: 6474 | Nga01104.01 | 171.35 | 145.49 | exocyst complex component 7 |
| SEQ ID NO: 6475 | Nga01101 | 3065.34 | 3258.10 | conserved unknown protein [Ectocarpus siliculosus] |
| SEQ ID NO: 6476 | Nga01102 | 1322.10 | 1161.77 | protein |
| SEQ ID NO: 6477 | Nga01105 | 0.00 | 7.33 | adenylate and guanylate cyclase catalytic domain protein |
| SEQ ID NO: 6478 | Nga05819.1 | 1067.43 | 958.50 | cdp-diacylglycerol--glycerol-3-phosphate 3-phosphatidyltransferase |
| SEQ ID NO: 6479 | Nga04657.02 | 553.42 | 557.82 | vesicle transport v- |
| SEQ ID NO: 6480 | Nga20292 | 509.57 | 578.44 | wd40 repeat-containing protein |
| SEQ ID NO: 6481 | Nga05820 | 2970.95 | 4120.54 | protein |
| SEQ ID NO: 6482 | Nga05824 | 491.28 | 669.94 | aminoglycoside phosphotransferase |
| SEQ ID NO: 6483 | Nga20659 | 405.09 | 549.04 | ---NA--- |
| SEQ ID NO: 6484 | Nga05821 | 10989.89 | 10063.12 | calmodulin |
| SEQ ID NO: 6485 | Nga05822 | 281.52 | 300.19 | conserved c2h2 zinc finger protein |
| SEQ ID NO: 6486 | Nga05817 | 377.84 | 322.71 | microcystin synthetase-associated thioesterase |
| SEQ ID NO: 6487 | Nga05818.1 | 586.84 | 778.60 | trehalose-phosphate synthase |
| SEQ ID NO: 6488 | Nga00915 | 767.68 | 827.93 | replication protein a 32 kda |
| SEQ ID NO: 6489 | Nga00917 | 820.48 | 973.68 | gtp-binding protein 1 |
| SEQ ID NO: 6490 | Nga20393 | 128.10 | 89.52 | helicase-like protein |
| SEQ ID NO: 6491 | Nga00916 | 822.41 | 926.09 | vacuolar protein sorting-associated protein 13 family protein |
| SEQ ID NO: 6492 | Nga20041 | 411.35 | 515.69 | tectonin beta-propeller repeat-containing protein 1-like |
| SEQ ID NO: 6493 | Nga20770 | 183.06 | 268.19 | conserved unknown protein [Ectocarpus siliculosus] |
| SEQ ID NO: 6494 | Nga20394 | 152.94 | 223.02 | protein |
| SEQ ID NO: 6495 | Nga20268 | 198.99 | 223.79 | vacuolar protein sorting-associated protein vps13 |
| SEQ ID NO: 6496 | Nga00913 | 1169.71 | 1219.71 | conserved hypothetical protein |
| SEQ ID NO: 6497 | Nga00914 | 94.71 | 111.01 | dead deah box rna |
| SEQ ID NO: 6498 | Nga01330 | 107.20 | 148.64 | protein |
| SEQ ID NO: 6499 | Nga01331.1 | 956.06 | 908.09 | nad-dependent epimerase dehydratase |
| SEQ ID NO: 6500 | Nga01332 | 172.26 | 179.02 | ---NA--- |
| SEQ ID NO: 6501 | Nga20592 | 138.76 | 347.26 | alpha-galactosidase |
| SEQ ID NO: 6502 | Nga21156 | 211.45 | 238.60 | alpha-galactosidase |
| SEQ ID NO: 6503 | Nga05245 | 710.47 | 861.55 | expressed unknown protein [Ectocarpus siliculosus] |
| SEQ ID NO: 6504 | Nga05247 | 742.08 | 649.45 | protein |
| SEQ ID NO: 6505 | Nga05248 | 367.87 | 485.33 | phosphatidylinositide phosphatase sac1 |
| SEQ ID NO: 6506 | Nga05246 | 1599.20 | 1774.27 | protein |
| SEQ ID NO: 6507 | Nga05249 | 894.61 | 1123.06 | ---NA--- |
| SEQ ID NO: 6508 | Nga05244 | 618.28 | 650.33 | uncharacterized protein c7orf50-like |
| SEQ ID NO: 6509 | Nga00968.02 | 54.57 | 59.11 | hypothetical protein PTSG_07517 [Salpingoeca sp. ATCC 50818] |
| SEQ ID NO: 6510 | Nga06291 | 1186.34 | 1368.81 | radical sam domain protein |
| SEQ ID NO: 6511 | Nga00967.02 | 484.45 | 507.08 | dna polymerase beta |
| SEQ ID NO: 6512 | Nga02278.2 | 881.63 | 1017.11 | fe-only |

FIGURE 24 CY

| # | Nga model | +N rpkb | -N rpkb | GO |
|---|---|---|---|---|
| SEQ ID NO: 6513 | Nga00985.1 | 231.15 | 248.73 | atpase type 13a1 |
| SEQ ID NO: 6514 | Nga00982.01 | 2877.19 | 2455.92 | ---NA--- |
| SEQ ID NO: 6515 | Nga20397 | 343.09 | 334.04 | duf89 fructose- -bisphosphatase |
| SEQ ID NO: 6516 | Nga00984 | 1098.97 | 1337.96 | protein |
| SEQ ID NO: 6517 | Nga00983.01 | 1637.10 | 1510.56 | peptidyl-prolyl cis-trans isomerase |
| SEQ ID NO: 6518 | Nga00981 | 331.99 | 549.75 | ---NA--- |
| SEQ ID NO: 6519 | Nga01117.02 | 2200.70 | 2327.30 | dual specificity protein phosphatase 10 |
| SEQ ID NO: 6520 | Nga01282 | 72.46 | 23.55 | ---NA--- |
| SEQ ID NO: 6521 | Nga01276 | 900.56 | 563.62 | ---NA--- |
| SEQ ID NO: 6522 | Nga01281 | 143.13 | 108.12 | ---NA--- |
| SEQ ID NO: 6523 | Nga01277 | 125.64 | 180.23 | protein |
| SEQ ID NO: 6524 | Nga21014 | 229.21 | 241.70 | peroxisome biogenesis factor 10 |
| SEQ ID NO: 6525 | Nga01279 | 175.36 | 220.75 | ring-1 like protein |
| SEQ ID NO: 6526 | Nga01280 | 153.69 | 169.85 | predicted protein [Thalassiosira pseudonana CCMP1335] |
| SEQ ID NO: 6527 | Nga20419.1 | 187.56 | 171.67 | protein |
| SEQ ID NO: 6528 | Nga20486.1 | 153.35 | 110.75 | ---NA--- |
| SEQ ID NO: 6529 | Nga03710 | 214.17 | 228.77 | protein |
| SEQ ID NO: 6530 | Nga20907 | 112.78 | 138.46 | ---NA--- |
| SEQ ID NO: 6531 | Nga02439.02 | 217.65 | 364.79 | ---NA--- |
| SEQ ID NO: 6532 | Nga00900 | 193.20 | 284.44 | protein |
| SEQ ID NO: 6533 | Nga00902 | 567.90 | 511.53 | predicted protein [Thalassiosira pseudonana CCMP1335] |
| SEQ ID NO: 6534 | Nga00899 | 1393.10 | 1060.82 | malonyl- :acp transacylase |
| SEQ ID NO: 6535 | Nga00894 | 520.00 | 416.27 | protein |
| SEQ ID NO: 6536 | Nga00897 | 763.53 | 736.89 | nitrite transporter nar1 |
| SEQ ID NO: 6537 | Nga00896 | 336.11 | 286.62 | mitochondrial matrix protein frataxin |
| SEQ ID NO: 6538 | Nga00903 | 944.14 | 804.13 | unknown [Picea sitchensis] |
| SEQ ID NO: 6539 | Nga00895 | 535.47 | 674.51 | abc transporter atp-binding protein |
| SEQ ID NO: 6540 | Nga00901 | 617.30 | 685.62 | hypothetical protein AURANDRAFT_70357 [Aureococcus anophagefferens] |
| SEQ ID NO: 6541 | Nga00898 | 327.00 | 267.38 | upf0551 protein mitochondrial-like |
| SEQ ID NO: 6542 | Nga21016 | 361.43 | 331.47 | nad-dependent epimerase dehydratase |
| SEQ ID NO: 6543 | Nga02272 | 93.66 | 74.60 | PREDICTED: hypothetical protein, partial [Strongylocentrotus purpuratus] |
| SEQ ID NO: 6544 | Nga02271 | 76.92 | 87.95 | ---NA--- |
| SEQ ID NO: 6545 | Nga01748 | 333.74 | 251.28 | potential abc transporter |
| SEQ ID NO: 6546 | Nga01747 | 4701.88 | 5746.79 | thiamine biosynthesis protein |
| SEQ ID NO: 6547 | Nga21175 | 238.37 | 233.02 | dual specificity protein |
| SEQ ID NO: 6548 | Nga01750 | 213.74 | 140.57 | ---NA--- |
| SEQ ID NO: 6549 | Nga01749 | 689.83 | 682.73 | ---NA--- |
| SEQ ID NO: 6550 | Nga02129 | 16.97 | 19.57 | outer dynein arm heavy chain beta |
| SEQ ID NO: 6551 | Nga02130 | 7.75 | 2.80 | flagellar outer dynein arm heavy chain beta |
| SEQ ID NO: 6552 | Nga04665.2 | 487.34 | 523.33 | dna-directed rna polymerases i and iii subunit rpac1 |
| SEQ ID NO: 6553 | Nga01918.01 | 520.47 | 576.46 | protein |
| SEQ ID NO: 6554 | Nga20936.1 | 4845.53 | 5109.62 | dynamin-like protein |
| SEQ ID NO: 6555 | Nga01916.01 | 4258.00 | 4114.80 | dynamin-like protein |
| SEQ ID NO: 6556 | Nga01917.01 | 1146.85 | 805.48 | dna-directed rna polymerases and iii subunit rpabc2 |
| SEQ ID NO: 6557 | Nga21018 | 107.87 | 143.62 | ---NA--- |
| SEQ ID NO: 6558 | Nga05804 | 201.75 | 214.98 | probable methyltransferase c20orf7 mitochondrial precursor |
| SEQ ID NO: 6559 | Nga05803 | 522.93 | 459.57 | protein |
| SEQ ID NO: 6560 | Nga20278 | 199.82 | 273.92 | trna pseudouridine synthase |
| SEQ ID NO: 6561 | Nga05805 | 1229.66 | 1724.36 | ---NA--- |
| SEQ ID NO: 6562 | Nga05807 | 959.24 | 1009.64 | ---NA--- |
| SEQ ID NO: 6563 | Nga05806 | 174.45 | 209.22 | ---NA--- |
| SEQ ID NO: 6564 | Nga00095 | 682.17 | 626.99 | tri-functional histidine biosynthesis protein |
| SEQ ID NO: 6565 | Nga00096 | 925.90 | 698.24 | udp-sugar transporter ust74c |
| SEQ ID NO: 6566 | Nga20768 | 875.11 | 885.58 | elongator complex protein 3 |
| SEQ ID NO: 6567 | Nga20938 | 569.32 | 517.92 | alpha beta hydrolase fold protein |
| SEQ ID NO: 6568 | Nga00113 | 185.68 | 166.65 | glutamine synthetase |
| SEQ ID NO: 6569 | Nga00103.01 | 2716.83 | 3062.52 | protein |
| SEQ ID NO: 6570 | Nga00091 | 1648.13 | 1942.21 | p-type atpase |
| SEQ ID NO: 6571 | Nga00110 | 626.43 | 663.55 | proteasome assembly chaperone 4-like |
| SEQ ID NO: 6572 | Nga00098 | 587.77 | 424.46 | dolichol-phosphate mannosyltransferase |
| SEQ ID NO: 6573 | Nga20373 | 495.11 | 455.38 | dna-directed rna polymerase iii subunit rpc2 |
| SEQ ID NO: 6574 | Nga00099.01 | 257.29 | 207.31 | protein |

FIGURE 24 CZ

| # | Nga model | +N rpkb | -N rpkb | GO |
|---|---|---|---|---|
| SEQ ID NO: 6575 | Nga00101 | 6070.18 | 6877.83 | elongation factor 2 |
| SEQ ID NO: 6576 | Nga00105 | 2736.60 | 3078.00 | mitochondrial processing peptidase |
| SEQ ID NO: 6577 | Nga00107 | 6547.31 | 4853.77 | ---NA--- |
| SEQ ID NO: 6578 | Nga00104 | 857.41 | 1046.65 | protein |
| SEQ ID NO: 6579 | Nga00094 | 517.51 | 378.09 | nicotinate phosphoribosyltransferase |
| SEQ ID NO: 6580 | Nga00112 | 308.14 | 233.02 | ---NA--- |
| SEQ ID NO: 6581 | Nga00111 | 3121.00 | 2480.56 | conserved hypothetical protein [Phytophthora infestans T30-4] |
| SEQ ID NO: 6582 | Nga00106 | 418.80 | 408.69 | small-conductance mechanosensitive channel |
| SEQ ID NO: 6583 | Nga00092 | 6991.55 | 7148.71 | heat shock protein 70 |
| SEQ ID NO: 6584 | Nga00100 | 1399.88 | 1333.52 | cytochrome p450 |
| SEQ ID NO: 6585 | Nga00109 | 381.47 | 426.43 | alpha-galactosidase |
| SEQ ID NO: 6586 | Nga00102 | 865.36 | 967.38 | protein |
| SEQ ID NO: 6587 | Nga00108 | 2652.13 | 2543.30 | ormdl family protein |
| SEQ ID NO: 6588 | Nga00097 | 1684.50 | 2533.38 | ngdn protein |
| SEQ ID NO: 6589 | Nga00093 | 805.18 | 738.63 | protein |
| SEQ ID NO: 6590 | Nga02035 | 342.83 | 292.52 | dolichyl-phosphate beta-glucosyltransferase isoform 1 |
| SEQ ID NO: 6591 | Nga01784.02 | 451.68 | 369.62 | dna-directed rna polymerase ii kda polypeptide |
| SEQ ID NO: 6592 | Nga01787.02 | 325.16 | 362.85 | charged multivesicular body protein 3 |
| SEQ ID NO: 6593 | Nga20075.1 | 420.11 | 497.58 | beta-lactamase domain protein |
| SEQ ID NO: 6594 | Nga01681.01 | 1100.15 | 1061.04 | rab18 -family small gtpase |
| SEQ ID NO: 6595 | Nga01682.01 | 481.50 | 549.59 | ---NA--- |
| SEQ ID NO: 6596 | Nga01684.01 | 424.39 | 547.78 | glucosamine-6-phosphate isomerase |
| SEQ ID NO: 6597 | Nga20571 | 131.34 | 229.63 | conserved unknown protein [Ectocarpus siliculosus] |
| SEQ ID NO: 6598 | Nga20202 | 214.87 | 256.32 | predicted protein [Thalassiosira pseudonana CCMP1335] |
| SEQ ID NO: 6599 | Nga01683 | 1010.46 | 1102.75 | urate oxidase |
| SEQ ID NO: 6600 | Nga06764 | 35.26 | 59.02 | protein |
| SEQ ID NO: 6601 | Nga06763 | 204.51 | 297.75 | ---NA--- |
| SEQ ID NO: 6602 | Nga06765 | 350.17 | 248.01 | ---NA--- |
| SEQ ID NO: 6603 | Nga06762 | 530.82 | 557.77 | mitogen-activated protein kinase kinase 2 |
| SEQ ID NO: 6604 | Nga06761 | 259.85 | 298.82 | protein |
| SEQ ID NO: 6605 | Nga01657 | 595.40 | 567.76 | protein |
| SEQ ID NO: 6606 | Nga20498.1 | 399.18 | 472.25 | ---NA--- |
| SEQ ID NO: 6607 | Nga06223 | 900.15 | 988.70 | periplasmic beta-glucosidase |
| SEQ ID NO: 6608 | Nga06221 | 525.33 | 651.36 | protein |
| SEQ ID NO: 6609 | Nga06220 | 1044.94 | 753.26 | protein |
| SEQ ID NO: 6610 | Nga06224 | 346.01 | 354.21 | tb2 dp1 hva22 family integral membrane protein that may be involved in membrane 3x transmembrane domains |
| SEQ ID NO: 6611 | Nga06219 | 786.09 | 735.67 | mitochondrial carrier |
| SEQ ID NO: 6612 | Nga06222 | 384.71 | 471.44 | tetratricopeptide repeat domain-containing protein |
| SEQ ID NO: 6613 | Nga20466 | 147.77 | 208.46 | g patch domain-containing protein 1 |
| SEQ ID NO: 6614 | Nga20317 | 133.48 | 163.24 | kif2a protein |
| SEQ ID NO: 6615 | Nga21061 | 144.58 | 172.27 | kinesin-like protein |
| SEQ ID NO: 6616 | Nga03575.01 | 352.24 | 224.19 | protein |
| SEQ ID NO: 6617 | Nga03574.01 | 344.22 | 390.16 | protein |
| SEQ ID NO: 6618 | Nga03570.2 | 262.11 | 255.67 | ---NA--- |
| SEQ ID NO: 6619 | Nga03576.01 | 333.33 | 350.46 | 60s ribosome subunit biogenesis protein nip7 homolog |
| SEQ ID NO: 6620 | Nga02317.01 | 2491.88 | 2067.26 | expressed unknown protein [Ectocarpus siliculosus] |
| SEQ ID NO: 6621 | Nga02319 | 299.29 | 237.68 | mitochondrial carrier family |
| SEQ ID NO: 6622 | Nga02318 | 22562.94 | 15306.00 | ---NA--- |
| SEQ ID NO: 6623 | Nga20788 | 326.72 | 291.52 | cs-domain containing conserved in apicomplexa |
| SEQ ID NO: 6624 | Nga06079.2 | 539.93 | 483.32 | mitochondrial carrier |
| SEQ ID NO: 6625 | Nga00877 | 1362.81 | 1463.10 | wd repeat protein |
| SEQ ID NO: 6626 | Nga00879 | 637.24 | 675.96 | polynucleotide adenylyltransferase region |
| SEQ ID NO: 6627 | Nga20100 | 1902.74 | 1691.56 | mitochondrial pyruvate dehydrogenase kinase |
| SEQ ID NO: 6628 | Nga00880 | 861.32 | 844.91 | mitochondrial import receptor subunit tom40 |
| SEQ ID NO: 6629 | Nga01848.01 | 817.03 | 538.20 | ---NA--- |
| SEQ ID NO: 6630 | Nga02393 | 568.78 | 670.50 | ---NA--- |
| SEQ ID NO: 6631 | Nga02023 | 9.17 | 11.74 | ---NA--- |
| SEQ ID NO: 6632 | Nga02083 | 304.88 | 332.46 | conserved unknown protein [Ectocarpus siliculosus] |
| SEQ ID NO: 6633 | Nga02086 | 193.35 | 186.08 | potassium channel modulatory factor 1 |
| SEQ ID NO: 6634 | Nga02084 | 862.30 | 784.01 | protein |
| SEQ ID NO: 6635 | Nga02085 | 111.57 | 131.37 | membrane-associated tyrosine- and threonine-specific cdc2-inhibitory kinase |

FIGURE 24 DA

| # | Nga model | +N rpkb | -N rpkb | GO |
|---|---|---|---|---|
| SEQ ID NO: 6636 | Nga20558.1 | 308.61 | 329.47 | b chain snapshots of the rna processing factor scaf8 bound to different phosphorylated forms of the carboxy-terminal domain of rna-polymerase ii |
| SEQ ID NO: 6637 | Nga04892.2 | 449.06 | 410.90 | protein |
| SEQ ID NO: 6638 | Nga01648 | 749.03 | 701.07 | saccharopine dehydrogenase |
| SEQ ID NO: 6639 | Nga05884 | 420.79 | 406.36 | inositol-3-phosphate synthase |
| SEQ ID NO: 6640 | Nga05882 | 287.44 | 354.97 | dead deah box rna |
| SEQ ID NO: 6641 | Nga05883 | 3646.90 | 3205.23 | ras-related protein rab-11b |
| SEQ ID NO: 6642 | Nga05885 | 670.23 | 587.17 | protein |
| SEQ ID NO: 6643 | Nga05881 | 247.02 | 184.02 | ---NA--- |
| SEQ ID NO: 6644 | Nga20188 | 265.60 | 266.04 | rna binding motif protein 19 |
| SEQ ID NO: 6645 | Nga20304 | 169.12 | 284.08 | probable rna-binding protein 19 |
| SEQ ID NO: 6646 | Nga20549 | 131.66 | 88.29 | trna rrna methyltransferase |
| SEQ ID NO: 6647 | Nga03930 | 1183.76 | 1185.08 | conserved unknown protein [Ectocarpus siliculosus] |
| SEQ ID NO: 6648 | Nga03929.01 | 1365.45 | 1483.05 | -dihydroxy-2-butanone 4-phosphate synthase |
| SEQ ID NO: 6649 | Nga03927 | 1448.96 | 1350.55 | atp-dependent clp protease proteolytic subunit |
| SEQ ID NO: 6650 | Nga03928 | 346.33 | 342.21 | tsa family domain-containing protein |
| SEQ ID NO: 6651 | Nga02254 | 420.36 | 336.67 | translation initiation factor if-3 |
| SEQ ID NO: 6652 | Nga02256 | 500.00 | 533.31 | cop9 constitutive photomorphogenic homolog subunit 8 |
| SEQ ID NO: 6653 | Nga02255 | 368.83 | 427.67 | protein |
| SEQ ID NO: 6654 | Nga20661 | 212.67 | 249.98 | aaa atpase domain-containing protein |
| SEQ ID NO: 6655 | Nga02250 | 133.33 | 101.10 | duf647 family protein |
| SEQ ID NO: 6656 | Nga02251 | 287.09 | 158.10 | protein |
| SEQ ID NO: 6657 | Nga03442 | 428.84 | 404.30 | 3 (2) -bisphosphate nucleotidase |
| SEQ ID NO: 6658 | Nga03450 | 4620.38 | 4566.75 | ---NA--- |
| SEQ ID NO: 6659 | Nga20991 | 647.06 | 477.90 | unidentified vitellogenin-linked transcript family member (uvt-5) |
| SEQ ID NO: 6660 | Nga03430.2 | 1044.76 | 980.40 | fkbp-type peptidyl-prolyl cis-trans isomerase |
| SEQ ID NO: 6661 | Nga03444 | 972.38 | 1006.83 | spx domain-containing membrane protein |
| SEQ ID NO: 6662 | Nga03439 | 21834.08 | 22200.65 | expressed unknown protein [Ectocarpus siliculosus] |
| SEQ ID NO: 6663 | Nga03448 | 636.79 | 601.23 | charged multivesicular body protein 2a |
| SEQ ID NO: 6664 | Nga03449 | 11.01 | 15.72 | mer3 meiotic cross-over helicase |
| SEQ ID NO: 6665 | Nga20869 | 614.26 | 567.07 | hypothetical protein DFA_11952 [Dictyostelium fasciculatum] |
| SEQ ID NO: 6666 | Nga03441 | 637.69 | 552.62 | stress-inducible protein |
| SEQ ID NO: 6667 | Nga03446 | 680.42 | 729.18 | conserved unknown protein [Ectocarpus siliculosus] |
| SEQ ID NO: 6668 | Nga03440 | 2636.40 | 3144.03 | kif1-binding protein homolog |
| SEQ ID NO: 6669 | Nga03447 | 341.43 | 469.45 | arginyl-trna synthetase |
| SEQ ID NO: 6670 | Nga03445 | 1548.15 | 1185.94 | fkbp-type peptidyl-prolyl cis-trans isomerase |
| SEQ ID NO: 6671 | Nga20159 | 558.38 | 601.62 | indoleamine -dioxygenase 2 |
| SEQ ID NO: 6672 | Nga20057 | 194.44 | 215.98 | rio kinase 1 |
| SEQ ID NO: 6673 | Nga20155 | 548.32 | 674.97 | hect e3 ubiquitin |
| SEQ ID NO: 6674 | Nga21054 | 193.66 | 282.25 | hect e3 ubiquitin |
| SEQ ID NO: 6675 | Nga21055 | 156.51 | 306.95 | hect e3 ubiquitin |
| SEQ ID NO: 6676 | Nga21128 | 76.51 | 98.30 | e3 ubiquitin-protein ligase mf123 |
| SEQ ID NO: 6677 | Nga02145 | 461.54 | 621.38 | dis3 mitotic control homolog |
| SEQ ID NO: 6678 | Nga02246 | 698.28 | 680.08 | protein |
| SEQ ID NO: 6679 | Nga02245 | 2954.23 | 3079.94 | heat shock protein hsp90 |
| SEQ ID NO: 6680 | Nga20259 | 121.18 | 139.22 | predicted protein [Phaeodactylum tricornutum CCAP 1055/1] |
| SEQ ID NO: 6681 | Nga04181 | 84.25 | 79.36 | ---NA--- |
| SEQ ID NO: 6682 | Nga04178 | 3021.12 | 2812.17 | ---NA--- |
| SEQ ID NO: 6683 | Nga04177 | 22890.19 | 11531.01 | light harvesting complex protein |
| SEQ ID NO: 6684 | Nga04180 | 181.97 | 185.14 | guanine nucleotide-binding protein subunit beta-like protein 1 |
| SEQ ID NO: 6685 | Nga04179 | 500.00 | 554.51 | ---NA--- |
| SEQ ID NO: 6686 | Nga07181.2 | 133.99 | 140.87 | glycosyl hydrolase |
| SEQ ID NO: 6687 | Nga00253.1 | 3745.67 | 1601.50 | ---NA--- |
| SEQ ID NO: 6688 | Nga00250 | 128.60 | 134.72 | myotubularin related protein 3 |
| SEQ ID NO: 6689 | Nga00251.01 | 8641.55 | 8947.81 | redoxin domain protein |
| SEQ ID NO: 6690 | Nga00255 | 263.31 | 251.84 | ---NA--- |
| SEQ ID NO: 6691 | Nga00258.01 | 3.62 | 27.47 | ---NA--- |
| SEQ ID NO: 6692 | Nga00254 | 435.24 | 517.47 | ubiquitin-like activating enzyme |
| SEQ ID NO: 6693 | Nga00256 | 753.44 | 1123.52 | ---NA--- |
| SEQ ID NO: 6694 | Nga20850 | 343.40 | 371.98 | ---NA--- |
| SEQ ID NO: 6695 | Nga00257.1 | 709.01 | 743.00 | ---NA--- |
| SEQ ID NO: 6696 | Nga00971.1 | 204.50 | 216.85 | glutamine-fructose-6-phosphate transaminase |
| SEQ ID NO: 6697 | Nga00970.01 | 3093.06 | 2547.48 | glutaredoxin type i |

FIGURE 24 DB

| # | Nga model | +N rpkb | -N rpkb | GO |
|---|---|---|---|---|
| SEQ ID NO: 6698 | Nga00974.1 | 69.99 | 107.07 | guanine deaminase |
| SEQ ID NO: 6699 | Nga00972 | 163.06 | 171.88 | dna mismatch repair protein |
| SEQ ID NO: 6700 | Nga00973 | 167.06 | 188.73 | ---NA--- |
| SEQ ID NO: 6701 | Nga06287.2 | 265.54 | 321.91 | ---NA--- |
| SEQ ID NO: 6702 | Nga04422 | 1722.66 | 1268.64 | ribonuclease p |
| SEQ ID NO: 6703 | Nga04425.01 | 316.04 | 226.10 | ---NA--- |
| SEQ ID NO: 6704 | Nga04423.1 | 220.40 | 345.89 | protein |
| SEQ ID NO: 6705 | Nga04426 | 298.67 | 381.30 | protein |
| SEQ ID NO: 6706 | Nga04424 | 133.62 | 122.95 | ---NA--- |
| SEQ ID NO: 6707 | Nga03065.02 | 525.64 | 552.61 | adenosine 3 -phospho 5 -phosphosulfate transporter 2 |
| SEQ ID NO: 6708 | Nga03066.02 | 1130.43 | 1118.00 | coiled-coil domain 6-like protein |
| SEQ ID NO: 6709 | Nga06389.1 | 645.23 | 635.62 | fact complex subunit |
| SEQ ID NO: 6710 | Nga06392 | 8319.44 | 8728.20 | 60s ribosomal protein l24 |
| SEQ ID NO: 6711 | Nga06393 | 864.46 | 888.30 | casein kinase ii beta subunit |
| SEQ ID NO: 6712 | Nga06391 | 742.29 | 654.48 | conserved unknown protein [Ectocarpus siliculosus] |
| SEQ ID NO: 6713 | Nga06388 | 2111.84 | 2020.37 | hig1 domain family member 2a |
| SEQ ID NO: 6714 | Nga20319 | 92.50 | 136.11 | protein |
| SEQ ID NO: 6715 | Nga05206 | 72.46 | 125.59 | protein |
| SEQ ID NO: 6716 | Nga05205 | 42.12 | 63.49 | protein |
| SEQ ID NO: 6717 | Nga05202 | 674.73 | 612.40 | ras-related gtp-binding protein |
| SEQ ID NO: 6718 | Nga05200 | 485.29 | 524.63 | dihydrolipoamide s-acetyltransferase |
| SEQ ID NO: 6719 | Nga05203 | 286.76 | 310.24 | kinesin heavy chain |
| SEQ ID NO: 6720 | Nga05201 | 44.17 | 67.09 | large subunit gtpase 1 |
| SEQ ID NO: 6721 | Nga05207 | 490.66 | 422.45 | protein |
| SEQ ID NO: 6722 | Nga00939.2 | 1862.83 | 2384.66 | protein |
| SEQ ID NO: 6723 | Nga21096 | 218.99 | 215.28 | protein |
| SEQ ID NO: 6724 | Nga02198.1 | 267.59 | 327.20 | inositol polyphosphate 5-phosphatase ocrl-1 |
| SEQ ID NO: 6725 | Nga04291 | 1502.38 | 1494.22 | choline dehydrogenase |
| SEQ ID NO: 6726 | Nga01807 | 632.52 | 903.10 | ribonuclease ii |
| SEQ ID NO: 6727 | Nga21216 | 473.56 | 580.36 | weakly cyanobacterial exoribonuclease ii |
| SEQ ID NO: 6728 | Nga01806 | 533.33 | 546.28 | protein |
| SEQ ID NO: 6729 | Nga04563 | 144.74 | 204.29 | protein |
| SEQ ID NO: 6730 | Nga04562 | 861.68 | 787.25 | ---NA--- |
| SEQ ID NO: 6731 | Nga04561 | 1605.70 | 1807.34 | hypothetical protein PHATRDRAFT_50624 [Phaeodactylum tricornutum CCAP 1055/1] |
| SEQ ID NO: 6732 | Nga04620 | 7112.40 | 10995.86 | ---NA--- |
| SEQ ID NO: 6733 | Nga04619 | 1618.76 | 1415.91 | enzyme of the cupin superfamily |
| SEQ ID NO: 6734 | Nga04621 | 622.93 | 593.09 | conserved unknown protein [Ectocarpus siliculosus] |
| SEQ ID NO: 6735 | Nga01795.1 | 993.21 | 1478.37 | protein |
| SEQ ID NO: 6736 | Nga21295 | 196.97 | 283.12 | ---NA--- |
| SEQ ID NO: 6737 | Nga01796 | 315.86 | 377.09 | l-serine ammonia-lyase |
| SEQ ID NO: 6738 | Nga20585 | 86.96 | 126.57 | protein |
| SEQ ID NO: 6739 | Nga04216 | 1101.55 | 1037.40 | ---NA--- |
| SEQ ID NO: 6740 | Nga04214 | 871.29 | 754.33 | trafficking protein particle complex 1 |
| SEQ ID NO: 6741 | Nga04215 | 772.77 | 785.90 | scavenger receptor class member 2 |
| SEQ ID NO: 6742 | Nga03748 | 339.25 | 320.48 | hypothetical protein CPC735_031960 [Coccidioides posadasii C735 delta SOWgp] |
| SEQ ID NO: 6743 | Nga03746 | 390.69 | 460.49 | patsas cg6618-pa |
| SEQ ID NO: 6744 | Nga03745 | 889.58 | 883.51 | heat shock protein |
| SEQ ID NO: 6745 | Nga03744 | 823.17 | 819.76 | udp-glucose pyrophosphorylase 2 |
| SEQ ID NO: 6746 | Nga03743 | 1469.72 | 1552.70 | cytochrome p450 |
| SEQ ID NO: 6747 | Nga03747 | 1753.83 | 1434.10 | ---NA--- |
| SEQ ID NO: 6748 | Nga03749 | 1667.88 | 1665.70 | c21orf57 isoform a protein |
| SEQ ID NO: 6749 | Nga20329 | 864.25 | 738.90 | scavenger receptor class member 2 |
| SEQ ID NO: 6750 | Nga03864 | 904.28 | 853.57 | ubiquitin-activating enzyme e1 |
| SEQ ID NO: 6751 | Nga03866 | 784.23 | 693.69 | ubiquitin activating enzyme |
| SEQ ID NO: 6752 | Nga03862 | 228.31 | 281.63 | cre-let-765 protein |
| SEQ ID NO: 6753 | Nga04754.2 | 1061.60 | 769.23 | protein |
| SEQ ID NO: 6754 | Nga04691 | 1391.49 | 1525.75 | 2-isopropylmalate synthase |
| SEQ ID NO: 6755 | Nga04690 | 500.98 | 510.94 | thioesterase superfamily member 2 |
| SEQ ID NO: 6756 | Nga04689 | 270.92 | 330.35 | alpha beta-hydrolase domain-containing protein |
| SEQ ID NO: 6757 | Nga04512 | 515.25 | 582.13 | beta-ketoacyl-coa synthase family protein |
| SEQ ID NO: 6758 | Nga21146 | 733.80 | 703.82 | protein containing a histone methylation dot1 motif |
| SEQ ID NO: 6759 | Nga04513.1 | 287.48 | 265.55 | tata-binding protein-associated-factor |

FIGURE 24 DC

| # | Nga model | +N rpkb | -N rpkb | GO |
|---|---|---|---|---|
| SEQ ID NO: 6760 | Nga02205 | 26.40 | 44.69 | heat repeat-containing protein 1 |
| SEQ ID NO: 6761 | Nga04431.2 | 381.55 | 374.70 | upf0598 protein c8orf82 homolog |
| SEQ ID NO: 6762 | Nga02203.01 | 2106.76 | 1790.83 | protein |
| SEQ ID NO: 6763 | Nga06339 | 1009.98 | 970.80 | ribosomal protein s15 |
| SEQ ID NO: 6764 | Nga06340 | 1070.96 | 922.39 | inorganic pyrophosphatase |
| SEQ ID NO: 6765 | Nga06341 | 352.49 | 284.99 | gscfa family protein |
| SEQ ID NO: 6766 | Nga06338 | 433.23 | 391.08 | protein |
| SEQ ID NO: 6767 | Nga06342 | 1996.83 | 2145.83 | ---NA--- |
| SEQ ID NO: 6768 | Nga01694.2 | 1476.45 | 1599.95 | g-rich sequence factor 1 |
| SEQ ID NO: 6769 | Nga05530 | 1671.26 | 2120.48 | cystathionine beta-synthase |
| SEQ ID NO: 6770 | Nga05535 | 238.19 | 218.75 | ---NA--- |
| SEQ ID NO: 6771 | Nga05533 | 841.87 | 932.27 | atlastin-like protein |
| SEQ ID NO: 6772 | Nga05528 | 1259.17 | 1061.78 | beta--endoglucanase |
| SEQ ID NO: 6773 | Nga20021 | 327.92 | 237.75 | o-succinylbenzoic acid synthetase |
| SEQ ID NO: 6774 | Nga20489 | 180.72 | 145.43 | 2-succinyl-6-hydroxy--cyclohexadiene-1-carboxylic acid synthase 2-oxoglutarate decarboxylase |
| SEQ ID NO: 6775 | Nga05531 | 7025.69 | 7907.54 | phosphoglycerate kinase |
| SEQ ID NO: 6776 | Nga20505 | 131.15 | 119.87 | ---NA--- |
| SEQ ID NO: 6777 | Nga20448 | 176.56 | 123.66 | 2-oxoglutarate decarboxylase hydro-lyase magnesium ion binding protein |
| SEQ ID NO: 6778 | Nga20232 | 99.33 | 139.51 | 2-succinyl-6-hydroxy--cyclohexadiene-1-carboxylic acid synthase 2-oxoglutarate decarboxylase |
| SEQ ID NO: 6779 | Nga05532 | 1137.97 | 1301.24 | transcription factor jmjc |
| SEQ ID NO: 6780 | Nga05534 | 5486.73 | 3721.82 | mesencephalic astrocyte-derived neurotrophic factor |
| SEQ ID NO: 6781 | Nga05536 | 306.83 | 249.14 | suppression of tumorigenicity 5 |
| SEQ ID NO: 6782 | Nga05529 | 337.96 | 401.69 | wd-40 repeat expressed |
| SEQ ID NO: 6783 | Nga02228.01 | 59.00 | 67.10 | protein unc-45 homolog a |
| SEQ ID NO: 6784 | Nga02078 | 10.29 | 11.14 | ---NA--- |
| SEQ ID NO: 6785 | Nga02077 | 6529.34 | 5202.50 | ---NA--- |
| SEQ ID NO: 6786 | Nga04614 | 174.04 | 207.70 | ---NA--- |
| SEQ ID NO: 6787 | Nga04615 | 329.60 | 262.31 | protein n-terminal glutamine amidohydrolase-like |
| SEQ ID NO: 6788 | Nga02858 | 1028.49 | 1001.99 | mitochondrial 3-hydroxyisobutyryl- hydrolase |
| SEQ ID NO: 6789 | Nga02866 | 818.99 | 703.08 | abc-1 domain protein |
| SEQ ID NO: 6790 | Nga02863 | 658.57 | 708.41 | aspartate kinase |
| SEQ ID NO: 6791 | Nga02861 | 727.76 | 688.49 | mgc152585 protein |
| SEQ ID NO: 6792 | Nga21164 | 621.69 | 491.59 | nad-dependent epimerase dehydratase |
| SEQ ID NO: 6793 | Nga02868 | 433.64 | 581.74 | protein |
| SEQ ID NO: 6794 | Nga02865 | 447.25 | 458.98 | polyprenyl synthetase |
| SEQ ID NO: 6795 | Nga02869 | 278.10 | 264.10 | ---NA--- |
| SEQ ID NO: 6796 | Nga02859 | 396.80 | 352.73 | ---NA--- |
| SEQ ID NO: 6797 | Nga02867 | 236.92 | 207.26 | mono-or diacylglycerol acyltransferase type 2 |
| SEQ ID NO: 6798 | Nga21132 | 155.89 | 146.22 | ---NA--- |
| SEQ ID NO: 6799 | Nga02864 | 5533.77 | 5630.93 | expressed unknown protein [Ectocarpus siliculosus] |
| SEQ ID NO: 6800 | Nga02860 | 1766.74 | 1475.12 | calmodulin binding |
| SEQ ID NO: 6801 | Nga02862 | 505.85 | 367.41 | predicted protein [Phaeodactylum tricornutum CCAP 1055/1] |
| SEQ ID NO: 6802 | Nga04243 | 552.99 | 563.60 | alpha beta hydrolase fold family |
| SEQ ID NO: 6803 | Nga04681 | 1918.44 | 1813.07 | ---NA--- |
| SEQ ID NO: 6804 | Nga04680 | 146.72 | 216.80 | ---NA--- |
| SEQ ID NO: 6805 | Nga21201.1 | 166.05 | 243.83 | ---NA--- |
| SEQ ID NO: 6806 | Nga20801.1 | 228.97 | 195.72 | pseudouridylate synthase 10 |
| SEQ ID NO: 6807 | Nga20834 | 2049.22 | 1340.01 | glycosyl transferase |
| SEQ ID NO: 6808 | Nga04076 | 1616.28 | 1728.24 | protein |
| SEQ ID NO: 6809 | Nga04078 | 300.00 | 286.28 | ---NA--- |
| SEQ ID NO: 6810 | Nga04077 | 2015.94 | 2421.91 | protein |
| SEQ ID NO: 6811 | Nga20146 | 717.64 | 725.54 | ---NA--- |
| SEQ ID NO: 6812 | Nga04121 | 226.97 | 243.80 | u6 snrna-associated sm-like protein lsm1 |
| SEQ ID NO: 6813 | Nga04119 | 1138.91 | 1101.42 | ring zinc finger-containing protein |
| SEQ ID NO: 6814 | Nga04122 | 196.81 | 197.31 | myosin-like protein |
| SEQ ID NO: 6815 | Nga04120 | 1022.57 | 809.37 | uroporphyrinogen decarboxylase |
| SEQ ID NO: 6816 | Nga20311 | 631.69 | 886.07 | homocysteine s-methyltransferase |
| SEQ ID NO: 6817 | Nga20815 | 594.96 | 457.80 | protein |
| SEQ ID NO: 6818 | Nga01945 | 45.75 | 58.06 | protein |
| SEQ ID NO: 6819 | Nga01946 | 357.27 | 391.00 | ---NA--- |
| SEQ ID NO: 6820 | Nga01944.1 | 114.12 | 138.29 | hect domain and rld 4 |

FIGURE 24 DD

| # | Nga model | +N rpkb | -N rpkb | GO |
|---|---|---|---|---|
| SEQ ID NO: 6821 | Nga01943.01 | 2224.59 | 2333.20 | bromodomain containing protein |
| SEQ ID NO: 6822 | Nga02012 | 1010.86 | 1142.80 | pheophorbide a oxygenase |
| SEQ ID NO: 6823 | Nga20925 | 4983.37 | 4587.03 | pyruvate kinase |
| SEQ ID NO: 6824 | Nga02011 | 439.11 | 618.38 | phosphoinositol transporter |
| SEQ ID NO: 6825 | Nga20982.1 | 177.24 | 154.07 | ---NA--- |
| SEQ ID NO: 6826 | Nga02013.01 | 121.38 | 210.93 | transducin -like 3 |
| SEQ ID NO: 6827 | Nga04940 | 46.80 | 46.99 | ---NA--- |
| SEQ ID NO: 6828 | Nga04939 | 630.43 | 562.55 | atp-dependent bile acid permease |
| SEQ ID NO: 6829 | Nga03590 | 336.31 | 251.47 | rad51-like 3 ( cerevisiae) |
| SEQ ID NO: 6830 | Nga06452 | 880.27 | 1048.81 | hypothetical protein Cpap_3608 [Clostridium papyrosolvens DSM 2782] |
| SEQ ID NO: 6831 | Nga04283.1 | 960.65 | 930.38 | protein |
| SEQ ID NO: 6832 | Nga00948 | 374.38 | 379.94 | cre-duo-3 protein |
| SEQ ID NO: 6833 | Nga00947 | 1311.11 | 1010.22 | phosphate transporter |
| SEQ ID NO: 6834 | Nga00949 | 776.00 | 515.62 | ---NA--- |
| SEQ ID NO: 6835 | Nga04919.2 | 1002.75 | 818.38 | protein nef1 |
| SEQ ID NO: 6836 | Nga02241 | 686.04 | 641.07 | autoinhibited calcium atpase |
| SEQ ID NO: 6837 | Nga01637.01 | 752.43 | 562.65 | meiotic nuclear division protein 1 homolog |
| SEQ ID NO: 6838 | Nga01638 | 263.16 | 215.38 | ---NA--- |
| SEQ ID NO: 6839 | Nga02047 | 359.89 | 449.36 | udp-n-acetylglucosamine pyrophosphorylase |
| SEQ ID NO: 6840 | Nga21300.1 | 473.47 | 530.56 | udp-n-acetylglucosamine pyrophosphorylase |
| SEQ ID NO: 6841 | Nga20745.1 | 496.50 | 545.40 | ---NA--- |
| SEQ ID NO: 6842 | Nga20221.1 | 202.55 | 164.21 | protein |
| SEQ ID NO: 6843 | Nga20167 | 187.24 | 260.26 | protein |
| SEQ ID NO: 6844 | Nga20020 | 1493.06 | 1436.79 | protein |
| SEQ ID NO: 6845 | Nga04992.01 | 200.00 | 256.04 | ---NA--- |
| SEQ ID NO: 6846 | Nga04991.1 | 177.95 | 180.89 | beta-catenin-like protein 1 |
| SEQ ID NO: 6847 | Nga01875 | 137.35 | 148.79 | dna mismatch repair protein |
| SEQ ID NO: 6848 | Nga01876 | 533.58 | 586.08 | conserved hypothetical protein [Neospora caninum Liverpool] |
| SEQ ID NO: 6849 | Nga02063 | 702.94 | 815.55 | 3-mercaptopyruvate sulfurtransferase |
| SEQ ID NO: 6850 | Nga21234 | 575.76 | 587.57 | ---NA--- |
| SEQ ID NO: 6851 | Nga02065 | 658.95 | 588.37 | conserved unknown protein [Ectocarpus siliculosus] |
| SEQ ID NO: 6852 | Nga02064 | 192.74 | 201.29 | regulator of chromosome condensation rcc1 |
| SEQ ID NO: 6853 | Nga20682 | 136.65 | 168.20 | ---NA--- |
| SEQ ID NO: 6854 | Nga05392 | 155.04 | 218.33 | ---NA--- |
| SEQ ID NO: 6855 | Nga05391 | 386.76 | 337.71 | ---NA--- |
| SEQ ID NO: 6856 | Nga05390 | 111.11 | 112.34 | ---NA--- |
| SEQ ID NO: 6857 | Nga00866 | 54.47 | 71.65 | ---NA--- |
| SEQ ID NO: 6858 | Nga00863.01 | 442.76 | 488.39 | deoxyhypusine hydroxylase monooxygenase |
| SEQ ID NO: 6859 | Nga00865.01 | 668.39 | 480.81 | expressed unknown protein [Ectocarpus siliculosus] |
| SEQ ID NO: 6860 | Nga00864.01 | 471.93 | 552.11 | ---NA--- |
| SEQ ID NO: 6861 | Nga00867 | 629.20 | 714.38 | telomerase activating protein est1 |
| SEQ ID NO: 6862 | Nga00868 | 1186.38 | 1207.48 | ---NA--- |
| SEQ ID NO: 6863 | Nga20079 | 318.18 | 388.14 | pre-mrna-splicing factor atp-dependent rna helicase prp16 |
| SEQ ID NO: 6864 | Nga01911 | 790.67 | 862.10 | u2 snrnp auxiliary small subunit |
| SEQ ID NO: 6865 | Nga01913 | 876.79 | 1138.85 | gelsolin precursor |
| SEQ ID NO: 6866 | Nga01912 | 423.12 | 409.97 | atp-binding sub-family c (cftr mrp) member partial |
| SEQ ID NO: 6867 | Nga01915 | 170.21 | 181.31 | atp-binding cassette protein c4-like |
| SEQ ID NO: 6868 | Nga01914 | 742.14 | 651.76 | protein |
| SEQ ID NO: 6869 | Nga03668 | 480.94 | 348.95 | mitochondrial substrate carrier family protein |
| SEQ ID NO: 6870 | Nga03667 | 553.96 | 243.53 | glutathione s-transferase |
| SEQ ID NO: 6871 | Nga20141 | 187.12 | 147.85 | tesmin tso1-like cxc domain-containing protein |
| SEQ ID NO: 6872 | Nga21134 | 209.55 | 281.58 | d111 g-patch domain-containing protein |
| SEQ ID NO: 6873 | Nga03549 | 448.95 | 519.39 | peptidylprolyl isomerase domain and wd repeat-containing protein 1 |
| SEQ ID NO: 6874 | Nga00996.2 | 483.73 | 464.08 | ---NA--- |
| SEQ ID NO: 6875 | Nga00996.1 | 483.73 | 464.08 | ---NA--- |
| SEQ ID NO: 6876 | Nga00997 | 346.72 | 388.12 | ethanolamine-phosphate cytidylyltransferase |
| SEQ ID NO: 6877 | Nga00995 | 301.39 | 241.52 | atp-binding cassette transporter |
| SEQ ID NO: 6878 | Nga20824 | 767.93 | 711.80 | 50s ribosomal protein l20 |
| SEQ ID NO: 6879 | Nga20601 | 374.60 | 130.68 | wd40 repeat-containing protein |
| SEQ ID NO: 6880 | Nga21023 | 169.81 | 143.07 | transducin wd domain-containing protein |
| SEQ ID NO: 6881 | Nga20903 | 242.99 | 172.10 | wd repeat protein pop3 |
| SEQ ID NO: 6882 | Nga20005 | 253.97 | 146.15 | likely wd40 component of tor1 and tor2 kinase complexes |
| SEQ ID NO: 6883 | Nga04245 | 173.61 | 173.02 | rrna-processing protein efg1 |
| SEQ ID NO: 6884 | Nga04628 | 946.08 | 899.66 | aspartyl-trna synthetase |

FIGURE 24 DE

| # | Nga model | +N rpkb | -N rpkb | GO |
|---|---|---|---|---|
| SEQ ID NO: 6885 | Nga04627 | 4467.55 | 3317.63 | iron-sulfur cluster assembly accessory protein |
| SEQ ID NO: 6886 | Nga01966 | 89.55 | 97.01 | ---NA--- |
| SEQ ID NO: 6887 | Nga04812 | 189.49 | 243.88 | et-dependent rrna methyltransferase spb1 |
| SEQ ID NO: 6888 | Nga04811 | 285.46 | 307.30 | choline ethanolamine kinase |
| SEQ ID NO: 6889 | Nga01864 | 655.67 | 613.88 | si:ch211- protein |
| SEQ ID NO: 6890 | Nga21183 | 655.46 | 568.93 | allantoicase |
| SEQ ID NO: 6891 | Nga21254 | 612.83 | 747.72 | allantoicase |
| SEQ ID NO: 6892 | Nga06579 | 163.96 | 130.77 | ubiquinone biosynthesis o-methyltransferase |
| SEQ ID NO: 6893 | Nga06580 | 437.92 | 449.92 | 3-demethylubiquinone-9 3-methyltransferase |
| SEQ ID NO: 6894 | Nga02403.01 | 9336.99 | 8769.55 | atp synthase subunit 5 |
| SEQ ID NO: 6895 | Nga02402 | 714.84 | 776.02 | conserved unknown protein [Ectocarpus siliculosus] |
| SEQ ID NO: 6896 | Nga02400 | 1060.31 | 965.26 | nmra-like family domain-containing protein 1-like |
| SEQ ID NO: 6897 | Nga02401 | 1437.99 | 1413.65 | protein phosphatase inhibitor |
| SEQ ID NO: 6898 | Nga04882 | 294.76 | 174.34 | protein |
| SEQ ID NO: 6899 | Nga04881 | 1811.64 | 2020.86 | 40s ribosomal protein s0 |
| SEQ ID NO: 6900 | Nga04414 | 206.06 | 196.95 | multidrug resistance-associated protein 4 |
| SEQ ID NO: 6901 | Nga04413 | 364.89 | 499.55 | multidrug resistance-associated protein |
| SEQ ID NO: 6902 | Nga04415 | 1576.27 | 1664.63 | multidrug resistance protein 1 (atp-binding cassette c1) |
| SEQ ID NO: 6903 | Nga06550 | 1993.72 | 2009.08 | protein |
| SEQ ID NO: 6904 | Nga06552 | 306.02 | 290.73 | protein |
| SEQ ID NO: 6905 | Nga06557 | 3885.71 | 3511.37 | ---NA--- |
| SEQ ID NO: 6906 | Nga06554 | 517.69 | 536.57 | ---NA--- |
| SEQ ID NO: 6907 | Nga05630.02 | 2018.06 | 2342.56 | apolipoprotein a-i-binding protein precursor |
| SEQ ID NO: 6908 | Nga06553 | 1701.12 | 1631.95 | ---NA--- |
| SEQ ID NO: 6909 | Nga21236 | 118.11 | 174.85 | signal transduction protein |
| SEQ ID NO: 6910 | Nga20280 | 193.62 | 197.40 | ---NA--- |
| SEQ ID NO: 6911 | Nga06551 | 2391.79 | 2542.64 | very long-chain acyl- synthetase isoform 1 |
| SEQ ID NO: 6912 | Nga06556 | 380.39 | 319.77 | sodium hydrogen exchanger |
| SEQ ID NO: 6913 | Nga01695 | 247.23 | 193.99 | ---NA--- |
| SEQ ID NO: 6914 | Nga01696 | 231.23 | 418.55 | mitogen-activated protein kinase kinase 2 |
| SEQ ID NO: 6915 | Nga01697 | 392.23 | 440.18 | hypothetical protein Esi_0538_0008 [Ectocarpus siliculosus] |
| SEQ ID NO: 6916 | Nga02096 | 293.14 | 234.28 | mitochondrial substrate carrier family protein |
| SEQ ID NO: 6917 | Nga02097 | 311.21 | 401.56 | ---NA--- |
| SEQ ID NO: 6918 | Nga05030 | 45.27 | 15.60 | ---NA--- |
| SEQ ID NO: 6919 | Nga05029 | 2119.12 | 2010.26 | hypothetical protein AURANDRAFT_60840 [Aureococcus anophagefferens] |
| SEQ ID NO: 6920 | Nga05699 | 112.61 | 146.38 | ---NA--- |
| SEQ ID NO: 6921 | Nga05695 | 518.38 | 567.50 | 17-beta-hydroxysteroid dehydrogenase type 6 |
| SEQ ID NO: 6922 | Nga05697 | 9107.71 | 3410.01 | light-harvesting protein |
| SEQ ID NO: 6923 | Nga05700 | 5207.57 | 4328.69 | AlNc14C52G4064 [Albugo laibachii Nc14] |
| SEQ ID NO: 6924 | Nga05698 | 189.63 | 247.14 | ---NA--- |
| SEQ ID NO: 6925 | Nga05694 | 1168.80 | 977.96 | protein |
| SEQ ID NO: 6926 | Nga05696 | 149.85 | 99.38 | dna cross-link repair protein snm1 |
| SEQ ID NO: 6927 | Nga05701 | 449.45 | 513.86 | ---NA--- |
| SEQ ID NO: 6928 | Nga03583 | 1066.84 | 1062.55 | gamma-tocopherol methyltransferase |
| SEQ ID NO: 6929 | Nga03581 | 17735.50 | 10534.34 | light harvesting complex protein |
| SEQ ID NO: 6930 | Nga00601.02 | 1153.05 | 973.71 | protein |
| SEQ ID NO: 6931 | Nga21227.1 | 293.56 | 255.08 | hexose-6-phosphate dehydrogenase (glucose 1-dehydrogenase) |
| SEQ ID NO: 6932 | Nga00617.02 | 240.08 | 208.48 | hexose-6-phosphate dehydrogenase (glucose 1-dehydrogenase) |
| SEQ ID NO: 6933 | Nga20007.1 | 373.20 | 415.19 | butyrylcholinesterase precursor |
| SEQ ID NO: 6934 | Nga02226.2 | 439.06 | 526.56 | far upstream binding protein |
| SEQ ID NO: 6935 | Nga21082 | 154.41 | 103.54 | rna helicase like protein |
| SEQ ID NO: 6936 | Nga06084 | 299.08 | 265.46 | ---NA--- |
| SEQ ID NO: 6937 | Nga06085.1 | 358.28 | 384.12 | ---NA--- |
| SEQ ID NO: 6938 | Nga02885.02 | 3260.95 | 3187.80 | small conserved protein |
| SEQ ID NO: 6939 | Nga06088.1 | 397.20 | 587.17 | glycerophosphoryl diester phosphodiesterase |
| SEQ ID NO: 6940 | Nga20442 | 220.62 | 171.45 | ---NA--- |
| SEQ ID NO: 6941 | Nga02227.02 | 599.18 | 542.06 | gluconolactonase |
| SEQ ID NO: 6942 | Nga07222 | 1234.02 | 1415.31 | protein |
| SEQ ID NO: 6943 | Nga02380 | 1231.35 | 1267.32 | major facilitator family transporter |
| SEQ ID NO: 6944 | Nga02381 | 3060.78 | 3375.23 | uncharacterized membrane permease |
| SEQ ID NO: 6945 | Nga04824 | 536.15 | 379.80 | expressed unknown protein [Ectocarpus siliculosus] |
| SEQ ID NO: 6946 | Nga04823 | 2258.29 | 1301.12 | rubredoxin-type fe 4 protein |
| SEQ ID NO: 6947 | Nga04825 | 630.24 | 530.76 | peptide methionine sulfoxide reductase |

FIGURE 24 DF

| # | Nga model | +N rpkb | -N rpkb | GO |
|---|---|---|---|---|
| SEQ ID NO: 6948 | Nga04578 | 279.91 | 305.91 | vacuolar protein sorting-associated protein 33-like protein |
| SEQ ID NO: 6949 | Nga04579 | 1266.41 | 1509.96 | magnesium transporter |
| SEQ ID NO: 6950 | Nga05047 | 98.81 | 166.98 | ---NA--- |
| SEQ ID NO: 6951 | Nga04841 | 361.26 | 407.83 | nucleolar protein 10 |
| SEQ ID NO: 6952 | Nga04842.01 | 173.78 | 173.92 | sulfate transporter |
| SEQ ID NO: 6953 | Nga01971.02 | 447.28 | 422.22 | nucleolar basal body binding protein bn46 S1 large subunit |
| SEQ ID NO: 6954 | Nga04900 | 133.33 | 154.59 | tubulin-specific chaperone d |
| SEQ ID NO: 6955 | Nga20914 | 108.70 | 102.04 | cobalamin 5 -phosphate synthase |
| SEQ ID NO: 6956 | Nga04898 | 309.76 | 296.34 | ---NA--- |
| SEQ ID NO: 6957 | Nga04962 | 148.58 | 80.48 | ---NA--- |
| SEQ ID NO: 6958 | Nga04359 | 656.88 | 664.52 | gtp-binding protein |
| SEQ ID NO: 6959 | Nga04360 | 9749.41 | 4888.64 | ---NA--- |
| SEQ ID NO: 6960 | Nga01675.02 | 238.79 | 327.29 | ---NA--- |
| SEQ ID NO: 6961 | Nga01962 | 51.28 | 66.66 | ---NA--- |
| SEQ ID NO: 6962 | Nga04911 | 291.73 | 345.17 | heavy metal p-type atpase |
| SEQ ID NO: 6963 | Nga04912 | 751.14 | 682.74 | heavy metal p-type atpase |
| SEQ ID NO: 6964 | Nga04507 | 440.82 | 474.52 | nucleoporin 205 |
| SEQ ID NO: 6965 | Nga04298 | 80.42 | 107.31 | protein |
| SEQ ID NO: 6966 | Nga00258.02 | 3.62 | 27.47 | ---NA--- |
| SEQ ID NO: 6967 | Nga20837 | 327.78 | 470.00 | major facilitator superfamily |
| SEQ ID NO: 6968 | Nga06426 | 785.69 | 829.60 | cockayne syndrome 1 |
| SEQ ID NO: 6969 | Nga06427 | 811.28 | 781.89 | calcium ion binding |
| SEQ ID NO: 6970 | Nga06425 | 423.31 | 474.02 | membrane protein |
| SEQ ID NO: 6971 | Nga06430 | 270.68 | 305.79 | loc495097 protein |
| SEQ ID NO: 6972 | Nga06428 | 3233.10 | 4170.07 | 2-oxoglutarate e1 component |
| SEQ ID NO: 6973 | Nga06429 | 297.36 | 285.84 | hypothetical protein [Monosiga brevicollis MX1] |
| SEQ ID NO: 6974 | Nga03516 | 186.05 | 162.35 | cop9 complex homolog subunit 3 |
| SEQ ID NO: 6975 | Nga03514 | 527.21 | 617.76 | protein |
| SEQ ID NO: 6976 | Nga03515 | 421.50 | 495.40 | ---NA--- |
| SEQ ID NO: 6977 | Nga02389 | 157.56 | 219.43 | ---NA--- |
| SEQ ID NO: 6978 | Nga04450 | 44.19 | 70.92 | ---NA--- |
| SEQ ID NO: 6979 | Nga21296 | 234.15 | 235.14 | srr1-like protein |
| SEQ ID NO: 6980 | Nga04449 | 910.11 | 1073.44 | scavenger receptor class member 2 |
| SEQ ID NO: 6981 | Nga06962 | 12705.60 | 13728.87 | ---NA--- |
| SEQ ID NO: 6982 | Nga06963 | 79.71 | 94.19 | ---NA--- |
| SEQ ID NO: 6983 | Nga06514 | 1606.74 | 1374.79 | cathepsin b |
| SEQ ID NO: 6984 | Nga20931 | 5968.00 | 7265.56 | transcript antisense to ribosomal rna protein |
| SEQ ID NO: 6985 | Nga06516 | 872.31 | 803.29 | ppgpp synthetase |
| SEQ ID NO: 6986 | Nga06515 | 1156.69 | 1156.37 | thioredoxin family trp26-like protein |
| SEQ ID NO: 6987 | Nga06517 | 1009.05 | 1019.04 | dead h (asp-glu-ala-asp his) box polypeptide 11 |
| SEQ ID NO: 6988 | Nga06518 | 525.53 | 627.82 | conserved hypothetical protein [Phytophthora infestans T30-4] |
| SEQ ID NO: 6989 | Nga02209.02 | 545.86 | 533.98 | mfs monosaccharide |
| SEQ ID NO: 6990 | Nga02311 | 521.34 | 781.19 | rna polymerase i-specific transcription initiation factor |
| SEQ ID NO: 6991 | Nga20395 | 168.94 | 259.74 | ---NA--- |
| SEQ ID NO: 6992 | Nga02310 | 329.41 | 327.52 | ---NA--- |
| SEQ ID NO: 6993 | Nga05664 | 276.04 | 406.21 | ---NA--- |
| SEQ ID NO: 6994 | Nga04608.02 | 2033.00 | 1573.72 | protein |
| SEQ ID NO: 6995 | Nga05661.01 | 362.80 | 297.24 | bacteriocin o-metyltransferase |
| SEQ ID NO: 6996 | Nga05661.02 | 362.80 | 297.24 | bacteriocin o-metyltransferase |
| SEQ ID NO: 6997 | Nga05663 | 169.47 | 230.99 | ---NA--- |
| SEQ ID NO: 6998 | Nga05660 | 337.37 | 413.49 | ---NA--- |
| SEQ ID NO: 6999 | Nga20547 | 129.87 | 344.67 | 3 -5 exoribonuclease rna-binding protein |
| SEQ ID NO: 7000 | Nga04609.2 | 635.63 | 716.60 | ---NA--- |
| SEQ ID NO: 7001 | Nga07059 | 278.96 | 333.73 | ---NA--- |
| SEQ ID NO: 7002 | Nga05487 | 268.75 | 294.50 | ---NA--- |
| SEQ ID NO: 7003 | Nga21091 | 1034.18 | 978.61 | family protein |
| SEQ ID NO: 7004 | Nga21058 | 245.33 | 250.56 | ---NA--- |
| SEQ ID NO: 7005 | Nga05484 | 562.07 | 453.95 | fanconi complementation group i |
| SEQ ID NO: 7006 | Nga05485 | 433.90 | 471.93 | had-superfamily hydrolase |
| SEQ ID NO: 7007 | Nga05482 | 256.19 | 214.44 | ---NA--- |
| SEQ ID NO: 7008 | Nga05488 | 177.30 | 176.70 | ---NA--- |
| SEQ ID NO: 7009 | Nga05483 | 147.37 | 184.07 | lysine-specific histone demethylase |
| SEQ ID NO: 7010 | Nga05486 | 646.99 | 407.47 | ---NA--- |
| SEQ ID NO: 7011 | Nga03878 | 129.30 | 129.78 | dna polymerase lambda |

FIGURE 24 DG

| # | Nga model | +N rpkb | -N rpkb | GO |
|---|---|---|---|---|
| SEQ ID NO: 7012 | Nga03877 | 615.48 | 487.80 | n -adenine-specific dna methyltransferase 1 |
| SEQ ID NO: 7013 | Nga20548 | 84.59 | 114.54 | ---NA--- |
| SEQ ID NO: 7014 | Nga06018 | 58.25 | 105.17 | ---NA--- |
| SEQ ID NO: 7015 | Nga06015 | 412.22 | 340.62 | chromosome 1 open reading frame 58 |
| SEQ ID NO: 7016 | Nga06016 | 325.98 | 424.80 | dipeptidyl peptidase 3 |
| SEQ ID NO: 7017 | Nga21282 | 217.39 | 329.68 | ---NA--- |
| SEQ ID NO: 7018 | Nga20579 | 258.33 | 126.38 | ---NA--- |
| SEQ ID NO: 7019 | Nga21087 | 7714.75 | 4637.71 | cytochrome b5 |
| SEQ ID NO: 7020 | Nga06014 | 351.18 | 344.16 | abc transporter g family member 29 |
| SEQ ID NO: 7021 | Nga06013 | 695.23 | 672.93 | hus1 checkpoint homolog ( pombe) |
| SEQ ID NO: 7022 | Nga06017 | 251.98 | 386.87 | predicted protein [Micromonas sp. RCC299] |
| SEQ ID NO: 7023 | Nga20462 | 71.91 | 119.28 | gtp-binding protein |
| SEQ ID NO: 7024 | Nga03212 | 2282.33 | 2369.57 | mucin-associated surface protein |
| SEQ ID NO: 7025 | Nga03213 | 922.08 | 984.76 | ---NA--- |
| SEQ ID NO: 7026 | Nga21157 | 674.99 | 765.43 | translocator of the inner chloroplast envelope membrane 110k |
| SEQ ID NO: 7027 | Nga00974.2 | 69.99 | 107.07 | guanine deaminase |
| SEQ ID NO: 7028 | Nga06416 | 210.42 | 198.59 | tyrosyl-dna phosphodiesterase 1 |
| SEQ ID NO: 7029 | Nga06417 | 1223.71 | 1751.00 | protein mitochondrial-like |
| SEQ ID NO: 7030 | Nga06415 | 858.97 | 847.14 | likely ras family gtp binding protein |
| SEQ ID NO: 7031 | Nga06418 | 200.80 | 169.66 | ---NA--- |
| SEQ ID NO: 7032 | Nga07136 | 5173.87 | 4039.95 | ---NA--- |
| SEQ ID NO: 7033 | Nga07137 | 580.09 | 722.16 | ---NA--- |
| SEQ ID NO: 7034 | Nga01968 | 880.29 | 747.92 | protein |
| SEQ ID NO: 7035 | Nga21065 | 124.09 | 181.86 | ribonuclease z |
| SEQ ID NO: 7036 | Nga21273 | 98.04 | 70.80 | ---NA--- |
| SEQ ID NO: 7037 | Nga04473.2 | 1877.24 | 2195.83 | protein |
| SEQ ID NO: 7038 | Nga20257 | 365.30 | 336.35 | conserved unknown protein [Ectocarpus siliculosus] |
| SEQ ID NO: 7039 | Nga04475 | 222.22 | 180.54 | ---NA--- |
| SEQ ID NO: 7040 | Nga04473.1 | 1877.24 | 2195.83 | loc398558 protein |
| SEQ ID NO: 7041 | Nga20693 | 153.37 | 148.42 | ---NA--- |
| SEQ ID NO: 7042 | Nga03951 | 127.80 | 160.30 | adenylate kinase |
| SEQ ID NO: 7043 | Nga20433 | 182.02 | 153.36 | conserved unknown protein [Ectocarpus siliculosus] |
| SEQ ID NO: 7044 | Nga03950 | 7941.40 | 5499.01 | lactoylglutathione lyase |
| SEQ ID NO: 7045 | Nga01170 | 524.43 | 418.66 | 3-like protein |
| SEQ ID NO: 7046 | Nga01168.1 | 652.21 | 843.10 | ---NA--- |
| SEQ ID NO: 7047 | Nga01169 | 468.11 | 575.47 | atp-binding sub-family b (mdr tap) member 10 |
| SEQ ID NO: 7048 | Nga01171 | 721.94 | 620.55 | integral membrane mpv17 pmp22 |
| SEQ ID NO: 7049 | Nga01167 | 1733.14 | 1888.73 | protein |
| SEQ ID NO: 7050 | Nga20752 | 107.78 | 188.11 | ---NA--- |
| SEQ ID NO: 7051 | Nga02419 | 169.26 | 228.25 | ---NA--- |
| SEQ ID NO: 7052 | Nga20153 | 234.14 | 186.16 | novel protein containing 10 heat domains |
| SEQ ID NO: 7053 | Nga02418 | 844.89 | 693.88 | 26s proteasome non-atpase regulatory subunit 12 |
| SEQ ID NO: 7054 | Nga02417 | 520.87 | 544.13 | ---NA--- |
| SEQ ID NO: 7055 | Nga06797 | 213.00 | 195.23 | signal peptide peptidase |
| SEQ ID NO: 7056 | Nga01605 | 517.35 | 696.36 | redoxin domain protein |
| SEQ ID NO: 7057 | Nga01603.01 | 228.78 | 321.85 | ---NA--- |
| SEQ ID NO: 7058 | Nga01604 | 153.10 | 145.90 | protein |
| SEQ ID NO: 7059 | Nga01602 | 754.29 | 762.05 | udp-glucuronic acid decarboxylase 1 |
| SEQ ID NO: 7060 | Nga07219 | 170.09 | 223.82 | ---NA--- |
| SEQ ID NO: 7061 | Nga07108 | 85.93 | 124.79 | heavy metal p-type atpase |
| SEQ ID NO: 7062 | Nga01703 | 233.81 | 220.75 | ---NA--- |
| SEQ ID NO: 7063 | Nga01702 | 244.90 | 317.39 | multidrug-resistance like protein isoform q |
| SEQ ID NO: 7064 | Nga20039 | 1908.56 | 2043.96 | conserved unknown protein [Ectocarpus siliculosus] |
| SEQ ID NO: 7065 | Nga01943.02 | 2224.59 | 2333.29 | bromodomain containing protein |
| SEQ ID NO: 7066 | Nga01944.2 | 114.12 | 138.24 | e3 isg15--protein ligase herc5 |
| SEQ ID NO: 7067 | Nga02235 | 365.63 | 270.31 | beta- -mannosyl-glycoprotein beta- -n-acetylglucosaminyltransferase |
| SEQ ID NO: 7068 | Nga21185 | 71.43 | 85.97 | ---NA--- |
| SEQ ID NO: 7069 | Nga21118 | 729.01 | 867.13 | ---NA--- |
| SEQ ID NO: 7070 | Nga20570 | 64.00 | 112.66 | like gtpase |
| SEQ ID NO: 7071 | Nga20576 | 103.66 | 102.38 | ---NA--- |
| SEQ ID NO: 7072 | Nga20251 | 651.45 | 572.98 | expressed unknown protein [Ectocarpus siliculosus] |
| SEQ ID NO: 7073 | Nga06873 | 1116.61 | 1268.09 | ---NA--- |
| SEQ ID NO: 7074 | Nga05598 | 2599.66 | 3970.65 | ---NA--- |
| SEQ ID NO: 7075 | Nga05601 | 399.35 | 313.01 | expressed unknown protein [Ectocarpus siliculosus] |

FIGURE 24 DH

| # | Nga model | +N rpkb | -N rpkb | GO |
|---|---|---|---|---|
| SEQ ID NO: 7076 | Nga05602 | 100.84 | 109.23 | ---NA--- |
| SEQ ID NO: 7077 | Nga05600 | 1307.28 | 1071.76 | expressed unknown protein [Ectocarpus siliculosus] |
| SEQ ID NO: 7078 | Nga05599 | 238.10 | 336.90 | hydrolase involved in interstrand cross-link repair |
| SEQ ID NO: 7079 | Nga04925.2 | 535.09 | 530.83 | ubiquitin conjugation factor e4 b |
| SEQ ID NO: 7080 | Nga04925.1 | 535.09 | 530.83 | ubiquitin conjugation factor e4 |
| SEQ ID NO: 7081 | Nga02016 | 79.23 | 97.67 | conserved hypothetical protein |
| SEQ ID NO: 7082 | Nga02015 | 177.09 | 150.13 | conserved hypothetical protein |
| SEQ ID NO: 7083 | Nga20406 | 89.64 | 142.42 | chaperone protein |
| SEQ ID NO: 7084 | Nga03701 | 795.24 | 717.00 | ---NA--- |
| SEQ ID NO: 7085 | Nga03702 | 850.65 | 661.19 | ---NA--- |
| SEQ ID NO: 7086 | Nga03697 | 180.19 | 170.08 | ---NA--- |
| SEQ ID NO: 7087 | Nga20135 | 338.51 | 341.61 | protein |
| SEQ ID NO: 7088 | Nga20015 | 193.72 | 229.69 | conserved unknown protein [Ectocarpus siliculosus] |
| SEQ ID NO: 7089 | Nga03698 | 639.76 | 716.51 | nt5c3l-b protein |
| SEQ ID NO: 7090 | Nga03703 | 337.00 | 301.56 | ---NA--- |
| SEQ ID NO: 7091 | Nga03700.01 | 801.22 | 1132.92 | n-acetyltransferase esco2 |
| SEQ ID NO: 7092 | Nga03699.1 | 613.38 | 865.78 | protein |
| SEQ ID NO: 7093 | Nga20449 | 322.03 | 415.72 | tho complex subunit |
| SEQ ID NO: 7094 | Nga20533 | 185.11 | 294.24 | tho complex subunit |
| SEQ ID NO: 7095 | Nga04513.2 | 287.48 | 265.55 | protein |
| SEQ ID NO: 7096 | Nga01446 | 709.15 | 674.96 | carboxyvinyl-carboxyphosphonate phosphorylmutase |
| SEQ ID NO: 7097 | Nga01447 | 196.34 | 217.16 | origin recognition complex subunit 4 |
| SEQ ID NO: 7098 | Nga01445.1 | 3746.55 | 4432.15 | succinate dehydrogenase |
| SEQ ID NO: 7099 | Nga04259 | 849.84 | 869.21 | dna mismatch repair protein msh2 |
| SEQ ID NO: 7100 | Nga05986.02 | 458.72 | 510.52 | alanine-glyoxylate aminotransferase 2-like 2 |
| SEQ ID NO: 7101 | Nga06776 | 299.48 | 256.70 | predicted protein [Thalassiosira pseudonana CCMP1335] |
| SEQ ID NO: 7102 | Nga06770 | 1753.96 | 2272.14 | protein |
| SEQ ID NO: 7103 | Nga05984.02 | 206.52 | 263.87 | protein |
| SEQ ID NO: 7104 | Nga05981.02 | 2019.73 | 2874.37 | ---NA--- |
| SEQ ID NO: 7105 | Nga05985.02 | 469.14 | 493.32 | tyrosine phosphatase |
| SEQ ID NO: 7106 | Nga05982.02 | 456.31 | 493.09 | triacylglycerol lipase |
| SEQ ID NO: 7107 | Nga05987.02 | 489.49 | 465.27 | ---NA--- |
| SEQ ID NO: 7108 | Nga05983.02 | 3140.04 | 2439.95 | ---NA--- |
| SEQ ID NO: 7109 | Nga06831 | 170.21 | 220.23 | ---NA--- |
| SEQ ID NO: 7110 | Nga06830 | 587.45 | 621.86 | uncharacterized protein |
| SEQ ID NO: 7111 | Nga01896.01 | 626.27 | 569.16 | arrestin domain protein |
| SEQ ID NO: 7112 | Nga01895 | 2246.12 | 2294.52 | branched-chain amino acid aminotransferase |
| SEQ ID NO: 7113 | Nga01894 | 1804.58 | 1667.85 | ---NA--- |
| SEQ ID NO: 7114 | Nga01893 | 2895.95 | 3301.91 | purple acid phosphatase |
| SEQ ID NO: 7115 | Nga07022 | 36.36 | 29.54 | ---NA--- |
| SEQ ID NO: 7116 | Nga02280 | 1232.01 | 1142.09 | tubulin-specific chaperone a |
| SEQ ID NO: 7117 | Nga06282.2 | 1803.52 | 2360.24 | biotin and thiamin synthesis associated |
| SEQ ID NO: 7118 | Nga02282 | 560.73 | 674.67 | small gtp-binding protein |
| SEQ ID NO: 7119 | Nga04071 | 271.86 | 236.34 | rab family gtpase |
| SEQ ID NO: 7120 | Nga04070 | 284.55 | 237.78 | conserved unknown protein [Ectocarpus siliculosus] |
| SEQ ID NO: 7121 | Nga06943 | 211.59 | 210.37 | ---NA--- |
| SEQ ID NO: 7122 | Nga05519 | 28.17 | 45.77 | ---NA--- |
| SEQ ID NO: 7123 | Nga05514 | 1130.03 | 1170.43 | glycoprotein fp21 |
| SEQ ID NO: 7124 | Nga05517 | 151.16 | 201.53 | ---NA--- |
| SEQ ID NO: 7125 | Nga05515 | 290.03 | 261.64 | ---NA--- |
| SEQ ID NO: 7126 | Nga05516 | 85.53 | 135.40 | ---NA--- |
| SEQ ID NO: 7127 | Nga02794 | 259.78 | 186.59 | kynureninase |
| SEQ ID NO: 7128 | Nga02790 | 20617.45 | 8748.27 | light-harvesting protein |
| SEQ ID NO: 7129 | Nga20467 | 340.77 | 357.76 | conserved unknown protein [Ectocarpus siliculosus] |
| SEQ ID NO: 7130 | Nga02791 | 309.34 | 302.27 | pseudouridine synthase |
| SEQ ID NO: 7131 | Nga02788 | 515.71 | 489.67 | phosphatidylinositol-4-phosphate 5-kinase |
| SEQ ID NO: 7132 | Nga02784 | 1812.98 | 1963.89 | protein phosphatase 2c containing protein |
| SEQ ID NO: 7133 | Nga02795 | 1475.53 | 1277.28 | protein |
| SEQ ID NO: 7134 | Nga02787 | 3976.80 | 3817.79 | p11915 nonspecific lipid-transfer protein |
| SEQ ID NO: 7135 | Nga02796 | 414.65 | 387.24 | diacylglycerol kinase |
| SEQ ID NO: 7136 | Nga02785 | 9248.51 | 2577.52 | light-harvesting protein |
| SEQ ID NO: 7137 | Nga20088 | 1037.09 | 883.92 | membrane protein |
| SEQ ID NO: 7138 | Nga02786 | 288.81 | 181.49 | bifunctional atp-dependent dihydroxyacetone kinase fad-amp lyase |
| SEQ ID NO: 7139 | Nga02797 | 354.57 | 362.36 | cdk5 and abl1 enzyme substrate 1 |

FIGURE 24 DI

| # | Nga model | +N rpkb | -N rpkb | GO |
|---|---|---|---|---|
| SEQ ID NO: 7140 | Nga02793 | 634.56 | 691.51 | expressed unknown protein [Ectocarpus siliculosus] |
| SEQ ID NO: 7141 | Nga02792 | 607.36 | 500.43 | tpr domain protein |
| SEQ ID NO: 7142 | Nga02789 | 1334.02 | 1385.69 | dnl-type zinc finger |
| SEQ ID NO: 7143 | Nga20858 | 644.32 | 657.61 | gualynate kinase-1 |
| SEQ ID NO: 7144 | Nga07012 | 7.30 | 31.63 | ---NA--- |
| SEQ ID NO: 7145 | Nga01303 | 82.47 | 122.84 | ---NA--- |
| SEQ ID NO: 7146 | Nga01301 | 286.68 | 277.66 | ---NA--- |
| SEQ ID NO: 7147 | Nga01299 | 169.54 | 206.06 | mitochondrial ornithine transporter 1 |
| SEQ ID NO: 7148 | Nga01300 | 248.69 | 202.28 | 16s ribosomal rna methyltransferase |
| SEQ ID NO: 7149 | Nga01302 | 394.62 | 355.82 | ncs1 nucleoside transporter family |
| SEQ ID NO: 7150 | Nga01298 | 1199.20 | 854.44 | nonclathrin coat protein zeta2-cop |
| SEQ ID NO: 7151 | Nga20376 | 146.74 | 188.39 | wd repeat protein 23 |
| SEQ ID NO: 7152 | Nga05950 | 542.25 | 608.70 | cation transporting |
| SEQ ID NO: 7153 | Nga05948 | 1820.49 | 1745.30 | predicted protein [Phaeodactylum tricornutum CCAP 1055/1] |
| SEQ ID NO: 7154 | Nga05949 | 1847.31 | 1520.54 | dolichyl-diphosphooligosaccharide-protein glycosyltransferase |
| SEQ ID NO: 7155 | Nga05952 | 201.45 | 211.50 | protein fra10ac1 homolog |
| SEQ ID NO: 7156 | Nga05951 | 341.33 | 410.18 | wd repeat domain isoform cra_c |
| SEQ ID NO: 7157 | Nga02222 | 347.88 | 474.00 | ---NA--- |
| SEQ ID NO: 7158 | Nga02220 | 807.39 | 913.51 | rossmann fold nucleotide-binding protein |
| SEQ ID NO: 7159 | Nga02221 | 156.44 | 191.06 | cg12909 |
| SEQ ID NO: 7160 | Nga20363 | 502.41 | 460.77 | lipase domain protein |
| SEQ ID NO: 7161 | Nga05921 | 1513.67 | 1833.01 | phosphoenolpyruvate carboxylase |
| SEQ ID NO: 7162 | Nga05919 | 677.42 | 641.90 | na+ h+ antiporter |
| SEQ ID NO: 7163 | Nga05922 | 11070.34 | 7973.53 | ---NA--- |
| SEQ ID NO: 7164 | Nga05923 | 451.17 | 441.86 | tudor-sn protein 1 |
| SEQ ID NO: 7165 | Nga05920 | 143.16 | 146.85 | dna mismatch repair protein msh6 |
| SEQ ID NO: 7166 | Nga03995 | 168.99 | 131.37 | ---NA--- |
| SEQ ID NO: 7167 | Nga03994 | 87.43 | 130.22 | ykl027w-like protein |
| SEQ ID NO: 7168 | Nga02211 | 258.93 | 220.52 | ---NA--- |
| SEQ ID NO: 7169 | Nga02210 | 1124.08 | 1303.79 | svop protein |
| SEQ ID NO: 7170 | Nga07158 | 3047.39 | 2388.50 | ---NA--- |
| SEQ ID NO: 7171 | Nga05256 | 4535.67 | 4791.75 | iojap-like protein |
| SEQ ID NO: 7172 | Nga05254 | 713.59 | 545.12 | vesicle transport protein |
| SEQ ID NO: 7173 | Nga05257 | 64.33 | 6.33 | ---NA--- |
| SEQ ID NO: 7174 | Nga05255 | 7482.23 | 4448.41 | phosphoglycerate kinase |
| SEQ ID NO: 7175 | Nga05253 | 6250.79 | 6086.80 | protein |
| SEQ ID NO: 7176 | Nga07270 | 704.18 | 588.11 | conserved unknown protein [Ectocarpus siliculosus] |
| SEQ ID NO: 7177 | Nga04834 | 351.94 | 345.96 | conserved hypothetical protein [Albugo laibachii Nc14] |
| SEQ ID NO: 7178 | Nga06921 | 1516.57 | 1304.08 | d-lactate dehydrogenase |
| SEQ ID NO: 7179 | Nga04483 | 290.13 | 254.62 | ---NA--- |
| SEQ ID NO: 7180 | Nga00857 | 6687.00 | 5909.04 | ---NA--- |
| SEQ ID NO: 7181 | Nga00859 | 622.81 | 516.28 | 26s proteasome non-atpase regulatory subunit |
| SEQ ID NO: 7182 | Nga00858 | 281.84 | 251.54 | rna-binding s4 |
| SEQ ID NO: 7183 | Nga00856 | 568.15 | 295.81 | ankyrin unc44 |
| SEQ ID NO: 7184 | Nga00855 | 996.32 | 1041.02 | chain structure of aminoadipate-semialdehyde dehydrogenase- phosphopantetheinyl transferase |
| SEQ ID NO: 7185 | Nga07267 | 1123.31 | 1059.75 | protein |
| SEQ ID NO: 7186 | Nga07314 | 372.70 | 361.08 | wd domain-containing |
| SEQ ID NO: 7187 | Nga06978 | 200.00 | 225.67 | ---NA--- |
| SEQ ID NO: 7188 | Nga06971 | 5321.50 | 4753.78 | cupin 2 barrel domain-containing protein |
| SEQ ID NO: 7189 | Nga21072 | 20.27 | 14.64 | snare associated golgi protein |
| SEQ ID NO: 7190 | Nga06523 | 6838.79 | 7207.12 | ribosomal protein srp1 |
| SEQ ID NO: 7191 | Nga06524 | 213.42 | 262.17 | la-related protein 4b |
| SEQ ID NO: 7192 | Nga06525 | 463.27 | 473.09 | ---NA--- |
| SEQ ID NO: 7193 | Nga02268 | 3284.76 | 1786.64 | nitrate reductase |
| SEQ ID NO: 7194 | Nga02267 | 6885.56 | 2084.81 | ferredoxin-nitrite reductase |
| SEQ ID NO: 7195 | Nga21027 | 404.49 | 430.86 | elicitin-like protein 6 precursor |
| SEQ ID NO: 7196 | Nga07259 | 8234.13 | 7070.05 | ---NA--- |
| SEQ ID NO: 7197 | Nga04437 | 109.59 | 115.00 | ---NA--- |
| SEQ ID NO: 7198 | Nga20844 | 366.58 | 289.06 | exosome component 5 |
| SEQ ID NO: 7199 | Nga02933 | 142.12 | 206.33 | sulfite reductase |
| SEQ ID NO: 7200 | Nga02928 | 1849.34 | 1844.81 | peptidyl-prolyl cis-trans isomerase ppi1 |
| SEQ ID NO: 7201 | Nga02935 | 256.15 | 270.27 | mucolipin-like protein |
| SEQ ID NO: 7202 | Nga02937 | 9.05 | 8.17 | type a von willebrand factor domain-containing protein |

FIGURE 24 DJ

| # | Nga model | +N rpkb | -N rpkb | GO |
|---|---|---|---|---|
| SEQ ID NO: 7203 | Nga02936 | 9.45 | 40.02 | midasin-like protein |
| SEQ ID NO: 7204 | Nga02927 | 469.05 | 344.41 | golgi snap receptor complex member 2 |
| SEQ ID NO: 7205 | Nga20218 | 19.05 | 59.32 | midasin-like protein |
| SEQ ID NO: 7206 | Nga20218 | 29.63 | 43.33 | midasin-like protein |
| SEQ ID NO: 7207 | Nga02931 | 1031.36 | 1179.12 | elongation factor tu |
| SEQ ID NO: 7208 | Nga21113 | 131.41 | 120.66 | protein |
| SEQ ID NO: 7209 | Nga02934 | 1224.90 | 1370.36 | elongation factor tu |
| SEQ ID NO: 7210 | Nga02930 | 328.07 | 384.15 | methionine synthase mitochondrial precursor-like protein |
| SEQ ID NO: 7211 | Nga02932 | 77.13 | 117.87 | protein |
| SEQ ID NO: 7212 | Nga02929 | 168.69 | 125.63 | programmed cell death protein 5 |
| SEQ ID NO: 7213 | Nga06840 | 83.33 | 40.12 | ---NA--- |
| SEQ ID NO: 7214 | Nga06839 | 116.33 | 92.09 | conserved unknown protein [Ectocarpus siliculosus] |
| SEQ ID NO: 7215 | Nga06829.1 | 48.85 | 54.47 | shq1 homolog ( cerevisiae) |
| SEQ ID NO: 7216 | Nga05819.2 | 1067.43 | 958.50 | cdp-diacylglycerol--glycerol-3-phosphate 3-phosphatidyltransferase |
| SEQ ID NO: 7217 | Nga04657.01 | 553.42 | 557.82 | vesicle transport v- |
| SEQ ID NO: 7218 | Nga21246 | 166.88 | 255.52 | cell division control protein |
| SEQ ID NO: 7219 | Nga20332 | 424.05 | 370.22 | protein |
| SEQ ID NO: 7220 | Nga02432 | 14878.71 | 9133.10 | mpv17-like protein |
| SEQ ID NO: 7221 | Nga02433 | 598.55 | 816.56 | ring finger protein 167 |
| SEQ ID NO: 7222 | Nga04067 | 164.10 | 249.98 | ---NA--- |
| SEQ ID NO: 7223 | Nga04066 | 323.53 | 427.30 | upf0652 protein |
| SEQ ID NO: 7224 | Nga06846 | 1647.89 | 1383.28 | secreted protein |
| SEQ ID NO: 7225 | Nga20676.1 | 24.19 | 87.36 | ---NA--- |
| SEQ ID NO: 7226 | Nga21261 | 37.31 | 56.59 | eukaryotic translation initiation factor 2-alpha kinase 4 |
| SEQ ID NO: 7227 | Nga20301 | 88.63 | 62.61 | protein kinase |
| SEQ ID NO: 7228 | Nga04724 | 158.33 | 81.24 | ---NA--- |
| SEQ ID NO: 7229 | Nga04723 | 140.22 | 107.92 | hypothetical protein PTSG_03639 [Salpingoeca sp. ATCC 50818] |
| SEQ ID NO: 7230 | Nga04805 | 991.48 | 935.60 | ---NA--- |
| SEQ ID NO: 7231 | Nga04815 | 172.99 | 187.39 | soluble nsf attachment protein gamma isoform |
| SEQ ID NO: 7232 | Nga04814.1 | 297.80 | 270.11 | ---NA--- |
| SEQ ID NO: 7233 | Nga06809 | 1013.28 | 1062.68 | conserved unknown protein [Ectocarpus siliculosus] |
| SEQ ID NO: 7234 | Nga07075 | 58.18 | 59.09 | ---NA--- |
| SEQ ID NO: 7235 | Nga07076 | 30.30 | 20.89 | ---NA--- |
| SEQ ID NO: 7236 | Nga20069 | 573.94 | 661.65 | trehalose synthase |
| SEQ ID NO: 7237 | Nga03635 | 348.02 | 652.39 | sodium hydrogen exchanger family protein |
| SEQ ID NO: 7238 | Nga03638 | 286.46 | 445.71 | ---NA--- |
| SEQ ID NO: 7239 | Nga03637 | 192.98 | 573.29 | monovalent cation:proton antiporter-1 family |
| SEQ ID NO: 7240 | Nga03636 | 210.67 | 181.98 | monovalent cation:proton antiporter-1 family |
| SEQ ID NO: 7241 | Nga06810 | 329.14 | 411.04 | aminophospholipid-transporting p-type atpase |
| SEQ ID NO: 7242 | Nga06899 | 83.87 | 74.06 | aminotransferase class-iii |
| SEQ ID NO: 7243 | Nga07284 | 868.87 | 659.27 | exported nucleotide-binding protein |
| SEQ ID NO: 7244 | Nga04959 | 2776.21 | 2415.86 | protein |
| SEQ ID NO: 7245 | Nga04960 | 172.00 | 137.49 | erythromycin esterase |
| SEQ ID NO: 7246 | Nga04185 | 380.95 | 443.61 | ---NA--- |
| SEQ ID NO: 7247 | Nga04184 | 626.21 | 557.39 | heme oxygenase |
| SEQ ID NO: 7248 | Nga21195 | 172.41 | 121.40 | ---NA--- |
| SEQ ID NO: 7249 | Nga06860 | 1743.39 | 1375.54 | ---NA--- |
| SEQ ID NO: 7250 | Nga05024 | 155.79 | 191.56 | ---NA--- |
| SEQ ID NO: 7251 | Nga03706.01 | 591.29 | 553.98 | protein |
| SEQ ID NO: 7252 | Nga07134 | 934.65 | 936.10 | ---NA--- |
| SEQ ID NO: 7253 | Nga07049 | 554.14 | 603.71 | histone h3 |
| SEQ ID NO: 7254 | Nga07039 | 50.30 | 102.44 | ---NA--- |
| SEQ ID NO: 7255 | Nga03298 | 32.26 | 0.00 | ---NA--- |
| SEQ ID NO: 7256 | Nga03302 | 1223.12 | 1278.33 | polyadenlyte binding protein |
| SEQ ID NO: 7257 | Nga03300 | 113.10 | 77.37 | rare lipoprotein a |
| SEQ ID NO: 7258 | Nga03296 | 1112.73 | 1486.33 | b chain crystal structure of the mile domain of poly -binding protein in complex with the binding region of paip2 |
| SEQ ID NO: 7259 | Nga03295 | 14.91 | 44.03 | ---NA--- |
| SEQ ID NO: 7260 | Nga20684 | 589.64 | 747.95 | disulfide isomerase |
| SEQ ID NO: 7261 | Nga03299 | 53.57 | 58.03 | ---NA--- |
| SEQ ID NO: 7262 | Nga03297 | 36.23 | 26.69 | p-loop containing nucleoside triphosphate hydrolase-like protein |
| SEQ ID NO: 7263 | Nga20443 | 122.30 | 124.69 | dna primase |
| SEQ ID NO: 7264 | Nga03301 | 67.71 | 43.25 | protein |
| SEQ ID NO: 7265 | Nga03294 | 193.28 | 200.87 | tfiih subunit |

FIGURE 24 DK

| # | Nga model | +N rpkb | -N rpkb | GO |
|---|---|---|---|---|
| SEQ ID NO: 7266 | Nga01499 | 712.75 | 890.77 | ankyrin repeat domain protein |
| SEQ ID NO: 7267 | Nga01498 | 902.96 | 893.45 | protein |
| SEQ ID NO: 7268 | Nga05017 | 729.37 | 818.68 | protein |
| SEQ ID NO: 7269 | Nga20266 | 504.30 | 425.09 | potential er nuclear membrane ubiquitin-protein ligase e3 |
| SEQ ID NO: 7270 | Nga01841 | 351.73 | 486.22 | glycosyl transferase family protein |
| SEQ ID NO: 7271 | Nga20611 | 348.80 | 390.03 | spindle pole body interacting protein |
| SEQ ID NO: 7272 | Nga20652 | 28.17 | 55.94 | wd repeat-containing protein 3 |
| SEQ ID NO: 7273 | Nga20960 | 741.41 | 561.31 | predicted protein [Thalassiosira pseudonana CCMP1335] |
| SEQ ID NO: 7274 | Nga01038 | 651.99 | 724.43 | 3-isopropylmalate dehydrogenase |
| SEQ ID NO: 7275 | Nga01039 | 156.72 | 288.32 | serine threonine protein |
| SEQ ID NO: 7276 | Nga03813 | 3.75 | 85.20 | protein |
| SEQ ID NO: 7277 | Nga03815 | 44.59 | 73.60 | potassium channel protein |
| SEQ ID NO: 7278 | Nga03812 | 111.11 | 114.89 | protein |
| SEQ ID NO: 7279 | Nga03816 | 66.67 | 55.22 | ---NA--- |
| SEQ ID NO: 7280 | Nga03814 | 169.31 | 126.09 | ---NA--- |
| SEQ ID NO: 7281 | Nga07002 | 112.09 | 126.69 | abc transporter atpase |
| SEQ ID NO: 7282 | Nga00234.02 | 163.78 | 204.54 | methyltransferase mett10d |
| SEQ ID NO: 7283 | Nga05367 | 283.38 | 336.48 | major facilitator superfamily domain-containing protein 9-like |
| SEQ ID NO: 7284 | Nga00232.02 | 3023.75 | 2957.22 | hypothetical protein tll0394 [Thermosynechococcus elongatus BP-1] |
| SEQ ID NO: 7285 | Nga00233.02 | 365.97 | 281.46 | ---NA--- |
| SEQ ID NO: 7286 | Nga00223.02 | 647.29 | 827.95 | serine acetyltransferase |
| SEQ ID NO: 7287 | Nga05366 | 1336.58 | 1265.25 | methylenetetrahydrofolate reductase |
| SEQ ID NO: 7288 | Nga00218.02 | 1682.69 | 1001.99 | protein |
| SEQ ID NO: 7289 | Nga00217.02 | 13677.11 | 13639.38 | myo-inositol 2-dehydrogenase |
| SEQ ID NO: 7290 | Nga00214.02 | 684.27 | 683.71 | pleckstrin domain-containing protein |
| SEQ ID NO: 7291 | Nga00227.02 | 631.30 | 781.54 | predicted protein [Thalassiosira pseudonana CCMP1335] |
| SEQ ID NO: 7292 | Nga07275 | 226.67 | 158.87 | ---NA--- |
| SEQ ID NO: 7293 | Nga20523 | 85.89 | 146.20 | translin-like protein |
| SEQ ID NO: 7294 | Nga20381 | 112.05 | 222.14 | ---NA--- |
| SEQ ID NO: 7295 | Nga03496 | 156.50 | 106.78 | necap-like protein cg9132 |
| SEQ ID NO: 7296 | Nga03493 | 231.43 | 192.70 | ---NA--- |
| SEQ ID NO: 7297 | Nga03497 | 1460.16 | 1210.05 | peptidyl-prolyl isomerase fkbp12 |
| SEQ ID NO: 7298 | Nga03494 | 920.19 | 969.32 | 3-dehydroquinate synthase |
| SEQ ID NO: 7299 | Nga20772.1 | 554.82 | 701.96 | protein |
| SEQ ID NO: 7300 | Nga03495 | 1976.30 | 1776.30 | proteasome subunit alpha type 5 |
| SEQ ID NO: 7301 | Nga03492 | 308.09 | 324.41 | alternative splicing type 3 |
| SEQ ID NO: 7302 | Nga03491.01 | 1636.64 | 1347.84 | ---NA--- |
| SEQ ID NO: 7303 | Nga07007 | 220.78 | 246.19 | er degradation-enhancing alpha-mannosidase-like protein |
| SEQ ID NO: 7304 | Nga06833 | 211.92 | 234.94 | ---NA--- |
| SEQ ID NO: 7305 | Nga06947 | 1502.85 | 1204.51 | predicted protein [Micromonas pusilla CCMP1545] |
| SEQ ID NO: 7306 | Nga20484 | 288.39 | 349.71 | protein |
| SEQ ID NO: 7307 | Nga04850 | 2687.19 | 2273.71 | glycerol-3-phosphate o-acyltransferase |
| SEQ ID NO: 7308 | Nga20220 | 1283.98 | 1338.11 | ornithine carbamoyltransferase |
| SEQ ID NO: 7309 | Nga04836 | 9682.24 | 8929.09 | ---NA--- |
| SEQ ID NO: 7310 | Nga06872 | 128.65 | 152.03 | ---NA--- |
| SEQ ID NO: 7311 | Nga04316 | 1219.93 | 1066.75 | ---NA--- |
| SEQ ID NO: 7312 | Nga04315 | 3148.30 | 2694.04 | ---NA--- |
| SEQ ID NO: 7313 | Nga20919 | 159.76 | 153.83 | ---NA--- |
| SEQ ID NO: 7314 | Nga06823 | 1837.16 | 1725.49 | conserved unknown protein [Ectocarpus siliculosus] |
| SEQ ID NO: 7315 | Nga06824 | 1374.69 | 1374.67 | ribosomal rna large subunit methyltransferase h |
| SEQ ID NO: 7316 | Nga04209 | 592.36 | 769.99 | conserved unknown protein [Ectocarpus siliculosus] |
| SEQ ID NO: 7317 | Nga04210 | 174.37 | 198.80 | ubiquitin-protein cullin 4 |
| SEQ ID NO: 7318 | Nga20345 | 192.07 | 137.95 | calcium calmodulin-dependent protein kinase kinase alpha |
| SEQ ID NO: 7319 | Nga20992 | 151.79 | 121.86 | protein kinase |
| SEQ ID NO: 7320 | Nga20552.1 | 125.33 | 178.18 | ---NA--- |
| SEQ ID NO: 7321 | Nga21140.1 | 134.71 | 151.07 | d-2-hydroxyglutarate mitochondrial precursor |
| SEQ ID NO: 7322 | Nga20751.1 | 250.64 | 261.76 | protein |
| SEQ ID NO: 7323 | Nga02446 | 1605.89 | 1315.05 | glycosyl hydrolase |
| SEQ ID NO: 7324 | Nga04018.2 | 2458.19 | 2300.51 | type iii effector protein |
| SEQ ID NO: 7325 | Nga06836 | 223.67 | 271.98 | ubiquinone menaquinone biosynthesis methyltransferase |
| SEQ ID NO: 7326 | Nga04160.02 | 2642.63 | 2382.10 | brain protein 44-like protein |
| SEQ ID NO: 7327 | Nga05788 | 282.92 | 442.43 | ---NA--- |
| SEQ ID NO: 7328 | Nga05791 | 167.74 | 172.39 | ---NA--- |
| SEQ ID NO: 7329 | Nga05790.1 | 953.02 | 993.35 | major facilitator superfamily mfs_1 |

FIGURE 24 DL

| # | Nga model | +N rpkb | -N rpkb | GO |
|---|---|---|---|---|
| SEQ ID NO: 7330 | Nga06895.2 | 912.42 | 1157.40 | ---NA--- |
| SEQ ID NO: 7331 | Nga05793 | 78.60 | 89.88 | emopamil binding |
| SEQ ID NO: 7332 | Nga06799 | 77.33 | 77.99 | 6-deoxyerythronolide-b synthase |
| SEQ ID NO: 7333 | Nga04398 | 1039.86 | 922.32 | conserved unknown protein [Ectocarpus siliculosus] |
| SEQ ID NO: 7334 | Nga04396 | 1985.88 | 1615.67 | ascorbate peroxidase |
| SEQ ID NO: 7335 | Nga04397 | 34.39 | 37.25 | ---NA--- |
| SEQ ID NO: 7336 | Nga04395 | 163.27 | 320.55 | ---NA--- |
| SEQ ID NO: 7337 | Nga20387 | 489.97 | 527.41 | zinc ion binding protein |
| SEQ ID NO: 7338 | Nga04889 | 175.70 | 126.29 | set translocation (myeloid leukemia-associated) a |
| SEQ ID NO: 7339 | Nga04365 | 828.33 | 947.99 | ---NA--- |
| SEQ ID NO: 7340 | Nga04364 | 174.48 | 189.00 | ---NA--- |
| SEQ ID NO: 7341 | Nga04501 | 428.36 | 371.53 | ---NA--- |
| SEQ ID NO: 7342 | Nga05288 | 287.79 | 261.36 | nad-dependent epimerase dehydratase |
| SEQ ID NO: 7343 | Nga05287 | 461.75 | 293.01 | charged multivesicular body protein |
| SEQ ID NO: 7344 | Nga05292 | 369.49 | 315.23 | transcription factor protein |
| SEQ ID NO: 7345 | Nga05291 | 931.40 | 643.66 | protein |
| SEQ ID NO: 7346 | Nga05294 | 826.53 | 751.63 | 24-dehydrocholesterol reductase |
| SEQ ID NO: 7347 | Nga05296 | 309.59 | 323.49 | ---NA--- |
| SEQ ID NO: 7348 | Nga05295 | 538.29 | 460.68 | udp-glucose ceramide glucosyltransferase-like 1 |
| SEQ ID NO: 7349 | Nga20131.1 | 392.55 | 476.35 | hypothetical protein AURANDRAFT_63258 [Aureococcus anophagefferens] |
| SEQ ID NO: 7350 | Nga05293 | 967.82 | 939.64 | 24-dehydrocholesterol reductase |
| SEQ ID NO: 7351 | Nga05289 | 67324.43 | 24008.93 | protein fucoxanthin chlorophyll a c protein |
| SEQ ID NO: 7352 | Nga05290 | 2588.24 | 2574.27 | protein |
| SEQ ID NO: 7353 | Nga01117.01 | 2200.70 | 2327.30 | dual specificity protein phosphatase 10 |
| SEQ ID NO: 7354 | Nga01118 | 1479.47 | 1562.05 | ---NA--- |
| SEQ ID NO: 7355 | Nga01116 | 912.61 | 1399.68 | dynactin 5 |
| SEQ ID NO: 7356 | Nga04739 | 579.30 | 576.28 | phosphatidylinositol kinase |
| SEQ ID NO: 7357 | Nga04741 | 2371.74 | 2793.78 | ---NA--- |
| SEQ ID NO: 7358 | Nga04740 | 3217.91 | 3286.30 | hyaluronan mrna binding family protein |
| SEQ ID NO: 7359 | Nga21062 | 329.87 | 301.05 | ---NA--- |
| SEQ ID NO: 7360 | Nga04738 | 690.22 | 715.14 | phosphatidylinositol kinase |
| SEQ ID NO: 7361 | Nga07060 | 128.74 | 129.49 | ---NA--- |
| SEQ ID NO: 7362 | Nga06614 | 5974.50 | 5232.48 | ---NA--- |
| SEQ ID NO: 7363 | Nga06615.1 | 346.69 | 382.52 | patched family protein |
| SEQ ID NO: 7364 | Nga06616 | 163.27 | 125.27 | ---NA--- |
| SEQ ID NO: 7365 | Nga01331.2 | 956.06 | 908.09 | nad-dependent epimerase dehydratase |
| SEQ ID NO: 7366 | Nga04533 | 151.80 | 180.23 | protein |
| SEQ ID NO: 7367 | Nga07095.1 | 625.00 | 780.99 | ---NA--- |
| SEQ ID NO: 7368 | Nga04430 | 80.00 | 139.62 | ---NA--- |
| SEQ ID NO: 7369 | Nga01822 | 2.49 | 10.78 | bacteriocin o-metyltransferase |
| SEQ ID NO: 7370 | Nga01823 | 145.48 | 131.58 | prematurely terminated mrna decay factor-like |
| SEQ ID NO: 7371 | Nga07019 | 936.87 | 839.78 | iduronate-2-sulfatase |
| SEQ ID NO: 7372 | Nga07018 | 2114.53 | 1719.62 | short-chain dehydrogenase reductase sdr |
| SEQ ID NO: 7373 | Nga01556 | 625.32 | 455.23 | methylenetetrahydrofolate dehydrogenase |
| SEQ ID NO: 7374 | Nga01555 | 94.07 | 170.57 | ---NA--- |
| SEQ ID NO: 7375 | Nga01045.02 | 3785.01 | 3574.55 | microcystin synthetase-associated thioesterase |
| SEQ ID NO: 7376 | Nga01042.02 | 765.33 | 615.28 | rae1-like protein |
| SEQ ID NO: 7377 | Nga01292 | 8888.07 | 9693.15 | 60s ribosomal protein l11 |
| SEQ ID NO: 7378 | Nga01296 | 1162.45 | 1165.50 | protein-s-isoprenylcysteine o-methyltransferase |
| SEQ ID NO: 7379 | Nga20734 | 946.67 | 772.71 | protein-s-isoprenylcysteine o-methyltransferase-like |
| SEQ ID NO: 7380 | Nga01290 | 6309.11 | 5550.10 | stress-inducible protein |
| SEQ ID NO: 7381 | Nga01291 | 295.02 | 351.12 | acyl- dehydrogenase domain protein |
| SEQ ID NO: 7382 | Nga01295 | 83.56 | 70.73 | ---NA--- |
| SEQ ID NO: 7383 | Nga02148 | 700.37 | 756.64 | ---NA--- |
| SEQ ID NO: 7384 | Nga20097.1 | 190.19 | 218.10 | type i inositol polyphosphate 5- |
| SEQ ID NO: 7385 | Nga06939 | 242.29 | 152.70 | ---NA--- |
| SEQ ID NO: 7386 | Nga07061 | 575.61 | 667.55 | atp-citrate synthase |
| SEQ ID NO: 7387 | Nga06907 | 432.60 | 522.05 | upf0082 protein pc1328 |
| SEQ ID NO: 7388 | Nga20389 | 352.83 | 273.28 | gpi mannosyltransferase 1 |
| SEQ ID NO: 7389 | Nga06908 | 296.86 | 258.89 | gpi mannosyltransferase 1 |
| SEQ ID NO: 7390 | Nga06273.02 | 77.78 | 96.29 | ---NA--- |
| SEQ ID NO: 7391 | Nga06271.02 | 2306.05 | 2335.27 | thiol-disulfide oxidoreductase dcc |
| SEQ ID NO: 7392 | Nga06269.02 | 1489.60 | 1356.36 | ---NA--- |

FIGURE 24 DM

| # | Nga model | +N rpkb | -N rpkb | GO |
|---|---|---|---|---|
| SEQ ID NO: 7393 | Nga01351.02 | 1830.59 | 2111.68 | eukaryotic translation initiation factor 3 subunit g |
| SEQ ID NO: 7394 | Nga05066.02 | 164.88 | 164.69 | ---NA--- |
| SEQ ID NO: 7395 | Nga05058.02 | 5137.54 | 3468.91 | ferredoxin-dependent bilin reductase |
| SEQ ID NO: 7396 | Nga05061.02 | 1195.18 | 788.67 | phosphoinositol transporter |
| SEQ ID NO: 7397 | Nga20921 | 110.41 | 157.19 | trna (adenine-n -)-methyltransferase catalytic |
| SEQ ID NO: 7398 | Nga21239 | 200.47 | 161.60 | protein |
| SEQ ID NO: 7399 | Nga21253 | 123.51 | 108.00 | diphthamide biosynthesis |
| SEQ ID NO: 7400 | Nga20386 | 143.28 | 140.80 | diphthamide biosynthesis protein |
| SEQ ID NO: 7401 | Nga21029 | 2030.73 | 1844.89 | hnh endonuclease |
| SEQ ID NO: 7402 | Nga07273 | 302.86 | 365.08 | protein |
| SEQ ID NO: 7403 | Nga04565 | 422.12 | 494.08 | protein |
| SEQ ID NO: 7404 | Nga03760 | 174.45 | 178.85 | ---NA--- |
| SEQ ID NO: 7405 | Nga20426 | 245.05 | 209.14 | ---NA--- |
| SEQ ID NO: 7406 | Nga03761 | 2288.22 | 3697.00 | bzip transcription factor |
| SEQ ID NO: 7407 | Nga20793 | 629.20 | 701.16 | protein |
| SEQ ID NO: 7408 | Nga20796 | 102.00 | 83.15 | related dnase |
| SEQ ID NO: 7409 | Nga07128 | 488.74 | 556.26 | histidine acid |
| SEQ ID NO: 7410 | Nga04776.01 | 2722.74 | 2796.39 | aquaporin sip1-2 |
| SEQ ID NO: 7411 | Nga04777.1 | 1441.20 | 1045.24 | protein |
| SEQ ID NO: 7412 | Nga01109.02 | 824.94 | 859.83 | ---NA--- |
| SEQ ID NO: 7413 | Nga01112.02 | 117.65 | 180.54 | ---NA--- |
| SEQ ID NO: 7414 | Nga01111.02 | 72.07 | 78.07 | ---NA--- |
| SEQ ID NO: 7415 | Nga05050 | 259.95 | 239.92 | integral membrane mpv17 pmp22 |
| SEQ ID NO: 7416 | Nga03571.2 | 1037.76 | 960.85 | protein |
| SEQ ID NO: 7417 | Nga04540 | 2153.59 | 2034.60 | protein |
| SEQ ID NO: 7418 | Nga04498.01 | 165.41 | 222.62 | conserved hypothetical protein [Phytophthora infestans T30-4] |
| SEQ ID NO: 7419 | Nga07231 | 496.82 | 492.17 | protein |
| SEQ ID NO: 7420 | Nga07062 | 446.88 | 398.31 | thioesterase superfamily member 4 |
| SEQ ID NO: 7421 | Nga02392.02 | 639.03 | 692.22 | cd4-specific ankyrin repeat protein |
| SEQ ID NO: 7422 | Nga02390.2 | 608.77 | 536.70 | ---NA--- |
| SEQ ID NO: 7423 | Nga04377 | 387.39 | 405.97 | protein |
| SEQ ID NO: 7424 | Nga04379.01 | 1007.44 | 1088.61 | ---NA--- |
| SEQ ID NO: 7425 | Nga04378.01 | 10024.63 | 8667.28 | like protein |
| SEQ ID NO: 7426 | Nga06275.02 | 1840.26 | 1797.89 | protein rer1a |
| SEQ ID NO: 7427 | Nga01375.02 | 437.80 | 290.24 | flap endonuclease 1 |
| SEQ ID NO: 7428 | Nga01377.02 | 421.05 | 445.24 | flap endonuclease-1 |
| SEQ ID NO: 7429 | Nga01376.02 | 265.65 | 284.10 | flap endonuclease-1 |
| SEQ ID NO: 7430 | Nga07056 | 5.49 | 59.52 | family transcriptional regulator |
| SEQ ID NO: 7431 | Nga03245.02 | 476.37 | 413.64 | e3 ubiquitin-protein ligase rnf14 |
| SEQ ID NO: 7432 | Nga03239.2 | 1841.42 | 2086.33 | protein |
| SEQ ID NO: 7433 | Nga03766.01 | 3999.10 | 3999.26 | nadh dehydrogenase |
| SEQ ID NO: 7434 | Nga03764.01 | 455.84 | 534.93 | 24-dehydrocholesterol reductase |
| SEQ ID NO: 7435 | Nga05615.2 | 654.91 | 1315.06 | phosphoribosylformylglycinamidine synthase |
| SEQ ID NO: 7436 | Nga02169 | 456.20 | 487.22 | aldose 1-epimerase |
| SEQ ID NO: 7437 | Nga02170 | 295.68 | 251.66 | transmembrane protein 184c |
| SEQ ID NO: 7438 | Nga02168 | 934.10 | 707.58 | signal recognition particle-docking protein |
| SEQ ID NO: 7439 | Nga20346 | 267.92 | 192.12 | ---NA--- |
| SEQ ID NO: 7440 | Nga20663 | 176.94 | 198.13 | carbohydrate fggy |
| SEQ ID NO: 7441 | Nga07006 | 505.65 | 544.68 | predicted protein [Phaeodactylum tricornutum CCAP 1055/1] |
| SEQ ID NO: 7442 | Nga04808.01 | 871.60 | 961.00 | mg-protoporphyrin ix methyl transferase |
| SEQ ID NO: 7443 | Nga04807.01 | 788.12 | 811.47 | uncharacterized protein |
| SEQ ID NO: 7444 | Nga04010.2 | 968.23 | 1108.62 | protein |
| SEQ ID NO: 7445 | Nga04011.02 | 136.51 | 204.59 | atp synthetase alpha chain -like |
| SEQ ID NO: 7446 | Nga04008.02 | 768.78 | 714.71 | emp24 gp25l p24 family protein |
| SEQ ID NO: 7447 | Nga04143 | 2615.97 | 3348.55 | tfiib zinc-binding family |
| SEQ ID NO: 7448 | Nga04938.2 | 648.41 | 700.47 | atp-dependent protease la |
| SEQ ID NO: 7449 | Nga03232 | 364.75 | 335.18 | ---NA--- |
| SEQ ID NO: 7450 | Nga05323.2 | 876.54 | 1084.57 | protein |
| SEQ ID NO: 7451 | Nga03225.01 | 843.56 | 1355.27 | nadph--cytochrome p450 reductase |
| SEQ ID NO: 7452 | Nga03235 | 158.46 | 166.04 | rrna methylase family |
| SEQ ID NO: 7453 | Nga03228.01 | 227.86 | 231.40 | calcium-dependent protein |
| SEQ ID NO: 7454 | Nga03237 | 69.98 | 51.35 | ---NA--- |
| SEQ ID NO: 7455 | Nga03234 | 974.27 | 902.40 | rho gtpase-activating protein 12 isoform 1 |
| SEQ ID NO: 7456 | Nga03230 | 1893.09 | 2076.53 | plastid atp adp translocase |

FIGURE 24 DN

| # | Nga model | +N rpkb | -N rpkb | GO |
|---|---|---|---|---|
| SEQ ID NO: 7457 | Nga03227 | 548.88 | 486.73 | septum site-determining protein |
| SEQ ID NO: 7458 | Nga05325.2 | 974.06 | 1018.31 | calpain 7 |
| SEQ ID NO: 7459 | Nga20719.1 | 255.14 | 341.29 | coiled-coil domain containing 76 |
| SEQ ID NO: 7460 | Nga03223.1 | 2371.74 | 2031.69 | hypothetical protein AURANDRAFT_64839 [Aureococcus anophageferens] |
| SEQ ID NO: 7461 | Nga03236.01 | 290.83 | 319.01 | ---NA--- |
| SEQ ID NO: 7462 | Nga03233.1 | 466.93 | 514.95 | blue cheese |
| SEQ ID NO: 7463 | Nga03226 | 2957.91 | 2251.74 | protein |
| SEQ ID NO: 7464 | Nga03224 | 521.59 | 512.51 | ---NA--- |
| SEQ ID NO: 7465 | Nga00175.02 | 273.43 | 269.47 | alpha beta hydrolase |
| SEQ ID NO: 7466 | Nga00183.2 | 199.22 | 194.04 | imidazoleglycerol phosphate cyclase subunit |
| SEQ ID NO: 7467 | Nga04642 | 964.13 | 850.10 | ---NA--- |
| SEQ ID NO: 7468 | Nga01813 | 109.52 | 101.45 | ---NA--- |
| SEQ ID NO: 7469 | Nga20696 | 245.54 | 261.59 | dnase domain containing 3 |
| SEQ ID NO: 7470 | Nga01814 | 69.65 | 61.98 | ---NA--- |
| SEQ ID NO: 7471 | Nga06865 | 713.25 | 788.32 | sam-dependent methyltransferase |
| SEQ ID NO: 7472 | Nga02827.2 | 233.58 | 222.41 | protein |
| SEQ ID NO: 7473 | Nga02826.2 | 58.44 | 112.54 | ---NA--- |
| SEQ ID NO: 7474 | Nga04868 | 500.00 | 314.98 | ---NA--- |
| SEQ ID NO: 7475 | Nga04867 | 814.13 | 909.16 | major facilitator superfamily mfs_1 |
| SEQ ID NO: 7476 | Nga04866 | 1381.73 | 1367.94 | protein |
| SEQ ID NO: 7477 | Nga07097.1 | 706.49 | 893.80 | gtp-binding protein |
| SEQ ID NO: 7478 | Nga07180 | 491.74 | 461.05 | ---NA--- |
| SEQ ID NO: 7479 | Nga00746.2 | 106.91 | 139.21 | kiaa1401 protein |
| SEQ ID NO: 7480 | Nga00747.02 | 1671.61 | 1771.89 | sugar transporter |
| SEQ ID NO: 7481 | Nga04733 | 72.80 | 94.63 | ribosome biogenesis protein |
| SEQ ID NO: 7482 | Nga20994 | 1113.80 | 949.18 | transport protein particle bet3 containing protein |
| SEQ ID NO: 7483 | Nga02173 | 233.99 | 205.44 | ---NA--- |
| SEQ ID NO: 7484 | Nga20714 | 21.74 | 64.76 | polyketide synthase |
| SEQ ID NO: 7485 | Nga01360.02 | 2706.83 | 2504.43 | transport protein sec61 alpha subunit |
| SEQ ID NO: 7486 | Nga01981.01 | 2059.33 | 2352.25 | ---NA--- |
| SEQ ID NO: 7487 | Nga01980.01 | 748.12 | 702.52 | alpha beta fold family protein |
| SEQ ID NO: 7488 | Nga20618.1 | 318.75 | 230.19 | ---NA--- |
| SEQ ID NO: 7489 | Nga01979 | 111.80 | 122.98 | sulphonylurea receptor 2b |
| SEQ ID NO: 7490 | Nga01978.01 | 1568.28 | 1993.29 | geranyl diphosphate synthase |
| SEQ ID NO: 7491 | Nga04049.1 | 808.42 | 789.84 | 5 -3 exoribonuclease 1 |
| SEQ ID NO: 7492 | Nga07241 | 581.03 | 773.39 | pseudouridine synthase |
| SEQ ID NO: 7493 | Nga04878 | 319.78 | 270.07 | ---NA--- |
| SEQ ID NO: 7494 | Nga04876 | 1055.59 | 1299.62 | predicted protein [Thalassiosira pseudonana CCMP1335] |
| SEQ ID NO: 7495 | Nga04877 | 1113.17 | 1850.57 | predicted protein [Thalassiosira pseudonana CCMP1335] |
| SEQ ID NO: 7496 | Nga20856 | 3621.17 | 3881.84 | conserved unknown protein [Ectocarpus siliculosus] |
| SEQ ID NO: 7497 | Nga07071.1 | 398.76 | 385.02 | tpr domain-containing protein |
| SEQ ID NO: 7498 | Nga02274 | 84.03 | 91.03 | ---NA--- |
| SEQ ID NO: 7499 | Nga02275 | 101.44 | 96.49 | predicted protein [Phaeodactylum tricornutum CCAP 1055/1] |
| SEQ ID NO: 7500 | Nga02273 | 306.35 | 300.19 | peptidase m50 |
| SEQ ID NO: 7501 | Nga06945 | 497.18 | 802.06 | peptidase u32 |
| SEQ ID NO: 7502 | Nga04704 | 515.90 | 534.60 | hypothetical protein VAS14_15709 [Vibrio angustum S14] |
| SEQ ID NO: 7503 | Nga04703 | 1522.45 | 1826.02 | diphthamide biosynthesis protein 1 |
| SEQ ID NO: 7504 | Nga01670.02 | 29.53 | 27.12 | ---NA--- |
| SEQ ID NO: 7505 | Nga01671.02 | 508.33 | 559.67 | ---NA--- |
| SEQ ID NO: 7506 | Nga04969 | 399.03 | 409.22 | protein |
| SEQ ID NO: 7507 | Nga04968 | 1894.64 | 2267.91 | ---NA--- |
| SEQ ID NO: 7508 | Nga04971 | 777.08 | 680.41 | protein |
| SEQ ID NO: 7509 | Nga04970 | 707.91 | 694.51 | protein |
| SEQ ID NO: 7510 | Nga00712.02 | 1387.79 | 1547.99 | ---NA--- |
| SEQ ID NO: 7511 | Nga04661 | 167.24 | 288.00 | conserved hypothetical protein [Phytophthora infestans T30-4] |
| SEQ ID NO: 7512 | Nga01681.02 | 1100.15 | 1061.04 | rab18 -family small gtpase |
| SEQ ID NO: 7513 | Nga01682.02 | 481.50 | 549.59 | ---NA--- |
| SEQ ID NO: 7514 | Nga01684.02 | 424.39 | 547.78 | glucosamine-6-phosphate isomerase |
| SEQ ID NO: 7515 | Nga20364 | 208.33 | 338.51 | like gtpase |
| SEQ ID NO: 7516 | Nga05768.2 | 229.01 | 219.40 | probable serca-type calcium atpase |
| SEQ ID NO: 7517 | Nga04326.01 | 428.11 | 438.60 | protein |
| SEQ ID NO: 7518 | Nga04327.01 | 178.06 | 211.06 | protein |
| SEQ ID NO: 7519 | Nga07088 | 586.21 | 728.38 | ---NA--- |

FIGURE 24 DO

| # | Nga model | +N rpkb | -N rpkb | GO |
|---|---|---|---|---|
| SEQ ID NO: 7520 | Nga20902 | 716.58 | 892.08 | 39s ribosomal protein mitochondrial-like |
| SEQ ID NO: 7521 | Nga21190 | 738.31 | 685.79 | protein |
| SEQ ID NO: 7522 | Nga02116 | 8090.45 | 8841.15 | 60s acidic ribosomal protein p0 |
| SEQ ID NO: 7523 | Nga02115.1 | 1490.61 | 1340.85 | d-galacturonic acid reductase |
| SEQ ID NO: 7524 | Nga04979 | 147.95 | 137.64 | peptidylprolyl isomerase-like 2 |
| SEQ ID NO: 7525 | Nga04978 | 525.46 | 677.17 | ---NA--- |
| SEQ ID NO: 7526 | Nga06903 | 546.64 | 676.35 | protein |
| SEQ ID NO: 7527 | Nga06904 | 768.71 | 636.19 | signal recognition particle protein |
| SEQ ID NO: 7528 | Nga00881.02 | 3447.70 | 3984.56 | succinate fumarate mitochondrial transporter |
| SEQ ID NO: 7529 | Nga00884.2 | 36.52 | 31.89 | dna replication atp-dependent helicase dna2 |
| SEQ ID NO: 7530 | Nga07163 | 458.11 | 496.24 | 6-4 photolyase |
| SEQ ID NO: 7531 | Nga04457.1 | 1102.61 | 1434.26 | protein |
| SEQ ID NO: 7532 | Nga03453.02 | 210.81 | 224.78 | structural maintenance of chromosomes protein 3 |
| SEQ ID NO: 7533 | Nga03458.02 | 2169.96 | 2504.33 | ---NA--- |
| SEQ ID NO: 7534 | Nga03946.1 | 7492.19 | 6006.61 | ---NA--- |
| SEQ ID NO: 7535 | Nga01204.02 | 11063.86 | 12214.44 | hypothetical protein THAPSDRAFT_268059 [Thalassiosira pseudonana CCMP1335] |
| SEQ ID NO: 7536 | Nga01201.02 | 567.13 | 655.45 | l-allo-threonine aldolase |
| SEQ ID NO: 7537 | Nga07193 | 446.67 | 500.09 | 4-hydroxyphenylpyruvate dioxygenase |
| SEQ ID NO: 7538 | Nga03681 | 1395.20 | 2017.21 | adhesin-like protein |
| SEQ ID NO: 7539 | Nga03679 | 1408.33 | 1211.87 | ---NA--- |
| SEQ ID NO: 7540 | Nga03680 | 2511.90 | 3301.28 | ---NA--- |
| SEQ ID NO: 7541 | Nga06852 | 285.17 | 356.00 | mitochondrial carnitine acylcarnitine carrier protein |
| SEQ ID NO: 7542 | Nga06853 | 17190.03 | 9384.65 | light-harvesting protein |
| SEQ ID NO: 7543 | Nga06854 | 660.98 | 576.49 | trna rrna methyltransferase |
| SEQ ID NO: 7544 | Nga03165.2 | 277.12 | 337.58 | glycoside hydrolase family 37 |
| SEQ ID NO: 7545 | Nga04712 | 76.99 | 74.03 | calcineurin-like phosphoesterase |
| SEQ ID NO: 7546 | Nga04845.01 | 295.92 | 316.77 | nadph dependent diflavin oxidoreductase 1 |
| SEQ ID NO: 7547 | Nga04844.01 | 224.19 | 218.08 | salicylate hydroxylase |
| SEQ ID NO: 7548 | Nga02139 | 555.16 | 613.02 | protein |
| SEQ ID NO: 7549 | Nga04370.1 | 676.10 | 700.21 | peroxisomal acyl-coenzyme a oxidase 1 |
| SEQ ID NO: 7550 | Nga01097.2 | 511.38 | 528.00 | conserved unknown protein [Ectocarpus siliculosus] |
| SEQ ID NO: 7551 | Nga04312.01 | 962.73 | 1403.02 | galactosamine (n-acetyl)-6-sulfate sulfatase-like |
| SEQ ID NO: 7552 | Nga04124.2 | 341.52 | 460.44 | transcription antitermination protein nusg |
| SEQ ID NO: 7553 | Nga04123.02 | 522.11 | 655.66 | ---NA--- |
| SEQ ID NO: 7554 | Nga00860.02 | 675.03 | 625.47 | ribosomal protein l22 |
| SEQ ID NO: 7555 | Nga06896 | 64.10 | 83.33 | ---NA--- |
| SEQ ID NO: 7556 | Nga05712.2 | 588.89 | 489.93 | cell cycle control protein 50a |
| SEQ ID NO: 7557 | Nga04753 | 471.82 | 507.60 | ---NA--- |
| SEQ ID NO: 7558 | Nga06973 | 1042.65 | 999.35 | protein |
| SEQ ID NO: 7559 | Nga04857.01 | 2722.67 | 2415.85 | signal peptidase complex catalytic subunit sec11a |
| SEQ ID NO: 7560 | Nga04858.1 | 142.86 | 152.42 | mgc83562 protein |
| SEQ ID NO: 7561 | Nga05826.2 | 245.43 | 257.05 | signal recognition particle receptor |
| SEQ ID NO: 7562 | Nga00667.2 | 895.95 | 1007.72 | lipoate-protein ligase b |
| SEQ ID NO: 7563 | Nga04269.02 | 42.42 | 52.52 | kinesin-like protein |
| SEQ ID NO: 7564 | Nga04238 | 1133.07 | 1016.76 | soluble nsf attachment protein receptor vesicle-associated membrane protein |
| SEQ ID NO: 7565 | Nga04239 | 239.51 | 263.90 | peptidase m28 family protein |
| SEQ ID NO: 7566 | Nga20577.1 | 202.70 | 146.38 | ---NA--- |
| SEQ ID NO: 7567 | Nga20401.1 | 232.88 | 204.03 | glutamate carboxypeptidase |
| SEQ ID NO: 7568 | Nga21068.1 | 156.10 | 195.51 | glutamate carboxypeptidase 2 |
| SEQ ID NO: 7569 | Nga04237 | 275.11 | 200.25 | chromosome 1 open reading frame 149 |
| SEQ ID NO: 7570 | Nga04757 | 644.40 | 598.01 | ---NA--- |
| SEQ ID NO: 7571 | Nga04756.01 | 1614.47 | 1104.61 | conserved unknown protein [Ectocarpus siliculosus] |
| SEQ ID NO: 7572 | Nga02181.1 | 494.41 | 529.25 | vesicle transport through interaction with t-snares homolog 1a |
| SEQ ID NO: 7573 | Nga02183 | 278.15 | 375.76 | protein |
| SEQ ID NO: 7574 | Nga02182 | 931.20 | 1190.30 | ---NA--- |
| SEQ ID NO: 7575 | Nga06880 | 916.31 | 754.42 | ---NA--- |
| SEQ ID NO: 7576 | Nga03072.02 | 1389.98 | 1476.54 | ---NA--- |
| SEQ ID NO: 7577 | Nga03063.02 | 1093.05 | 887.31 | ---NA--- |
| SEQ ID NO: 7578 | Nga04730.1 | 247.45 | 315.99 | ---NA--- |
| SEQ ID NO: 7579 | Nga04404.01 | 605.65 | 741.74 | alpha beta hydrolase fold-3 domain protein |
| SEQ ID NO: 7580 | Nga04403.01 | 6167.72 | 5668.70 | conserved unknown protein [Ectocarpus siliculosus] |
| SEQ ID NO: 7581 | Nga04950 | 69.48 | 66.69 | recombinase a |

FIGURE 24 DP

| # | Nga model | +N rpkb | -N rpkb | GO |
|---|---|---|---|---|
| SEQ ID NO: 7582 | Nga04949 | 2206.95 | 1947.00 | thioredoxin 1 |
| SEQ ID NO: 7583 | Nga01905 | 590.20 | 704.46 | hormone-sensitive lipase |
| SEQ ID NO: 7584 | Nga01907 | 833.33 | 844.29 | ---NA--- |
| SEQ ID NO: 7585 | Nga01908 | 592.43 | 513.87 | ---NA--- |
| SEQ ID NO: 7586 | Nga01906 | 405.11 | 383.48 | fatty acid hydroxylase-like protein |
| SEQ ID NO: 7587 | Nga04827 | 406.01 | 343.41 | trauco protein |
| SEQ ID NO: 7588 | Nga20213 | 430.46 | 392.90 | protein |
| SEQ ID NO: 7589 | Nga04500 | 34.55 | 79.01 | ---NA--- |
| SEQ ID NO: 7590 | Nga07081 | 191.49 | 212.55 | ---NA--- |
| SEQ ID NO: 7591 | Nga21120.1 | 134.62 | 160.24 | bromodomain phd finger transcription factor |
| SEQ ID NO: 7592 | Nga02104 | 446.70 | 428.89 | ---NA--- |
| SEQ ID NO: 7593 | Nga02101 | 12610.66 | 7352.70 | extrinsic protein in photosystem ii |
| SEQ ID NO: 7594 | Nga02103 | 233.33 | 238.87 | ---NA--- |
| SEQ ID NO: 7595 | Nga02102 | 728.66 | 643.32 | glutathione peroxidase |
| SEQ ID NO: 7596 | Nga07073 | 379.88 | 265.12 | ccd43_dicdi ame: full=coiled-coil domain-containing protein 43 homolog |
| SEQ ID NO: 7597 | Nga04816 | 212.45 | 271.80 | ---NA--- |
| SEQ ID NO: 7598 | Nga04273 | 1144.81 | 994.20 | protein |
| SEQ ID NO: 7599 | Nga02395 | 246.58 | 195.38 | ---NA--- |
| SEQ ID NO: 7600 | Nga06324.02 | 2670.06 | 2608.04 | dna repair protein nse1 |
| SEQ ID NO: 7601 | Nga07105 | 324.59 | 316.45 | transcription initiation protein spt5 |
| SEQ ID NO: 7602 | Nga04454 | 6146.40 | 6599.43 | protein |
| SEQ ID NO: 7603 | Nga06975 | 3611.11 | 3992.96 | ---NA--- |
| SEQ ID NO: 7604 | Nga07210 | 5.21 | 1.61 | beta tubulin |
| SEQ ID NO: 7605 | Nga07209 | 372.65 | 672.78 | protein |
| SEQ ID NO: 7606 | Nga20168.1 | 528.19 | 655.30 | protein |
| SEQ ID NO: 7607 | Nga20308.1 | 251.62 | 386.07 | protein |
| SEQ ID NO: 7608 | Nga20607.1 | 124.63 | 208.93 | e3 ubiquitin-protein ligase ubr4 |
| SEQ ID NO: 7609 | Nga01741.01 | 975.28 | 958.57 | pap fibrillin family protein |
| SEQ ID NO: 7610 | Nga01742 | 397.01 | 485.03 | ---NA--- |
| SEQ ID NO: 7611 | Nga07237 | 216.00 | 207.98 | ---NA--- |
| SEQ ID NO: 7612 | Nga05674.02 | 1894.78 | 1273.98 | light harvesting complex protein |
| SEQ ID NO: 7613 | Nga02363.1 | 196.23 | 182.86 | alpha- -glucosyltransferase alg10-a-like |
| SEQ ID NO: 7614 | Nga02362 | 194.84 | 257.96 | protein |
| SEQ ID NO: 7615 | Nga01160.02 | 45.20 | 57.53 | ---NA--- |
| SEQ ID NO: 7616 | Nga01157.02 | 962.03 | 991.06 | ---NA--- |
| SEQ ID NO: 7617 | Nga04224.02 | 7724.92 | 8189.01 | hybrid cluster protein |
| SEQ ID NO: 7618 | Nga06980 | 167.13 | 263.98 | ---NA--- |
| SEQ ID NO: 7619 | Nga20916.1 | 595.98 | 459.41 | protein |
| SEQ ID NO: 7620 | Nga07177 | 310.04 | 390.20 | acyl- -binding |
| SEQ ID NO: 7621 | Nga07197 | 446.67 | 500.09 | transcriptional family protein |
| SEQ ID NO: 7622 | Nga07041 | 311.91 | 330.63 | ---NA--- |
| SEQ ID NO: 7623 | Nga03454.02 | 651.79 | 688.18 | protein |
| SEQ ID NO: 7624 | Nga01215 | 752.94 | 777.38 | histone acetyltransferase complex component |
| SEQ ID NO: 7625 | Nga01213 | 279.56 | 319.52 | two-pore calcium channel |
| SEQ ID NO: 7626 | Nga01217 | 1031.07 | 887.40 | predicted protein [Phaeodactylum tricornutum CCAP 1055/1] |
| SEQ ID NO: 7627 | Nga01216 | 937.01 | 844.41 | protein |
| SEQ ID NO: 7628 | Nga01212 | 420.95 | 465.36 | cyclin b2 |
| SEQ ID NO: 7629 | Nga01214 | 961.69 | 965.99 | protein kinase |
| SEQ ID NO: 7630 | Nga06804 | 1372.90 | 1514.50 | wd40 repeat-containing protein |
| SEQ ID NO: 7631 | Nga00303.2 | 394.52 | 401.64 | cytochrome c biogenesis protein transmembrane region |
| SEQ ID NO: 7632 | Nga01938 | 1032.99 | 1027.33 | aldo-keto reductase |
| SEQ ID NO: 7633 | Nga01940 | 917.30 | 751.46 | n-acetyltransferase 5 |
| SEQ ID NO: 7634 | Nga06825 | 149.87 | 207.13 | ---NA--- |
| SEQ ID NO: 7635 | Nga06731.2 | 552.46 | 538.02 | sorbitol oxidase |
| SEQ ID NO: 7636 | Nga06814 | 243.00 | 296.84 | transducin family protein wd-40 repeat family protein |
| SEQ ID NO: 7637 | Nga20295.1 | 569.74 | 470.34 | jmjc domain-containing protein 4-like |
| SEQ ID NO: 7638 | Nga03692 | 918.97 | 917.66 | mitochondrial energy transfer protein |
| SEQ ID NO: 7639 | Nga21245 | 602.81 | 458.80 | protein |
| SEQ ID NO: 7640 | Nga20674 | 90.45 | 87.09 | ---NA--- |
| SEQ ID NO: 7641 | Nga21037 | 1132.96 | 1088.31 | small multidrug export protein |
| SEQ ID NO: 7642 | Nga06795 | 221.17 | 241.63 | white-brown-complex abc transporter family |
| SEQ ID NO: 7643 | Nga06794 | 396.48 | 367.81 | conserved unknown protein [Ectocarpus siliculosus] |
| SEQ ID NO: 7644 | Nga20113.1 | 756.98 | 779.68 | transcription initiation factor tfiid subunit |

FIGURE 24 DQ

| # | Nga model | +N rpkb | -N rpkb | GO |
|---|---|---|---|---|
| SEQ ID NO: 7645 | Nga03126.02 | 9669.35 | 7501.52 | protein |
| SEQ ID NO: 7646 | Nga07261 | 677.61 | 790.06 | taf5 rna polymerase tata box binding protein -associated factor |
| SEQ ID NO: 7647 | Nga02002.2 | 273.62 | 277.56 | sorting nexin 1 |
| SEQ ID NO: 7648 | Nga04671 | 104.58 | 129.80 | fad dependent oxidoreductase |
| SEQ ID NO: 7649 | Nga04672 | 215.19 | 308.52 | ---NA--- |
| SEQ ID NO: 7650 | Nga01150.2 | 730.51 | 797.24 | ll-diaminopimelate aminotransferase |
| SEQ ID NO: 7651 | Nga01154.02 | 513.59 | 528.86 | class 3 |
| SEQ ID NO: 7652 | Nga02700.02 | 1149.43 | 1155.17 | violaxanthin de-epoxidase |
| SEQ ID NO: 7653 | Nga02696.02 | 1319.67 | 1235.29 | hypothetical protein Dole_0419 [Desulfococcus oleovorans Hxd3] |
| SEQ ID NO: 7654 | Nga07037 | 970.99 | 923.30 | nitric oxide dioxygenase |
| SEQ ID NO: 7655 | Nga07038 | 649.77 | 653.93 | protein |
| SEQ ID NO: 7656 | Nga06798 | 709.68 | 454.26 | ---NA--- |
| SEQ ID NO: 7657 | Nga03334.2 | 481.17 | 513.48 | protein of hypothetical function duf482 |
| SEQ ID NO: 7658 | Nga03340.02 | 605.67 | 647.71 | mitotic checkpoint protein |
| SEQ ID NO: 7659 | Nga01884.1 | 524.67 | 603.25 | s-adenosyl-l-methionine-dependent methyltransferase domain-containing protein |
| SEQ ID NO: 7660 | Nga06406.2 | 4746.49 | 4117.57 | fatty acid elongase |
| SEQ ID NO: 7661 | Nga01885.01 | 3082.19 | 1211.39 | ---NA--- |
| SEQ ID NO: 7662 | Nga02365 | 417.18 | 403.17 | ring u-box domain-containing protein |
| SEQ ID NO: 7663 | Nga01493.02 | 10521.37 | 10349.58 | triosephosphate isomerase |
| SEQ ID NO: 7664 | Nga02189.1 | 538.65 | 556.27 | violaxanthin de-epoxidase-related protein |
| SEQ ID NO: 7665 | Nga00143.02 | 842.33 | 907.80 | conserved uncharacterized protein |
| SEQ ID NO: 7666 | Nga00149.02 | 1285.98 | 1034.00 | ---NA--- |
| SEQ ID NO: 7667 | Nga00779.02 | 5335.74 | 3704.86 | ribulose-phosphate 3-epimerase |
| SEQ ID NO: 7668 | Nga04461.01 | 698.16 | 611.27 | deah (asp-glu-ala-his) box polypeptide 35 |
| SEQ ID NO: 7669 | Nga00669.02 | 324.26 | 434.28 | sumo ligase |
| SEQ ID NO: 7670 | Nga00688.2 | 444.61 | 587.43 | protein |
| SEQ ID NO: 7671 | Nga04546.2 | 609.28 | 509.25 | tetratricopeptide repeat domain-containing protein |
| SEQ ID NO: 7672 | Nga03594.01 | 586.49 | 374.75 | protein |
| SEQ ID NO: 7673 | Nga04389 | 4671.93 | 3990.78 | ---NA--- |
| SEQ ID NO: 7674 | Nga04388 | 8332.87 | 6872.00 | ---NA--- |
| SEQ ID NO: 7675 | Nga02428 | 66.97 | 44.52 | ---NA--- |
| SEQ ID NO: 7676 | Nga02427 | 128.46 | 113.65 | protein |
| SEQ ID NO: 7677 | Nga04768.01 | 315.63 | 389.84 | ---NA--- |
| SEQ ID NO: 7678 | Nga04801 | 2199.10 | 2458.26 | protein |
| SEQ ID NO: 7679 | Nga03925.02 | 1104.40 | 1177.48 | ---NA--- |
| SEQ ID NO: 7680 | Nga03920.02 | 772.96 | 741.56 | cytochrome c oxidase assembly mitochondrial |
| SEQ ID NO: 7681 | Nga03921.2 | 4067.70 | 4165.82 | 40s ribosomal protein s7 |
| SEQ ID NO: 7682 | Nga05039 | 590.80 | 640.86 | ---NA--- |
| SEQ ID NO: 7683 | Nga05041 | 1159.82 | 1553.13 | methylcrotonyl- carboxylase biotin-containing subunit |
| SEQ ID NO: 7684 | Nga20928 | 1188.60 | 1378.18 | myc-induced nuclear antigen |
| SEQ ID NO: 7685 | Nga21153 | 87.79 | 103.36 | ---NA--- |
| SEQ ID NO: 7686 | Nga05040 | 1147.36 | 1530.53 | carboxylase:pyruvate acetyl-coa propionyl-coa |
| SEQ ID NO: 7687 | Nga03857.2 | 105.93 | 100.30 | 72 kda inositol polyphosphate 5-phosphatase-like |
| SEQ ID NO: 7688 | Nga07205 | 55.56 | 55.16 | coiled-coil domain-containing protein 65-like |
| SEQ ID NO: 7689 | Nga03696.02 | 1150.15 | 933.60 | ---NA--- |
| SEQ ID NO: 7690 | Nga07145 | 254.81 | 214.31 | nucleotidyltransferase-like protein |
| SEQ ID NO: 7691 | Nga02493.2 | 102.33 | 114.38 | glutamine |
| SEQ ID NO: 7692 | Nga02330.01 | 2612.90 | 2387.77 | nadh-ubiquinone oxidoreductase kda subunit |
| SEQ ID NO: 7693 | Nga20189.1 | 117.34 | 185.91 | conserved unknown protein [Ectocarpus siliculosus] |
| SEQ ID NO: 7694 | Nga03125.02 | 120.22 | 139.10 | ---NA--- |
| SEQ ID NO: 7695 | Nga20273 | 293.45 | 261.73 | protein |
| SEQ ID NO: 7696 | Nga05831.02 | 1936.49 | 1515.83 | pentapeptide repeat protein |
| SEQ ID NO: 7697 | Nga00081.02 | 451.40 | 552.43 | cyclin dependent kinase |
| SEQ ID NO: 7698 | Nga04797 | 412.18 | 393.31 | phosphatidylinositide phosphatase sac1 |
| SEQ ID NO: 7699 | Nga02218 | 361.78 | 287.13 | abc1 family protein |
| SEQ ID NO: 7700 | Nga00397.02 | 144.85 | 165.12 | fidgetin-like protein |
| SEQ ID NO: 7701 | Nga20048.1 | 923.93 | 819.54 | nudix hydrolase |
| SEQ ID NO: 7702 | Nga20722 | 42.65 | 46.20 | ---NA--- |
| SEQ ID NO: 7703 | Nga01484.02 | 310.61 | 434.34 | mitochondrial phosphate carrier protein 2 |
| SEQ ID NO: 7704 | Nga03849 | 612.78 | 584.38 | ---NA--- |
| SEQ ID NO: 7705 | Nga03846 | 1958.88 | 1520.66 | membrane-associated protein in eicosanoid and glutathione metabolism |
| SEQ ID NO: 7706 | Nga03848.01 | 156.46 | 132.64 | ankyrin repeat-containing protein |

FIGURE 24 DR

| # | Nga model | +N rpkb | -N rpkb | GO |
|---|---|---|---|---|
| SEQ ID NO: 7707 | Nga03845.01 | 493.55 | 405.34 | AF391290_4unknown [Branchiostoma floridae] |
| SEQ ID NO: 7708 | Nga02323.01 | 2494.69 | 2768.12 | elongation factor 1- |
| SEQ ID NO: 7709 | Nga02322 | 1582.21 | 1823.69 | protein |
| SEQ ID NO: 7710 | Nga04994.01 | 756.49 | 695.19 | stromal cell-derived factor 2 |
| SEQ ID NO: 7711 | Nga04996.01 | 1387.65 | 1414.89 | ntp pyrophosphohydrolase |
| SEQ ID NO: 7712 | Nga04995.01 | 2294.03 | 2284.03 | nad-dependent epimerase dehydratase |
| SEQ ID NO: 7713 | Nga05007 | 313.73 | 435.42 | cdp-alcohol phosphatidyltransferase family protein |
| SEQ ID NO: 7714 | Nga05008 | 1831.28 | 1903.46 | protein |
| SEQ ID NO: 7715 | Nga05009 | 101.85 | 70.21 | ---NA--- |
| SEQ ID NO: 7716 | Nga01866 | 598.30 | 732.56 | protein |
| SEQ ID NO: 7717 | Nga05105.2 | 914.78 | 737.06 | ---NA--- |
| SEQ ID NO: 7718 | Nga00965.02 | 26928.68 | 20938.84 | oxygen-evolving enhancer protein |
| SEQ ID NO: 7719 | Nga00966.2 | 738.21 | 652.14 | mitogen-activated protein kinase |
| SEQ ID NO: 7720 | Nga03311 | 221.35 | 267.99 | threonyl-trna synthetase |
| SEQ ID NO: 7721 | Nga03313 | 221.35 | 267.99 | dihydropteroate synthase |
| SEQ ID NO: 7722 | Nga03315 | 221.35 | 267.99 | acetyl-carboxylase |
| SEQ ID NO: 7723 | Nga03316 | 221.35 | 267.99 | aspartate aminotransferase |
| SEQ ID NO: 7724 | Nga03314 | 221.35 | 267.99 | glutamyl-trna amidotransferase subunit a |
| SEQ ID NO: 7725 | Nga03312 | 221.35 | 267.99 | cytidine and deoxycytidylate deaminase family protein |
| SEQ ID NO: 7726 | Nga07084 | 159.17 | 136.77 | predicted protein [Phaeodactylum tricornutum CCAP 1055/1] |
| SEQ ID NO: 7727 | Nga20511 | 175.37 | 189.97 | ---NA--- |
| SEQ ID NO: 7728 | Nga07083 | 168.04 | 125.33 | ---NA--- |
| SEQ ID NO: 7729 | Nga20479 | 277.72 | 288.70 | protein |
| SEQ ID NO: 7730 | Nga04553 | 1097.85 | 1210.19 | eukaryotic translation initiation factor 3 |
| SEQ ID NO: 7731 | Nga20092 | 338.11 | 378.47 | low-co2-inducible protein |
| SEQ ID NO: 7732 | Nga01995 | 49.65 | 53.78 | ---NA--- |
| SEQ ID NO: 7733 | Nga01994 | 2155.14 | 2136.95 | caltractin |
| SEQ ID NO: 7734 | Nga01993 | 806.14 | 814.72 | s-formylglutathione hydrolase |
| SEQ ID NO: 7735 | Nga04569 | 757.58 | 652.40 | ---NA--- |
| SEQ ID NO: 7736 | Nga20300 | 162.62 | 170.08 | methyltransferase-like protein mitochondrial-like |
| SEQ ID NO: 7737 | Nga20470 | 502.48 | 469.22 | e3 ubiquitin-protein ligase upl6 |
| SEQ ID NO: 7738 | Nga20371 | 329.60 | 489.58 | ---NA--- |
| SEQ ID NO: 7739 | Nga04568 | 414.36 | 443.29 | phosphoenolpyruvate carboxylase family protein |
| SEQ ID NO: 7740 | Nga21163.1 | 233.08 | 154.75 | myb-like dna-binding |
| SEQ ID NO: 7741 | Nga01975 | 1652.73 | 1534.90 | ---NA--- |
| SEQ ID NO: 7742 | Nga01973 | 460.09 | 491.87 | swib complex baf60b domain-containing protein |
| SEQ ID NO: 7743 | Nga04897.2 | 463.73 | 488.96 | dnaj-like protein |
| SEQ ID NO: 7744 | Nga05758 | 48.39 | 54.36 | transcription factor |
| SEQ ID NO: 7745 | Nga05761 | 755.60 | 776.30 | ---NA--- |
| SEQ ID NO: 7746 | Nga05757 | 370.27 | 376.69 | protein |
| SEQ ID NO: 7747 | Nga05756 | 1174.35 | 1042.14 | like domain-containing protein |
| SEQ ID NO: 7748 | Nga05752 | 335.44 | 498.33 | phosphoribosylamine--glycine ligase |
| SEQ ID NO: 7749 | Nga05754 | 1135.11 | 1198.99 | e3 ubiquitin-protein ligase rnf8 |
| SEQ ID NO: 7750 | Nga05753 | 504.20 | 694.85 | ---NA--- |
| SEQ ID NO: 7751 | Nga05750 | 863.79 | 826.46 | alanyl-trna synthetase |
| SEQ ID NO: 7752 | Nga05760 | 451.22 | 359.98 | ---NA--- |
| SEQ ID NO: 7753 | Nga05751 | 968.95 | 1052.15 | methylmalonyl coenzyme a mutase |
| SEQ ID NO: 7754 | Nga21045 | 596.74 | 600.89 | signal peptide peptidase |
| SEQ ID NO: 7755 | Nga20265 | 253.15 | 278.76 | predicted protein [Thalassiosira pseudonana CCMP1335] |
| SEQ ID NO: 7756 | Nga05749 | 615.18 | 617.28 | leucyl-trna synthetase |
| SEQ ID NO: 7757 | Nga05759 | 398.55 | 366.33 | myb-like dna-binding shaqkyf class family protein |
| SEQ ID NO: 7758 | Nga05755 | 17316.27 | 15548.33 | transketolase |
| SEQ ID NO: 7759 | Nga05762 | 507.64 | 560.93 | zinc-protease albf |
| SEQ ID NO: 7760 | Nga05748 | 732.66 | 702.46 | ---NA--- |
| SEQ ID NO: 7761 | Nga20370.1 | 283.02 | 324.46 | autophagy ubiquitin-activating enzyme |
| SEQ ID NO: 7762 | Nga04989.01 | 994.89 | 888.85 | protein |
| SEQ ID NO: 7763 | Nga01196.02 | 576.98 | 703.95 | cop9 signalosome complex subunit 2 |
| SEQ ID NO: 7764 | Nga00848.01 | 912.07 | 750.95 | ubiquitin-conjugating enzyme |
| SEQ ID NO: 7765 | Nga00847 | 509.43 | 562.06 | hypothetical protein AURANDRAFT_63946 [Aureococcus anophagefferens] |
| SEQ ID NO: 7766 | Nga00851.01 | 151.62 | 199.44 | ---NA--- |
| SEQ ID NO: 7767 | Nga00850.1 | 1465.64 | 1654.48 | ---NA--- |
| SEQ ID NO: 7768 | Nga00846.01 | 193.32 | 915.00 | ---NA--- |
| SEQ ID NO: 7769 | Nga00845.01 | 388.86 | 398.35 | at4g35080-like protein |

FIGURE 24 DS

| # | Nga model | +N rpkb | -N rpkb | GO |
|---|---|---|---|---|
| SEQ ID NO: 7770 | Nga00849.01 | 242.17 | 287.01 | set domain-containing protein |
| SEQ ID NO: 7771 | Nga03576.02 | 333.33 | 350.46 | 60s ribosome subunit biogenesis protein nip7 homolog |
| SEQ ID NO: 7772 | Nga06988 | 10.42 | 22.57 | ---NA--- |
| SEQ ID NO: 7773 | Nga04873.1 | 4269.75 | 3098.89 | ---NA--- |
| SEQ ID NO: 7774 | Nga04419.01 | 1411.92 | 1395.58 | trigger factor |
| SEQ ID NO: 7775 | Nga04420 | 24341.74 | 25732.61 | ---NA--- |
| SEQ ID NO: 7776 | Nga07283 | 656.86 | 727.47 | ---NA--- |
| SEQ ID NO: 7777 | Nga07282 | 258.59 | 299.64 | kynurenine-oxoglutarate transaminase |
| SEQ ID NO: 7778 | Nga04735.2 | 258.05 | 349.26 | aldehyde dehydrogenase family |
| SEQ ID NO: 7779 | Nga04088 | 208.59 | 250.32 | ---NA--- |
| SEQ ID NO: 7780 | Nga01508.2 | 2612.36 | 3093.51 | threonine aldolase |
| SEQ ID NO: 7781 | Nga04090 | 1417.81 | 1758.64 | threonine aldolase |
| SEQ ID NO: 7782 | Nga01081 | 223.50 | 215.49 | duf1253 domain-containing protein |
| SEQ ID NO: 7783 | Nga01080 | 1151.73 | 1030.43 | conserved unknown protein [Ectocarpus siliculosus] |
| SEQ ID NO: 7784 | Nga01083 | 4160.56 | 3647.33 | stress-induced protein sti1 |
| SEQ ID NO: 7785 | Nga01082 | 2228.90 | 1823.67 | amino acid dehydrogenase family protein |
| SEQ ID NO: 7786 | Nga01084 | 194.33 | 223.66 | dhhc zinc finger domain containing protein |
| SEQ ID NO: 7787 | Nga04683 | 169.40 | 134.17 | ---NA--- |
| SEQ ID NO: 7788 | Nga02247.2 | 695.04 | 664.81 | histone deacetylase |
| SEQ ID NO: 7789 | Nga04686 | 279.07 | 214.13 | chloride channel protein 7 |
| SEQ ID NO: 7790 | Nga04682 | 1089.17 | 1282.42 | glutathione reductase |
| SEQ ID NO: 7791 | Nga04685 | 280.25 | 227.00 | monovalent cation:proton antiporter1 family |
| SEQ ID NO: 7792 | Nga20446 | 172.13 | 216.65 | predicted protein [Thalassiosira pseudonana CCMP1335] |
| SEQ ID NO: 7793 | Nga01595 | 215.69 | 252.95 | serine threonine protein kinase |
| SEQ ID NO: 7794 | Nga01596 | 212.45 | 261.88 | mitogen activated protein kinase-like protein |
| SEQ ID NO: 7795 | Nga01593 | 597.08 | 623.68 | aspartylglucosaminidase |
| SEQ ID NO: 7796 | Nga01594 | 1463.39 | 1319.91 | proteasome subunit |
| SEQ ID NO: 7797 | Nga01871 | 2281.25 | 2286.07 | ---NA--- |
| SEQ ID NO: 7798 | Nga01872 | 171.25 | 168.48 | 2-phosphodiesterase 12- partial |
| SEQ ID NO: 7799 | Nga04537 | 76.50 | 102.60 | u3 small nucleolar rna-associated protein 10 and nuc211 domain-containing protein |
| SEQ ID NO: 7800 | Nga02484.2 | 8670.94 | 10558.30 | Aardvark [Ectocarpus siliculosus] |
| SEQ ID NO: 7801 | Nga04666 | 257.73 | 247.54 | protein |
| SEQ ID NO: 7802 | Nga01620 | 7413.76 | 6265.04 | beta-ig-h3 fasciclin |
| SEQ ID NO: 7803 | Nga01621 | 87.41 | 141.22 | adaptor protein kanadaptin |
| SEQ ID NO: 7804 | Nga01619 | 339.74 | 361.30 | rna polymerase ii associated protein 2 |
| SEQ ID NO: 7805 | Nga01419.2 | 357.51 | 406.42 | cullin-associated nedd8-dissociated protein 1 |
| SEQ ID NO: 7806 | Nga01418.02 | 692.90 | 666.08 | protein |
| SEQ ID NO: 7807 | Nga20421.1 | 323.89 | 350.85 | ---NA--- |
| SEQ ID NO: 7808 | Nga01579 | 312.29 | 433.65 | ---NA--- |
| SEQ ID NO: 7809 | Nga01582.01 | 532.14 | 464.71 | ---NA--- |
| SEQ ID NO: 7810 | Nga03017.2 | 404.03 | 455.47 | protein |
| SEQ ID NO: 7811 | Nga01580 | 287.48 | 331.09 | splicing factor 3a |
| SEQ ID NO: 7812 | Nga04279 | 355.04 | 307.34 | ---NA--- |
| SEQ ID NO: 7813 | Nga04280 | 5.21 | 16.93 | ---NA--- |
| SEQ ID NO: 7814 | Nga00267.02 | 818.78 | 835.86 | px domain containing protein |
| SEQ ID NO: 7815 | Nga00264.02 | 515.77 | 588.97 | ccr4-not transcription complex subunit 10 |
| SEQ ID NO: 7816 | Nga20976.1 | 455.05 | 416.63 | conserved hypothetical protein [Phytophthora infestans T30-4] |
| SEQ ID NO: 7817 | Nga04254 | 4281.71 | 3874.40 | 30s ribosomal protein s21 |
| SEQ ID NO: 7818 | Nga04479 | 161.62 | 166.56 | protein |
| SEQ ID NO: 7819 | Nga04480 | 128.21 | 126.72 | protein |
| SEQ ID NO: 7820 | Nga05005 | 980.23 | 1531.01 | ---NA--- |
| SEQ ID NO: 7821 | Nga04872 | 1396.32 | 1556.02 | ---NA--- |
| SEQ ID NO: 7822 | Nga02127 | 1599.40 | 2262.83 | protein |
| SEQ ID NO: 7823 | Nga02128.1 | 271.83 | 466.39 | ---NA--- |
| SEQ ID NO: 7824 | Nga01898.01 | 25470.99 | 15573.13 | light-harvesting protein |
| SEQ ID NO: 7825 | Nga01899.1 | 238.90 | 301.24 | autophagy-related protein 7 |
| SEQ ID NO: 7826 | Nga01900.01 | 3330.41 | 3329.94 | protein |
| SEQ ID NO: 7827 | Nga03733.1 | 793.96 | 825.93 | obtusifoliol 14-alpha demethylase |
| SEQ ID NO: 7828 | Nga03732 | 827.66 | 708.65 | signal peptidase i |
| SEQ ID NO: 7829 | Nga02805.2 | 1504.93 | 1312.22 | uncharacterized fam18-like protein cg5021 |
| SEQ ID NO: 7830 | Nga03146.2 | 107.14 | 107.46 | ---NA--- |
| SEQ ID NO: 7831 | Nga03152.2 | 319.58 | 293.59 | hydrolase-like protein |
| SEQ ID NO: 7832 | Nga21117 | 126.69 | 118.94 | protein |

FIGURE 24 DT

| # | Nga model | +N rpkb | -N rpkb | GO |
|---|---|---|---|---|
| SEQ ID NO: 7833 | Nga20550 | 160.00 | 205.81 | ---NA--- |
| SEQ ID NO: 7834 | Nga04380 | 5927.89 | 6519.30 | ---NA--- |
| SEQ ID NO: 7835 | Nga04517 | 571.63 | 460.95 | peptidyl-prolyl cis-trans isomerase b precursor |
| SEQ ID NO: 7836 | Nga06678.1 | 3382.79 | 2908.75 | protein |
| SEQ ID NO: 7837 | Nga20649 | 131.94 | 173.02 | ---NA--- |
| SEQ ID NO: 7838 | Nga20018 | 48.00 | 60.66 | ---NA--- |
| SEQ ID NO: 7839 | Nga06682 | 3057.97 | 2960.84 | unnamed protein product [Blastocystis hominis] |
| SEQ ID NO: 7840 | Nga03817.02 | 595.45 | 658.24 | soluble pyridine nucleotide transhydrogenase |
| SEQ ID NO: 7841 | Nga06679 | 612.01 | 632.57 | nuclear cap-binding protein subunit 1 |
| SEQ ID NO: 7842 | Nga03818.02 | 401.53 | 394.66 | cop9 complex subunit 7a |
| SEQ ID NO: 7843 | Nga06677 | 765.06 | 883.40 | nitrite transporter nar1 |
| SEQ ID NO: 7844 | Nga06681 | 558.68 | 443.80 | protein |
| SEQ ID NO: 7845 | Nga06683.1 | 417.18 | 427.24 | ufm1-specific protease |
| SEQ ID NO: 7846 | Nga06676 | 1832.86 | 1118.11 | protein |
| SEQ ID NO: 7847 | Nga03820.2 | 594.71 | 774.65 | predicted protein [Thalassiosira pseudonana CCMP1335] |
| SEQ ID NO: 7848 | Nga04907 | 474.78 | 532.11 | ran gtpase activating protein 1 |
| SEQ ID NO: 7849 | Nga20009 | 553.01 | 563.52 | dual-specificity tyrosine- -phosphorylation regulated kinase 1b |
| SEQ ID NO: 7850 | Nga02198.2 | 267.59 | 327.20 | inositol polyphosphate 5-phosphatase ocrl-1 |
| SEQ ID NO: 7851 | Nga01848.02 | 817.03 | 538.20 | ---NA--- |
| SEQ ID NO: 7852 | Nga01689 | 3811.04 | 4211.57 | sigma 54 modulation protein ribosomal protein s30ea |
| SEQ ID NO: 7853 | Nga01688 | 515.24 | 465.10 | protein |
| SEQ ID NO: 7854 | Nga01691 | 157.94 | 152.49 | ribosomal pseudouridine |
| SEQ ID NO: 7855 | Nga01690 | 1668.47 | 2127.86 | sigma 54 modulation protein ribosomal protein s30ea |
| SEQ ID NO: 7856 | Nga01692 | 357.04 | 377.51 | ---NA--- |
| SEQ ID NO: 7857 | Nga21095 | 352.59 | 338.25 | major facilitator superfamily |
| SEQ ID NO: 7858 | Nga01734 | 219.88 | 177.32 | 3-dehydroquinate synthase |
| SEQ ID NO: 7859 | Nga00788 | 1562.80 | 1582.11 | sulfate transporter |
| SEQ ID NO: 7860 | Nga00789 | 588.59 | 442.84 | protein |
| SEQ ID NO: 7861 | Nga01413 | 390.90 | 272.62 | protein |
| SEQ ID NO: 7862 | Nga01415 | 331.89 | 333.66 | ---NA--- |
| SEQ ID NO: 7863 | Nga01414 | 186.44 | 190.59 | drug metabolite transporter superfamily |
| SEQ ID NO: 7864 | Nga20630 | 74.20 | 103.35 | phytoene dehydrogenase |
| SEQ ID NO: 7865 | Nga01412 | 9647.34 | 10464.74 | protein |
| SEQ ID NO: 7866 | Nga07004 | 1041.21 | 1174.87 | h aca ribonucleoprotein complex subunit 1 |
| SEQ ID NO: 7867 | Nga03397.2 | 957.21 | 1058.84 | ribulose-phosphate 3-epimerase |
| SEQ ID NO: 7868 | Nga20136 | 556.89 | 660.97 | glycine oxidase |
| SEQ ID NO: 7869 | Nga07052 | 212.70 | 354.20 | ---NA--- |
| SEQ ID NO: 7870 | Nga06952 | 132.13 | 201.68 | ---NA--- |
| SEQ ID NO: 7871 | Nga03770 | 1866.04 | 2662.90 | ---NA--- |
| SEQ ID NO: 7872 | Nga04630 | 418.70 | 473.36 | fatty acid desaturase |
| SEQ ID NO: 7873 | Nga06739.2 | 1392.58 | 1334.65 | dihydroceramide delta -desaturase |
| SEQ ID NO: 7874 | Nga04550 | 2787.04 | 2693.04 | histone h3 |
| SEQ ID NO: 7875 | Nga04549 | 295.00 | 337.61 | mitochondrial inner membrane protease subunit 1-like |
| SEQ ID NO: 7876 | Nga20987 | 301.08 | 205.78 | ---NA--- |
| SEQ ID NO: 7877 | Nga20391 | 193.55 | 244.60 | wd repeat domain 61 |
| SEQ ID NO: 7878 | Nga21064 | 131.81 | 139.67 | ---NA--- |
| SEQ ID NO: 7879 | Nga04016 | 120.55 | 207.74 | conserved unknown protein [Ectocarpus siliculosus] |
| SEQ ID NO: 7880 | Nga02342 | 94.86 | 85.47 | zinc-binding dehydrogenase |
| SEQ ID NO: 7881 | Nga04346.01 | 876.42 | 824.31 | dna replication complex gins protein psf3 |
| SEQ ID NO: 7882 | Nga04347 | 207.65 | 221.97 | u2 snrnp component ist3 |
| SEQ ID NO: 7883 | Nga04100 | 72.00 | 58.74 | conserved domain protein |
| SEQ ID NO: 7884 | Nga01685 | 424.39 | 547.78 | ---NA--- |
| SEQ ID NO: 7885 | Nga04435 | 185.33 | 271.85 | ---NA--- |
| SEQ ID NO: 7886 | Nga02201.2 | 474.15 | 494.31 | gpn-loop gtpase 2 |
| SEQ ID NO: 7887 | Nga04695 | 844.91 | 1040.61 | ---NA--- |
| SEQ ID NO: 7888 | Nga04694 | 56.79 | 101.64 | ---NA--- |
| SEQ ID NO: 7889 | Nga04692 | 50.96 | 71.30 | ---NA--- |
| SEQ ID NO: 7890 | Nga04693 | 510.52 | 720.79 | expulsion defective family member (exp-2) |
| SEQ ID NO: 7891 | Nga04020.02 | 723.88 | 825.90 | short chain dehydrogenase reductase family |
| SEQ ID NO: 7892 | Nga02071 | 201.14 | 178.83 | ---NA--- |
| SEQ ID NO: 7893 | Nga02070 | 668.07 | 732.02 | protein |
| SEQ ID NO: 7894 | Nga02073 | 257.98 | 249.20 | ---NA--- |
| SEQ ID NO: 7895 | Nga02072 | 23646.06 | 17587.78 | ---NA--- |
| SEQ ID NO: 7896 | Nga04838.1 | 179.49 | 147.21 | ---NA--- |

FIGURE 24 DU

| # | Nga model | +N rpkb | -N rpkb | GO |
|---|---|---|---|---|
| SEQ ID NO: 7897 | Nga01546.2 | 686.04 | 739.21 | ---NA--- |
| SEQ ID NO: 7898 | Nga04830 | 35.21 | 61.03 | ---NA--- |
| SEQ ID NO: 7899 | Nga03988 | 633.15 | 584.30 | ---NA--- |
| SEQ ID NO: 7900 | Nga03986 | 976.83 | 784.28 | conserved hypothetical protein |
| SEQ ID NO: 7901 | Nga03987 | 288.85 | 332.52 | |
| SEQ ID NO: 7902 | Nga20979 | 686.24 | 770.15 | hit-type zinc finger protein |
| SEQ ID NO: 7903 | Nga03985 | 713.93 | 578.67 | myb-like dna-binding |
| SEQ ID NO: 7904 | Nga20324 | 59.21 | 117.59 | ---NA--- |
| SEQ ID NO: 7905 | Nga03989 | 822.53 | 1059.82 | selenocysteine-specific elongation factor |
| SEQ ID NO: 7906 | Nga04772 | 445.90 | 507.88 | ---NA--- |
| SEQ ID NO: 7907 | Nga07054.2 | 473.03 | 488.39 | ---NA--- |
| SEQ ID NO: 7908 | Nga04771 | 225.98 | 181.35 | predicted protein [Micromonas pusilla CCMP1545] |
| SEQ ID NO: 7909 | Nga04250 | 421.05 | 541.62 | ---NA--- |
| SEQ ID NO: 7910 | Nga03715 | 593.50 | 714.33 | ---NA--- |
| SEQ ID NO: 7911 | Nga03712 | 667.32 | 753.19 | taurine dioxygenase |
| SEQ ID NO: 7912 | Nga20222 | 217.35 | 198.42 | methyltransferase like 8 |
| SEQ ID NO: 7913 | Nga03714 | 1523.95 | 1741.61 | ---NA--- |
| SEQ ID NO: 7914 | Nga03713 | 48.03 | 73.37 | urease |
| SEQ ID NO: 7915 | Nga20144 | 360.43 | 338.10 | morn repeat-containing protein |
| SEQ ID NO: 7916 | Nga04749 | 1111.11 | 1152.01 | ---NA--- |
| SEQ ID NO: 7917 | Nga07264 | 31.86 | 20.20 | inorganic phosphate |
| SEQ ID NO: 7918 | Nga07033 | 113.82 | 296.49 | ---NA--- |
| SEQ ID NO: 7919 | Nga04342.02 | 517.79 | 528.12 | dna-directed rna polymerases and iii kda polypeptide |
| SEQ ID NO: 7920 | Nga04343.02 | 18888.24 | 14347.11 | ---NA--- |
| SEQ ID NO: 7921 | Nga01725 | 244.05 | 267.58 | 6-pyruvoyl tetrahydropterin synthase |
| SEQ ID NO: 7922 | Nga01726 | 166.89 | 134.86 | beta-lactamase |
| SEQ ID NO: 7923 | Nga01724 | 167.35 | 202.65 | ap4a phosphorylase ii |
| SEQ ID NO: 7924 | Nga21260 | 126.48 | 119.88 | protein |
| SEQ ID NO: 7925 | Nga04586 | 1903.95 | 2170.40 | ---NA--- |
| SEQ ID NO: 7926 | Nga06887 | 238.64 | 255.57 | zinc finger ran-binding domain-containing protein 3 |
| SEQ ID NO: 7927 | Nga06888 | 213.81 | 182.70 | bis(5 -adenosyl)-triphosphatase |
| SEQ ID NO: 7928 | Nga01188 | 113.06 | 145.70 | conserved unknown protein [Ectocarpus siliculosus] |
| SEQ ID NO: 7929 | Nga01189 | 270.33 | 299.43 | alanine--glyoxylate transaminase |
| SEQ ID NO: 7930 | Nga20239 | 322.96 | 298.49 | aminotransferase class-iii |
| SEQ ID NO: 7931 | Nga03398.02 | 2625.09 | 3123.45 | ---NA--- |
| SEQ ID NO: 7932 | Nga03395.02 | 617.11 | 421.31 | alkaline phosphatase d |
| SEQ ID NO: 7933 | Nga06949 | 28.04 | 60.74 | ---NA--- |
| SEQ ID NO: 7934 | Nga01718.01 | 1024.82 | 1024.72 | glutathione s-transferase |
| SEQ ID NO: 7935 | Nga01716 | 6781.52 | 6113.98 | -epimerase 4-reductase |
| SEQ ID NO: 7936 | Nga01717 | 4875.75 | 4644.83 | protein |
| SEQ ID NO: 7937 | Nga20050 | 281.76 | 207.13 | vacuolar amino acid transporter 6 |
| SEQ ID NO: 7938 | Nga04455 | 6215.19 | 6309.40 | 60s ribosomal protein l31 |
| SEQ ID NO: 7939 | Nga05471 | 209.82 | 257.91 | lipoate-protein ligase b |
| SEQ ID NO: 7940 | Nga05473 | 194.69 | 92.67 | ---NA--- |
| SEQ ID NO: 7941 | Nga05479.01 | 231.58 | 228.05 | ---NA--- |
| SEQ ID NO: 7942 | Nga05475 | 406.14 | 435.33 | short-chain dehydrogenase reductase sdr |
| SEQ ID NO: 7943 | Nga05472 | 4134.40 | 4151.57 | conserved unknown protein [Ectocarpus siliculosus] |
| SEQ ID NO: 7944 | Nga05469 | 412.30 | 455.25 | peptide methionine sulfoxide reductase |
| SEQ ID NO: 7945 | Nga05474 | 444.44 | 404.41 | heat shock protein atpase subunit |
| SEQ ID NO: 7946 | Nga05476 | 644.96 | 725.51 | pyridoxamine phosphate |
| SEQ ID NO: 7947 | Nga05477 | 487.91 | 590.15 | atp-dependent protease atp-binding subunit |
| SEQ ID NO: 7948 | Nga05468 | 167.21 | 232.12 | uncharacterized protein yjr111c |
| SEQ ID NO: 7949 | Nga05470 | 2328.47 | 2825.37 | domain-containing protein |
| SEQ ID NO: 7950 | Nga02423.1 | 477.62 | 861.12 | methylenetetrahydrofolate dehydrogenase |
| SEQ ID NO: 7951 | Nga02425.01 | 694.25 | 646.35 | er lumen protein retaining receptor |
| SEQ ID NO: 7952 | Nga06601.2 | 394.31 | 433.70 | ribonucleoside triphosphate reductase |
| SEQ ID NO: 7953 | Nga04701 | 177.72 | 227.76 | ---NA--- |
| SEQ ID NO: 7954 | Nga04464 | 202.49 | 236.22 | conserved unknown protein [Ectocarpus siliculosus] |
| SEQ ID NO: 7955 | Nga02088.01 | 2302.26 | 2571.78 | protein |
| SEQ ID NO: 7956 | Nga21060 | 449.75 | 535.37 | protein |
| SEQ ID NO: 7957 | Nga03623 | 151.30 | 104.20 | ferroxidase |
| SEQ ID NO: 7958 | Nga07044 | 688.52 | 414.35 | histone h4 |
| SEQ ID NO: 7959 | Nga02813.02 | 226.29 | 307.50 | protein |
| SEQ ID NO: 7960 | Nga02819.02 | 385.71 | 330.13 | ---NA--- |

FIGURE 24 DV

| # | Nga model | +N rpkb | -N rpkb | GO |
|---|---|---|---|---|
| SEQ ID NO: 7961 | Nga02820.2 | 871.08 | 761.16 | ---NA--- |
| SEQ ID NO: 7962 | Nga02817.02 | 1953.22 | 1704.03 | polymerase ii (dna directed) polypeptide e |
| SEQ ID NO: 7963 | Nga01057.02 | 382.95 | 325.41 | protein |
| SEQ ID NO: 7964 | Nga04452.01 | 3876.38 | 5172.26 | ---NA--- |
| SEQ ID NO: 7965 | Nga01642 | 295.88 | 405.71 | ---NA--- |
| SEQ ID NO: 7966 | Nga01266.02 | 264.81 | 275.18 | dhhc zinc finger domain-containing protein |
| SEQ ID NO: 7967 | Nga01990 | 2460.18 | 2358.19 | ---NA--- |
| SEQ ID NO: 7968 | Nga03564 | 909.60 | 843.03 | ---NA--- |
| SEQ ID NO: 7969 | Nga03560 | 1356.82 | 1317.11 | ubiquitin-like protein nedd8 |
| SEQ ID NO: 7970 | Nga03563 | 628.32 | 642.27 | ---NA--- |
| SEQ ID NO: 7971 | Nga20170 | 269.84 | 302.88 | conserved unknown protein [Ectocarpus siliculosus] |
| SEQ ID NO: 7972 | Nga03565 | 495.31 | 734.69 | ribosomal protein l11 methyltransferase |
| SEQ ID NO: 7973 | Nga03561 | 184.50 | 206.85 | atp phosphoribosyltransferase |
| SEQ ID NO: 7974 | Nga20619 | 97.87 | 106.02 | tetratricopeptide repeat protein |
| SEQ ID NO: 7975 | Nga20504 | 60.84 | 94.73 | ---NA--- |
| SEQ ID NO: 7976 | Nga21233 | 67.01 | 117.26 | tpr domain-containing protein |
| SEQ ID NO: 7977 | Nga03562 | 954.35 | 1437.10 | 30s ribosomal protein s9 |
| SEQ ID NO: 7978 | Nga07244 | 475.47 | 380.15 | ---NA--- |
| SEQ ID NO: 7979 | Nga07245 | 287.15 | 229.84 | mmpl domain protein |
| SEQ ID NO: 7980 | Nga04162.02 | 351.85 | 272.24 | ---NA--- |
| SEQ ID NO: 7981 | Nga04719 | 61.47 | 35.85 | ---NA--- |
| SEQ ID NO: 7982 | Nga04720 | 77.80 | 109.07 | ---NA--- |
| SEQ ID NO: 7983 | Nga04261.1 | 719.39 | 1022.90 | adenosine deaminase |
| SEQ ID NO: 7984 | Nga00028.02 | 32.92 | 84.70 | ---NA--- |
| SEQ ID NO: 7985 | Nga00029.02 | 164.38 | 136.85 | mmp37-like mitochondrial precursor |
| SEQ ID NO: 7986 | Nga00923 | 567.52 | 549.29 | nitrilase member 2 |
| SEQ ID NO: 7987 | Nga00920 | 765.38 | 700.92 | conserved unknown protein [Ectocarpus siliculosus] |
| SEQ ID NO: 7988 | Nga00919 | 1813.44 | 1669.20 | long-chain acyl- synthetase 7 |
| SEQ ID NO: 7989 | Nga00924 | 4435.03 | 4967.37 | ribosomal protein rpl30 |
| SEQ ID NO: 7990 | Nga00922 | 169.08 | 99.43 | nuclear prelamin a recognition factor-like protein |
| SEQ ID NO: 7991 | Nga00921 | 916.21 | 895.79 | protein |
| SEQ ID NO: 7992 | Nga01152.02 | 187.30 | 257.91 | ---NA--- |
| SEQ ID NO: 7993 | Nga06934 | 205.61 | 245.68 | amino acid transport protein |
| SEQ ID NO: 7994 | Nga21206 | 138.24 | 127.44 | predicted protein [Phaeodactylum tricornutum CCAP 1055/1] |
| SEQ ID NO: 7995 | Nga21111 | 339.39 | 481.10 | expressed unknown protein [Ectocarpus siliculosus] |
| SEQ ID NO: 7996 | Nga02665.02 | 6477.17 | 6628.01 | conserved hypothetical protein [Phytophthora infestans T30-4] |
| SEQ ID NO: 7997 | Nga01346 | 134.22 | 149.48 | myotubularin related protein 3 |
| SEQ ID NO: 7998 | Nga00257.2 | 709.01 | 743.00 | ---NA--- |
| SEQ ID NO: 7999 | Nga01349 | 1020.83 | 1145.29 | protein |
| SEQ ID NO: 8000 | Nga01348 | 13756.91 | 15883.44 | ---NA--- |
| SEQ ID NO: 8001 | Nga01350 | 26779.69 | 27727.40 | ---NA--- |
| SEQ ID NO: 8002 | Nga01347 | 275.30 | 293.83 | ---NA--- |
| SEQ ID NO: 8003 | Nga04505.01 | 1002.05 | 1358.48 | ankyrin |
| SEQ ID NO: 8004 | Nga04504.01 | 4897.14 | 5041.69 | 3-ketoacyl- mitochondrial |
| SEQ ID NO: 8005 | Nga02057 | 306.78 | 257.23 | 5-methyltetrahydropteroyltriglutamate--homocysteine s-methyltransferase |
| SEQ ID NO: 8006 | Nga02058 | 310.10 | 271.75 | ---NA--- |
| SEQ ID NO: 8007 | Nga04374 | 1280.00 | 1335.99 | protein |
| SEQ ID NO: 8008 | Nga04013.1 | 410.44 | 447.00 | peroxisome biosynthesis protein (pas1 peroxin-1) |
| SEQ ID NO: 8009 | Nga03870 | 146.48 | 213.65 | alpha beta domain protein |
| SEQ ID NO: 8010 | Nga03872 | 422.74 | 375.82 | uncharacterized protein hp_0274 |
| SEQ ID NO: 8011 | Nga03871 | 453.37 | 408.66 | ---NA--- |
| SEQ ID NO: 8012 | Nga05011 | 1133.76 | 917.64 | translation initiation factor 2 alpha |
| SEQ ID NO: 8013 | Nga05010 | 1880.07 | 2385.69 | activating transcription factor 6 |
| SEQ ID NO: 8014 | Nga05012 | 1356.81 | 1362.94 | eukaryotic translation initiation factor subunit 1 alpha |
| SEQ ID NO: 8015 | Nga05774.2 | 266.18 | 279.07 | protein |
| SEQ ID NO: 8016 | Nga03919.02 | 883.08 | 870.36 | like protein |
| SEQ ID NO: 8017 | Nga03917.02 | 409.64 | 453.68 | structural maintenance of chromosomes 1 |
| SEQ ID NO: 8018 | Nga02242.02 | 502.99 | 507.89 | drug metabolite transporter superfamily |
| SEQ ID NO: 8019 | Nga04679 | 140.74 | 176.53 | ---NA--- |
| SEQ ID NO: 8020 | Nga04477 | 7022.60 | 7652.60 | large subunit ribosomal protein l10e |
| SEQ ID NO: 8021 | Nga01713 | 130.26 | 158.47 | mutl homolog colon nonpolyposis type 2 ( coli) |
| SEQ ID NO: 8022 | Nga01714 | 230.28 | 150.35 | protein |
| SEQ ID NO: 8023 | Nga06240.02 | 938.43 | 1181.71 | glucose-methanol-choline oxidoreductase |

FIGURE 24 DW

| # | Nga model | +N rpkb | -N rpkb | GO |
|---|---|---|---|---|
| SEQ ID NO: 8024 | Nga04308 | 1169.30 | 1191.21 | small gtp-binding protein |
| SEQ ID NO: 8025 | Nga00448.02 | 26082.30 | 12065.79 | light harvesting complex protein |
| SEQ ID NO: 8026 | Nga07220 | 1185.86 | 1199.22 | glycosyl bnr protein |
| SEQ ID NO: 8027 | Nga01460.01 | 97.11 | 36.96 | riken cdna 6720467c03 isoform cra_a |
| SEQ ID NO: 8028 | Nga21224.1 | 93.62 | 69.14 | conserved unknown protein [Ectocarpus siliculosus] |
| SEQ ID NO: 8029 | Nga01459.01 | 828.36 | 775.11 | methionine aminopeptidase |
| SEQ ID NO: 8030 | Nga01458.01 | 7968.76 | 9166.47 | delta-9 acyl-desaturase |
| SEQ ID NO: 8031 | Nga01457.01 | 2910.32 | 2344.79 | ---NA--- |
| SEQ ID NO: 8032 | Nga20764.1 | 329.59 | 273.85 | tubulin tyrosine ligase |
| SEQ ID NO: 8033 | Nga20162 | 295.51 | 380.13 | protein |
| SEQ ID NO: 8034 | Nga20819 | 269.04 | 356.40 | conserved unknown protein [Ectocarpus siliculosus] |
| SEQ ID NO: 8035 | Nga01630 | 623.03 | 538.20 | splicing factor 3 subunit |
| SEQ ID NO: 8036 | Nga20191 | 400.53 | 355.83 | kinesin family member 2c |
| SEQ ID NO: 8037 | Nga01970 | 189.91 | 163.93 | ---NA--- |
| SEQ ID NO: 8038 | Nga01969 | 10683.75 | 11280.18 | ribosomal protein l19 |
| SEQ ID NO: 8039 | Nga05775.2 | 126.41 | 162.74 | rep helicase |
| SEQ ID NO: 8040 | Nga04786.01 | 69.89 | 75.71 | ---NA--- |
| SEQ ID NO: 8041 | Nga00735 | 652.75 | 432.21 | ---NA--- |
| SEQ ID NO: 8042 | Nga00736 | 151.79 | 48.36 | ---NA--- |
| SEQ ID NO: 8043 | Nga04113 | 106.71 | 142.86 | low quality protein: uncharacterized protein kiaa0564-like |
| SEQ ID NO: 8044 | Nga04111 | 2798.80 | 2630.40 | ubiquitin family protein |
| SEQ ID NO: 8045 | Nga20114 | 580.61 | 541.88 | polymyositis scleroderma autoantigen 1 |
| SEQ ID NO: 8046 | Nga04112 | 1040.75 | 1186.22 | dihydropteridine reductase |
| SEQ ID NO: 8047 | Nga20565 | 92.49 | 62.61 | ---NA--- |
| SEQ ID NO: 8048 | Nga03834 | 184.19 | 158.91 | wsc domain containing 1 |
| SEQ ID NO: 8049 | Nga03833 | 256.16 | 220.12 | chaperone protein |
| SEQ ID NO: 8050 | Nga06812 | 3180.74 | 4098.64 | ---NA--- |
| SEQ ID NO: 8051 | Nga20589 | 140.85 | 91.54 | cathepsin c |
| SEQ ID NO: 8052 | Nga06608 | 437.13 | 546.94 | protein |
| SEQ ID NO: 8053 | Nga06610 | 4206.79 | 5004.96 | 60s ribosomal protein l3 |
| SEQ ID NO: 8054 | Nga20729 | 345.38 | 360.31 | protein transport protein sec24b-like |
| SEQ ID NO: 8055 | Nga06611 | 239.32 | 370.34 | ---NA--- |
| SEQ ID NO: 8056 | Nga06609 | 24.69 | 13.37 | ---NA--- |
| SEQ ID NO: 8057 | Nga03531 | 176.74 | 189.81 | ---NA--- |
| SEQ ID NO: 8058 | Nga03533 | 183.80 | 276.71 | voltage-gated ion channel superfamily |
| SEQ ID NO: 8059 | Nga03529 | 870.65 | 705.99 | acyl- -binding protein |
| SEQ ID NO: 8060 | Nga03532 | 254.72 | 235.04 | ---NA--- |
| SEQ ID NO: 8061 | Nga03530 | 125.00 | 126.81 | ---NA--- |
| SEQ ID NO: 8062 | Nga06884.1 | 304.21 | 253.28 | soluble pyridine nucleotide transhydrogenase |
| SEQ ID NO: 8063 | Nga05183.2 | 314.78 | 411.62 | protein |
| SEQ ID NO: 8064 | Nga06883 | 320.63 | 281.98 | soluble pyridine nucleotide transhydrogenase |
| SEQ ID NO: 8065 | Nga02260 | 146.50 | 262.18 | ---NA--- |
| SEQ ID NO: 8066 | Nga02259 | 216.56 | 183.99 | derlin (degradation in endoplasmic reticulum protein ) (der1-like protein) |
| SEQ ID NO: 8067 | Nga02261 | 925.61 | 657.81 | ---NA--- |
| SEQ ID NO: 8068 | Nga02258 | 3750.68 | 2491.73 | hypothetical protein [Gracilariopsis andersonii] |
| SEQ ID NO: 8069 | Nga04427 | 923.08 | 999.91 | acylphosphatase erythrocyte type isoform cra_a |
| SEQ ID NO: 8070 | Nga04783 | 76.92 | 77.15 | ---NA--- |
| SEQ ID NO: 8071 | Nga04782 | 211.59 | 222.83 | methyltransferase family |
| SEQ ID NO: 8072 | Nga01030.02 | 2352.40 | 2701.89 | ---NA--- |
| SEQ ID NO: 8073 | Nga01951 | 208.89 | 163.69 | anaphase promoting complex subunit 3 |
| SEQ ID NO: 8074 | Nga04355 | 78.63 | 96.29 | ---NA--- |
| SEQ ID NO: 8075 | Nga02356 | 260.45 | 306.51 | ---NA--- |
| SEQ ID NO: 8076 | Nga02355 | 776.14 | 539.22 | protein-tyrosine low molecular weight |
| SEQ ID NO: 8077 | Nga02358 | 584.36 | 624.69 | hypothetical protein GOALK_097_02160 [Gordonia alkanivorans NBRC 16433] |
| SEQ ID NO: 8078 | Nga02357 | 259.02 | 354.56 | ---NA--- |
| SEQ ID NO: 8079 | Nga04714 | 1287.96 | 1010.02 | gdp-fucose transporter 1-like |
| SEQ ID NO: 8080 | Nga05027 | 1146.84 | 1179.37 | p-type had subfamily ic |
| SEQ ID NO: 8081 | Nga04921 | 848.33 | 1200.58 | leukocyte receptor cluster member 8-like protein |
| SEQ ID NO: 8082 | Nga04922 | 199.31 | 178.68 | ---NA--- |
| SEQ ID NO: 8083 | Nga02239.02 | 275.29 | 249.66 | protein |
| SEQ ID NO: 8084 | Nga00490.02 | 783.65 | 773.93 | adenine phosphoribosyltransferase |
| SEQ ID NO: 8085 | Nga00493.02 | 4304.25 | 4488.03 | mago nashi |

FIGURE 24 DX

| # | Nga model | +N rpkb | -N rpkb | GO |
|---|---|---|---|---|
| SEQ ID NO: 8086 | Nga00494.02 | 791.11 | 849.77 | serine threonine protein phosphatase |
| SEQ ID NO: 8087 | Nga00743 | 352.53 | 354.99 | fungal specific transcription factor domain-containing protein |
| SEQ ID NO: 8088 | Nga00742 | 956.63 | 702.81 | violaxanthin de-epoxidase |
| SEQ ID NO: 8089 | Nga00744 | 119.15 | 135.89 | pentatricopeptide repeat-containing protein |
| SEQ ID NO: 8090 | Nga00741 | 839.70 | 691.53 | solute carrier family 31 (copper transporters) member 1 |
| SEQ ID NO: 8091 | Nga06093 | 85.96 | 106.79 | ---NA--- |
| SEQ ID NO: 8092 | Nga06092 | 445.45 | 459.55 | ---NA--- |
| SEQ ID NO: 8093 | Nga06090 | 263.64 | 324.97 | ---NA--- |
| SEQ ID NO: 8094 | Nga06091 | 475.35 | 416.31 | hypothetical protein CHLNCDRAFT_138448 [Chlorella variabilis] |
| SEQ ID NO: 8095 | Nga07202 | 4983.41 | 5411.27 | nadh dehydrogenase |
| SEQ ID NO: 8096 | Nga07201 | 765.10 | 719.73 | ---NA--- |
| SEQ ID NO: 8097 | Nga03621 | 142.86 | 87.05 | ---NA--- |
| SEQ ID NO: 8098 | Nga03620.01 | 513.86 | 614.05 | endonuclease exonuclease phosphatase |
| SEQ ID NO: 8099 | Nga06864 | 154.22 | 161.83 | ---NA--- |
| SEQ ID NO: 8100 | Nga20809 | 323.63 | 320.96 | phosphatidylglycerophosphate synthase 1 |
| SEQ ID NO: 8101 | Nga05316 | 499.25 | 518.21 | phosphatidylinositol-3-phosphate 5-kinase |
| SEQ ID NO: 8102 | Nga05319 | 297.40 | 488.60 | gram domain containing 1c |
| SEQ ID NO: 8103 | Nga05320 | 730.50 | 626.12 | protein |
| SEQ ID NO: 8104 | Nga05317 | 819.92 | 1054.18 | gram domain-containing protein |
| SEQ ID NO: 8105 | Nga05315 | 640.24 | 780.72 | exosome complex exonuclease rrp44 |
| SEQ ID NO: 8106 | Nga05318 | 1303.03 | 1595.31 | ---NA--- |
| SEQ ID NO: 8107 | Nga07306 | 900.65 | 833.04 | ---NA--- |
| SEQ ID NO: 8108 | Nga07305 | 350.04 | 310.00 | pseudouridine synthase |
| SEQ ID NO: 8109 | Nga04293 | 267.44 | 289.70 | 40 kda peptidyl-prolyl cis-trans isomerase |
| SEQ ID NO: 8110 | Nga04294 | 248.06 | 260.31 | 20 kda cyclophilin |
| SEQ ID NO: 8111 | Nga02723.02 | 176.80 | 214.25 | expressed unknown protein [Ectocarpus siliculosus] |
| SEQ ID NO: 8112 | Nga02725.02 | 954.08 | 1002.07 | ---NA--- |
| SEQ ID NO: 8113 | Nga02735.02 | 456.21 | 452.27 | conserved unknown protein [Ectocarpus siliculosus] |
| SEQ ID NO: 8114 | Nga02731.02 | 1963.61 | 1938.16 | hypothetical protein VOLCADRAFT_89537 [Volvox carteri f. nagariensis] |
| SEQ ID NO: 8115 | Nga01260 | 456.71 | 536.93 | uncharacterized protein |
| SEQ ID NO: 8116 | Nga01261 | 253.77 | 257.06 | ---NA--- |
| SEQ ID NO: 8117 | Nga06923 | 172.04 | 330.02 | protein |
| SEQ ID NO: 8118 | Nga01852.2 | 640.29 | 945.30 | ctd small phosphatase-like |
| SEQ ID NO: 8119 | Nga06399 | 901.23 | 704.77 | ---NA--- |
| SEQ ID NO: 8120 | Nga03683 | 88.12 | 103.76 | ---NA--- |
| SEQ ID NO: 8121 | Nga03682 | 526.04 | 468.27 | ---NA--- |
| SEQ ID NO: 8122 | Nga04887 | 544.74 | 544.17 | aldo keto reductase |
| SEQ ID NO: 8123 | Nga04886 | 420.21 | 442.84 | ---NA--- |
| SEQ ID NO: 8124 | Nga01825.2 | 561.69 | 637.75 | conserved hypothetical protein [Phytophthora infestans T30-4] |
| SEQ ID NO: 8125 | Nga01800.01 | 3475.90 | 4617.92 | gcn5-related n-acetyltransferase |
| SEQ ID NO: 8126 | Nga07089 | 586.21 | 728.38 | glutathione s-transferase |
| SEQ ID NO: 8127 | Nga02092.01 | 1547.45 | 2155.74 | alternative nadh-dehydrogenase |
| SEQ ID NO: 8128 | Nga02151 | 1267.20 | 1143.41 | adp-ribosylation factor |
| SEQ ID NO: 8129 | Nga02150 | 940.64 | 1093.13 | ---NA--- |
| SEQ ID NO: 8130 | Nga02179 | 49.65 | 46.10 | ---NA--- |
| SEQ ID NO: 8131 | Nga02177 | 216.58 | 199.28 | atp-dependent bile acid permease |
| SEQ ID NO: 8132 | Nga02178 | 127.07 | 125.68 | ---NA--- |
| SEQ ID NO: 8133 | Nga04883 | 302.43 | 276.60 | protein |
| SEQ ID NO: 8134 | Nga02026.01 | 127.45 | 159.30 | ---NA--- |
| SEQ ID NO: 8135 | Nga05586.2 | 296.20 | 249.87 | diacylglycerol kinase |
| SEQ ID NO: 8136 | Nga02111.01 | 525.58 | 463.05 | carbohydratebinding protein |
| SEQ ID NO: 8137 | Nga20321 | 330.53 | 330.74 | hypothetical protein AURANDRAFT_62846 [Aureococcus anophagefferens] |
| SEQ ID NO: 8138 | Nga03658 | 293.83 | 304.91 | ---NA--- |
| SEQ ID NO: 8139 | Nga03657 | 347.26 | 243.23 | protein |
| SEQ ID NO: 8140 | Nga03660 | 491.02 | 415.13 | ---NA--- |
| SEQ ID NO: 8141 | Nga03656 | 265.81 | 270.27 | ---NA--- |
| SEQ ID NO: 8142 | Nga03659 | 4714.47 | 4022.26 | ---NA--- |
| SEQ ID NO: 8143 | Nga20790 | 1553.57 | 811.04 | protein |
| SEQ ID NO: 8144 | Nga01257 | 8706.87 | 9058.67 | ---NA--- |
| SEQ ID NO: 8145 | Nga01256 | 8271.83 | 8983.21 | 60s acidic ribosomal protein |
| SEQ ID NO: 8146 | Nga01254 | 412.29 | 367.03 | patatin-like phospholipase domain-containing protein |
| SEQ ID NO: 8147 | Nga04584.2 | 488.89 | 422.59 | 4-diphosphocytidyl-2c-methyl-d-erythritol kinase |
| SEQ ID NO: 8148 | Nga03793 | 982.30 | 1047.63 | protein |

FIGURE 24 DY

| # | Nga model | +N rpkb | -N rpkb | GO |
|---|---|---|---|---|
| SEQ ID NO: 8149 | Nga20845 | 100.70 | 91.33 | protein kinase domain containing protein |
| SEQ ID NO: 8150 | Nga20383 | 170.05 | 236.44 | isoform f |
| SEQ ID NO: 8151 | Nga04842.02 | 173.78 | 173.92 | sulfate transporter |
| SEQ ID NO: 8152 | Nga02376 | 213.25 | 243.25 | ---NA--- |
| SEQ ID NO: 8153 | Nga00988 | 430.35 | 485.03 | rna-binding protein 8a |
| SEQ ID NO: 8154 | Nga03962 | 12.39 | 32.22 | hnh endonuclease family protein |
| SEQ ID NO: 8155 | Nga02348.01 | 345.29 | 397.21 | sam-dependent methyltransferase |
| SEQ ID NO: 8156 | Nga21081 | 418.44 | 414.86 | ---NA--- |
| SEQ ID NO: 8157 | Nga20794 | 481.17 | 614.89 | nucleosome binding protein |
| SEQ ID NO: 8158 | Nga02333.1 | 316.07 | 324.09 | dna polymerase delta catalytic subunit |
| SEQ ID NO: 8159 | Nga03597 | 1948.54 | 3075.15 | kazal-type serine protease inhibitor domain |
| SEQ ID NO: 8160 | Nga03600 | 4740.11 | 5178.94 | ---NA--- |
| SEQ ID NO: 8161 | Nga03599 | 286.28 | 480.65 | unnamed protein product [Blastocystis hominis] |
| SEQ ID NO: 8162 | Nga03598 | 408.90 | 694.62 | ---NA--- |
| SEQ ID NO: 8163 | Nga06983 | 506.88 | 498.27 | proprotein convertase subtilisin kexin type 9 preproprotein |
| SEQ ID NO: 8164 | Nga04219 | 1464.90 | 1876.03 | cytokine-induced anti-apoptosis inhibitor fe-s biogenesis |
| SEQ ID NO: 8165 | Nga06036.2 | 598.46 | 518.61 | uncharacterized protein |
| SEQ ID NO: 8166 | Nga04108 | 750.00 | 654.45 | ---NA--- |
| SEQ ID NO: 8167 | Nga04104 | 134.42 | 168.46 | pre-mrna-splicing factor 38b |
| SEQ ID NO: 8168 | Nga04105 | 473.15 | 428.93 | ---NA--- |
| SEQ ID NO: 8169 | Nga04103 | 1142.34 | 1196.16 | ribosomal rna small subunit methyltransferase b |
| SEQ ID NO: 8170 | Nga04596 | 161.76 | 355.77 | ---NA--- |
| SEQ ID NO: 8171 | Nga04595 | 622.79 | 748.22 | glycosyl family 43 |
| SEQ ID NO: 8172 | Nga04597 | 28.99 | 70.65 | ---NA--- |
| SEQ ID NO: 8173 | Nga04819 | 521.94 | 569.43 | conserved unknown protein [Ectocarpus siliculosus] |
| SEQ ID NO: 8174 | Nga04197.02 | 2880.82 | 2549.74 | protein |
| SEQ ID NO: 8175 | Nga04698 | 2015.17 | 1873.88 | thylakoid lumenal kda chloroplast |
| SEQ ID NO: 8176 | Nga07289 | 162.96 | 147.11 | ---NA--- |
| SEQ ID NO: 8177 | Nga07102 | 1942.51 | 2117.53 | ---NA--- |
| SEQ ID NO: 8178 | Nga03912 | 409.21 | 657.57 | sjchgc05773 protein |
| SEQ ID NO: 8179 | Nga03910 | 468.76 | 480.97 | atp-binding cassette sub-family e member 1 |
| SEQ ID NO: 8180 | Nga03911 | 290.87 | 288.63 | acyl-coenzyme a binding domain containing 6 |
| SEQ ID NO: 8181 | Nga03908 | 404.87 | 334.27 | protein phosphatase 2c |
| SEQ ID NO: 8182 | Nga03909 | 361.55 | 429.85 | protein phosphatase |
| SEQ ID NO: 8183 | Nga03606.1 | 1402.08 | 1990.44 | agc ndr protein kinase |
| SEQ ID NO: 8184 | Nga02051.02 | 393.85 | 450.84 | ---NA--- |
| SEQ ID NO: 8185 | Nga03605.1 | 115.03 | 112.27 | cg3476-pa |
| SEQ ID NO: 8186 | Nga00907 | 422.62 | 381.34 | conserved unknown protein [Ectocarpus siliculosus] |
| SEQ ID NO: 8187 | Nga00908 | 52.08 | 78.99 | ---NA--- |
| SEQ ID NO: 8188 | Nga20841 | 195.95 | 253.24 | alpha beta hydrolase fold protein |
| SEQ ID NO: 8189 | Nga07121 | 84.80 | 78.22 | zinc knuckle (cchc-type) family protein |
| SEQ ID NO: 8190 | Nga07119 | 175.49 | 184.79 | family protein |
| SEQ ID NO: 8191 | Nga07120 | 608.70 | 768.27 | conserved unknown protein [Ectocarpus siliculosus] |
| SEQ ID NO: 8192 | Nga03589 | 1451.86 | 1434.78 | ---NA--- |
| SEQ ID NO: 8193 | Nga03588 | 131.31 | 114.11 | protein kinase |
| SEQ ID NO: 8194 | Nga03587 | 129.17 | 130.89 | protein kinase |
| SEQ ID NO: 8195 | Nga04003 | 183.29 | 195.62 | conserved oligomeric golgi complex subunit 7 |
| SEQ ID NO: 8196 | Nga03800 | 1348.84 | 1252.70 | dolichol-phosphate mannosyltransferase subunit 3-like |
| SEQ ID NO: 8197 | Nga03799 | 256.73 | 226.78 | ---NA--- |
| SEQ ID NO: 8198 | Nga04545 | 436.63 | 441.87 | ---NA--- |
| SEQ ID NO: 8199 | Nga02018 | 230.61 | 242.99 | vacuolar protein sorting-associated protein 11 homolog |
| SEQ ID NO: 8200 | Nga05835.2 | 267.36 | 292.12 | ring zinc finger-containing protein |
| SEQ ID NO: 8201 | Nga02019 | 384.62 | 274.55 | fatty acid desaturase |
| SEQ ID NO: 8202 | Nga00819.02 | 590.02 | 455.69 | uncharacterized protein conserved in bacteria with a cystatin-like fold |
| SEQ ID NO: 8203 | Nga20945 | 1036.04 | 1400.68 | cug-bp- and etr-3-like |
| SEQ ID NO: 8204 | Nga02158 | 366.67 | 333.18 | u4 u6 small nuclear ribonucleoprotein prp31 |
| SEQ ID NO: 8205 | Nga02157 | 575.90 | 700.12 | ---NA--- |
| SEQ ID NO: 8206 | Nga01385 | 7582.38 | 9595.54 | histone h4 |
| SEQ ID NO: 8207 | Nga01092.01 | 455.84 | 478.35 | rpa-interacting protein a |
| SEQ ID NO: 8208 | Nga01090.01 | 3969.61 | 4630.68 | transketolase |
| SEQ ID NO: 8209 | Nga01091.01 | 876.21 | 843.98 | ---NA--- |
| SEQ ID NO: 8210 | Nga01810 | 1273.84 | 1273.93 | u6 snrna-associated sm-like |
| SEQ ID NO: 8211 | Nga04792 | 906.86 | 865.53 | lactoylglutathione lyase glyoxalase i-like protein |
| SEQ ID NO: 8212 | Nga03830 | 759.07 | 900.47 | protein |

FIGURE 24 DZ

| # | Nga model | +N rpkb | -N rpkb | GO |
|---|---|---|---|---|
| SEQ ID NO: 8213 | Nga03831 | 278.39 | 226.17 | ---NA--- |
| SEQ ID NO: 8214 | Nga03829 | 1995.46 | 2006.81 | protein |
| SEQ ID NO: 8215 | Nga03202 | 495.12 | 565.03 | dna mismatch repair protein msh2 |
| SEQ ID NO: 8216 | Nga04972.2 | 198.76 | 224.27 | ---NA--- |
| SEQ ID NO: 8217 | Nga03203 | 344.71 | 362.31 | dna mismatch repair protein msh2 |
| SEQ ID NO: 8218 | Nga03204 | 206.45 | 258.58 | ---NA--- |
| SEQ ID NO: 8219 | Nga03201.01 | 325.52 | 340.66 | trigger factor |
| SEQ ID NO: 8220 | Nga03206 | 409.52 | 402.34 | protein homolog 2a |
| SEQ ID NO: 8221 | Nga04973.2 | 902.78 | 1079.76 | px domain containing protein |
| SEQ ID NO: 8222 | Nga03205 | 187.50 | 101.55 | ---NA--- |
| SEQ ID NO: 8223 | Nga03197 | 338.88 | 385.11 | alpha beta hydrolase |
| SEQ ID NO: 8224 | Nga03200 | 756.36 | 584.07 | protein |
| SEQ ID NO: 8225 | Nga04050 | 347.17 | 363.80 | ---NA--- |
| SEQ ID NO: 8226 | Nga01561 | 126.82 | 182.42 | ---NA--- |
| SEQ ID NO: 8227 | Nga01563 | 282.35 | 360.47 | lipid a export atp-binding permease protein msba |
| SEQ ID NO: 8228 | Nga20851 | 293.04 | 265.85 | at2g36910-like protein |
| SEQ ID NO: 8229 | Nga20388 | 218.21 | 272.08 | atp-binding sub-family b (mdr tap) member 10 |
| SEQ ID NO: 8230 | Nga01562 | 362.16 | 267.88 | kh domain-containing protein |
| SEQ ID NO: 8231 | Nga20481 | 339.26 | 377.99 | conserved unknown protein [Ectocarpus siliculosus] |
| SEQ ID NO: 8232 | Nga02005 | 4235.74 | 4559.02 | ---NA--- |
| SEQ ID NO: 8233 | Nga02006 | 1318.66 | 1265.30 | adp-ribosylation factor gtpase-activating protein agd8 |
| SEQ ID NO: 8234 | Nga02007 | 225.56 | 196.19 | phosphatidylinositol 4-kinase |
| SEQ ID NO: 8235 | Nga04149 | 250.64 | 280.68 | block of proliferation 1 |
| SEQ ID NO: 8236 | Nga01147 | 352.86 | 334.63 | phosphatidylinositol phosphatase |
| SEQ ID NO: 8237 | Nga20644 | 251.80 | 183.14 | ---NA--- |
| SEQ ID NO: 8238 | Nga01148 | 183.51 | 192.79 | trna-splicing endonuclease positive effector-related protein |
| SEQ ID NO: 8239 | Nga01572 | 883.07 | 993.51 | predicted protein [Thalassiosira pseudonana CCMP1335] |
| SEQ ID NO: 8240 | Nga01573 | 171.30 | 130.39 | ---NA--- |
| SEQ ID NO: 8241 | Nga01571 | 438.64 | 441.21 | ---NA--- |
| SEQ ID NO: 8242 | Nga06948 | 1065.45 | 1284.26 | ---NA--- |
| SEQ ID NO: 8243 | Nga04375 | 14.71 | 10.62 | ---NA--- |
| SEQ ID NO: 8244 | Nga04798 | 250.46 | 215.45 | para-aminobenzoate synthase |
| SEQ ID NO: 8245 | Nga21259 | 116.13 | 209.66 | p-aminobenzoic acid synthase |
| SEQ ID NO: 8246 | Nga04039 | 1591.57 | 1582.75 | ---NA--- |
| SEQ ID NO: 8247 | Nga04041 | 1805.77 | 1734.31 | dihydrolipoamide acetyltransferase |
| SEQ ID NO: 8248 | Nga04043 | 1234.57 | 1105.52 | branched-chain alpha-keto acid dehydrogenase subunit e2 |
| SEQ ID NO: 8249 | Nga04042 | 1582.46 | 1500.08 | endoribonuclease l-psp |
| SEQ ID NO: 8250 | Nga04040 | 1717.28 | 1553.01 | branched-chain alpha-keto acid dehydrogenase subunit e2 |
| SEQ ID NO: 8251 | Nga02483.02 | 1542.86 | 1293.69 | peptide methionine sulfoxide reductase |
| SEQ ID NO: 8252 | Nga02482.02 | 461.49 | 468.30 | pre-mrna-splicing factor syf1 |
| SEQ ID NO: 8253 | Nga06756 | 1143.39 | 1183.42 | phosphoethanolamine n-methyltransferase |
| SEQ ID NO: 8254 | Nga00771 | 182.74 | 203.45 | ---NA--- |
| SEQ ID NO: 8255 | Nga00772 | 119.34 | 160.48 | ---NA--- |
| SEQ ID NO: 8256 | Nga00773 | 112.46 | 135.87 | ---NA--- |
| SEQ ID NO: 8257 | Nga06264 | 190.48 | 276.67 | ---NA--- |
| SEQ ID NO: 8258 | Nga06265 | 237.29 | 238.68 | ---NA--- |
| SEQ ID NO: 8259 | Nga06261 | 434.98 | 390.22 | ---NA--- |
| SEQ ID NO: 8260 | Nga06260 | 70.87 | 79.61 | ---NA--- |
| SEQ ID NO: 8261 | Nga06263 | 398.37 | 537.21 | ---NA--- |
| SEQ ID NO: 8262 | Nga06262 | 50.26 | 65.91 | ---NA--- |
| SEQ ID NO: 8263 | Nga04421 | 1349.36 | 1446.35 | hypothetical protein AURANDRAFT_71238 [Aureococcus anophagefferens] |
| SEQ ID NO: 8264 | Nga05735 | 2361.34 | 3298.63 | proline oxidase |
| SEQ ID NO: 8265 | Nga05734 | 331.83 | 375.37 | beta-adrenergic receptor kinase |
| SEQ ID NO: 8266 | Nga05731 | 447.14 | 707.76 | ---NA--- |
| SEQ ID NO: 8267 | Nga05730 | 630.38 | 684.30 | protein |
| SEQ ID NO: 8268 | Nga05736 | 85.31 | 65.03 | aec family transporter; auxin efflux |
| SEQ ID NO: 8269 | Nga05728 | 800.00 | 640.31 | axonemal dynein beta heavy chain |
| SEQ ID NO: 8270 | Nga21074 | 267.86 | 177.96 | endonuclease fl j39025-like |
| SEQ ID NO: 8271 | Nga20946 | 243.96 | 481.16 | sulfate transporter family domain-containing protein |
| SEQ ID NO: 8272 | Nga05732 | 1894.32 | 2003.89 | protein |
| SEQ ID NO: 8273 | Nga05733 | 931.25 | 964.76 | ---NA--- |
| SEQ ID NO: 8274 | Nga05729 | 2218.27 | 2490.89 | dna-directed rna polymerase ii kda polypeptide |
| SEQ ID NO: 8275 | Nga05737 | 1297.05 | 1105.34 | eukaryotic translation initiation factor |

FIGURE 24 EA

| # | Nga model | +N rpkb | -N rpkb | GO |
|---|---|---|---|---|
| SEQ ID NO: 8276 | Nga05942 | 282.77 | 263.71 | ---NA--- |
| SEQ ID NO: 8277 | Nga05941 | 297.39 | 269.04 | sodium-dependent glucose transporter 1 |
| SEQ ID NO: 8278 | Nga05940 | 447.80 | 466.05 | hydroxyacyl glutathione hydrolase |
| SEQ ID NO: 8279 | Nga20359.1 | 1231.91 | 1166.44 | ---NA--- |
| SEQ ID NO: 8280 | Nga20400.1 | 81.76 | 74.94 | ---NA--- |
| SEQ ID NO: 8281 | Nga20583.1 | 42.33 | 85.97 | protein |
| SEQ ID NO: 8282 | Nga00930 | 607.23 | 616.01 | ---NA--- |
| SEQ ID NO: 8283 | Nga20270 | 262.82 | 288.86 | serine threonine kinase 25 (ste20 yeast) |
| SEQ ID NO: 8284 | Nga00931 | 130.28 | 119.71 | wd repeat-containing protein 91 |
| SEQ ID NO: 8285 | Nga01668 | 180.54 | 196.52 | asparaginase |
| SEQ ID NO: 8286 | Nga00831 | 371.17 | 399.84 | protein |
| SEQ ID NO: 8287 | Nga00832 | 293.23 | 317.64 | o-phosphoseryl-trna selenium transferase |
| SEQ ID NO: 8288 | Nga00830 | 209.91 | 304.48 | o-phosphoseryl-trna selenium transferase |
| SEQ ID NO: 8289 | Nga00765 | 301.08 | 350.89 | ---NA--- |
| SEQ ID NO: 8290 | Nga20086.1 | 274.61 | 437.68 | serine threonine protein |
| SEQ ID NO: 8291 | Nga04910 | 1187.64 | 1583.00 | protein kinase |
| SEQ ID NO: 8292 | Nga01780 | 116.35 | 122.63 | dna replication licensing factor mcm3 |
| SEQ ID NO: 8293 | Nga20855.1 | 288.76 | 417.76 | ---NA--- |
| SEQ ID NO: 8294 | Nga00792.02 | 188.24 | 194.48 | nmda receptor regulated 1-like |
| SEQ ID NO: 8295 | Nga01374 | 98.36 | 88.79 | ---NA--- |
| SEQ ID NO: 8296 | Nga01372 | 189.57 | 246.79 | protein |
| SEQ ID NO: 8297 | Nga01373 | 336.02 | 329.05 | 5-formyltetrahydrofolate cyclo-ligase |
| SEQ ID NO: 8298 | Nga02438 | 553.08 | 572.83 | ---NA--- |
| SEQ ID NO: 8299 | Nga02440 | 485.48 | 408.27 | ubiquitin thioesterase otub1 |
| SEQ ID NO: 8300 | Nga02439.01 | 217.65 | 364.79 | ---NA--- |
| SEQ ID NO: 8301 | Nga00889 | 1207.01 | 1163.44 | 50s ribosomal protein l24 |
| SEQ ID NO: 8302 | Nga01340 | 1016.08 | 1188.89 | protein |
| SEQ ID NO: 8303 | Nga01342.01 | 7.94 | 30.09 | urease accessory protein ured |
| SEQ ID NO: 8304 | Nga01339 | 258.95 | 258.87 | myo-inositol monophosphatase 1 |
| SEQ ID NO: 8305 | Nga01338 | 526.56 | 520.40 | threonyl-trna synthetase |
| SEQ ID NO: 8306 | Nga01341 | 1037.88 | 937.57 | nucleolar protein nop56 |
| SEQ ID NO: 8307 | Nga06457 | 347.39 | 271.90 | ---NA--- |
| SEQ ID NO: 8308 | Nga06456 | 617.95 | 276.19 | ---NA--- |
| SEQ ID NO: 8309 | Nga07310 | 2056.17 | 1684.98 | zeta-carotene desaturase |
| SEQ ID NO: 8310 | Nga01475 | 1032.83 | 921.07 | histone deacetylase 1 |
| SEQ ID NO: 8311 | Nga01478 | 167.99 | 161.01 | ---NA--- |
| SEQ ID NO: 8312 | Nga01476 | 369.59 | 400.75 | cathepsin l-like proteinase |
| SEQ ID NO: 8313 | Nga01477 | 456.29 | 535.78 | rCG22628 [Rattus norvegicus] |
| SEQ ID NO: 8314 | Nga06910 | 161.13 | 227.17 | ---NA--- |
| SEQ ID NO: 8315 | Nga06909 | 280.51 | 272.29 | atp dependent rna helicase |
| SEQ ID NO: 8316 | Nga02117 | 3893.33 | 3816.59 | glutamate decarboxylase |
| SEQ ID NO: 8317 | Nga02118 | 693.07 | 695.34 | protein |
| SEQ ID NO: 8318 | Nga02119 | 187.92 | 141.77 | ---NA--- |
| SEQ ID NO: 8319 | Nga05571 | 3318.39 | 3102.78 | ---NA--- |
| SEQ ID NO: 8320 | Nga05573 | 11330.25 | 12414.41 | ---NA--- |
| SEQ ID NO: 8321 | Nga05574 | 458.33 | 558.54 | 3-oxoacid - b subunit |
| SEQ ID NO: 8322 | Nga05572 | 174.13 | 172.46 | ---NA--- |
| SEQ ID NO: 8323 | Nga05570 | 753.13 | 542.59 | uncharacterized protein |
| SEQ ID NO: 8324 | Nga01795.2 | 993.21 | 1478.37 | phosphatidylinositol kinase (pik-f) |
| SEQ ID NO: 8325 | Nga03522 | 506.26 | 368.18 | t-complex protein 1 subunit gamma |
| SEQ ID NO: 8326 | Nga03524 | 1411.11 | 2044.10 | ---NA--- |
| SEQ ID NO: 8327 | Nga03523 | 375.85 | 363.84 | asparagine synthase |
| SEQ ID NO: 8328 | Nga03525 | 194.84 | 215.72 | beta-tubulin isotype 2 |
| SEQ ID NO: 8329 | Nga03519 | 867.89 | 884.21 | atp synthase protein i |
| SEQ ID NO: 8330 | Nga20528 | 275.77 | 274.58 | arginine serine rich splicing factor sf4 |
| SEQ ID NO: 8331 | Nga03520 | 428.77 | 321.88 | beta-tubulin [Holocryphia eucalypti] |
| SEQ ID NO: 8332 | Nga03526 | 254.90 | 237.89 | ---NA--- |
| SEQ ID NO: 8333 | Nga02197.2 | 43.30 | 47.78 | dmt superfamily drug metabolite transporter |
| SEQ ID NO: 8334 | Nga02196.02 | 1176.23 | 1143.45 | ---NA--- |
| SEQ ID NO: 8335 | Nga04529 | 60.61 | 93.79 | ---NA--- |
| SEQ ID NO: 8336 | Nga06994 | 88771.93 | 47391.05 | light harvesting complex protein |
| SEQ ID NO: 8337 | Nga05964 | 78.82 | 133.40 | ---NA--- |
| SEQ ID NO: 8338 | Nga04762.02 | 191.69 | 140.79 | ---NA--- |
| SEQ ID NO: 8339 | Nga04763.02 | 1319.20 | 1103.65 | ---NA--- |

FIGURE 24 EB

| # | Nga model | +N rpkb | -N rpkb | GO |
|---|---|---|---|---|
| SEQ ID NO: 8340 | Nga05965 | 594.71 | 523.32 | protein |
| SEQ ID NO: 8341 | Nga20098 | 622.64 | 559.50 | purple acid phosphatase isoform b2 |
| SEQ ID NO: 8342 | Nga05960 | 784.42 | 880.66 | acetylglucosaminyl-transferase |
| SEQ ID NO: 8343 | Nga05961 | 219.05 | 242.44 | ---NA--- |
| SEQ ID NO: 8344 | Nga20894 | 137.61 | 154.04 | protein kinase domain containing protein |
| SEQ ID NO: 8345 | Nga05959 | 146.85 | 172.96 | ---NA--- |
| SEQ ID NO: 8346 | Nga04052 | 516.26 | 394.10 | polymerase (dna directed) delta regulatory subunit |
| SEQ ID NO: 8347 | Nga06173 | 40.94 | 38.01 | ---NA--- |
| SEQ ID NO: 8348 | Nga01182 | 752.09 | 633.65 | ---NA--- |
| SEQ ID NO: 8349 | Nga03807 | 175.64 | 181.05 | ---NA--- |
| SEQ ID NO: 8350 | Nga02132.2 | 327.33 | 357.83 | dynamin like protein |
| SEQ ID NO: 8351 | Nga01917.02 | 1146.85 | 805.48 | dna-directed rna polymerases and iii subunit rpabc2 |
| SEQ ID NO: 8352 | Nga01012 | 132.01 | 239.53 | ---NA--- |
| SEQ ID NO: 8353 | Nga01013 | 149.04 | 121.52 | hypothetical protein ANI_1_1318134 [Aspergillus niger CBS 513.88] |
| SEQ ID NO: 8354 | Nga04904.2 | 134.02 | 174.96 | cysteine protease family |
| SEQ ID NO: 8355 | Nga05154 | 104.90 | 159.08 | trna rrna methyltransferase -like protein |
| SEQ ID NO: 8356 | Nga05158 | 906.03 | 762.67 | ke2 family protein |
| SEQ ID NO: 8357 | Nga05155 | 3480.28 | 5403.60 | phosphate dikinase |
| SEQ ID NO: 8358 | Nga05160 | 375.07 | 441.79 | potential uroporphyrin-3 c-methyltransferase |
| SEQ ID NO: 8359 | Nga05156 | 520.75 | 595.44 | 3-hydroxyisobutyrate dehydrogenase |
| SEQ ID NO: 8360 | Nga05157 | 309.11 | 420.20 | nodulin 21 -like transporter family protein |
| SEQ ID NO: 8361 | Nga05159 | 510.42 | 678.43 | serine threonine-protein kinase dclk3 |
| SEQ ID NO: 8362 | Nga05153 | 2048.39 | 2009.22 | ---NA--- |
| SEQ ID NO: 8363 | Nga04028 | 1613.77 | 2256.20 | ---NA--- |
| SEQ ID NO: 8364 | Nga04029 | 462.26 | 403.66 | glutathione s- |
| SEQ ID NO: 8365 | Nga04031 | 138.66 | 138.06 | alpha beta hydrolase fold protein |
| SEQ ID NO: 8366 | Nga02412.2 | 517.93 | 535.71 | eukaryotic translation initiation factor |
| SEQ ID NO: 8367 | Nga04059 | 331.92 | 304.47 | signal recognition particle 54 kda protein |
| SEQ ID NO: 8368 | Nga04057 | 111.11 | 159.18 | ---NA--- |
| SEQ ID NO: 8369 | Nga04055 | 108.16 | 140.21 | ---NA--- |
| SEQ ID NO: 8370 | Nga04056 | 1648.60 | 2157.57 | ---NA--- |
| SEQ ID NO: 8371 | Nga04058 | 1038.61 | 922.07 | ---NA--- |
| SEQ ID NO: 8372 | Nga07269 | 118.61 | 194.94 | protein |
| SEQ ID NO: 8373 | Nga06193 | 133.33 | 156.47 | ---NA--- |
| SEQ ID NO: 8374 | Nga06190 | 839.38 | 689.98 | ---NA--- |
| SEQ ID NO: 8375 | Nga06191 | 368.83 | 230.71 | ribosomal rna methyltransferase |
| SEQ ID NO: 8376 | Nga06192 | 212.87 | 225.23 | ---NA--- |
| SEQ ID NO: 8377 | Nga01104.02 | 171.35 | 145.49 | exocyst complex component 7 |
| SEQ ID NO: 8378 | Nga01103.2 | 1040.00 | 1014.42 | endoribonuclease l-psp |
| SEQ ID NO: 8379 | Nga06502 | 494.86 | 525.88 | conserved unknown protein [Ectocarpus siliculosus] |
| SEQ ID NO: 8380 | Nga06504 | 507.19 | 561.96 | conserved hypothetical protein [Neospora caninum Liverpool] |
| SEQ ID NO: 8381 | Nga06506 | 706.78 | 790.09 | protein |
| SEQ ID NO: 8382 | Nga21141 | 238.26 | 506.77 | protein |
| SEQ ID NO: 8383 | Nga06505 | 85.98 | 101.57 | exocyst complex |
| SEQ ID NO: 8384 | Nga06507 | 141.84 | 164.13 | abc transporter g family member 7 |
| SEQ ID NO: 8385 | Nga06503 | 418.18 | 397.84 | mannose-p-dolichol utilization defect 1 |
| SEQ ID NO: 8386 | Nga01928 | 163.35 | 136.66 | ---NA--- |
| SEQ ID NO: 8387 | Nga05044.2 | 479.70 | 517.63 | homing endonuclease rb16 2 |
| SEQ ID NO: 8388 | Nga01927 | 131.27 | 117.11 | ---NA--- |
| SEQ ID NO: 8389 | Nga03185 | 202.61 | 339.84 | ---NA--- |
| SEQ ID NO: 8390 | Nga03184 | 1611.65 | 1461.84 | ribulose- -bisphosphate carboxylase oxygenase small subunit n-methyltransferase i |
| SEQ ID NO: 8391 | Nga03186 | 56.74 | 84.51 | ---NA--- |
| SEQ ID NO: 8392 | Nga03182 | 281.32 | 373.88 | peroxin pex14 |
| SEQ ID NO: 8393 | Nga03183 | 158.70 | 168.22 | serine arginine repetitive matrix 1 |
| SEQ ID NO: 8394 | Nga03188 | 1130.40 | 1118.78 | ribulose- -bisphosphate carboxylase oxygenase small subunit n-methyltransferase i |
| SEQ ID NO: 8395 | Nga03642 | 256.70 | 157.17 | ---NA--- |
| SEQ ID NO: 8396 | Nga03641 | 298.33 | 239.57 | rna binding protein |
| SEQ ID NO: 8397 | Nga01785.01 | 1113.07 | 1258.03 | protein |
| SEQ ID NO: 8398 | Nga01789 | 273.18 | 336.64 | protein kiaa0664 homolog |
| SEQ ID NO: 8399 | Nga01788 | 85.34 | 79.38 | adp-ribosylation crystallin j1 |
| SEQ ID NO: 8400 | Nga01786 | 628.57 | 722.16 | eukaryotic translation initiation factor 3 |
| SEQ ID NO: 8401 | Nga01784.01 | 451.68 | 369.62 | dna-directed rna polymerase ii kda polypeptide |

FIGURE 24 EC

| # | Nga model | +N rpkb | -N rpkb | GO |
|---|---|---|---|---|
| SEQ ID NO: 8402 | Nga01787.01 | 325.16 | 362.85 | charged multivesicular body protein 3 |
| SEQ ID NO: 8403 | Nga20102 | 1629.24 | 1700.23 | predicted protein [Phaeodactylum tricornutum CCAP 1055/1] |
| SEQ ID NO: 8404 | Nga03978 | 903.14 | 850.71 | ---NA--- |
| SEQ ID NO: 8405 | Nga03979 | 981.84 | 940.63 | secreted protein |
| SEQ ID NO: 8406 | Nga04760.2 | 284.95 | 241.69 | uncharacterized protein |
| SEQ ID NO: 8407 | Nga01654 | 314.34 | 310.63 | conserved hypothetical protein [Phytophthora infestans T30-4] |
| SEQ ID NO: 8408 | Nga05457 | 67.25 | 101.36 | tbc domain containing protein |
| SEQ ID NO: 8409 | Nga05456 | 150.30 | 149.68 | telomerase cajal body protein 1 |
| SEQ ID NO: 8410 | Nga05460 | 106.28 | 147.57 | mrna processing protein |
| SEQ ID NO: 8411 | Nga05455 | 712.17 | 605.37 | 2-hydroxy-3-oxopropionate reductase |
| SEQ ID NO: 8412 | Nga05458 | 488.26 | 391.59 | atp-binding cassette transporter |
| SEQ ID NO: 8413 | Nga05462 | 118.12 | 163.01 | protease do-like 2 |
| SEQ ID NO: 8414 | Nga05459 | 528.43 | 511.88 | cg1824 |
| SEQ ID NO: 8415 | Nga05461 | 438.60 | 323.07 | atp-binding cassette sub-family b member 5-like |
| SEQ ID NO: 8416 | Nga05454 | 2050.73 | 2138.99 | transcription elongation factor b polypeptide 1 |
| SEQ ID NO: 8417 | Nga20755 | 29.41 | 47.79 | wd repeat and fyve domain-containing protein |
| SEQ ID NO: 8418 | Nga21162.1 | 119.45 | 129.40 | lysine ornithine decarboxylase |
| SEQ ID NO: 8419 | Nga02232.1 | 22.22 | 6.88 | conserved unknown protein [Ectocarpus siliculosus] |
| SEQ ID NO: 8420 | Nga02231 | 354.67 | 376.23 | ---NA--- |
| SEQ ID NO: 8421 | Nga02233 | 12.58 | 27.25 | ---NA--- |
| SEQ ID NO: 8422 | Nga02337 | 33.47 | 4.53 | ---NA--- |
| SEQ ID NO: 8423 | Nga03750.2 | 134.00 | 198.72 | pstvd rna-biding virp1 |
| SEQ ID NO: 8424 | Nga04780 | 125.98 | 145.00 | ---NA--- |
| SEQ ID NO: 8425 | Nga01637.02 | 752.43 | 562.65 | meiotic nuclear division protein 1 homolog |
| SEQ ID NO: 8426 | Nga06465 | 929.03 | 950.45 | ---NA--- |
| SEQ ID NO: 8427 | Nga06466 | 666.67 | 594.27 | ---NA--- |
| SEQ ID NO: 8428 | Nga06077 | 524.46 | 695.30 | ---NA--- |
| SEQ ID NO: 8429 | Nga06078 | 552.06 | 555.45 | chaperone protein |
| SEQ ID NO: 8430 | Nga06079.1 | 539.93 | 483.32 | mitochondrial carrier |
| SEQ ID NO: 8431 | Nga06080 | 160.39 | 156.01 | ---NA--- |
| SEQ ID NO: 8432 | Nga04465 | 695.89 | 920.01 | ---NA--- |
| SEQ ID NO: 8433 | Nga21002.1 | 133.52 | 184.64 | phytochelatin synthase |
| SEQ ID NO: 8434 | Nga03738 | 100.00 | 74.99 | ---NA--- |
| SEQ ID NO: 8435 | Nga01439.01 | 6.01 | 9.76 | mismatch repair protein 5 |
| SEQ ID NO: 8436 | Nga01434.01 | 1309.20 | 1273.96 | zip zinc transporter family protein |
| SEQ ID NO: 8437 | Nga01435.01 | 321.71 | 320.46 | protein polybromo-1 |
| SEQ ID NO: 8438 | Nga01436.01 | 370.20 | 472.56 | inosine triphosphate pyrophosphatase |
| SEQ ID NO: 8439 | Nga01437.01 | 304.95 | 306.79 | alpha beta hydrolase fold family |
| SEQ ID NO: 8440 | Nga01438.01 | 276.63 | 247.29 | protein phosphatase 1 beta |
| SEQ ID NO: 8441 | Nga06030 | 80.14 | 84.29 | kiaa0562 protein |
| SEQ ID NO: 8442 | Nga06029 | 285.71 | 308.30 | magnesium ion transporter mrs2 |
| SEQ ID NO: 8443 | Nga06032 | 8.40 | 18.21 | ---NA--- |
| SEQ ID NO: 8444 | Nga06031 | 333.99 | 341.89 | uncharacterized protein kiaa0562 |
| SEQ ID NO: 8445 | Nga06028 | 201.55 | 283.10 | potential dead box rna helicase |
| SEQ ID NO: 8446 | Nga01396 | 756.49 | 934.61 | hypothetical protein MYCGRDRAFT_99199 [Mycosphaerella graminicola IPO323] |
| SEQ ID NO: 8447 | Nga01398 | 574.74 | 688.71 | 5 -3 exoribonuclease |
| SEQ ID NO: 8448 | Nga01399 | 283.02 | 314.01 | protein |
| SEQ ID NO: 8449 | Nga01397 | 94.88 | 123.33 | ---NA--- |
| SEQ ID NO: 8450 | Nga05564 | 105.26 | 190.04 | ---NA--- |
| SEQ ID NO: 8451 | Nga05563 | 611.65 | 462.74 | ---NA--- |
| SEQ ID NO: 8452 | Nga05560 | 287.97 | 306.06 | deah (asp-glu-ala-his) box polypeptide 9 |
| SEQ ID NO: 8453 | Nga05561 | 385.96 | 456.10 | ---NA--- |
| SEQ ID NO: 8454 | Nga05565 | 257.50 | 288.48 | ---NA--- |
| SEQ ID NO: 8455 | Nga05562 | 71.65 | 67.49 | protein kinase |
| SEQ ID NO: 8456 | Nga02524.02 | 18205.19 | 18242.25 | predicted protein [Phaeodactylum tricornutum CCAP 1055/1] |
| SEQ ID NO: 8457 | Nga04248 | 134.64 | 162.54 | ---NA--- |
| SEQ ID NO: 8458 | Nga06059.2 | 1347.35 | 1430.84 | protein |
| SEQ ID NO: 8459 | Nga03888 | 140.70 | 168.74 | ---NA--- |
| SEQ ID NO: 8460 | Nga03886 | 1025.81 | 838.63 | cytochrome c6 |
| SEQ ID NO: 8461 | Nga03885 | 1996.79 | 1746.09 | atp-binding cassette |
| SEQ ID NO: 8462 | Nga03884 | 1064.37 | 919.73 | protein |
| SEQ ID NO: 8463 | Nga02237 | 984.99 | 1070.02 | short-chain dehydrogenase reductase sdr |
| SEQ ID NO: 8464 | Nga20715 | 185.76 | 154.27 | ---NA--- |

FIGURE 24 ED

| # | Nga model | +N rpkb | -N rpkb | GO |
|---|---|---|---|---|
| SEQ ID NO: 8465 | Nga02238 | 777.29 | 684.31 | r- vamp71-family |
| SEQ ID NO: 8466 | Nga20917 | 81.08 | 78.07 | ---NA--- |
| SEQ ID NO: 8467 | Nga20514 | 53.85 | 20.83 | peptide chain release factor 2 |
| SEQ ID NO: 8468 | Nga04334 | 253.05 | 297.23 | ---NA--- |
| SEQ ID NO: 8469 | Nga21137 | 156.61 | 197.92 | ---NA--- |
| SEQ ID NO: 8470 | Nga04559 | 137.25 | 140.18 | ---NA--- |
| SEQ ID NO: 8471 | Nga05576 | 2770.94 | 2662.18 | peptidoglycan-binding lysin domain |
| SEQ ID NO: 8472 | Nga04670 | 795.13 | 810.10 | ---NA--- |
| SEQ ID NO: 8473 | Nga21286 | 149.51 | 161.95 | trna-specific adenosine deaminase subunit tad3 |
| SEQ ID NO: 8474 | Nga04187 | 883.36 | 1031.01 | conserved protein |
| SEQ ID NO: 8475 | Nga04188 | 1315.57 | 1073.05 | ---NA--- |
| SEQ ID NO: 8476 | Nga04189 | 445.08 | 361.08 | short-chain dehydrogenase reductase sdr |
| SEQ ID NO: 8477 | Nga21228 | 187.50 | 206.67 | exosome complex rna-binding protein rrp42 |
| SEQ ID NO: 8478 | Nga02352 | 72.92 | 62.06 | ---NA--- |
| SEQ ID NO: 8479 | Nga04082 | 387.10 | 404.93 | ---NA--- |
| SEQ ID NO: 8480 | Nga02408 | 52.53 | 42.68 | serologically defined colon cancer antigen 10 |
| SEQ ID NO: 8481 | Nga02409 | 566.73 | 643.60 | ---NA--- |
| SEQ ID NO: 8482 | Nga02410 | 177.01 | 219.14 | ---NA--- |
| SEQ ID NO: 8483 | Nga02407 | 146.10 | 241.23 | rna (guanine-9-)-methyltransferase domain-containing protein 2 |
| SEQ ID NO: 8484 | Nga05171 | 798.59 | 694.72 | ubiquitin carrier protein |
| SEQ ID NO: 8485 | Nga05169 | 385.40 | 301.02 | ---NA--- |
| SEQ ID NO: 8486 | Nga05173 | 39.22 | 35.40 | ---NA--- |
| SEQ ID NO: 8487 | Nga05172 | 806.34 | 705.28 | cytochrome b5 |
| SEQ ID NO: 8488 | Nga05170 | 235.99 | 236.46 | ---NA--- |
| SEQ ID NO: 8489 | Nga06493 | 679.50 | 686.01 | ---NA--- |
| SEQ ID NO: 8490 | Nga06492 | 899.92 | 819.96 | short-chain dehydrogenase reductase |
| SEQ ID NO: 8491 | Nga06497 | 59.17 | 25.64 | ---NA--- |
| SEQ ID NO: 8492 | Nga06499 | 86.21 | 112.06 | ---NA--- |
| SEQ ID NO: 8493 | Nga06498 | 63.49 | 34.39 | ---NA--- |
| SEQ ID NO: 8494 | Nga06496 | 79.77 | 40.12 | protein |
| SEQ ID NO: 8495 | Nga06495 | 79.84 | 69.19 | protein |
| SEQ ID NO: 8496 | Nga06494 | 137.21 | 138.55 | ---NA--- |
| SEQ ID NO: 8497 | Nga07035 | 303.03 | 393.90 | ---NA--- |
| SEQ ID NO: 8498 | Nga00231.02 | 129.11 | 317.85 | phd zinc finger-containing protein |
| SEQ ID NO: 8499 | Nga00224.02 | 2630.54 | 2139.15 | alanine-2-oxoglutarate aminotransferase 2 |
| SEQ ID NO: 8500 | Nga00230.02 | 292.04 | 421.79 | amino acid permease family protein |
| SEQ ID NO: 8501 | Nga00225.2 | 267.29 | 320.52 | protein |
| SEQ ID NO: 8502 | Nga02384 | 265.50 | 245.62 | nudix hydrolase |
| SEQ ID NO: 8503 | Nga04336 | 315.97 | 274.57 | nuclear nucleic acid-binding protein c1d-like |
| SEQ ID NO: 8504 | Nga02294 | 2855.39 | 3174.96 | ---NA--- |
| SEQ ID NO: 8505 | Nga02296 | 1469.61 | 1349.89 | protein |
| SEQ ID NO: 8506 | Nga02295 | 517.06 | 525.92 | metalloprotease family |
| SEQ ID NO: 8507 | Nga01588 | 1293.75 | 1360.52 | ---NA--- |
| SEQ ID NO: 8508 | Nga21069 | 60.98 | 46.24 | ---NA--- |
| SEQ ID NO: 8509 | Nga01587 | 324.03 | 232.45 | tat pathway signal sequence domain protein |
| SEQ ID NO: 8510 | Nga01589 | 311.93 | 407.45 | ---NA--- |
| SEQ ID NO: 8511 | Nga01699 | 123.81 | 96.29 | cyclophilin |
| SEQ ID NO: 8512 | Nga01698 | 302.42 | 323.22 | cycloeucalenol cycloisomerase |
| SEQ ID NO: 8513 | Nga04356 | 468.92 | 630.21 | ---NA--- |
| SEQ ID NO: 8514 | Nga06719 | 2958.59 | 3107.04 | elongation factor 3 |
| SEQ ID NO: 8515 | Nga06723 | 393.94 | 326.61 | autophagy protein 12 |
| SEQ ID NO: 8516 | Nga06717 | 2964.56 | 2699.58 | protein |
| SEQ ID NO: 8517 | Nga06720 | 3402.56 | 3419.13 | mrna export factor elf1 |
| SEQ ID NO: 8518 | Nga01709.2 | 390.27 | 366.35 | major facilitator protein |
| SEQ ID NO: 8519 | Nga06722 | 138.08 | 148.40 | pre-mrna-splicing factor cwc2 |
| SEQ ID NO: 8520 | Nga06718.1 | 2232.10 | 2335.05 | mrna export factor elf1 |
| SEQ ID NO: 8521 | Nga06133.2 | 325.74 | 374.63 | dna replication complex gins protein psf2 |
| SEQ ID NO: 8522 | Nga20164 | 1099.91 | 1062.88 | protein |
| SEQ ID NO: 8523 | Nga01755.02 | 547.76 | 711.60 | ---NA--- |
| SEQ ID NO: 8524 | Nga01757.02 | 527.21 | 633.73 | 2-oxoisovalerate dehydrogenase alpha mitochondrial expressed |
| SEQ ID NO: 8525 | Nga04385 | 446.19 | 326.96 | protein |
| SEQ ID NO: 8526 | Nga03042.02 | 75.30 | 123.56 | protein |
| SEQ ID NO: 8527 | Nga00960 | 965.09 | 1049.87 | adp-ribosylation factor gtpase-activating protein agd14 |
| SEQ ID NO: 8528 | Nga00961 | 348.88 | 342.77 | fha domain containing protein |

FIGURE 24 EE

| # | Nga model | +N rpkb | -N rpkb | GO |
|---|---|---|---|---|
| SEQ ID NO: 8529 | Nga00963 | 1993.60 | 2049.96 | epsilon subunit of mitochondrial f1-atpase |
| SEQ ID NO: 8530 | Nga00962 | 649.72 | 608.94 | 50s ribosomal protein l13 |
| SEQ ID NO: 8531 | Nga06802 | 161.96 | 233.17 | ---NA--- |
| SEQ ID NO: 8532 | Nga06801 | 568.81 | 724.64 | protein |
| SEQ ID NO: 8533 | Nga00458.02 | 9447.11 | 8268.63 | chaperonin 10 |
| SEQ ID NO: 8534 | Nga00461.02 | 902.98 | 815.05 | abc subfamily abcg |
| SEQ ID NO: 8535 | Nga02486.2 | 775.30 | 706.74 | ankyrin-2 isoform 1 |
| SEQ ID NO: 8536 | Nga04303.01 | 490.09 | 462.59 | n-ethylmaleimide-sensitive fusion protein |
| SEQ ID NO: 8537 | Nga04302.01 | 284.54 | 377.94 | pak1ip1 protein |
| SEQ ID NO: 8538 | Nga04304.01 | 390.41 | 650.43 | protein |
| SEQ ID NO: 8539 | Nga06996 | 352.68 | 431.52 | regulatory-associated protein of mtor |
| SEQ ID NO: 8540 | Nga01769.1 | 448.64 | 619.83 | 5-oxoprolinase |
| SEQ ID NO: 8541 | Nga01768.01 | 13904.11 | 18448.36 | heat shock protein hsp20 |
| SEQ ID NO: 8542 | Nga01770.01 | 189.25 | 218.98 | zinc transport |
| SEQ ID NO: 8543 | Nga01310.02 | 1417.46 | 1344.22 | mfs transporter |
| SEQ ID NO: 8544 | Nga04488 | 285.19 | 391.17 | ---NA--- |
| SEQ ID NO: 8545 | Nga04487 | 3339.20 | 4071.49 | argininosuccinate synthase |
| SEQ ID NO: 8546 | Nga04489 | 497.44 | 466.62 | armadillo repeat-containing protein |
| SEQ ID NO: 8547 | Nga07013 | 7.30 | 31.63 | nadh-quinone oxidoreductase |
| SEQ ID NO: 8548 | Nga04341 | 2207.28 | 2742.98 | protein |
| SEQ ID NO: 8549 | Nga20368.1 | 1223.30 | 1139.32 | transthyretin family protein |
| SEQ ID NO: 8550 | Nga04204.01 | 12867.52 | 15623.75 | acyl- dehydrogenase |
| SEQ ID NO: 8551 | Nga04205.01 | 1129.97 | 1359.07 | ---NA--- |
| SEQ ID NO: 8552 | Nga01793.02 | 333.88 | 304.94 | protein |
| SEQ ID NO: 8553 | Nga01792.02 | 1814.89 | 1902.29 | expressed unknown protein [Ectocarpus siliculosus] |
| SEQ ID NO: 8554 | Nga01794.02 | 1708.62 | 1941.74 | ---NA--- |
| SEQ ID NO: 8555 | Nga02303 | 1410.31 | 1323.03 | uracil-5-carboxylate decarboxylase |
| SEQ ID NO: 8556 | Nga02304 | 417.53 | 549.11 | thioredoxin-like protein |
| SEQ ID NO: 8557 | Nga02305 | 377.98 | 498.52 | ribosomal rna methyltransferase nop2 |
| SEQ ID NO: 8558 | Nga01934 | 177.67 | 166.86 | nadh:flavin oxidoreductase nadh oxidase |
| SEQ ID NO: 8559 | Nga01935 | 559.78 | 721.17 | ---NA--- |
| SEQ ID NO: 8560 | Nga21213 | 457.87 | 459.46 | ---NA--- |
| SEQ ID NO: 8561 | Nga01936 | 1210.14 | 990.61 | protein |
| SEQ ID NO: 8562 | Nga01933 | 2305.07 | 2532.19 | pyrroline-5-carboxylate reductase |
| SEQ ID NO: 8563 | Nga01729 | 1477.19 | 1757.80 | pyruvate carboxylase |
| SEQ ID NO: 8564 | Nga01730 | 318.25 | 270.81 | retinol retinaldehyde reductase |
| SEQ ID NO: 8565 | Nga07146 | 1529.41 | 1390.59 | protein |
| SEQ ID NO: 8566 | Nga20139 | 863.11 | 1198.76 | prolyl 4- alpha subunit domain protein |
| SEQ ID NO: 8567 | Nga07147 | 809.88 | 1005.28 | calcium-independent phospholipase a2-gamma |
| SEQ ID NO: 8568 | Nga05428.02 | 459.75 | 494.95 | aminotransferase class i and ii |
| SEQ ID NO: 8569 | Nga01646.2 | 1423.30 | 1713.42 | iojap-related protein |
| SEQ ID NO: 8570 | Nga01645.02 | 604.10 | 504.81 | lysophospholipase-like protein |
| SEQ ID NO: 8571 | Nga20646.1 | 237.20 | 195.62 | ---NA--- |
| SEQ ID NO: 8572 | Nga00508.02 | 6980.90 | 6051.63 | glutathione peroxidase |
| SEQ ID NO: 8573 | Nga00500.02 | 4996.24 | 4992.33 | glutaryl- mitochondrial precursor |
| SEQ ID NO: 8574 | Nga00512.02 | 74.11 | 81.85 | ---NA--- |
| SEQ ID NO: 8575 | Nga00499.02 | 3887.18 | 3369.14 | ---NA--- |
| SEQ ID NO: 8576 | Nga05420.02 | 13110.33 | 13438.71 | ribosomal protein l27 |
| SEQ ID NO: 8577 | Nga05415.02 | 1324.32 | 1401.09 | protein |
| SEQ ID NO: 8578 | Nga20622 | 65.75 | 80.13 | conserved unknown protein [Ectocarpus siliculosus] |
| SEQ ID NO: 8579 | Nga07152 | 106.80 | 91.15 | ---NA--- |
| SEQ ID NO: 8580 | Nga07150 | 408.47 | 489.82 | tyrosyl-trna synthetase |
| SEQ ID NO: 8581 | Nga07151 | 2242.83 | 1910.60 | 58 kda |
| SEQ ID NO: 8582 | Nga01821 | 212.66 | 198.47 | cln3-like protein |
| SEQ ID NO: 8583 | Nga01820 | 265.82 | 233.10 | protein |
| SEQ ID NO: 8584 | Nga21067 | 269.33 | 348.47 | ---NA--- |
| SEQ ID NO: 8585 | Nga07125 | 444.80 | 357.63 | ubiquinone biosynthesis protein |
| SEQ ID NO: 8586 | Nga04439 | 145.56 | 182.25 | protein |
| SEQ ID NO: 8587 | Nga20210.1 | 152.67 | 150.91 | transcription factor iiic-gamma subunit |
| SEQ ID NO: 8588 | Nga20424 | 313.87 | 266.20 | duf726 domain protein |
| SEQ ID NO: 8589 | Nga20227 | 317.68 | 220.38 | ---NA--- |
| SEQ ID NO: 8590 | Nga00134 | 1936.36 | 1472.57 | protein |
| SEQ ID NO: 8591 | Nga00142 | 266.83 | 247.24 | protein |
| SEQ ID NO: 8592 | Nga00138 | 621.64 | 649.37 | autophagy protein 16 |

FIGURE 24 EF

| # | Nga model | +N rpkb | -N rpkb | GO |
|---|---|---|---|---|
| SEQ ID NO: 8593 | Nga00135 | 1868.46 | 1696.82 | conserved unknown protein [Ectocarpus siliculosus] |
| SEQ ID NO: 8594 | Nga00129 | 1274.04 | 707.88 | ---NA--- |
| SEQ ID NO: 8595 | Nga20276 | 808.06 | 751.28 | alpha-ketoglutarate-dependent taurine dioxygenase |
| SEQ ID NO: 8596 | Nga20840 | 186.48 | 210.84 | c2h2 zinc finger protein |
| SEQ ID NO: 8597 | Nga20119 | 533.23 | 554.16 | erd (early-responsive to dehydration stress) family protein |
| SEQ ID NO: 8598 | Nga00139 | 292.60 | 354.64 | duf221 domain |
| SEQ ID NO: 8599 | Nga00130 | 2123.92 | 2144.62 | ---NA--- |
| SEQ ID NO: 8600 | Nga00132 | 521.59 | 667.57 | atp-binding cassette superfamily |
| SEQ ID NO: 8601 | Nga00137 | 349.87 | 336.57 | conserved unknown protein [Ectocarpus siliculosus] |
| SEQ ID NO: 8602 | Nga00127 | 730.57 | 913.77 | wd repeat-containing protein 43 |
| SEQ ID NO: 8603 | Nga20742 | 457.50 | 456.41 | ---NA--- |
| SEQ ID NO: 8604 | Nga00131 | 328.66 | 459.19 | rna 3 -terminal phosphate cyclase family protein |
| SEQ ID NO: 8605 | Nga00140 | 3504.04 | 3267.22 | ---NA--- |
| SEQ ID NO: 8606 | Nga20432 | 89.80 | 69.25 | armadillo-like helical domain-containing protein |
| SEQ ID NO: 8607 | Nga00125 | 8248.34 | 8201.31 | alpha tubulin 1 |
| SEQ ID NO: 8608 | Nga21097 | 732.58 | 826.90 | bromodomain containing protein |
| SEQ ID NO: 8609 | Nga00128 | 476.74 | 530.82 | wd repeat domain 76 |
| SEQ ID NO: 8610 | Nga00136 | 1434.46 | 1562.78 | nuclear lim interactor-interacting protein |
| SEQ ID NO: 8611 | Nga21248 | 599.54 | 518.07 | mannosyl-oligosaccharide glucosidase |
| SEQ ID NO: 8612 | Nga00126 | 2048.23 | 1908.23 | protein |
| SEQ ID NO: 8613 | Nga00133 | 810.31 | 845.85 | u3 small nucleolar rna-associated protein |
| SEQ ID NO: 8614 | Nga07301 | 208.67 | 167.33 | conserved hypothetical protein [Albugo laibachii Nc14] |
| SEQ ID NO: 8615 | Nga03835 | 1252.08 | 1067.44 | purple acid phosphatase |
| SEQ ID NO: 8616 | Nga03836 | 213.94 | 153.63 | ---NA--- |
| SEQ ID NO: 8617 | Nga21176 | 259.46 | 357.17 | ---NA--- |
| SEQ ID NO: 8618 | Nga02285 | 35442.74 | 23984.62 | photosystem ii reaction center m plastid precursor |
| SEQ ID NO: 8619 | Nga06312 | 562.77 | 576.79 | ---NA--- |
| SEQ ID NO: 8620 | Nga06311 | 3585.68 | 2936.64 | ---NA--- |
| SEQ ID NO: 8621 | Nga00376.02 | 2173.73 | 2140.08 | centrin 3 |
| SEQ ID NO: 8622 | Nga00379.02 | 689.68 | 757.11 | protein |
| SEQ ID NO: 8623 | Nga04337 | 315.97 | 274.57 | hydrophobe amphiphile efflux-1 family |
| SEQ ID NO: 8624 | Nga00022.02 | 707.38 | 651.38 | hemolysin iii |
| SEQ ID NO: 8625 | Nga00027.02 | 6926.51 | 8021.43 | fad-dependent pyridine nucleotide-disulfide oxidoreductase |
| SEQ ID NO: 8626 | Nga00447 | 2010.50 | 2027.90 | 2-dehydro-3-deoxyphosphoheptonate aldolase 3-deoxy-d-arabino-heptulosonate 7-phosphate synthetase |
| SEQ ID NO: 8627 | Nga01570 | 254.39 | 215.38 | phosphoacetylglucosamine mutase |
| SEQ ID NO: 8628 | Nga00192 | 141.67 | 234.70 | ---NA--- |
| SEQ ID NO: 8629 | Nga20124 | 520.39 | 507.56 | heat repeat containing 2 |
| SEQ ID NO: 8630 | Nga00802 | 2918.70 | 2730.10 | ---NA--- |
| SEQ ID NO: 8631 | Nga00062.1 | 197.39 | 174.17 | biopterin transport-related protein bt1 |
| SEQ ID NO: 8632 | Nga05112 | 228.41 | 262.51 | alcohol oxidase |
| SEQ ID NO: 8633 | Nga03822.01 | 8692.90 | 8393.50 | gtp-binding nuclear protein ran |
| SEQ ID NO: 8634 | Nga05506.01 | 360.95 | 301.25 | ---NA--- |
| SEQ ID NO: 8635 | Nga02743 | 430.94 | 553.59 | serine palmitoyltransferase |
| SEQ ID NO: 8636 | Nga06381 | 1955.70 | 2136.48 | fatty acid desaturase a |
| SEQ ID NO: 8637 | Nga20478 | 748.06 | 779.06 | membrane protein |
| SEQ ID NO: 8638 | Nga03996 | 362.03 | 389.77 | ---NA--- |
| SEQ ID NO: 8639 | Nga20090 | 289.98 | 291.67 | kiaa0789 protein |
| SEQ ID NO: 8640 | Nga00878 | 858.60 | 635.73 | pantoate beta-alanine ligase |
| SEQ ID NO: 8641 | Nga00066 | 2393.81 | 2295.95 | nadh dehydrogenase 1 alpha subcomplex subunit 8 |
| SEQ ID NO: 8642 | Nga01454.2 | 106.36 | 85.99 | phosphopantothenate--cysteine ligase |
| SEQ ID NO: 8643 | Nga00838.1 | 940.72 | 973.95 | uv excision repair protein rad23 |
| SEQ ID NO: 8644 | Nga03138 | 515.75 | 387.47 | protein |
| SEQ ID NO: 8645 | Nga00581.01 | 395.78 | 432.88 | dna polymerase v family |
| SEQ ID NO: 8646 | Nga01059 | 294.53 | 308.06 | histone deacetylase superfamily |
| SEQ ID NO: 8647 | Nga03451 | 1041.55 | 1062.54 | fg-gap repeat domain protein |
| SEQ ID NO: 8648 | Nga01255 | 60.87 | 65.94 | ---NA--- |
| SEQ ID NO: 8649 | Nga06472 | 816.59 | 938.97 | snf1-related protein kinase catalytic subunit alpha kin10 |
| SEQ ID NO: 8650 | Nga03082 | 256.64 | 245.13 | hypothetical protein [Magnaporthe oryzae 70-15] |
| SEQ ID NO: 8651 | Nga01124.01 | 1733.86 | 1392.93 | mannose-p-dolichol utilization defect 1 |
| SEQ ID NO: 8652 | Nga03284 | 768.74 | 830.40 | conserved hypothetical protein [Phytophthora infestans T30-4] |
| SEQ ID NO: 8653 | Nga03068 | 258.02 | 282.84 | lariat debranching enzyme |
| SEQ ID NO: 8654 | Nga05679 | 1265.28 | 1358.45 | eukaryotic translation initiation factor 2 subunit 3 |
| SEQ ID NO: 8655 | Nga00552 | 219.24 | 165.98 | translesion dna polymerase-rev1 deoxycytidyl transferase |

FIGURE 24 EG

| # | Nga model | +N rpkb | -N rpkb | GO |
|---|---|---|---|---|
| SEQ ID NO: 8656 | Nga01472 | 61.62 | 69.79 | ---NA--- |
| SEQ ID NO: 8657 | Nga03187 | 755.12 | 871.20 | beta-glucan synthesis-associated |
| SEQ ID NO: 8658 | Nga00495 | 1697.29 | 1688.12 | transmembrane protein 184c |
| SEQ ID NO: 8659 | Nga00728 | 997.98 | 982.12 | nuclear receptor corepressor 2 |
| SEQ ID NO: 8660 | Nga06424 | 937.50 | 1154.27 | protein |
| SEQ ID NO: 8661 | Nga00182 | 456.20 | 449.81 | retinol retinaldehyde reductase |
| SEQ ID NO: 8662 | Nga05994 | 271.55 | 278.59 | protein |
| SEQ ID NO: 8663 | Nga20156 | 503.89 | 463.16 | ph domain-containing protein |

FIGURE 24 EH

USE OF ENDOGENOUS PROMOTERS IN GENETIC ENGINEERING OF *NANNOCHLOROPSIS GADITANA*

CROSS REFERENCE TO RELATED APPLICATIONS

This application claims benefit of priority pursuant to 35 U.S.C. §119(e) of U.S. provisional patent application No. 61/548,157, filed 17 Oct. 2011 and U.S. provisional patent application No. 61/578,110, filed 20 Dec. 2011, both of which are hereby incorporated by reference in their entirety.

SEQUENCE LISTING

A Sequence Listing submitted in computer readable form (CRF) is hereby incorporated by reference. The CRF file is named 229741-US-2_ST25-v1.txt, was created on Oct. 17, 2012, and contains 9380 kilobytes.

TECHNICAL FIELD

This disclosure is directed to the production of biomass and lipids from algae. Specifically, this disclosure is directed to isolated microalgae nucleic acid control and coding sequences and variants thereof, methods of modifying microalgae, and use of modified microalgae for the production of biomass and lipids.

BACKGROUND

In recent years, a detailed understanding of the many biosynthetic pathways that can be used for the production of biofuel feedstocks and higher value bioproducts has emerged, and novel pathways for the production of specific bioenergy carriers are continuously being discovered in a variety of organisms. (Steen, E. J. et al. Microbial production of fatty-acid-derived fuels and chemicals from plant biomass. Nature 463, 559-562 (2010); Radakovits, R., Jinkerson, R. E., Darzins, A. & Posewitz, M. C. Genetic engineering of algae for enhanced biofuel production. Eukaryotic Cell 9, 486-501 (2010); Rude, M. A. & Schirmer, A. New microbial fuels: a biotech perspective. Current Opinion in Microbiology 12, 274-281 (2009); Jang, Y.-S. et al. Engineering of microorganisms for the production of biofuels and perspectives based on systems metabolic engineering approaches. Biotechnology Advances (2011); Li, H., Cann, A. F. & Liao, J. C. Biofuels: Biomolecular engineering fundamentals and advances. Annual Review of Chemical and Biomolecular Engineering 1, 19-36 (2010)).

Further improvements in strain productivity have been hampered by the lack of a genetically tractable model system for these highly productive oleaginous algae. Currently, the algal model species are the green alga *Chlamydomonas reinhardtii* and the diatom *Phaeodactylum tricornutum*, both of which have genome sequences and established transformation methods. (Merchant, S. S. et al. The *Chlamydomonas* genome reveals the evolution of key animal and plant functions. *Science*, 245-250 (2007); Bowler, C. et al. The *Phaeodactylum* genome reveals the evolutionary history of diatom genomes. *Nature*, 239-244 (2008); Siaut, M. et al. Molecular toolbox for studying diatom biology in *Phaeodactylum tricornutum*. *Gene*, 23-35 (2007); Zaslayskaia, L. A., Lippmeier, J. C., Kroth, P. G., Grossman, A. R. & Apt, K. E. Transformation of the diatom *Phaeodactylum tricornutum* (Bacillariophyceae) with a variety of selectable marker and reporter genes. *Journal of Phycology*, 379-386 (2000); Boynton, J. et al. Chloroplast transformation in *Chlamydomonas* with high velocity microprojectiles. *Science*, 1534-1538 (1988); Kindle, K. L. High-frequency nuclear transformation of *Chlamydomonas reinhardtii*. *Proceedings of the National Academy of Sciences*, 1228-1232 (1990)). Genetic engineering approaches have been used to improve biofuel phenotypes in both of these organisms (Radakovits, R., Eduafo, P. M. & Posewitz, M. C. Genetic engineering of fatty acid chain length in *Phaeodactylum tricornutum*. *Metabolic Engineering*, 89-95 (2011); Work, V. H. et al. Increased lipid accumulation in the *Chlamydomonas reinhardtii* sta7-10 starchless isoamylase mutant and increased carbohydrate synthesis in complemented strains. *Eukaryotic Cell*, 1251-1261 (2010); Wang, Z. T., Ullrich, N., Joo, S., Waffenschmidt, S. & Goodenough, U. Algal Lipid Bodies: Stress induction, purification, and biochemical characterization in wild-type and starchless *Chlamydomonas reinhardtii*. *Eukaryotic Cell*, 1856-1868 (2009); Li, Y. et al. *Chlamydomonas* starchless mutant defective in ADP-glucose pyrophosphorylase hyper-accumulates triacylglycerol. *Metabolic Engineering*, 387-391 (2010)), unfortunately neither of these algae in their native form produce high amounts of biomass or lipids and as such, extensive genetic modifications will be needed prior to their use in biofuel applications.

*Nannochloropsis* is an algae that can accumulate biomass through photoautotrophy, it also stores lipids (Rodolfi, L. et al. Microalgae for oil: Strain selection, induction of lipid synthesis and outdoor mass cultivation in a low-cost photobioreactor. *Biotechnology and Bioengineering*, 100-112 (2009); Converti, A., Casazza, A. A., Ortiz, E. Y., Perego, P. & Del Borghi, M. Effect of temperature and nitrogen concentration on the growth and lipid content of *Nannochloropsis oculata* and *Chlorella vulgaris* for biodiesel production. *Chemical Engineering and Processing: Process Intensification*, 1146-1151 (2009); Gouveia, L. & Oliveira, A. Microalgae as a raw material for biofuels production. *Journal of Industrial Microbiology & Biotechnology*, 269-274 (2009); Pal, D., Khozin-Goldberg, I., Cohen, Z. & Boussiba, S. The effect of light, salinity, and nitrogen availability on lipid production by *Nannochloropsis* sp. *Applied Microbiology and Biotechnology*, 1429-1441 (2011); Zou, N., Zhang, C., Cohen, Z. & Richmond, A. Production of cell mass and eicosapentaenoic acid (EPA) in ultrahigh cell density cultures of *Nannochloropsis* sp. (Eustigmatophyceae). *European Journal of Phycology*, 127-133 (2000)) and may be cultivated using natural sunlight in either open ponds or enclosed systems by companies such as Solix Biofuels (Fort Collins, Colo.), Seambiotic (Tel Aviv, Israel), Hairong Electric Company/Seambiotic (Penglai, China) and Proviron (Antwerp, Belgium).

What is needed is an alga that has high lipid and biomass production, whose genome sequence is know, with established protocols for genetic manipulation, and can be cultivated at commercial scale.

SUMMARY

The present disclosure relates to novel polynucleotide control sequences that regulate transcription. In addition novel polypeptide sequences, polynucleotides that encode those polypeptides, and antibodies directed to those polypeptides are disclosed. Expression vectors comprising the disclosed polynucleotides are also described. The present invention also relates to transgenic alga, methods for growing transgenic alga, and methods for obtaining biomass from transgenic alga.

Described herein are purified polynucleotides comprising nucleotide sequences homologous to sequences selected from SEQ ID NOs: 1-8663; wherein said nucleotide sequence has transcriptional promoter activity. In some variations, the described nucleotide sequences are operably linked to coding sequences that encode polypeptides selected from SEQ ID NOs:8664-8838. In some variations, the described nucleotide sequences can regulate a polynucleotide encoding a polypeptide in a lipid biosynthetic pathway, or a polypeptide that regulates a lipid biosynthetic pathway.

Also described are purified polynucleotides comprising nucleotide sequences that encode polypeptides selected from SEQ ID NOs:8664-8838. The disclosed polypeptides can be operably linked to nucleotide sequences selected from SEQ ID NOs:1-8663. Polynucleotide sequences that hybridize to nucleic acid sequences coding for the disclosed polypeptides are also described.

Methods of obtaining algae are described, wherein the methods comprise, placing at least one alga in a medium, wherein the alga comprises a purified polynucleotide sequence selected from SEQ ID NOs:8664-8838, operably linked to a polynucleotide sequence encoding a polypeptide; allowing the alga to reach a stationary phase; and separating the algae from the medium to obtain a purified algae. The disclosed method can also include steps for reducing the nitrogen content of the media.

Methods of modifying at least one alga is also described, the method comprising, a) introducing a purified polynucleotide sequence selected from SEQ ID NOs:8664-8838, or a purified polynucleotide sequence encoding a polypeptide selected from SEQ ID NO:8664-8838 into at least one alga; and b) contacting the transformed algae with a medium.

BRIEF DESCRIPTION OF THE DRAWINGS

FIG. 1A is a list of Chlorophyll (tetrapyrrole), carotenoid and sterol biosynthesis genes. The list of FIG. 1A is continued on FIG. 1B-FIG. 1C. In FIGS. 1A-1C, "a" designates *N. gaditana* gene model encoding corresponding enzyme; "b" indicates if given gene model has transcript support from RNAseq of a pool of conditions including: +/−nitrate, logarithmic phase, stationary phase, heat shocked culture (2 h at 37° C.), cold treated culture (2 h at 4° C.), culture after 12 h dark, +/−$CO_2$; "c" indicates if the gene model is located in the nuclear genome (N) or chloroplast genome (C).

FIG. 2*a* is *Nannochloropsis gaditana* production of biomass, lipids, protein and sugars quantified during continuous growth over a period of three months in 50% salinity seawater medium supplemented with nitrate, phosphate and $CO_2$ grown with continuous 1000 μE light. Every week half of the culture was harvested and replaced with fresh medium. FIG. 2*b* is a chart illustrating harvested biomass compositions, the majority of which consists of lipids even under nutrient replete conditions. FIG. 2*c* is a table describing the yield in mg/l/d and the biomass composition as a % of total. FIG. 2*d* shows a comparison of *N. gaditana* lipid production rates with other algae examined in this work. FIG. 2*e* is a comparison of *N. gaditana* large scale production rates with other biofuel production platforms. Bars in green indicate our estimations; bars in gray indicate estimations by Atsumi et al. 2009. The values for *N. gaditana* have been extrapolated from 1 L cultures and adjusted for our observed productivity in 12 h/12 h light/dark cycles. The *S. elongatus* production values are for 24 h light and would presumably be lower in 12 h/12 h light/dark cycles.

FIG. 3*a* shows lipid droplets in cells during logarithmic growth. FIG. 3*b* shows lipid droplets in cells during stationary phase. Lipid droplets are fluorescently labeled with BODIPY (492/503) (green), chlorophyll autofluorescence (red). FIG. 3*c* is a GC-FID chromatogram showing a typical *N. gaditana* fatty acid profile.

FIG. 6A is a table comparing the chloroplast gene content of several different organisms with *N. gaditana*. The table of FIG. 6 A is continued on FIGS. 6B-6E.

FIG. 8A is a table of various gene clusters from *N. gaditana*. The table of FIG. 8A is continued on FIGS. 8B-8C. In FIGS. 8A-8C, "a" is the gene ontology (GO) term that defines gene cluster; "b" is the gene ontology term description; "c" is the name of contig that gene cluster is found on; "d" is the corresponding *N. gaditana* gene model; "e" is the *N. gaditana* gene model description; "f" is the gene location in cluster.

FIG. 9*a* is a schematic phylogenetic tree of stramenopiles and photosynthetic algae. The tree is adapted from Eisenreich et al., 2004 and Tyler et al. 2006. Filled green circles on the right indicate photosynthetic species. The inset cladogram outlines the relationship between the different species of *Nannochloropsis* based on 18S rRNA. FIG. 9*b* is a Venn diagram representation of shared/unique genes in comparison of *N. gaditana* with brown algae, diatoms, red algae and green algae. FIG. 9*c* is a pie chart showing the StramenopilePhotoCut of genes common to photosynthetic and absent in non-photosynthetic stramenopiles. Green sector: fraction of the StramenopilePhotoCut that is also found in the GreenCut2 of genes common to the green lineage; yellow sector: genes unique for the photosynthetic Stramenopiles (not found in green or red lineages).

FIG. 11A is the first view of a table of "StramenopilePhotoCut" genes. FIGS. 11B-11S are continuation views of FIG. 11A. In FIG. 11A-FIG. 11S, "a" is the name given to *N. gaditana* gene model by manual curation, "b" is the conserved protein domain(s) ID assigned from NCBI-curated domains, Pfam, SMART, COG, PRK, or TIGRFAM databases, "c" is a description(s) of conserved protein domain given, "d" is algal lineages with homologs to *N. gaditana* gene model. B—Brown, D—diatom, R—red, G—green, "e" indicates if *N. gaditana* gene model has homology to a Green-Cut2 gene. P229741.US.03 Use of Endogenous Promoters FIG. 12*a* is a chart showing the "StramenopilePhotoCut" of genes comparing photosynthetic and nonphotosynthetic stramenopiles. Green indicates the fraction of the "StramenopilePhotoCut" which are found in the GreenCut2 of photosynthetic genes; yellow indicates the "StramenopilePhotoCut" genes that are found in diatom and brown algal lineages, but not found in red or green algal lineages; red indicates the "StramenopilePhotoCut" genes that are found in diatom, brown, and red algal lineages; light green indicates the "StramenopilePhotoCut" genes that are found in diatom, brown, and green algal lineages, but not in GreenCut2; purple indicates the "StramenopilePhotoCut" genes that are found in diatom, brown, red, and green algal lineages, but not in GreenCut2. FIG. 12b is a chart showing the number of "StramenopilePhotoCut" genes with select Gene Ontology (GO) terms. The organisms that were included in the analysis of the "StramenopilePhotoCut" include *N. gaditana* and the photosynthetic stramenopile algae *Ectocarpus siliculosus, Aureococcus.anophagefferens, Phaeodactylum tricornutum,* and *Thalassiosira pseudonana*, the nonphotosynthetic stramenopiles *Phytophtora sojae, Phytophtora ramorum, Phytophtora infestans, Blastocystis hominis,* and *Albugo laibachii*. In addition the red alga *Cyanidioschyzon merolae* and the green algae *Chlamydomonas reinhardtii, Chlorella variabilis* NC64, and *Ostreococcus lucimarinus*, were used to determine if "StramenopilePhotoCut" genes are found in other algal lineages.

FIG. 15A is a table listing lipid metabolic pathway genes. The table of FIG. 15A is continued on FIGS. 15B-15C. In FIGS. 15A-15C, "a" is the candidate *N. gaditana* gene model encoding corresponding enzyme; "b' Indicates if given gene model has transcript support from RNAseq of a pool of conditions including: +/−nitrate, logarithmic phase, stationary phase, heat shocked culture (2 h at 37° C.), cold treated culture (2 h at 4° C.), culture after 12 h dark, +/−$CO_2$.

FIG. 17 is a table comparing lipid metabolic genes in various organisms. "a" is a comparison of the number of copies of lipid metabolic genes that are homologous between *N. gaditana*, brown algae (*E. siliculosus*), diatoms (*P. tricornutum*), red algae (*C. merolae*) and green algae (*C. reinhardtii*), "b" Total number of genes in this organism, "c" Category of lipid metabolic genes, sorted by fatty acid biosynthesis, TAG assembly and lipid degradation, "d" Total number of genes that are listed in specified category of the lipid metabolism, "e" Total number of genes in all listed categories of lipid metabolic pathways.

FIG. 18 is a table of selected GO-term expansions/reductions. "a" are the expansions and reduction of GO-terms. Green indicates over-representation in comparison with both *P. tricornutum* and *C. reinhardtii*, while red indicates under-representation. Lighter green and red indicates over-representation and underrepresentation in comparison with *C. reinhardtii* alone, "b" is the gene ontology term description, "c" signifies whether the GO-term is over- or under-represented in comparison with *P. tricornutum* and *C. reinhardtii*, "d" is the probability for over/under-representation in comparison with *C. reinhardtii* and *P. tricornutum* calculated by Fisher exact test.

FIG. 19 is a list of over-representation of amino acid metabolic GO-terms. "a" expansions and reduction of GO-terms relating to amino acid metabolism. Green indicates overrepresentation in comparison with both *P. tricornutum* and *C. reinhardtii*, while red indicates under-representation, "b" is the gene ontology term description, "c" signifies whether the GO-term is over- or under-represented in comparison with *P. tricornutum* and *C. reinhardtii*, "d" Probability for over/under-representation in comparison with *C. reinhardtii* and *P. tricornutum* calculated by Fisher exact test.

FIG. 20A is a list depicting transcriptional regulation of metabolic pathways. The list of FIG. 20A is continued on FIGS. 20B-20H. In FIGS. 20A-20H, "a" *N. gaditana* gene models differentially regulated during nitrogen deprivation, "b" fold regulation of gene, >1 signifies up-regulation, <1 signifies down-regulation, "c" *N. gaditana* gene model description. A green label indicates a function in photosynthesis; a blue label indicates a function in nitrogen utilization or protein degradation/recycling, "d" conserved protein domain ID assigned from NCBI-curated domains, Pfam, SMART, COG, PRK, or TIGRFAM databases, "e" is a description of conserved protein domain given.

FIG. 22a Genomic PCR confirmation of the presence of the transgene. FIG. 22b Southern blot indicating the nuclear incorporation and copy number of the Zeocin resistance gene in three different transformants (lanes 1-3), and the lack of the transgene in a wildtype control (WT lane).

FIG. 23 is a list of polypeptide sequences and their corresponding SEQ ID NOs, and reference names.

FIG. 24 A is a list of polynucleotides and their corresponding SEQ ID NOs. The list of FIG. 24 A is continued on FIGS. 24 B-24 EH. FIGS. 24 A-24 EH also present reference names and the relative expression levels of these genes under control of their native promoters.

DETAILED DESCRIPTION

Figure 2:
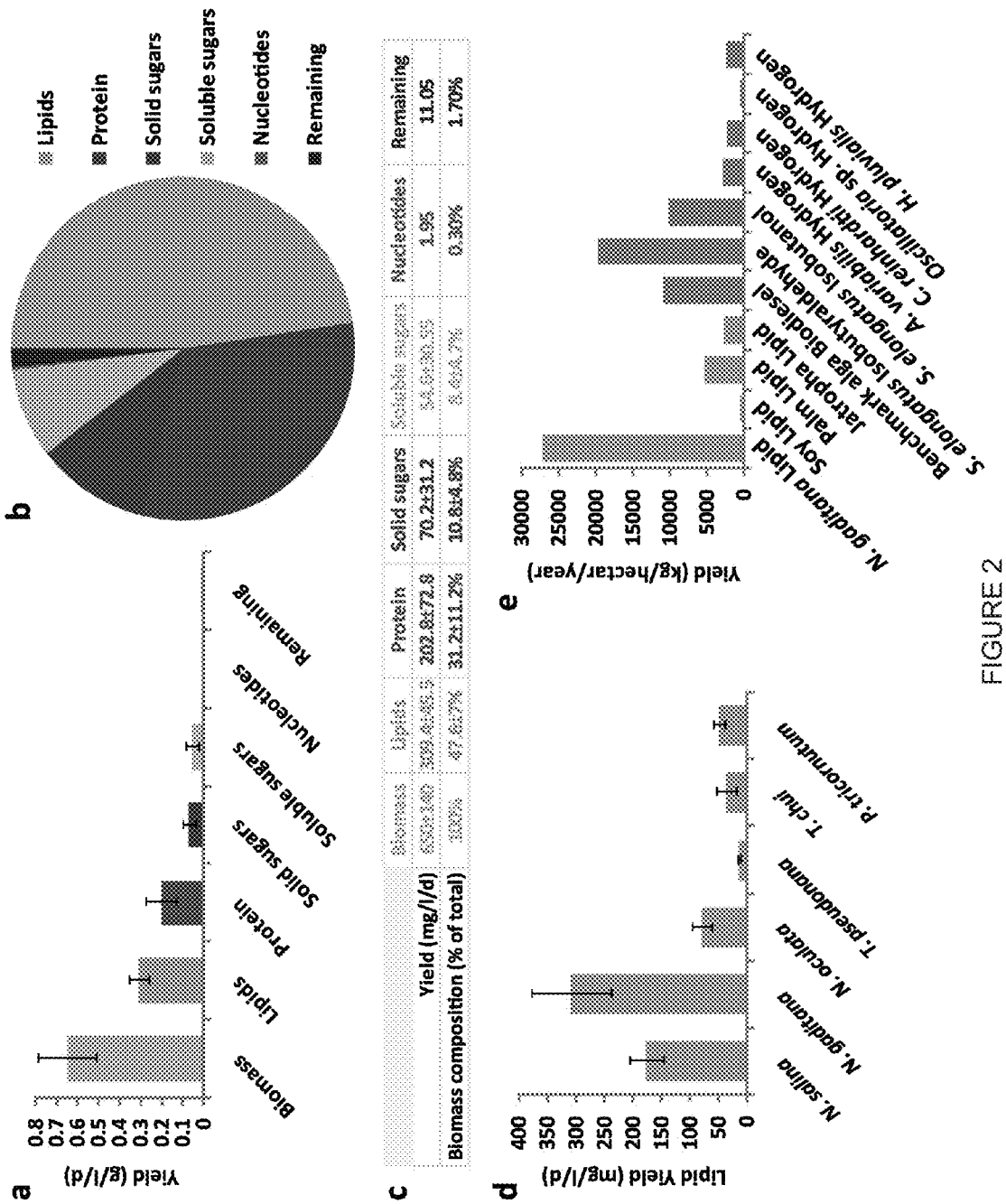
FIG. 2 depicts biomass production by *N. gaditana*.

Disclosed herein are polynucleotides and polypeptides of the algae *N. gaditana*. The disclosed sequences comprise control regions and polypeptides implicated in biomass biosynthesis. In some cases the control regions comprise expression and transcription regulatory sequences, promoter sequences, enhancers, and transcription factor binding sequences that can aid in controlling the expression of operably linked gene sequences. Also disclosed are amino acid sequences involved in biosynthesis of biofuels and biomass, and nucleotide sequences that encode the amino acid sequences.

Also disclosed herein are methods of introducing nucleic acids into algae to create transgenic algae. The nucleic acids can comprise control regions and coding sequences. The transgenic algae can be used to produce lipids, proteins, and other valuable products for use in biofuel and biomass.

The present disclosure relates to novel polynucleotide control sequences that regulate transcription. In addition novel polypeptide sequences, polynucleotides that encode those polypeptides, and antibodies directed to those polypeptides are disclosed. Expression vectors comprising the disclosed polynucleotides are also described. The present invention also relates to transgenic alga, methods for growing transgenic alga, and methods for obtaining biomass from transgenic alga.

Described herein are polynucleotides comprising nucleotide sequences homologous to sequences selected from SEQ ID NOs:1-8663; wherein said nucleotide sequence has transcriptional regulatory activity. In some variations, the described nucleotide sequences are operably linked to coding sequences that encode polypeptides selected from SEQ ID NOs:8664-8838. In some variations, the described nucleotide sequences can regulate a polynucleotide encoding a polypeptide in a lipid biosynthetic pathway, or a polypeptide that regulates a lipid biosynthetic pathway.

Also described are polynucleotides comprising nucleotide sequences that encode polypeptides selected from SEQ ID NOs:8664-8838. The disclosed polypeptides can be operably linked to nucleotide sequences selected from SEQ ID NOs:1-8663. Polynucleotide sequences that hybridize to nucleic acid sequences coding for the disclosed polypeptides are also described.

Methods of obtaining algae are also described. Methods of obtaining algae can comprise, placing at least one alga in a medium, wherein the alga comprises a control polynucleotide sequence selected from SEQ ID NOs:1-8663. In various cases the control polynucleotide can be operably linked to a polynucleotide sequence encoding a polypeptide. The method may further comprise allowing the alga to reach a stationary phase, and separating the alga from the medium to obtain a purified alga. The disclosed method can also include steps for reducing the nitrogen content of the media. In other cases, methods are disclosed for using algae that have been modified to allow biomass and biofuel production during the growth phase.

Methods of modifying algae are also described. Methods of modifying algae can comprise introducing a control polynucleotide sequence selected from SEQ ID NOs:1-8663, or a purified polynucleotide sequence encoding a polypeptide selected from SEQ ID NOs:8664-8838 into at least one alga and then contacting the transformed algae with a medium.

Homologous Nucleotide Sequences Aligned with BLASTn

In one case, the disclosed nucleotide sequences homologous to SEQ ID NOs:1-8663. In various cases, the nucleotide sequences can be identical to the sequences of SEQ ID NOs:1-8663. In other cases, the nucleotide sequences can be homologous to a portion of SEQ ID NOs:1-8663, for example more than about 5 nt, 10 nt, 15 nt, 20 nt, 25 nt, 30 nt, 35 nt, 40 nt, 45 nt, 50 nt, 60 nt, 70 nt, 80 nt, 90 nt, 100 nt, 150 nt, 200 nt, 300 nt, 400 nt, 500 nt, or 600 nt, and/or less than about 700 nt, 600 nt, 500 nt, 400 nt, 300 nt, 200 nt, 150 nt, 90 nt, 80 nt, 70 nt, 60 nt, 55 nt, 50 nt, 45 nt, 40 nt, 35 nt, 30 nt, 25 nt, 20 nt, 15 nt, 10 nt, or 5 nt. In various cases, the homologous sequences can include deleted nucleotides or inserted nucleotides.

In various cases the homologous nucleotide sequences can be aligned by a nucleotide sequence alignment algorithm. For example, blastn for aligning two nucleotide sequences, wherein the program is optimized for highly similar sequences (megablast) or for somewhat similar sequences (blastn; this can be useful where sequences have less than about 90% identity or the sequences have low complexity). In various cases the maximum target sequence is set to the length of the longer of the two sequences to be aligned, the expected threshold can be 10, the word size can be 28, the match/mismatch scores can be −1, −2 and the gap costs linear. In various cases of homology between nucleotide sequences, homology can be expressed as percent identity.

In some variations the nucleotide sequences, when aligned with the sequences of SEQ ID NOs:1-8663, can have identity of more than about 40%, 45%, 50%, 55%, 60%, 65%, 70%, 75%, 80%, 85%, 90%, or 95% and/or less than about 100%, 95%, 90%, 85%, 80%, 75%, 70%, 65%, 60%, 55%, 50%, or 45% identities. In various cases the sequence alignment can have gaps of less than about 15%, 14%, 13%, 12%, 11%, 10%, 9%, 8%, 7%, 6%, 5%, 4%, 3%, 2%, 1%.

Homology Based on Hybridization

In some cases, the inventive nucleotide sequences can hybridize to the sequences of SEQ ID NOs:1-8663. Hybridization can occur under various stringency conditions. Stringency refers to the binding of two single stranded nucleic acids via complementary base pairing. Extensive guides to the hybridization of nucleic acids can be found in: Tijssen, Laboratory Techniques in Biochemistry and Molecular Biology-Hybridization with Nucleic Acid Probes Part I, Ch. 2, "Overview of principles of hybridization and the strategy of nucleic acid probe assays" (1993), Elsevier, N.Y.; and Sambrook et al., Molecular Cloning: A Laboratory Manual (3rd ed.) Vol. 1-3 (2001), Cold Spring Harbor Laboratory, Cold Spring Harbor Press, N.Y. The phrases "hybridizing specifically to", "specific hybridization", and "selectively hybridize to", refer to the preferential binding, duplexing, or hybridizing of a nucleic acid molecule to a particular probe under stringent conditions. The term "stringent conditions" refers to hybridization conditions under which a probe will hybridize preferentially to its target subsequence, and to a lesser extent, or not at all, to other sequences in a mixed population (e.g., a DNA preparation from a tissue biopsy). "Stringent hybridization" and "stringent hybridization wash conditions" are sequence-dependent and are different under different environmental parameters.

Generally, highly stringent hybridization and wash conditions are selected to be about 5° C. lower than the thermal melting point (Tm) for a specific sequence at a defined ionic strength and pH. The Tm is the temperature at which 50% of the target sequence hybridizes to a perfectly matched probe. Very stringent conditions are selected to be equal to the Tm for a particular probe. Often, a high stringency wash is preceded by a low stringency wash to remove background probe signal. An example of stringent hybridization conditions for hybridization of complementary nucleic acids which have more than 100 complementary residues on an array is 42° C. using standard hybridization solutions, with the hybridization being carried out overnight. An example of highly stringent wash conditions is a 0.15 M NaCl wash at 72° C. for 15 minutes. An example of stringent wash conditions is a wash in 0.2× Standard Saline Citrate (SSC) buffer at 65° C. for 15 minutes. An example of a medium stringency wash for a duplex of, for example, more than 100 nucleotides, is 1×SSC at 45° C. for 15 minutes. An example of a low stringency wash for a duplex of, for example, more than 100 nucleotides, is 4× to 6×SSC at 40° C. for 15 minutes.

In some cases, the disclosed inventive nucleic acid sequences can bind to *N. gaditana* control sequences with low stringency.

Nucleotide Sequence Form

In various cases the homologous nucleotide sequences can be single-stranded, double stranded, or a combination thereof. In some variations, the nucleotide sequences can comprise natural nucleic acids, synthetic nucleic acids, non-natural nucleic acids, and/or nucleic acid analogs. The nucleotide sequences can further comprise other non-nucleic acid molecules such as amino acids, and other monomers.

In various cases, the nucleic acids of the disclosed nucleotide sequences can include nucleotides that are metabolized in a manner similar to naturally occurring nucleotides. Also included are nucleic-acid-like structures with synthetic backbone analogues including, without limitation, phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs) (see, e.g.: "Oligonucleotides and Analogues, a Practical Approach," edited by F. Eckstein, IRL Press at Oxford University Press (1991); "Antisense Strategies," Annals of the New York Academy of Sciences, Volume 600, Eds. Baserga and Denhardt (NYAS 1992); Milligan (1993) J. Med. Chem. 36:1923-1937; and "Antisense Research and Applications" (1993, CRC Press)). PNAs contain non-ionic backbones, such as N-(2-aminoethyl) glycine units. Phosphorothioate linkages are described in: WO 97/03211; WO 96/39154; and Mata (1997) Toxicol. Appl. Pharmacol. 144:189-197. Other synthetic backbones encompassed by this term include methyl-phosphonate linkages or alternating methyl-phosphonate and phosphodiester linkages (Strauss-Soukup (1997) Biochemistry 36: 8692-8698), and benzyl-phosphonate linkages (Samstag (1996) Antisense Nucleic Acid Drug Dev 6: 153-156).

Control Activity of Nucleotide Sequences

In various cases the disclosed nucleotide sequences comprise control sequences having transcriptional regulatory activity. Control sequences with transcriptional regulatory activity can include sequences that can affect transcription or expression of a nearby or distal transcribed sequences. In various cases, the disclosed control sequences can enhance or suppress transcription from nearby or distal genes and coding sequences. In various cases, specific sequences can be used to enhance and/or suppress transcription from a nearby gene. In various cases, these nucleic acid sequences can provide binding or recognition sequences for proteins and enzymes involved in transcription, for example TATA binding protein, RNA polymerase (I, II, or III) and DNA binding proteins, such as transcription factors. Disclosed nucleotide sequences can comprise core promoter sites, transcription initiation sites, proximal promoter sites, or distal promoter sites.

In various cases, control activity of a nucleotide sequence can be tested by the use of a coding sequence operatively connected to the nucleotide sequence. In various cases the coding sequence can be a reporter gene. In various cases the reporter can be screenable or selectable. Selectable reporters can be required for survival in certain media, for example in the presence of an antibiotic. Screenable reporters can be observed visually, or easily assayed.

In various cases, less than the entire control region can be used to regulate transcriptional expression of a nearby gene. In various cases portions of the disclosed control regions ranging from less than about 700 nt (nucleotides), 600 nt, 500 nt, 400 nt, 300 nt, 200 nt, 100 nt, 90 nt, 80 nt, 70 nt, 60 nt, 50 nt or 40 nt, and/or in various cases more than about 50 nt, 60 nt, 70 nt, 80 nt, 90 nt, 100 nt, 200 nt, 300 nt, 400 nt, 500 nt, or 600 nt can aid in regulating gene expression. In various cases the described control sequence can be a contiguous sequence. In other cases non-contiguous portions of a control sequence can be connected, and internal portions removed. In various cases portions of a control sequence can be inverted relative to their native orientation. In various cases the control sequences can have internal nucleotides removed. In other cases, nucleotides can be added, or deleted, or the identity of a nucleotide changed.

The disclosed control regions can comprise nucleotide sequence from more than one control region. In various cases the multiple control regions can be operably linked. In various cases the operably linked control regions can be in the same orientation, for example a direct repeat. In other cases, the control regions can be oriented in opposite directions.

In various cases, the disclosed control regions can be modified to include binding sites for specific proteins or enzymes, for example N. gaditana, or non-N. gaditana proteins or transcription factors. In various cases, control regions can be modified to include binding sites for transcription factors and proteins that maybe regulated. In various cases, regulated transcription factors can suppress or enhance transcription from nearby genes in response to environmental stimuli or specific molecules and/or intra-cellular and inter-cellular signals.

The disclosed control regions can be used with promoters, enhancers, and other genetic regulatory elements from different control regions.

In various cases the inventive control sequence is all or a portion of: SEQ ID NO:8336, Nga06994; SEQ ID NO:2473, Nga02045; SEQ ID NO:1992, Nga00934; SEQ ID NO:2325, Nga00965.01; SEQ ID NO:5027, Nga02886; SEQ ID NO:1069, Nga02524.01; SEQ ID NO:2171, Nga00078; SEQ ID NO:3600, Nga04463.1; SEQ ID NO:6398, Nga00714; SEQ ID NO:4944, Nga00519; SEQ ID NO:3025, Nga01286; SEQ ID NO:1712, Nga03241; SEQ ID NO:5909, Nga05308; SEQ ID NO:8316, Nga02117; SEQ ID NO:928, Nga02604; SEQ ID NO:1397, Nga06559; SEQ ID NO:3381, Nga03303; SEQ ID NO:5521, Nga06692; SEQ ID NO:6585, Nga00109; SEQ ID NO:5453, Nga02544.

In various cases, the polynucleotides can have transcriptional promoter activity. In these cases, the control regions can initiate transcription of an operably linked nucleic acid sequence, in various cases the linked nucleic acid is a coding sequence, gene, or non-coding sequence. In some variations, transcription can initiate within the control sequence, in other cases, transcription initiates at an operably linked nucleic acid sequence. In various cases, the coding sequence can code for an N-terminal methionine of an operably linked coding sequence.

Operably Linked Nucleic Acid Sequences and Transgenes

In various cases, the disclosed nucleotide sequences can be operably linked to a coding sequence. Operable linking of nucleic acid sequences can include where a nucleic acid is placed into a functional relationship with another nucleic acid sequence.

In various cases operably linking two or more nucleic acid sequences can form a transgene. In various cases, transgenes can include transcriptional and translational regulatory nucleic acid sequences and nucleic acid sequences encoding a polypeptide. In some variations, the transcriptional and translational regulatory sequences can include promoter sequences, ribosomal binding sites, transcriptional start and stop sequences, translational start and stop sequences, and enhancer or activator sequences. In various cases, the operably linked nucleic acid sequences can comprise an expression cassette. An expression cassette can comprise one or more coding sequences and control sequences that regulate expression of the coding sequence. In various cases, the control sequence can be a promoter sequence, and the coding sequence can comprise untranslated sequence or region that can further comprise a polyadenylation site. In various cases, the expression cassette can be contained on a plasmid or vector. In various cases, expression cassettes further comprise nucleic acid sequences allow for selection or retention of the cassette within the organism.

In various cases, the nucleotide sequences comprising a transgene can be incorporated into a genome of a cell, or can be an unincorporated plasmid or vector. In various cases, a plasmid or vector introduced into a cell can later become incorporated into the cell's genome. In various cases, genome can refer to nucleic acids including coding, non-coding, and regulatory sequences in linear or circular form. In various cases a genome can be one or several chromosomes. In various cases a genome can reside in the cytoplasm, nucleus, or organelles such as mitochondria or chloroplast.

In some cases, the disclosed nucleotide sequences can be operably linked to non-heterologous *N. gaditana* or non-*N. gaditana* coding regions. In some cases control regions operatively linked to coding regions can result in greater or lesser expression of a specific gene. In some cases, the control/promoter region can result in the gene being expressed in response to specific stimuli, for example, a coding sequence that was previously not highly expressed during nitrogen starvation can become highly expressed during nitrogen starvation when operably linked to one or more the disclosed nucleotide sequences.

In various cases, non-*N. gaditana* nucleic acid sequences can be operably linked to the disclosed *N. gaditana* nucleic acid sequences. In various cases, non-*N. gaditana* can refer to other *Nannochloropsis* algae (e.g. *N. gaditana, N. salina, N. oculata, N. oceanica, N. granulate, N. limnetica, N. Nannochloropsis* W2J3B), other photosynthetic algae (e.g. *Chlamydomonas reinhardtii, Chlorella protothecoides*), other eustigmatophytes, and stramenopiles (e.g. *Phaeodactylum tricornutum, Thalassiosira pseudonana, Phytophtora* sp., *Ectocarpus siliculosus, Aureococcus anophageﬀerens*). In various cases, non-*N. gaditana* can refer to sequences from bacteria, fungi and higher plants as well as sequences that have been synthesized to be codon optimized for expression in *Nannochloropsis*.

Disclosed herein are polypeptides sequences homologous to SEQ ID NOs: 8664-8838, as well as nucleotide sequences that encode polypeptides of SEQ ID NOs: 8664-8838. Polypeptides disclosed herein can include amino acid sequences that are identical to the disclosed amino acid sequences. In other cases, the claimed polypeptides include amino acid sequences that can comprise conservative amino acid substitutions as compared to the disclosed sequence. Conservative amino acid substitutions can include amino acids that share characteristics with the substituted amino acid. In various cases, substitution can be made without significant change in the structure or function of the polypeptide.

Conservative amino acid substitutions can be made on the basis of relative similarity of side-chain size, charge, hydrophobicity, hydrophilicity, etc. In various cases, substitutions can be assayed for their effect on the function of the protein by routine testing. Conserved amino acid substitutions include amino acids with similar hydrophilicity value, as wherein amino acids have a hydropathic index which can be based upon an amino acid's hydrophobicity and charge. In various cases, conserved amino acid substitutions can be made between amino acids of the same class, for example non-polar amino acids, acidic amino acids, basic amino acids, and neutral amino acids. Conservative substitutions can also be based upon size or volume. Amino acids can also be classified based upon their ability to form or break a given structure, such as an alpha helix, beta sheet, or intra- or inter-molecular interaction. In various cases conservative amino acid substitutions are based upon more than one characteristic.

Currently disclosed polypeptides can include both natural and non-natural amino acids. In various cases, natural amino acid side chains can be substituted with non-natural side chains. In various cases, amino acids can be derivatised.

The disclosed polypeptides include polypeptides that are homologous to the sequences of SEQ ID NOs:8664-8838. Homology can be expressed as % identity or % similar or % positive. In various cases, % identity is a percentage of amino acids that are identical between two aligned polypeptides, and % similar or % positive is a percentage of amino acids that are non-identical but represent conservative substitutions; for example, lysine to arginine can be considered a conservative substitution where charge is considered.

In various cases, two polypeptides can be aligned by algorithms, for example BLASTp. In various cases, the BLASTp perameters can be set with a maximum target sequence length equal to, greater, or less than the length of the longer of the two polypeptides, the expect threshold can be set to 10, the word size to 3, and scoring matrix can be BLOSUM62, with gap costs of 11 for existence and 1 for extension. BLASTp can report homology of aligned polypeptides as "Identities" and "Positives." The aligned sequences can include gaps to achieve the alignment.

In various cases, homology of amino acid sequences can reflect the percentage of identity or positives when optimally aligned as described above. In various cases, the % homology (% positive) or % identity can be calculated by dividing the number of aligned amino acids within a comparison window. A comparison window can be the entire length of one or the other polypeptides, if the two polypeptides are of unequal length. In other cases, the comparison window can be a portion of one of the polypeptides. In various cases the comparison window for measuring homology or identity of two polypeptide sequences is greater than about 40 aa (amino acids), 45 aa, 50 aa, 55 aa, 60 aa, 65 aa, 70 aa, 75 aa, 80 aa, 85 aa, 90 aa, 95 aa, 100 aa, 150 aa, or 200 aa, and/or less than about 200 aa, 150 aa, 100 aa, 95 aa, 90 aa, 85 aa, 80 aa, 75 aa, 70 aa, 65 aa, 60 aa, 55 aa, 50 aa, or 45 aa.

In various cases, the claimed amino acid sequences can have % identity or % homology (% positive) over a given comparison window, that is greater than about 60%, 65%, 70%, 75%, 80%, 85%, 90%, 91%, 92%, 93%, 94%, 95%, 96%, 97%, 98%, or 99% and/or less than about 100%, 99%, 98%, 97%, 96%, 95%, 94%, 93%, 92%, 91%, 90%, 85%, 80%, 75%, or 70%.

In various cases, a sequence alignment can be performed using various algorithms, including dynamic, local, and global alignment. For example, the algorithm of Smith and Waterman, 1981, Adv. Appl. Math 2: 482; the alignment algorithm of Needleman and Wunsch, 1970, J. Mol. Biol. 48:443; the similarity method of Pearson and Lipman, 1988, Proc. Natl. Acad. Sci. USA 85: 2444. In various cases, computer programs can implement these algorithms (such as EMBOSS, GAP, BESTFIT, FASTA, TFASTA BLAST, BLOSUM, etc.).

In alternative cases, conserved amino acid substitutions can be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In some cases, conserved amino acid substitutions can be made where an amino acid residue is substituted for another having a similar hydrophilicity value (e.g., within a value of plus or minus 2.0), where the following can be an amino acid having a hydropathic index of about −1.6 such as Tyr (−1.3) or Pro (−1.6)s are assigned to amino acid residues: Arg (+3.0); Lys (+3.0); Asp (+3.0); Glu (+3.0); Ser (+0.3); Asn (+0.2); Gin (+0.2); Gly (O); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative cases, conserved amino acid substitutions can be made where an amino acid residue is substituted for another having a similar hydropathic index (e.g., within a value of plus or minus 2.0). In such cases, each amino acid residue can be assigned a hydropathic index on the basis of its hydrophobicity and charge characteristics, as follows: lie (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); H is (−3.2); Glu (−3.5); Gln (−3.5); Asp (−3.5); Asn (−3.5); Lys (−3.9); and Arg (−4.5).

In alternative cases, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (J. Mol. Bio. 179:125-142, 184). Genetically encoded hydrophobic amino acids include Gly, Ala, Phe, Val, Leu, lie, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which can contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR, etc., where R is independently (C$_1$-C$_6$) alkyl, substituted (C$_1$-C$_6$) alkyl, (C$_0$-C$_6$) alkenyl, substituted (C$_1$-C$_6$) alkenyl, (C$_1$-C$_6$) alkynyl, substituted (C$_0$-C$_6$) alkynyl, (C$_5$-C$_{20}$) aryl, substituted (C$_0$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Tryp.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

A % amino acid sequence identity value is determined by the number of matching identical residues divided by the total number of residues of the "longer" sequence in the comparison window. The "longer" sequence is the one having the most actual residues in the comparison window (gaps introduced by WU-Blast-2 to maximize the alignment score are ignored).

The alignment can include the introduction of gaps in the sequences to be aligned. In addition, for sequences which contain either more or fewer amino acids than the protein encoded by the sequence the disclosed polypeptide, it is understood that in one case, the percentage of sequence identity will be determined based on the number of identical amino acids in relation to the total number of amino acids. In percent identity calculations relative weight is not assigned to various manifestations of sequence variation, such as, insertions, deletions, substitutions, etc.

In one case, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Coding Sequences

In various cases, nucleotide sequences encoding the polypeptide sequences of SEQ ID NOS:8664-8838 are included. These nucleotide coding sequences can be translated into a polypeptide having an amino acid sequence identical to the disclosed polypeptide sequence. The inventive coding sequences can further comprise untranslated sequences, for example poly-adenylation sequences. The inventive coding sequences can also comprise intron or intervening, non-translated, sequence that are spliced out of a transcribed mRNA prior to translation. In various cases the transcribed mRNA can be capped with a terminal 7-methylguanosine.

In some variations, due to the degeneracy of the genetic code, multiple nucleotide coding sequences can encode the same polypeptide sequence. These inventive nucleic acid coding sequences can also be homologous to nucleotide sequences that encode the disclosed polypeptides. The nucleotide coding sequences can be aligned by BLASTn, as described above. In various cases the homology (or identities in BLASTn) of these aligned nucleotide sequences can be greater than about 40%, 45%, 50%, 55%, 60%, 65%, 70%, 75%, 80%, 85%, 90%, or 95% and/or less than about 100%, 95%, 90%, 85%, 80%, 75%, 70%, 65%, 60%, 55%, 50%, or 45%. In various cases, the homologous aligned sequences can be less than about 700 nt, 600 nt, 500 nt, 400 nt, 300 nt, 200 nt, 100 nt, 90 nt, 80 nt, 70 nt, 60 nt, 50 nt or 40 nt, and/or more than about 50 nt, 60 nt, 70 nt, 80 nt, 90 nt, 100 nt, 200 nt, 300 nt, 400 nt, 500 nt, or 600 nt.

In various cases, the coding sequence directs transcription of a ribonucleic acid sequence that can be translated into amino acid sequence according to the standard genetic code. In various cases, the code can include variations to the canonical code. In some variations, the coding sequence can include introns, or intervening sequences that do not code for amino acids, but can be transcribed and later removed before the ribonucleic acid is translated into a polypeptide.

Sequences Related to Biofuel and Biomass Biosynthesis.

The disclosed nucleic acid sequences, amino acid sequences, organisms, and method can be involved in lipid biosynthesis. In various cases, lipid biosynthesis can include lipid metabolism, such as synthesis of fatty acids, assembly of triacylglycerides, and activation of lipids. In various cases the disclosed nucleic acid sequences and amino acid sequences are related to lipid metabolic pathway genes, fatty acids biosynthetic genes, triacylglycerides assembly genes, lipid activation genes, and genes can regulate transcription and translation of these genes, as well as proteins that regulate these genes and proteins that regulate the enzymes in these pathways. Some exemplary genes are described in FIG. 1. In various cases, lipid metabolic pathway genes include transcription factors and other regulatory genes and polypeptides. In various cases the coding sequences to be expressed include, thioesterases, acetyl-CoA carboxylase, acyl-transferases, carbonic anhydrases, bicarbonate transporters, nitrate transporters, nitrite transporters, ammonium transporters, glycerol 3-phosphate dehydrogenase, lipases, acyl-CoA oxidases, malic enzyme, malate dehydrogenase, pyruvate dehydrogenase and PEP carboxylase.

Transgenic Organisms

Transgenic organisms are also described. In various cases the described nucleic acid sequences can be introduced into various organisms to create transgeneic organisms. In various cases, the nucleic acid sequences introduced into the organism can be control sequences, coding sequences, or both. In various cases where a transgenic organism comprises both control and coding sequences, the control and coding sequences can be operably linked, for example on an expression cassette.

In various cases, the nucleic acid sequences are incorporated into the genome of the transgenic organism, or are included on a plasmid or vector in the transgenic organism. The inventive nucleic acid sequences can be translocated, re-arranged, deleted, or duplicated within the transgenic organisms. Nucleic acid sequences that are translocated, re-arranged, deleted, or duplicated include single derivatised nucleotides, native nucleotides, single nucleotides, and multiple nucleotides. In various cases, the disclosed transgenic organisms can further comprise native or non-native nucleic acid sequences.

Stably integrated nucleic acid sequences can be passed to progeny. In various cases, stably integrated nucleic acids can have selectable markers that can aid in selecting transgenic organisms. In various cases, selectable markers may be retained by the progeny. In various cases, a selectable marker can confer resistance to a drug or chemical, which can retard the growth of organisms which lack the resistance selectable marker. In various cases, the selectable marker can be an antibiotic resistance gene.

In various cases the transgenic organism can be algae, e.g. *N. gaditana, N. salina, N. oceanica, N. oculata, N. limnetica, N. granulata*, Nannochloropsis W2J3B, *Phaeodactylum tricornutum, Thalassiosira pseudonana, Fragilariopsis cylindrusl, Ectocarpus ciliculosus, Aureococcus anophagefferens*.

Production of Biofuel and Biomass

In various cases, the described compositions and methods are useful in the production of biofuel and biomass. Biofuels can be fuels used for electricity, heat, and fuel that can be derived from renewable resource, including plants and microbes. Biofuels can include alcohols, alkanes, lipids, isoprenoids, fatty acid methyl/ethyl esters, oils, and gases. In various cases, the described organisms can be induced to produce biofuel during a relatively high lipid production stage, or stationary phase. In various cases, the stationary phase can follow a logarithmic growth phase, in which the number of organisms is growing rapidly. The logarithmic phase can be a stage of lower lipid production stage than the stationary phase. In various cases, a stationary phase can be induced. In various cases, the stationary phase can be induced by low nitrate levels. Low nitrate levels can be achieved by nitrogen depletion, removal, sequestration, or lowering the amount of nitrogen being added to a given environment. In various cases, a modified organism may be used that may allow high lipid production state during rapid growth. In various cases, these modified organisms may be genetically engineered to allow high lipid production during rapid growth. In various cases the genetic engineering may include expression cassettes comprising the claimed nucleotide sequences. In various cases, the modified organisms may comprise modified control sequences.

The described organisms can be grown in a liquid environment. In various cases the liquid is a culture medium. In various cases the culture medium is a defined medium. Other liquid medium include fresh water, salt water, waste water, and treated water. In various cases, nutrients and other substances can be added to the liquid medium. In various cases antibiotics are added to the water.

*Nannochloropsis gaditana* CCMP526 (Provasoli-Guillard National Center for Culture of Marine Phytoplankton, West Boothbay Harbor, Me. (CCMP)) was cultivated in either f/2 medium or artificial seawater medium as indicated. The f/2 medium was made using Boothbay Harbor seawater (CCMP) diluted to 50% salinity with $diH_2O$ and supplemented with f/2 trace metals, 8.82 mM $NaNO_3$ and 0.1448 mM $NaH_2PO_4$. A defined artificial seawater medium (ASW) was prepared as follows: 15 g/l NaCl, 6.6 g/l $MgSO_4.7H_2O$, 5.6 g/l $MgCl_2.6H_2O$, 0.5 g/l $CaCl_2.2H_2O$, 1.45 g/l $KNO_3$, 0.12 g/l $KH_2PO_4$, 0.04 g/l $NaHCO_3$, 0.01 g/l $FeCl_3.6H_2O$, 0.035 g/l $Na_2$-EDTA, 0.25 ml/13.64 mM $MnCl_2.4H_2O$, and 0.5 ml/l trace metal mix (20 mg/l $CoCl_2.6H_2O$, 12 mg/l $Na_2MoO_4.2H_2O$, 44 mg/l $ZnSO_4.7H_2O$, 20 mg/l $CuSO_4.5H2O$, 7.8 g/l $Na_2$-EDTA). The pH of the trace metal mix was adjusted to 7.5 and the final pH of the ASW was adjusted to 7.3. No significant difference in growth was observed between the f/2 and ASW media. In various cases seawater or brackish water from any source can be used. In various cases, the total salt concentration in the medium can be reduced to as low as 4 g/l with no NaCl. In various cases, fresh water with added trace metals and minerals can be used.

Methods of Transformation

The claimed nucleic acid sequences can be introduced into an organism, for example an alga. In various cases nucleic acids can be introduced into an alga by electroporation. In various cases, field strength can be greater than about 10,500 V/cm, 10,600 V/cm, 10,700 V/cm, 10,800 V/cm, 10,900 V/cm, 11,000 V/cm, 11,100 V/cm, 11,200 V/cm, 11,300 V/cm, 11,400 V/cm, 11,500 V/cm, 11,600 V/cm, 11,700 V/cm, 11,800 V/cm, 11,900 V/cm, or 12,000 V/cm, and/or in some case, the field strength can be less than about 13,00 V/cm, 12,900 V/cm, 12,800 V/cm, 12,700 V/cm, 12,600 V/cm, 12,500 V/cm, 12,400 V/cm, 12,300 V/cm, 12,200 V/cm, 12,100 V/cm, 12,000 V/cm, 11,900 V/cm, 11,800 V/cm, 11,700 V/cm, 11,600 V/cm, 11,500 V/cm, 11,400 V/cm, 11,300 V/cm, 11,200 V/cm, 11,100 V/cm, or 11,000 V/cm. In various cases, the field strength can be between 10,500 V/cm and 12,00 V/cm.

In some cases, transformation can include various enzyme mixes for creation of protoplasts prior to transformation.

Genetic Transformation of *N. gaditana*

Genomic DNA from an axenic culture of *N. gaditana* (CCMP526, Provasoli-Guillard National Center for Culture of Marine Phytoplankton) was purified as previously described using a phenol/chloroform extraction protocol (Radakovits). A full 454 sequencing run was used to generate a preliminary Newbler assembly of the *N. gaditana* genome. BLASTx was used to annotate the obtained sequence and identify potential genes by homology. The *N. gaditana* genome is similar to the genomes of *P. tricornutum* and *T. pseudonana* in that many genes have 0-2 introns, this characteristic allowed us to identify many full length genes including their upstream promoter regions. From the identified full length genes that included an upstream promoter region we selected three for testing in transformation experiments.

For these experiments the following upstream control regions were obtained: a 608 bp portion from the heat shock protein 70 gene (HSP), a 520 bp portion from the beta-tubulin gene (TUB), and a 710 bp portion from the ubiquitin extension protein (UEP). The control regions were amplified and purified from the genomic *N. gaditana* DNA using the following primers:

```
HSP forward primer:
ATGCTCCGGAGCC GAAGCCCTGTCG ACCAC

HSP reverse primer:
AGCTTGGCCATGTTAGTCTGTCAAAAAATGACGTTGCG

TUB forward primer:
ATGCTCCGGAACTGCGCATGGATTGACCGA

TUB reverse primer:
AGCTTGGCCATGCTTCACAAAAAAGACAGCTTCTTGAT

UEP forward primer:
ATGCTCCGGAGCTGCTGCCCCGACCGTATC

UEP reverse primer:
AGCTTGGCCATCCT GCTGTATGATTTTGGCACAACG.
```

The amplified, purified fragments were inserted into the pPha-T1 plasmid in front of a bleomycin (ble) resistance gene by replacing the *P. tricornutum* fcpB promoter to create the pPha-T1-HSP, pPha-T1-TUB and the pPhaT1-UEP plasmids.

*N. gaditana* was grown in f/2 50% seawater medium under cool white fluorescent lights at 100 μE (24 h illumination). After two weeks of growth $5\times10^8$ cells were harvested for each transformation experiment. Cells were washed twice with 375 mM sorbitol before resuspension in 100 μl 375 mM sorbitol containing 5 μg plasmid DNA linearized with ScaI. Electroporation was done using a ECM630 BTX electroporator (Harvard Apparatus, Inc., Holliston, Mass.) set at 500 Ω, 50 μF and either 900, 1050 or 1200 V using a 1 mm cuvette, resulting in a single 17-20 ms pulse. After electroporation cells were resuspended in 10 ml f/2 medium and kept overnight on a shaker at RT in low light ($50\,\mu\text{mmol}\,\text{m}^{-2}\,\text{s}^{-1}$) before plating on f/2 zeocin selection plates. $5\times10^7$ cells were plated per 10 cm plate containing 3 μg/ml zeocin. Zeocin-resistant colonies were detected after 5-6 weeks and picked after 7-8 weeks. No colonies grew on control plates with cells electroporated without plasmid and survival of cells plated without zeocin appeared unaffected even at the highest voltage. The highest number of zeocin-resistant colonies was generated using 1200 V (12000 V/cm field strength) and the promoter with the highest number of transformants was TUB followed by UEP.

In some embodiments a plasmid may comprise a control sequence operably linked to coding sequence, wherein the coding sequences is a nucleotide sequence coding for a polypeptide. In some embodiments the plasmid may be the pPha-T1 plasmid, or a similar plasmid. In some embodiments the control sequence may be selected from SEQ ID NOs:1-8663. In some embodiments the coding sequence may be selected from SEQ ID NOs:8664-8838. In some embodiments, introduction of a plasmid, comprising a control sequence and a coding sequence, into an organism such as *N. gaditana* may aid in the production of biomass and/or biofuel.

Confirmation of Successful Transformation by Genomic PCR and Southern Blot

Picked colonies were grown in f/2 liquid media and $10^9$ cells were harvested for verification of transgene incorporation into the genome of the zeocin resistant colonies. Genomic DNA was purified as described previously (Radakovits) and either used for genomic PC or digested with the StuI and ClaI restriction enzymes over night for Southern blot analysis. The resulting DNA fragments were separated on a 0.7% agarose gel before transfer onto a nitrocellulose membrane which was used for hybridization with a 371 bp DNA probe specific for the ble resistance gene. The ble probe was generated by PCR using the following primers: ble forward primer: CCGGGACTTCGTGGAGGACGAC; ble reverse primer: GCTGCTCGCCGATCTCGGTCAT. Probe synthesis and hybridization were performed using the AlkPhos Direct Labeling and Detection Systems as described previously, according to the manufacturer's instructions (Amersham Biosciences). The chemilumiscent signal was detected by a LAS-4010 imaging system (GE Healthcare Life Sciences), 20 h exposures gave good results. The differences in the size of the bands indicate random insertion of the transgene while the presence of multiple bands in some mutants signifies multiple insertions.

Disclosed herein are nucleotide sequences and polynucleotide sequences of an alga that may be genetically manipulated to possess desirable biomass production characteristics. The alga has been successfully cultivated outdoors at commercial scale. *Nannochloropsis gaditana*, *N. gaditana*, is a stramenopile alga of the Eustigmatophyceae class.

Photosynthetic algae have long been considered a possible renewable feedstock for biofuel production and have recently experienced intense interest due to diminishing petroleum reserves and increasing atmospheric levels of $CO_2$. One of the main challenges has been the lack of a genetically tractable model alga capable of industrial biofuels production. Described herein is engineered *N. gaditana*, *N. gaditana*-derived sequences, methods of engineering *N. gaditana*, and methods of using engineered *N. gaditana* for the synthesis of biofuels and biomass.

*N. gaditana* is a model organism for oleaginous algal biofuel and biomass production. Modification of *N. gaditana* provides a cost competitive system for photoautotrophic production of biofuels.

Figure 3:
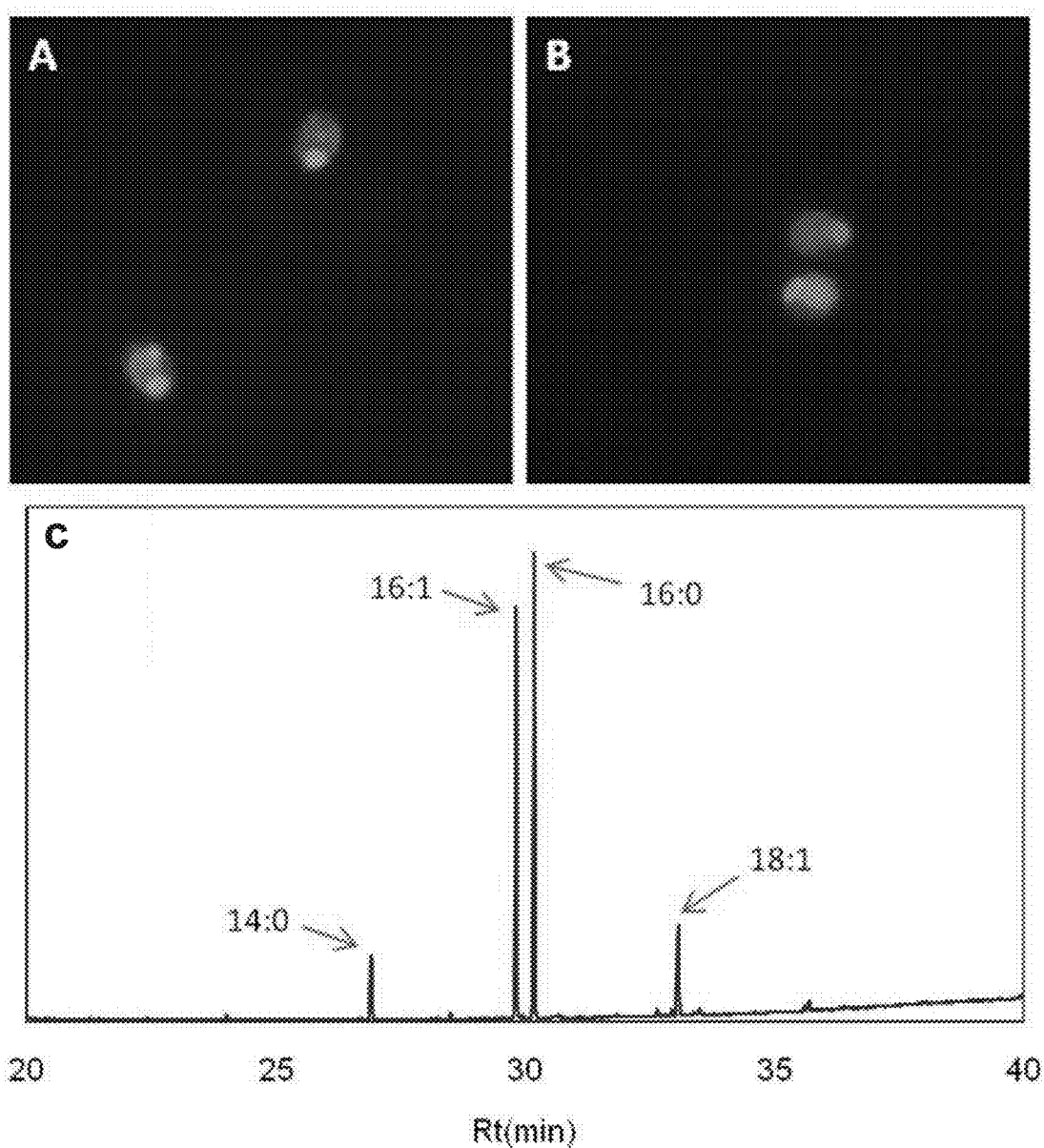
FIG. 3 depicts characterization of *N. gaditana* lipid content.

*N. gaditana* is an oleaginous microalga and can store lipid, in the form of triacylglycerides (TAG), even during logarithmic growth (FIG. 2 and FIG. 3). Various strains of *Nannochloropsis* have been investigated for their biomass and lipid production characteristics and several isolates have been grown for aquaculture purposes. *Nannochloropsis salina*, *N. oculata* and *N. gaditana* have received attention due to their exceptional lipid production characteristics. (Converti, A., Casazza, A. A., Ortiz, E. Y., Perego, P. & Del Borghi, M. Effect of temperature and nitrogen concentration on the growth and lipid content of *Nannochloropsis oculata* and *Chlorella vulgaris* for biodiesel production. *Chemical Engi-* neering and Processing: Process Intensification, 1146-1151 (2009); Simionato, D. et al. Acclimation of *Nannochloropsis gaditana* to different illumination regimes: Effects on lipids accumulation. *Bioresource Technology*, 6026-6032 (2011); Boussiba, S., Vonshak, A., Cohen, Z., Avissar, Y. & Richmond, A. Lipid and biomass production by the halotolerant microalga *Nannochloropsis salina*. *Biomass*, 37-47 (1987)) *Nannochloropsis gaditana* uses photoautotrophy to accumulate biomass and lipids, and can grow to densities of >10 g/l, while tolerating various pH, temperature, and salinity. *N. gaditana* may be a good candidate for development into a model organism for algal biofuel production and the availability of a genome sequence and reliable transformation protocols are steps in this direction. In addition, there are some suggestions that homologous recombination can be more tractable in eustigmatophyte algae than in green algae. (Kilian, O. & Vick, B. Homologous recombination in an algal nuclear genome, Patent number: US 2011/0091977 A1 (2011)). This present disclosure indicates that *N. gaditana* may be a model species.

Current algal model organisms are not robust producers of biomass and lipids. Described herein is a highly productive engineered microalga, *N. gaditana* for use as a new model organism for biofuel production. Further described are methods of genetically engineering *N. gaditana*, including transgenic expression of genes. Also described is the identification and characterization of native *N. gaditana* promoters for the expression of transgenic coding sequences. The disclosed method can be used to express both native and foreign genes for the production of biofuel and other high value products.

Current algal model species are not competitive production strains. Here we present a draft genome sequence, nucleotide and polypeptide sequences, transgene constructs, and a method for genetic transformation of the marine microalga, *N. gaditana*, CCMP526.

The genome assembly of *N. gaditana* includes nuclear (~28 Mb) and organellar genomes, and contains 9,052 gene models. The genes associated with glycerolipid biogenesis are defined and the differential regulation of many genes during nitrogen limited lipid biosynthesis is detailed.

Phylogenomic analysis identified genetic attributes of *N. gaditana*, including unique stramenopile photosynthesis genes and gene expansions, that can explain the distinguishing photoautotrophic phenotypes observed. The availability of a genome sequence and transformation methods can facilitate investigations into *N. gaditana* lipid biosynthesis and can aid in creating genetic engineering strategies to further improve this naturally productive algal strain.

In an effort to transform an oleaginous alga into a model system for biofuel production, the genome of *N. gaditana* was sequenced, and a method for genetic transformation of microalga, *Nannochloropsis gaditana* CCMP5 was developed. Biofuel production rates of *N. gaditana* were compared with several other marine microalga and other biofuel production systems to demonstrate that this alga has favorable biofuel production characteristics.

Despite its ability to produce biofuel, relatively little is known about the metabolic pathways and adaptations that allow *N. gaditana* to reach the cell densities it does, while accumulating lipids. The lipid metabolic pathways in *N. gaditana* both on a genomic and transcriptomic level have been investigated and characterized by quantifying gene expression levels during a relatively low lipid production stage, (logarithmic growth), and a high lipid production stage, (stationary phase) after nitrate depletion. Additionally we have conducted comparative and phylogenomic analysis among other algal lineages to determine genes unique to *N. gaditana* and also to identify sets of conserved proteins across photosynthetic stramenopiles. The genome sequence, its analysis, and the development of genetic transformation in *N. gaditana* are beneficial steps in improving this industrially proven, oleaginous algal fuel biofuel production.

In some cases of nucleic acid sequences that can function as control regions, the sequences can be modified to create higher or lower affinity binding sites for DNA-binding proteins. In some cases, control regions can be modified to bind fewer or more DNA-binding proteins.

In some cases of inventive nucleic acid sequences which code for proteins, the sequences can be non-identical to *N. gaditana* sequences disclosed herein but can code for proteins, peptides, and/or fragments thereof with greater than about 95%, greater than about 90%, greater than about 85%, greater than about 80%, greater than about 75%, greater than about 70%, greater than about 65%, greater than about 60%, greater than about 55%, greater than about 50%, greater than about 45%, greater than about 40%, greater than about 35%, greater than about 30%, or greater than about 25% identity to *N. gaditana* proteins, peptides, and/or fragments thereof.

EXAMPLES

Example 1

Analysis of Biomass and Lipid Yields from High Density Cultures of *N. gaditana*

The yields from *N. gaditana* cultures grown in f/2 medium at 50% salinity are shown in FIG. 2a-c. Yields of 0.65 g/l/d biomass and 0.31 g/l/d total lipids were achieved over a period of three months in 1 L Roux Flasks sparged with air/2% $CO_2$, when half the cultures were exchanged for fresh medium every week. Lipid body accumulation can be triggered/enhanced in algae by nitrogen deprivation or other stress conditions (Hu, Q. et al. Microalgal triacylglycerols as feedstocks for biofuel production: perspectives and advances. *The Plant Journal*, 621-639 (2008)), and the lipid content (47.6%) in actively growing cultures of *N. gaditana* is likely facilitated by the rapid depletion of nitrate in dense cultures (3-8 g/l) during growth. The laboratory productivity numbers have been extrapolated to calculate potential lipid yields in comparison with other algae (FIG. 2d) and to other biofuel production platforms (FIG. 2e). In FIG. 2e, the green bars indicate our extrapolations, while gray bars indicate estimations originally provided by Atsumi et al. (Atsumi, S., Higashide, W. & Liao, J. C. Direct photosynthetic recycling of carbon dioxide to isobutyraldehyde. *Nature Biotechnology*, 1177-1180 (2009)). The yields from *Nannochloropsis* scale from 25 ml cultures to 8 L cultures under laboratory conditions, to 10 hectare outdoor ponds where it is grown on a commercial scale (Hairong Electric Company, Penglai, China and Seambiotic, Tel Aviv, Israel).

*Nannochloropsis gaditana* is a producer of both biomass and lipids under a wide array of culture conditions, including minimal f/2 seawater medium and artificial seawater (10-120% seawater salinity, pH 7-10) supplemented with nitrate, phosphate and $CO_2$. The key components to achieving high yields are the augmented supply of $CO_2$ (1-2%), high concentrations of nitrate (8.9 mM), and inoculums above 3 g/l. Optimal lipid yields were obtained with a starting culture density of ~3.6 g/l. It is likely that self shading is the main limiting factor at higher starting densities. Low density cultures (<0.5 g/l) can be growth inhibited by high light (>200 μE) but the higher density cultures have good production between 1,000 μE and 2,000 μE. For medium to high density cultures (3-10 g/l), no substantial increase in productivity is observed upon increasing the light from 1,000 µE to 2,000 µE, supporting the hypothesis that self shading becomes the limiting factor at these densities. The yields from cultures grown in f/2 medium at 50% salinity are shown in FIG. 2a-c. Yields of 0.65 g/l/d biomass and 0.31 g/l/d total lipids were achieved over a period of three months in Roux Flasks bubbled with 2% $CO_2$ with half the cultures being exchanged for fresh medium every week. Lipid body accumulation can be triggered in algae by nitrogen deprivation and other stress conditions, and the lipid content (47.6%) in these actively growing cultures is likely facilitated by the rapid depletion of nitrate in these dense cultures (3-8 g/l) during the growth cycle. These productivity numbers have been extrapolated to calculate theoretical lipid yields in comparison with other algae (FIG. 2d) and to other biofuel production platforms (FIG. 2e). In FIG. 2e the green bars indicate our extrapolations, while gray bars indicate estimations originally provided by Atsumi et al.4. It is noted that some of the values represent actual production yields from large scale cultivation (Soy, Palm)$_3$, 41, while other values are extrapolated from small scale cultures with 24 h light (*S. elongatus* Isobutyraldehyde and Isobutanol). The *N. gaditana* lipid production yields have been derived from small scale cultures with 12 h light/12 h dark cycles and therefore provide a more realistic estimation relative to *S. elongatus*. The yields from *N. gaditana* scale from 25 ml cultures to 8 L cultures under laboratory conditions, to 10 hectare outdoor ponds where it is grown on a commercial scale (Hairong Electric Company, Penglai, China and Seambiotic, Tel Aviv, Israel). The lipid content of *N. gaditana* cells is apparent upon fluorescent labeling of algal triglycerides with the lipophilic dye, bodipy. Actively growing cells have a constitutive lipid droplet that expands within cells in stationary phase or during nitrogen deprivation (FIGS. 3a and b, respectively). Some of the lipids in *N. gaditana* are composed of palmitic and palmitoleic acid with a minor content of myristic and oleic acid (FIG. 3c), resulting in a relatively simple fatty acid profile, and these fatty acids can be used for the production of biodiesel or biopetrol.

Example 2

Sequencing, Assembly, and Analysis of *N. gaditana* Genome

DNA sequencing reads obtained using both Roche and Illumina (including both unpaired and LIPES protocols) technologies were trimmed for quality, and then assembled separately. These assemblies were merged, followed by removal of scaffolds of bacterial contaminant(s), producing a genome assembly of 2,087 scaffolds, with an N50 of 253 and an L50 of 38,300 nts (TABLE 1). There are 35 scaffolds longer than 100 kb, a total of 561 longer than 20 kb, and a total of 1,447 that are longer than 2 kb.

TABLE 1

| Assembly Statistics | |
| --- | --- |
| Number of assembled contigs | 2,087 |
| Estimated genome size | 28.4 Mbp |
| Contig N50 | 253 |
| Contig L50 | 38,300 bp |
| Genomic G + C content | 54.20% |
| Gene Statistics | |
| Predicted number of genes | 9,052 |
| Chloroplast genes | 124 |

TABLE 1-continued

| Mitochondrial genes | 36 |
| --- | --- |
| Genes supported by ESTs | 8,359 (92.3%) |
| Genes supported by homology (Blast e-value cutoff <$e^{-10}$) | 6,308 (69.7%) |
| Unique genes | 2,744 (30.3%) |
| Average coding sequence length | 1069 bp |
| Average intron length | 220 bp |
| Introns per gene | 1.62 |

Figure 4:
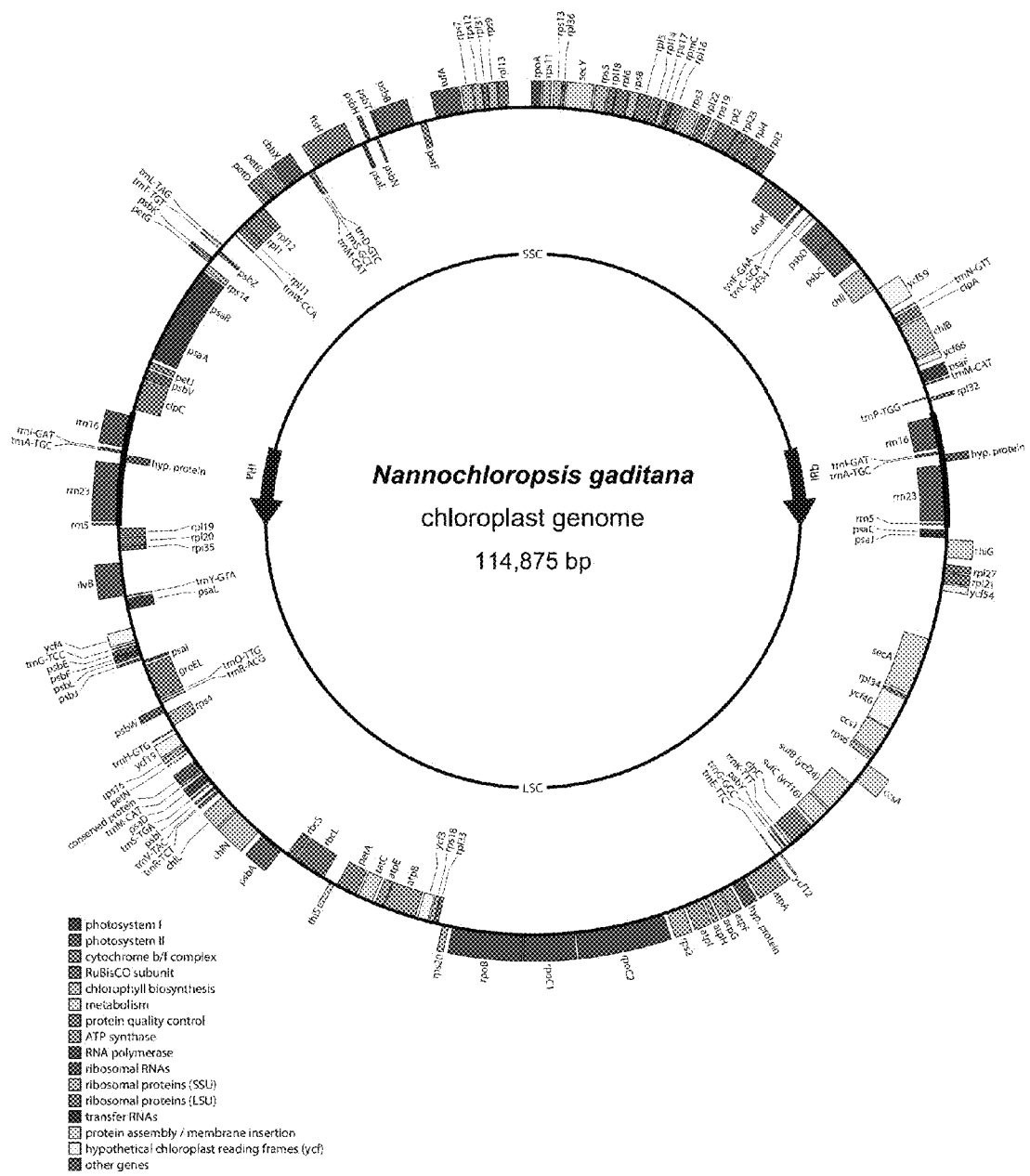
FIG. 4 depicts the *N. gaditana* chloroplast genome. Genes on the inside are transcribed clockwise, and genes on the outside are transcribed counter-clockwise.
Figure 5:
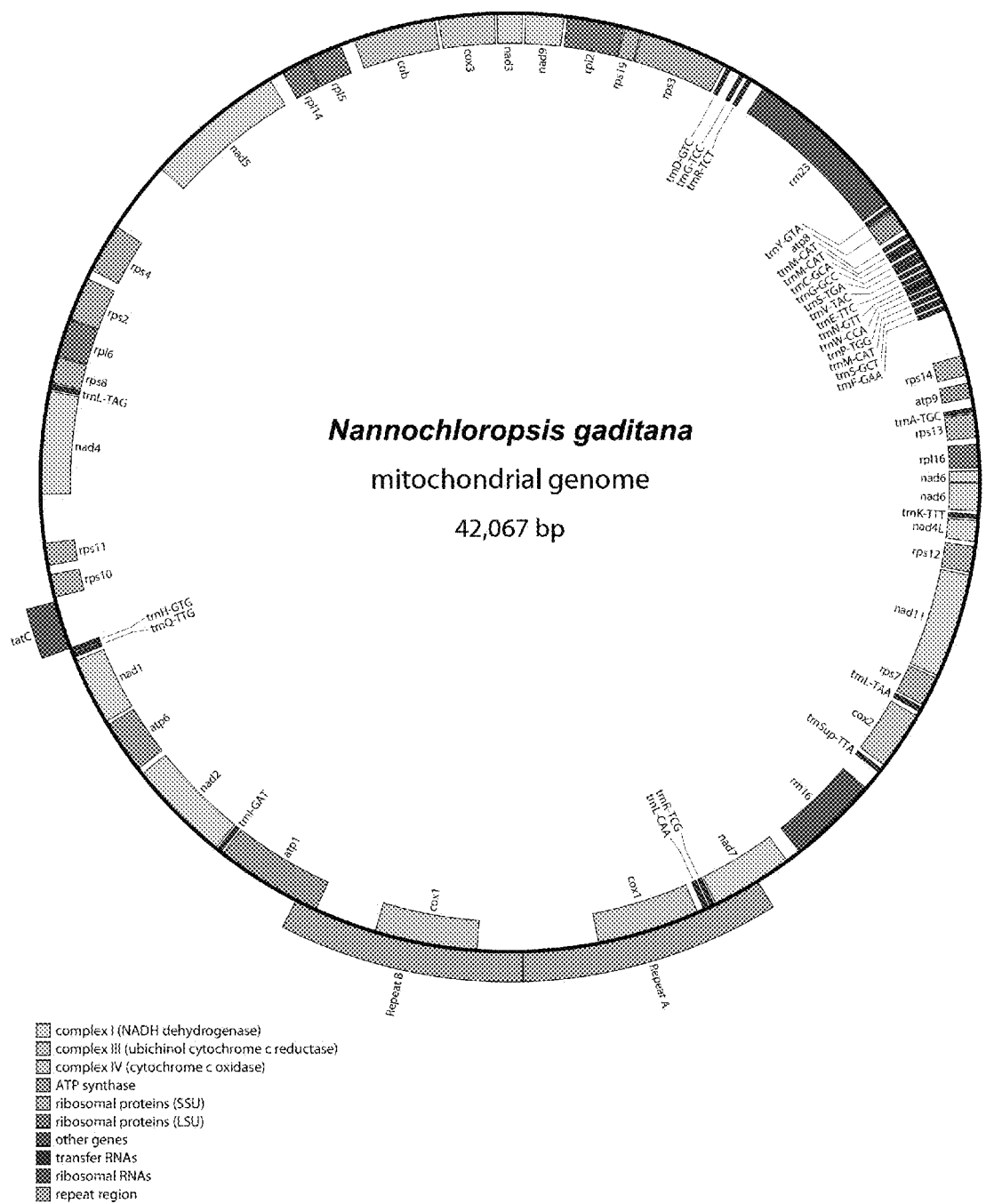
FIG. 5 depicts the *N. gaditana* mitochondrial genome. Genes on the inside are transcribed clockwise, and genes on the outside are transcribed counter-clockwise.

In addition to the nuclear genome, the plastid and mitochondrial genomes were also sequenced, assembled and annotated (FIG. 4 and FIG. 5). Relative to the organellar genomes of *P. tricornutum* and *T. pseudonana*, significant conservation of gene content and gene organization was observed, with some notable exceptions. (Oudot-Le Secq, M.-P. et al. Chloroplast genomes of the diatoms *Phaeodactylum tricornutum* and *Thalassiosira pseudonana* comparison with other plastid genomes of the red lineage. *Molecular Genetics and Genomics*, 427-439 (2007))

Plastid and Mitochondrial Genomes The circular chloroplast genome is 114,785 bp, which is similar in size to those of *P. tricornutum*, *T. pseudonana* and *E. siliculosus*, (Oudot-Le Secq, M.-P. et al. Chloroplast genomes of the diatoms *Phaeodactylum tricornutum* and *Thalassiosira pseudonana* comparison with other plastid genomes of the red lineage. *Molecular Genetics and Genomics* 277, 427-439 (2007); Le Corguille, G. et al. Plastid genomes of two brown algae, *Ectocarpus siliculosus* and *Fucus vesiculosus*: further insights on the evolution of red-algal derived plastids. *BMC Evolutionary Biology* 9, 253 (2009)) and contains 124 protein-encoding genes as well as those for 5S, 16S and 23S rRNAs, and 27 tRNA, which satisfy all translational requirements. Due to the close phylogenetic relationship between *N. gaditana* and diatoms we compared the plastid and mitochondrial genomes with *P. tricornutum*, *T. pseudonana* and *E. siliculosus* (FIG. 6). The gene order is not strictly conserved but there are a number of conserved gene clusters, such as that of ribosomal genes. The *N. gaditana* chloroplast genome contains all the subunits of the light-independent protochlorophyllide reductase (chlB, chlL, and chlN) which is needed for chlorophyll synthesis. Neither chloroplast genomes of *P. tricornutum* or *T. pseudonana* encode these subunits, while the chloroplast genome of the evolutionarily more distant green alga *C. reinhardtii* does. (Li, J., Goldschmidt-Clermont, M. & Timko, M. P. Chloroplast-encoded chlB is required for light-independent protochlorophyllide reductase activity in *Chlamydomonas reinhardtii*. *The Plant Cell* 5, 1817-1829 (1993)) The circular mitochondrial genome is 42,067 bp, which is similar in size to those of *T. pseudonana* and *P. tricornutum*, and contains 36 protein-encoding genes as well as those for 16S and 23S rRNAs and 27 tRNAs, which satisfy all translational requirements except for tRNA-Thr, which is also missing in other heterokonts. (Oudot-Le Secq, M.-P. & Green, B. R. Complex repeat structures and novel feature in the mitochondrial genomes of the diatoms *Phaeodactylum tricornutum* and *Thalassiosira pseudonana*. *Gene* 476, 20-26 (2011)) The *N. gaditana* mitochondrial genome has two complete copies of the cox1 gene lacking introns in two duplicated regions. This is a different configuration than what is found in *P. tricornutum* or *T. pseudonana* where the cox1 gene instead is split into exons and introns. This change in configuration can suggest that the duplicated cox1 gene in *N. gaditana* is an older configuration which has been modified in *P. tricornutum* and *T. pseudonana*. Heterokontophyte brown algae have only a single intron-less copy of cox1. (Oudot-Le Secq, M.-P., Loiseaux-de Goër, S., Stam, W. &

Olsen, J. Complete mitochondrial genomes of the three brown algae (Heterokonta: Phaeophyceae) *Dictyota dichotoma, Fucus vesiculosus, Desmarestia viridis. Current Genetics* 49, 47-58 (2006))

Genome Annotation

A variety of methods were used, including ab initio predictions, homology detection, and RNAseq matching to the genome assembly, and then these were reconciled into a single gene set using Maker. Contigs from the transcript assembly that had strong homology support but were otherwise not part of the Maker gene set were added in to form gene set version 1.1 with 9,052 members (TABLE 2).

TABLE 2

*N. gaditana* Genome Statistics

| Assembly Statistics | |
| --- | --- |
| Number of assembled contigs | 2,087 |
| Estimated genome size | 28.4 Mbp |
| Contig N50 | 253 |
| Contig L50 | 38,300 bp |
| Genomic G + C content | 54.20% |
| Gene Statistics | |
| Predicted number of genes | 9,052 |
| Chloroplast genes | 124 |
| Mitochondrial genes | 36 |
| Genes supported by ESTs | 8,359 (92.3%) |
| Genes supported by homology (Blast e-value cutoff <e−10) | 6,308 (69.7%) |
| Unique genes | 2,733 (30.2%) |
| Avg coding sequence length | 1069 bp |
| Average intron length | 220 bp |
| Introns per gene | 1.62 |

Figure 7:
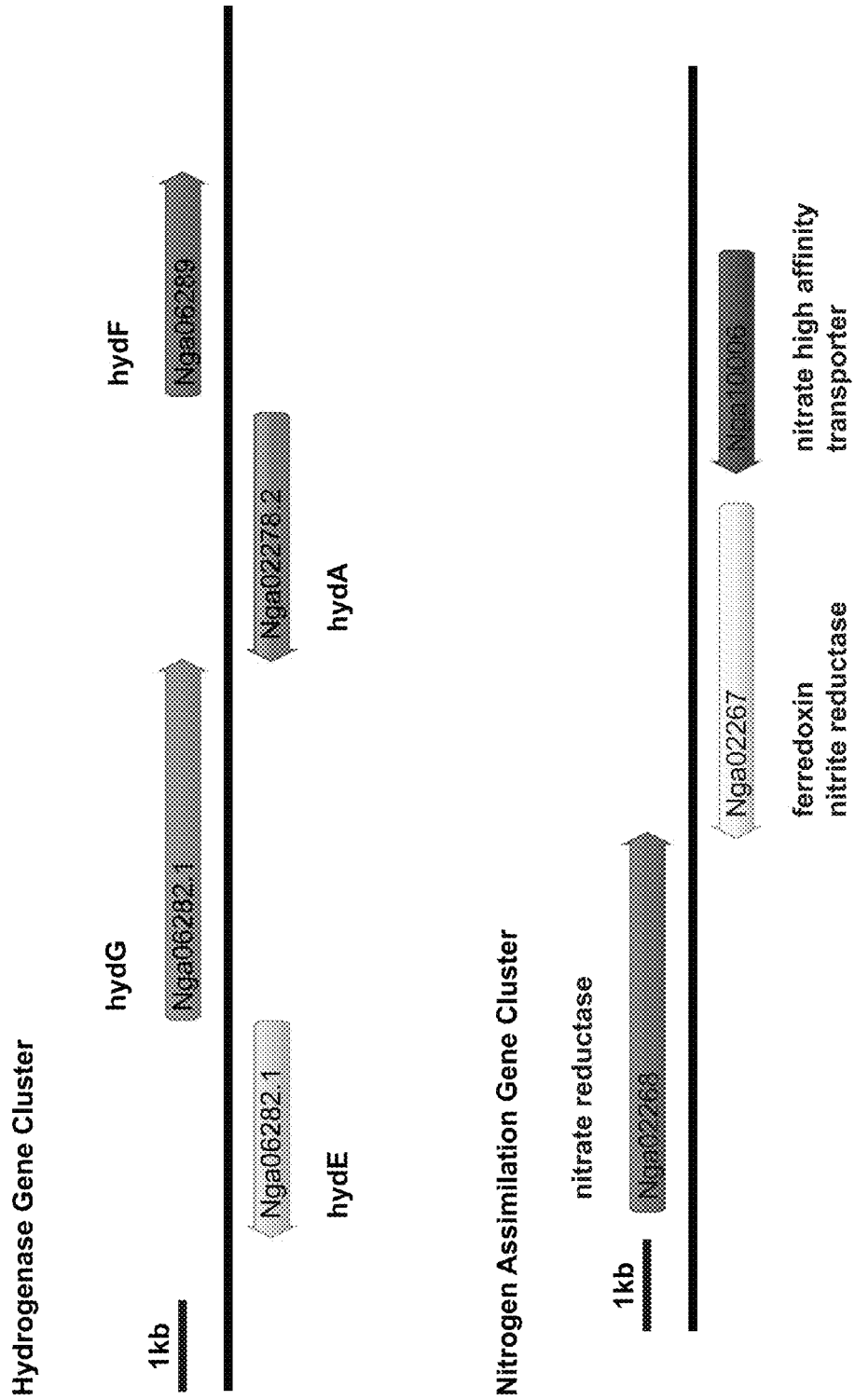
FIG. 7 depicts two functional gene clusters, involved in hydrogen metabolism and nitrogen assimilation, identified in the *N. gaditana* nuclear genome. Arrows indicate gene direction.

Several uniquely organized functional gene clusters have been identified, including a cluster of four genes involved in hydrogenase function (HYDA1, HYDE, HYDF and HYDG) and a cluster of three genes involved in nitrogen assimilation (nitrate reductase, nitrite reductase and a nitrate transporter) (FIG. 7). Clusters of genes with similar ontology annotations are observed in *E. siliculosus*. (Marchler-Bauer, A. et al. CDD: a Conserved Domain Database for the functional annotation of proteins. Nucleic Acids Research 39, 225-229 (2011)). However, while a similar cluster of nitrogen assimilation genes can be observed in prasinophytes and *C. reinhardtii* (Emanuelsson, O., Brunak, S., von Heijne, G. & Nielsen, H. Locating proteins in the cell using TargetP, SignalP and related tools. Nature Protocols 2, 953-971 (2007); Götz, S. et al. High-throughput functional annotation and data mining with the Blast2GO suite. Nucleic Acids Research 36, 3420-3435 (2008)), no such cluster can be observed in the more closely related *E. siliculosus*. (Marchler-Bauer, A. et al. CDD: a Conserved Domain Database for the functional annotation of proteins. Nucleic Acids Research 39, 225-229 (2011)). An expanded analysis of functional gene clusters can be found in FIG. 8.

Comparative Genomics

Figure 9:
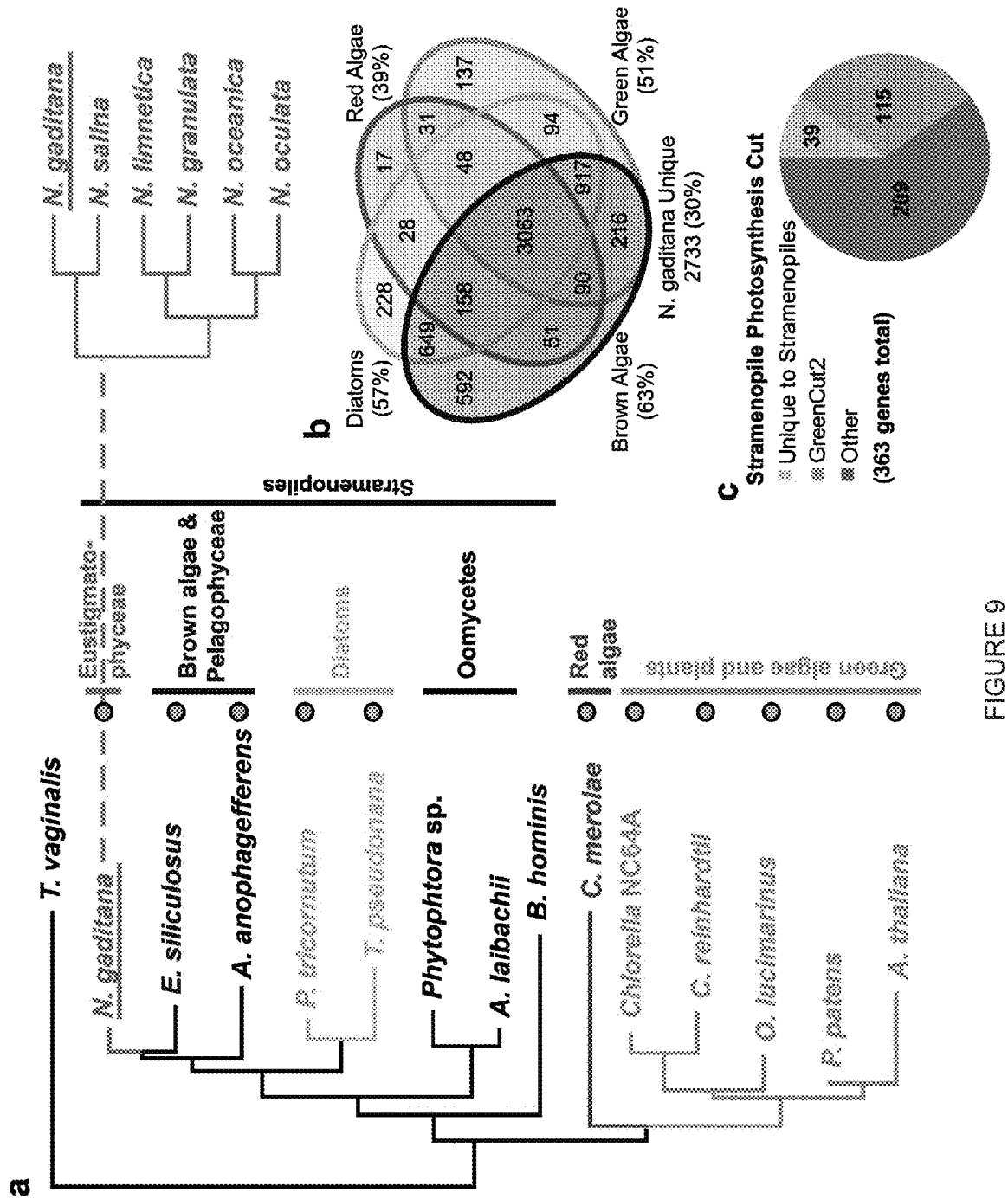
FIG. 9 shows characterization of *N. gaditana* relatedness to other organisms.
Figure 10:
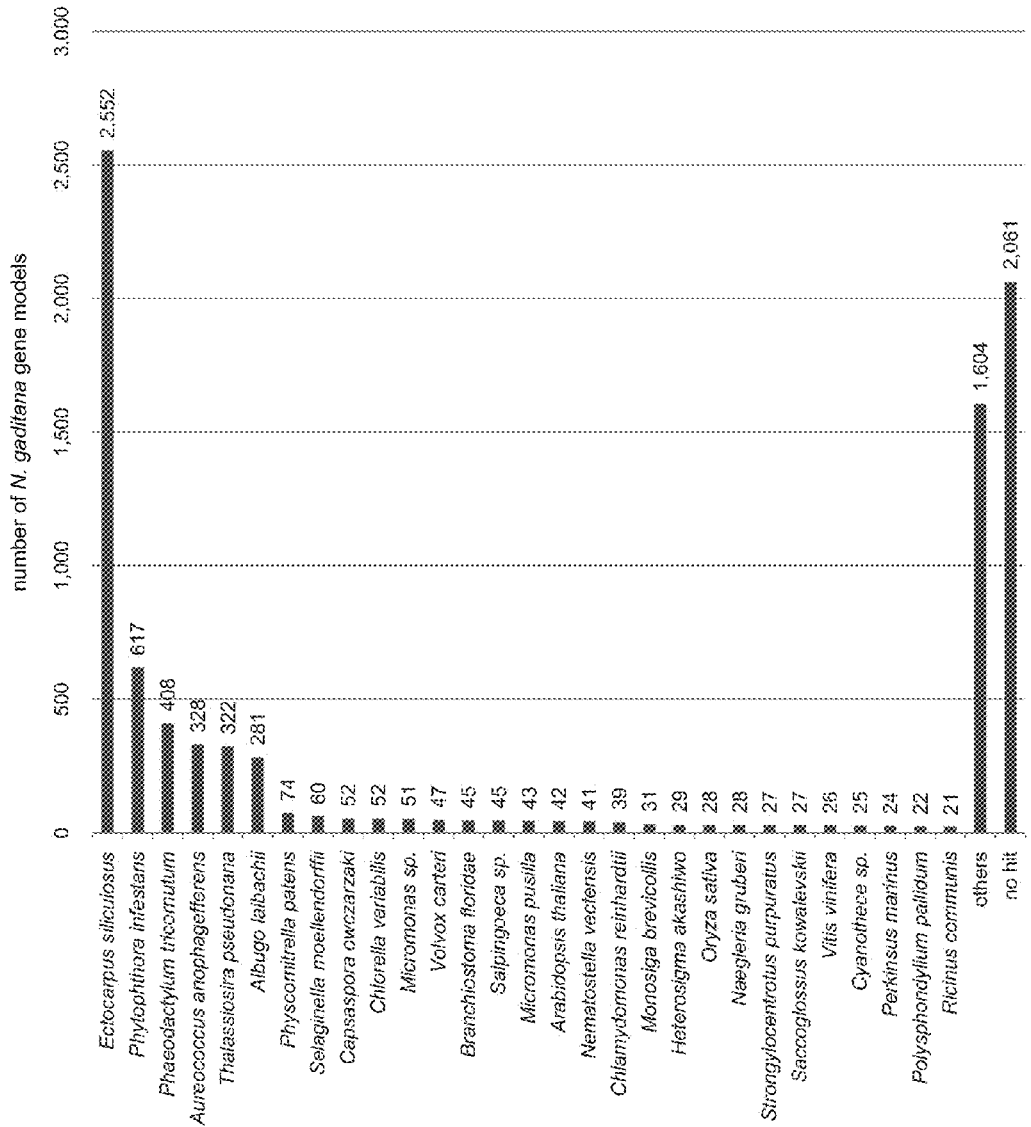
FIG. 10 depicts *N. gaditana* gene models from BLASTp top-hit by organism. *N. gaditana* gene models were compared to all previously sequenced genomes in the nonredundant (nr) protein database using BLASTp. The number of times an organism was the top BLASTp hits (e-value less than 1E-3) of a *N. gaditana* gene model is indicated.

*Nannochloropsis gaditana* is a eustigmatophyte alga that is closely related to the Phaeophyceae (brown algae), with the closely related organism having a fully sequenced genome being the multicellular brown alga, *Ectocarpus siliculosus* (FIG. 9a; Cock, J. M. et al. The Ectocarpus genome and the independent evolution of multicellularity in brown algae. Nature, 617-621 (2010)). To identify novel features of the *N. gaditana* genome, we determined which *N. gaditana* genes have homologs found in brown algae (Cock, J. M. et al. The Ectocarpus genome and the independent evolution of multicellularity in brown algae. Nature, 617-621 (2010)) and the pelagophyte *A. anophagefferens* (Gobler, C. J. et al. Niche of harmful alga *Aureococcus anophagefferens* revealed through ecogenomics. Proceedings of the National Academy of Sciences, 4352-4357 (2011)), green algae (*Chlorella variabilis* NC64A and *Chlamydomonas reinhardtii* Blanc, G. et al. The *Chlorella variabilis* NC64A genome reveals adaptation to photosymbiosis, coevolution with viruses, and cryptic sex. The Plant Cell (2010), Merchant, S. S. et al. The *Chlamydomonas* genome reveals the evolution of key animal and plant functions. Science, 245-250 (2007)), red algae (*C. merolae*; Matsuzaki, M. et al. Genome sequence of the ultrasmall unicellular red alga *Cyanidioschyzon merolae* 10D. Nature, 653-657 (2004)), and diatoms (*T. pseudonana* and *P. tricornutum*; (Armbrust, E. V. et al. The genome of the diatom *Thalassiosira pseudonana*: Ecology, evolution, and metabolism. Science, 79-86 (2004), Bowler, C. et al. The *Phaeodactylum* genome reveals the evolutionary history of diatom genomes. Nature, 239-244 (2008)). This analysis confirms the close evolutionary proximity between the Eustigmatophyceae and Phaeophyceae (FIG. 9b), and provides us with 2,744 genes that may be unique to *N. gaditana*, not found in the other algal genomes queried. This corresponds to 30.3% of the total gene repertoire in *N. gaditana*, which is similar to the fraction of unique genes found in *T. pseudonana, E. siliculosus* and *P. tricornutum*. (Bowler, C. et al. The *Phaeodactylum* genome reveals the evolutionary history of diatom genomes. Nature, 239-244 (2008); Cock, J. M. et al. The Ectocarpus genome and the independent evolution of multicellularity in brown algae. Nature, 617-621 (2010), Armbrust, E. V. et al. The genome of the diatom *Thalassiosira pseudonana*: Ecology, evolution, and metabolism. Science, 79-86 (2004)). Comparison of *N. gaditana* gene models to the non-redundant protein database (BLASTp) yielded top hits from a variety of organisms, the most frequent being stramenopiles (FIG. 10), which was expected based on the phylogeny of *N. gaditana*.

Figure 12:
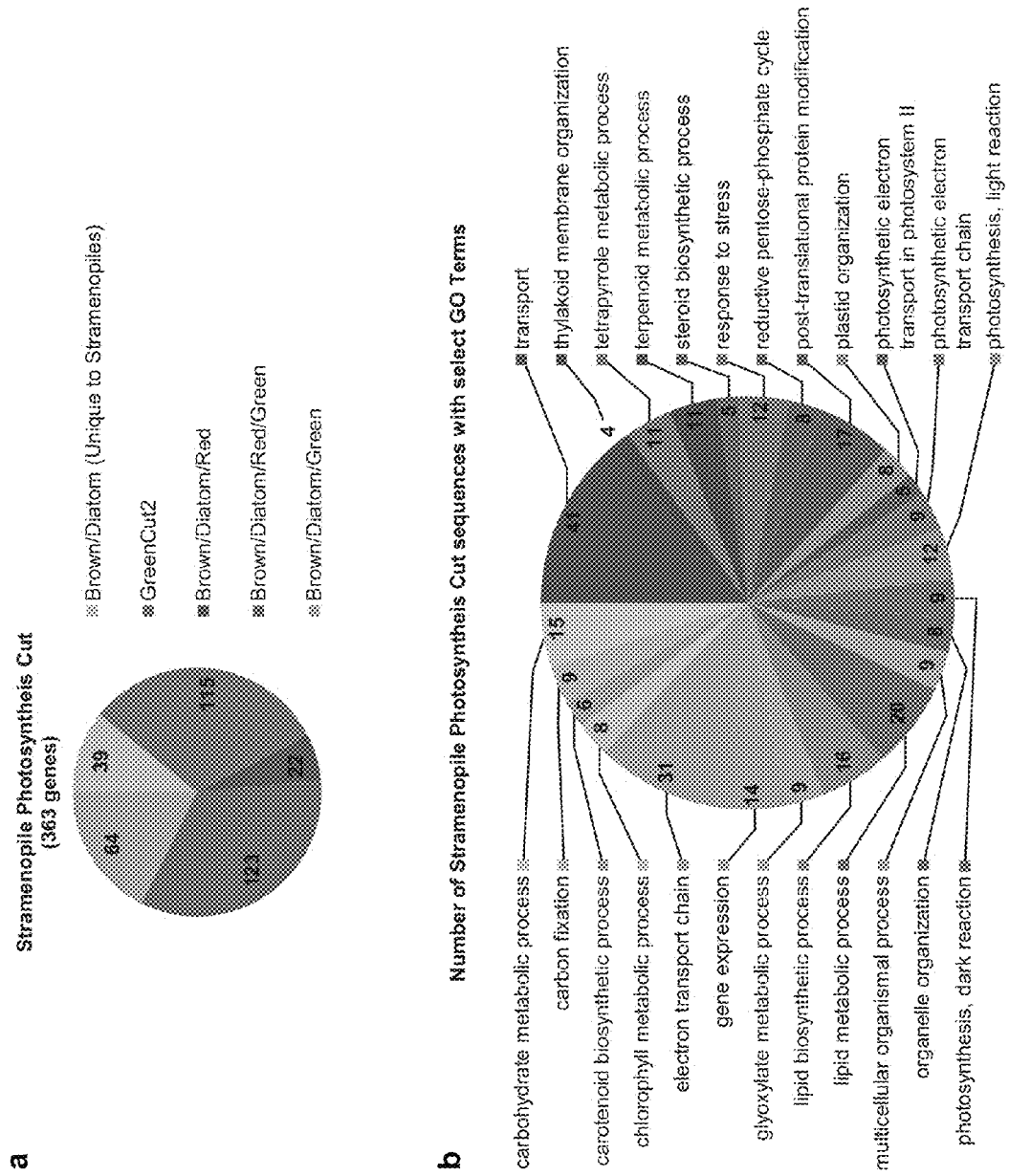
FIG. 12 depicts an expanded version of "StramenopilePhotoCut".

Previous attempts have been made at establishing the minimal essential set of genes needed for photosynthesis, the "GreenCut" of photosynthetic genes, which is a set of 597 orthologs that are conserved in plant and green algal lineages, but not in non-photosynthetic organisms. (Merchant, S. S. et al. The *Chlamydomonas* genome reveals the evolution of key animal and plant functions. Science, 245-250 (2007), Karpowicz, S. J., Prochnik, S. E., Grossman, A. R. & Merchant, S. S. The GreenCut2 resource, a phylogenomically derived inventory of proteins specific to the plant lineage. Journal of Biological Chemistry, 21427-21439 (2011)) We decided to take advantage of the fact that there are both photosynthetic and non-photosynthetic stramenopiles to generate an analogous set of genes conserved in photosynthetic stramenopiles. To establish this "StramenopilePhotoCut" of photosynthetic genes, orthologs common to *N. gaditana* and four photosynthetic stramenopiles (*E. siliculosus, A. anophagefferens, T. pseudonana* and *P. tricornutum*), but not present in non-photosynthetic stramenopiles (*P. sojae, P. ramorum, P. infestans, A. laibachii* or *B. hominis*), were selected, resulting in a list of 363 genes. (FIG. 9c and FIG. 11). The majority of these genes have orthologs in the green and red algal lineages and 115 are found in the "GreenCut2" (Karpowicz, S. J., Prochnik, S. E., Grossman, A. R. & Merchant, S. S. The GreenCut2 resource, a phylogenomically derived inventory of proteins specific to the plant lineage. Journal of Biological Chemistry, 21427-21439 (2011)); see FIG. 12 for an expanded characterization of the genes in the "StramenopilePhotoCut"). However, 39 genes with homologs found in photosynthetic stramenopiles are present in the genome (FIG. 11). Similar to many genes found in the "GreenCut", some of the 39 stramenopile-specific "StramenopilePhotoCut" genes are of completely unknown function, but several of the genes have known domains, including several peptidases/proteases, DNA-binding proteins/transcription factors and transport proteins, as well as genes that are thought to directly interact with the photosystems. Due to the photoautotrophic growth rates exhibited by N. gaditana we also characterized the complete pathways for synthesis of chlorophyll and accessory pigments (FIG. 1). All expected genes could be identified except for those encoding the mevalonate pathway for isopentenyl-pyrophosphate biosynthesis (see analysis of bioenergy metabolic pathways).

Bioenergy Metabolic Pathways

Figure 13:
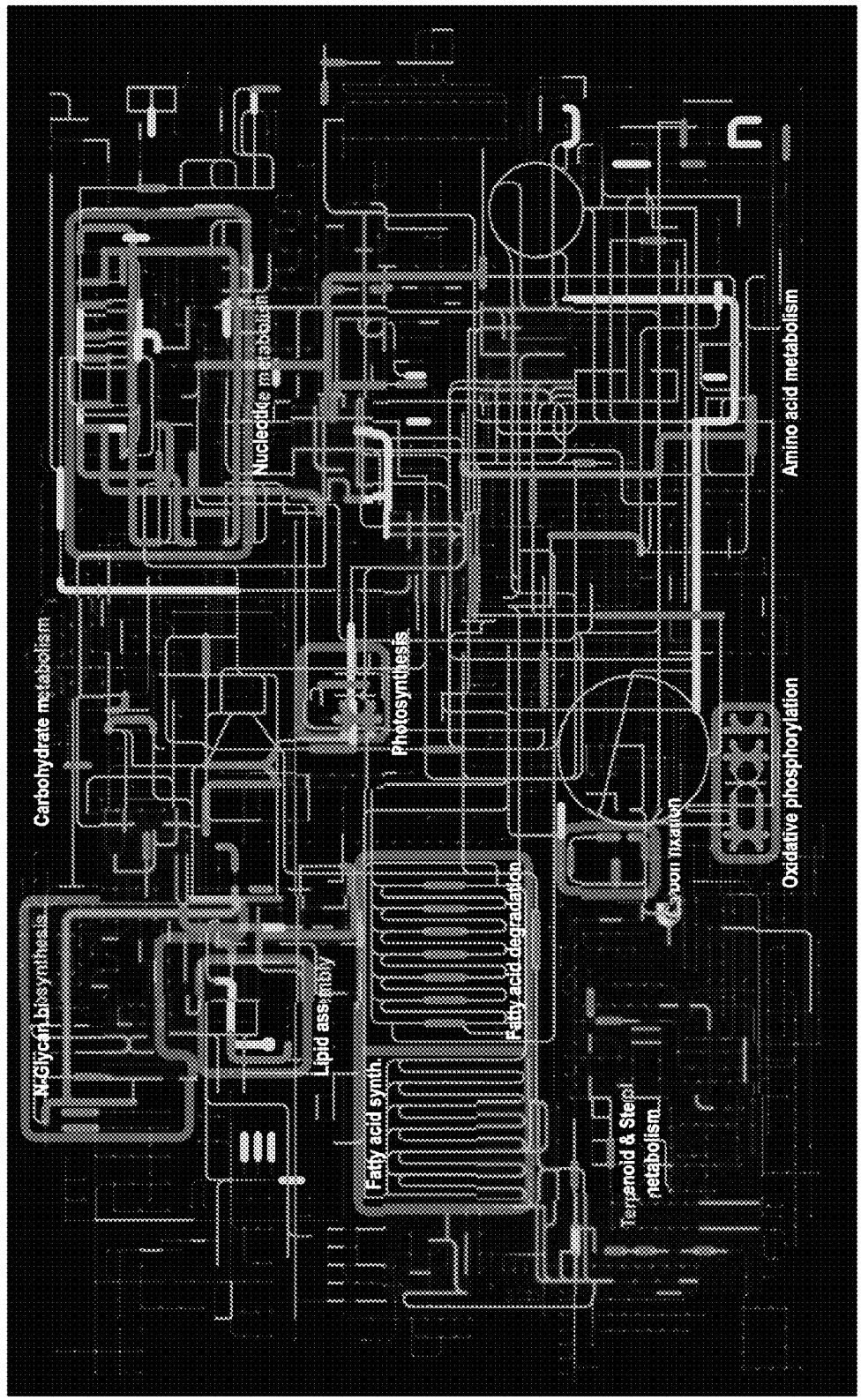
FIG. 13 depicts metabolic pathway map of genes found in *N. gaditana* genome in green. Genes that are up- or down-regulated during nitrogen deprivation are labeled in yellow and blue, respectively. Light gray background traces indicate KEGG pathways not encoded by the *N. gaditana* genome.
Figure 14:
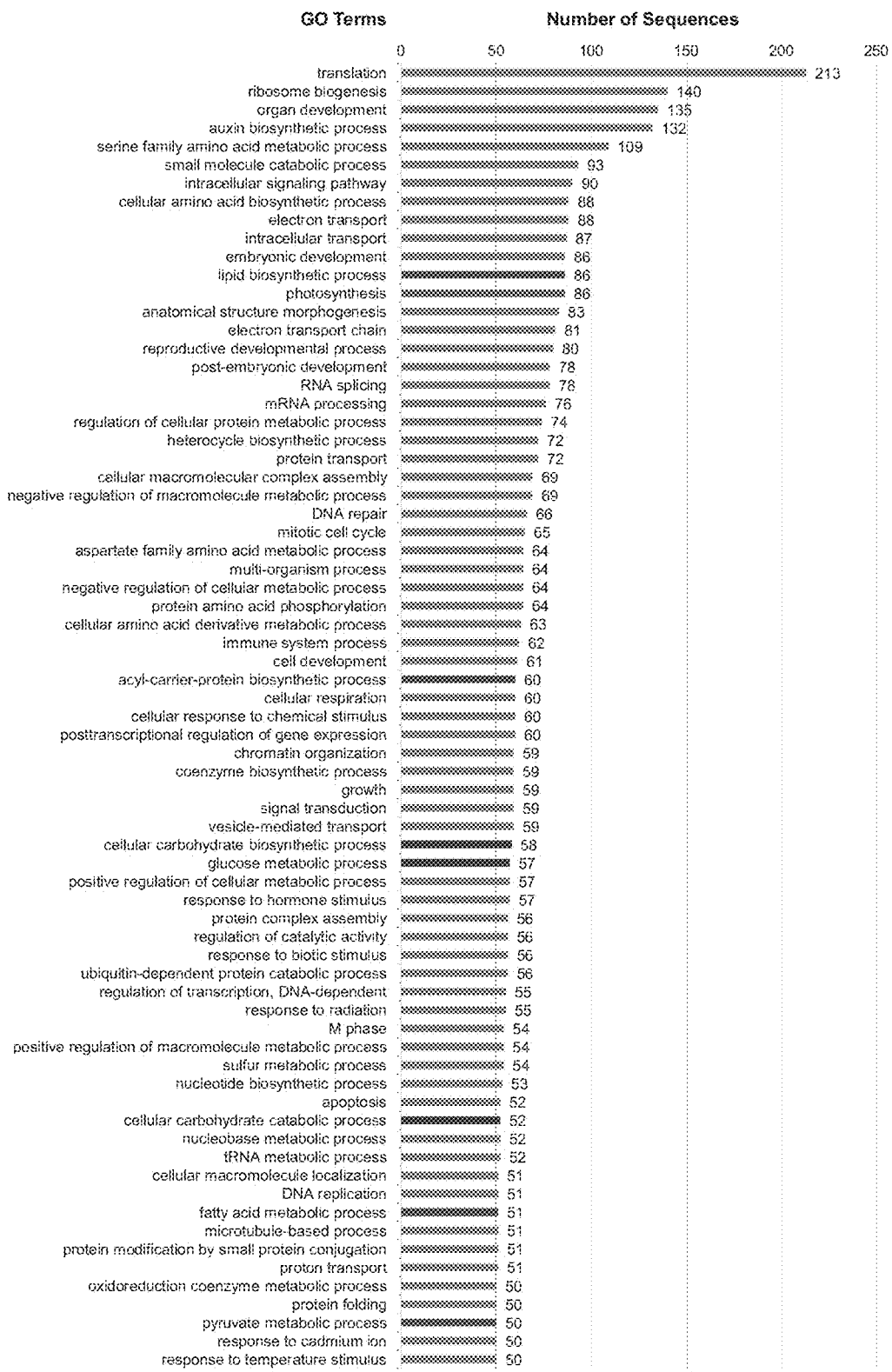
FIG. 14 is a bar graph of the most abundant GO terms assigned to *N. gaditana* gene models. Number of gene models assigned to specified GO term. GO terms associated with lipids (red), carbohydrates (purple), and photosynthesis (green).
Figure 16:
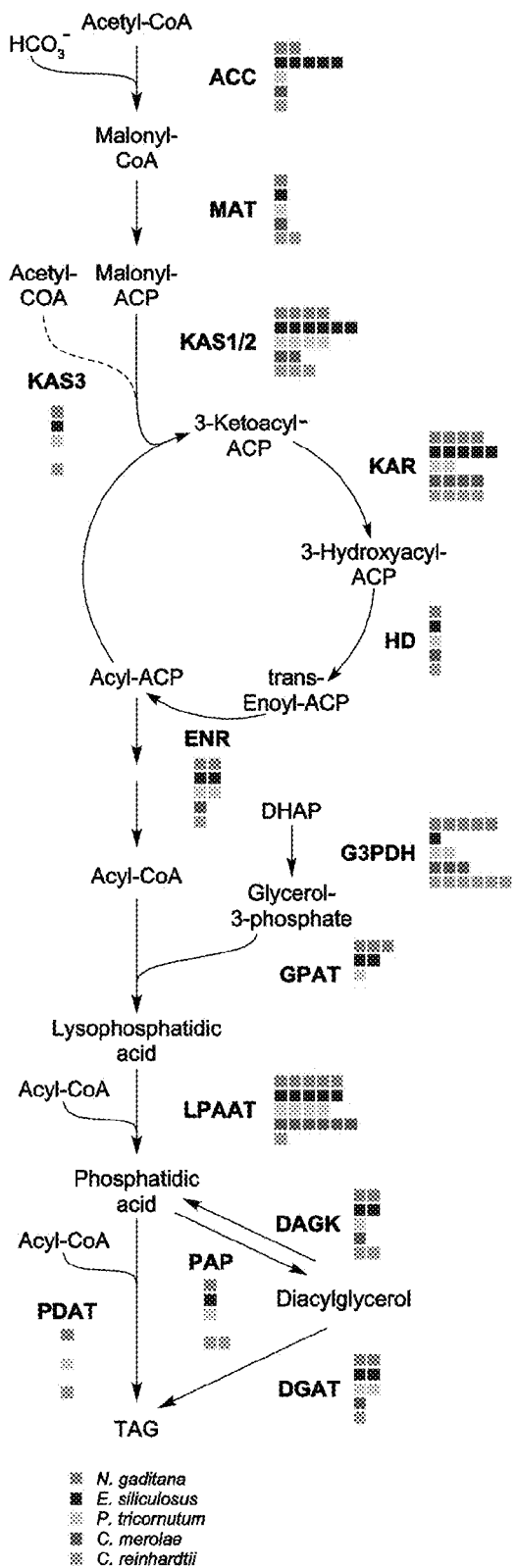
FIG. 16 shows the number of gene homologs in the TAG biosynthetic pathways in *N. gaditana* as compared to a brown alga (*E. siliculosus*), a diatom (*P. tricornutum*), a red alga (*C. merolae*) and a green alga (*C. reinhardtii*). For each reaction, colored squares denote the number of homologous genes in *N. gaditana* (orange), *E. siliculosus* (brown), *P. tricornutum* (yellow), *C. merolae* (red), *C. reinhardtii* (green). See the table at FIG. 18 for an overview of these gene homologs.

To investigate metabolic pathways of interest for biofuel production functional annotations were assigned to N. gaditana gene models. Gene Ontology terms were assigned to 3,838 gene models, from which 2,766 genes were identified as performing enzyme-catalyzed reactions representing 700 unique EC numbers that were in turn used to populate metabolic pathway maps (FIG. 13). Some of the most frequent Gene Ontology terms, aside from housekeeping functions, are terms involved in auxin biosynthesis, photosynthesis, and lipid biosynthesis (FIG. 14). Due to the exemplary lipid production by N. gaditana cultures we focused on characterizing lipid metabolic pathway genes, including those involved in fatty acid biosynthesis, TAG assembly and lipid activation/degradation (FIG. 15). BLASTp was used to identify homologs of the N. gaditana lipid metabolic genes in red/green/brown algae and diatoms. Comparison of the number of genes in each step of the lipid metabolic pathways suggests that N. gaditana has an expanded repertoire of genes involved in both TAG assembly and lipid degradation, including glycerol 3-phosphate dehydrogenase (G3PDH), glycerol 3-phosphate acyltransferase (GPAT), long-chain acyl-CoA ligase (ACSL) and acyl-CoA oxidase (ACOX) (FIG. 16 and FIG. 17). This increased number of lipid metabolic pathway genes is likely significant considering that N. gaditana has fewer total genes than all other algae used for this comparison, with the exception of C. merolae. To further examine the expansion of gene families in N. gaditana we compared the prevalence of gene ontology terms (GO-terms) with P. tricornutum and C. reinhardtii using the Fisher exact test. A selected list of over- and under-represented terms is shown in FIG. 18. This analysis confirms the overrepresentation of the GO-term for acyl-carrier protein biosynthetic processes and also indicates the expansion of several other gene families that can be of importance for the exemplary biomass production phenotype of N. gaditana.

For further analysis of the expansion of gene families/enrichment of gene ontology terms (GOtems) in N. gaditana we compared the prevalence of GO-terms with P. tricornutum and C. reinhardtii. Gene Ontology terms were assigned with Blast2GO and the complete gene ontologies for P. tricornutum and C. reinhardtii were obtained from B2G-FAR database. (Götz, S. et al. High-throughput functional annotation and data mining with the Blast2GO suite. Nucleic Acids Research 36, 3420-3435 (2008), Götz, S. et al. B2G-FAR, a species centered GO annotation repository. Bioinformatics (2011)). The Fisher exact test was used to analyze the significance of the expansions/reductions through the use of the built in Gossip algorithm. (Conesa, A. et al. Blast2GO: a universal tool for annotation, visualization and analysis in functional genomics research. Bioinformatics 21, 3674-3676 (2005), Blüthgen, N. et al. Profiling of gene groups utilizing gene ontology—A statistical framework. arXiv:q-bio (2004)). A selected list of over- and under-represented GO-terms with a maximum P-Value of $4 \times 10^{-03}$ and maximum false discovery rate of $5 \times 10^{-02}$ are shown in FIG. 18. Several expanded gene families that can be of importance for the exemplary biomass and lipid production characteristics of N. gaditana include those for acyl-carrier protein biosynthetic processes, auxin biosynthetic processes related to the production of plant growth hormones, carbon utilization, response to stress (including chemical, temperature and salt), and pyruvate metabolic processes. A large number of GO-terms associated with amino acid metabolism are also overrepresented (FIG. 19). In addition, GO-terms for chlorinated/halogenated hydrocarbon metabolic processes are also expanded, which is also observed in E. siliculosus, Cock, J. M. et al. The Ectocarpus genome and the independent evolution of multicellularity in brown algae. Nature 465, 617-621 (2010), where it is thought that these genes can protect against halogenated compounds produced by kelps as defense molecules, allowing epiphytic growth on these organisms, Cock, J. M. et al. The Ectocarpus genome and the independent evolution of multicellularity in brown algae. Nature 465, 617-621 (2010). Nannochloropsis gaditana, Merchant, S. S. et al. The Chlamydomonas genome reveals the evolution of key animal and plant functions. Science 318, 245-250 (2007), growth does not rely on exogenous sources of vitamins, which is reflected in the underrepresentation of genes involved in vitamin binding.

Example 3

Sequencing and Analysis of N. gaditana Transcriptomes

RNA was isolated from a variety of culturing conditions and growth phases, converted into cDNA, then sequenced using the Illumina SIPES protocol, followed by assembly of these reads using the commercial package from CLC Bio (Katrinebjerg, Denmark) into 37,055 contigs.

To assist in the identification of genes and to improve metabolic pathway maps of N. gaditana we sequenced the transcriptome (RNAseq) under a variety of physiological conditions. Additionally, transcriptome sequencing was conducted during logarithmic growth (low lipid production) and during stationary phase due to nitrate deprivation (high lipid production) to discover how transcriptional changes in N. gaditana modulate increased metabolic flux into lipid biosynthesis during nutrient deprivation. Genes that are strongly regulated during these different conditions are shown in FIG. 20. Similar to the findings in C. reinhardtii37, some of the up-regulated genes are involved in nitrogen assimilation and protein degradation/recycling, while some of the down-regulated genes are involved in photosynthesis. In addition, we annotated some regulated pathways on the metabolic pathway map (FIG. 13). This map highlights the decreased expression of genes involved in photosynthesis, carbon fixation, and oxidative phosphorylation that would be expected during stationary phase due to nutrient deprivation. Surprisingly, few genes that are directly involved in lipid biosynthesis are transcriptionally up-regulated to a significant extent. Because N. gaditana constitutively produces TAG, even during logarithmic growth, a possible explanation for this low amount of differential transcript accumulation is that the lipid production machinery can already be abundant within the cell, and existing levels can manage increased metabolic flux. In support of this hypothesis, we found that genes assigned with the GO-term for posttranscriptional regulation of gene expression were overrepresented in N. gaditana in comparison with P. tricornutum and C. reinhardtii, while the GO-term for transcription factor activity was underrepresented (FIG.

18). These results demonstrate that genes involved in gluconeogenesis (fructose-1,6-bisphosphatase, fructose-1,6-bisphosphate aldolase and phosphoglycerate kinase) are down-regulated, which could help direct carbon flux away from carbohydrate biosynthesis into lipid biosynthesis. To determine the exact mechanisms of lipid accumulation during nutrient deprivation further transcriptomic, proteomic, and metabolomic investigations are needed.

Other pathways that are of interest for bioenergy applications are the two isoprenoid biosynthesis pathways, the mevalonate (MVA) and the non-mevalonate pathways (DXP). Ancestral eukaryotes generally have the MVA pathway while many photosynthetic organisms have acquired the DXP pathway, most likely through a cyanobacterial endosymbiont or secondarily through a red algal symbiont. (Zaslayskaia, L. A., Lippmeier, J. C., Kroth, P. G., Grossman, A. R. & Apt, K. E. Transformation of the diatom *Phaeodactylum tricornutum* (Bacillariophyceae) with a variety of selectable marker and reporter genes. Journal of Phycology 36, 379-386 (2000).

Figure 21:
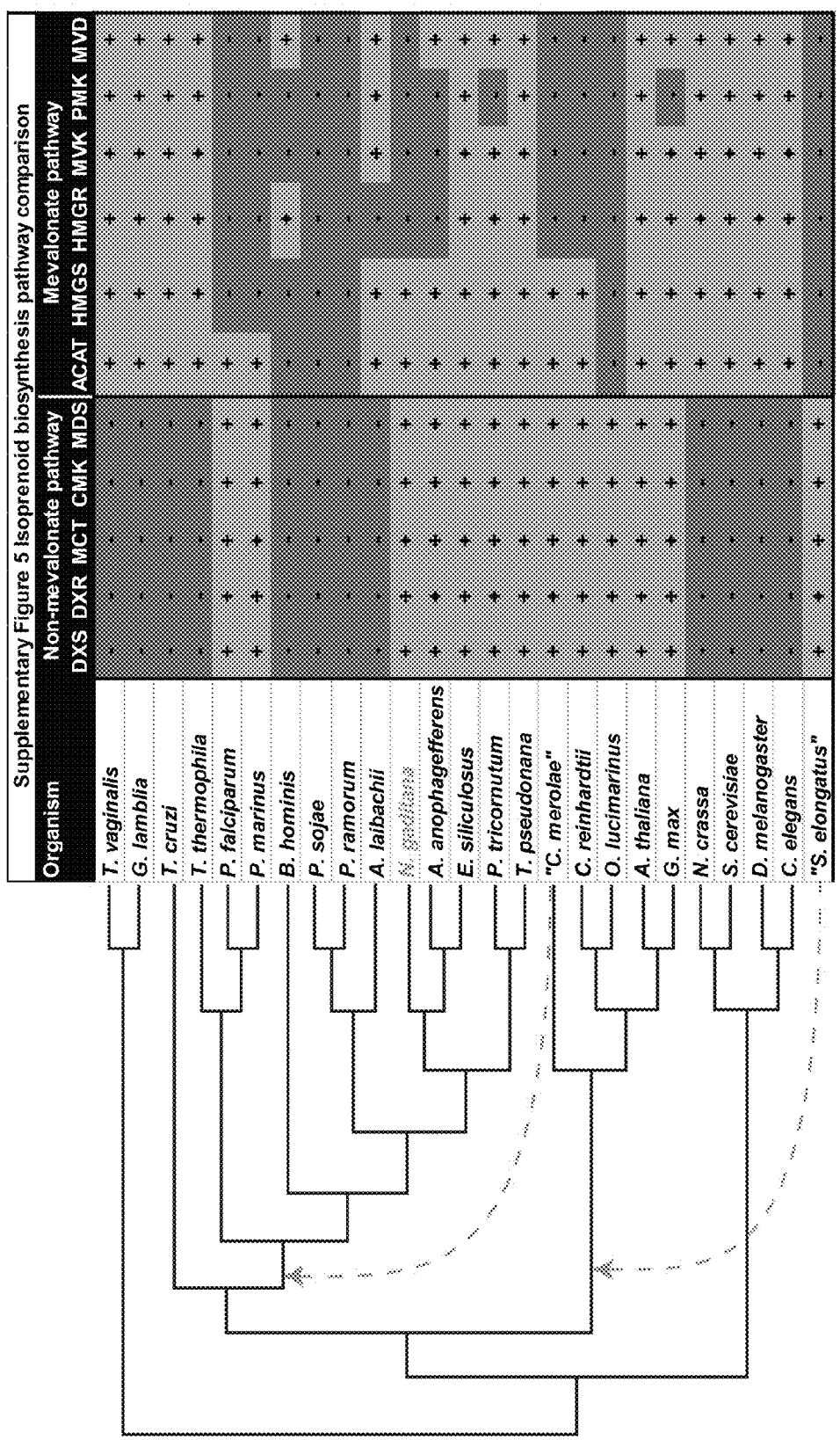
FIG. 21 is a comparison of isoprenoid biosynthesis pathway. Simplified phylogenetic cladogram and table showing the relationship between organisms with different sets of isoprenoid biosynthesis pathway genes. Green arrows indicate the acquisition of photosynthetic symbionts thought to have brought the DXP pathway into modern plants and algae. The names of *S. elongatus* and *C. merolae* appear in quotes to indicate that the symbiotic events do not refer to the *S. elongatus* or *C. merolae* but rather unknown relatives of these species.

Some higher plants have kept both the MVA and DXP pathways, while the green and red algae (*C. reinhardtii, O. lucimarinus, C. merolae*) have kept the more recently acquired DXP pathway and eliminated the more ancestral MVA pathway. In a similar fashion, stramenopiles that most likely acquired the DXP pathway from a red algal symbiont have in the case of diatoms and brown algae (*P. tricornutum, T. pseudonana, E. siliculosus*) kept both the MVA and DXP pathways, while *N. gaditana* and *A. anophagefferens* have the DXP pathway (FIG. 21 and FIG. 1). Parasitic chromalveolates, including stramenopiles, seem to differ in their isoprenoid biosynthesis capacity depending on whether they have kept at least a remnant plastid. Both *P. marinus* (has a functional plastid) and *P. falciparum* (has a remnant plastid) have kept the DXP pathway, while *P. sojae, P. ramorum* and *A. laibachii* (no plastid) have lost both the MVA and DXP pathways.

Example 4

Genetic Transformation of *N. gaditana* Using Electroporation

Transformation protocols for common laboratory model algae, such as *C. reinhardtii* and *P. tricornutum* have been available for more than a decade, (Zaslayskaia, L. A., Lippmeier, J. C., Kroth, P. G., Grossman, A. R. & Apt, K. E. Transformation of the diatom *Phaeodactylum tricornutum* (Bacillariophyceae) with a variety of selectable marker and reporter genes. *Journal of Phycology*, 379-386 (2000); Boynton, J. et al. Chloroplast transformation in *Chlamydomonas* with high velocity microprojectiles. *Science*, 1534-1538 (1988); Kindle, K. L. High-frequency nuclear transformation of *Chlamydomonas reinhardtii*. *Proceedings of the National Academy of Sciences*, 1228-1232 (1990), Apt, K. E., Grossman, A. R. & Kroth-Pancic, P. G. Stable nuclear transformation of the diatom *Phaeodactylum tricornutum*. Molecular and General Genetics, 572-579 (1996)), but relatively low biomass production rates in some of these strains have kept them from becoming industrially relevant. There have been reports of successful genetic transformation of *Nannochloropsis oculata*. (Chen, H. L., Li, S. S., Huang, R. & Tsai, H.-J. Conditional production of a functional fish growth hormone in the transgenic line of *Nannochloropsis oculata* (Eustigmatophyceae). *Journal of Phycology*, 768-776 (2008); Li, S.-S. & Tsai, H.-J. Transgenic microalgae as a non-antibiotic bactericide producer to defend against bacterial pathogen infection in the fish digestive tract. *Fish & Shellfish Immunology*, 316-325 (2009)) However, 99% of the transformants lost the transgene after 1.5 months of cultivation, indicating that the majority of the transformants had not truly incorporated the transgene into the genome. These earlier attempts at transformation of *N. oculata* relied on the use of foreign promoters, from *P. tricornutum, C. reinhardtii* or viral promoters and did not utilize antibiotic selection. Here we show for the first time the successful transformation of *N. gaditana*. Transformation efficiency was greatly improved by the use of endogenous promoters, identified through preliminary sequencing of the *N. gaditana* genome, to drive the expression of a bleomycin resistance gene. In addition, previously described protocols for the transformation of *N. oculata* involve the use of various enzyme mixes for creation of protoplasts prior to transformation, (Chen, H. L., Li, S. S., Huang, R. & Tsai, H.-J. Conditional production of a functional fish growth hormone in the transgenic line of *Nannochloropsis oculata* (Eustigmatophyceae). *Journal of Phycology*, 768-776 (2008); Li, S.-S. & Tsai, H.-J. Transgenic microalgae as a non-antibiotic bactericide producer to defend against bacterial pathogen infection in the fish digestive tract. *Fish & Shellfish Immunology*, 316-325 (2009)), while our protocol simply relies on the use of electroporation at high field strength. We selected three promoters for use in our transformations, which included the promoters from the genes encoding beta-tubulin (TUB, Nga00092), heat shock protein 70 (HSP, Nga07210) and the ubiquitin extension protein (UEP, Nga02115.1). The efficiency of the transformations was strongly affected by the promoter used (Table 3) and efficient transformation was achieved using the TUB promoter which resulted in an efficiency of $12.5*10^{-6}$. This was achieved using a very high 12,000 V/cm field strength during the electroporation. Use of lower field strength (10,500 V/cm) resulted in 5-fold lower transformation efficiency ($60*10^{-6}$). We also attempted using the fucoxanthin binding protein B (FcpB) promoter from *P. tricornutum* without success. The highest efficiency achieved, ($12.5*10^{-6}$) is comparable to the efficiency ($10*10^{-6}$) observed with transformations of *P. tricornutum*. (Apt, K. E., Grossman, A. R. & Kroth-Pancic, P. G. Stable nuclear transformation of the diatom *Phaeodactylum tricornutum*. Molecular and General Genetics, 572-579 (1996).

TABLE 3

Number of clones generated by different promoter constructs and field strengths

| Promoter construct[a] | 9,000 V/cm[b] | 10,500 V/cm[b] | 12,000 V/cm[b] | 12,000 V/cm efficiencies[c] | +N RNA quant[d] | −N RNA quant[d] |
|---|---|---|---|---|---|---|
| No plasmid[e] | 0 | 0 | 0 | 0 | N/A | N/A |
| TUB Nga00092 | 0 | 3 | 40 | 12.5 * 10-6 | 6,992 | 7,149 |
| UEP Nga02115.1 | 0 | 8 | 18 | 27.8 * 10-6 | 1,491 | 1,341 |

TABLE 3-continued

Number of clones generated by different promoter constructs and field strengths

| Promoter construct[a] | 9,000 V/cm[b] | 10,500 V/cm[b] | 12,000 V/cm[b] | 12,000 V/cm efficiencies[c] | +N RNA quant[d] | −N RNA quant[d] |
|---|---|---|---|---|---|---|
| HSP Nga07210 | 0 | 3 | 3 | 166.7 * 10-6 | 5 | 2 |
| pPha-T1-fcpB[f] | 0 | 0 | 0 | 0 | N/A | N/A |

[a]The promoter used for transformation.
[b]Number of colonies generated at the different field strengths used during electroporation.
[c]Efficiencies of electroporation, colonies generated per electroporated cell.
[d]Normalized RNAseq quantification measured in number of reads per kb of the corresponding genes during normal and nitrogen deprived growth.
[e]Negative control went through entire electroporation protocol without any plasmid DNA. Survival appeared unaffected on positive control plates without zeocin.
[f]pPha-T1-fcpB indicates use of the *P. tricornutum* fcpB promoter.

Figure 22:
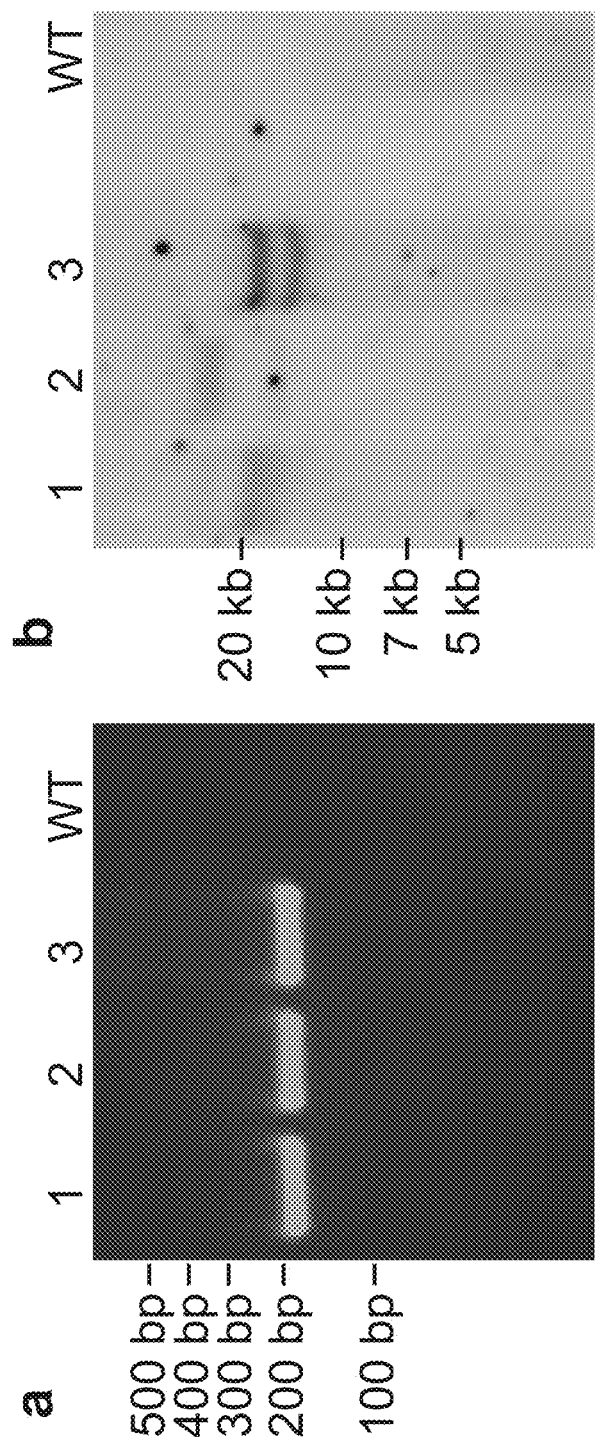
FIG. 22 shows successful transformation of *N. gaditana* by electroporation.

Confirmation of successful *N. gaditana* transformation was done after 4-5 months of growth with antibiotic selection. Genomic PCR confirmed the presence of the transgene in selected colonies and Southern blot analysis confirmed successful incorporation of the transgene into the nuclear genomes of the mutant colonies (FIG. 22). The Southern blots also indicated that in various cases multiple insertions of the transgene occurred, and that integration into the genome with the construct used is random. Our results demonstrate a straight forward approach to genetically modify this oleaginous alga, and we anticipate that the ability to further engineer *N. gaditana* will allow this organism to emerge as an important model species for algal biofuel production.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the nucleic acid, polynucleotide, amino acid, and polypeptide sequences are specifically embraced by the present invention and are disclosed herein just as if each and every combination was individually and explicitly disclosed, to the extent that such combinations embrace operably sequences (i.e., sequences that produce the desired effect and can be tested for biological activity). In addition, all sub-combinations of the sequences listed in the embodiments describing such variables are also specifically embraced by the present invention and are disclosed herein just as if each and every such sub-combination of sequence was individually and explicitly disclosed herein.

All cited references are herein expressly incorporated by reference in their entirety.

Although certain preferred cases of the invention have been specifically described herein, it will be apparent to those skilled in the art to which the invention pertains that variations and modifications of the various cases shown and described herein can be made without departing from the spirit and scope of the invention. Accordingly, it is intended that the invention be limited only to the extent required by the appended claims and the applicable rules of law.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08709766B2). An electronic copy of the "Sequence Listing" will also be available from the USPTO upon request and payment of the fee set forth in 37 CFR 1.19(b)(3).

What is claimed is:

1. A transgenic algae of the genus *Nannochloropsis* transformed with a purified polynucleotide sequence comprising the *Nannochloropsis* control sequence of SEQ ID NO:7604 operably linked to a polypeptide coding sequence, said purified polynucleotide sequence further comprising a selectable marker.

2. The algae of claim 1, wherein the polypeptide is a lipid biosynthetic pathway polypeptide or regulates a lipid biosynthetic pathway.

3. The algae of claim 2, wherein the lipid is triacylglyceride.

4. The algae of claim 1, wherein the coding sequence is SEQ ID NO:8719.

5. The algae of claim 4, wherein the control sequence is SEQ ID NO:7604.

6. The algae of claim 4, wherein the control sequence increases or decreases the number of copies of coding sequence transcript during logarithmic growth and/or when nitrogen is not limiting, than during non-logarithmic growth and/or when nitrogen is limiting.

7. The algae of claim 6, wherein the control sequence increases the number of copies of coding sequence transcript during logarithmic growth and/or when nitrogen is not limiting.

8. A method of making a transgenic algae comprising:

a) transforming an alga of the genus *Nannochloropsis* by introducing a purified polynucleotide sequence comprising the *Nannochloropsis* control sequence of SEQ ID NO:7604 operably linked to a polypeptide coding sequence, said purified polynucleotide sequence further comprising a selectable marker; and b) contacting the at least one transformed alga with a medium.

9. The method of claim 8, wherein the purified polynucleotide sequence is stably integrated into the genome of the algae.

10. The method of claim 8, wherein the introducing is by electroporation.

11. The method of claim 10, wherein electroporation is performed at high field strength.

12. The method of claim 11, wherein the field strength is 12,000 V/cm.

13. A method of using the transgenic algae of claim 1 for obtaining lipid or biomass comprising:
  a) growing the transgenic algae in a liquid medium;
  b) allowing the transgenic algae to grow to a stationary phase and/or reducing the nitrogen concentration in the liquid medium and/or a gas environment in contact with the liquid medium;
  c) maintaining the transgenic algae in the liquid medium;
  d) collecting the transgenic algae;
  e) separating the algae from the liquid medium;
  f) extracting lipids or biomass from the algae, thereby
  g) obtaining lipid or biomass.

\* \* \* \* \*